US012690385B2

(12) United States Patent
Stoessel

(10) Patent No.: US 12,690,385 B2
(45) Date of Patent: Jul. 21, 2026

(54) INDOLO[3.2.1-JK]CARBAZOLE-6-CARBONITRILE DERIVATIVES AS BLUE FLUORESCENT EMITTERS FOR USE IN OLEDS

(71) Applicant: UDC IRELAND LIMITED, Dublin (IE)

(72) Inventor: Philipp Stoessel, Darmstadt (DE)

( * ) Notice: Subject to any disclaimer, the term of this patent is extended or adjusted under 35 U.S.C. 154(b) by 0 days.

(21) Appl. No.: 18/266,832

(22) PCT Filed: Dec. 15, 2021

(86) PCT No.: PCT/EP2021/085803

§ 371 (c)(1),
(2) Date: Jun. 13, 2023

(87) PCT Pub. No.: WO2022/129116

PCT Pub. Date: Jun. 23, 2022

(65) Prior Publication Data

US 2024/0114782 A1 Apr. 4, 2024

(30) Foreign Application Priority Data

Dec. 18, 2020 (EP) .................................... 20215734

(51) Int. Cl.
*H10K 85/60* (2023.01)
*C07D 471/08* (2006.01)
(Continued)

(52) U.S. Cl.
CPC ....... *H10K 85/6572* (2023.02); *C07D 471/08* (2013.01); *C07D 471/16* (2013.01); *C07D 487/06* (2013.01); *C07D 487/16* (2013.01); *C07D 487/18* (2013.01); *C07D 487/22* (2013.01); *C07D 491/16* (2013.01); *C07D 491/20* (2013.01); *C07D 491/22* (2013.01); *C07D 495/16* (2013.01); *C07D 495/22* (2013.01); *C07D 498/22* (2013.01); *C07F 7/0814* (2013.01); *C09K 11/02* (2013.01); *C09K 11/06* (2013.01); *H10K 85/40* (2023.02); *H10K 85/615* (2023.02); *H10K 85/624* (2023.02); *H10K 85/654* (2023.02); *H10K 85/657* (2023.02); *C07B 2200/05* (2013.01); *C09K 2211/1007* (2013.01);
(Continued)

(58) Field of Classification Search
CPC .................................................. H10K 85/6572
See application file for complete search history.

(56) References Cited

U.S. PATENT DOCUMENTS

2019/0221747 A1 * 7/2019 Takahashi .......... H10K 85/6574

FOREIGN PATENT DOCUMENTS

WO 2019/111971 A1 6/2019
WO 2019/194617 A1 10/2019

OTHER PUBLICATIONS

Henry et al., "Specific indolo [3, 2, 1-jk] carbazole conducting thin-film materials production by selective substitution", The Journal of Physical Chemistry A 115, 2011, pp. 5435-5442.
(Continued)

*Primary Examiner* — William D Young
(74) *Attorney, Agent, or Firm* — DUANE MORRIS LLP

(57) ABSTRACT

The present invention relates to aromatic compounds suitable for use in electronic devices, and to electronic devices, especially organic electroluminescent devices, comprising these compounds.

19 Claims, 1 Drawing Sheet

PL spectra, about $10^{-5}$ M in toluene

(51) Int. Cl.

| | |
|---|---|
| ***C07D 471/16*** | (2006.01) |
| ***C07D 487/06*** | (2006.01) |
| ***C07D 487/16*** | (2006.01) |
| ***C07D 487/18*** | (2006.01) |
| ***C07D 487/22*** | (2006.01) |
| ***C07D 491/16*** | (2006.01) |
| ***C07D 491/20*** | (2006.01) |
| ***C07D 491/22*** | (2006.01) |
| ***C07D 495/16*** | (2006.01) |
| ***C07D 495/22*** | (2006.01) |
| ***C07D 498/22*** | (2006.01) |
| ***C07F 7/08*** | (2006.01) |
| ***C09K 11/02*** | (2006.01) |
| ***C09K 11/06*** | (2006.01) |
| ***H10K 50/11*** | (2023.01) |
| ***H10K 85/40*** | (2023.01) |

(52) U.S. Cl.

CPC ................. *C09K 2211/1011* (2013.01); *C09K 2211/1018* (2013.01); *H10K 50/11* (2023.02)

(56) References Cited

OTHER PUBLICATIONS

International Search Report and Written Opinion received for PCT Patent Application No. PCT/EP2021/085803, mailed on Feb. 22, 2022, 14 pages (3 pages of English Translation and 11 pages of Original Document).

* cited by examiner

PL spectra, about $10^{-5}$ M in toluene
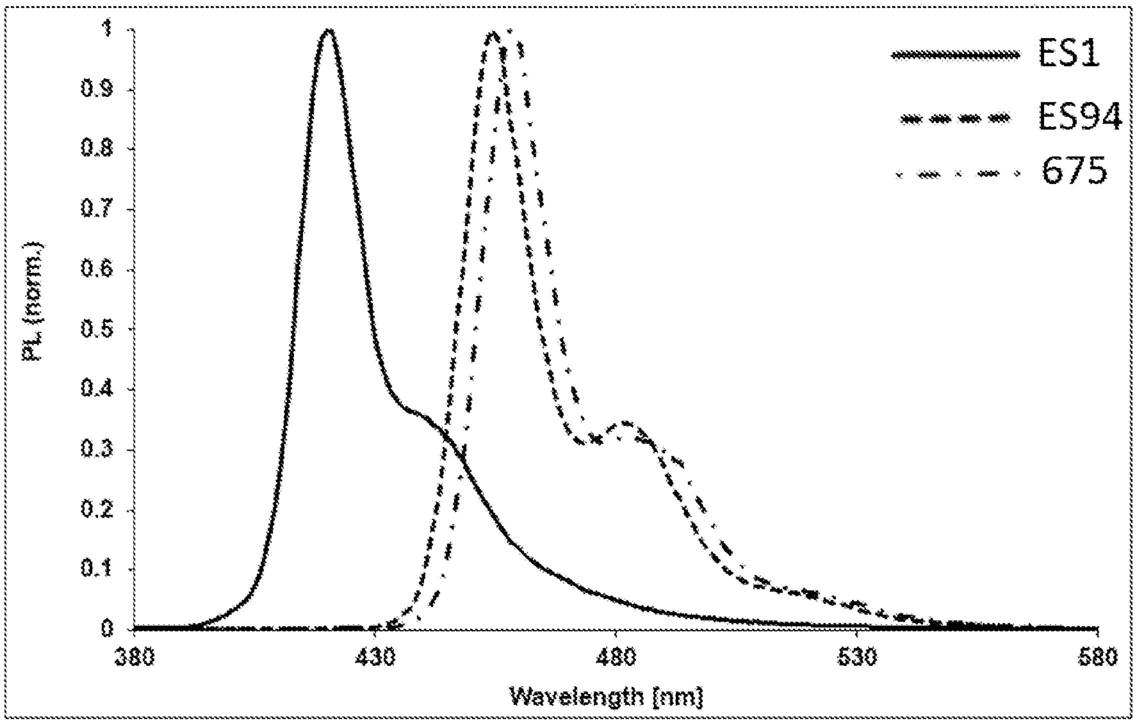

INDOLO[3.2.1-JK]CARBAZOLE-6-CARBONITRILE DERIVATIVES AS BLUE FLUORESCENT EMITTERS FOR USE IN OLEDS

CROSS-REFERENCE TO RELATED APPLICATIONS

This application is a National stage application (under 35 U.S.C. § 371) of PCT/EP2021/085803, filed Dec. 15, 2021, which claims benefit of European Application No. 20215734.3, filed Dec. 18, 2020, both of which are incorporated herein by reference in their entirety.

The present invention relates to aromatic compounds for use in electronic devices, especially in organic electroluminescent devices, and to electronic devices, especially organic electroluminescent devices comprising these aromatic compounds.

Emitting materials used in organic electroluminescent devices are frequently phosphorescent organometallic complexes or fluorescent compounds. There is generally still a need for improvement in electroluminescent devices.

US 2010/0051928, WO 2010/104047 A1, US 2014/319507 A1, WO 2017/175690, US 2019/0393439, CN 110452226 A, WO 2019/132506 A1 and WO 2020/064666 A1 disclose polycyclic compounds that can be used in organic electroluminescent devices.

In general terms, there is still a need for improvement in these heterocyclic compounds, for example for use as emitters, especially as fluorescent emitters, particularly in relation to lifetime and colour purity, but also in relation to the efficiency and operating voltage of the device.

It is therefore an object of the present invention to provide compounds which are suitable for use in an organic electronic device, especially in an organic electroluminescent device, and which lead to good device properties when used in this device, and to provide the corresponding electronic device.

More particularly, the problem addressed by the present invention is that of providing compounds which lead to a high lifetime, good efficiency and low operating voltage.

In addition, the compounds should have excellent processability, and the compounds should especially show good solubility.

A further problem addressed by the present invention can be considered that of providing compounds suitable for use in phosphorescent or fluorescent electroluminescent devices, especially as emitter. A particular problem addressed by the present invention is that of providing emitters suitable for red, green or blue electroluminescent devices, preferably for blue electroluminescent devices.

In addition, the compounds, especially when they are used as emitters in organic electroluminescent devices, should lead to devices having excellent colour purity.

A further problem can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, this object is achieved by particular compounds described in detail below that are of very good suitability for use in preferably electroluminescent devices and lead to organic electroluminescent devices that show very good properties, especially in relation to lifetime, colour purity, efficiency and operating voltage. The present invention therefore provides these compounds and electronic devices, especially organic electroluminescent devices, comprising such compounds.

BRIEF DESCRIPTION OF FIGURE

FIG. 1 shows the photoluminescence spectra (PL spectra) of compounds ES1, ES94 and 675, measured with a Hitachi F-4500 PL spectrometer in about $10^{-5}$ molar degassed toluene solution at room temperature (about 25° C.).

The present invention provides a compound comprising at least one structure of the formula (I), preferably a compound of the formula (I), Formula (I)

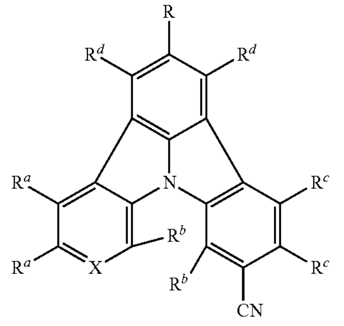

where the symbols used are as follows:

X is the same or different at each instance and is N, C—CN, C—Y—$R^y$ or $CR^b$, preferably N, C—CN or C—Y—$R^y$, more preferably C—CN;

Y is the same or different at each instance and is CO, P(═O)$R^a$, SO, $SO_2$, C(O)O, C(S)O, C(O)S, C(═O)N$R^a$, C(═O)NAr, preferably CO, P(═O)$R^a$, SO, $SO_2$, more preferably CO;

R is the same or different at each instance and is H, D, OH, F, Cl, Br, I, CN, $NO_2$, $N(Ar)_2$, $N(Re)_2$, C(═O)$N(Ar)_2$, C(═O)$N(Re)_2$, $C(Ar)_3$, $C(Re)_3$, $Si(Ar)_3$, $Si(Re)_3$, $B(Ar)_2$, $B(Re)_2$, C(═O)Ar, C(═O)Re, P(═O)$(Ar)_2$, P(═O)$(Re)_2$, $P(Ar)_2$, $P(Re)_2$, S(═O)Ar, S(═O)Re, S$(═O)_2$Ar, S$(═O)_2R^e$, $OSO_2Ar$, $OSO_2R^e$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may each be substituted by one or more Re radicals, where one or more nonadjacent $CH_2$ groups may be replaced by $R^eC$═$CR^e$, C≡C, $Si(R^e)_2$, C═O, C═S, C═Se, C═$NR^e$, —C(═O)O—, —C(═O)$NR^e$—, $NR^e$, P(═O)($R^e$), —O—, —S—, SO or $SO_2$, or an aromatic or heteroaromatic ring system which has 5 to 60 aromatic ring atoms and may be substituted in each case by one or more Re radicals, or an aryloxy or heteroaryloxy group which has 5 to 60 aromatic ring atoms and may be substituted by one or more $R^e$ radicals, or an arylthio or heteroarylthio group which has 5 to 60 aromatic ring atoms and may be substituted by one or more $R^e$ radicals, or a diarylamino, arylheteroarylamino, diheteroarylamino group which has 5 to 60 aromatic ring atoms and may be substituted by one or more $R^e$ radicals, or an arylalkyl or heteroarylalkyl group which has 5 to 60 aromatic ring atoms and 1 to 10 carbon atoms in the alkyl radical and may be substituted by one or more $R^e$ radicals; at the same time, any R radical may form a ring system with a further group, preferably $R^d$;

Ar is the same or different at each instance and is an aromatic or heteroaromatic ring system which has 5 to 60 aromatic ring atoms and may be substituted by one or more $R^e$ radicals; at the same time, it is possible for two Ar radicals bonded to the same carbon atom, silicon atom, nitrogen atom, phosphorus atom or boron atom also to be joined together via a bridge by a single bond or a bridge selected from $B(R^e)$, $C(R^e)_2$, $Si(R^e)_2$, C═O, C═$NR^e$, C═$C(R^e)_2$, O, S, S═O, $SO_2$, $N(R^e)$, $P(R^e)$ and P(═O)$R^e$;

$R^a$, $R^b$, $R^c$, $R^d$, $R^e$ is the same or different at each instance and is H, D, OH, F, Cl, Br, I, CN, $NO_2$, $N(Ar')_2$, $N(R^1)_2$, C(═O)$N(Ar')_2$, C(═O)$N(R^1)_2$, $C(Ar')_3$, $C(R^1)_3$, $Si(Ar')_3$, $Si(R^1)_3$, $B(Ar')_2$, $B(R^1)_2$, C(═O)Ar', C(═O)$R^1$, P(═O)$(Ar')_2$, P(═O)$(R^1)_2$, $P(Ar')_2$, $P(R^1)_2$, S(═O)Ar', S(═O)$R^1$, S(═O)$_2$Ar', S(═O)$_2R^1$, $OSO_2Ar'$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^1$ radicals, where one or more nonadjacent $CH_2$ groups may be replaced by $R^1C$═$CR^1$, C≡C, $Si(R^1)_2$, C═O, C═S, C═Se, C═$NR^1$, —C(═O)O—, —C(═O)$NR^1$—, $NR^1$, P(═O)($R^1$), —O—, —S—, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two $R^a$, $R^b$, $R^c$, $R^d$, $R^e$ radicals may also form a ring system together or with a further group, preferably R or $R^y$;

$R^y$ is the same or different at each instance and is $C(Ar')_3$, $C(R^1)_3$, $Si(Ar')_3$, $Si(R^1)_3$, $N(Ar')_2$, $N(R^1)_2$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^1$ radicals, where one or more nonadjacent $CH_2$ groups may be replaced by $R^1C$═$CR^1$, C≡C, $Si(R^1)_2$, C═O, C═S, C═Se, C═$NR^1$, —C(═O)O—, —C(═O)$NR^1$—, $NR^1$, P(═O)($R^1$), —O—, —S—, SO or $SO_2$, where any $CH_2$ group bonded to the Y radical may not be replaced by C═O, C═S, C═Se, C═$NR^1$, —C(═O)O—, —C(═O)$NR^1$—, P(═O)($R^1$), SO or $SO_2$, where any $CH_2$ group bonded to the Y radical may more preferably not be replaced by $Si(R^1)_2$, C═O, C═S, C═Se, C═$NR^1$, —C(═O)O—, —C(═O)$NR^1$—, $NR^1$, P(═O)($R^1$), —O—, —S—, SO or $SO_2$, or an aromatic or heteroaromatic ring system which has 5 to 60 aromatic ring atoms and may be substituted in each case by one or more $R^1$ radicals; at the same time, two $R^y$ radicals may also form a ring system with one another, or one $R^y$ radical together with one $R^a$, $R^b$, $R^c$, $R^d$, $R^e$ radical, preferably an $R^a$ radical;

Ar' is the same or different at each instance and is an aromatic or heteroaromatic ring system which has 5 to 60 aromatic ring atoms and may be substituted by one or more $R^1$ radicals; at the same time, it is possible for two Ar' radicals bonded to the same carbon atom, silicon atom, nitrogen atom, phosphorus atom or boron atom also to be joined together via a bridge by a single bond or a bridge selected from $B(R^1)$, $C(R^1)_2$, $Si(R^1)_2$, C═O, C═$NR^1$, C═$C(R^1)_2$, O, S, S═O, $SO_2$, $N(R^1)$, $P(R^1)$ and P(═O)$R^1$;

$R^1$ is the same or different at each instance and is H, D, F, Cl, Br, I, CN, $NO_2$, $N(Ar'')_2$, $N(R^2)_2$, C(═O)Ar'', C(═O)$R^2$, P(═O)$(Ar'')_2$, $P(Ar'')_2$, $B(Ar'')_2$, $B(R^2)_2$, $C(Ar'')_3$, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by —$R^2C$═$CR^2$—, —C≡C—, $Si(R^2)_2$, C═O, C═S, C═Se, C═$NR^2$, —C(═O)O—, —C(═O)$NR^2$—, $NR^2$, P(═O)($R^2$), —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more, preferably adjacent $R^1$ radicals together may form a ring system; at the same time, one or more $R^1$ radicals may form a ring system with a further part of the compound;

Ar'' is the same or different at each instance and is an aromatic or heteroaromatic ring system which has 5 to 30 aromatic ring atoms and may be substituted by one or more $R^2$ radicals; at the same time, it is possible for two Ar'' radicals bonded to the same carbon atom, silicon atom, nitrogen atom, phosphorus atom or boron atom also to be joined together via a bridge by a single bond or a bridge selected from $B(R^2)$, $C(R^2)_2$, $Si(R^2)_2$, C═O, C═$NR^2$, C═$C(R^2)_2$, O, S, S═O, $SO_2$, $N(R^2)$, $P(R^2)$ and P(═O)$R^2$;

$R^2$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, two or more, preferably adjacent substituents $R^2$ together may form a ring system.

It may preferably be the case that at least one, preferably at least two, of the R, $R^a$, $R^b$, $R^c$, $R^d$, $R^e$ radicals are not H, preferably not H, D, OH, $NO_2$, F, Cl, Br, I. Accordingly, R is preferably selected from CN, $N(Ar)_2$, $N(R^e)_2$, C(═O)$N(Ar)_2$, C(═O)$N(R^e)_2$, $C(Ar)_3$, $C(R^e)_3$, $Si(Ar)_3$, $Si(R^e)_3$, $B(Ar)_2$, $B(R^e)_2$, C(═O)Ar, C(═O)$R^e$, P(═O)$(Ar)_2$, P(═O)$(R^e)_2$, $P(Ar)_2$, $P(R^e)_2$, S(═O)Ar, S(═O)$R^e$, S(═O)$_2$Ar, S(═O)$_2R^e$, $OSO_2Ar$, $OSO_2R^e$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^e$ radicals, where one or more nonadjacent $CH_2$ groups may be replaced by $R^eC{=}CR^e$, C≡C, $Si(R^e)_2$, C═O, C═S, C═Se, $C{=}NR^e$, —C(═O)O—, —C(═O)$NR^e$—, $NR^e$, P(═O)($R^e$), —O—, —S—, SO or $SO_2$, or an aromatic or heteroaromatic ring system which has 5 to 60 aromatic ring atoms and may be substituted in each case by one or more $R^e$ radicals, or an aryloxy or heteroaryloxy group which has 5 to 60 aromatic ring atoms and may be substituted by one or more $R^e$ radicals, or an arylthio or heteroarylthio group which has 5 to 60 aromatic ring atoms and may be substituted by one or more $R^e$ radicals, or a diarylamino, arylheteroarylamino, diheteroarylamino group which has 5 to 60 aromatic ring atoms and may be substituted by one or more $R^e$ radicals, or an arylalkyl or heteroarylalkyl group which has 5 to 60 aromatic ring atoms and 1 to 10 carbon atoms in the alkyl radical and may be substituted by one or more $R^e$ radicals; at the same time, an R radical may form a ring system with a further group, preferably $R^d$; and/or at least one of the $R^a$, $R^b$, $R^c$, $R^d$, $R^e$ radicals is preferably the same or different at each instance and is selected from CN, $N(Ar')_2$, $N(R^1)_2$, $C(=O)N(Ar')_2$, $C(=O)N(R^1)_2$, $C(Ar')_3$, $C(R^1)_3$, $Si(Ar')_3$, $Si(R^1)_3$, $B(Ar')_2$, $B(R^1)_2$, C(═O)Ar', C(═O)$R^1$, $P(=O)(Ar')_2$, $P(=O)(R^1)_2$, $P(Ar')_2$, $P(R^1)_2$, S(═O)Ar', S(═O)$R^1$, $S(=O)_2Ar'$, $S(=O)_2R^1$, $OSO_2Ar'$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^1$ radicals, where one or more nonadjacent $CH_2$ groups may be replaced by $R^1C{=}CR^1$, CC, $Si(R^1)_2$, C═O, C═S, C═Se, C═$NR^1$, —C(═O)O—, —C(═O)$NR^1$—, $NR^1$, P(═O)($R^1$), —O—, —S—, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two $R^a$, $R^b$, $R^c$, $R^d$, $R^e$ radicals may also form a ring system together or with a further group.

It may preferably be the case that at least one of the $R^a$ radicals, preferably both $R^a$ radicals, is/are not H, where, more preferably, at least one of the $R^a$ radicals, preferably both $R^a$ radicals, is/are not H, D, F, Cl, Br, I. In this context, the details set out above with regard to preferred $R^a$ radicals should be taken into account.

It may preferably further be the case that at least one of the $R^c$ radicals, preferably both $R^c$ radicals, is/are not H, where, more preferably, at least one of the $R^c$ radicals, preferably both $R^c$ radicals, is/are not H, D, F, Cl, Br, I. In this context, the details set out above with regard to preferred $R^c$ radicals should be taken into account.

More preferably, it may further be the case that at least one of the $R^a$ radicals and at least one of the $R^c$ radicals is not H, preferably not H, D, F, Cl, Br, I. Especially preferably, both $R^a$ radicals and both $R^c$ radicals are not H, preferably not H, D, F, Cl, Br, I In this context, the details set out above with regard to preferred $R^a$ and $R^c$ radicals should be taken into account.

It may preferably further be the case that at least one, preferably at least two, of the $R^a$, $R^c$ radicals is/are a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^1$ radicals, where one or more nonadjacent $CH_2$ groups may be replaced by $R^1C{=}CR^1$, C≡C, $Si(R^1)_2$, C═O, C═S, C═Se, C═$NR^1$, —C(═O)O—, —C(═O)$NR^1$—, $NR^1$, P(═O)($R^1$), —O—, —S—, SO or $SO_2$.

In a preferred configuration, it may be the case that the R radical is an aromatic or heteroaromatic ring system which has 5 to 13 aromatic ring atoms and may be substituted by one or more $R^e$ radicals.

In a further-preferred configuration, it may be the case that two $R^a$ radicals together with the further groups to which the two $R^a$ radicals bind form a fused ring, preferably an aliphatic or heteroaliphatic ring having 3 to 20, preferably 5 to 18, ring atoms or an aromatic or heteroaromatic ring having 5 to 13 ring atoms, more preferably an aliphatic or heteroaliphatic ring which has 3 to 20, preferably 5 to 18, ring atoms and may be substituted in each case by one or more $R^1$ radicals, where $R^1$ has the definition given above.

Furthermore, it may preferably be the case that two $R^c$ radicals together with the further groups to which the two $R^c$ radicals bind form a fused ring, preferably an aliphatic or heteroaliphatic ring having 3 to 20, preferably 5 to 18, ring atoms or an aromatic or heteroaromatic ring having 5 to 13 ring atoms, more preferably an aliphatic or heteroaliphatic ring which has 3 to 20, preferably 5 to 18, ring atoms and may be substituted in each case by one or more $R^1$ radicals, where $R^1$ has the definition given above.

In an especially preferred embodiment, the R radical comprises an aromatic or heteroaromatic ring system which has 5 to 13 aromatic ring atoms and may be substituted by one or more $R^e$ radicals, and at least two $R^a$, $R^c$ radicals together with the further groups to which the two $R^a$, $R^c$ radicals bind form a fused ring that may be substituted in each case by one or more $R^1$ radicals. Preferably, a compound/structure of the invention accordingly comprises at least one, preferably two, fused rings that are formed by the two $R^a$ and/or $R^c$ radicals together with the further groups to which the two $R^a$, $R^c$ radicals bind, and the R radical is an aromatic or heteroaromatic ring system having 5 to 13 aromatic ring atoms. Fused rings here may be aliphatic, heteroaliphatic, aromatic or heteroaromatic, with preferred configurations set out above and hereinafter, preferably with formation of an aliphatic or heteroaliphatic ring having 3 to 20, preferably 5 to 18, ring atoms or an aromatic or heteroaromatic ring having 5 to 13 ring atoms, more preferably an aliphatic or heteroaliphatic ring which has 3 to 20, preferably 5 to 18, ring atoms and may be substituted in each case by one or more $R^1$ radicals.

If X is a C—Y—$R^y$ group, it may preferably be the case that:

$R^y$ is the same or different at each instance and is $C(Ar')_3$, $C(R^1)_3$, $Si(Ar')_3$, $Si(R^1)_3$, a straight-chain alkyl group having 1 to 40 carbon atoms or an alkenyl or alkynyl group having 2 to 40 carbon atoms or a branched or cyclic alkyl group having 3 to 20 carbon atoms, where the alkyl, alkenyl or alkynyl group may be substituted in each case by one or more $R^1$ radicals, where one or more nonadjacent $CH_2$ groups may be replaced by $R^1C{=}CR^1$, C≡C, $Si(R^1)_2$, C═O, C═S, C═Se, C═$NR^1$, —C(═O)O—, —C(═O)$NR^1$—, $NR^1$, P(═O)($R^1$), —O—, —S—, SO or $SO_2$, where any $CH_2$ group bonded to the Y radical may not be replaced by the groups mentioned, or an aromatic or heteroaromatic ring system which has 5 to 60 aromatic ring atoms and may be substituted in each case by one or more $R^1$ radicals; at the same time, two $R^y$ radicals may also form a ring system with one another, or one $R^y$ radical together with one $R^a$, $R^b$, $R^c$, $R^d$, $R^e$ radical, preferably an $R^a$ radical.

In addition, it may preferably be the case that the $R^y$ radical bonded to the Y group and the $R^a$ radical adjacent to the group, together with the further groups to which the two $R^y$, $R^a$ radicals bind, form a fused ring, preferably an aliphatic or heteroaliphatic ring having 3 to 20, preferably 5 to 18, ring atoms or an aromatic or heteroaromatic ring having 5 to 13 ring atoms, more preferably an aliphatic or heteroaliphatic ring which has 3 to 20, preferably 5 to 18, ring atoms and may be substituted by one or more $R^1$ radicals, where $R^1$ has the definition given above. In addition, it is also possible for one $R^b$ radical and one $R^y$ radical together with the further groups to which the two $R^y$, $R^a$ radicals bind to form a fused ring, as set out above for the $R^a$ radical, preference being given to ring formation via an $R^a$ radical.

In addition, it may more preferably be the case that the $R^y$ radical bonded to the Y group adjacent to the Y group does not have an acidic proton, preferably ruling out keto-enol tautomerism in the case that Y is C═O. An acidic proton in this context is a proton having a high pKa, where the pKa of a proton is preferably at least 21, more preferably at least 22 and especially preferably at least 25. Preferably, an $R^y$ radical bonded to the Y group and the $R^a$ or $R^b$ radical adjacent to the group, together with the further groups to which the two $R^y$, $R^a$ radicals bind, form a fused, bridged ring that satisfies Bredt's rule, with the bridging atom binding directly to the Y group.

An aryl group in the context of this invention contains 6 to 40 carbon atoms, a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An electron-deficient heteroaryl group in the context of the present invention is a heteroaryl group having at least one heteroaromatic six-membered ring having at least one nitrogen atom. Further aromatic or heteroaromatic five-membered or six-membered rings may be fused onto this six-membered ring. Examples of electron-deficient heteroaryl groups are pyridine, pyrimidine, pyrazine, pyridazine, triazine, quinoline, quinazoline or quinoxaline.

An aromatic ring system in the context of this invention contains 6 to 60 carbon atoms in the ring system, preferably 6 to 40 carbon atoms in the ring system. A heteroaromatic ring system in the context of this invention contains 2 to 60 carbon atoms, preferably 3 to 40 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferably, the aromatic ring system is selected from fluorene, 9,9'-spirobifluorene, 9,9-diarylamine or groups in which two or more aryl and/or heteroaryl groups are joined to one another by single bonds.

In the context of the present invention, an aliphatic hydrocarbyl radical or an alkyl group or an alkenyl or alkynyl group which may contain 1 to 20 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more non-adjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 or 5-40 aromatic ring atoms and may also be substituted in each case by the abovementioned radicals and which may be joined to the aromatic or heteroaromatic system via any desired positions is understood to mean especially groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

The wording that two or more radicals together may form a ring, in the context of the present description, should be understood to mean, inter alia, that the two radicals are joined to one another by a chemical bond with formal elimination of two hydrogen atoms. This is illustrated by the following scheme:

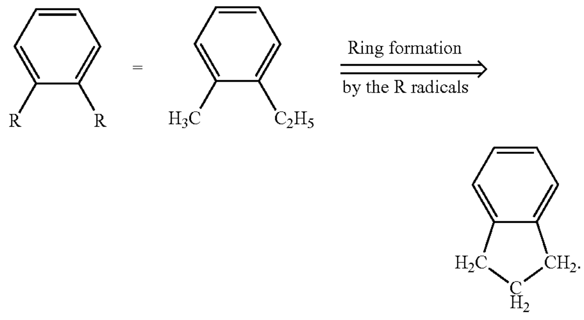

In addition, however, the abovementioned wording shall also be understood to mean that, if one of the two radicals is hydrogen, the second radical binds to the position to which the hydrogen atom was bonded, forming a ring. This shall be illustrated by the following scheme:

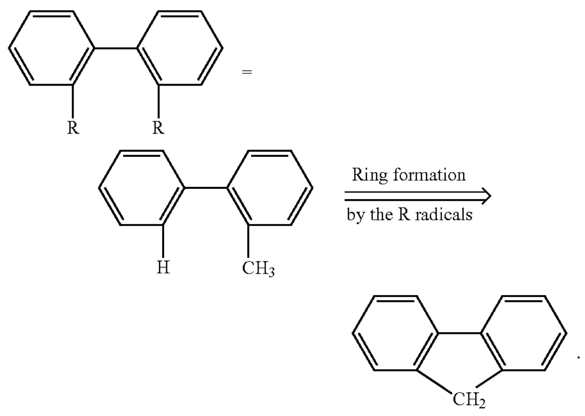

In a preferred configuration, the compounds of the invention may comprise a structure of the formulae (I-1) to (I-81); more preferably, the compounds of the invention may be selected from the compounds of the formulae (I-1) to (I-83):

Formula (I-1)

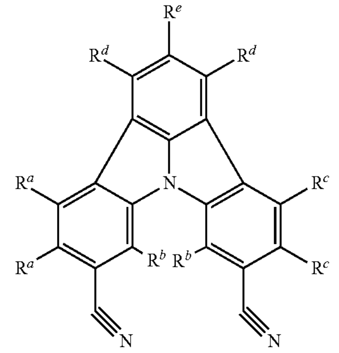

Formula (I-2)

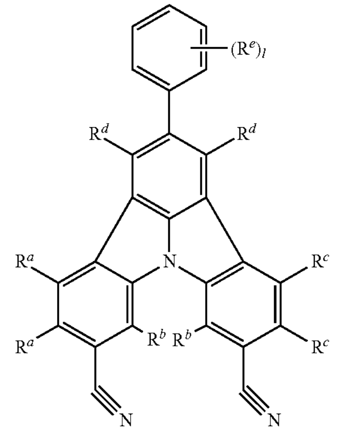

Formula (I-3)

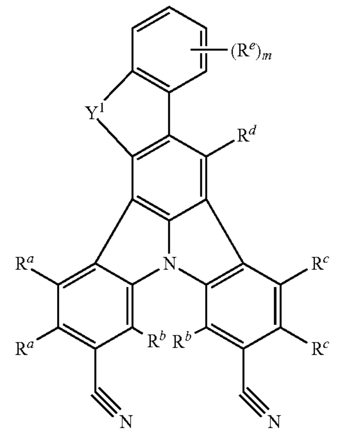

Formula (I-4)

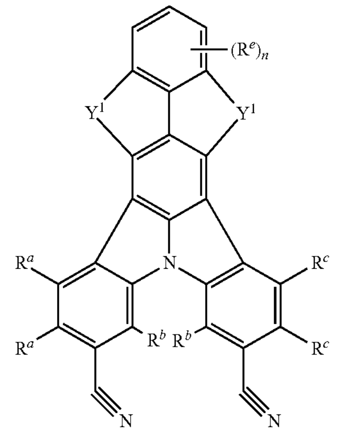

-continued
Formula (I-5)
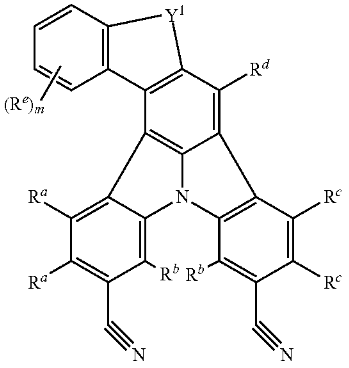
Formula (I-6)
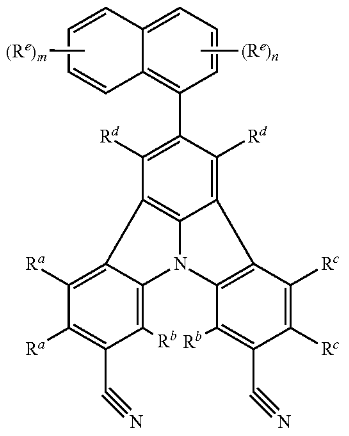
Formula (I-7)
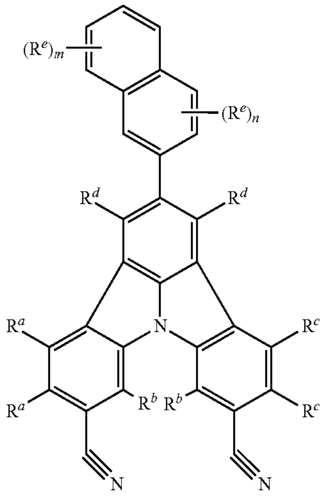
-continued
Formula (I-8)
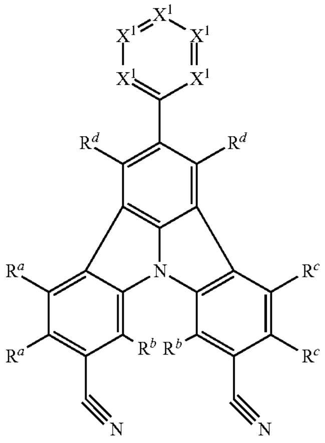
Formula (I-9)
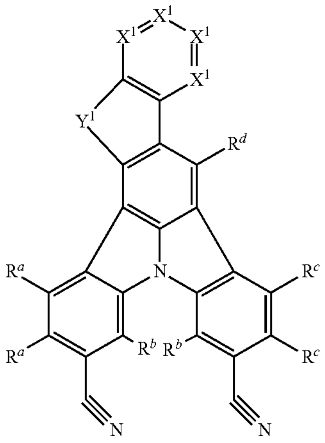
Formula (I-10)
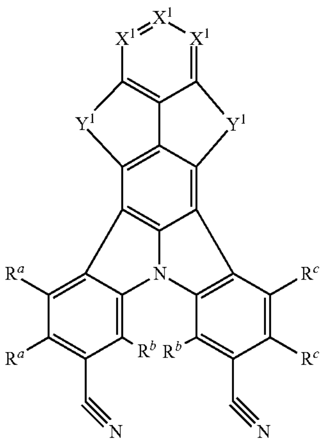

-continued
Formula (I-11)
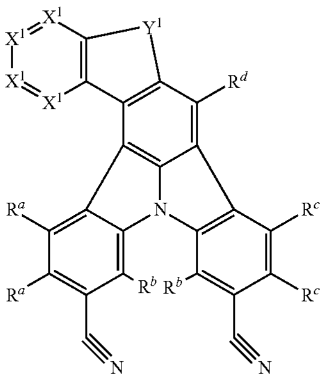
Formula (I-12)
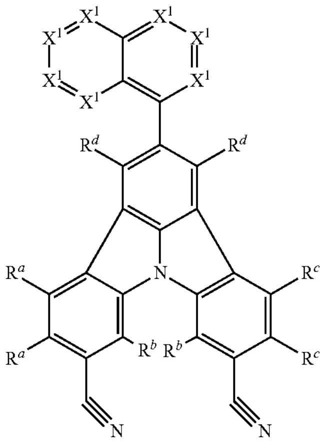
Formula (I-13)
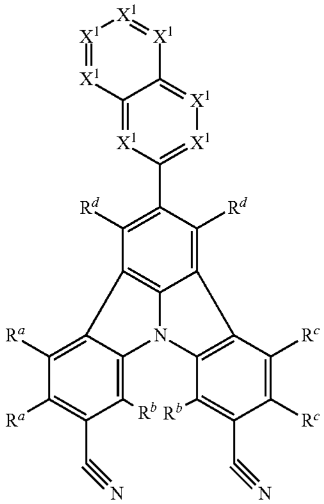
-continued
Formula (I-14)
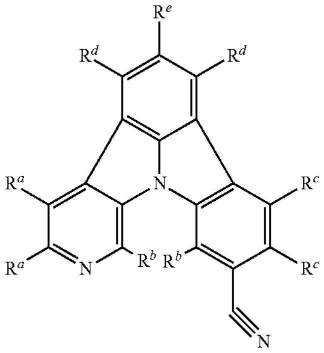
Formula (I-15)
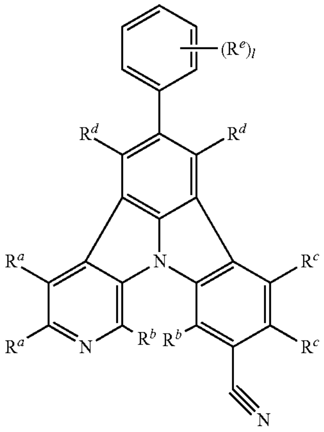
Formula (I-16)
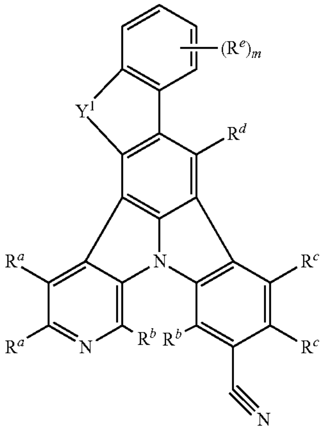
Formula (I-17)
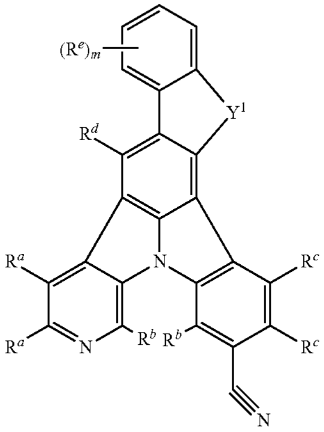

Formula (I-18)
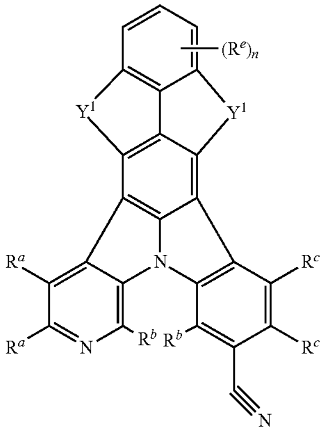
Formula (I-19)
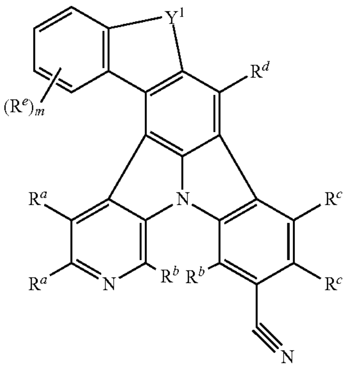
Formula (I-20)
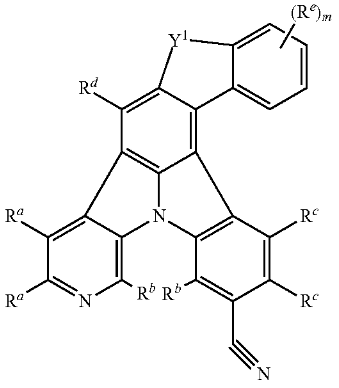
Formula (I-21)
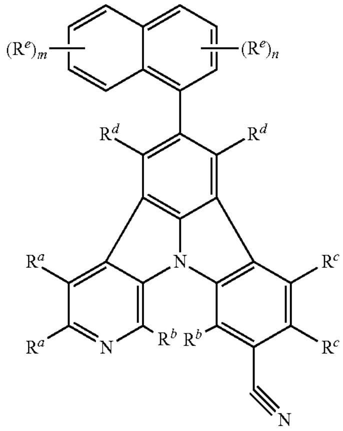
Formula (I-22)
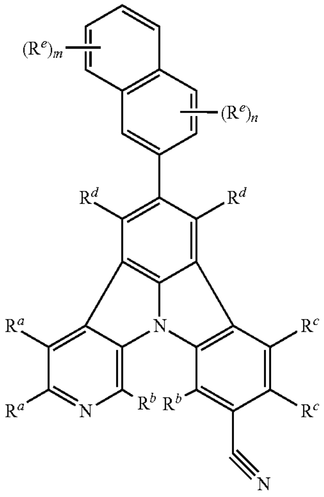
Formula (I-23)
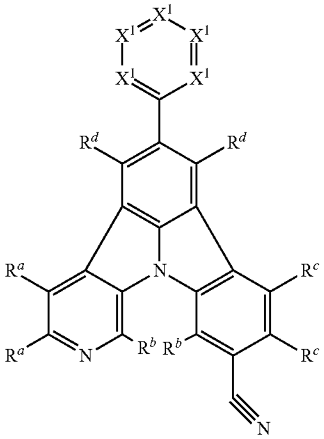
Formula (I-24)
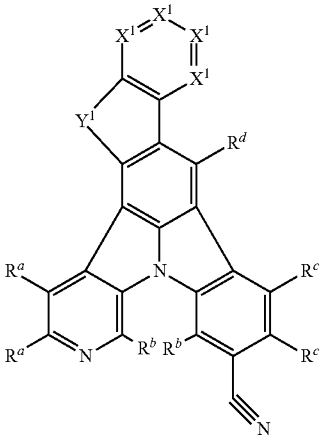

-continued
Formula (I-25)
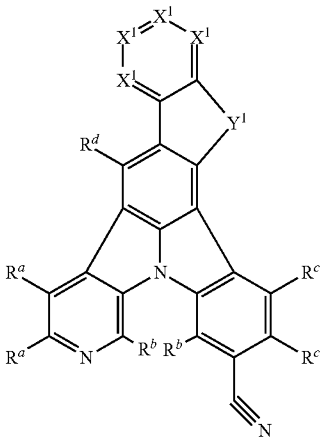
Formula (I-26)
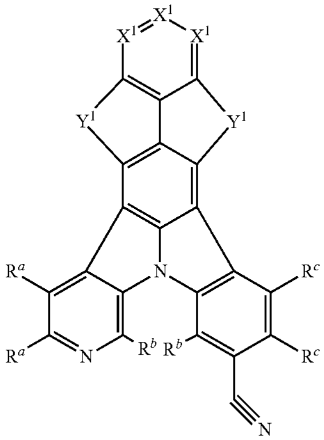
Formula (I-27)
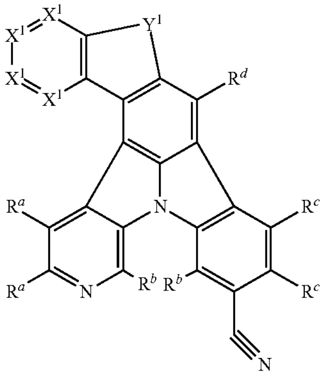
Formula (I-28)
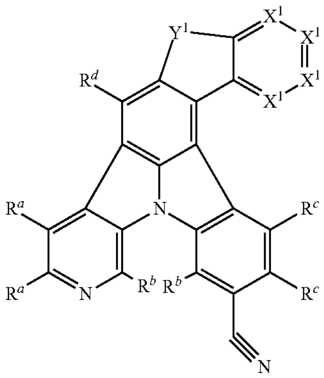
-continued
Formula (I-29)
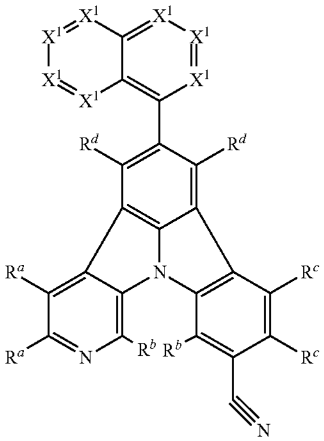
Formula (I-30)
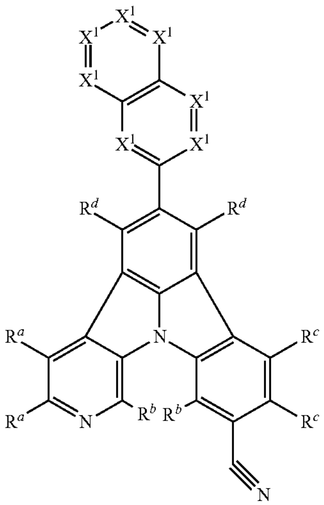
Formula (I-31)
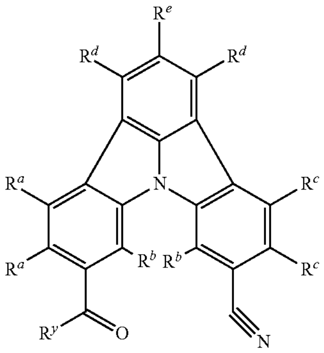

-continued
Formula (I-32)
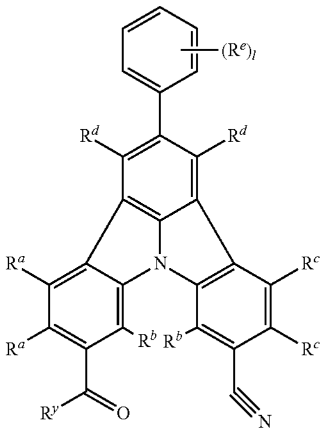
Formula (I-33)
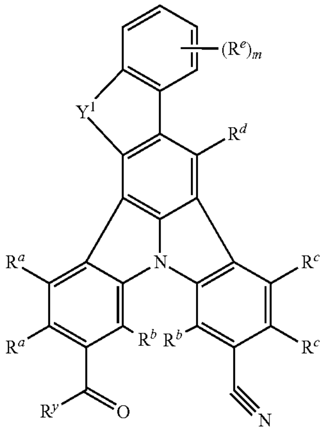
Formula (I-34)
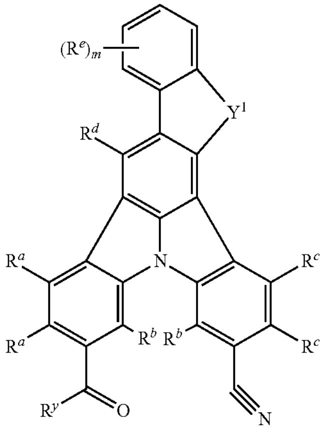
-continued
Formula (I-35)
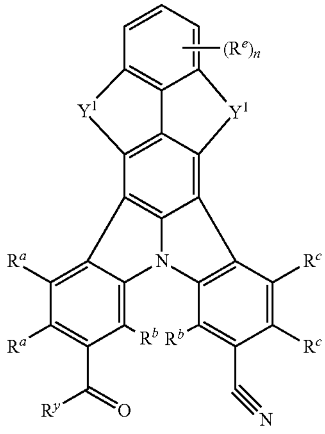
Formula (I-36)
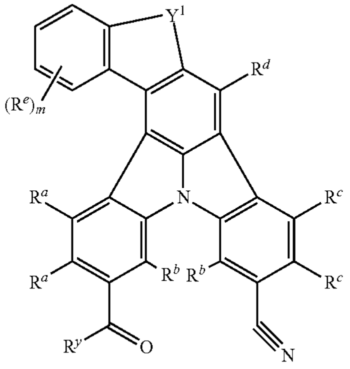
Formula (I-37)
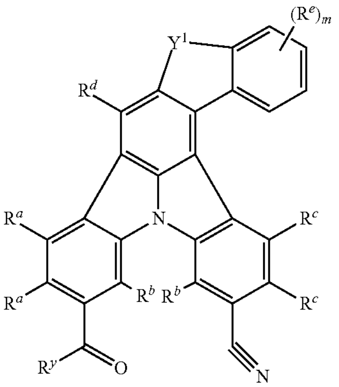
Formula (I-38)
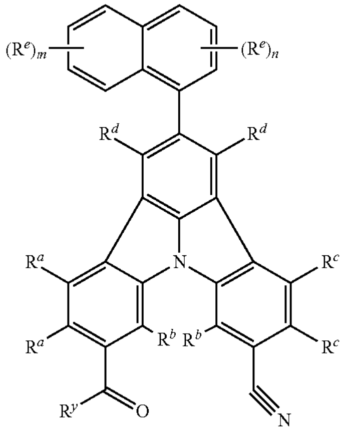

-continued
Formula (I-39)
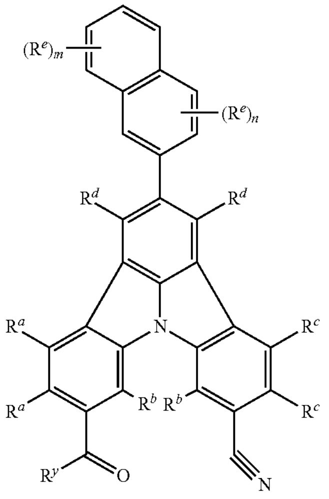
Formula (I-40)
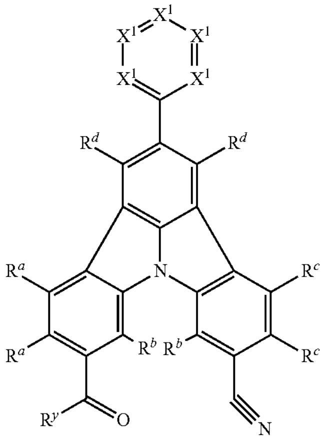
Formula (I-41)
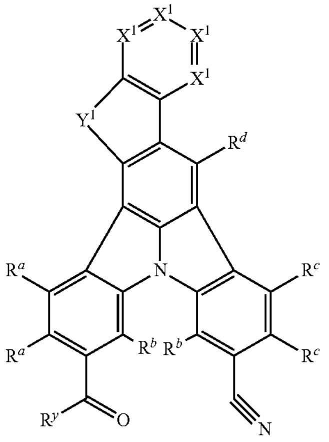
-continued
Formula (I-42)
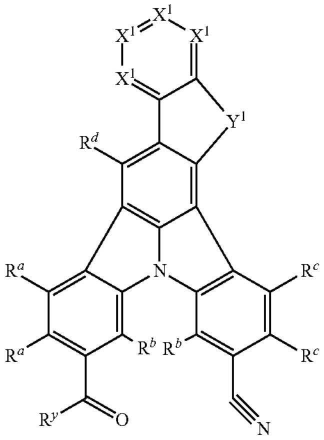
Formula (I-43)
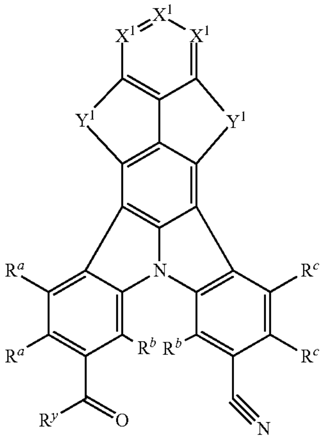
Formula (I-44)
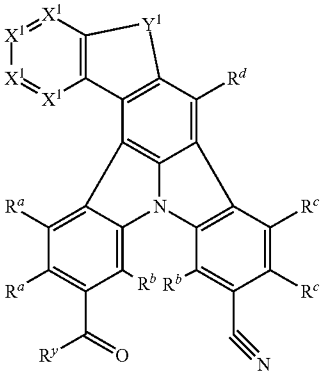
Formula (I-45)
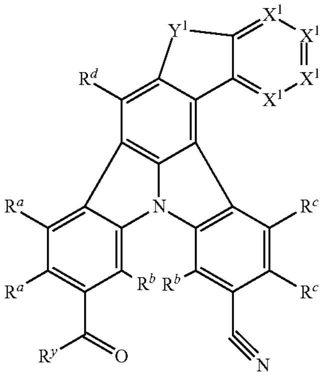

-continued
Formula (I-46)
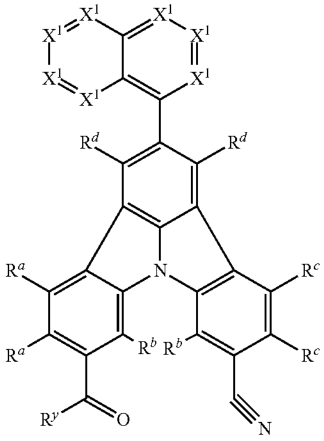
Formula (I-47)
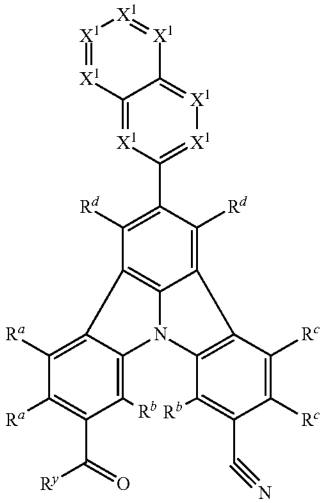
Formula (I-48)
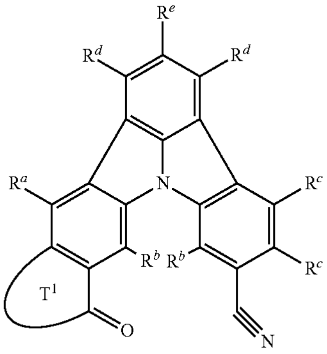
-continued
Formula (I-49)
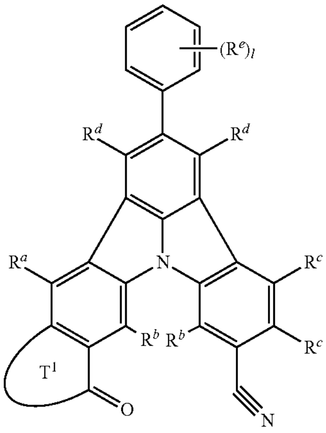
Formula (I-50)
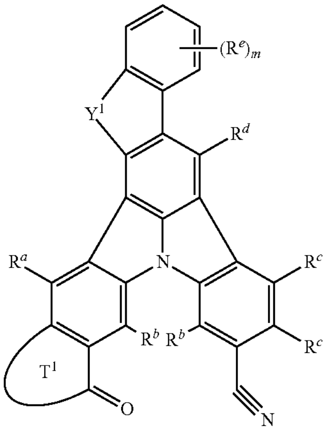
Formula (I-51)
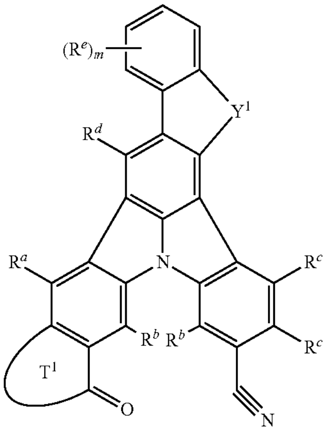

-continued
Formula (I-52)
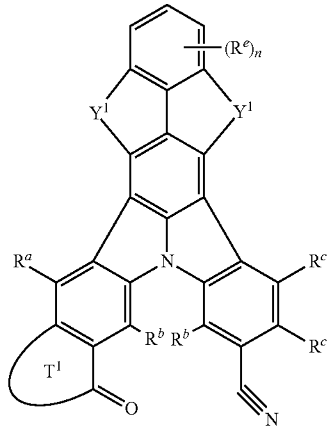
Formula (I-53)
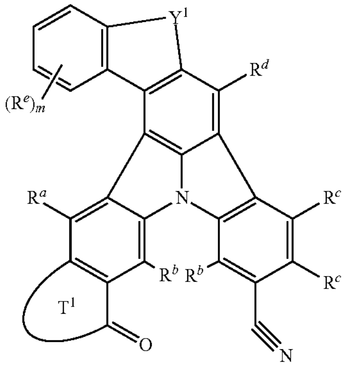
Formula (I-54)
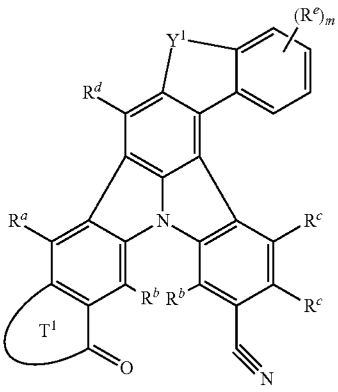
Formula (I-55)
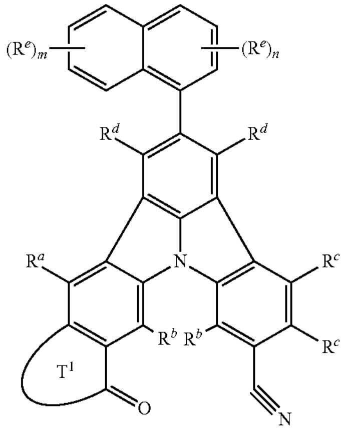
-continued
Formula (I-56)
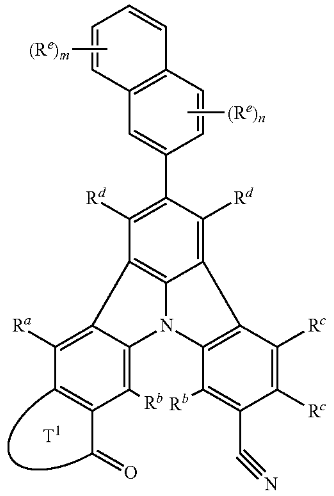
Formula (I-57)
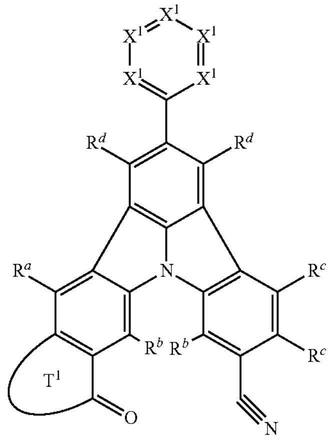
Formula (I-58)
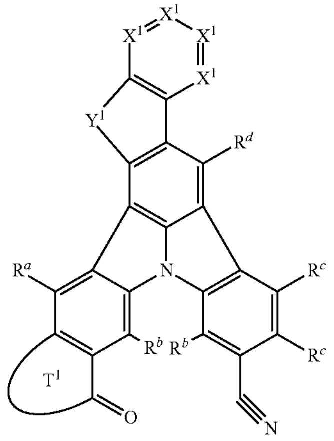

-continued
Formula (I-59)
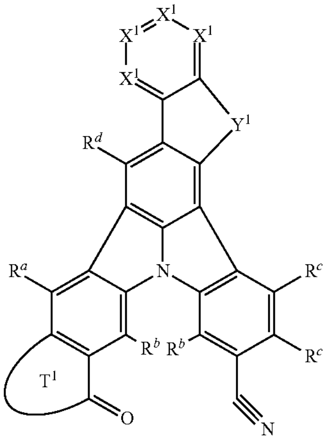
Formula (I-60)
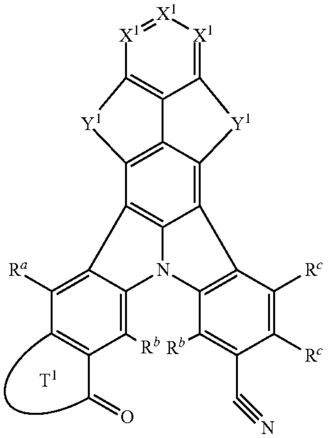
Formula (I-61)
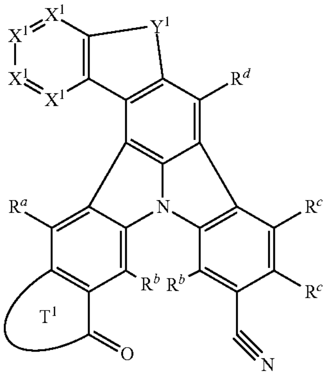
Formula (I-62)
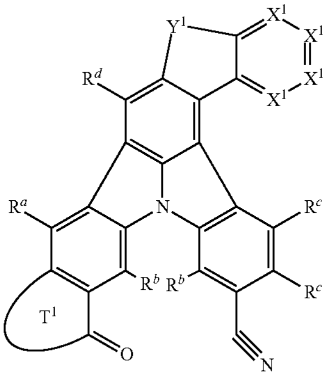
-continued
Formula (I-63)
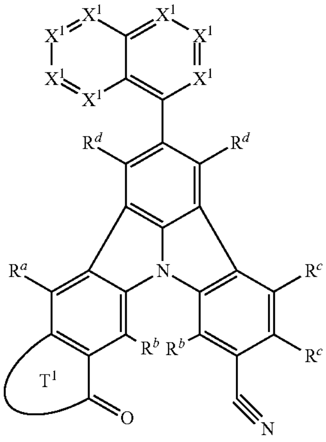
Formula (I-64)
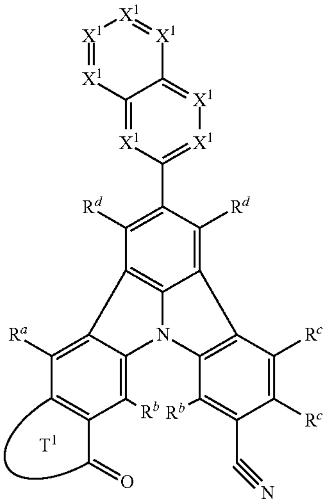
Formula (I-65)
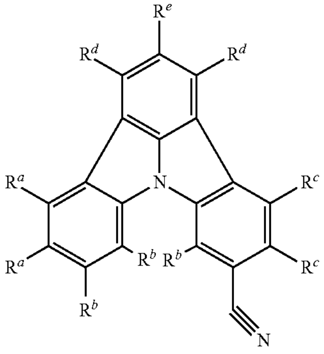

-continued
Formula (I-66)
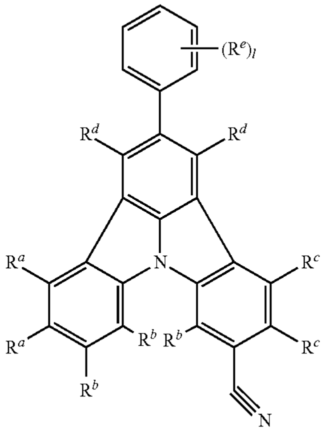
Formula (I-67)
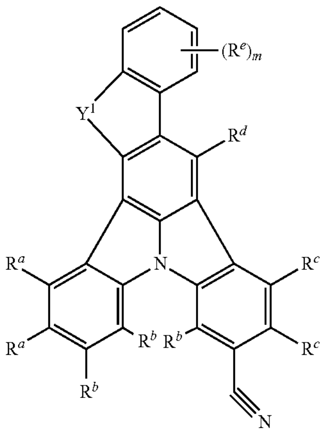
Formula (I-68)
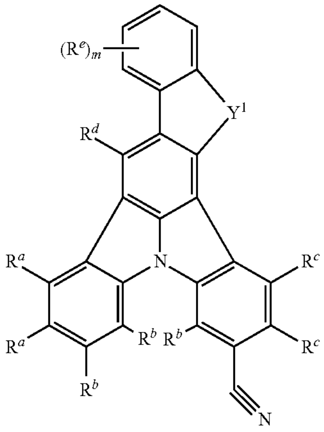
-continued
Formula (I-69)
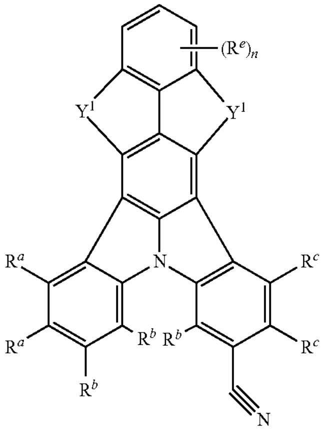
Formula (I-70)
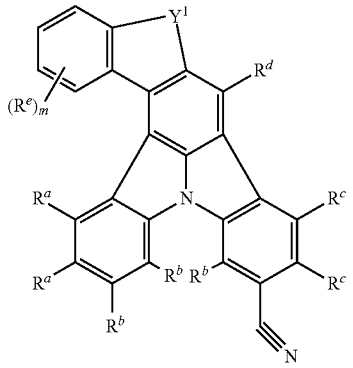
Formula (I-71)
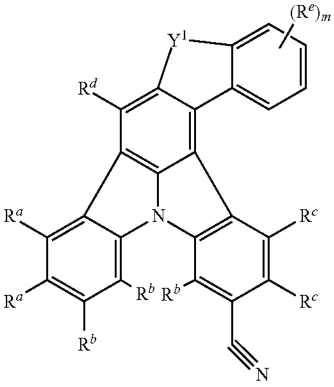
Formula (I-72)
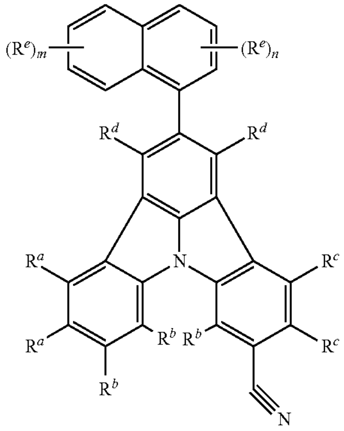

-continued
Formula (I-73)
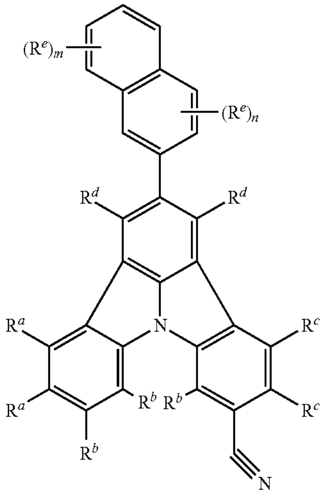
Formula (I-74)
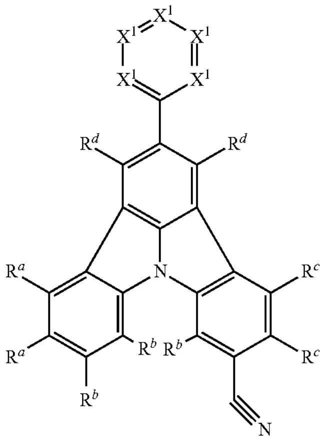
Formula (I-75)
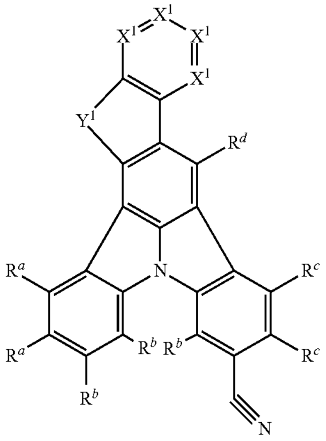
-continued
Formula (I-76)
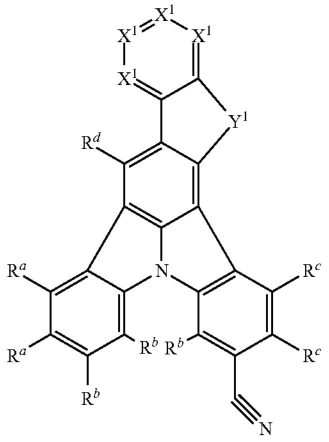
Formula (I-77)
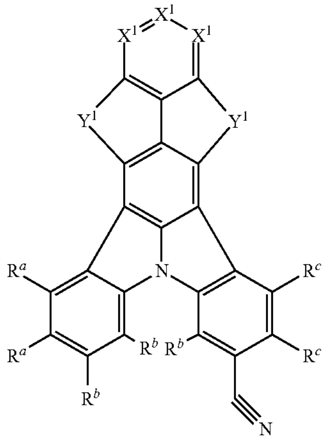
Formula (I-78)
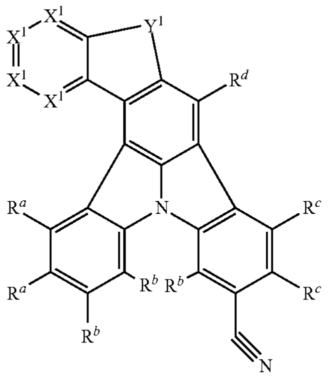
Formula (I-79)
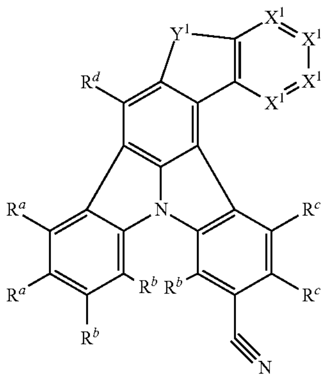

-continued

Formula (I-80)

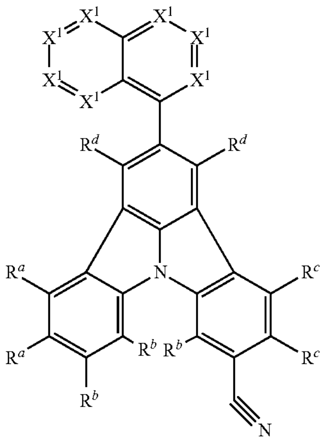

Formula (I-81)

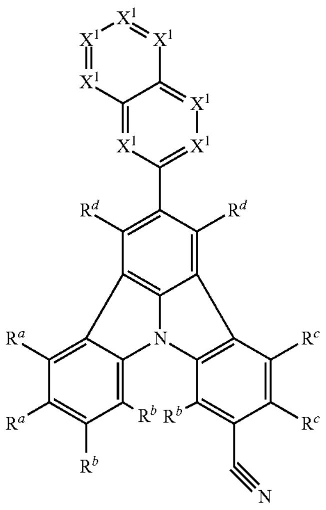

Formula (I-82)

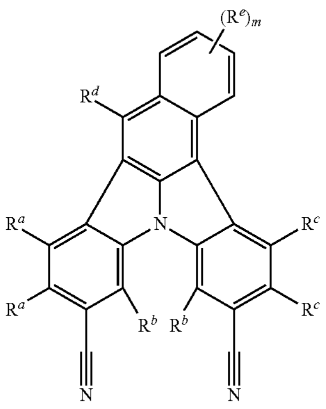

-continued

Formula (I-83)

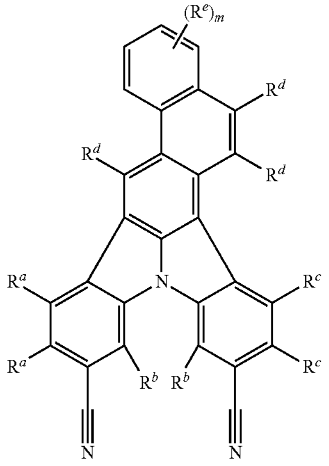

where the symbols $R^a$, $R^b$, $R^c$, $R^d$, $R^e$ and $R^y$ have the definitions given above, especially for formula (I), and the further symbols and indices used are as follows:

$X^1$ is the same or different at each instance and is N or $CR^e$, preferably $CR^e$, with the proviso that not more than two of the $X^1$ groups in one cycle are N;

$Y^1$ is the same or different at each instance and is $C(R^e)_2$, $(R^e)_2C—C(R^e)_2$ $(R^e)C{=}C(R^e)$, $NR^e$, NAr', O, S, SO, $SO_2$, Se, $P(O)R^e$, $BR^e$ or $Si(R^e)_2$, preferably $C(R^e)_2$, $(R^e)_2C—C(R^e)_2$, $(R^e)C{=}C(R^e)$, O or S, more preferably $C(R^e)_2$;

$T^1$ is the same or different at each instance and is a fused ring, preferably an aliphatic or heteroaliphatic ring having 3 to 20, preferably 5 to 18, ring atoms or an aromatic or heteroaromatic ring having 5 to 13 ring atoms, more preferably an aliphatic or heteroaliphatic ring having 3 to 20, preferably 5 to 18, ring atoms, which may be substituted by one or more $R^1$ radicals, where $R^1$ has the definition given above, especially for formula (I);

n is 0, 1, 2 or 3, preferably 0, 1 or 2;

m is 0, 1, 2, 3 or 4, preferably 0, 1 or 2.

Surprisingly, compounds/structures in which the symbol X in formula (I) is C—CN show unexpected advantages with regard to performance, especially in relation to colour purity, such that compounds having two cyano substituents on the aromatic rings show distinctly narrower emission spectra. Surprisingly, preference is given to the structures/compounds of the formulae (I-1) to (I-13), and particular preference to structures/compounds of the formulae (I-1) to (I-7).

In a preferred configuration of the present invention, it may be the case that at least two R, $R^a$, $R^b$, $R^c$, $R^d$, $R^e$, $R^y$ radicals together with the further groups to which the two R, $R^a$, $R^b$, $R^c$, $R^d$, $R^e$, $R^y$ radicals bind form a fused ring, where the two R, $R^a$, $R^b$, $R^c$, $R^d$, $R^e$, $R^y$ radicals form at least one structure of the following formulae (Cy-1) to (Cy-10)

Formula (Cy-1)

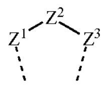

Formula (Cy-2)

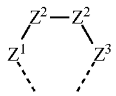

-continued

Formula (Cy-3)

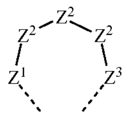

Formula (Cy-4)

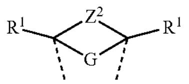

Formula (Cy-5)

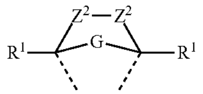

Formula (Cy-6)

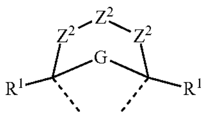

Formula (Cy-7)

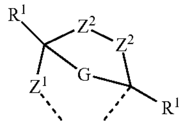

Formula (Cy-8)

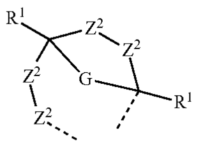

Formula (Cy-9)

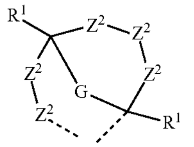

Formula (Cy-10)

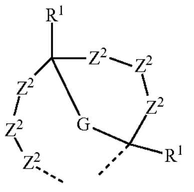

where $R^1$ and $R^2$ have the definitions set out above, the dotted bonds represent the sites of attachment to the atoms of the groups to which the two R, $R^a$, $R^b$, $R^c$, $R^d$, $R^e$, $R^y$ radicals bind, and in addition:

$Z^1$, $Z^3$ is the same or different at each instance and is $C(R^3)_2$, $Si(R^3)_2$, O, S, $NR^3$ or C(═O);

$Z^2$ is $C(R^1)_2$, $Si(R^1)_2$, O, S, $NR^1$ or C(═O), where two adjacent groups $Z^2$ represent —$CR^1$═$CR^1$— or an ortho-bonded arylene or heteroarylene group having 5 to 14 aromatic ring atoms which may be substituted by one or more $R^1$ radicals;

G is an alkylene group which has 1, 2 or 3 carbon atoms and may be substituted by one or more $R^1$ radicals, —$CR^1$═$CR^1$— or an ortho-bonded arylene or heteroarylene group which has 5 to 14 aromatic ring atoms and may be substituted by one or more $R^1$ radicals;

$R^1$ is the same or different at each instance and is H, D, F, Cl, Br, I, CN, $NO_2$, $N(Ar'')_2$, $N(R^2)_2$, C(═O)Ar'', C(═O)$R^2$, P(═O)$(Ar'')_2$, $P(Ar'')_2$, $B(Ar'')_2$, $B(R^2)_2$, $C(Ar'')_3$, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by —$R^2C$═$CR^2$—, —C≡C—, $Si(R^2)_2$, C═O, C═S, C═Se, C═$NR^2$, —C(═O)O—, —C(═O)$NR^2$—, $NR^2$, P(═O)($R^2$), —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two $R^3$ radicals which are bonded to the same carbon atom together may form an aliphatic or aromatic ring system and thus span a spiro system; in addition, $R^3$ may form a ring system, preferably an aliphatic ring system, with a preferably adjacent R, $R^a$, $R^c$, $R^d$, $R^e$ or $R^1$ radical;

with the proviso that no two heteroatoms in these groups are bonded directly to one another and no two C═O groups are bonded directly to one another.

In a preferred embodiment of the invention, $R^3$ is not H and/or D.

When adjacent radicals in the structures of the invention form an aliphatic ring system, it is preferable when the latter does not have any acidic benzylic protons. Benzylic protons are understood to mean protons which bind to an alkyl carbon atom bonded directly to an aryl or heteroaryl group. This can be achieved by virtue of the carbon atoms in the aliphatic ring system which bind directly to an aryl or heteroaryl group being fully substituted and not containing any bonded hydrogen atoms. Thus, the absence of acidic benzylic protons in the formulae (Cy-1) to (Cy-3) is achieved by virtue of $Z^1$ and $Z^3$, when they are $C(R^3)_2$, being defined such that $R^3$ is not hydrogen. This can additionally also be achieved by virtue of the carbon atoms in the aliphatic ring system which bind directly to an aryl or heteroaryl group being the bridgeheads in a bi- or polycyclic structure. The protons bonded to bridgehead carbon atoms, because of the spatial structure of the bi- or polycycle, are significantly less acidic than benzylic protons on carbon atoms which are not bonded within a bi- or polycyclic structure, and are regarded as non-acidic protons in the context of the present invention. Thus, the absence of acidic benzylic protons in formulae (Cy-4) to (Cy-10) is achieved by virtue of this being a bicyclic structure, as a result of which $R^1$, when it is H, is much less acidic than benzylic protons since the corresponding anion of the bicyclic structure is not mesomerically stabilized. Even when $R^1$ in formulae (Cy-4) to (Cy-10) is H, this is therefore a non-acidic proton in the context of the present application.

It may preferably be the case that, especially in formulae (Cy-1) to (Cy-3):

$R^1$ is the same or different at each instance and is F, Cl, Br, I, CN, $NO_2$, $N(Ar'')_2$, $N(R^2)_2$, C(═O)Ar'', C(═O)$R^2$, P(═O)$(Ar'')_2$, $P(Ar'')_2$, $B(Ar'')_2$, $B(R^2)_2$, $C(Ar'')_3$, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more non-adjacent $CH_2$ groups may be replaced by $—R^2C═CR^2—$, $—C≡C—$, $Si(R^2)_2$, $C═O$, $C═S$, $C═Se$, $C═NR^2$, $—C(═O)O—$, $—C(═O)NR^2—$, $NR^2$, $P(═O)(R^2)$, $—O—$, $—S—$, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two $R^3$ radicals which are bonded to the same carbon atom together may form an aliphatic or aromatic ring system and thus span a spiro system; in addition, $R^3$ may form a ring system, preferably an aliphatic ring system, with a preferably adjacent R, $R^a$, $R^c$, $R^d$, $R^e$, $R^1$ radical or with a further group.

It may preferably be the case that, especially in formulae (Cy-1) to (Cy-3):

$R^3$ is the same or different at each instance and is F, a straight-chain alkyl, alkoxy or thioalkoxy group having 1 to 40 carbon atoms or an alkyl or alkenyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^2$ radicals, where one or more adjacent $CH_2$ groups may be replaced by $R^2C═CR^2$, $C≡C$, $Si(R^2)_2$, $C═O$, $C═S$, $C═Se$, $C═NR^2$, $—C(═O)O—$, $—C(═O)NR^2—$, $NR^2$, $P(═O)(R^1)$, $—O—$, $—S—$, SO or $SO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals; at the same time, it is also possible for two $R^3$ radicals together or one $R^3$ radical together with an R, $R^a$, $R^c$, $R^d$, $R^e$, $R^1$ radical or together with a further group to form a ring system, preferably an aliphatic ring system.

In a preferred embodiment of the structure of the formulae (Cy-1) to (Cy-10), not more than one of the $Z^1$, $Z^2$ and $Z^3$ groups is a heteroatom, especially O or $NR^3$, or O or $NR^1$, and the other groups are $C(R^3)_2$ or $C(R^1)_2$, or $Z^1$ and $Z^3$ are the same or different at each instance and are 0 or $NR^3$ and $Z^2$ is $C(R^1)_2$. In a particularly preferred embodiment of the invention, $Z^1$ and $Z^3$ are the same or different at each instance and are $C(R^3)_2$, and $Z^2$ is $C(R^1)_2$ and more preferably $C(R^3)_2$ or $CH_2$.

In a preferred embodiment of the invention, the $R^1$ radical bonded to the bridgehead atom, preferably to the bridgehead atom in formulae (Cy-4) to (Cy-10), is the same or different at each instance and is selected from the group consisting of H, D, F, a straight-chain alkyl group which has 1 to 10 carbon atoms and may be substituted by one or more $R^2$ radicals, but is preferably unsubstituted, a branched or cyclic alkyl group which has 3 to 10 carbon atoms and may be substituted by one or more $R^2$ radicals, but is preferably unsubstituted, or an aromatic or heteroaromatic ring system which has 5 to 12 aromatic ring atoms and may be substituted in each case by one or more $R^2$ radicals. More preferably, the $R^1$ radical bonded to the bridgehead atom in formula (CY-4) is the same or different at each instance and is selected from the group consisting of H, F, a straight-chain alkyl group having 1 to 4 carbon atoms, a branched alkyl group having 3 or 4 carbon atoms and a phenyl group which may be substituted by an alkyl group having 1 to 4 carbon atoms, but is preferably unsubstituted. Most preferably, the $R^1$ radical is the same or different at each instance and is selected from the group consisting of H, methyl and tert-butyl.

In a preferred development of the present invention, it may be the case that at least two R, $R^a$, $R^b$, $R^c$, $R^d$, $R^e$, $R^y$ radicals together with the further groups to which the two R, $R^a$, $R^b$, $R^c$, $R^d$, $R^e$, $R^y$ radicals bind form a fused ring, where the two R, $R^a$, $R^b$, $R^c$, $R^d$, $R^e$, $R^y$ radicals form at least one structure of the formulae (RA-1) to (RA-13)

Formula RA-1

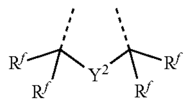

Formula RA-2

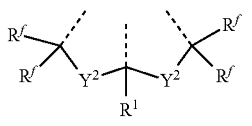

Formula RA-3

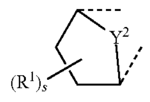

Formula RA-4

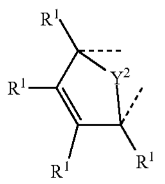

Formula RA-5

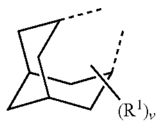

Formula RA-6

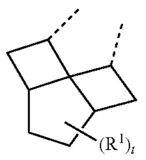

Formula RA-7

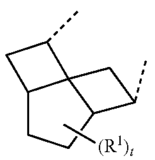

Formula RA-8

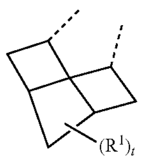

-continued

Formula RA-9

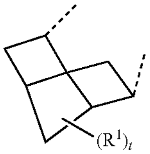

Formula RA-10

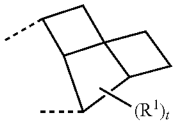

Formula RA-11

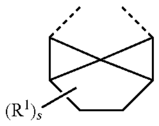

Formula RA-12

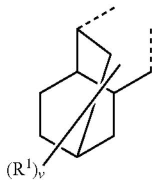

Formula RA-13

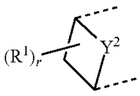

where $R^1$ has the definition set out above, the dotted bonds represent the sites of attachment via which the two R, $R^a$, $R^b$, $R^c$, $R^d$, $R^e$, $R^y$ radicals bind, and the further symbols have the following definition:

$Y^2$ is the same or different at each instance and is $C(R^1)_2$, $(R^1)_2C—C(R^1)_2$, $(R^1)C{=}C(R^1)$, $NR^1$, NAr', O or S, preferably $C(R^1)_2$, $(R^1)_2C—C(R^1)_2$, $(R^1)C{=}C(R^1)$, O or S;

$R^f$ is the same or different at each instance and is F, a straight-chain alkyl, alkoxy or thioalkoxy group having 1 to 40 carbon atoms or an alkyl or alkenyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^2$ radicals, where one or more nonadjacent $CH_2$ groups may be replaced by $R^2C{=}CR^2$, C≡C, $Si(R^2)_2$, C=O, C=S, C=Se, $C{=}NR^2$, —C(=O)O—, $—C(=O)NR^2—$, $NR^2$, $P(=O)(R^1)$, —O—, —S—, SO or $SO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals; at the same time, it is also possible for two $R^f$ radicals together or one $R^f$ radical together with an $R^1$ radical or together with a further group to form a ring system;

r is 0, 1, 2, 3 or 4, preferably 0, 1 or 2, more preferably 0 or 1;

s is 0, 1, 2, 3, 4, 5 or 6, preferably 0, 1, 2, 3 or 4, more preferably 0, 1 or 2;

t is 0, 1, 2, 3, 4, 5, 6, 7 or 8, preferably 0, 1, 2, 3 or 4, more preferably 0, 1 or 2;

v is 0, 1, 2, 3, 4, 5, 6, 7, 8 or 9, preferably 0, 1, 2, 3 or 4, more preferably 0, 1 or 2.

Preference is given here to structures of the formulae RA-1, RA-3, RA-4 and RA-5, and particular preference to structures of the formulae RA-4 and RA-5.

In a preferred embodiment of the present invention, at least two R, $R^a$, $R^b$, $R^c$, $R^d$, $R^e$, $R^y$ radicals together with the further groups to which the two R, $R^a$, $R^b$, $R^c$, $R^d$, $R^e$, $R^y$ radicals bind form a fused ring, where the two R, $R^a$, $R^b$, $R^c$, $R^d$, $R^e$, $R^y$ radicals preferably form at least one of the structures of the formulae (RA-1a) to (RA-4f)

Formula RA-1a

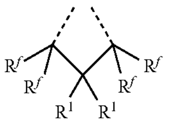

Formula RA-1b

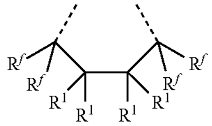

Formula RA-1c

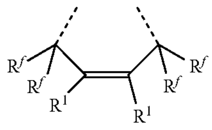

Formula RA-2a

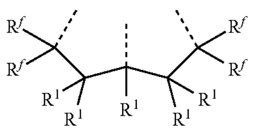

Formula RA-2b

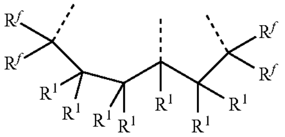

Formula RA-2c

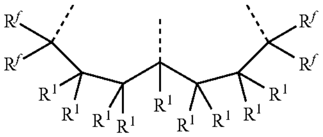

Formula RA-3a

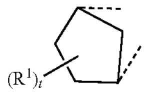

Formula RA-3b

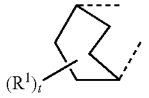

Formula RA-4a

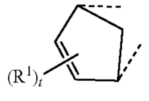

Formula RA-4b

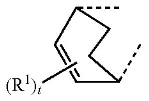

-continued

Formula RA-4c

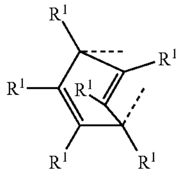

Formula RA-4d

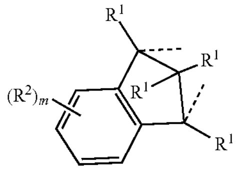

Formula RA-4e

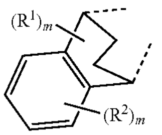

Formula RA-4f

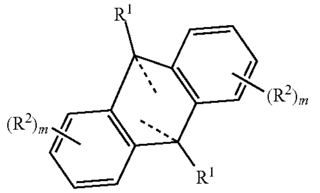

where the dotted bonds represent the sites of attachment via which the two R, $R^a$, $R^b$, RC, $R^d$, $R^e$, $R^y$ radicals bind, the index m is 0, 1, 2, 3 or 4, preferably 0, 1 or 2, and the symbols $R^1$, $R^2$, $R^f$ and indices s and t have the definition given above, especially for formula (I) and/or formulae (RA-1) to (RA-13).

Preference is given here to structures of the formula RA-4f.

It may further be the case that two $R^a$ radicals form the structures of the formulae (Cy-1) to (Cy-10), (RA-1) to (RA-13) and/or (RA-1a) to (RA-4f) and form a fused ring.

In addition, it may be the case that one $R^a$ radical and one $R^y$ radical form structures of the formulae (Cy-1) to (Cy-10), (RA-1) to (RA-13) and/or (RA-1a) to (RA-4f) and form a fused ring, where the $R^a$ radical and the $R^y$ radical are preferably adjacent. Furthermore, one $R^b$ radical and one $R^y$ radical may also form structures of the formulae (Cy-1) to (Cy-10), (RA-1) to (RA-13) and/or (RA-1a) to (RA-4f) and form a fused ring, preference being given to ring formation via an $R^a$ radical.

It may additionally be the case that two $R^c$ radicals form the structures of the formulae (Cy-1) to (Cy-10), (RA-1) to (RA-13) and/or (RA-1a) to (RA-4f) and form a fused ring.

In a further configuration, it may be the case that two $R^b$ radicals form the structures of the formulae (Cy-1) to (Cy-10), (RA-1) to (RA-13) and/or (RA-1a) to (RA-4f) and form a fused ring, where the $R^b$ radicals are preferably adjacent. In addition, the two $R^b$ radicals may also come from different rings, in which case the rings each bind to the nitrogen atom of the base skeleton.

It may further be the case that one $R^d$ radical together with one R or $R^e$ radical form the structures of the formulae (Cy-1) to (Cy-10), (RA-1) to (RA-13) and/or (RA-1a) to (RA-4f) and form a fused ring.

It may additionally be the case that two $R^e$ radicals form the structures of the formulae (Cy-1) to (Cy-10), (RA-1) to (RA-13) and/or (RA-1a) to (RA-4f) and form a fused ring, where the $R^e$ radicals are preferably adjacent.

In this case, preferably two $R^a$ radicals, two $R^c$ radicals, one $R^d$ radical together with one R or $R^e$ radical or two $R^e$ radicals form the structures of the formulae (Cy-1) to (Cy-10), (RA-1) to (RA-13) and/or (RA-1a) to (RA-4f) and form at least one fused ring, more preferably two $R^a$ radicals and/or two $R^c$ radicals. Especially preferably, two $R^a$ radicals and two $R^c$ radicals each form a fused ring.

In a further-preferred configuration, at least two R, $R^a$, $R^b$, $R^c$, $R^d$, $R^e$, $R^y$ radicals together with the further groups to which the two R, $R^a$, $R^b$, $R^c$, $R^d$, $R^e$, $R^y$ radicals bind form a fused ring, where the two R, $R^a$, $R^b$, $R^c$, $R^d$, $R^e$, $R^y$ radicals form structures of the formula (RB), Formula RB

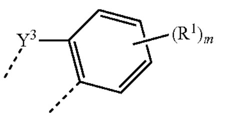

where $R^1$ has the definition given above, especially for formula (I), the dotted bonds represent the bonding sites via which the two R, $R^a$, $R^b$, $R^c$, $R^d$, $R^e$, $R^y$ radicals bind, the index m is 0, 1, 2, 3 or 4, preferably 0, 1 or 2, and $Y^3$ is $C(R^1)_2$, $NR^1$, NAr', $BR^1$, BAr', O or S, preferably $C(R^1)_2$, NAr' or O, where Ar' has the definition given above, especially for formula (I).

It may be the case here that one $R^d$ radical together with one R or $R^e$ radical form the structures of the formula (RB) and form a fused ring. It may further be the case that two $R^e$ radicals form the structures of the formula (RB) and form a fused ring, where the $R^e$ radicals are preferably adjacent.

More particularly, it may be the case that, in preferred structures/compounds, the sum total of the indices r, s, t, v, m and n is preferably 0, 1, 2 or 3, more preferably 1 or 2.

It may preferably be the case that the compounds have at least two fused rings, where at least one fused ring is formed by structures of the formulae (RA-1) to (RA-13) and/or (RA-1a) to (RA-4f) and a further ring by structures of the formulae (RA-1) to (RA-13), (RA-1a) to (RA-4f) or (RB).

If the compounds have at least two fused rings, preferably two $R^a$ radicals, two $R^c$ radicals, one $R^d$ radical together with one R or $R^e$ radical or two $R^e$ radicals form the structures of the formulae (Cy-1) to (Cy-10), (RA-1) to (RA-13) and/or (RA-1a) to (RA-4f) and each form at least one fused ring, more preferably two $R^a$ radicals and two $R^c$ radicals.

In addition, it may preferably be the case that the fused ring $T^1$, shown in formulae including (I-48) to (I-64), is selected from a structure of the formulae (TCY-1) to (TRA-13) or (TRA-4f)

Formula (TCY-1)

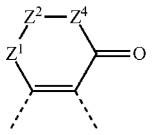

Formula (TCY-2)

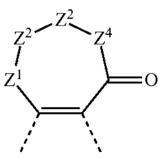

-continued
Formula (TCY-3)
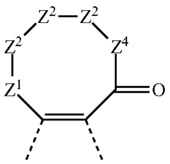
Formula (TCY-4)
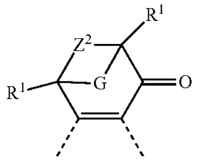
Formula (TCY-5)
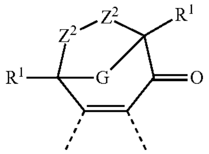
Formula (TCY-6)
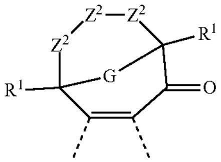
Formula (TCY-7)
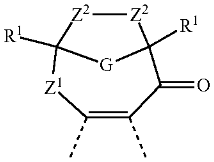
Formula (TCY-8)
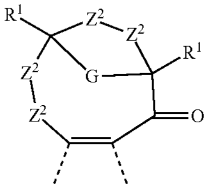
Formula (TCY-9)
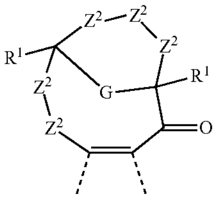
Formula (TCY-10)
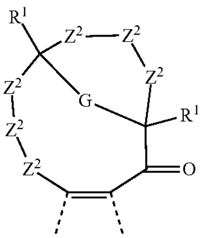
-continued
Formula TRA-1
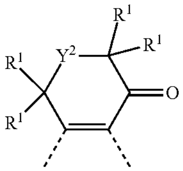
Formula TRA-2
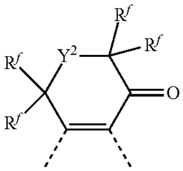
Formula TRA-3
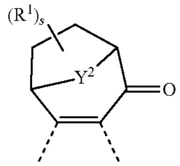
Formula TRA-4
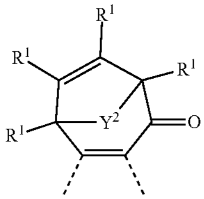
Formula TRA-5
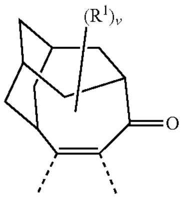
Formula TRA-6
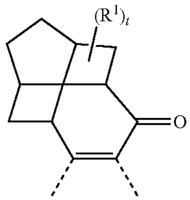
Formula TRA-7
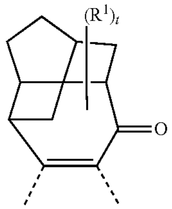
Formula TRA-8
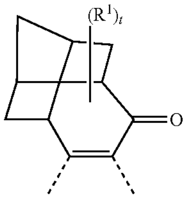

-continued
Formula TRA-9
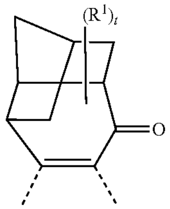
Formula TRA-10
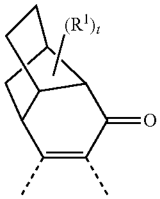
Formula TRA-11
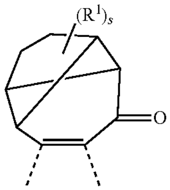
Formula TRA-12
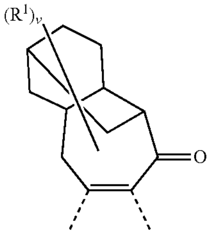
Formula TRA-13
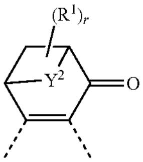
Formula TRA-1a
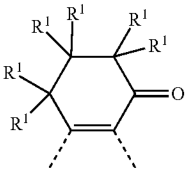
Formula TRA-1b
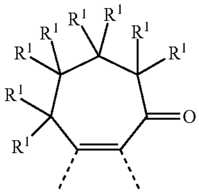
Formula TRA-1c
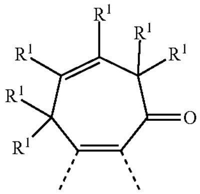
-continued
Formula TRA-2a
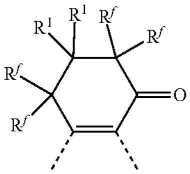
Formula TRA-2b
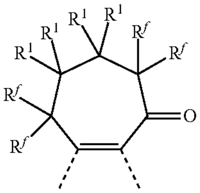
Formula TRA-2c
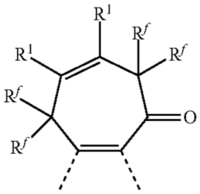
Formula TRA-3a
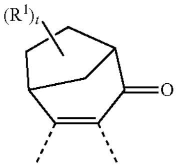
Formula TRA-3b
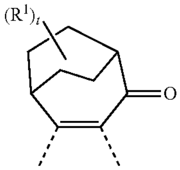
Formula TRA-4a
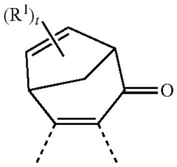
Formula TRA-4b
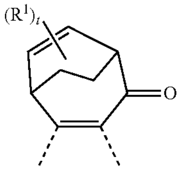
Formula TRA-4c
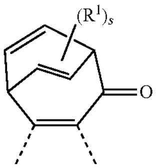

-continued

Formula TRA-4d

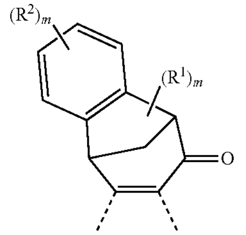

Formula TRA-4e

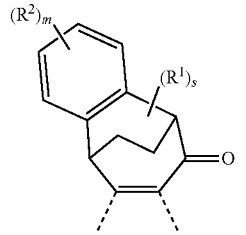

Formula TRA-4f

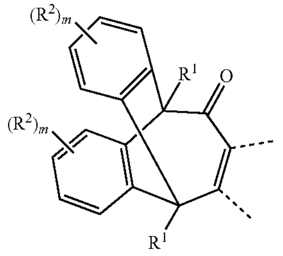

where the symbols $R^1$ and $R^2$ have the definitions set out above, especially for formula (I), the symbols $Z^1$, $Z^2$, G and $R^3$ have the definition set out above, especially for formulae (Cy-1) to (Cy-10), and $Z^4$ is the same or different at each instance and is $C(R^3)_2$, O, S or $NR^3$, and is preferably the same or different at each instance and is $C(R^3)_2$, with the proviso that, in these groups, no two heteroatoms are bonded directly to one another and no two C═O groups are bonded directly to one another, the symbols $Y^2$ and $R^f$ and the indices r, s, t and v have the definitions given above, especially for formulae (RA-1) to (RA-13), the index m is 0, 1, 2, 3 or 4, preferably 0, 1 or 2, and the dotted bonds represent the sites of attachment of the fused ring to the further groups.

It may additionally be the case that the substituents R, $R^a$, $R^b$, $R^c$, $R^d$, $R^e$, $R^f$, $R^y$, $R^1$ and $R^2$ according to the above formulae do not form a fused aromatic or heteroaromatic ring system with the ring atoms of the ring system to which the substituents R, $R^a$, $R^b$, $R^c$, $R^d$, $R^e$, $R^f$, $R^y$, $R^1$ and $R^2$ bind. This includes the formation of a fused aromatic or heteroaromatic ring system with possible substituents $R^1$ and $R^2$ that may be bonded to the R, $R^a$, $R^b$, RC, $R^d$, $R^e$, $R^f$, $R^y$ and $R^1$ radicals.

When the compound of the invention is substituted by aromatic or heteroaromatic R, $R^a$, $R^b$, $R^c$, $R^d$, $R^e$, $R^f$, $R^y$, $R^1$ or $R^2$ groups, it is preferable when these do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

It may therefore preferably be the case that the R radical does not have any through-conjugated anthracene group; preferably, none of the R, $R^a$, $R^b$, $R^c$, $R^d$, $R^e$, $R^f$, $R^y$, $R^1$, $R^2$ radicals comprises a through-conjugated anthracene group.

Through-conjugation of the anthracene group is formed if direct bonds are formed between the anthracene group, the base skeleton of the invention shown in formula (I), and an optional aromatic or heteroaromatic connecting group. A further bond between the aforementioned conjugated groups, for example via a sulfur, nitrogen or oxygen atom or a carbonyl group, is not detrimental to conjugation. In the case of a fluorene system, the two aromatic rings are bonded directly, where the $sp^3$-hybridized carbon atom in position 9 does prevent fusion of these rings, but conjugation is possible, since this $sp^3$-hybridized carbon atom in position 9 does not necessarily lie between the groups connected via a connecting group. In contrast, in the case of a spirobifluorene structure, through-conjugation can be formed if the bond between the groups connected via the spirobifluorene group is via the same phenyl group in the spirobifluorene structure or via phenyl groups in the spirobifluorene structure that are bonded directly to one another and are in one plane. If the bond between the groups connected via a spirobifluorene group is via different phenyl groups in the second spirobifluorene structure bonded via the $sp^3$-hybridized carbon atom in position 9, the conjugation is interrupted.

It may also be particularly preferable that the R radical does not comprise any anthracene group; preferably, none of the R, $R^a$, $R^b$, $R^c$, $R^d$, $R^e$, $R^f$, $R^y$, $R^1$, $R^2$ radicals comprises an anthracene group.

Very especially preferably, it may further be the case that the R radical does not comprise any aromatic or heteroaromatic ring system having three linear-condensed aromatic 6-membered rings, where preferably none of the R, $R^a$, $R^b$, $R^c$, $R^d$, $R^e$, $R^f$, $R^y$, $R^1$, $R^2$ radicals comprises an aromatic or heteroaromatic ring system having three linear-condensed aromatic 6-membered rings.

It may further be the case that the $R^y$ radical does not comprise or form a fluorenone group; preferably, none of the radicals R, $R^a$, $R^b$, $R^c$, $R^d$, $R^e$ comprises or forms a fluorenone group. This includes substituents that bind to the R, $R^a$, $R^b$, $R^c$, $R^d$, $R^e$, $R^y$ radicals. A fluorenone comprises a 5-membered ring with a CO group to which two aromatic 6-membered rings are fused.

When two radicals that may especially be selected from R, $R^a$, $R^b$, $R^c$, $R^d$, $R^e$, $R^f$, $R^y$, $R^1$ and $R^2$ form a ring system with one another, this ring system may be mono- or polycyclic, aliphatic, heteroaliphatic, aromatic or heteroaromatic. In this case, the radicals which together form a ring system may be adjacent, meaning that these radicals are bonded to the same carbon atom or to carbon atoms directly bonded to one another, or they may be further removed from one another. In addition, the ring systems provided with the substituents R, $R^a$, $R^b$, $R^c$, $R^d$, $R^e$, $R^f$, $R^y$, $R^1$ and/or $R^2$ may also be joined to one another via a bond, such that this can bring about a ring closure. In this case, each of the corresponding bonding sites has preferably been provided with a substituent R, $R^a$, $R^b$, $R^c$, $R^d$, $R^e$, $R^f$, $R^y$, $R^1$ and/or $R^2$.

It may preferably be the case that the structure/compound is symmetric in relation to the $R^a$ and $R^c$ radicals. It may additionally be the case that the structure/compound is symmetric in relation to the $R^a$, $R^b$ and $R^c$ radicals. It may further be the case that the structure/compound is symmetric in relation to the $R^a$, $R^b$, $R^c$ and $R^d$ radicals.

What is meant more particularly by symmetric in relation to the $R^a$ and $R^c$ radicals is that the corresponding $R^a$ and $R^c$ radicals are the same and do not differ. In this case, the sameness relates to both radicals $R^a$ and $R^c$. If two $R^a$ radicals, for example, form a ring of the structure RA-1, the two $R^c$ radicals form an identical ring of structure RA-1.

Structures/compounds in which the $R^a$ and $R^c$ radicals are symmetric are notable for surprisingly high colour purity which is reflected particularly in a narrow emission spectrum.

In a further configuration, the structure/compound may be asymmetric in relation to the $R^a$ and $R^c$ radicals.

It may further be the case that the R radical represents, comprises, or forms together with an $R^d$ radical, at least one group selected from $C(Ar)_3$, $C(R^e)_3$, $N(Ar)_2$, $N(R^e)_2$, $Si(Ar)_3$, $Si(R^e)_3$, $B(R^e)_2$, preferably selected from $C(Ar)_3$, $C(R^e)_3$, $N(Ar)_2$, $Si(Ar)_3$, $Si(R^e)_3$, more preferably a fluorene group that may be substituted by one or more $R^e$ radicals.

It may additionally be the case that the $R^e$ and/or $R^d$ radical represents, comprises, or forms together with an $R^d$ or $R^e$ radical, at least one group selected from $C(Ar')_3$, $C(R^1)_3$, $N(Ar')_2$, $N(R^1)_2$, $Si(Ar')_3$, $Si(R^1)_3$, $B(R^1)_2$, preferably selected from $C(Ar')_3$, $C(R^1)_3$, $N(Ar')_2$, $Si(Ar')_3$, $Si(R^1)_3$, more preferably a fluorene group that may be substituted by one or more $R^1$ radicals.

Structures/compounds having one of the aforementioned groups selected from $C(Ar')_3$, $C(R^1)_3$, $Si(Ar')_3$, $Si(R^1)_3$, $N(Ar')_2$, $N(R^1)_2$, $B(R^1)_2$, more preferably a fluorene group, are notable for surprisingly high efficiency.

In a preferred configuration, a compound of the invention can be represented by at least one of the structures of formula (I) and/or (I-1) to (I-83). Preferably, compounds of the invention, preferably comprising structures of formula (I) and/or (I-1) to (I-83), have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

Preferred aromatic or heteroaromatic ring systems Ar, R, $R^a$, $R^b$, $R^c$, $R^d$, $R^e$, $R^f$ and/or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3, 4 or 9 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^e$, $R^1$ or $R^2$ radicals.

It may preferably be the case that at least one substituent R, $R^a$, $R^b$, $R^c$, $R^d$, $R^e$ is the same or different at each instance and is selected from the group consisting of H, D, a branched or cyclic alkyl, alkoxy or thioalkoxy group having 3 to 20 carbon atoms or an aromatic or heteroaromatic ring system selected from the groups of the following formulae Ar-1 to Ar-75, where the substituents R, $R^a$, $R^b$, $R^c$, $R^d$, $R^e$ preferably either form a ring according to the structures of the formulae (RA-1) to (RA-13), (RA-1a) to (RA-4f) or (RB) or the substituent R, $R^a$, $R^b$, $R^c$, $R^d$, $R^e$ is the same or different at each instance and is selected from the group consisting of H, D or an aromatic or heteroaromatic ring system selected from the groups of the following formulae Ar-1 to Ar-75, and/or the Ar' group is the same or different at each instance and is selected from the groups of the following formulae Ar-1 to Ar-75:

Ar-1

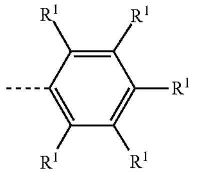

Ar-2

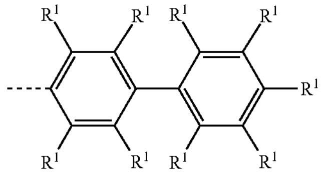

Ar-3

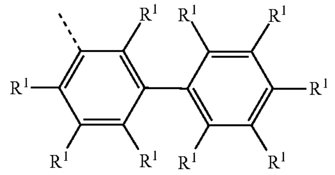

Ar-4

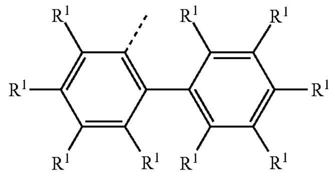

Ar-5

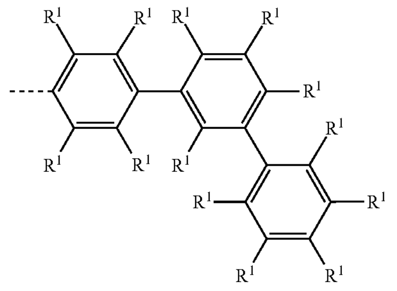

Ar-6

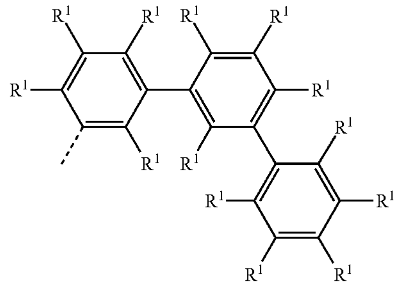

-continued
Ar-7
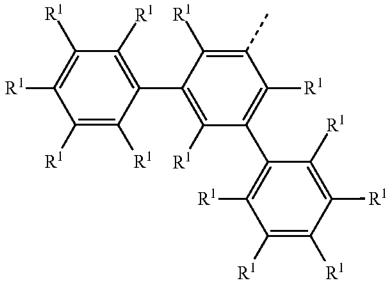
Ar-8
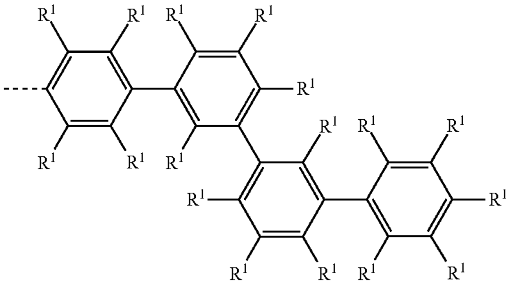
Ar-9
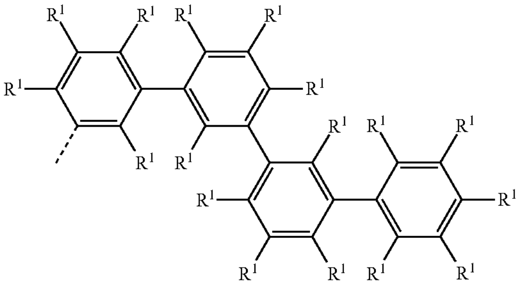
Ar-10
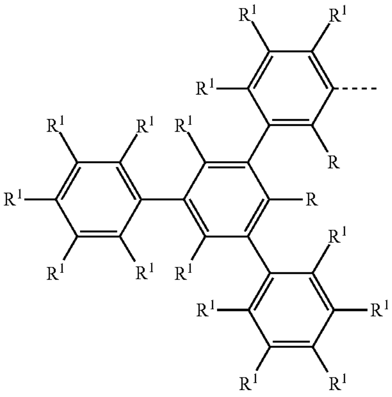
-continued
Ar-11
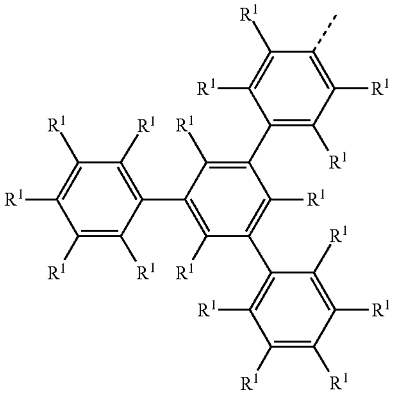
Ar-12
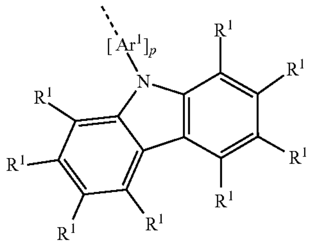
Ar-13
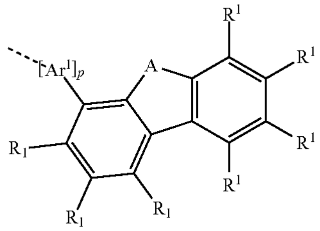
Ar-14
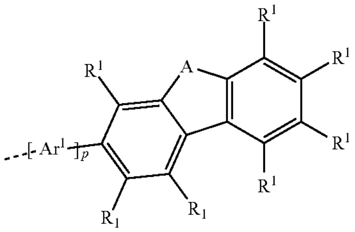
Ar-15
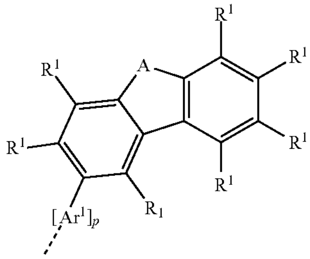
Ar-16
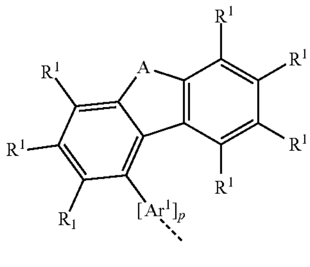

-continued
Ar-17
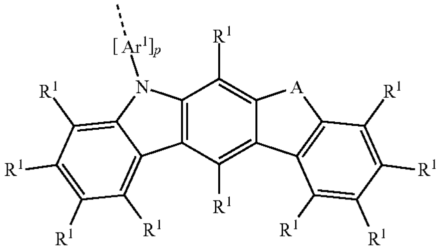
Ar-18
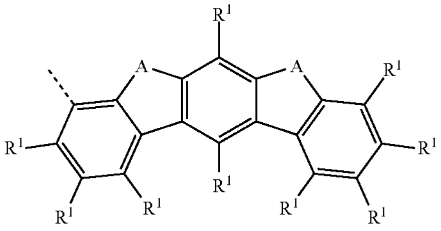
Ar-19
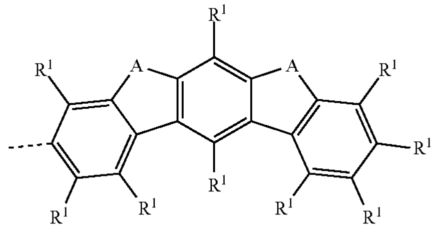
Ar-20
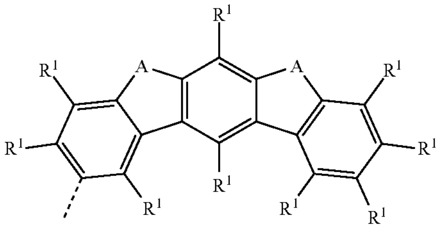
Ar-21
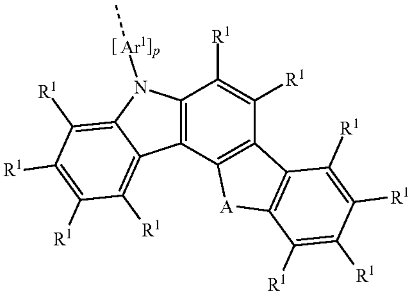
Ar-22
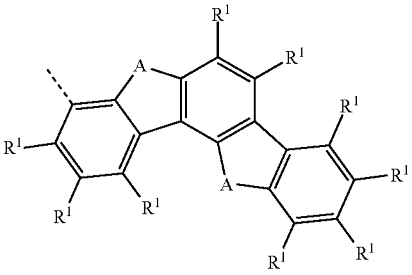
-continued
Ar-23
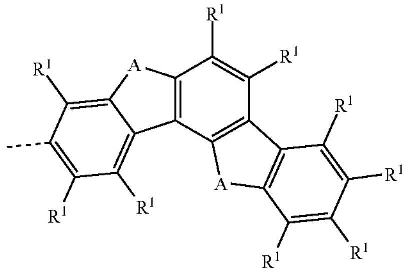
Ar-24
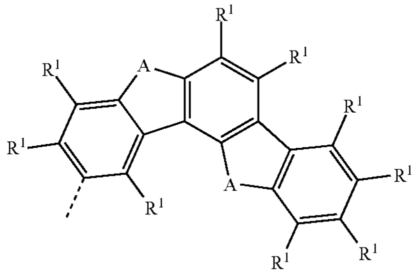
Ar-25
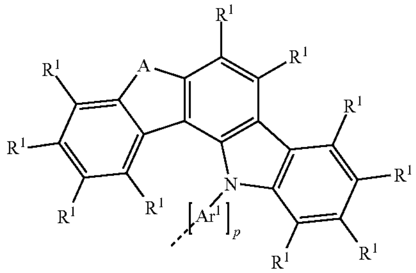
Ar-26
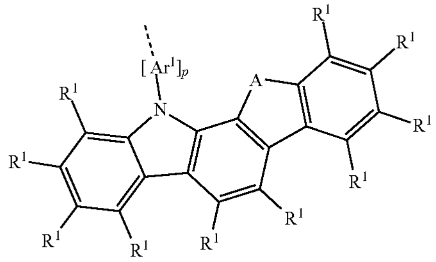
Ar-27
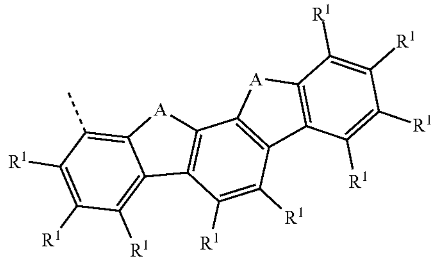
Ar-28
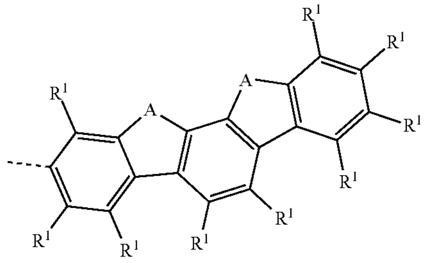

-continued
Ar-29
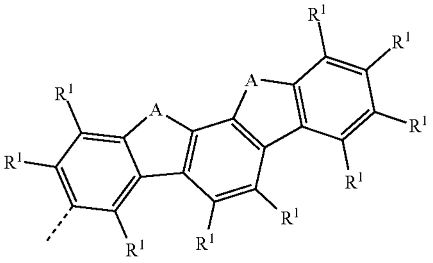
Ar-30
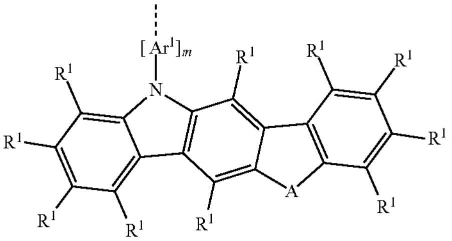
Ar-31
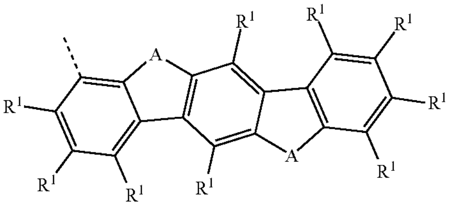
Ar-32
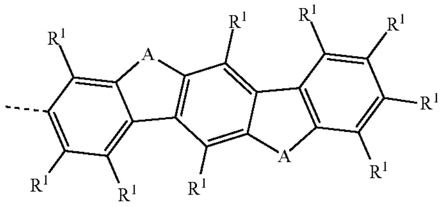
Ar-33
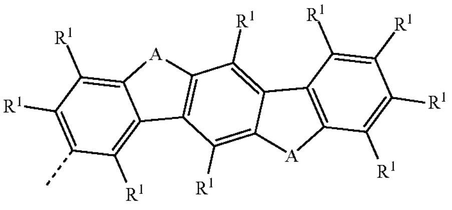
Ar-34
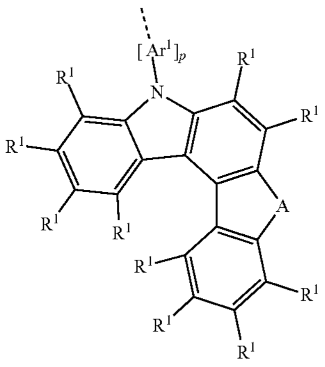
-continued
Ar-35
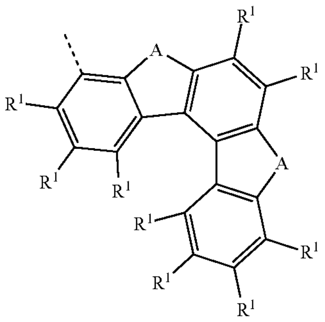
Ar-36
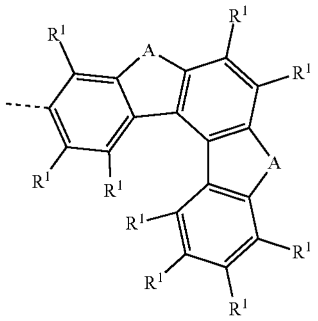
Ar-37
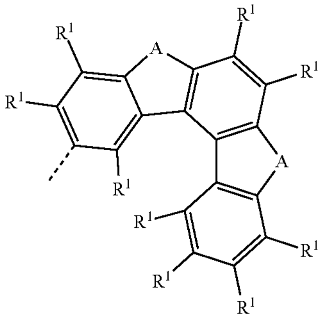
Ar-38
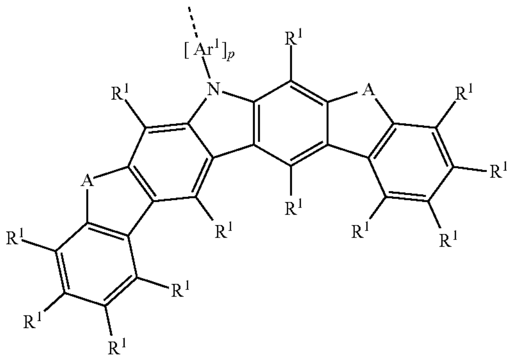

-continued
Ar-39
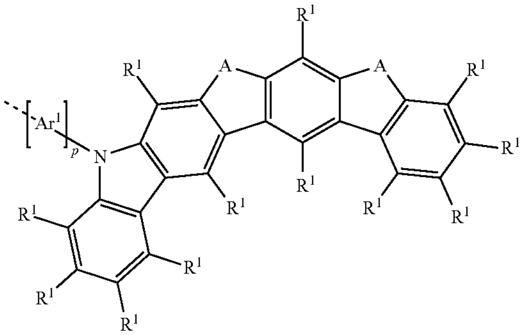
Ar-40
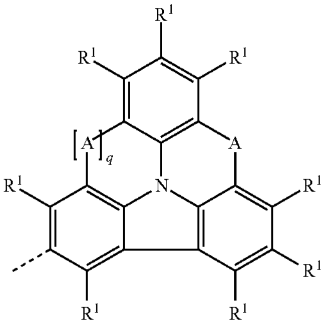
Ar-41
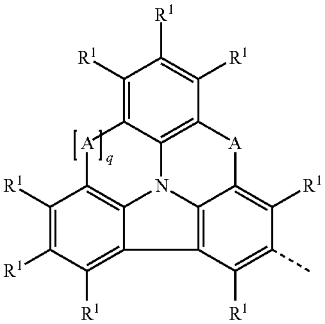
Ar-42
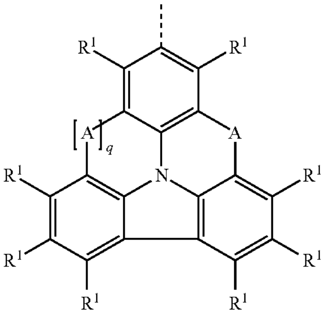
Ar-43
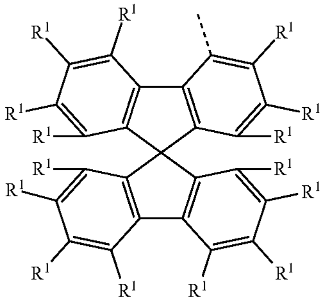
-continued
Ar-44
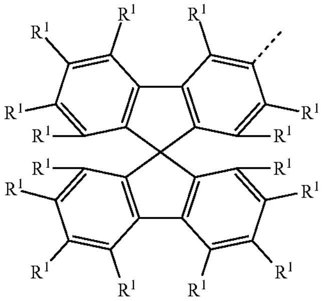
Ar-45
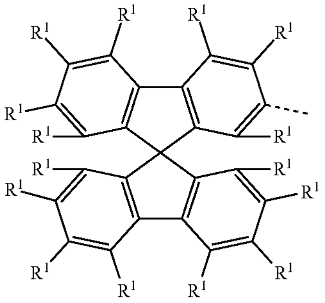
Ar-46
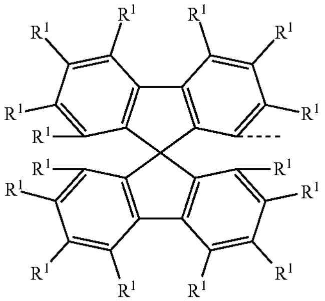
Ar-47
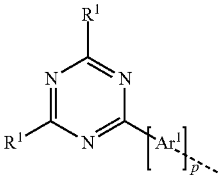
Ar-48
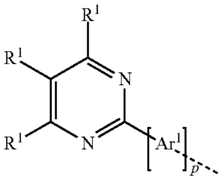
Ar-49
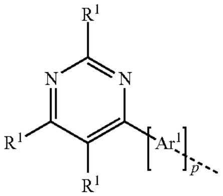

-continued
Ar-50
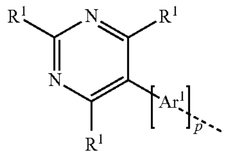
Ar-51
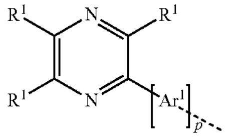
Ar-52
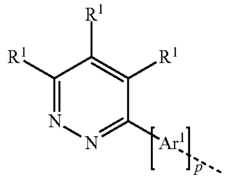
Ar-53
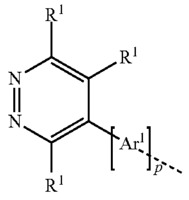
Ar-54
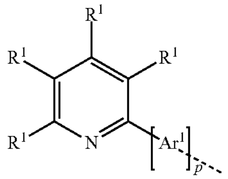
Ar-55
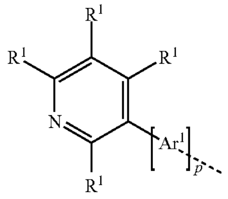
Ar-56
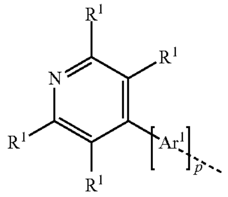
Ar-57
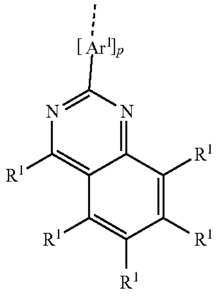
-continued
Ar-58
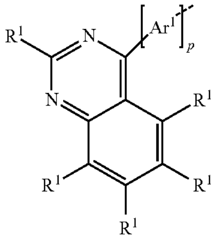
Ar-59
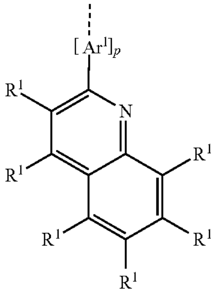
Ar-60
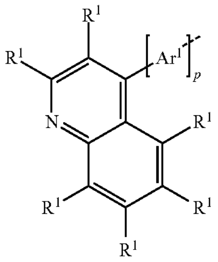
Ar-61
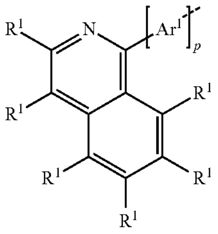
Ar-62
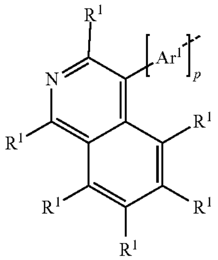
Ar-63
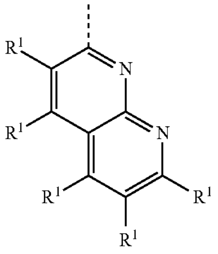

-continued
Ar-64
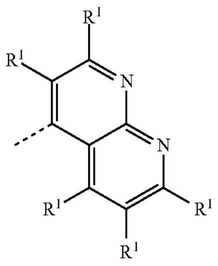
Ar-65
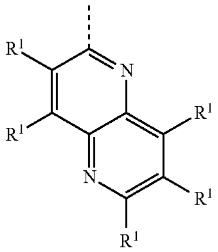
Ar-66
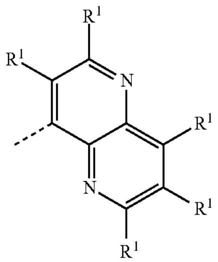
Ar-67
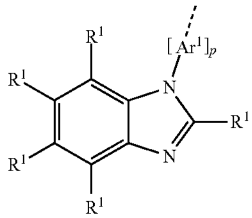
Ar-68
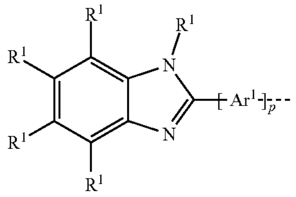
Ar-69
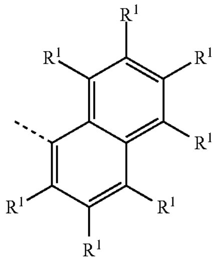
-continued
Ar-70
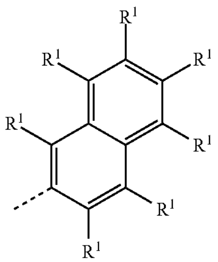
Ar-71
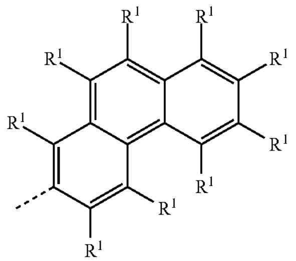
Ar-72
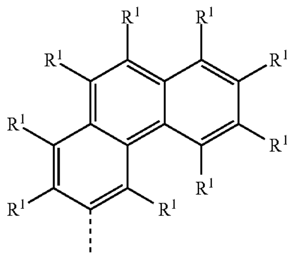
Ar-73
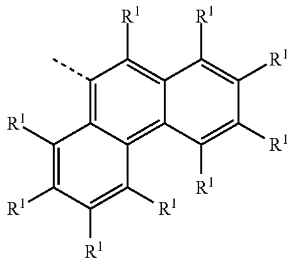
Ar-74
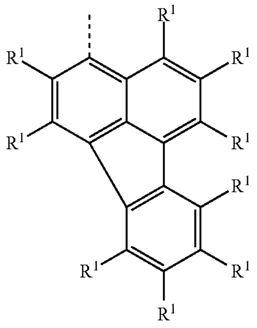

-continued

Ar-75

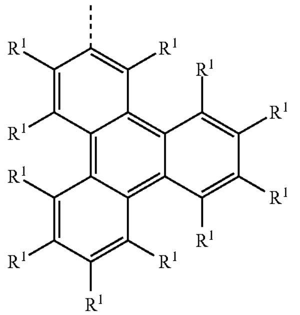

where $R^1$ has the definitions given above, the dotted bond represents the site of attachment to the corresponding group and in addition:

$Ar^1$ is the same or different at each instance and is a bivalent aromatic or heteroaromatic ring system which has 6 to 18 aromatic ring atoms and may be substituted in each case by one or more $R^1$ radicals; A is the same or different at each instance and is $C(R^1)_2$, $NR^1$, O or S;

p is 0 or 1, where p=0 means that the $Ar^1$ group is absent and that the corresponding aromatic or heteroaromatic group is bonded directly to the corresponding radical;

q is 0 or 1, where q=0 means that no A group is bonded at this position and the $R^1$ radicals thereof are bonded to the corresponding carbon atoms instead.

In this case, preference is given to structures of the formulae (Ar-1), (Ar-2), (Ar-3), (Ar-12), (Ar-13), (Ar-14), (Ar-15), (Ar-16), (Ar-40), (Ar-41), (Ar-42), (Ar-43), (Ar-44), (Ar-45), (Ar-46), (Ar-69), (Ar-70), (Ar-75), and particular preference to structures of the formulae (Ar-1), (Ar-2), (Ar-3), (Ar-12), (Ar-13), (Ar-14), (Ar-15), (Ar-16).

When the abovementioned groups for Ar have two or more A groups, possible options for these include all combinations from the definition of A. Preferred embodiments in that case are those in which one A group is $NR^1$ and the other A group is $C(R^1)_2$ or in which both A groups are $NR^1$ or in which both A groups are O.

When A is $NR^1$, the substituent $R^1$ bonded to the nitrogen atom is preferably an aromatic or heteroaromatic ring system which has 5 to 24 aromatic ring atoms and may also be substituted by one or more $R^2$ radicals. In a particularly preferred embodiment, this $R^1$ substituent is the same or different at each instance and is an aromatic or heteroaromatic ring system which has 6 to 24 aromatic ring atoms, especially 6 to 18 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^2$ radicals. Preference is given to phenyl, biphenyl, terphenyl and quaterphenyl having bonding patterns as listed above for Ar-1 to Ar-11, where these structures, rather than by $R^1$, may be substituted by one or more $R^2$ radicals, but are preferably unsubstituted. Preference is further given to triazine, pyrimidine and quinazoline as listed above for Ar-47 to Ar-50, Ar-57 and Ar-58, where these structures, rather than by $R^1$, may be substituted by one or more $R^2$ radicals.

There follows a description of preferred substituents R, $R^a$, $R^b$, $R^c$, $R^d$, $R^e$ and $R^f$.

In a preferred embodiment of the invention, R, $R^a$, $R^b$, $R^c$, $R^d$, $R^e$ are the same or different at each instance and are selected from the group consisting of H, D, F, CN, $NO_2$, $Si(R^1)_3$, $B(OR^1)_2$, a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^1$ radicals.

In a further-preferred embodiment of the invention, substituent R, $R^a$, $R^b$, $R^c$, $R^d$, $R^e$ is the same or different at each instance and is selected from the group consisting of H, D, F, a straight-chain alkyl group having 1 to 20 carbon atoms or a branched or cyclic alkyl group having 3 to 20 carbon atoms, where the alkyl group may be substituted in each case by one or more $R^1$ radicals, or an aromatic or heteroaromatic ring system which has 5 to 60 aromatic ring atoms, preferably 5 to 40 aromatic ring atoms, and may be substituted in each case by one or more $R^1$ radicals.

It may further be the case that at least one substituent R, $R^a$, $R^b$, $R^c$, $R^d$, $R^e$ is the same or different at each instance and is selected from the group consisting of H, D, an aromatic or heteroaromatic ring system which has 6 to 30 aromatic ring atoms and may be substituted by one or more $R^1$ radicals, and an $N(Ar')_2$ group. In a further-preferred embodiment of the invention, the substituents R, $R^a$, $R^b$, $R^c$, $R^d$, $R^e$ either form a ring according to the structures of the formulae (RA-1) to (RA-13), (RA-1a) to (RA-4f) or (RB), or R, $R^a$, $R^b$, $R^c$, $R^d$, $R^e$ is the same or different at each instance and is selected from the group consisting of H, D, an aromatic or heteroaromatic ring system which has 6 to 30 aromatic ring atoms and may be substituted by one or more $R^1$ radicals, or an $N(Ar')_2$ group. More preferably, substituent R, $R^a$, $R^b$, $R^c$, $R^d$, $R^e$ is the same or different at each instance and is selected from the group consisting of H or an aromatic or heteroaromatic ring system having 6 to 24 aromatic ring atoms, preferably having 6 to 18 aromatic ring atoms, more preferably having 6 to 13 aromatic ring atoms, each of which may be substituted by one or more $R^1$ radicals.

In a preferred embodiment of the invention $R^f$ is the same or different at each instance and are selected from the group consisting of a straight-chain alkyl group having 1 to 20 carbon atoms or a branched or cyclic alkyl group having 3 to 20 carbon atoms, where the alkyl group may be substituted in each case by one or more $R^2$ radicals, or an aromatic or heteroaromatic ring system which has 5 to 60 aromatic ring atoms, preferably 5 to 40 aromatic ring atoms, and may be substituted in each case by one or more $R^2$ radicals.

In a further-preferred embodiment of the invention, $R^f$ is the same or different at each instance and are selected from the group consisting of a straight-chain alkyl group having 1 to 10 carbon atoms or a branched or cyclic alkyl group having 3 to 10 carbon atoms, where the alkyl group may be substituted in each case by one or more $R^2$ radicals, an aromatic or heteroaromatic ring system which has 6 to 30 aromatic ring atoms and may be substituted by one or more $R^2$ radicals. More preferably, $R^a$ is the same or different at each instance and are selected from the group consisting of a straight-chain alkyl group having 1 to 5 carbon atoms or a branched or cyclic alkyl group having 3 to 5 carbon atoms, where the alkyl group may be substituted in each case by one or more $R^2$ radicals, or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more $R^2$ radicals.

In a preferred embodiment of the invention, $R^f$ is the same or different at each instance and is selected from the group consisting of a straight-chain alkyl group having 1 to 6 carbon atoms or a cyclic alkyl group having 3 to 6 carbon atoms, where the alkyl group may be substituted in each case by one or more $R^2$ radicals, or an aromatic or heteroaromatic ring system which has 6 to 24 aromatic ring atoms and may be substituted in each case by one or more $R^2$ radicals; at the same time, two $R^f$ radicals together may also form a ring system. More preferably, $R^f$ is the same or different at each instance and is selected from the group consisting of a straight-chain alkyl group having 1, 2, 3 or 4 carbon atoms or a branched or cyclic alkyl group having 3 to 6 carbon atoms, where the alkyl group may be substituted in each case by one or more $R^2$ radicals, but is preferably unsubstituted, or an aromatic ring system which has 6 to 12 aromatic ring atoms, especially 6 aromatic ring atoms, and may be substituted in each case by one or more preferably nonaromatic $R^2$ radicals, but is preferably unsubstituted; at the same time, two $R^f$ radicals together may form a ring system. Most preferably, $R^f$ is the same or different at each instance and is selected from the group consisting of a straight-chain alkyl group having 1, 2, 3 or 4 carbon atoms, or a branched alkyl group having 3 to 6 carbon atoms. Most preferably, $R^f$ is a methyl group or is a phenyl group, where two phenyl groups together may form a ring system, preference being given to a methyl group over a phenyl group.

Preferred aromatic or heteroaromatic ring systems represented by the substituents R, $R^a$, $R^b$, $R^c$, $R^d$, $R^e$, $R^f$ or Ar, Ar' or Ar" are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^e$, $R^1$ or $R^2$ radicals. Particular preference is given to the structures Ar-1 to Ar-75 shown above, preference being given to structures of the formulae (Ar-1), (Ar-2), (Ar-3), (Ar-12), (Ar-13), (Ar-14), (Ar-15), (Ar-16), (Ar-40), (Ar-41), (Ar-42), (Ar-43), (Ar-44), (Ar-45), (Ar-46), (Ar-69), (Ar-70), (Ar-75), and particular preference to structures of the formulae (Ar-1), (Ar-2), (Ar-3), (Ar-12), (Ar-13), (Ar-14), (Ar-15), (Ar-16). With regard to the structures Ar-1 to Ar-75, it should be stated that these are shown with a substituent $R^1$. In the case of the ring system Ar, these substituents $R^1$ should be replaced by $R^e$, and in the case of Ar", $R^f$, these substituents $R^1$ should be replaced by $R^2$.

Further suitable R, $R^a$, $R^b$, $R^c$, $R^d$, $R^e$ groups are groups of the formula —$Ar^4$—$N(Ar^2)(Ar^3)$ where $Ar^2$, $Ar^3$ and $Ar^4$ are the same or different at each instance and are an aromatic or heteroaromatic ring system which has 5 to 24 aromatic ring atoms and may be substituted in each case by one or more $R^1$ radicals. The total number of aromatic ring atoms in $Ar^2$, $Ar^3$ and $Ar^4$ here is not more than 60 and preferably not more than 40.

In this case, $Ar^4$ and $Ar^2$ may also be bonded to one another and/or $Ar^2$ and $Ar^3$ to one another by a group selected from $C(R^1)_2$, $NR^1$, O and S. Preferably, $Ar^4$ and $Ar^2$ are joined to one another and $Ar^2$ and $Ar^3$ to one another in the respective ortho position to the bond to the nitrogen atom. In a further embodiment of the invention, none of the $Ar^2$, $Ar^3$ and $Ar^4$ groups are bonded to one another.

Preferably, $Ar^4$ is an aromatic or heteroaromatic ring system which has 6 to 24 aromatic ring atoms, preferably 6 to 12 aromatic ring atoms, and may be substituted in each case by one or more $R^1$ radicals. More preferably, $Ar^4$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^4$ is an unsubstituted phenylene group.

Preferably, $Ar^2$ and $Ar^3$ are the same or different at each instance and are an aromatic or heteroaromatic ring system which has 6 to 24 aromatic ring atoms and may be substituted in each case by one or more $R^1$ radicals. Particularly preferred $Ar^2$ and $Ar^3$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene or triphenylene, each of which may be substituted by one or more $R^1$ radicals. Most preferably, $Ar^2$ and $Ar^3$ are the same or different at each instance and are selected from the group consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

In a further preferred embodiment of the invention, $R^1$ is the same or different at each instance and is selected from the group consisting of H, D, F, CN, a straight-chain alkyl group having 1 to 10 carbon atoms or a branched or cyclic alkyl group having 3 to 10 carbon atoms, where the alkyl group may be substituted in each case by one or more $R^2$ radicals, or an aromatic or heteroaromatic ring system which has 6 to 24 aromatic ring atoms and may be substituted in each case by one or more $R^2$ radicals. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 13 aromatic ring atoms and may be substituted in each case by one or more $R^2$ radicals, but is preferably unsubstituted.

In a further preferred embodiment of the invention, $R^2$ is the same or different at each instance and is H, an alkyl group having 1 to 4 carbon atoms or an aryl group having 6 to 10 carbon atoms, which may be substituted by an alkyl group having 1 to 4 carbon atoms, but is preferably unsubstituted.

At the same time, in compounds of the invention that are processed by vacuum evaporation, the alkyl groups preferably have not more than five carbon atoms, more preferably not more than 4 carbon atoms, most preferably not more than 1 carbon atom. For compounds that are processed from solution, suitable compounds are also those substituted by alkyl groups, especially branched alkyl groups, having up to 10 carbon atoms or those substituted by oligoarylene groups, for example ortho-, meta- or para-terphenyl or branched terphenyl or quaterphenyl groups.

Furthermore, it may be the case that the compound comprises exactly two or exactly three structures of formula (I) and/or (I-1) to (I-83), where preferably one of the aromatic or heteroaromatic ring systems that can be represented by at least one of the R, $R^d$, $R^e$ groups or to which the R, $R^d$, $R^e$ groups bind is shared by the two structures.

In a preferred configuration, the compounds are selected from compounds of the formula (D-1), (D-2) or (D-3)

Formula (D-1)

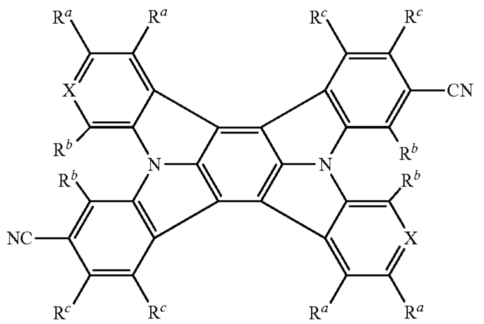

Formula (D-2)

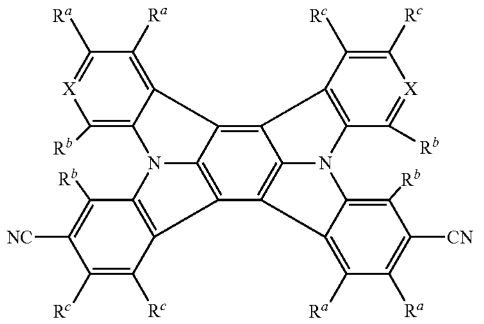

Formula (D-3)

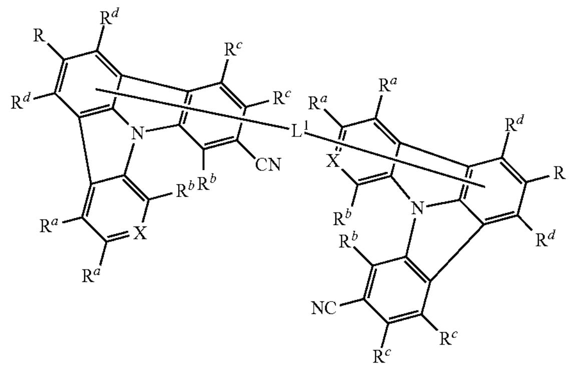

where the $L^1$ group is a connecting group, preferably a bond or an aromatic or heteroaromatic ring system which has 5 to 40, preferably 5 to 30, aromatic ring atoms and may be substituted by one or more $R^1$ radicals, and $R^1$ and the further symbols used have the definitions given above, especially for formula (I).

In a further preferred embodiment of the invention, $L^1$ is a bond or an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (I). More preferably, $L^1$ is an aromatic ring system having 6 to 10 aromatic ring atoms or a heteroaromatic ring system having 6 to 13 heteroaromatic ring atoms, each of which may be substituted by one or more $R^2$ radicals, but is preferably unsubstituted, where $R^2$ may have the definition given above, especially for formula (I).

Further preferably, the symbol $L^1$ shown in formula (D3) inter alia is the same or different at each instance and is a bond or an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded to the respective atom of the further group directly, i.e. via an atom of the aromatic or heteroaromatic group.

It may additionally be the case that the $L^1$ group shown in formula (D3) comprises an aromatic ring system having not more than two fused aromatic and/or heteroaromatic 6-membered rings, preferably does not comprise any fused aromatic or heteroaromatic ring system. Accordingly, naphthyl structures are preferred over anthracene structures. In addition, fluorenyl, spirobifluorenyl, dibenzofuranyl and/or dibenzothienyl structures are preferred over naphthyl structures.

Particular preference is given to structures having no fusion, for example phenyl, biphenyl, terphenyl and/or quaterphenyl structures.

Examples of suitable aromatic or heteroaromatic ring systems $L^1$ are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more $R^1$ radicals, but are preferably unsubstituted.

The abovementioned preferred embodiments may be combined with one another as desired within the restrictions defined in claim 1. In a particularly preferred embodiment of the invention, the abovementioned preferences occur simultaneously.

In a further configuration of the present invention, preference is given to compounds comprising a structure of formula (I), preferably compounds of formula (I), in which the $R^a$ radicals together form a ring, where these compounds have the following properties:

| Formula of the ring formed by $R^a$ radicals | $Z^1$ | $Z^2$ | $Z^3$ |
|---|---|---|---|
| Cy-1 | $C(R^3)_2$ | $C(R^1)_2$ | $C(R^3)_2$ |
| Cy-2 | $C(R^3)_2$ | $C(R^1)_2$ | $C(R^3)_2$ |
| Cy-3 | $C(R^3)_2$ | $C(R^1)_2$ | $C(R^3)_2$ |
| Cy-1 | $Si(R^3)_2$ | $C(R^1)_2$ | $Si(R^3)_2$ |
| Cy-2 | $Si(R^3)_2$ | $C(R^1)_2$ | $Si(R^3)_2$ |
| Cy-3 | $Si(R^3)_2$ | $C(R^1)_2$ | $Si(R^3)_2$ |

In a further configuration of the present invention, preference is given to compounds comprising a structure of formula (I), preferably compounds of formula (I), in which the $R^a$ radicals together form a ring, where these compounds have the following properties:

| Formula of the ring formed by $R^a$ radicals | G | $R^1$ | $Z^2$ |
|---|---|---|---|
| Cy-4 | Alkylene group having 1, 2 or 3 carbon atoms | H, methyl or Ar-1 to Ar-75, preferably H | $C(R^1)_2$ |
| Cy-5 | Alkylene group having 1, 2 or 3 carbon atoms | H, methyl or Ar-1 to Ar-75, preferably H | $C(R^1)_2$ |
| Cy-6 | Alkylene group having 1, 2 or 3 carbon atoms | H, methyl or Ar-1 to Ar-75, preferably H | $C(R^1)_2$ |
| Cy-7 | Alkylene group having 1, 2 or 3 carbon atoms | H, methyl or Ar-1 to Ar-75, preferably H | $C(R^1)_2$ |
| Cy-8 | Alkylene group having 1, 2 or 3 carbon atoms | H or Ar-1 to H, methyl or Ar-1 to Ar-75, preferably H | $C(R^1)_2$ |
| Cy-9 | Alkylene group having 1, 2 or 3 carbon atoms | H, methyl or Ar-1 to Ar-75, preferably H | $C(R^1)_2$ |
| Cy-10 | Alkylene group having 1, 2 or 3 carbon atoms | H, methyl or Ar-1 to Ar-75, preferably H | $C(R^1)_2$ |
| Cy-4 | —CR1═CR1— | H, methyl or Ar-1 to Ar-75, preferably H | $C(R^1)_2$ |
| Cy-5 | —CR1═CR1— | H, methyl or Ar-1 to Ar-75, preferably H | $C(R^1)_2$ |
| Cy-6 | —CR1═CR1— | H, methyl or Ar-1 to Ar-75, preferably H | $C(R^1)_2$ |
| Cy-7 | —CR1═CR1— | H, methyl or Ar-1 to Ar-75, preferably H | $C(R^1)_2$ |
| Cy-8 | —CR1═CR1— | H or Ar-1 to H, methyl or Ar-1 to Ar-75, preferably H | $C(R^1)_2$ |
| Cy-9 | —CR1═CR1— | H, methyl or Ar-1 to Ar-75, preferably H | $C(R^1)_2$ |
| Cy-10 | —CR1═CR1— | H, methyl or Ar-1 to Ar-75, preferably H | $C(R^1)_2$ |
| Cy-4 | Arylene or heteroarylene group having 5 to 14 aromatic ring atoms | H, methyl or Ar-1 to Ar-75, preferably H | $C(R^1)_2$ |
| Cy-5 | Arylene or heteroarylene group having 5 to 14 aromatic ring atoms | H, methyl or Ar-1 to Ar-75, preferably H | $C(R^1)_2$ |
| Cy-6 | Arylene or heteroarylene group having 5 to 14 aromatic ring atoms | H, methyl or Ar-1 to Ar-75, preferably H | $C(R^1)_2$ |
| Cy-7 | Arylene or heteroarylene group having 5 to 14 aromatic ring atoms | H, methyl or Ar-1 to Ar-75, preferably H | $C(R^1)_2$ |
| Cy-8 | Arylene or heteroarylene group having 5 to 14 aromatic ring atoms | H or Ar-1 to H, methyl or Ar-1 to Ar-75, preferably H | $C(R^1)_2$ |

-continued

| Formula of the ring formed by $R^a$ radicals | G | $R^1$ | $Z^2$ |
|---|---|---|---|
| Cy-9 | Arylene or heteroarylene group having 5 to 14 aromatic ring atoms | H, methyl or Ar-1 to Ar-75, preferably H | $C(R^1)_2$ |
| Cy-10 | Arylene or heteroarylene group having 5 to 14 aromatic ring atoms | H, methyl or Ar-1 to Ar-75, preferably H | $C(R^1)_2$ |

In a further configuration, the preferences set out above with regard to ring formation between two $R^a$ radicals to form structures of the formulae (Cy-1) to (Cy-10) are applicable to two $R^c$ radicals.

In a further configuration, the preferences set out above with regard to ring formation between two $R^a$ radicals to form structures of the formulae (Cy-1) to (Cy-10) are applicable to two $R^e$ radicals.

In a further configuration of the present invention, preference is given to compounds comprising a structure of formula (I-1), preferably compounds of formula (I-1), where the two $R^a$ radicals form a ring, the two $R^c$ radicals form a ring, and in which the $R^a$, $R^b$, $R^c$, $R^d$ and $R^e$ radicals have the following definitions:

| $R^a$ | $R^b$ | $R^c$ | $R^d$ | $R^e$ |
|---|---|---|---|---|
| RA-5 | H, D, alkyl | RA-5 | H, D, alkyl | H, D, alkyl |
| RA-4 | H, D, alkyl | RA-4 | H, D, alkyl | H, D, alkyl |
| RA-4f | H, D, alkyl | RA-4f | H, D, alkyl | H, D, alkyl |
| RA-3 | H, D, alkyl | RA-3 | H, D, alkyl | H, D, alkyl |
| RB | H, D, alkyl | RB | H, D, alkyl | H, D, alkyl |
| RA-5 | H, D, alkyl | RA-5 | H, D, alkyl and phenyl ring formation with $R^e$ | Phenyl ring formation with $R^d$ |
| RA-5 | H, D, alkyl | RA-5 | Aryl, heteroaryl, and phenyl ring formation with $R^e$ | Phenyl ring formation with $R^d$ |
| RA-4 | H, D, alkyl | RA-4 | H, D, alkyl and phenyl ring formation with $R^e$ | Phenyl ring formation with $R^d$ |
| RA-4 | H, D, alkyl | RA-4 | Aryl, heteroaryl, and phenyl ring formation with $R^e$ | Phenyl ring formation with $R^d$ |
| RA-4f | H, D, alkyl | RA-4f | H, D, alkyl and phenyl ring formation with $R^e$ | Phenyl ring formation with $R^d$ |
| RA-4f | H, D, alkyl | RA-4f | Aryl, heteroaryl, and phenyl ring formation with $R^e$ | Phenyl ring formation with $R^d$ |
| RA-3 | H, D, alkyl | RA-3 | H, D, alkyl and phenyl ring formation with $R^e$ | Phenyl ring formation with $R^d$ |
| RA-3 | H, D, alkyl | RA-3 | Aryl, heteroaryl, and phenyl ring formation with $R^e$ | Phenyl ring formation with $R^d$ |
| RB | H, D, alkyl | RB | H, D, alkyl and phenyl ring formation with $R^e$ | Phenyl ring formation with $R^d$ |

-continued

| $R^a$ | $R^b$ | $R^c$ | $R^d$ | $R^e$ |
|---|---|---|---|---|
| RB | H, D, alkyl | RB | Aryl, heteroaryl, and phenyl ring formation with $R^e$ | Phenyl ring formation with $R^d$ |
| RA-5 | H, D, alkyl | RA-5 | H, D, alkyl and heteroaryl ring formation with $R^e$ | Heteroaryl ring formation with $R^d$ |
| RA-5 | H, D, alkyl | RA-5 | Aryl, heteroaryl, and heteroaryl ring formation with $R^e$ | Heteroaryl ring formation with $R^d$ |
| RA-4 | H, D, alkyl | RA-4 | H, D, alkyl and heteroaryl ring formation with $R^e$ | Heteroaryl ring formation with $R^d$ |
| RA-4 | H, D, alkyl | RA-4 | Aryl, heteroaryl, and heteroaryl ring formation with $R^e$ | Heteroaryl ring formation with $R^d$ |
| RA-4f | H, D, alkyl | RA-4f | H, D, alkyl and heteroaryl ring formation with $R^e$ | Heteroaryl ring formation with $R^d$ |
| RA-4f | H, D, alkyl | RA-4f | Aryl, heteroaryl, and heteroaryl ring formation with $R^e$ | Heteroaryl ring formation with $R^d$ |
| RA-3 | H, D, alkyl | RA-3 | H, D, alkyl and heteroaryl ring formation with $R^e$ | Heteroaryl ring formation with $R^d$ |
| RA-3 | H, D, alkyl | RA-3 | Aryl, heteroaryl, and heteroaryl ring formation with $R^e$ | Heteroaryl ring formation with $R^d$ |
| RB | H, D, alkyl | RB | H, D, alkyl and heteroaryl ring formation with $R^e$ | Heteroaryl ring formation with $R^d$ |
| RB | H, D, alkyl | RB | Aryl, heteroaryl, and heteroaryl ring formation with $R^e$ | Heteroaryl ring formation with $R^d$ |
| RA-5 | H, D, alkyl | RA-5 | H, D, alkyl | $C(Ar')_3$, $Si(Ar')_3$ |
| RA-4 | H, D, alkyl | RA-4 | H, D, alkyl | $C(Ar')_3$, $Si(Ar')_3$ |
| RA-4f | H, D, alkyl | RA-4f | H, D, alkyl | $C(Ar')_3$, $Si(Ar')_3$ |
| RA-3 | H, D, alkyl | RA-3 | H, D, alkyl | $C(Ar')_3$, $Si(Ar')_3$ |
| RB | H, D, alkyl | RB | H, D, alkyl | $C(Ar')_3$, $Si(Ar')_3$ |
| RA-5 | H, D, alkyl | RA-5 | H, D, alkyl and ring formation with $R^e$ | $C(Ar')_3$, $Si(Ar')_3$ |
| RA-4 | H, D, alkyl | RA-4 | H, D, alkyl and ring formation with $R^e$ | $C(Ar')_3$, $Si(Ar')_3$ |
| RA-4f | H, D, alkyl | RA-4f | H, D, alkyl and ring formation with $R^e$ | $C(Ar')_3$, $Si(Ar')_3$ |
| RA-3 | H, D, alkyl | RA-3 | H, D, alkyl and ring formation with $R^e$ | $C(Ar')_3$, $Si(Ar')_3$ |
| RB | H, D, alkyl | RB | H, D, alkyl and ring formation with $R^e$ | $C(Ar')_3$, $Si(Ar')_3$ |
| RA-5 | H, D, alkyl | RA-5 | H, D, alkyl | $N(Ar')_3$, $N(R^1)_3$ |
| RA-4 | H, D, alkyl | RA-4 | H, D, alkyl | $N(Ar')_3$, $N(R^1)_3$ |
| RA-4f | H, D, alkyl | RA-4f | H, D, alkyl | $N(Ar')_3$, $N(R^1)_3$ |
| RA-3 | H, D, alkyl | RA-3 | H, D, alkyl | $N(Ar')_3$, $N(R^1)_3$ |
| RB | H, D, alkyl | RB | H, D, alkyl | $N(Ar')_3$, $N(R^1)_3$ |
| RA-5 | H, D, alkyl | RA-5 | H, D, alkyl and ring formation with $R^e$ | $N(Ar')_3$, $N(R^1)_3$ |
| RA-4 | H, D, alkyl | RA-4 | H, D, alkyl and ring formation with $R^e$ | $N(Ar')_3$, $N(R^1)_3$ |

-continued

| $R^a$ | $R^b$ | $R^c$ | $R^d$ | $R^e$ |
|---|---|---|---|---|
| RA-4f | H, D, alkyl | RA-4f | H, D, alkyl and ring formation with $R^e$ | $N(Ar')_3$, $N(R^1)_3$ |
| RA-3 | H, D, alkyl | RA-3 | H, D, alkyl and ring formation with $R^e$ | $N(Ar')_3$, $N(R^1)_3$ |
| RB | H, D, alkyl | RB | H, D, alkyl and ring formation with $R^e$ | $N(Ar')_3$, $N(R^1)_3$ |
| RA-5 | H, D, alkyl | RA-5 | H, D, alkyl and RA-5 ring formation with $R^e$ | RA-5 ring formation with $R^d$ |
| RA-4 | H, D, alkyl | RA-4 | H, D, alkyl and RA-4 ring formation with $R^e$ | RA-4 ring formation with $R^d$ |
| RA-4f | H, D, alkyl | RA-4f | H, D, alkyl and RA-4f ring formation with $R^e$ | RA-4f ring formation with $R^d$ |
| RA-3 | H, D, alkyl | RA-3 | H, D, alkyl and RA-3 ring formation with $R^e$ | RA-3 ring formation with $R^d$ |
| RB | H, D, alkyl | RB | H, D, alkyl and RB ring formation with $R^e$ | RB ring formation with $R^d$ |
| RA-5 | H, D, alkyl | RA-5 | H, D, alkyl | Ar-1 to Ar-75 |
| RA-4 | H, D, alkyl | RA-4 | H, D, alkyl | Ar-1 to Ar-75 |
| RA-4f | H, D, alkyl | RA-4f | H, D, alkyl | Ar-1 to Ar-75 |
| RA-3 | H, D, alkyl | RA-3 | H, D, alkyl | Ar-1 to Ar-75 |
| RB | H, D, alkyl | RB | H, D, alkyl | Ar-1 to Ar-75 |
| RA-5 | H, D, alkyl | RA-5 | RA-2, RA-2c | RA-2, RA-2c |
| RA-4 | H, D, alkyl | RA-4 | RA-2, RA-2c | RA-2, RA-2c |
| RA-4f | H, D, alkyl | RA-4f | RA-2, RA-2c | RA-2, RA-2c |
| RA-3 | H, D, alkyl | RA-3 | RA-2, RA-2c | RA-2, RA-2c |
| RB | H, D, alkyl | RB | RA-2, RA-2c | RA-2, RA-2c |

In a further configuration of the present invention, preference is given to compounds comprising a structure of formula (I-14), preferably compounds of formula (I-14), where the two $R^a$ radicals form a ring, the two $R^c$ radicals form a ring, and in which the $R^a$, $R^b$, $R^c$, $R^d$ and $R^e$ radicals have the following definitions:

| $R^a$ | all $R^b$ | $R^c$ | $R^d$ | $R^e$ |
|---|---|---|---|---|
| RA-5 | H, D, alkyl | RA-5 | H, D, alkyl | H, D, alkyl |
| RA-4 | H, D, alkyl | RA-4 | H, D, alkyl | H, D, alkyl |
| RA-4f | H, D, alkyl | RA-4f | H, D, alkyl | H, D, alkyl |
| RA-3 | H, D, alkyl | RA-3 | H, D, alkyl | H, D, alkyl |
| RB | H, D, alkyl | RB | H, D, alkyl | H, D, alkyl |
| RA-5 | H, D, alkyl | RA-5 | H, D, alkyl and phenyl ring formation with $R^e$ | Phenyl ring formation with $R^d$ |
| RA-5 | H, D, alkyl | RA-5 | Aryl, heteroaryl, and phenyl ring formation with $R^e$ | Phenyl ring formation with $R^d$ |
| RA-4 | H, D, alkyl | RA-4 | H, D, alkyl and phenyl ring formation with $R^e$ | Phenyl ring formation with $R^d$ |
| RA-4 | H, D, alkyl | RA-4 | Aryl, heteroaryl, and phenyl ring formation with $R^e$ | Phenyl ring formation with $R^d$ |
| RA-4f | H, D, alkyl | RA-4f | H, D, alkyl and phenyl ring formation with $R^e$ | Phenyl ring formation with $R^d$ |
| RA-4f | H, D, alkyl | RA-4f | Aryl, heteroaryl, and phenyl ring formation with $R^e$ | Phenyl ring formation with $R^d$ |

-continued

| $R^a$ | all $R^b$ | $R^c$ | $R^d$ | $R^e$ |
|---|---|---|---|---|
| RA-3 | H, D, alkyl | RA-3 | H, D, alkyl and phenyl ring formation with $R^e$ | Phenyl ring formation with $R^d$ |
| RA-3 | H, D, alkyl | RA-3 | Aryl, heteroaryl, and phenyl ring formation with $R^e$ | Phenyl ring formation with $R^d$ |
| RB | H, D, alkyl | RB | H, D, alkyl and phenyl ring formation with $R^e$ | Phenyl ring formation with $R^d$ |
| RB | H, D, alkyl | RB | Aryl, heteroaryl, and phenyl ring formation with $R^e$ | Phenyl ring formation with $R^d$ |
| RA-5 | H, D, alkyl | RA-5 | H, D, alkyl and heteroaryl ring formation with $R^e$ | Heteroaryl ring formation with $R^d$ |
| RA-5 | H, D, alkyl | RA-5 | Aryl, heteroaryl, and heteroaryl ring formation with $R^e$ | Heteroaryl ring formation with $R^d$ |
| RA-4 | H, D, alkyl | RA-4 | H, D, alkyl and heteroaryl ring formation with $R^e$ | Heteroaryl ring formation with $R^d$ |
| RA-4 | H, D, alkyl | RA-4 | Aryl, heteroaryl, and heteroaryl ring formation with $R^e$ | Heteroaryl ring formation with $R^d$ |
| RA-4f | H, D, alkyl | RA-4f | H, D, alkyl and heteroaryl ring formation with $R^e$ | Heteroaryl ring formation with $R^d$ |
| RA-4f | H, D, alkyl | RA-4f | Aryl, heteroaryl, and heteroaryl ring formation with $R^e$ | Heteroaryl ring formation with $R^d$ |
| RA-3 | H, D, alkyl | RA-3 | H, D, alkyl and heteroaryl ring formation with $R^e$ | Heteroaryl ring formation with $R^d$ |
| RA-3 | H, D, alkyl | RA-3 | Aryl, heteroaryl, and heteroaryl ring formation with $R^e$ | Heteroaryl ring formation with $R^d$ |
| RB | H, D, alkyl | RB | H, D, alkyl and heteroaryl ring formation with $R^e$ | Heteroaryl ring formation with $R^d$ |
| RB | H, D, alkyl | RB | Aryl, heteroaryl, and heteroaryl ring formation with $R^e$ | Heteroaryl ring formation with $R^d$ |
| RA-5 | H, D, alkyl | RA-5 | H, D, alkyl | $C(Ar')_3$, $Si(Ar')_3$ |
| RA-4 | H, D, alkyl | RA-4 | H, D, alkyl | $C(Ar')_3$, $Si(Ar')_3$ |
| RA-4f | H, D, alkyl | RA-4f | H, D, alkyl | $C(Ar')_3$, $Si(Ar')_3$ |
| RA-3 | H, D, alkyl | RA-3 | H, D, alkyl | $C(Ar')_3$, $Si(Ar')_3$ |
| RB | H, D, alkyl | RB | H, D, alkyl | $C(Ar')_3$, $Si(Ar')_3$ |
| RA-5 | H, D, alkyl | RA-5 | H, D, alkyl and ring formation with $R^e$ | $C(Ar')_3$, $Si(Ar')_3$ |
| RA-4 | H, D, alkyl | RA-4 | H, D, alkyl and ring formation with $R^e$ | $C(Ar')_3$, $Si(Ar')_3$ |
| RA-4f | H, D, alkyl | RA-4f | H, D, alkyl and ring formation with $R^e$ | $C(Ar')_3$, $Si(Ar')_3$ |
| RA-3 | H, D, alkyl | RA-3 | H, D, alkyl and ring formation with $R^e$ | $C(Ar')_3$, $Si(Ar')_3$ |
| RB | H, D, alkyl | RB | H, D, alkyl and ring formation with $R^e$ | $C(Ar')_3$, $Si(Ar')_3$ |
| RA-5 | H, D, alkyl | RA-5 | H, D, alkyl | $N(Ar')_3$, $N(R^1)_3$ |
| RA-4 | H, D, alkyl | RA-4 | H, D, alkyl | $N(Ar')_3$, $N(R^1)_3$ |
| RA-4f | H, D, alkyl | RA-4f | H, D, alkyl | $N(Ar')_3$, $N(R^1)_3$ |
| RA-3 | H, D, alkyl | RA-3 | H, D, alkyl | $N(Ar')_3$, $N(R^1)_3$ |
| RB | H, D, alkyl | RB | H, D, alkyl | $N(Ar')_3$, $N(R^1)_3$ |
| RA-5 | H, D, alkyl | RA-5 | H, D, alkyl and ring formation with $R^e$ | $N(Ar')_3$, $N(R^1)_3$ |
| RA-4 | H, D, alkyl | RA-4 | H, D, alkyl and ring formation with $R^e$ | $N(Ar')_3$, $N(R^1)_3$ |
| RA-4f | H, D, alkyl | RA-4f | H, D, alkyl and ring formation with $R^e$ | $N(Ar')_3$, $N(R^1)_3$ |
| RA-3 | H, D, alkyl | RA-3 | H, D, alkyl and ring formation with $R^e$ | $N(Ar')_3$, $N(R^1)_3$ |
| RB | H, D, alkyl | RB | H, D, alkyl and ring formation with $R^e$ | $N(Ar')_3$, $N(R^1)_3$ |
| RA-5 | H, D, alkyl | RA-5 | H, D, alkyl and RA-5 ring formation with $R^e$ | RA-5 ring formation with $R^d$ |
| RA-4 | H, D, alkyl | RA-4 | H, D, alkyl and RA-4 ring formation with $R^e$ | RA-4 ring formation with $R^d$ |
| RA-4f | H, D, alkyl | RA-4f | H, D, alkyl and RA-4f ring formation with $R^e$ | RA-4f ring formation with $R^d$ |
| RA-3 | H, D, alkyl | RA-3 | H, D, alkyl and RA-3 ring formation with $R^e$ | RA-3 ring formation with $R^d$ |
| RB | H, D, alkyl | RB | H, D, alkyl and RB ring formation with $R^e$ | RB ring formation with $R^d$ |
| RA-5 | H, D, alkyl | RA-5 | H, D, alkyl | Ar-1 to Ar-75 |
| RA-4 | H, D, alkyl | RA-4 | H, D, alkyl | Ar-1 to Ar-75 |
| RA-4f | H, D, alkyl | RA-4f | H, D, alkyl | Ar-1 to Ar-75 |
| RA-3 | H, D, alkyl | RA-3 | H, D, alkyl | Ar-1 to Ar-75 |
| RB | H, D, alkyl | RB | H, D, alkyl | Ar-1 to Ar-75 |
| RA-5 | H, D, alkyl | RA-5 | RA-2, RA-2c | RA-2, RA-2c |
| RA-4 | H, D, alkyl | RA-4 | RA-2, RA-2c | RA-2, RA-2c |
| RA-4f | H, D, alkyl | RA-4f | RA-2, RA-2c | RA-2, RA-2c |
| RA-3 | H, D, alkyl | RA-3 | RA-2, RA-2c | RA-2, RA-2c |
| RB | H, D, alkyl | RB | RA-2, RA-2c | RA-2, RA-2c |

In a further configuration of the present invention, preference is given to compounds comprising a structure of formula (I-2), preferably compounds of formula (I-2), where the two $R^a$ radicals form a ring, the two $R^c$ radicals form a ring, where the index I is preferably not more than 3, more preferably 0, 1 or 2 and especially preferably 0 or 1, and in which the $R^a$, $R^b$, $R^c$, $R^d$ and $R^e$ radicals have the following definitions:

| $R^a$ | $R^b$ | $R^c$ | $R^d$ | $R^e$ (only if I is not 0 is at least one radical $R^e$, otherwise all $R^e$ are H) |
|---|---|---|---|---|
| RA-5 | H, D, alkyl | RA-5 | H, D, alkyl | D, alkyl |
| RA-4 | H, D, alkyl | RA-4 | H, D, alkyl | D, alkyl |
| RA-4f | H, D, alkyl | RA-4f | H, D, alkyl | D, alkyl |
| RA-3 | H, D, alkyl | RA-3 | H, D, alkyl | D, alkyl |
| RB | H, D, alkyl | RB | H, D, alkyl | D, alkyl |
| RA-5 | H, D, alkyl | RA-5 | H, D, alkyl | Ar-1 to Ar-75 |
| RA-4 | H, D, alkyl | RA-4 | H, D, alkyl | Ar-1 to Ar-75 |
| RA-4f | H, D, alkyl | RA-4f | H, D, alkyl | Ar-1 to Ar-75 |
| RA-3 | H, D, alkyl | RA-3 | H, D, alkyl | Ar-1 to Ar-75 |
| RB | H, D, alkyl | RB | H, D, alkyl | Ar-1 to Ar-75 |
| RA-5 | H, D, alkyl | RA-5 | Ar-1 to Ar-75 | D, alkyl |
| RA-4 | H, D, alkyl | RA-4 | Ar-1 to Ar-75 | D, alkyl |
| RA-4f | H, D, alkyl | RA-4f | Ar-1 to Ar-75 | D, alkyl |
| RA-3 | H, D, alkyl | RA-3 | Ar-1 to Ar-75 | D, alkyl |
| RB | H, D, alkyl | RB | Ar-1 to Ar-75 | D, alkyl |
| RA-5 | H, D, alkyl | RA-5 | Ar-1 to Ar-75 | Ar-1 to Ar-75 |
| RA-4 | H, D, alkyl | RA-4 | Ar-1 to Ar-75 | Ar-1 to Ar-75 |
| RA-4f | H, D, alkyl | RA-4f | Ar-1 to Ar-75 | Ar-1 to Ar-75 |

-continued

| $R^a$ | $R^b$ | $R^c$ | $R^d$ | $R^e$ (only if I is not 0 is at least one radical $R^e$, otherwise all $R^e$ are H) |
|---|---|---|---|---|
| RA-3 | H, D, alkyl | RA-3 | Ar-1 to Ar-75 | Ar-1 to Ar-75 |
| RB | H, D, alkyl | RB | Ar-1 to Ar-75 | Ar-1 to Ar-75 |
| RA-5 | H, D, alkyl | RA-5 | H, D, alkyl and Ar-1 to Ar-75 | D, alkyl |
| RA-4 | H, D, alkyl | RA-4 | H, D, alkyl and Ar-1 to Ar-75 | D, alkyl |
| RA-4f | H, D, alkyl | RA-4f | H, D, alkyl and Ar-1 to Ar-75 | D, alkyl |
| RA-3 | H, D, alkyl | RA-3 | H, D, alkyl and Ar-1 to Ar-75 | D, alkyl |
| RB | H, D, alkyl | RB | H, D, alkyl and Ar-1 to Ar-75 | D, alkyl |
| RA-5 | H, D, alkyl | RA-5 | H, D, alkyl and Ar-1 to Ar-75 | Ar-1 to Ar-75 |
| RA-4 | H, D, alkyl | RA-4 | H, D, alkyl and Ar-1 to Ar-75 | Ar-1 to Ar-75 |
| RA-4f | H, D, alkyl | RA-4f | H, D, alkyl and Ar-1 to Ar-75 | Ar-1 to Ar-75 |
| RA-3 | H, D, alkyl | RA-3 | H, D, alkyl and Ar-1 to Ar-75 | Ar-1 to Ar-75 |
| RB | H, D, alkyl | RB | H, D, alkyl and Ar-1 to Ar-75 | Ar-1 to Ar-75 |
| RA-5 | H, D, alkyl | RA-5 | H, D, alkyl | $C(Ar')_3$, $Si(Ar')_3$ |
| RA-4 | H, D, alkyl | RA-4 | H, D, alkyl | $C(Ar')_3$, $Si(Ar')_3$ |
| RA-4f | H, D, alkyl | RA-4f | H, D, alkyl | $C(Ar')_3$, $Si(Ar')_3$ |
| RA-3 | H, D, alkyl | RA-3 | H, D, alkyl | $C(Ar')_3$, $Si(Ar')_3$ |
| RB | H, D, alkyl | RB | H, D, alkyl | $C(Ar')_3$, $Si(Ar')_3$ |
| RA-5 | H, D, alkyl | RA-5 | Ar-1 to Ar-75 | $C(Ar')_3$, $Si(Ar')_3$ |
| RA-4 | H, D, alkyl | RA-4 | Ar-1 to Ar-75 | $C(Ar')_3$, $Si(Ar')_3$ |
| RA-4f | H, D, alkyl | RA-4f | Ar-1 to Ar-75 | $C(Ar')_3$, $Si(Ar')_3$ |
| RA-3 | H, D, alkyl | RA-3 | Ar-1 to Ar-75 | $C(Ar')_3$, $Si(Ar')_3$ |
| RB | H, D, alkyl | RB | Ar-1 to Ar-75 | $C(Ar')_3$, $Si(Ar')_3$ |
| RA-5 | H, D, alkyl | RA-5 | H, D, alkyl and Ar-1 to Ar-75 | $C(Ar')_3$, $Si(Ar')_3$ |
| RA-4 | H, D, alkyl | RA-4 | H, D, alkyl and Ar-1 to Ar-75 | $C(Ar')_3$, $Si(Ar')_3$ |
| RA-4f | H, D, alkyl | RA-4f | H, D, alkyl and Ar-1 to Ar-75 | $C(Ar')_3$, $Si(Ar')_3$ |
| RA-3 | H, D, alkyl | RA-3 | H, D, alkyl and Ar-1 to Ar-75 | $C(Ar')_3$, $Si(Ar')_3$ |
| RB | H, D, alkyl | RB | H, D, alkyl and Ar-1 to Ar-75 | $C(Ar')_3$, $Si(Ar')_3$ |
| RA-5 | H, D, alkyl | RA-5 | H, D, alkyl | $N(Ar')_3$, $N(R^1)_3$ |
| RA-4 | H, D, alkyl | RA-4 | H, D, alkyl | $N(Ar')_3$, $N(R^1)_3$ |
| RA-4f | H, D, alkyl | RA-4f | H, D, alkyl | $N(Ar')_3$, $N(R^1)_3$ |
| RA-3 | H, D, alkyl | RA-3 | H, D, alkyl | $N(Ar')_3$, $N(R^1)_3$ |
| RB | H, D, alkyl | RB | H, D, alkyl | $N(Ar')_3$, $N(R^1)_3$ |
| RA-5 | H, D, alkyl | RA-5 | Ar-1 to Ar-75 | $N(Ar')_3$, $N(R^1)_3$ |
| RA-4 | H, D, alkyl | RA-4 | Ar-1 to Ar-75 | $N(Ar')_3$, $N(R^1)_3$ |
| RA-4f | H, D, alkyl | RA-4f | Ar-1 to Ar-75 | $N(Ar')_3$, $N(R^1)_3$ |
| RA-3 | H, D, alkyl | RA-3 | Ar-1 to Ar-75 | $N(Ar')_3$, $N(R^1)_3$ |
| RB | H, D, alkyl | RB | Ar-1 to Ar-75 | $N(Ar')_3$, $N(R^1)_3$ |
| RA-5 | H, D, alkyl | RA-5 | H, D, alkyl and Ar-1 to Ar-75 | $N(Ar')_3$, $N(R^1)_3$ |
| RA-4 | H, D, alkyl | RA-4 | H, D, alkyl and Ar-1 to Ar-75 | $N(Ar')_3$, $N(R^1)_3$ |
| RA-4f | H, D, alkyl | RA-4f | H, D, alkyl and Ar-1 to Ar-75 | $N(Ar')_3$, $N(R^1)_3$ |
| RA-3 | H, D, alkyl | RA-3 | H, D, alkyl and Ar-1 to Ar-75 | $N(Ar')_3$, $N(R^1)_3$ |
| RB | H, D, alkyl | RB | H, D, alkyl and Ar-1 to Ar-75 | $N(Ar')_3$, $N(R^1)_3$ |

In a further configuration of the present invention, preference is given to compounds comprising a structure of formula (I-3), preferably compounds of formula (I-3), where the two $R^a$ radicals form a ring, the two $R^c$ radicals form a ring, where the index m is preferably 0, 1 or 2 and more preferably 0 or 1, and in which $R^b$ is H, D, alkyl and the $R^a$, RC, $R^d$, $R^e$ and $Y^1$ radicals have the following definitions:

| $R^a$ | $R^c$ | $R^d$ | $R^e$ on the phenyl ring (only if m is not 0 is at least one radical $R^e$, otherwise all $R^e$ are H) | $Y^1$ |
|---|---|---|---|---|
| RA-5 | RA-5 | H, D, alkyl | D, alkyl | $C(R^e)_2$ |
| RA-4 | RA-4 | H, D, alkyl | D, alkyl | $C(R^e)_2$ |
| RA-4f | RA-4f | H, D, alkyl | D, alkyl | $C(R^e)_2$ |
| RA-3 | RA-3 | H, D, alkyl | D, alkyl | $C(R^e)_2$ |
| RB | RB | H, D, alkyl | D, alkyl | $C(R^e)_2$ |
| RA-5 | RA-5 | H, D, alkyl | Ar-1 to Ar-75 | $C(R^e)_2$ |
| RA-4 | RA-4 | H, D, alkyl | Ar-1 to Ar-75 | $C(R^e)_2$ |
| RA-4f | RA-4f | H, D, alkyl | Ar-1 to Ar-75 | $C(R^e)_2$ |
| RA-3 | RA-3 | H, D, alkyl | Ar-1 to Ar-75 | $C(R^e)_2$ |
| RB | RB | H, D, alkyl | Ar-1 to Ar-75 | $C(R^e)_2$ |
| RA-5 | RA-5 | Ar-1 to Ar-75 | D, alkyl | $C(R^e)_2$ |
| RA-4 | RA-4 | Ar-1 to Ar-75 | D, alkyl | $C(R^e)_2$ |
| RA-4f | RA-4f | Ar-1 to Ar-75 | D, alkyl | $C(R^e)_2$ |
| RA-3 | RA-3 | Ar-1 to Ar-75 | D, alkyl | $C(R^e)_2$ |
| RB | RB | Ar-1 to Ar-75 | D, alkyl | $C(R^e)_2$ |
| RA-5 | RA-5 | Ar-1 to Ar-75 | Ar-1 to Ar-75 | $C(R^e)_2$ |
| RA-4 | RA-4 | Ar-1 to Ar-75 | Ar-1 to Ar-75 | $C(R^e)_2$ |
| RA-4f | RA-4f | Ar-1 to Ar-75 | Ar-1 to Ar-75 | $C(R^e)_2$ |
| RA-3 | RA-3 | Ar-1 to Ar-75 | Ar-1 to Ar-75 | $C(R^e)_2$ |
| RB | RB | Ar-1 to Ar-75 | Ar-1 to Ar-75 | $C(R^e)_2$ |
| RA-5 | RA-5 | H, D, alkyl | Phenyl ring formation by 2 $R^e$ | $C(R^e)_2$ |
| RA-4 | RA-4 | H, D, alkyl | Phenyl ring formation by 2 $R^e$ | $C(R^e)_2$ |
| RA-4f | RA-4f | H, D, alkyl | Phenyl ring formation by 2 $R^e$ | $C(R^e)_2$ |
| RA-3 | RA-3 | H, D, alkyl | Phenyl ring formation by 2 $R^e$ | $C(R^e)_2$ |
| RB | RB | H, D, alkyl | Phenyl ring formation by 2 $R^e$ | $C(R^e)_2$ |
| RA-5 | RA-5 | Ar-1 to Ar-75 | Phenyl ring formation by 2 $R^e$ | $C(R^e)_2$ |
| RA-4 | RA-4 | Ar-1 to Ar-75 | Phenyl ring formation by 2 $R^e$ | $C(R^e)_2$ |
| RA-4f | RA-4f | Ar-1 to Ar-75 | Phenyl ring formation by 2 $R^e$ | $C(R^e)_2$ |
| RA-3 | RA-3 | Ar-1 to Ar-75 | Phenyl ring formation by 2 $R^e$ | $C(R^e)_2$ |
| RB | RB | Ar-1 to Ar-75 | Phenyl ring formation by 2 $R^e$ | $C(R^e)_2$ |
| RA-5 | RA-5 | H, D, alkyl | $C(Ar')_3$, $Si(Ar')_3$ | $C(R^e)_2$ |
| RA-4 | RA-4 | H, D, alkyl | $C(Ar')_3$, $Si(Ar')_3$ | $C(R^e)_2$ |
| RA-4f | RA-4f | H, D, alkyl | $C(Ar')_3$, $Si(Ar')_3$ | $C(R^e)_2$ |
| RA-3 | RA-3 | H, D, alkyl | $C(Ar')_3$, $Si(Ar')_3$ | $C(R^e)_2$ |
| RE | RB | H, D, alkyl | $C(Ar')_3$, $Si(Ar')_3$ | $C(R^e)_2$ |
| RA-5 | RA-5 | Ar-1 to Ar-75 | $C(Ar')_3$, $Si(Ar')_3$ | $C(R^e)_2$ |
| RA-4 | RA-4 | Ar-1 to Ar-75 | $C(Ar')_3$, $Si(Ar')_3$ | $C(R^e)_2$ |
| RA-4f | RA-4f | Ar-1 to Ar-75 | $C(Ar')_3$, $Si(Ar')_3$ | $C(R^e)_2$ |
| RA-3 | RA-3 | Ar-1 to Ar-75 | $C(Ar')_3$, $Si(Ar')_3$ | $C(R^e)_2$ |
| RB | RB | Ar-1 to Ar-75 | $C(Ar')_3$, $Si(Ar')_3$ | $C(R^e)_2$ |
| RA-5 | RA-5 | H, D, alkyl | $N(Ar')_3$, $N(R^1)_3$ | $C(R^e)_2$ |
| RA-4 | RA-4 | H, D, alkyl | $N(Ar')_3$, $N(R^1)_3$ | $C(R^e)_2$ |
| RA-4f | RA-4f | H, D, alkyl | $N(Ar')_3$, $N(R^1)_3$ | $C(R^e)_2$ |
| RA-3 | RA-3 | H, D, alkyl | $N(Ar')_3$, $N(R^1)_3$ | $C(R^e)_2$ |
| RB | RB | H, D, alkyl | $N(Ar')_3$, $N(R^1)_3$ | $C(R^e)_2$ |
| RA-5 | RA-5 | Ar-1 to Ar-75 | $N(Ar')_3$, $N(R^1)_3$ | $C(R^e)_2$ |
| RA-4 | RA-4 | Ar-1 to Ar-75 | $N(Ar')_3$, $N(R^1)_3$ | $C(R^e)_2$ |
| RA-4f | RA-4f | Ar-1 to Ar-75 | $N(Ar')_3$, $N(R^1)_3$ | $C(R^e)_2$ |
| RA-3 | RA-3 | Ar-1 to Ar-75 | $N(Ar')_3$, $N(R^1)_3$ | $C(R^e)_2$ |
| RB | RB | Ar-1 to Ar-75 | $N(Ar')_3$, $N(R^1)_3$ | $C(R^e)_2$ |
| RA-5 | RA-5 | H, D, alkyl | D, alkyl | O, S |
| RA-4 | RA-4 | H, D, alkyl | D, alkyl | O, S |
| RA-4f | RA-4f | H, D, alkyl | D, alkyl | O, S |
| RA-3 | RA-3 | H, D, alkyl | D, alkyl | O, S |

-continued

| $R^a$ | $R^c$ | $R^d$ | $R^e$ on the phenyl ring (only if m is not 0 is at least one radical $R^e$, otherwise all $R^e$ are H) | $Y^1$ |
|---|---|---|---|---|
| RB | RB | H, D, alkyl | D, alkyl | O, S |
| RA-5 | RA-5 | H, D, alkyl | Ar-1 to Ar-75 | O, S |
| RA-4 | RA-4 | H, D, alkyl | Ar-1 to Ar-75 | O, S |
| RA-4f | RA-4f | H, D, alkyl | Ar-1 to Ar-75 | O, S |
| RA-3 | RA-3 | H, D, alkyl | Ar-1 to Ar-75 | O, S |
| RB | RE | H, D, alkyl | Ar-1 to Ar-75 | O, S |
| RA-5 | RA-5 | Ar-1 to Ar-75 | D, alkyl | O, S |
| RA-4 | RA-4 | Ar-1 to Ar-75 | D, alkyl | O, S |
| RA-4f | RA-4f | Ar-1 to Ar-75 | D, alkyl | O, S |
| RA-3 | RA-3 | Ar-1 to Ar-75 | D, alkyl | O, S |
| RB | RB | Ar-1 to Ar-75 | D, alkyl | O, S |
| RA-5 | RA-5 | Ar-1 to Ar-75 | Ar-1 to Ar-75 | O, S |
| RA-4 | RA-4 | Ar-1 to Ar-75 | Ar-1 to Ar-75 | O, S |
| RA-4f | RA-4f | Ar-1 to Ar-75 | Ar-1 to Ar-75 | O, S |
| RA-3 | RA-3 | Ar-1 to Ar-75 | Ar-1 to Ar-75 | O, S |
| RE | RE | Ar-1 to Ar-75 | Ar-1 to Ar-75 | O, S |
| RA-5 | RA-5 | H, D, alkyl | Phenyl ring formation by 2 $R^e$ | O, S |
| RA-4 | RA-4 | H, D, alkyl | Phenyl ring formation by 2 $R^e$ | O, S |
| RA-4f | RA-4f | H, D, alkyl | Phenyl ring formation by 2 $R^e$ | O, S |
| RA-3 | RA-3 | H, D, alkyl | Phenyl ring formation by 2 $R^e$ | O, S |
| RB | RB | H, D, alkyl | Phenyl ring formation by 2 $R^e$ | O, S |
| RA-5 | RA-5 | Ar-1 to Ar-75 | Phenyl ring formation by 2 $R^e$ | O, S |
| RA-4 | RA-4 | Ar-1 to Ar-75 | Phenyl ring formation by 2 $R^e$ | O, S |
| RA-4f | RA-4f | Ar-1 to Ar-75 | Phenyl ring formation by 2 $R^e$ | O, S |
| RA-3 | RA-3 | Ar-1 to Ar-75 | Phenyl ring formation by 2 $R^e$ | O, S |
| RB | RB | Ar-1 to Ar-75 | Phenyl ring formation by 2 $R^e$ | O, S |
| RA-5 | RA-5 | H, D, alkyl | $C(Ar')_3$, $Si(Ar')_3$ | O, S |
| RA-4 | RA-4 | H, D, alkyl | $C(Ar')_3$, $Si(Ar')_3$ | O, S |
| RA-4f | RA-4f | H, D, alkyl | $C(Ar')_3$, $Si(Ar')_3$ | O, S |
| RA-3 | RA-3 | H, D, alkyl | $C(Ar')_3$, $Si(Ar')_3$ | O, S |
| RB | RB | H, D, alkyl | $C(Ar')_3$, $Si(Ar')_3$ | O, S |
| RA-5 | RA-5 | Ar-1 to Ar-75 | $C(Ar')_3$, $Si(Ar')_3$ | O, S |
| RA-4 | RA-4 | Ar-1 to Ar-75 | $C(Ar')_3$, $Si(Ar')_3$ | O, S |
| RA-4f | RA-4f | Ar-1 to Ar-75 | $C(Ar')_3$, $Si(Ar')_3$ | O, S |
| RA-3 | RA-3 | Ar-1 to Ar-75 | $C(Ar')_3$, $Si(Ar')_3$ | O, S |
| RB | RB | Ar-1 to Ar-75 | $C(Ar')_3$, $Si(Ar')_3$ | O, S |
| RA-5 | RA-5 | H, D, alkyl | $N(Ar')_3$, $N(R^1)_3$ | O, S |
| RA-4 | RA-4 | H, D, alkyl | $N(Ar')_3$, $N(R^1)_3$ | O, S |
| RA-4f | RA-4f | H, D, alkyl | $N(Ar')_3$, $N(R^1)_3$ | O, S |
| RA-3 | RA-3 | H, D, alkyl | $N(Ar')_3$, $N(R^1)_3$ | O, S |
| RB | RB | H, D, alkyl | $N(Ar')_3$, $N(R^1)_3$ | O, S |
| RA-5 | RA-5 | Ar-1 to Ar-75 | $N(Ar')_3$, $N(R^1)_3$ | O, S |
| RA-4 | RA-4 | Ar-1 to Ar-75 | $N(Ar')_3$, $N(R^1)_3$ | O, S |
| RA-4f | RA-4f | Ar-1 to Ar-75 | $N(Ar')_3$, $N(R^1)_3$ | O, S |
| RA-3 | RA-3 | Ar-1 to Ar-75 | $N(Ar')_3$, $N(R^1)_3$ | O, S |
| RB | RB | Ar-1 to Ar-75 | $N(Ar')_3$, $N(R^1)_3$ | O, S |
| RA-5 | RA-5 | H, D, alkyl | D, alkyl | N(Ar') |
| RA-4 | RA-4 | H, D, alkyl | D, alkyl | N(Ar') |
| RA-4f | RA-4f | H, D, alkyl | D, alkyl | N(Ar') |
| RA-3 | RA-3 | H, D, alkyl | D, alkyl | N(Ar') |
| RB | RB | H, D, alkyl | D, alkyl | N(Ar') |
| RA-5 | RA-5 | H, D, alkyl | Ar-1 to Ar-75 | N(Ar') |

-continued

| $R^a$ | $R^c$ | $R^d$ | $R^e$ on the phenyl ring (only if m is not 0 is at least one radical $R^e$, otherwise all $R^e$ are H) | $Y^1$ |
|---|---|---|---|---|
| RA-4 | RA-4 | H, D, alkyl | Ar-1 to Ar-75 | N(Ar') |
| RA-4f | RA-4f | H, D, alkyl | Ar-1 to Ar-75 | N(Ar') |
| RA-3 | RA-3 | H, D, alkyl | Ar-1 to Ar-75 | N(Ar') |
| RB | RB | H, D, alkyl | Ar-1 to Ar-75 | N(Ar') |
| RA-5 | RA-5 | Ar-1 to Ar-75 | D, alkyl | N(Ar') |
| RA-4 | RA-4 | Ar-1 to Ar-75 | D, alkyl | N(Ar') |
| RA-4f | RA-4f | Ar-1 to Ar-75 | D, alkyl | N(Ar') |
| RA-3 | RA-3 | Ar-1 to Ar-75 | D, alkyl | N(Ar') |
| RB | RB | Ar-1 to Ar-75 | D, alkyl | N(Ar') |
| RA-5 | RA-5 | Ar-1 to Ar-75 | Ar-1 to Ar-75 | N(Ar') |
| RA-4 | RA-4 | Ar-1 to Ar-75 | Ar-1 to Ar-75 | N(Ar') |
| RA-4f | RA-4f | Ar-1 to Ar-75 | Ar-1 to Ar-75 | N(Ar') |
| RA-3 | RA-3 | Ar-1 to Ar-75 | Ar-1 to Ar-75 | N(Ar') |
| RB | RB | Ar-1 to Ar-75 | Ar-1 to Ar-75 | N(Ar') |
| RA-5 | RA-5 | H, D, alkyl | Phenyl ring formation by 2 $R^e$ | N(Ar') |
| RA-4 | RA-4 | H, D, alkyl | Phenyl ring formation by 2 $R^e$ | N(Ar') |
| RA-4f | RA-4f | H, D, alkyl | Phenyl ring formation by 2 $R^e$ | N(Ar') |
| RA-3 | RA-3 | H, D, alkyl | Phenyl ring formation by 2 $R^e$ | N(Ar') |
| RB | RB | H, D, alkyl | Phenyl ring formation by 2 $R^e$ | N(Ar') |
| RA-5 | RA-5 | Ar-1 to Ar-75 | Phenyl ring formation by 2 $R^e$ | N(Ar') |
| RA-4 | RA-4 | Ar-1 to Ar-75 | Phenyl ring formation by 2 $R^e$ | N(Ar') |
| RA-4f | RA-4f | Ar-1 to Ar-75 | Phenyl ring formation by 2 $R^e$ | N(Ar') |
| RA-3 | RA-3 | Ar-1 to Ar-75 | Phenyl ring formation by 2 $R^e$ | N(Ar') |
| RB | RB | Ar-1 to Ar-75 | Phenyl ring formation by 2 $R^e$ | N(Ar') |
| RA-5 | RA-5 | H, D, alkyl | $C(Ar')_3$, $Si(Ar')_3$ | N(Ar') |
| RA-4 | RA-4 | H, D, alkyl | $C(Ar')_3$, $Si(Ar')_3$ | N(Ar') |
| RA-4f | RA-4f | H, D, alkyl | $C(Ar')_3$, $Si(Ar')_3$ | N(Ar') |
| RA-3 | RA-3 | H, D, alkyl | $C(Ar')_3$, $Si(Ar')_3$ | N(Ar') |
| RB | RB | H, D, alkyl | $C(Ar')_3$, $Si(Ar')_3$ | N(Ar') |
| RA-5 | RA-5 | Ar-1 to Ar-75 | $C(Ar')_3$, $Si(Ar')_3$ | N(Ar') |
| RA-4 | RA-4 | Ar-1 to Ar-75 | $C(Ar')_3$, $Si(Ar')_3$ | N(Ar') |
| RA-4f | RA-4f | Ar-1 to Ar-75 | $C(Ar')_3$, $Si(Ar')_3$ | N(Ar') |
| RA-3 | RA-3 | Ar-1 to Ar-75 | $C(Ar')_3$, $Si(Ar')_3$ | N(Ar') |
| RB | RB | Ar-1 to Ar-75 | $C(Ar')_3$, $Si(Ar')_3$ | N(Ar') |
| RA-5 | RA-5 | H, D, alkyl | $N(Ar')_3$, $N(R^1)_3$ | N(Ar') |
| RA-4 | RA-4 | H, D, alkyl | $N(Ar')_3$, $N(R^1)_3$ | N(Ar') |
| RA-4f | RA-4f | H, D, alkyl | $N(Ar')_3$, $N(R^1)_3$ | N(Ar') |
| RA-3 | RA-3 | H, D, alkyl | $N(Ar')_3$, $N(R^1)_3$ | N(Ar') |
| RB | RB | H, D, alkyl | $N(Ar')_3$, $N(R^1)_3$ | N(Ar') |
| RA-5 | RA-5 | Ar-1 to Ar-75 | $N(Ar')_3$, $N(R^1)_3$ | N(Ar') |
| RA-4 | RA-4 | Ar-1 to Ar-75 | $N(Ar')_3$, $N(R^1)_3$ | N(Ar') |
| RA-4f | RA-4f | Ar-1 to Ar-75 | $N(Ar')_3$, $N(R^1)_3$ | N(Ar') |
| RA-3 | RA-3 | Ar-1 to Ar-75 | $N(Ar')_3$, $N(R^1)_3$ | N(Ar') |
| RB | RB | Ar-1 to Ar-75 | $N(Ar')_3$, $N(R^1)_3$ | N(Ar') |
| RA-5 | RA-5 | H, D, alkyl | D, alkyl | $(R^e)_2C—C(R^e)_2$, $(R^e)C=C(R^e)$ |
| RA-4 | RA-4 | H, D, alkyl | D, alkyl | $(R^e)_2C—C(R^e)_2$, $(R^e)C=C(R^e)$ |
| RA-4f | RA-4f | H, D, alkyl | D, alkyl | $(R^e)_2C—C(R^e)_2$, $(R^e)C=C(R^e)$ |
| RA-3 | RA-3 | H, D, alkyl | D, alkyl | $(R^e)_2C—C(R^e)_2$, $(R^e)C=C(R^e)$ |

-continued

| $R^a$ | $R^c$ | $R^d$ | $R^e$ on the phenyl ring (only if m is not 0 is at least one radical $R^e$, otherwise all $R^e$ are H) | $Y^1$ |
|---|---|---|---|---|
| RB | RB | H, D, alkyl | D, alkyl | $(R^e)_2C-C(R^e)_2$, $(R^e)C=C(R^e)$ |
| RA-5 | RA-5 | H, D, alkyl | Ar-1 to Ar-75 | $(R^e)_2C-C(R^e)_2$, $(R^e)C=C(R^e)$ |
| RA-4 | RA-4 | H, D, alkyl | Ar-1 to Ar-75 | $(R^e)_2C-C(R^e)_2$, $(R^e)C=C(R^e)$ |
| RA-4f | RA-4f | H, D, alkyl | Ar-1 to Ar-75 | $(R^e)_2C-C(R^e)_2$, $(R^e)C=C(R^e)$ |
| RA-3 | RA-3 | H, D, alkyl | Ar-1 to Ar-75 | $(R^e)_2C-C(R^e)_2$, $(R^e)C=C(R^e)$ |
| RB | RB | H, D, alkyl | Ar-1 to Ar-75 | $(R^e)_2C-C(R^e)_2$, $(R^e)C=C(R^e)$ |
| RA-5 | RA-5 | Ar-1 to Ar-75 | D, alkyl | $(R^e)_2C-C(R^e)_2$, $(R^e)C=C(R^e)$ |
| RA-4 | RA-4 | Ar-1 to Ar-75 | D, alkyl | $(R^e)_2C-C(R^e)_2$, $(R^e)C=C(R^e)$ |
| RA-4f | RA-4f | Ar-1 to Ar-75 | D, alkyl | $(R^e)_2C-C(R^e)_2$, $(R^e)C=C(R^e)$ |
| RA-3 | RA-3 | Ar-1 to Ar-75 | D, alkyl | $(R^e)_2C-C(R^e)_2$, $(R^e)C=C(R^e)$ |
| RB | RB | Ar-1 to Ar-75 | D, alkyl | $(R^e)_2C-C(R^e)_2$, $(R^e)C=C(R^e)$ |
| RA-5 | RA-5 | Ar-1 to Ar-75 | Ar-1 to Ar-75 | $(R^e)_2C-C(R^e)_2$, $(R^e)C=C(R^e)$ |
| RA-4 | RA-4 | Ar-1 to Ar-75 | Ar-1 to Ar-75 | $(R^e)_2C-C(R^e)_2$, $(R^e)C=C(R^e)$ |
| RA-4f | RA-4f | Ar-1 to Ar-75 | Ar-1 to Ar-75 | $(R^e)_2C-C(R^e)_2$, $(R^e)C=C(R^e)$ |
| RA-3 | RA-3 | Ar-1 to Ar-75 | Ar-1 to Ar-75 | $(R^e)_2C-C(R^e)_2$, $(R^e)C=C(R^e)$ |
| RB | RB | Ar-1 to Ar-75 | Ar-1 to Ar-75 | $(R^e)_2C-C(R^e)_2$, $(R^e)C=C(R^e)$ |
| RA-5 | RA-5 | H, D, alkyl | Phenyl ring formation by 2 $R^e$ | $(R^e)_2C-C(R^e)_2$, $(R^e)C=C(R^e)$ |
| RA-4 | RA-4 | H, D, alkyl | Phenyl ring formation by 2 $R^e$ | $(R^e)_2C-C(R^e)_2$, $(R^e)C=C(R^e)$ |
| RA-4f | RA-4f | H, D, alkyl | Phenyl ring formation by 2 $R^e$ | $(R^e)_2C-C(R^e)_2$, $(R^e)C=C(R^e)$ |
| RA-3 | RA-3 | H, D, alkyl | Phenyl ring formation by 2 $R^e$ | $(R^e)_2C-C(R^e)_2$, $(R^e)C=C(R^e)$ |
| RB | RB | H, D, alkyl | Phenyl ring formation by 2 $R^e$ | $(R^e)_2C-C(R^e)_2$, $(R^e)C=C(R^e)$ |
| RA-5 | RA-5 | Ar-1 to Ar-75 | Phenyl ring formation by 2 $R^e$ | $(R^e)_2C-C(R^e)_2$, $(R^e)C=C(R^e)$ |
| RA-4 | RA-4 | Ar-1 to Ar-75 | Phenyl ring formation by 2 $R^e$ | $(R^e)_2C-C(R^e)_2$, $(R^e)C=C(R^e)$ |
| RA-4f | RA-4f | Ar-1 to Ar-75 | Phenyl ring formation by 2 $R^e$ | $(R^e)_2C-C(R^e)_2$, $(R^e)C=C(R^e)$ |
| RA-3 | RA-3 | Ar-1 to Ar-75 | Phenyl ring formation by 2 $R^e$ | $(R^e)_2C-C(R^e)_2$, $(R^e)C=C(R^e)$ |
| RB | RB | Ar-1 to Ar-75 | Phenyl ring formation by 2 $R^e$ | $(R^e)_2C-C(R^e)_2$, $(R^e)C=C(R^e)$ |
| RA-5 | RA-5 | H, D, alkyl | $C(Ar')_3$, $Si(Ar')_3$ | $(R^e)_2C-C(R^e)_2$, $(R^e)C=C(R^e)$ |
| RA-4 | RA-4 | H, D, alkyl | $C(Ar')_3$, $Si(Ar')_3$ | $(R^e)_2C-C(R^e)_2$, $(R^e)C=C(R^e)$ |
| RA-4f | RA-4f | H, D, alkyl | $C(Ar')_3$, $Si(Ar')_3$ | $(R^e)_2C-C(R^e)_2$, $(R^e)C=C(R^e)$ |
| RA-3 | RA-3 | H, D, alkyl | $C(Ar')_3$, $Si(Ar')_3$ | $(R^e)_2C-C(R^e)_2$, $(R^e)C=C(R^e)$ |
| RB | RB | H, D, alkyl | $C(Ar')_3$, $Si(Ar')_3$ | $(R^e)_2C-C(R^e)_2$, $(R^e)C=C(R^e)$ |

-continued

| $R^a$ | $R^c$ | $R^d$ | $R^e$ on the phenyl ring (only if m is not 0 is at least one radical $R^e$, otherwise all $R^e$ are H) | $Y^1$ |
|---|---|---|---|---|
| RA-5 | RA-5 | Ar-1 to Ar-75 | $C(Ar')_3$, $Si(Ar')_3$ | $(R^e)_2C-C(R^e)_2$, $(R^e)C=C(R^e)$ |
| RA-4 | RA-4 | Ar-1 to Ar-75 | $C(Ar')_3$, $Si(Ar')_3$ | $(R^e)_2C-C(R^e)_2$, $(R^e)C=C(R^e)$ |
| RA-4f | RA-4f | Ar-1 to Ar-75 | $C(Ar')_3$, $Si(Ar')_3$ | $(R^e)_2C-C(R^e)_2$, $(R^e)C=C(R^e)$ |
| RA-3 | RA-3 | Ar-1 to Ar-75 | $C(Ar')_3$, $Si(Ar')_3$ | $(R^e)_2C-C(R^e)_2$, $(R^e)C=C(R^e)$ |
| RB | RB | Ar-1 to Ar-75 | $C(Ar')_3$, $Si(Ar')_3$ | $(R^e)_2C-C(R^e)_2$, $(R^e)C=C(R^e)$ |
| RA-5 | RA-5 | H, D, alkyl | $N(Ar')_3$, $N(R^1)_3$ | $(R^e)_2C-C(R^e)_2$, $(R^e)C=C(R^e)$ |
| RA-4 | RA-4 | H, D, alkyl | $N(Ar')_3$, $N(R^1)_3$ | $(R^e)_2C-C(R^e)_2$, $(R^e)C=C(R^e)$ |
| RA-4f | RA-4f | H, D, alkyl | $N(Ar')_3$, $N(R^1)_3$ | $(R^e)_2C-C(R^e)_2$, $(R^e)C=C(R^e)$ |
| RA-3 | RA-3 | H, D, alkyl | $N(Ar')_3$, $N(R^1)_3$ | $(R^e)_2C-C(R^e)_2$, $(R^e)C=C(R^e)$ |
| RB | RB | H, D, alkyl | $N(Ar')_3$, $N(R^1)_3$ | $(R^e)_2C-C(R^e)_2$, $(R^e)C=C(R^e)$ |
| RA-5 | RA-5 | Ar-1 to Ar-75 | $N(Ar')_3$, $N(R^1)_3$ | $(R^e)_2C-C(R^e)_2$, $(R^e)C=C(R^e)$ |
| RA-4 | RA-4 | Ar-1 to Ar-75 | $N(Ar')_3$, $N(R^1)_3$ | $(R^e)_2C-C(R^e)_2$, $(R^e)C=C(R^e)$ |
| RA-4f | RA-4f | Ar-1 to Ar-75 | $N(Ar')_3$, $N(R^1)_3$ | $(R^e)_2C-C(R^e)_2$, $(R^e)C=C(R^e)$ |
| RA-3 | RA-3 | Ar-1 to Ar-75 | $N(Ar')_3$, $N(R^1)_3$ | $(R^e)_2C-C(R^e)_2$, $(R^e)C=C(R^e)$ |
| RB | RB | Ar-1 to Ar-75 | $N(Ar')_3$, $N(R^1)_3$ | $(R^e)_2C-C(R^e)_2$, $(R^e)C=C(R^e)$ |

In the above tables, the radicals specified in the column under the $R^e$ group are the substituents on the phenyl ring of the base skeleton which is likewise substituted by the $R^d$ radical mentioned (see, for example, formula (I-1)), or are the substituents on the phenyl ring that binds to the phenyl ring of the base skeleton which is likewise substituted by the $R^d$ radical specified (see, for example, formula (I-2) and (I-3)). In the $C(R^e)_2$ group, the $R^e$ radical is especially the groups detailed above, where $R^e$ in the $C(R^e)_2$ group is preferably the same or different at each instance and is a linear alkyl group having 1 to 10 carbon atoms or a branched or cyclic alkyl group having 3 to 10 carbon atoms or an aromatic or heteroaromatic ring system having 5 to 24, preferably 5 to 13, aromatic ring atoms, which may also be substituted by one or more $R^1$ radicals. Most preferably, $R^e$ is a methyl group or a phenyl group. It is also possible here for the $R^e$ radicals to form a ring system with one another, which leads to a spiro system. In the $(R^e)_2C-C(R^e)_2$, $(R^e)C=C(R^e)$ groups, the $R^e$ radical is especially the groups detailed above, where $R^e$ in $(R^e)_2C-C(R^e)_2$, $(R^e)C=C(R^e)$ groups is preferably H, $C_1$ to $C_4$-alkyl, or an aryl or heteroaryl group having 5 to 13 carbon atoms, where the aryl or heteroaryl group may be linked. In this case, it is possible for two $R^e$ groups in the $(R^e)_2C-C(R^e)_2$ or $(R^e)C=C(R^e)$ group to form a fused ring system.

In a further configuration of the present invention, preference is given to compounds comprising a structure of formula (I-4), preferably compounds of formula (I-4), where the two $R^a$ radicals form a ring, the two $R^c$ radicals form a ring, where the index n is preferably 0, 1 or 2 and more preferably 0 or 1, and in which the $R^a$, $R^b$, $R^c$, $R^e$ and $Y^1$ radicals have the following definitions:

| $R^a$ | $R^b$ | $R^c$ | $R^e$ on the phenyl ring (only if m is not 0 is at least one radical $R^e$, otherwise all $R^e$ are H) | $Y^1$ |
|---|---|---|---|---|
| RA-5 | H, D, alkyl | RA-5 | D, alkyl | $C(R^e)_2$ |
| RA-4 | H, D, alkyl | RA-4 | D, alkyl | $C(R^e)_2$ |
| RA-4f | H, D, alkyl | RA-4f | D, alkyl | $C(R^e)_2$ |
| RA-3 | H, D, alkyl | RA-3 | D, alkyl | $C(R^e)_2$ |
| RB | H, D, alkyl | RB | D, alkyl | $C(R^e)_2$ |
| RA-5 | H, D, alkyl | RA-5 | Ar-1 to Ar-75 | $C(R^e)_2$ |
| RA-4 | H, D, alkyl | RA-4 | Ar-1 to Ar-75 | $C(R^e)_2$ |
| RA-4f | H, D, alkyl | RA-4f | Ar-1 to Ar-75 | $C(R^e)_2$ |
| RA-3 | H, D, alkyl | RA-3 | Ar-1 to Ar-75 | $C(R^e)_2$ |
| RB | H, D, alkyl | RB | Ar-1 to Ar-75 | $C(R^e)_2$ |
| RA-5 | H, D, alkyl | RA-5 | Phenyl ring formation by 2 $R^e$ | $C(R^e)_2$ |
| RA-4 | H, D, alkyl | RA-4 | Phenyl ring formation by 2 $R^e$ | $C(R^e)_2$ |
| RA-4f | H, D, alkyl | RA-4f | Phenyl ring formation by 2 $R^e$ | $C(R^e)_2$ |
| RA-3 | H, D, alkyl | RA-3 | Phenyl ring formation by 2 $R^e$ | $C(R^e)_2$ |
| RB | H, D, alkyl | RB | Phenyl ring formation by 2 $R^e$ | $C(R^e)_2$ |
| RA-5 | H, D, alkyl | RA-5 | $C(Ar')_3$, $Si(Ar')_3$ | $C(R^e)_2$ |
| RA-4 | H, D, alkyl | RA-4 | $C(Ar')_3$, $Si(Ar')_3$ | $C(R^e)_2$ |
| RA-4f | H, D, alkyl | RA-4f | $C(Ar')_3$, $Si(Ar')_3$ | $C(R^e)_2$ |
| RA-3 | H, D, alkyl | RA-3 | $C(Ar')_3$, $Si(Ar')_3$ | $C(R^e)_2$ |
| RB | H, D, alkyl | RB | $C(Ar')_3$, $Si(Ar')_3$ | $C(R^e)_2$ |
| RA-5 | H, D, alkyl | RA-5 | $N(Ar')_3$, $N(R^1)_3$ | $C(R^e)_2$ |
| RA-4 | H, D, alkyl | RA-4 | $N(Ar')_3$, $N(R^1)_3$ | $C(R^e)_2$ |
| RA-4f | H, D, alkyl | RA-4f | $N(Ar')_3$, $N(R^1)_3$ | $C(R^e)_2$ |
| RA-3 | H, D, alkyl | RA-3 | $N(Ar')_3$, $N(R^1)_3$ | $C(R^e)_2$ |
| RB | H, D, alkyl | RB | $N(Ar')_3$, $N(R^1)_3$ | $C(R^e)_2$ |
| RA-5 | H, D, alkyl | RA-5 | D, alkyl | $(R^e)_2C{-}C(R^e)_2$, $(R^e)C{=}C(R^e)$ |
| RA-4 | H, D, alkyl | RA-4 | D, alkyl | $(R^e)_2C{-}C(R^e)_2$, $(R^e)C{=}C(R^e)$ |
| RA-4f | H, D, alkyl | RA-4f | D, alkyl | $(R^e)_2C{-}C(R^e)_2$, $(R^e)C{=}C(R^e)$ |
| RA-3 | H, D, alkyl | RA-3 | D, alkyl | $(R^e)_2C{-}C(R^e)_2$, $(R^e)C{=}C(R^e)$ |
| RB | H, D, alkyl | RB | D, alkyl | $(R^e)_2C{-}C(R^e)_2$, $(R^e)C{=}C(R^e)$ |
| RA-5 | H, D, alkyl | RA-5 | Ar-1 to Ar-75 | $(R^e)_2C{-}C(R^e)_2$, $(R^e)C{=}C(R^e)$ |
| RA-4 | H, D, alkyl | RA-4 | Ar-1 to Ar-75 | $(R^e)_2C{-}C(R^e)_2$, $(R^e)C{=}C(R^e)$ |
| RA-4f | H, D, alkyl | RA-4f | Ar-1 to Ar-75 | $(R^e)_2C{-}C(R^e)_2$, $(R^e)C{=}C(R^e)$ |
| RA-3 | H, D, alkyl | RA-3 | Ar-1 to Ar-75 | $(R^e)_2C{-}C(R^e)_2$, $(R^e)C{=}C(R^e)$ |
| RB | H, D, alkyl | RB | Ar-1 to Ar-75 | $(R^e)_2C{-}C(R^e)_2$, $(R^e)C{=}C(R^e)$ |
| RA-5 | H, D, alkyl | RA-5 | Phenyl ring formation by 2 $R^e$ | $(R^e)_2C{-}C(R^e)_2$, $(R^e)C{=}C(R^e)$ |
| RA-4 | H, D, alkyl | RA-4 | Phenyl ring formation by 2 $R^e$ | $(R^e)_2C{-}C(R^e)_2$, $(R^e)C{=}C(R^e)$ |
| RA-4f | H, D, alkyl | RA-4f | Phenyl ring formation by 2 $R^e$ | $(R^e)_2C{-}C(R^e)_2$, $(R^e)C{=}C(R^e)$ |
| RA-3 | H, D, alkyl | RA-3 | Phenyl ring formation by 2 $R^e$ | $(R^e)_2C{-}C(R^e)_2$, $(R^e)C{=}C(R^e)$ |
| RB | H, D, alkyl | RB | Phenyl ring formation by 2 $R^e$ | $(R^e)_2C{-}C(R^e)_2$, $(R^e)C{=}C(R^e)$ |
| RA-5 | H, D, alkyl | RA-5 | $C(Ar')_3$, $Si(Ar')_3$ | $(R^e)_2C{-}C(R^e)_2$, $(R^e)C{=}C(R^e)$ |
| RA-4 | H, D, alkyl | RA-4 | $C(Ar')_3$, $Si(Ar')_3$ | $(R^e)_2C{-}C(R^e)_2$, $(R^e)C{=}C(R^e)$ |

-continued

| $R^a$ | $R^b$ | $R^c$ | $R^e$ on the phenyl ring (only if m is not 0 is at least one radical $R^e$, otherwise all $R^e$ are H) | $Y^1$ |
|---|---|---|---|---|
| RA-4f | H, D, alkyl | RA-4f | $C(Ar')_3$, $Si(Ar')_3$ | $(R^e)_2C{-}C(R^e)_2$, $(R^e)C{=}C(R^e)$ |
| RA-3 | H, D, alkyl | RA-3 | $C(Ar')_3$, $Si(Ar')_3$ | $(R^e)_2C{-}C(R^e)_2$, $(R^e)C{=}C(R^e)$ |
| RB | H, D, alkyl | RB | $C(Ar')_3$, $Si(Ar')_3$ | $(R^e)_2C{-}C(R^e)_2$, $(R^e)C{=}C(R^e)$ |
| RA-5 | H, D, alkyl | RA-5 | $N(Ar')_3$, $N(R^1)_3$ | $(R^e)_2C{-}C(R^e)_2$, $(R^e)C{=}C(R^e)$ |
| RA-4 | H, D, alkyl | RA-4 | $N(Ar')_3$, $N(R^1)_3$ | $(R^e)_2C{-}C(R^e)_2$, $(R^e)C{=}C(R^e)$ |
| RA-4f | H, D, alkyl | RA-4f | $N(Ar')_3$, $N(R^1)_3$ | $(R^e)_2C{-}C(R^e)_2$, $(R^e)C{=}C(R^e)$ |
| RA-3 | H, D, alkyl | RA-3 | $N(Ar')_3$, $N(R^1)_3$ | $(R^e)_2C{-}C(R^e)_2$, $(R^e)C{=}C(R^e)$ |
| RB | H, D, alkyl | RB | $N(Ar')_3$, $N(R^1)_3$ | $(R^e)_2C{-}C(R^e)_2$, $(R^e)C{=}C(R^e)$ |
| RA-5 | H, D, alkyl | RA-5 | D, alkyl | O, S |
| RA-4 | H, D, alkyl | RA-4 | D, alkyl | O, S |
| RA-4f | H, D, alkyl | RA-4f | D, alkyl | O, S |
| RA-3 | H, D, alkyl | RA-3 | D, alkyl | O, S |
| RB | H, D, alkyl | RB | D, alkyl | O, S |
| RA-5 | H, D, alkyl | RA-5 | Ar-1 to Ar-75 | O, S |
| RA-4 | H, D, alkyl | RA-4 | Ar-1 to Ar-75 | O, S |
| RA-4f | H, D, alkyl | RA-4f | Ar-1 to Ar-75 | O, S |
| RA-3 | H, D, alkyl | RA-3 | Ar-1 to Ar-75 | O, S |
| RB | H, D, alkyl | RE | Ar-1 to Ar-75 | O, S |
| RA-5 | H, D, alkyl | RA-5 | Phenyl ring formation by 2 $R^e$ | O, S |
| RA-4 | H, D, alkyl | RA-4 | Phenyl ring formation by 2 $R^e$ | O, S |
| RA-4f | H, D, alkyl | RA-4f | Phenyl ring formation by 2 $R^e$ | O, S |
| RA-3 | H, D, alkyl | RA-3 | Phenyl ring formation by 2 $R^e$ | O, S |
| RB | H, D, alkyl | RB | Phenyl ring formation by 2 $R^e$ | O, S |
| RA-5 | H, D, alkyl | RA-5 | $C(Ar')_3$, $Si(Ar')_3$ | O, S |
| RA-4 | H, D, alkyl | RA-4 | $C(Ar')_3$, $Si(Ar')_3$ | O, S |
| RA-4f | H, D, alkyl | RA-4f | $C(Ar')_3$, $Si(Ar')_3$ | O, S |
| RA-3 | H, D, alkyl | RA-3 | $C(Ar')_3$, $Si(Ar')_3$ | O, S |
| RB | H, D, alkyl | RB | $C(Ar')_3$, $Si(Ar')_3$ | O, S |
| RA-5 | H, D, alkyl | RA-5 | $N(Ar')_3$, $N(R^1)_3$ | O, S |
| RA-4 | H, D, alkyl | RA-4 | $N(Ar')_3$, $N(R^1)_3$ | O, S |
| RA-4f | H, D, alkyl | RA-4f | $N(Ar')_3$, $N(R^1)_3$ | O, S |
| RA-3 | H, D, alkyl | RA-3 | $N(Ar')_3$, $N(R^1)_3$ | O, S |
| RB | H, D, alkyl | RB | $N(Ar')_3$, $N(R^1)_3$ | O, S |
| RA-5 | H, D, alkyl | RA-5 | D, alkyl | O, S and $C(R^e)_2$ |
| RA-4 | H, D, alkyl | RA-4 | D, alkyl | O, S and $C(R^e)_2$ |
| RA-4f | H, D, alkyl | RA-4f | D, alkyl | O, S and $C(R^e)_2$ |
| RA-3 | H, D, alkyl | RA-3 | D, alkyl | O, S and $C(R^e)_2$ |
| RB | H, D, alkyl | RB | D, alkyl | O, S and $C(R^e)_2$ |
| RA-5 | H, D, alkyl | RA-5 | Ar-1 to Ar-75 | O, S and $C(R^e)_2$ |
| RA-4 | H, D, alkyl | RA-4 | Ar-1 to Ar-75 | O, S and $C(R^e)_2$ |
| RA-4f | H, D, alkyl | RA-4f | Ar-1 to Ar-75 | O, S and $C(R^e)_2$ |
| RA-3 | H, D, alkyl | RA-3 | Ar-1 to Ar-75 | O, S and $C(R^e)_2$ |
| RB | H, D, alkyl | RB | Ar-1 to Ar-75 | O, S and $C(R^e)_2$ |
| RA-5 | H, D, alkyl | RA-5 | Phenyl ring formation by 2 $R^e$ | O, S and $C(R^e)_2$ |
| RA-4 | H, D, alkyl | RA-4 | Phenyl ring formation by 2 $R^e$ | O, S and $C(R^e)_2$ |
| RA-4f | H, D, alkyl | RA-4f | Phenyl ring formation by 2 $R^e$ | O, S and $C(R^e)_2$ |

-continued

| $R^a$ | $R^b$ | $R^c$ | $R^e$ on the phenyl ring (only if m is not 0 is at least one radical $R^e$, otherwise all $R^e$ are H) | $Y^1$ |
|---|---|---|---|---|
| RA-3 | H, D, alkyl | RA-3 | Phenyl ring formation by 2 $R^e$ | O, S and $C(R^e)_2$ |
| RB | H, D, alkyl | RB | Phenyl ring formation by 2 $R^e$ | O, S and $C(R^e)_2$ |
| RA-5 | H, D, alkyl | RA-5 | $C(Ar')_3$, $Si(Ar')_3$ | O, S and $C(R^e)_2$ |
| RA-4 | H, D, alkyl | RA-4 | $C(Ar')_3$, $Si(Ar')_3$ | O, S and $C(R^e)_2$ |
| RA-4f | H, D, alkyl | RA-4f | $C(Ar')_3$, $Si(Ar')_3$ | O, S and $C(R^e)_2$ |
| RA-3 | H, D, alkyl | RA-3 | $C(Ar')_3$, $Si(Ar')_3$ | O, S and $C(R^e)_2$ |
| RE | H, D, alkyl | RE | $C(Ar')_3$, $Si(Ar')_3$ | O, S and $C(R^e)_2$ |
| RA-5 | H, D, alkyl | RA-5 | $N(Ar')_3$, $N(R^1)_3$ | O, S and $C(R^e)_2$ |
| RA-4 | H, D, alkyl | RA-4 | $N(Ar')_3$, $N(R^1)_3$ | O, S and $C(R^e)_2$ |
| RA-4f | H, D, alkyl | RA-4f | $N(Ar')_3$, $N(R^1)_3$ | O, S and $C(R^e)_2$ |
| RA-3 | H, D, alkyl | RA-3 | $N(Ar')_3$, $N(R^1)_3$ | O, S and $C(R^e)_2$ |
| RB | H, D, alkyl | RE | $N(Ar')_3$, $N(R^1)_3$ | O, S and $C(R^e)_2$ |
| RA-5 | H, D, alkyl | RA-5 | D, alkyl | $(R^e)_2C{-}C(R^e)_2$, $(Re)C{=}C(R^e)$ and $C(R^e)_2$ |
| RA-4 | H, D, alkyl | RA-4 | D, alkyl | $(R^e)_2C{-}C(R^e)_2$, $(Re)C{=}C(R^e)$ and $C(R^e)_2$ |
| RA-4f | H, D, alkyl | RA-4f | D, alkyl | $(R^e)_2C{-}C(R^e)_2$, $(Re)C{=}C(R^e)$ and $C(R^e)_2$ |
| RA-3 | H, D, alkyl | RA-3 | D, alkyl | $(R^e)_2C{-}C(R^e)_2$, $(Re)C{=}C(R^e)$ and $C(R^e)_2$ |
| RB | H, D, alkyl | RB | D, alkyl | $(R^e)_2C{-}C(R^e)_2$, $(Re)C{=}C(R^e)$ and $C(R^e)_2$ |
| RA-5 | H, D, alkyl | RA-5 | Ar-1 to Ar-75 | $(R^e)_2C{-}C(R^e)_2$, $(Re)C{=}C(R^e)$ and $C(R^e)_2$ |
| RA-4 | H, D, alkyl | RA-4 | Ar-1 to Ar-75 | $(R^e)_2C{-}C(R^e)_2$, $(Re)C{=}C(R^e)$ and $C(R^e)_2$ |
| RA-4f | H, D, alkyl | RA-4f | Ar-1 to Ar-75 | $(R^e)_2C{-}C(R^e)_2$, $(Re)C{=}C(R^e)$ and $C(R^e)_2$ |
| RA-3 | H, D, alkyl | RA-3 | Ar-1 to Ar-75 | $(R^e)_2C{-}C(R^e)_2$, $(Re)C{=}C(R^e)$ and $C(R^e)_2$ |
| RB | H, D, alkyl | RB | Ar-1 to Ar-75 | $(R^e)_2C{-}C(R^e)_2$, $(Re)C{=}C(R^e)$ and $C(R^e)_2$ |
| RA-5 | H, D, alkyl | RA-5 | Phenyl ring formation by 2 $R^e$ | $(R^e)_2C{-}C(R^e)_2$, $(Re)C{=}C(R^e)$ and $C(R^e)_2$ |
| RA-4 | H, D, alkyl | RA-4 | Phenyl ring formation by 2 $R^e$ | $(R^e)_2C{-}C(R^e)_2$, $(Re)C{=}C(R^e)$ and $C(R^e)_2$ |
| RA-4f | H, D, alkyl | RA-4f | Phenyl ring formation by 2 $R^e$ | $(R^e)_2C{-}C(R^e)_2$, $(Re)C{=}C(R^e)$ and $C(R^e)_2$ |
| RA-3 | H, D, alkyl | RA-3 | Phenyl ring formation by 2 $R^e$ | $(R^e)_2C{-}C(R^e)_2$, $(Re)C{=}C(R^e)$ and $C(R^e)_2$ |
| RB | H, D, alkyl | RB | Phenyl ring formation by 2 $R^e$ | $(R^e)_2C{-}C(R^e)_2$, $(Re)C{=}C(R^e)$ and $C(R^e)_2$ |
| RA-5 | H, D, alkyl | RA-5 | $C(Ar')_3$, $Si(Ar')_3$ | $(R^e)_2C{-}C(R^e)_2$, $(Re)C{=}C(R^e)$ and $C(R^e)_2$ |
| RA-4 | H, D, alkyl | RA-4 | $C(Ar')_3$, $Si(Ar')_3$ | $(R^e)_2C{-}C(R^e)_2$, $(Re)C{=}C(R^e)$ and $C(R^e)_2$ |
| RA-4f | H, D, alkyl | RA-4f | $C(Ar')_3$, $Si(Ar')_3$ | $(R^e)_2C{-}C(R^e)_2$, $(Re)C{=}C(R^e)$ and $C(R^e)_2$ |

-continued

| $R^a$ | $R^b$ | $R^c$ | $R^e$ on the phenyl ring (only if m is not 0 is at least one radical $R^e$, otherwise all $R^e$ are H) | $Y^1$ |
|---|---|---|---|---|
| RA-3 | H, D, alkyl | RA-3 | $C(Ar')_3$, $Si(Ar')_3$ | $(R^e)_2C{-}C(R^e)_2$, $(Re)C{=}C(R^e)$ and $C(R^e)_2$ |
| RB | H, D, alkyl | RB | $C(Ar')_3$, $Si(Ar')_3$ | $(R^e)_2C{-}C(R^e)_2$, $(Re)C{=}C(R^e)$ and $C(R^e)_2$ |
| RA-5 | H, D, alkyl | RA-5 | $N(Ar')_3$, $N(R^1)_3$ | $(R^e)_2C{-}C(R^e)_2$, $(Re)C{=}C(R^e)$ and $C(R^e)_2$ |
| RA-4 | H, D, alkyl | RA-4 | $N(Ar')_3$, $N(R^1)_3$ | $(R^e)_2C{-}C(R^e)_2$, $(Re)C{=}C(R^e)$ and $C(R^e)_2$ |
| RA-4f | H, D, alkyl | RA-4f | $N(Ar')_3$, $N(R^1)_3$ | $(R^e)_2C{-}C(R^e)_2$, $(Re)C{=}C(R^e)$ and $C(R^e)_2$ |
| RA-3 | H, D, alkyl | RA-3 | $N(Ar')_3$, $N(R^1)_3$ | $(R^e)_2C{-}C(R^e)_2$, $(Re)C{=}C(R^e)$ and $C(R^e)_2$ |
| RE | H, D, alkyl | RB | $N(Ar')_3$, $N(R^1)_3$ | $(R^e)_2C{-}C(R^e)_2$, $(Re)C{=}C(R^e)$ and $C(R^e)_2$ |
| RA-5 | H, D, alkyl | RA-5 | D, alkyl | O, S and $(R^e)_2C{-}C(R^e)_2$, $(R^e)C{=}C(R^e)$ |
| RA-4 | H, D, alkyl | RA-4 | D, alkyl | O, S and $(R^e)_2C{-}C(R^e)_2$, $(R^e)C{=}C(R^e)$ |
| RA-4f | H, D, alkyl | RA-4f | D, alkyl | O, S and $(R^e)_2C{-}C(R^e)_2$, $(R^e)C{=}C(R^e)$ |
| RA-3 | H, D, alkyl | RA-3 | D, alkyl | O, S and $(R^e)_2C{-}C(R^e)_2$, $(R^e)C{=}C(R^e)$ |
| RB | H, D, alkyl | RB | D, alkyl | O, S and $(R^e)_2C{-}C(R^e)_2$, $(R^e)C{=}C(R^e)$ |
| RA-5 | H, D, alkyl | RA-5 | Ar-1 to Ar-75 | O, S and $(R^e)_2C{-}C(R^e)_2$, $(R^e)C{=}C(R^e)$ |
| RA-4 | H, D, alkyl | RA-4 | Ar-1 to Ar-75 | O, S and $(R^e)_2C{-}C(R^e)_2$, $(R^e)C{=}C(R^e)$ |
| RA-4f | H, D, alkyl | RA-4f | Ar-1 to Ar-75 | O, S and $(R^e)_2C{-}C(R^e)_2$, $(R^e)C{=}C(R^e)$ |
| RA-3 | H, D, alkyl | RA-3 | Ar-1 to Ar-75 | O, S and $(R^e)_2C{-}C(R^e)_2$, $(R^e)C{=}C(R^e)$ |
| RB | H, D, alkyl | RB | Ar-1 to Ar-75 | O, S and $(R^e)_2C{-}C(R^e)_2$, $(R^e)C{=}C(R^e)$ |
| RA-5 | H, D, alkyl | RA-5 | Phenyl ring formation by 2 $R^e$ | O, S and $(R^e)_2C{-}C(R^e)_2$, $(R^e)C{=}C(R^e)$ |
| RA-4 | H, D, alkyl | RA-4 | Phenyl ring formation by 2 $R^e$ | O, S and $(R^e)_2C{-}C(R^e)_2$, $(R^e)C{=}C(R^e)$ |
| RA-4f | H, D, alkyl | RA-4f | Phenyl ring formation by 2 $R^e$ | O, S and $(R^e)_2C{-}C(R^e)_2$, $(R^e)C{=}C(R^e)$ |
| RA-3 | H, D, alkyl | RA-3 | Phenyl ring formation by 2 $R^e$ | O, S and $(R^e)_2C{-}C(R^e)_2$, $(R^e)C{=}C(R^e)$ |
| RB | H, D, alkyl | RB | Phenyl ring formation by 2 $R^e$ | O, S and $(R^e)_2C{-}C(R^e)_2$, $(R^e)C{=}C(R^e)$ |
| RA-5 | H, D, alkyl | RA-5 | $C(Ar')_3$, $Si(Ar')_3$ | O, S and $(R^e)_2C{-}C(R^e)_2$, $(R^e)C{=}C(R^e)$ |

-continued

| $R^a$ | $R^b$ | $R^c$ | $R^e$ on the phenyl ring (only if m is not 0 is at least one radical $R^e$, otherwise all $R^e$ are H) | $Y^1$ |
|---|---|---|---|---|
| RA-4 | H, D, alkyl | RA-4 | $C(Ar')_3$, $Si(Ar')_3$ | O, S and $(R^e)_2C—C(R^e)_2$, $(R^e)C═C(R^e)$ |
| RA-4f | H, D, alkyl | RA-4f | $C(Ar')_3$, $Si(Ar')_3$ | O, S and $(R^e)_2C—C(R^e)_2$, $(R^e)C═C(R^e)$ |
| RA-3 | H, D, alkyl | RA-3 | $C(Ar')_3$, $Si(Ar')_3$ | O, S and $(R^e)_2C—C(R^e)_2$, $(R^e)C═C(R^e)$ |
| RB | H, D, alkyl | RB | $C(Ar')_3$, $Si(Ar')_3$ | O, S and $(R^e)_2C—C(R^e)_2$, $(R^e)C═C(R^e)$ |
| RA-5 | H, D, alkyl | RA-5 | $N(Ar')_3$, $N(R^1)_3$ | O, S and $(R^e)_2C—C(R^e)_2$, $(R^e)C═C(R^e)$ |
| RA-4 | H, D, alkyl | RA-4 | $N(Ar')_3$, $N(R^1)_3$ | O, S and $(R^e)_2C—C(R^e)_2$, $(R^e)C═C(R^e)$ |
| RA-4f | H, D, alkyl | RA-4f | $N(Ar')_3$, $N(R^1)_3$ | O, S and $(R^e)_2C—C(R^e)_2$, $(R^e)C═C(R^e)$ |
| RA-3 | H, D, alkyl | RA-3 | $N(Ar')_3$, $N(R^1)_3$ | O, S and $(R^e)_2C—C(R^e)_2$, $(R^e)C═C(R^e)$ |
| RB | H, D, alkyl | RB | $N(Ar')_3$, $N(R^1)_3$ | O, S and $(R^e)_2C—C(R^e)_2$, $(R^e)C═C(R^e)$ |

In the $C(R^e)_2$ group, the $R^e$ radical is especially the groups detailed above, where $R^e$ in the $C(R^e)_2$ group is preferably the same or different at each instance and is a linear alkyl group having 1 to 10 carbon atoms or a branched or cyclic alkyl group having 3 to 10 carbon atoms or an aromatic or heteroaromatic ring system having 5 to 24, preferably 5 to 13, aromatic ring atoms, which may also be substituted by one or more $R^1$ radicals. Most preferably, $R^e$ is a methyl group or a phenyl group. It is also possible here for the $R^e$ radicals to form a ring system with one another, which leads to a spiro system. In the $(R^e)_2C—C(R^e)_2$, $(R^e)C═C(R^e)$ groups, the $R^e$ radical is especially the groups detailed above, where $R^e$ in $(R^e)_2C—C(R^e)_2$, $(R^e)C═C(R^e)$ groups is preferably H, $C_1$ to $C_4$-alkyl, or an aryl or heteroaryl group having 5 to 13 carbon atoms, where the aryl or heteroaryl group may be linked. In this case, it is possible for two $R^e$ groups in the $(R^e)_2C—C(R^e)_2$ or $(R^e)C═C(R^e)$ group to form a fused ring system.

In a further configuration of the present invention, preference is given to compounds comprising a structure of formula (I-5), preferably compounds of formula (I-5), where the two $R^a$ radicals form a ring, the two $R^c$ radicals form a ring, where the index m is preferably 0, 1 or 2 and more preferably 0 or 1, and in which $R^b$ is H, D, alkyl and the $R^a$, RC, $R^d$, $R^e$ and $Y^1$ radicals have the following definitions:

| $R^a$ | $R^c$ | $R^d$ | $R^e$ on the phenyl ring (only if I is not 0 is at least one radical $R^e$, otherwise all $R^e$ are H) | $Y^1$ |
|---|---|---|---|---|
| RA-5 | RA-5 | H, D, alkyl | D, alkyl | $C(R^e)_2$ |
| RA-4 | RA-4 | H, D, alkyl | D, alkyl | $C(R^e)_2$ |

-continued

| $R^a$ | $R^c$ | $R^d$ | $R^e$ on the phenyl ring (only if I is not 0 is at least one radical $R^e$, otherwise all $R^e$ are H) | $Y^1$ |
|---|---|---|---|---|
| RA-4f | RA-4f | H, D, alkyl | D, alkyl | $C(R^e)_2$ |
| RA-3 | RA-3 | H, D, alkyl | D, alkyl | $C(R^e)_2$ |
| RB | RB | H, D, alkyl | D, alkyl | $C(R^e)_2$ |
| RA-5 | RA-5 | H, D, alkyl | Ar-1 to Ar-75 | $C(R^e)_2$ |
| RA-4 | RA-4 | H, D, alkyl | Ar-1 to Ar-75 | $C(R^e)_2$ |
| RA-4f | RA-4f | H, D, alkyl | Ar-1 to Ar-75 | $C(R^e)_2$ |
| RA-3 | RA-3 | H, D, alkyl | Ar-1 to Ar-75 | $C(R^e)_2$ |
| RB | RB | H, D, alkyl | Ar-1 to Ar-75 | $C(R^e)_2$ |
| RA-5 | RA-5 | Ar-1 to Ar-75 | D, alkyl | $C(R^e)_2$ |
| RA-4 | RA-4 | Ar-1 to Ar-75 | D, alkyl | $C(R^e)_2$ |
| RA-4f | RA-4f | Ar-1 to Ar-75 | D, alkyl | $C(R^e)_2$ |
| RA-3 | RA-3 | Ar-1 to Ar-75 | D, alkyl | $C(R^e)_2$ |
| RB | RB | Ar-1 to Ar-75 | D, alkyl | $C(R^e)_2$ |
| RA-5 | RA-5 | Ar-1 to Ar-75 | Ar-1 to Ar-75 | $C(R^e)_2$ |
| RA-4 | RA-4 | Ar-1 to Ar-75 | Ar-1 to Ar-75 | $C(R^e)_2$ |
| RA-4f | RA-4f | Ar-1 to Ar-75 | Ar-1 to Ar-75 | $C(R^e)_2$ |
| RA-3 | RA-3 | Ar-1 to Ar-75 | Ar-1 to Ar-75 | $C(R^e)_2$ |
| RB | RB | Ar-1 to Ar-75 | Ar-1 to Ar-75 | $C(R^e)_2$ |
| RA-5 | RA-5 | H, D, alkyl | Phenyl ring formation by 2 $R^e$ | $C(R^e)_2$ |
| RA-4 | RA-4 | H, D, alkyl | Phenyl ring formation by 2 $R^e$ | $C(R^e)_2$ |
| RA-4f | RA-4f | H, D, alkyl | Phenyl ring formation by 2 $R^e$ | $C(R^e)_2$ |
| RA-3 | RA-3 | H, D, alkyl | Phenyl ring formation by 2 $R^e$ | $C(R^e)_2$ |
| RB | RB | H, D, alkyl | Phenyl ring formation by 2 $R^e$ | $C(R^e)_2$ |
| RA-5 | RA-5 | Ar-1 to Ar-75 | Phenyl ring formation by 2 $R^e$ | $C(R^e)_2$ |
| RA-4 | RA-4 | Ar-1 to Ar-75 | Phenyl ring formation by 2 $R^e$ | $C(R^e)_2$ |
| RA-4f | RA-4f | Ar-1 to Ar-75 | Phenyl ring formation by 2 $R^e$ | $C(R^e)_2$ |
| RA-3 | RA-3 | Ar-1 to Ar-75 | Phenyl ring formation by 2 $R^e$ | $C(R^e)_2$ |
| RB | RB | Ar-1 to Ar-75 | Phenyl ring formation by 2 $R^e$ | $C(R^e)_2$ |
| RA-5 | RA-5 | H, D, alkyl | $C(Ar')_3$, $Si(Ar')_3$ | $C(R^e)_2$ |
| RA-4 | RA-4 | H, D, alkyl | $C(Ar')_3$, $Si(Ar')_3$ | $C(R^e)_2$ |
| RA-4f | RA-4f | H, D, alkyl | $C(Ar')_3$, $Si(Ar')_3$ | $C(R^e)_2$ |
| RA-3 | RA-3 | H, D, alkyl | $C(Ar')_3$, $Si(Ar')_3$ | $C(R^e)_2$ |
| RB | RB | H, D, alkyl | $C(Ar')_3$, $Si(Ar')_3$ | $C(R^e)_2$ |
| RA-5 | RA-5 | Ar-1 to Ar-75 | $C(Ar')_3$, $Si(Ar')_3$ | $C(R^e)_2$ |
| RA-4 | RA-4 | Ar-1 to Ar-75 | $C(Ar')_3$, $Si(Ar')_3$ | $C(R^e)_2$ |
| RA-4f | RA-4f | Ar-1 to Ar-75 | $C(Ar')_3$, $Si(Ar')_3$ | $C(R^e)_2$ |
| RA-3 | RA-3 | Ar-1 to Ar-75 | $C(Ar')_3$, $Si(Ar')_3$ | $C(R^e)_2$ |
| RB | RB | Ar-1 to Ar-75 | $C(Ar')_3$, $Si(Ar')_3$ | $C(R^e)_2$ |
| RA-5 | RA-5 | H, D, alkyl | $N(Ar')_3$, $N(R^1)_3$ | $C(R^e)_2$ |
| RA-4 | RA-4 | H, D, alkyl | $N(Ar')_3$, $N(R^1)_3$ | $C(R^e)_2$ |
| RA-4f | RA-4f | H, D, alkyl | $N(Ar')_3$, $N(R^1)_3$ | $C(R^e)_2$ |
| RA-3 | RA-3 | H, D, alkyl | $N(Ar')_3$, $N(R^1)_3$ | $C(R^e)_2$ |
| RB | RB | H, D, alkyl | $N(Ar')_3$, $N(R^1)_3$ | $C(R^e)_2$ |
| RA-5 | RA-5 | Ar-1 to Ar-75 | $N(Ar')_3$, $N(R^1)_3$ | $C(R^e)_2$ |
| RA-4 | RA-4 | Ar-1 to Ar-75 | $N(Ar')_3$, $N(R^1)_3$ | $C(R^e)_2$ |
| RA-4f | RA-4f | Ar-1 to Ar-75 | $N(Ar')_3$, $N(R^1)_3$ | $C(R^e)_2$ |
| RA-3 | RA-3 | Ar-1 to Ar-75 | $N(Ar')_3$, $N(R^1)_3$ | $C(R^e)_2$ |
| RB | RB | Ar-1 to Ar-75 | $N(Ar')_3$, $N(R^1)_3$ | $C(R^e)_2$ |
| RA-5 | RA-5 | H, D, alkyl | D, alkyl | O, S |
| RA-4 | RA-4 | H, D, alkyl | D, alkyl | O, S |
| RA-4f | RA-4f | H, D, alkyl | D, alkyl | O, S |

-continued

| $R^a$ | $R^c$ | $R^d$ | $R^e$ on the phenyl ring (only if I is not 0 is at least one radical $R^e$, otherwise all $R^e$ are H) | $Y^1$ |
|---|---|---|---|---|
| RA-3 | RA-3 | H, D, alkyl | D, alkyl | O, S |
| RB | RB | H, D, alkyl | D, alkyl | O, S |
| RA-5 | RA-5 | H, D, alkyl | Ar-1 to Ar-75 | O, S |
| RA-4 | RA-4 | H, D, alkyl | Ar-1 to Ar-75 | O, S |
| RA-4f | RA-4f | H, D, alkyl | Ar-1 to Ar-75 | O, S |
| RA-3 | RA-3 | H, D, alkyl | Ar-1 to Ar-75 | O, S |
| RB | RB | H, D, alkyl | Ar-1 to Ar-75 | O, S |
| RA-5 | RA-5 | Ar-1 to Ar-75 | D, alkyl | O, S |
| RA-4 | RA-4 | Ar-1 to Ar-75 | D, alkyl | O, S |
| RA-4f | RA-4f | Ar-1 to Ar-75 | D, alkyl | O, S |
| RA-3 | RA-3 | Ar-1 to Ar-75 | D, alkyl | O, S |
| RB | RB | Ar-1 to Ar-75 | D, alkyl | O, S |
| RA-5 | RA-5 | Ar-1 to Ar-75 | Ar-1 to Ar-75 | O, S |
| RA-4 | RA-4 | Ar-1 to Ar-75 | Ar-1 to Ar-75 | O, S |
| RA-4f | RA-4f | Ar-1 to Ar-75 | Ar-1 to Ar-75 | O, S |
| RA-3 | RA-3 | Ar-1 to Ar-75 | Ar-1 to Ar-75 | O, S |
| RB | RB | Ar-1 to Ar-75 | Ar-1 to Ar-75 | O, S |
| RA-5 | RA-5 | H, D, alkyl | Phenyl ring formation by 2 $R^e$ | O, S |
| RA-4 | RA-4 | H, D, alkyl | Phenyl ring formation by 2 $R^e$ | O, S |
| RA-4f | RA-4f | H, D, alkyl | Phenyl ring formation by 2 $R^e$ | O, S |
| RA-3 | RA-3 | H, D, alkyl | Phenyl ring formation by 2 $R^e$ | O, S |
| RB | RB | H, D, alkyl | Phenyl ring formation by 2 $R^e$ | O, S |
| RA-5 | RA-5 | Ar-1 to Ar-75 | Phenyl ring formation by 2 $R^e$ | O, S |
| RA-4 | RA-4 | Ar-1 to Ar-75 | Phenyl ring formation by 2 $R^e$ | O, S |
| RA-4f | RA-4f | Ar-1 to Ar-75 | Phenyl ring formation by 2 $R^e$ | O, S |
| RA-3 | RA-3 | Ar-1 to Ar-75 | Phenyl ring formation by 2 $R^e$ | O, S |
| RB | RB | Ar-1 to Ar-75 | Phenyl ring formation by 2 $R^e$ | O, S |
| RA-5 | RA-5 | H, D, alkyl | $C(Ar')_3$, $Si(Ar')_3$ | O, S |
| RA-4 | RA-4 | H, D, alkyl | $C(Ar')_3$, $Si(Ar')_3$ | O, S |
| RA-4f | RA-4f | H, D, alkyl | $C(Ar')_3$, $Si(Ar')_3$ | O, S |
| RA-3 | RA-3 | H, D, alkyl | $C(Ar')_3$, $Si(Ar')_3$ | O, S |
| RB | RB | H, D, alkyl | $C(Ar')_3$, $Si(Ar')_3$ | O, S |
| RA-5 | RA-5 | Ar-1 to Ar-75 | $C(Ar')_3$, $Si(Ar')_3$ | O, S |
| RA-4 | RA-4 | Ar-1 to Ar-75 | $C(Ar')_3$, $Si(Ar')_3$ | O, S |
| RA-4f | RA-4f | Ar-1 to Ar-75 | $C(Ar')_3$, $Si(Ar')_3$ | O, S |
| RA-3 | RA-3 | Ar-1 to Ar-75 | $C(Ar')_3$, $Si(Ar')_3$ | O, S |
| RB | RB | Ar-1 to Ar-75 | $C(Ar')_3$, $Si(Ar')_3$ | O, S |
| RA-5 | RA-5 | H, D, alkyl | $N(Ar')_3$, $N(R^1)_3$ | O, S |
| RA-4 | RA-4 | H, D, alkyl | $N(Ar')_3$, $N(R^1)_3$ | O, S |
| RA-4f | RA-4f | H, D, alkyl | $N(Ar')_3$, $N(R^1)_3$ | O, S |
| RA-3 | RA-3 | H, D, alkyl | $N(Ar')_3$, $N(R^1)_3$ | O, S |
| RE | RB | H, D, alkyl | $N(Ar')_3$, $N(R^1)_3$ | O, S |
| RA-5 | RA-5 | Ar-1 to Ar-75 | $N(Ar')_3$, $N(R^1)_3$ | O, S |
| RA-4 | RA-4 | Ar-1 to Ar-75 | $N(Ar')_3$, $N(R^1)_3$ | O, S |
| RA-4f | RA-4f | Ar-1 to Ar-75 | $N(Ar')_3$, $N(R^1)_3$ | O, S |
| RA-3 | RA-3 | Ar-1 to Ar-75 | $N(Ar')_3$, $N(R^1)_3$ | O, S |
| RE | RB | Ar-1 to Ar-75 | $N(Ar')_3$, $N(R^1)_3$ | O, S |
| RA-5 | RA-5 | H, D, alkyl | D, alkyl | N(Ar) |
| RA-4 | RA-4 | H, D, alkyl | D, alkyl | N(Ar) |
| RA-4f | RA-4f | H, D, alkyl | D, alkyl | N(Ar) |
| RA-3 | RA-3 | H, D, alkyl | D, alkyl | N(Ar) |

-continued

| $R^a$ | $R^c$ | $R^d$ | $R^e$ on the phenyl ring (only if I is not 0 is at least one radical $R^e$, otherwise all $R^e$ are H) | $Y^1$ |
|---|---|---|---|---|
| RB | RB | H, D, alkyl | D, alkyl | N(Ar) |
| RA-5 | RA-5 | H, D, alkyl | Ar-1 to Ar-75 | N(Ar) |
| RA-4 | RA-4 | H, D, alkyl | Ar-1 to Ar-75 | N(Ar) |
| RA-4f | RA-4f | H, D, alkyl | Ar-1 to Ar-75 | N(Ar) |
| RA-3 | RA-3 | H, D, alkyl | Ar-1 to Ar-75 | N(Ar) |
| RE | RB | H, D, alkyl | Ar-1 to Ar-75 | N(Ar) |
| RA-5 | RA-5 | Ar-1 to Ar-75 | D, alkyl | N(Ar) |
| RA-4 | RA-4 | Ar-1 to Ar-75 | D, alkyl | N(Ar) |
| RA-4f | RA-4f | Ar-1 to Ar-75 | D, alkyl | N(Ar) |
| RA-3 | RA-3 | Ar-1 to Ar-75 | D, alkyl | N(Ar) |
| RB | RB | Ar-1 to Ar-75 | D, alkyl | N(Ar) |
| RA-5 | RA-5 | Ar-1 to Ar-75 | Ar-1 to Ar-75 | N(Ar) |
| RA-4 | RA-4 | Ar-1 to Ar-75 | Ar-1 to Ar-75 | N(Ar) |
| RA-4f | RA-4f | Ar-1 to Ar-75 | Ar-1 to Ar-75 | N(Ar) |
| RA-3 | RA-3 | Ar-1 to Ar-75 | Ar-1 to Ar-75 | N(Ar) |
| RB | RB | Ar-1 to Ar-75 | Ar-1 to Ar-75 | N(Ar) |
| RA-5 | RA-5 | H, D, alkyl | Phenyl ring formation by 2 $R^e$ | N(Ar) |
| RA-4 | RA-4 | H, D, alkyl | Phenyl ring formation by 2 $R^e$ | N(Ar) |
| RA-4f | RA-4f | H, D, alkyl | Phenyl ring formation by 2 $R^e$ | N(Ar) |
| RA-3 | RA-3 | H, D, alkyl | Phenyl ring formation by 2 $R^e$ | N(Ar) |
| RB | RB | H, D, alkyl | Phenyl ring formation by 2 $R^e$ | N(Ar) |
| RA-5 | RA-5 | Ar-1 to Ar-75 | Phenyl ring formation by 2 $R^e$ | N(Ar) |
| RA-4 | RA-4 | Ar-1 to Ar-75 | Phenyl ring formation by 2 $R^e$ | N(Ar) |
| RA-4f | RA-4f | Ar-1 to Ar-75 | Phenyl ring formation by 2 $R^e$ | N(Ar) |
| RA-3 | RA-3 | Ar-1 to Ar-75 | Phenyl ring formation by 2 $R^e$ | N(Ar) |
| RB | RB | Ar-1 to Ar-75 | Phenyl ring formation by 2 $R^e$ | N(Ar) |
| RA-5 | RA-5 | H, D, alkyl | $C(Ar')_3$, $Si(Ar')_3$ | N(Ar) |
| RA-4 | RA-4 | H, D, alkyl | $C(Ar')_3$, $Si(Ar')_3$ | N(Ar) |
| RA-4f | RA-4f | H, D, alkyl | $C(Ar')_3$, $Si(Ar')_3$ | N(Ar) |
| RA-3 | RA-3 | H, D, alkyl | $C(Ar')_3$, $Si(Ar')_3$ | N(Ar) |
| RB | RB | H, D, alkyl | $C(Ar')_3$, $Si(Ar')_3$ | N(Ar) |
| RA-5 | RA-5 | Ar-1 to Ar-75 | $C(Ar')_3$, $Si(Ar')_3$ | N(Ar) |
| RA-4 | RA-4 | Ar-1 to Ar-75 | $C(Ar')_3$, $Si(Ar')_3$ | N(Ar) |
| RA-4f | RA-4f | Ar-1 to Ar-75 | $C(Ar')_3$, $Si(Ar')_3$ | N(Ar) |
| RA-3 | RA-3 | Ar-1 to Ar-75 | $C(Ar')_3$, $Si(Ar')_3$ | N(Ar) |
| RB | RB | Ar-1 to Ar-75 | $C(Ar')_3$, $Si(Ar')_3$ | N(Ar) |
| RA-5 | RA-5 | H, D, alkyl | $N(Ar')_3$, $N(R^1)_3$ | N(Ar) |
| RA-4 | RA-4 | H, D, alkyl | $N(Ar')_3$, $N(R^1)_3$ | N(Ar) |
| RA-4f | RA-4f | H, D, alkyl | $N(Ar')_3$, $N(R^1)_3$ | N(Ar) |
| RA-3 | RA-3 | H, D, alkyl | $N(Ar')_3$, $N(R^1)_3$ | N(Ar) |
| RB | RB | H, D, alkyl | $N(Ar')_3$, $N(R^1)_3$ | N(Ar) |
| RA-5 | RA-5 | Ar-1 to Ar-75 | $N(Ar')_3$, $N(R^1)_3$ | N(Ar) |
| RA-4 | RA-4 | Ar-1 to Ar-75 | $N(Ar')_3$, $N(R^1)_3$ | N(Ar) |
| RA-4f | RA-4f | Ar-1 to Ar-75 | $N(Ar')_3$, $N(R^1)_3$ | N(Ar) |
| RA-3 | RA-3 | Ar-1 to Ar-75 | $N(Ar')_3$, $N(R^1)_3$ | N(Ar) |
| RB | RB | Ar-1 to Ar-75 | $N(Ar')_3$, $N(R^1)_3$ | N(Ar) |
| RA-5 | RA-5 | H, D, alkyl | D, alkyl | $(R^e)_2C{-}C(R^e)_2$, $(R^e)C{=}C(R^e)$ |
| RA-4 | RA-4 | H, D, alkyl | D, alkyl | $(R^e)_2C{-}C(R^e)_2$, $(R^e)C{=}C(R^e)$ |

-continued

| $R^a$ | $R^c$ | $R^d$ | $R^e$ on the phenyl ring (only if I is not 0 is at least one radical $R^e$, otherwise all $R^e$ are H) | $Y^1$ |
|---|---|---|---|---|
| RA-4f | RA-4f | H, D, alkyl | D, alkyl | $(R^e)_2C—C(R^e)_2$, $(R^e)C{=}C(R^e)$ |
| RA-3 | RA-3 | H, D, alkyl | D, alkyl | $(R^e)_2C—C(R^e)_2$, $(R^e)C{=}C(R^e)$ |
| RB | RB | H, D, alkyl | D, alkyl | $(R^e)_2C—C(R^e)_2$, $(R^e)C{=}C(R^e)$ |
| RA-5 | RA-5 | H, D, alkyl | Ar-1 to Ar-75 | $(R^e)_2C—C(R^e)_2$, $(R^e)C{=}C(R^e)$ |
| RA-4 | RA-4 | H, D, alkyl | Ar-1 to Ar-75 | $(R^e)_2C—C(R^e)_2$, $(R^e)C{=}C(R^e)$ |
| RA-4f | RA-4f | H, D, alkyl | Ar-1 to Ar-75 | $(R^e)_2C—C(R^e)_2$, $(R^e)C{=}C(R^e)$ |
| RA-3 | RA-3 | H, D, alkyl | Ar-1 to Ar-75 | $(R^e)_2C—C(R^e)_2$, $(R^e)C{=}C(R^e)$ |
| RB | RB | H, D, alkyl | Ar-1 to Ar-75 | $(R^e)_2C—C(R^e)_2$, $(R^e)C{=}C(R^e)$ |
| RA-5 | RA-5 | Ar-1 to Ar-75 | D, alkyl | $(R^e)_2C—C(R^e)_2$, $(R^e)C{=}C(R^e)$ |
| RA-4 | RA-4 | Ar-1 to Ar-75 | D, alkyl | $(R^e)_2C—C(R^e)_2$, $(R^e)C{=}C(R^e)$ |
| RA-4f | RA-4f | Ar-1 to Ar-75 | D, alkyl | $(R^e)_2C—C(R^e)_2$, $(R^e)C{=}C(R^e)$ |
| RA-3 | RA-3 | Ar-1 to Ar-75 | D, alkyl | $(R^e)_2C—C(R^e)_2$, $(R^e)C{=}C(R^e)$ |
| RB | RB | Ar-1 to Ar-75 | D, alkyl | $(R^e)_2C—C(R^e)_2$, $(R^e)C{=}C(R^e)$ |
| RA-5 | RA-5 | Ar-1 to Ar-75 | Ar-1 to Ar-75 | $(R^e)_2C—C(R^e)_2$, $(R^e)C{=}C(R^e)$ |
| RA-4 | RA-4 | Ar-1 to Ar-75 | Ar-1 to Ar-75 | $(R^e)_2C—C(R^e)_2$, $(R^e)C{=}C(R^e)$ |
| RA-4f | RA-4f | Ar-1 to Ar-75 | Ar-1 to Ar-75 | $(R^e)_2C—C(R^e)_2$, $(R^e)C{=}C(R^e)$ |
| RA-3 | RA-3 | Ar-1 to Ar-75 | Ar-1 to Ar-75 | $(R^e)_2C—C(R^e)_2$, $(R^e)C{=}C(R^e)$ |
| RB | RB | Ar-1 to Ar-75 | Ar-1 to Ar-75 | $(R^e)_2C—C(R^e)_2$, $(R^e)C{=}C(R^e)$ |
| RA-5 | RA-5 | H, D, alkyl | Phenyl ring formation by 2 $R^e$ | $(R^e)_2C—C(R^e)_2$, $(R^e)C{=}C(R^e)$ |
| RA-4 | RA-4 | H, D, alkyl | Phenyl ring formation by 2 $R^e$ | $(R^e)_2C—C(R^e)_2$, $(R^e)C{=}C(R^e)$ |
| RA-4f | RA-4f | H, D, alkyl | Phenyl ring formation by 2 $R^e$ | $(R^e)_2C—C(R^e)_2$, $(R^e)C{=}C(R^e)$ |
| RA-3 | RA-3 | H, D, alkyl | Phenyl ring formation by 2 $R^e$ | $(R^e)_2C—C(R^e)_2$, $(R^e)C{=}C(R^e)$ |
| RE | RB | H, D, alkyl | Phenyl ring formation by 2 $R^e$ | $(R^e)_2C—C(R^e)_2$, $(R^e)C{=}C(R^e)$ |
| RA-5 | RA-5 | Ar-1 to Ar-75 | Phenyl ring formation by 2 $R^e$ | $(R^e)_2C—C(R^e)_2$, $(R^e)C{=}C(R^e)$ |
| RA-4 | RA-4 | Ar-1 to Ar-75 | Phenyl ring formation by 2 $R^e$ | $(R^e)_2C—C(R^e)_2$, $(R^e)C{=}C(R^e)$ |
| RA-4f | RA-4f | Ar-1 to Ar-75 | Phenyl ring formation by 2 $R^e$ | $(R^e)_2C—C(R^e)_2$, $(R^e)C{=}C(R^e)$ |
| RA-3 | RA-3 | Ar-1 to Ar-75 | Phenyl ring formation by 2 $R^e$ | $(R^e)_2C—C(R^e)_2$, $(R^e)C{=}C(R^e)$ |
| RB | RB | Ar-1 to Ar-75 | Phenyl ring formation by 2 $R^e$ | $(R^e)_2C—C(R^e)_2$, $(R^e)C{=}C(R^e)$ |
| RA-5 | RA-5 | H, D, alkyl | $C(Ar')_3$, $Si(Ar')_3$ | $(R^e)_2C—C(R^e)_2$, $(R^e)C{=}C(R^e)$ |
| RA-4 | RA-4 | H, D, alkyl | $C(Ar')_3$, $Si(Ar')_3$ | $(R^e)_2C—C(R^e)_2$, $(R^e)C{=}C(R^e)$ |

-continued

| $R^a$ | $R^c$ | $R^d$ | $R^e$ on the phenyl ring (only if I is not 0 is at least one radical $R^e$, otherwise all $R^e$ are H) | $Y^1$ |
|---|---|---|---|---|
| RA-4f | RA-4f | H, D, alkyl | $C(Ar')_3$, $Si(Ar')_3$ | $(R^e)_2C—C(R^e)_2$, $(R^e)C{=}C(R^e)$ |
| RA-3 | RA-3 | H, D, alkyl | $C(Ar')_3$, $Si(Ar')_3$ | $(R^e)_2C—C(R^e)_2$, $(R^e)C{=}C(R^e)$ |
| RB | RB | H, D, alkyl | $C(Ar')_3$, $Si(Ar')_3$ | $(R^e)_2C—C(R^e)_2$, $(R^e)C{=}C(R^e)$ |
| RA-5 | RA-5 | Ar-1 to Ar-75 | $C(Ar')_3$, $Si(Ar')_3$ | $(R^e)_2C—C(R^e)_2$, $(R^e)C{=}C(R^e)$ |
| RA-4 | RA-4 | Ar-1 to Ar-75 | $C(Ar')_3$, $Si(Ar')_3$ | $(R^e)_2C—C(R^e)_2$, $(R^e)C{=}C(R^e)$ |
| RA-4f | RA-4f | Ar-1 to Ar-75 | $C(Ar')_3$, $Si(Ar')_3$ | $(R^e)_2C—C(R^e)_2$, $(R^e)C{=}C(R^e)$ |
| RA-3 | RA-3 | Ar-1 to Ar-75 | $C(Ar')_3$, $Si(Ar')_3$ | $(R^e)_2C—C(R^e)_2$, $(R^e)C{=}C(R^e)$ |
| RB | RB | Ar-1 to Ar-75 | $C(Ar')_3$, $Si(Ar')_3$ | $(R^e)_2C—C(R^e)_2$, $(R^e)C{=}C(R^e)$ |
| RA-5 | RA-5 | H, D, alkyl | $N(Ar')_3$, $N(R^1)_3$ | $(R^e)_2C—C(R^e)_2$, $(R^e)C{=}C(R^e)$ |
| RA-4 | RA-4 | H, D, alkyl | $N(Ar')_3$, $N(R^1)_3$ | $(R^e)_2C—C(R^e)_2$, $(R^e)C{=}C(R^e)$ |
| RA-4f | RA-4f | H, D, alkyl | $N(Ar')_3$, $N(R^1)_3$ | $(R^e)_2C—C(R^e)_2$, $(R^e)C{=}C(R^e)$ |
| RA-3 | RA-3 | H, D, alkyl | $N(Ar')_3$, $N(R^1)_3$ | $(R^e)_2C—C(R^e)_2$, $(R^e)C{=}C(R^e)$ |
| RB | RB | H, D, alkyl | $N(Ar')_3$, $N(R^1)_3$ | $(R^e)_2C—C(R^e)_2$, $(R^e)C{=}C(R^e)$ |
| RA-5 | RA-5 | Ar-1 to Ar-75 | $N(Ar')_3$, $N(R^1)_3$ | $(R^e)_2C—C(R^e)_2$, $(R^e)C{=}C(R^e)$ |
| RA-4 | RA-4 | Ar-1 to Ar-75 | $N(Ar')_3$, $N(R^1)_3$ | $(R^e)_2C—C(R^e)_2$, $(R^e)C{=}C(R^e)$ |
| RA-4f | RA-4f | Ar-1 to Ar-75 | $N(Ar')_3$, $N(R^1)_3$ | $(R^e)_2C—C(R^e)_2$, $(R^e)C{=}C(R^e)$ |
| RA-3 | RA-3 | Ar-1 to Ar-75 | $N(Ar')_3$, $N(R^1)_3$ | $(R^e)_2C—C(R^e)_2$, $(R^e)C{=}C(R^e)$ |
| RB | RB | Ar-1 to Ar-75 | $N(Ar')_3$, $N(R^1)_3$ | $(R^e)_2C—C(R^e)_2$, $(R^e)C{=}C(R^e)$ |

In the above table, the radicals that are specified in the column under the $R^e$ group are the substituents on the phenyl ring bonded to the $Y^1$ group. In the $C(R^e)_2$ group, the $R^e$ radical is especially the groups detailed above, where $R^e$ in the $C(R^e)_2$ group is preferably the same or different at each instance and is a linear alkyl group having 1 to 10 carbon atoms or a branched or cyclic alkyl group having 3 to 10 carbon atoms or an aromatic or heteroaromatic ring system having 5 to 24, preferably 5 to 13, aromatic ring atoms, which may also be substituted by one or more $R^1$ radicals. Most preferably, $R^e$ is a methyl group or a phenyl group. It is also possible here for the $R^e$ radicals to form a ring system with one another, which leads to a spiro system.

In the $(R^e)_2C—C(R^e)_2$, $(R^e)C{=}C(R^e)$ groups, the $R^e$ radical is especially the groups detailed above, where $R^e$ in $(R^e)_2C—C(R^e)_2$, $(R^e)C{=}C(R^e)$ groups is preferably H, $C_1$ to $C_4$-alkyl, or an aryl or heteroaryl group having 5 to 13 carbon atoms, where the aryl or heteroaryl group may be linked. In this case, it is possible for two $R^e$ groups in the $(R^e)_2C—C(R^e)_2$ or $(R^e)C{=}C(R^e)$ group to form a fused ring system.

In a further configuration of the present invention, preference is given to compounds comprising a structure of formula (I-6), preferably compounds of formula (I-6), where the two $R^a$ radicals form a ring, the two $R^c$ radicals form a ring, where the sum total of the indices m and n is preferably not more than 4, more preferably 0, 1 or 2 and especially preferably 0 or 1, and in which the $R^a$, $R^b$, $R^c$, $R^d$ and $R^e$ radicals have the following definitions:

| $R^a$ | $R^b$ | $R^c$ | $R^d$ | $R^e$ (only if n or m is not 0 is at least one radical $R^e$, otherwise all $R^e$ are H) |
|---|---|---|---|---|
| RA-5 | H, D, alkyl | RA-5 | H, D, alkyl | D, alkyl |
| RA-4 | H, D, alkyl | RA-4 | H, D, alkyl | D, alkyl |
| RA-4f | H, D, alkyl | RA-4f | H, D, alkyl | D, alkyl |
| RA-3 | H, D, alkyl | RA-3 | H, D, alkyl | D, alkyl |
| RB | H, D, alkyl | RB | H, D, alkyl | D, alkyl |
| RA-5 | H, D, alkyl | RA-5 | H, D, alkyl | Ar-1 to Ar-75 |
| RA-4 | H, D, alkyl | RA-4 | H, D, alkyl | Ar-1 to Ar-75 |
| RA-4f | H, D, alkyl | RA-4f | H, D, alkyl | Ar-1 to Ar-75 |
| RA-3 | H, D, alkyl | RA-3 | H, D, alkyl | Ar-1 to Ar-75 |
| RB | H, D, alkyl | RB | H, D, alkyl | Ar-1 to Ar-75 |
| RA-5 | H, D, alkyl | RA-5 | Ar-1 to Ar-75 | D, alkyl |
| RA-4 | H, D, alkyl | RA-4 | Ar-1 to Ar-75 | D, alkyl |
| RA-4f | H, D, alkyl | RA-4f | Ar-1 to Ar-75 | D, alkyl |
| RA-3 | H, D, alkyl | RA-3 | Ar-1 to Ar-75 | D, alkyl |
| RB | H, D, alkyl | RB | Ar-1 to Ar-75 | D, alkyl |
| RA-5 | H, D, alkyl | RA-5 | Ar-1 to Ar-75 | Ar-1 to Ar-75 |
| RA-4 | H, D, alkyl | RA-4 | Ar-1 to Ar-75 | Ar-1 to Ar-75 |
| RA-4f | H, D, alkyl | RA-4f | Ar-1 to Ar-75 | Ar-1 to Ar-75 |
| RA-3 | H, D, alkyl | RA-3 | Ar-1 to Ar-75 | Ar-1 to Ar-75 |
| RB | H, D, alkyl | RB | Ar-1 to Ar-75 | Ar-1 to Ar-75 |
| RA-5 | H, D, alkyl | RA-5 | H, D, alkyl and Ar-1 to Ar-75 | D, alkyl |
| RA-4 | H, D, alkyl | RA-4 | H, D, alkyl and Ar-1 to Ar-75 | D, alkyl |
| RA-4f | H, D, alkyl | RA-4f | H, D, alkyl and Ar-1 to Ar-75 | D, alkyl |
| RA-3 | H, D, alkyl | RA-3 | H, D, alkyl and Ar-1 to Ar-75 | D, alkyl |
| RB | H, D, alkyl | RB | H, D, alkyl and Ar-1 to Ar-75 | D, alkyl |
| RA-5 | H, D, alkyl | RA-5 | H, D, alkyl and Ar-1 to Ar-75 | Ar-1 to Ar-75 |
| RA-4 | H, D, alkyl | RA-4 | H, D, alkyl and Ar-1 to Ar-75 | Ar-1 to Ar-75 |
| RA-4f | H, D, alkyl | RA-4f | H, D, alkyl and Ar-1 to Ar-75 | Ar-1 to Ar-75 |
| RA-3 | H, D, alkyl | RA-3 | H, D, alkyl and Ar-1 to Ar-75 | Ar-1 to Ar-75 |
| RB | H, D, alkyl | RB | H, D, alkyl and Ar-1 to Ar-75 | Ar-1 to Ar-75 |
| RA-5 | H, D, alkyl | RA-5 | H, D, alkyl | $C(Ar')_3$, $Si(Ar')_3$ |
| RA-4 | H, D, alkyl | RA-4 | H, D, alkyl | $C(Ar')_3$, $Si(Ar')_3$ |
| RA-4f | H, D, alkyl | RA-4f | H, D, alkyl | $C(Ar')_3$, $Si(Ar')_3$ |
| RA-3 | H, D, alkyl | RA-3 | H, D, alkyl | $C(Ar')_3$, $Si(Ar')_3$ |
| RB | H, D, alkyl | RB | H, D, alkyl | $C(Ar')_3$, $Si(Ar')_3$ |
| RA-5 | H, D, alkyl | RA-5 | Ar-1 to Ar-75 | $C(Ar')_3$, $Si(Ar')_3$ |
| RA-4 | H, D, alkyl | RA-4 | Ar-1 to Ar-75 | $C(Ar')_3$, $Si(Ar')_3$ |
| RA-4f | H, D, alkyl | RA-4f | Ar-1 to Ar-75 | $C(Ar')_3$, $Si(Ar')_3$ |
| RA-3 | H, D, alkyl | RA-3 | Ar-1 to Ar-75 | $C(Ar')_3$, $Si(Ar')_3$ |
| RB | H, D, alkyl | RB | Ar-1 to Ar-75 | $C(Ar')_3$, $Si(Ar')_3$ |
| RA-5 | H, D, alkyl | RA-5 | H, D, alkyl and Ar-1 to Ar-75 | $C(Ar')_3$, $Si(Ar')_3$ |
| RA-4 | H, D, alkyl | RA-4 | H, D, alkyl and Ar-1 to Ar-75 | $C(Ar')_3$, $Si(Ar')_3$ |
| RA-4f | H, D, alkyl | RA-4f | H, D, alkyl and Ar-1 to Ar-75 | $C(Ar')_3$, $Si(Ar')_3$ |
| RA-3 | H, D, alkyl | RA-3 | H, D, alkyl and Ar-1 to Ar-75 | $C(Ar')_3$, $Si(Ar')_3$ |
| RB | H, D, alkyl | RB | H, D, alkyl and Ar-1 to Ar-75 | $C(Ar')_3$, $Si(Ar')_3$ |
| RA-5 | H, D, alkyl | RA-5 | H, D, alkyl | $N(Ar')_3$, $N(R^1)_3$ |
| RA-4 | H, D, alkyl | RA-4 | H, D, alkyl | $N(Ar')_3$, $N(R^1)_3$ |
| RA-4f | H, D, alkyl | RA-4f | H, D, alkyl | $N(Ar')_3$, $N(R^1)_3$ |
| RA-3 | H, D, alkyl | RA-3 | H, D, alkyl | $N(Ar')_3$, $N(R^1)_3$ |
| RB | H, D, alkyl | RB | H, D, alkyl | $N(Ar')_3$, $N(R^1)_3$ |
| RA-5 | H, D, alkyl | RA-5 | Ar-1 to Ar-75 | $N(Ar')_3$, $N(R^1)_3$ |
| RA-4 | H, D, alkyl | RA-4 | Ar-1 to Ar-75 | $N(Ar')_3$, $N(R^1)_3$ |
| RA-4f | H, D, alkyl | RA-4f | Ar-1 to Ar-75 | $N(Ar')_3$, $N(R^1)_3$ |
| RA-3 | H, D, alkyl | RA-3 | Ar-1 to Ar-75 | $N(Ar')_3$, $N(R^1)_3$ |
| RB | H, D, alkyl | RB | Ar-1 to Ar-75 | $N(Ar')_3$, $N(R^1)_3$ |

-continued

| $R^a$ | $R^b$ | $R^c$ | $R^d$ | $R^e$ (only if n or m is not 0 is at least one radical $R^e$, otherwise all $R^e$ are H) |
|---|---|---|---|---|
| RA-5 | H, D, alkyl | RA-5 | H, D, alkyl and Ar-1 to Ar-75 | $N(Ar')_3$, $N(R^1)_3$ |
| RA-4 | H, D, alkyl | RA-4 | H, D, alkyl and Ar-1 to Ar-75 | $N(Ar')_3$, $N(R^1)_3$ |
| RA-4f | H, D, alkyl | RA-4f | H, D, alkyl and Ar-1 to Ar-75 | $N(Ar')_3$, $N(R^1)_3$ |
| RA-3 | H, D, alkyl | RA-3 | H, D, alkyl and Ar-1 to Ar-75 | $N(Ar')_3$, $N(R^1)_3$ |
| RB | H, D, alkyl | RB | H, D, alkyl and Ar-1 to Ar-75 | $N(Ar')_3$, $N(R^1)_3$ |

The expression "alkyl" in the above tables especially encompasses straight-chain alkyl groups or branched or cyclic alkyl groups according to the definition set out above for the respective group.

The expression "aryl, heteroaryl" in the above tables especially encompasses aryl or heteroaryl groups having 5 to 40 aromatic ring atoms according to the definition set out above for the respective group, where the aryl groups preferably have 6 to 12 and more preferably 6 ring atoms and the heteroaryl groups preferably have 5 to 13 and more preferably 5 ring atoms. More preferably, heteroaryl groups comprise one or two heteroatoms, preferably N, O or S.

The designations "RA-3", "RA-4", "RA-4f", "RA-5", "Ar-1", "Ar-75" relate to the structural formulae shown above and hereinafter.

What is meant by ring formation with a group is that the two groups together form a phenyl group that may in each case be substituted by $R^1$ radicals according to the definition set out above for the respective group.

Typically, this results in formation of a naphthyl group with the phenyl group which is bonded to the nitrogen atom and is substituted by the $R^d$ and R or $R^e$ radicals. The same applies to the further definitions of ring formation.

What is meant by the word "and", particularly in the description of preferred $R^d$ groups, is that the two radicals are different, where one of the $R^d$ radicals conforms to a first definition and the second $R^d$ radical to a second definition. What is meant by the expression "aryl, heteroaryl, and phenyl ring formation with $R^e$" is that one of the $R^d$ radicals is an aryl or heteroaryl group and the second $R^d$ radical forms a phenyl ring with $R^e$. If a field does not include any word "and", all radicals represent a corresponding group. The expression "Ar-1 to Ar-75" for the $R^d$ group means that both $R^d$ radicals are an aryl or heteroaryl radical according to the formulae Ar-1 to Ar-75 above or hereinafter.

The same applies to the further use of the word "and" in the above tables.

The preferences set out for the formulae (I-1), (I-2), (I-3), (I-4), (I-5), (I-6) with regard to the different substituents $R^a$, $R^b$, $R^c$, $R^d$ and $R^e$ and if appropriate $Y^1$ are of course also applicable to the further formulae (I-7), (I-8), (I-9), (I-10), (I-11), (I-12) and (I-13) shown above.

It should also be emphasized that these preferences set out for the formulae (I-1), (I-2), (I-3), (I-4), (I-5), (I-6) with regard to the different substituents $R^a$, $R^b$, $R^c$, $R^d$ and $R^e$ and if appropriate $Y^1$ are additionally applicable to compounds with X═N, C—Y—$R^y$, $CR^b$ according to formulae (I-15) to (I-47) and (I-65) to (I-83).

If X is C—Y—$R^y$ and the $R^y$ group together with an adjacent $R^a$ radical forms a ring of formula ($T^1$), the preferences set out for the formulae (I-1), (I-2), (I-3), (I-4), (I-5), (I-6) with regard to the different substituents $R^a$, $R^b$, $R^c$, $R^d$ and $R^e$ and if appropriate $Y^1$ are correspondingly applicable, preference being given to formation of a ring between the $R^c$ groups according to the above definitions and a $T^1$ ring according to the corresponding formulae (TCY-1) to (TRA-13) or (TRA-4f), in which case, for example, a ring between two $R^c$ as per the formula (CY-1) corresponds to a $T^1$ ring as per formula (TCY-1).

Furthermore, the preferences set out above for the formulae (I-1), (I-2), (I-3), (I-4), (I-5), (I-6), especially with regard to the different substituents $R^b$, $R^d$ and $R^e$ and if appropriate $Y^1$, are applicable if the two pairs of substituents $R^a$, $R^c$ do not form a ring or a ring of the formulae (Cy-1) to (Cy-10), (RA-1) to (RA-13), (RA-1a) to (RA-4f) which is unspecified in the tables. Moreover, these preferences are applicable if both pairs of substituents $R^a$, $R^c$ form different rings of the formulae (Cy-1) to (Cy-10), (RA-1) to (RA-13), (RA-1a) to (RA-4f).

If the two pairs of substituents $R^a$, $R^c$ do not form a ring, these substituents $R^a$, $R^c$ are preferably selected from H, D, alkyl, aryl, heteroaryl as per the definition set out above for the $R^a$, $R^c$ groups.

The preferences set out above, especially for the formulae (I-1), (I-2), (I-3), (I-4), (I-5), (I-6), with regard to the different substituents $R^a$, $R^b$, $R^c$, $R^d$ and $R^e$ and if appropriate $Y^1$ and the preferences set out hereinafter in this regard for formulae (I-7) to (I-83), and in the case that the substituents $R^a$, $R^c$ do not form a ring or a ring of the formulae (Cy-1) to (Cy-10), (RA-1) to (RA-13), (RA-1a) to (RA-4f) which is unspecified in the tables, are still correspondingly applicable to compounds having exactly two or three structures of formula (I) and/or (I-1) to (I-83).

Examples of preferred compounds according to the embodiments detailed above are the compounds shown in the following table:

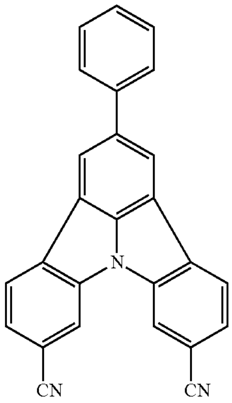 [SMILES: N#Cc1ccc2c3cc(-c4ccccc4)cc4c5ccc(C#N)cc5n(c2c1)c34]

1

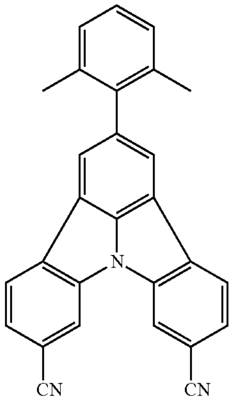 [SMILES: Cc1cccc(C)c1-c1cc2c3ccc(C#N)cc3n3c4cc(C#N)ccc4c(c1)c23]

2

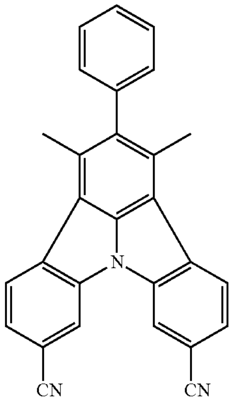 [SMILES: Cc1c(-c2ccccc2)c(C)c2c3ccc(C#N)cc3n3c4cc(C#N)ccc4c1c23]

3

-continued
4
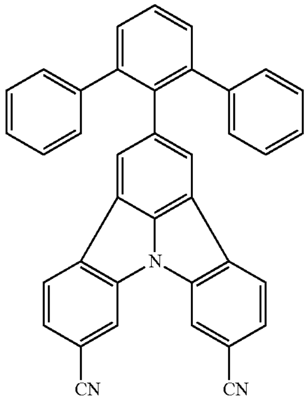 [SMILES: N#Cc1ccc2c3cc(-c4c(-c5ccccc5)cccc4-c4ccccc4)cc4c5ccc(C#N)cc5n(c2c1)c34]
5
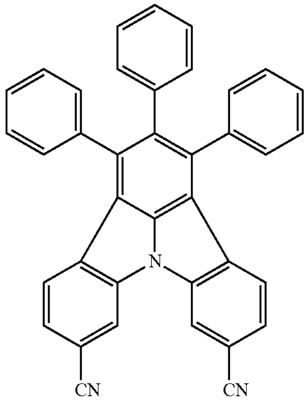 [SMILES: N#Cc1ccc2c3c(-c4ccccc4)c(-c4ccccc4)c(-c4ccccc4)c4c5ccc(C#N)cc5n(c2c1)c34]
6
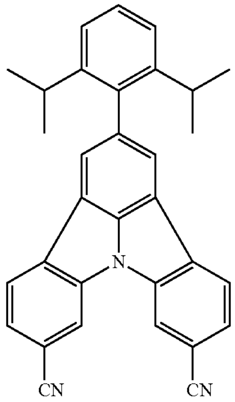 [SMILES: CC(C)c1cccc(C(C)C)c1-c1cc2c3ccc(C#N)cc3n3c4cc(C#N)ccc4c(c1)c23]
7
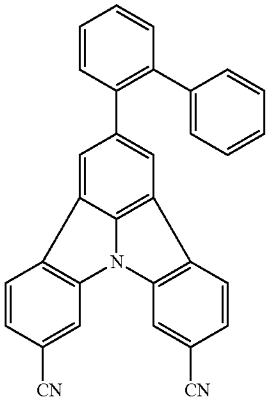 [SMILES: N#Cc1ccc2c3cc(-c4ccccc4-c4ccccc4)cc4c5ccc(C#N)cc5n(c2c1)c34]

-continued
8
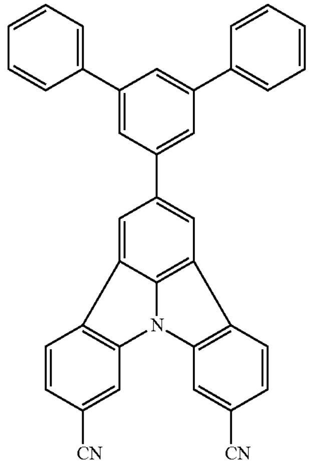 [SMILES: N#Cc1ccc2c3cc(-c4cc(-c5ccccc5)cc(-c5ccccc5)c4)cc4c5ccc(C#N)cc5n(c2c1)c34]
9
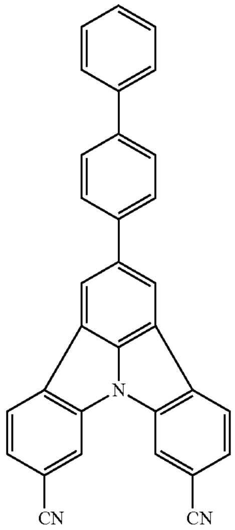 [SMILES: N#Cc1ccc2c3cc(-c4ccc(-c5ccccc5)cc4)cc4c5ccc(C#N)cc5n(c2c1)c34]
10
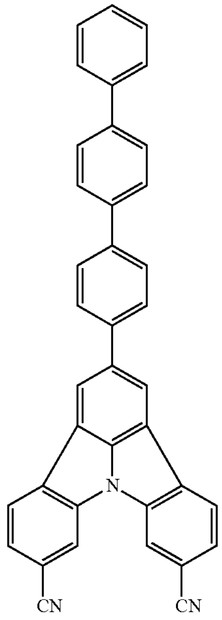 [SMILES: N#Cc1ccc2c3cc(-c4ccc(-c5ccc(-c6ccccc6)cc5)cc4)cc4c5ccc(C#N)cc5n(c2c1)c34]

-continued
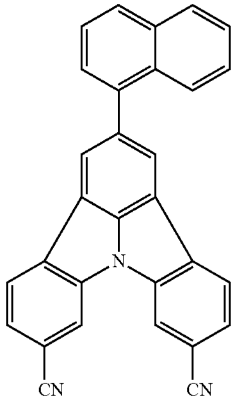 [SMILES: N#Cc1ccc2c3cc(-c4cccc5ccccc45)cc4c5ccc(C#N)cc5n(c2c1)c34]
11
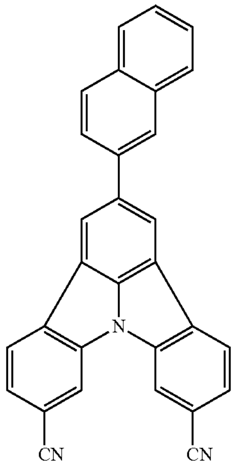 [SMILES: N#Cc1ccc2c3cc(-c4ccc5ccccc5c4)cc4c5ccc(C#N)cc5n(c2c1)c34]
12
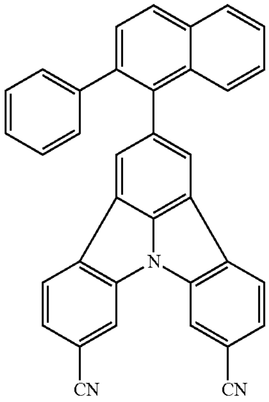 [SMILES: N#Cc1ccc2c3cc(-c4c(-c5ccccc5)ccc5ccccc45)cc4c5ccc(C#N)cc5n(c2c1)c34]
13

-continued
14
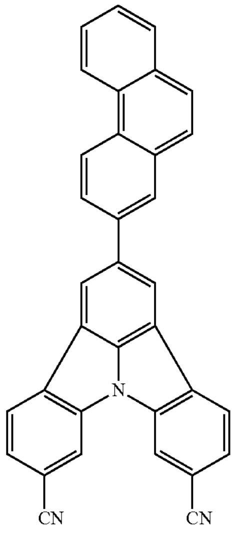 [SMILES: N#Cc1ccc2c3cc(-c4ccc5c(ccc6ccccc65)c4)cc4c5ccc(C#N)cc5n(c2c1)c34]
15
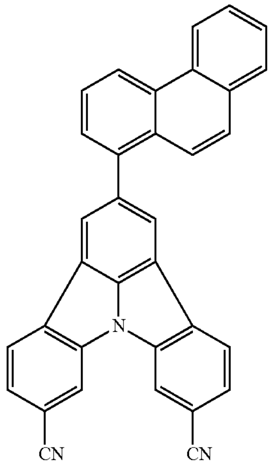 [SMILES: N#Cc1ccc2c3cc(-c4cccc5c4ccc4ccccc45)cc4c5ccc(C#N)cc5n(c2c1)c34]
16
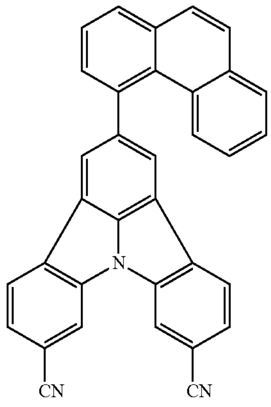 [SMILES: N#Cc1ccc2c3cc(-c4cccc5ccc6ccccc6c45)cc4c5ccc(C#N)cc5n(c2c1)c34]

-continued
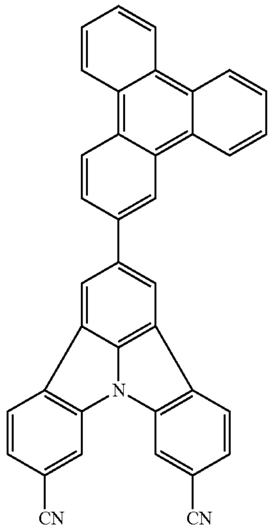 [SMILES: N#Cc1ccc2c3cc(-c4ccc5c6ccccc6c6ccccc6c5c4)cc4c5ccc(C#N)cc5n(c2c1)c34]
17
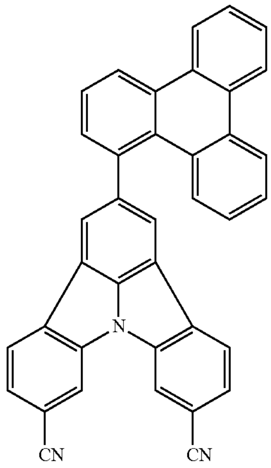 [SMILES: N#Cc1ccc2c3cc(-c4cccc5c6ccccc6c6ccccc6c45)cc4c5ccc(C#N)cc5n(c2c1)c34]
18
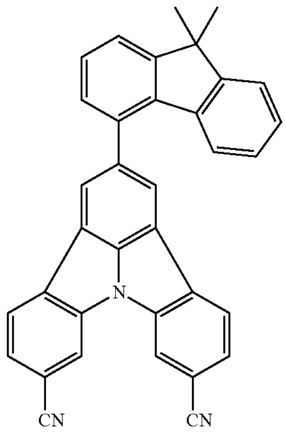 [SMILES: CC1(C)c2ccccc2-c2c(-c3cc4c5ccc(C#N)cc5n5c6cc(C#N)ccc6c(c3)c45)cccc21]
19

-continued
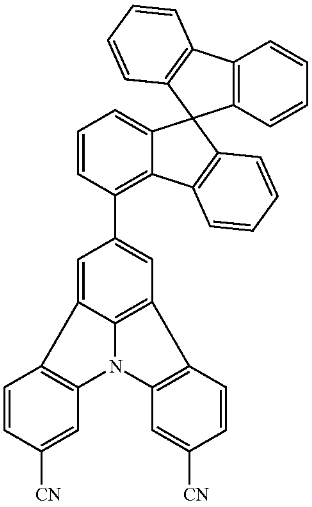 [SMILES: N#Cc1ccc2c3cc(-c4cccc5c4-c4ccccc4C54c5ccccc5-c5ccccc54)cc4c5ccc(C#N)cc5n(c2c1)c34]
20
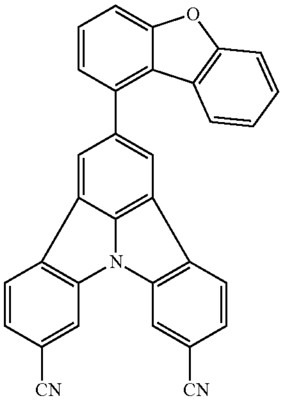 [SMILES: N#Cc1ccc2c3cc(-c4cccc5oc6ccccc6c45)cc4c5ccc(C#N)cc5n(c2c1)c34]
21
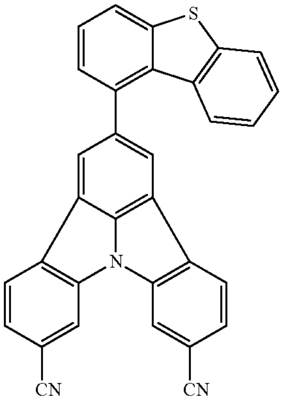 [SMILES: N#Cc1ccc2c3cc(-c4cccc5sc6ccccc6c45)cc4c5ccc(C#N)cc5n(c2c1)c34]
22

-continued
23
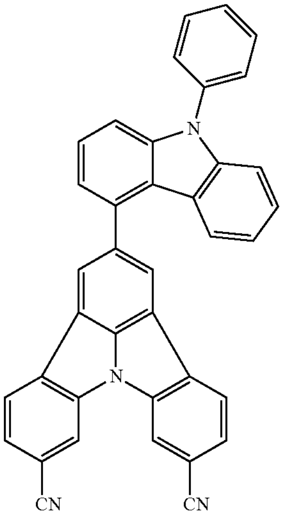 [SMILES: N#Cc1ccc2c3cc(-c4cccc5c4c4ccccc4n5-c4ccccc4)cc4c5ccc(C#N)cc5n(c2c1)c34]
24
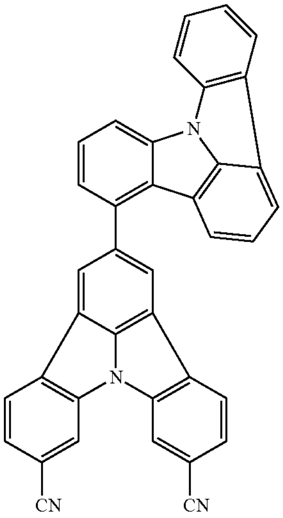 [SMILES: N#Cc1ccc2c3cc(-c4cccc5c4c4cccc6c7ccccc7n5c64)cc4c5ccc(C#N)cc5n(c2c1)c34]
25
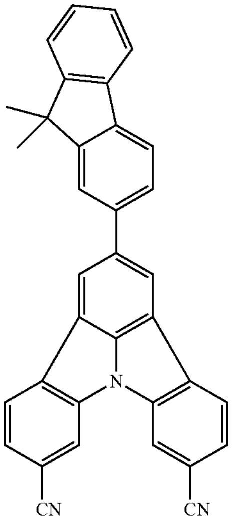 [SMILES: CC1(C)c2ccccc2-c2ccc(-c3cc4c5ccc(C#N)cc5n5c6cc(C#N)ccc6c(c3)c45)cc21]

-continued
26
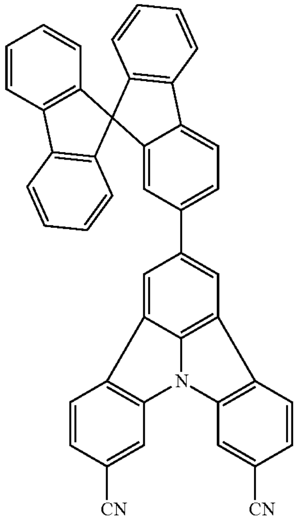 [SMILES: N#Cc1ccc2c3cc(-c4ccc5c(c4)C4(c6ccccc6-c6ccccc64)c4ccccc4-5)cc4c5ccc(C#N)cc5n(c2c1)c34]
27
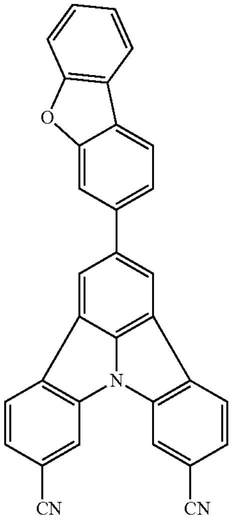 [SMILES: N#Cc1ccc2c3cc(-c4ccc5c(c4)oc4ccccc45)cc4c5ccc(C#N)cc5n(c2c1)c34]
28
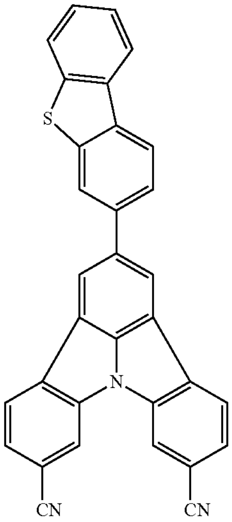 [SMILES: N#Cc1ccc2c3cc(-c4ccc5c(c4)sc4ccccc45)cc4c5ccc(C#N)cc5n(c2c1)c34]

-continued
29
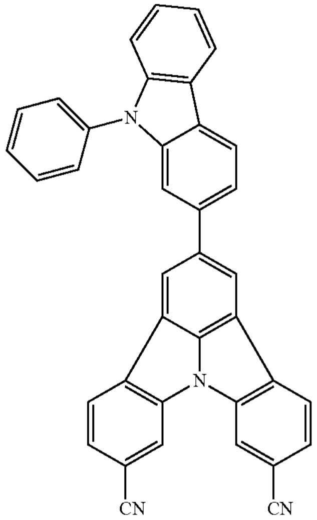 [SMILES: N#Cc1ccc2c3cc(-c4ccc5c6ccccc6n(-c6ccccc6)c5c4)cc4c5ccc(C#N)cc5n(c2c1)c34]
30
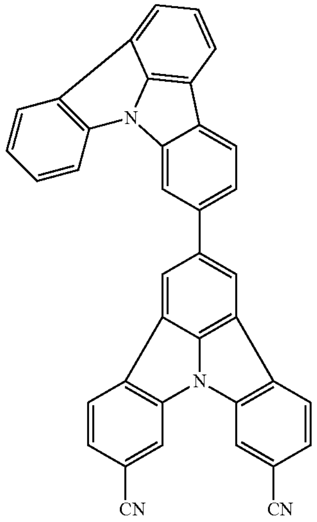 [SMILES: N#Cc1ccc2c3cc(-c4ccc5c6cccc7c8ccccc8n(c5c4)c76)cc4c5ccc(C#N)cc5n(c2c1)c34]
31
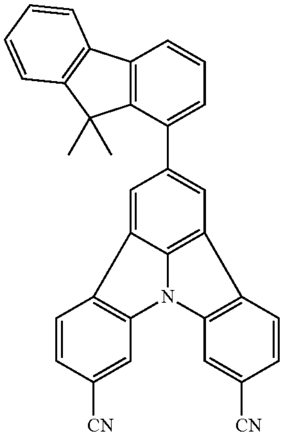 [SMILES: CC1(C)c2ccccc2-c2cccc(-c3cc4c5ccc(C#N)cc5n5c6cc(C#N)ccc6c(c3)c45)c21]

-continued
32
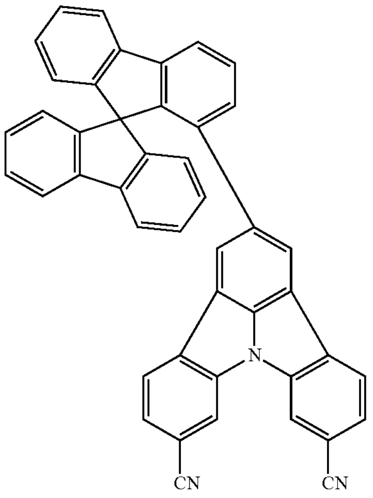 [SMILES: N#Cc1ccc2c3cc(-c4cccc5c4C4(c6ccccc6-c6ccccc64)c4ccccc4-5)cc4c5ccc(C#N)cc5n(c2c1)c34]
33
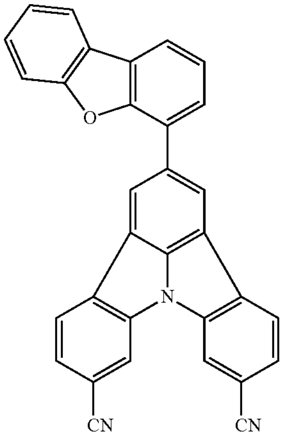 [SMILES: N#Cc1ccc2c3cc(-c4cccc5c4oc4ccccc45)cc4c5ccc(C#N)cc5n(c2c1)c34]
34
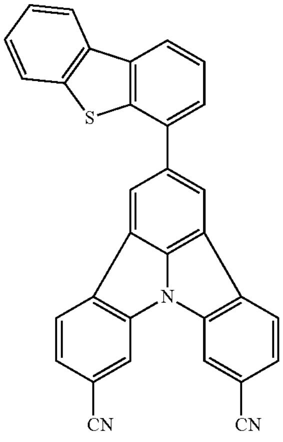 [SMILES: N#Cc1ccc2c3cc(-c4cccc5c4sc4ccccc45)cc4c5ccc(C#N)cc5n(c2c1)c34]

-continued
35
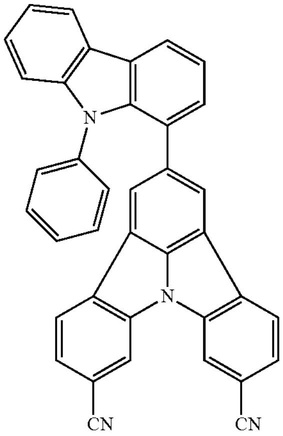 [SMILES: N#Cc1ccc2c3cc(-c4cccc5c6ccccc6n(-c6ccccc6)c45)cc4c5ccc(C#N)cc5n(c2c1)c34]
36
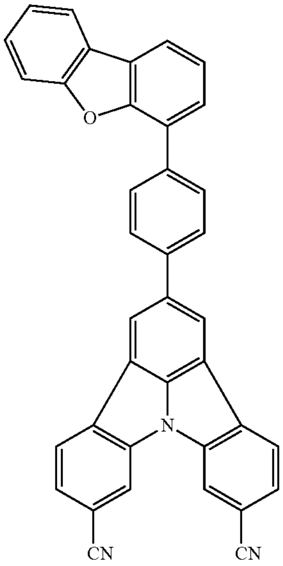 [SMILES: N#Cc1ccc2c3cc(-c4ccc(-c5cccc6c5oc5ccccc56)cc4)cc4c5ccc(C#N)cc5n(c2c1)c34]
37
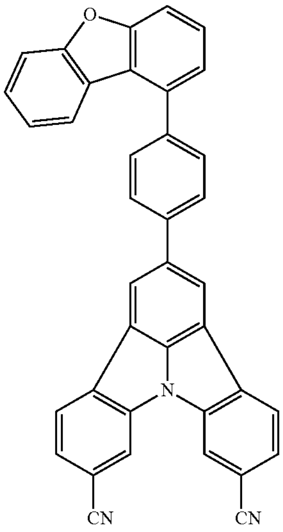 [SMILES: N#Cc1ccc2c3cc(-c4ccc(-c5cccc6oc7ccccc7c56)cc4)cc4c5ccc(C#N)cc5n(c2c1)c34]

-continued
38
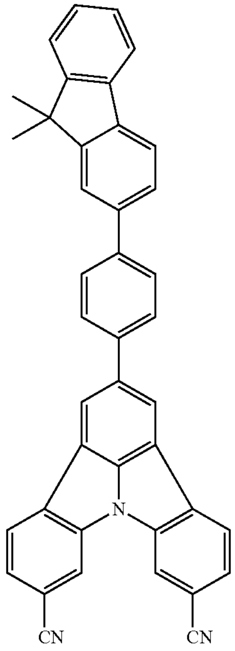 [SMILES: CC1(C)c2ccccc2-c2ccc(-c3ccc(-c4cc5c6ccc(C#N)cc6n6c7cc(C#N)ccc7c(c4)c56)cc3)cc21]
39
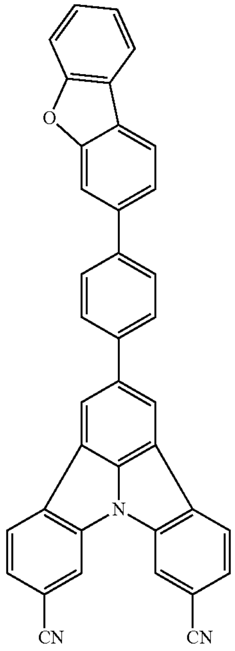 [SMILES: N#Cc1ccc2c3cc(-c4ccc(-c5ccc6c(c5)oc5ccccc56)cc4)cc4c5ccc(C#N)cc5n(c2c1)c34]

-continued
40
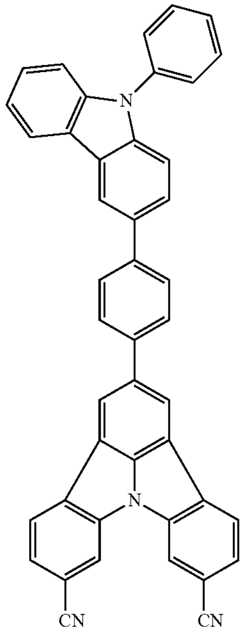 [SMILES: N#Cc1ccc2c3cc(-c4ccc(-c5ccc6c(c5)c5ccccc5n6-c5ccccc5)cc4)cc4c5ccc(C#N)cc5n(c2c1)c34]
41
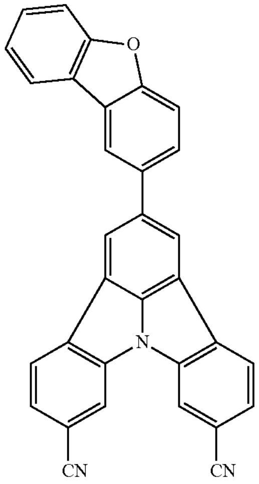 [SMILES: N#Cc1ccc2c3cc(-c4ccc5oc6ccccc6c5c4)cc4c5ccc(C#N)cc5n(c2c1)c34]
42
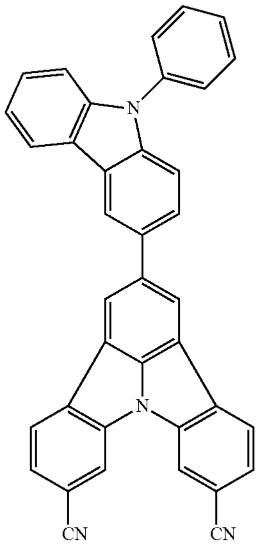 [SMILES: N#Cc1ccc2c3cc(-c4ccc5c(c4)c4ccccc4n5-c4ccccc4)cc4c5ccc(C#N)cc5n(c2c1)c34]

-continued
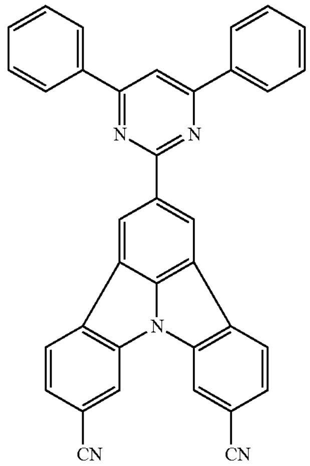 [SMILES: N#Cc1ccc2c3cc(-c4nc(-c5ccccc5)cc(-c5ccccc5)n4)cc4c5ccc(C#N)cc5n(c2c1)c34]
43
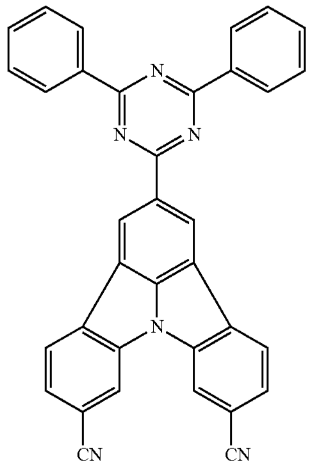 [SMILES: N#Cc1ccc2c3cc(-c4nc(-c5ccccc5)nc(-c5ccccc5)n4)cc4c5ccc(C#N)cc5n(c2c1)c34]
44
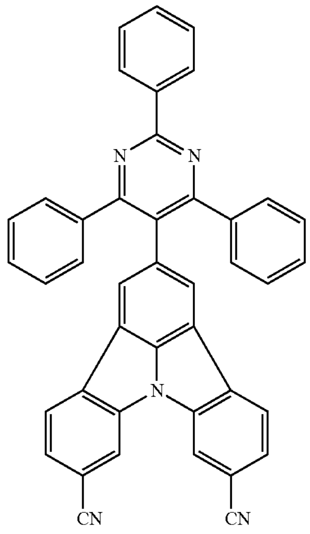 [SMILES: N#Cc1ccc2c3cc(-c4c(-c5ccccc5)nc(-c5ccccc5)nc4-c4ccccc4)cc4c5ccc(C#N)cc5n(c2c1)c34]
45

-continued
46
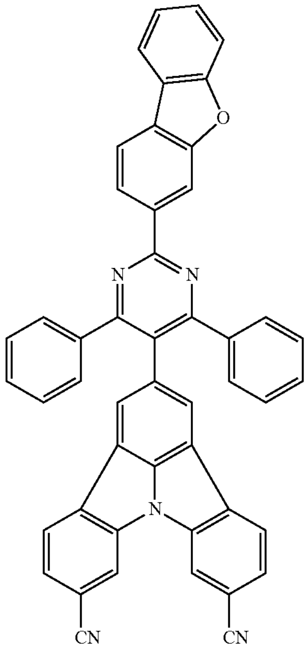 [SMILES: N#Cc1ccc2c3cc(-c4c(-c5ccccc5)nc(-c5ccc6c(c5)oc5ccccc56)nc4-c4ccccc4)cc4c5ccc(C#N)cc5n(c2c1)c34]
47
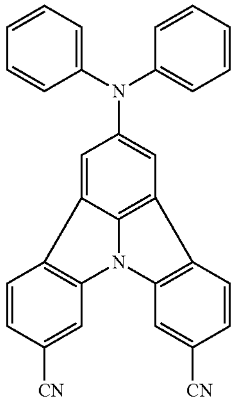 [SMILES: N#Cc1ccc2c3cc(N(c4ccccc4)c4ccccc4)cc4c5ccc(C#N)cc5n(c2c1)c34]
48
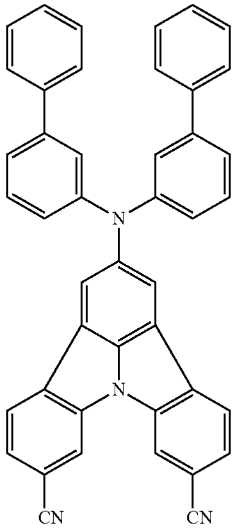 [SMILES: N#Cc1ccc2c3cc(N(c4cccc(-c5ccccc5)c4)c4cccc(-c5ccccc5)c4)cc4c5ccc(C#N)cc5n(c2c1)c34]

-continued
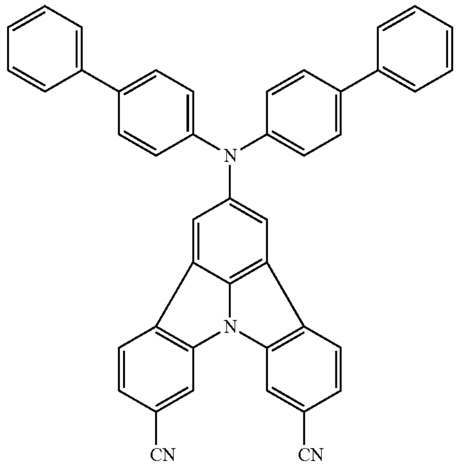 [SMILES: N#Cc1ccc2c3cc(N(c4ccc(-c5ccccc5)cc4)c4ccc(-c5ccccc5)cc4)cc4c5ccc(C#N)cc5n(c2c1)c34]
49
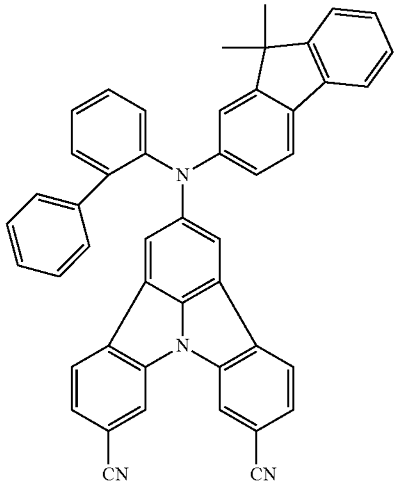 [SMILES: CC1(C)c2ccccc2-c2ccc(N(c3cc4c5ccc(C#N)cc5n5c6cc(C#N)ccc6c(c3)c45)c3ccccc3-c3ccccc3)cc21]
50
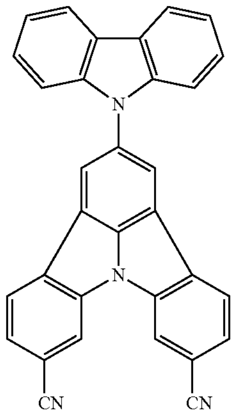 [SMILES: N#Cc1ccc2c3cc(-n4c5ccccc5c5ccccc54)cc4c5ccc(C#N)cc5n(c2c1)c34]
51

-continued
51
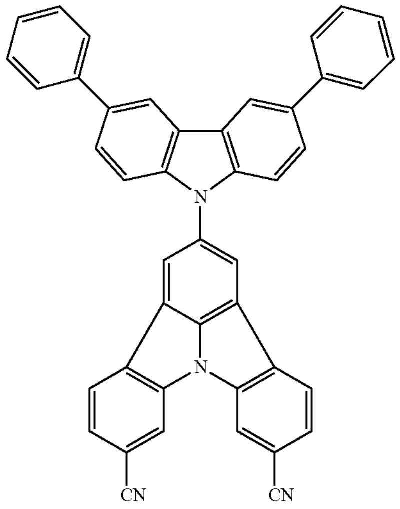 [SMILES: N#Cc1ccc2c3cc(-n4c5ccc(-c6ccccc6)cc5c5cc(-c6ccccc6)ccc54)cc4c5ccc(C#N)cc5n(c2c1)c34]
52
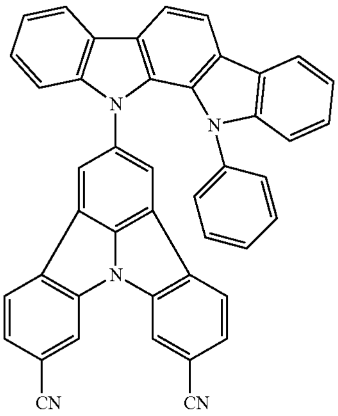 [SMILES: N#Cc1ccc2c3cc(-n4c5ccccc5c5ccc6c7ccccc7n(-c7ccccc7)c6c54)cc4c5ccc(C#N)cc5n(c2c1)c34]
53
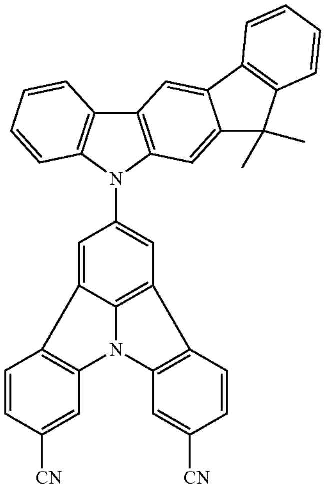 [SMILES: CC1(C)c2ccccc2-c2cc3c4ccccc4n(-c4cc5c6ccc(C#N)cc6n6c7cc(C#N)ccc7c(c4)c56)c3cc21]

-continued
54
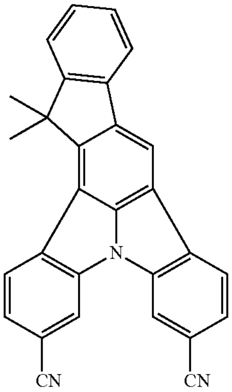 [SMILES: CC1(C)c2ccccc2-c2cc3c4ccc(C#N)cc4n4c5cc(C#N)ccc5c(c21)c34]
55
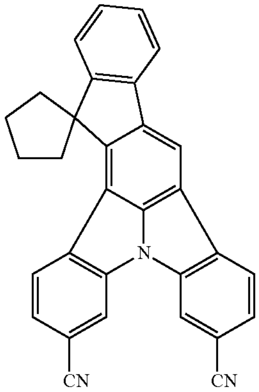 [SMILES: N#Cc1ccc2c3cc4c(c5c6ccc(C#N)cc6n(c2c1)c35)C1(CCCC1)c1ccccc1-4]
56
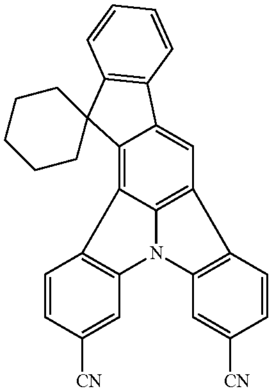 [SMILES: N#Cc1ccc2c3cc4c(c5c6ccc(C#N)cc6n(c2c1)c35)C1(CCCCC1)c1ccccc1-4]
57
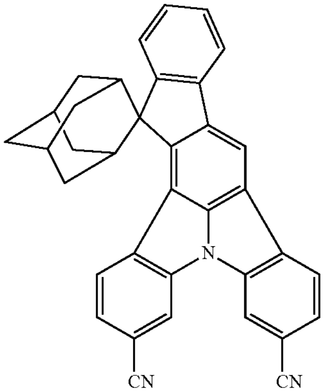 [SMILES: N#Cc1ccc2c3cc4c(c5c6ccc(C#N)cc6n(c2c1)c35)C1(c2ccccc2-4)C2CC3CC(C2)CC1C3]

-continued
58
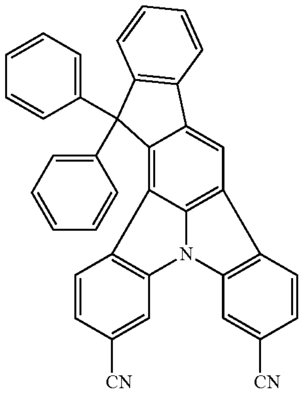 [SMILES: N#Cc1ccc2c3cc4c(c5c6ccc(C#N)cc6n(c2c1)c35)C(c1ccccc1)(c1ccccc1)c1ccccc1-4]
59
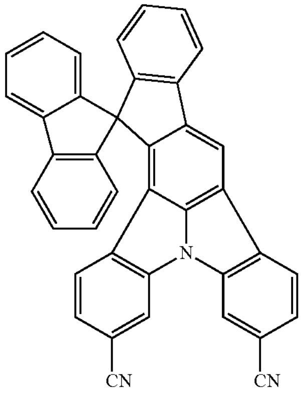 [SMILES: N#Cc1ccc2c3cc4c(c5c6ccc(C#N)cc6n(c2c1)c35)C1(c2ccccc2-c2ccccc21)c1ccccc1-4]
60
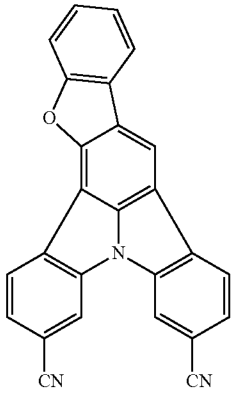 [SMILES: N#Cc1ccc2c3cc4c5ccccc5oc4c4c5ccc(C#N)cc5n(c2c1)c34]
61
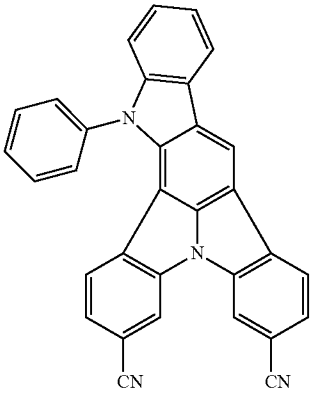 [SMILES: N#Cc1ccc2c3cc4c5ccccc5n(-c5ccccc5)c4c4c5ccc(C#N)cc5n(c2c1)c34]

-continued
62
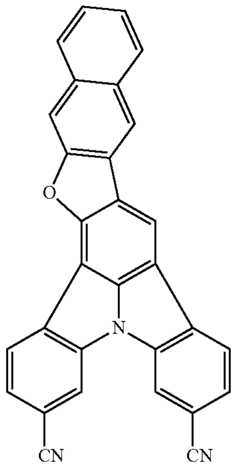 [SMILES: N#Cc1ccc2c3cc4c5cc6ccccc6cc5oc4c4c5ccc(C#N)cc5n(c2c1)c34]
63
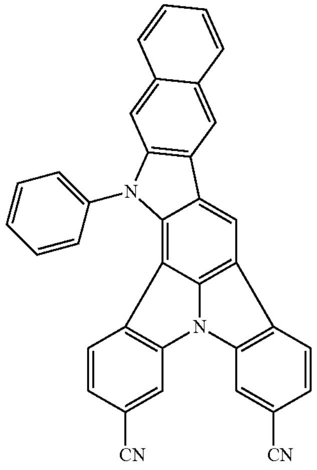 [SMILES: N#Cc1ccc2c3cc4c5cc6ccccc6cc5n(-c5ccccc5)c4c4c5ccc(C#N)cc5n(c2c1)c34]
64
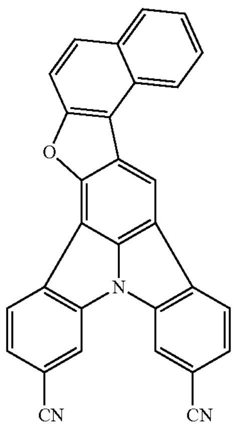 [SMILES: N#Cc1ccc2c3cc4c(oc5ccc6ccccc6c54)c4c5ccc(C#N)cc5n(c2c1)c34]

-continued
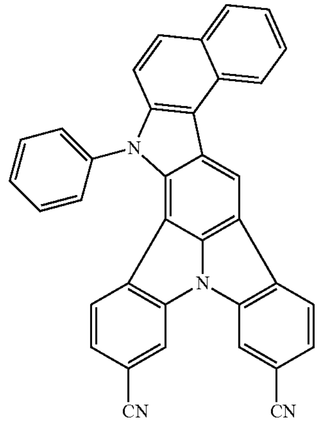 [SMILES: N#Cc1ccc2c3cc4c5c6ccccc6ccc5n(-c5ccccc5)c4c4c5ccc(C#N)cc5n(c2c1)c34]
65
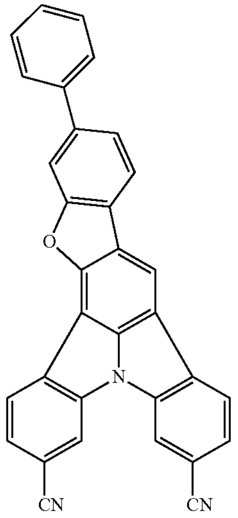 [SMILES: N#Cc1ccc2c3cc4c5ccc(-c6ccccc6)cc5oc4c4c5ccc(C#N)cc5n(c2c1)c34]
66
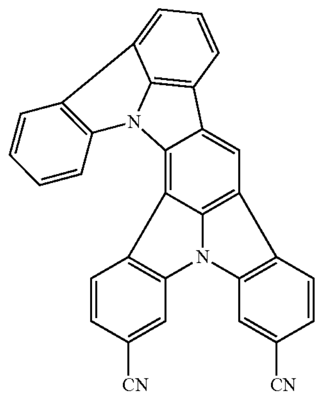 [SMILES: N#Cc1ccc2c3cc4c5cccc6c7ccccc7n(c65)c4c4c5ccc(C#N)cc5n(c2c1)c34]
67

-continued
68
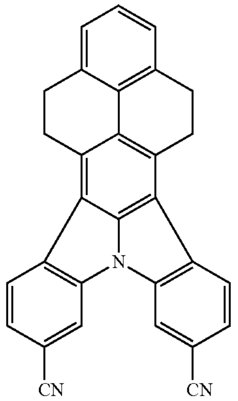 [SMILES: N#Cc1ccc2c3c4c5c(c6c7ccc(C#N)cc7n(c2c1)c36)CCc1cccc(c1-5)CC4]
69
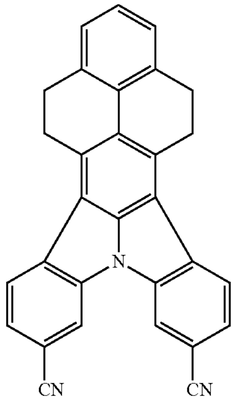 [SMILES: N#Cc1ccc2c3c4c5c(c6c7ccc(C#N)cc7n(c2c1)c36)CCc1cccc(c1-5)CC4]
70
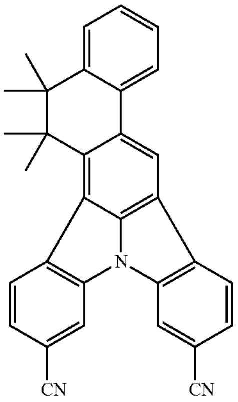 [SMILES: CC1(C)c2ccccc2-c2cc3c4ccc(C#N)cc4n4c5cc(C#N)ccc5c(c2C1(C)C)c34]
71
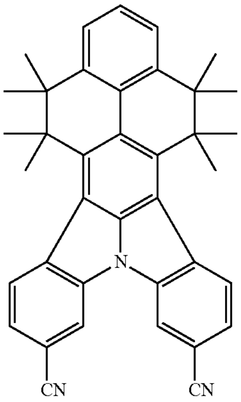

-continued
72
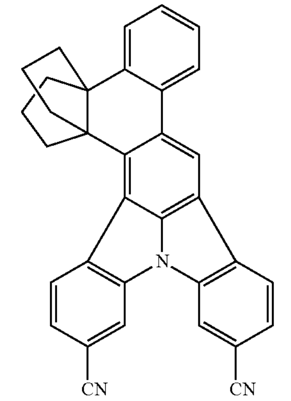 [SMILES: N#Cc1ccc2c3cc4c(c5c6ccc(C#N)cc6n(c2c1)c35)C12CCCC1(CCC2)c1ccccc1-4]
73
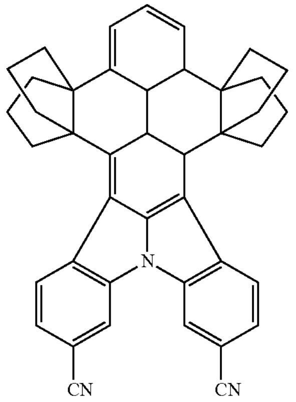 [SMILES: N#Cc1ccc2c3c4c(c5ccc(C#N)cc5n4c2c1)=C1C2C4C(=CC=CC4C45CCCC4(CCC5)C32)C23CCCC12CCC3]
74
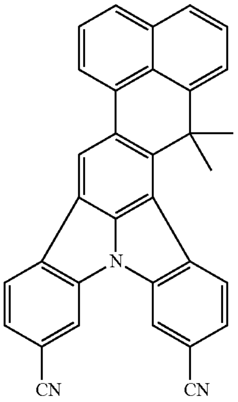 [SMILES: CC1(C)c2cccc3cccc(c23)-c2cc3c4ccc(C#N)cc4n4c5cc(C#N)ccc5c(c21)c34]
75
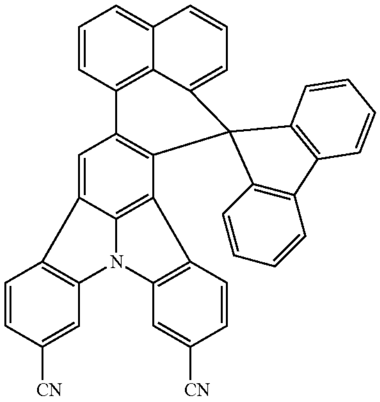 [SMILES: N#Cc1ccc2c3cc4c(c5c6ccc(C#N)cc6n(c2c1)c35)C1(c2ccccc2-c2ccccc21)c1cccc2cccc-4c12]

-continued
76
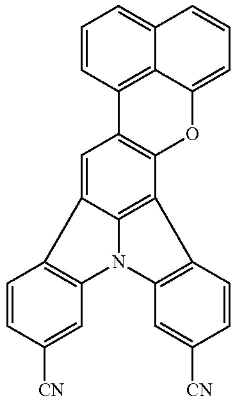 [SMILES: N#Cc1ccc2c3cc4c5cccc6cccc(oc4c4c7ccc(C#N)cc7n(c2c1)c34)c65]
77
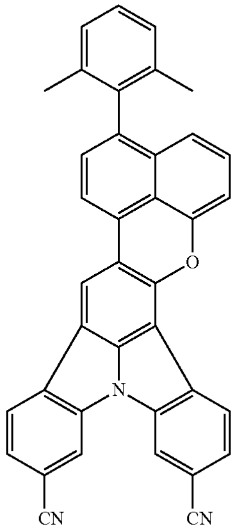 [SMILES: Cc1cccc(C)c1-c1ccc2c3cc4c5ccc(C#N)cc5n5c6cc(C#N)ccc6c(c3oc3cccc1c32)c45]
78
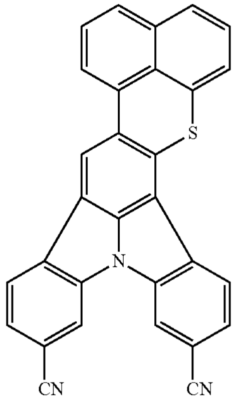

-continued
79
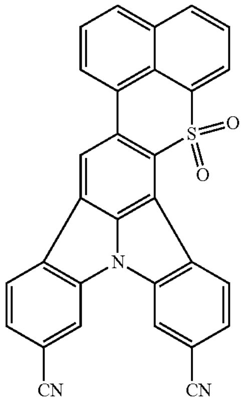 [SMILES: N#Cc1ccc2c3cc4c(c5c6ccc(C#N)cc6n(c2c1)c35)S(=O)(=O)c1cccc2cccc-4c12]
80
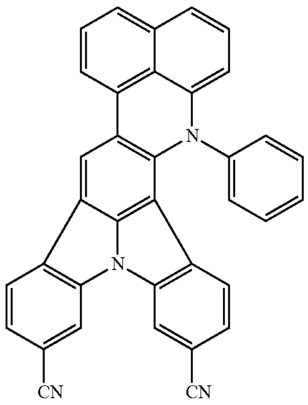 [SMILES: N#Cc1ccc2c3cc4c5cccc6cccc(c65)n(-c5ccccc5)c4c4c5ccc(C#N)cc5n(c2c1)c34]
81
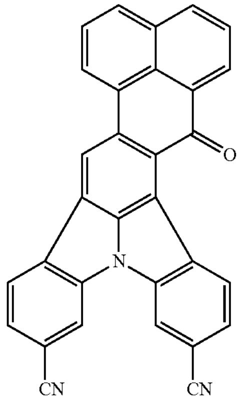 [SMILES: N#Cc1ccc2c3cc4c5cccc6cccc(c(=O)c4c4c7ccc(C#N)cc7n(c2c1)c34)c65]
82
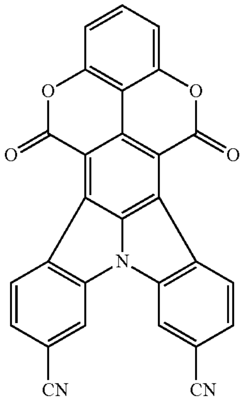 [SMILES: N#Cc1ccc2c3c4c(=O)oc5cccc6oc(=O)c(c4c56)c4c5ccc(C#N)cc5n(c2c1)c34]

-continued
83
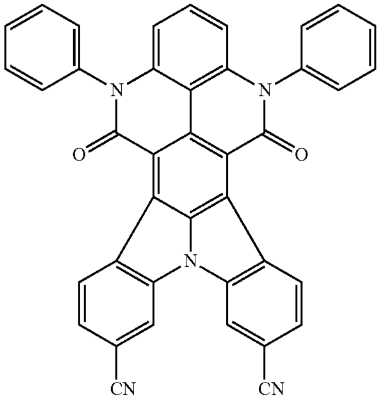 [SMILES: N#Cc1ccc2c3c4c(=O)n(-c5ccccc5)c5cccc6c5c4c(c(=O)n6-c4ccccc4)c4c5ccc(C#N)cc5n(c2c1)c34]
84
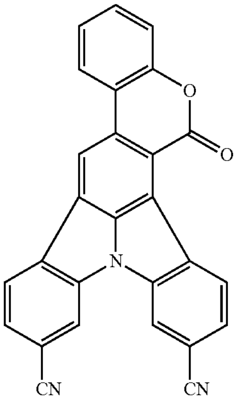 [SMILES: N#Cc1ccc2c3cc4c5ccccc5oc(=O)c4c4c5ccc(C#N)cc5n(c2c1)c34]
85
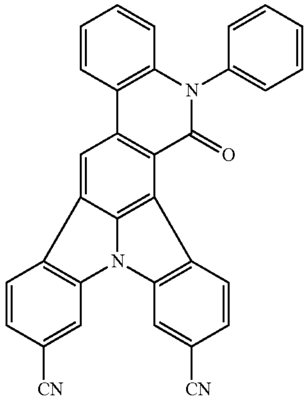 [SMILES: N#Cc1ccc2c3cc4c5ccccc5n(-c5ccccc5)c(=O)c4c4c5ccc(C#N)cc5n(c2c1)c34]
86
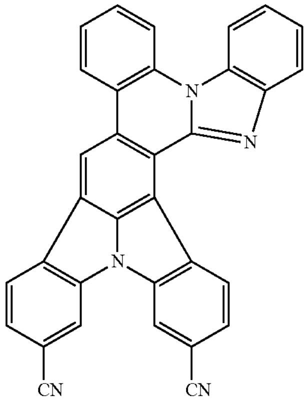 [SMILES: N#Cc1ccc2c3cc4c5ccccc5n5c6ccccc6nc5c4c4c5ccc(C#N)cc5n(c2c1)c34]

-continued
87
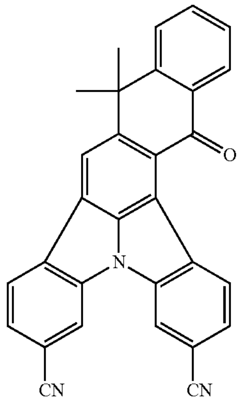 [SMILES: CC1(C)c2ccccc2C(=O)c2c1cc1c3ccc(C#N)cc3n3c4cc(C#N)ccc4c2c13]
88
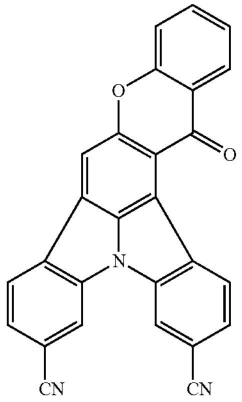 [SMILES: N#Cc1ccc2c3cc4oc5ccccc5c(=O)c4c4c5ccc(C#N)cc5n(c2c1)c34]
89
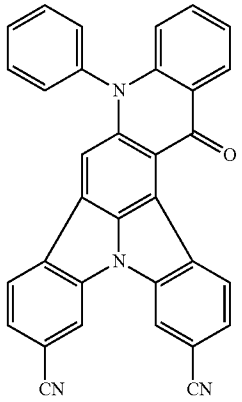 [SMILES: N#Cc1ccc2c3cc4c(c(=O)c5ccccc5n4-c4ccccc4)c4c5ccc(C#N)cc5n(c2c1)c34]
90
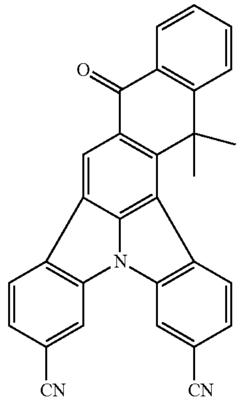 [SMILES: CC1(C)c2ccccc2C(=O)c2cc3c4ccc(C#N)cc4n4c5cc(C#N)ccc5c(c21)c34]

-continued
91
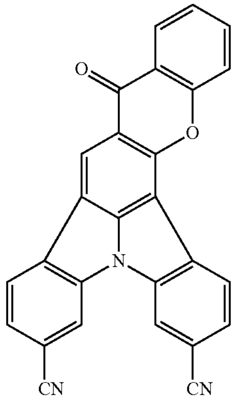 [SMILES: N#Cc1ccc2c3cc4c(=O)c5ccccc5oc4c4c5ccc(C#N)cc5n(c2c1)c34]
92
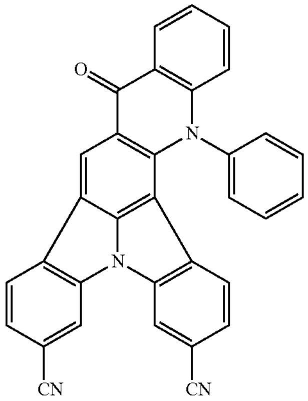 [SMILES: N#Cc1ccc2c3cc4c(=O)c5ccccc5n(-c5ccccc5)c4c4c5ccc(C#N)cc5n(c2c1)c34]
93
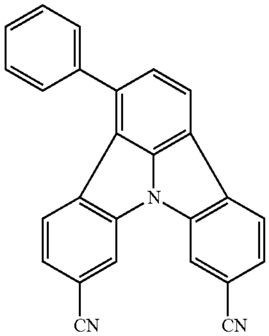 [SMILES: N#Cc1ccc2c3ccc(-c4ccccc4)c4c5ccc(C#N)cc5n(c2c1)c34]
94
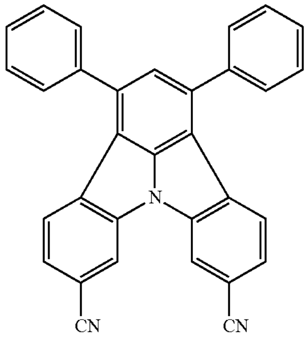 [SMILES: N#Cc1ccc2c3c(-c4ccccc4)cc(-c4ccccc4)c4c5ccc(C#N)cc5n(c2c1)c34]

-continued
95
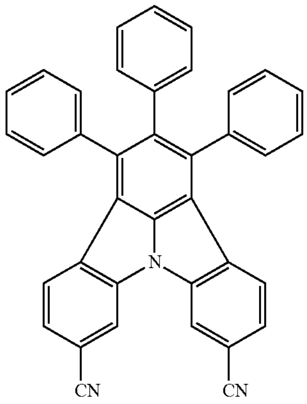 [SMILES: N#Cc1ccc2c3c(-c4ccccc4)c(-c4ccccc4)c(-c4ccccc4)c4c5ccc(C#N)cc5n(c2c1)c34]
96
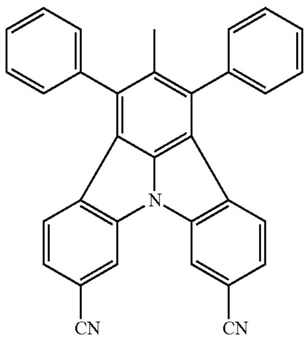 [SMILES: Cc1c(-c2ccccc2)c2c3ccc(C#N)cc3n3c4cc(C#N)ccc4c(c1-c1ccccc1)c23]
97
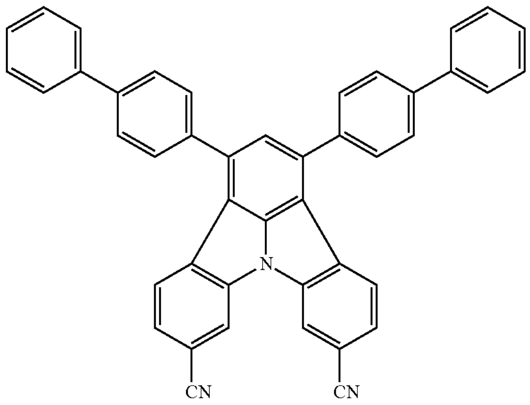 [SMILES: N#Cc1ccc2c3c(-c4ccc(-c5ccccc5)cc4)cc(-c4ccc(-c5ccccc5)cc4)c4c5ccc(C#N)cc5n(c2c1)c34]
98
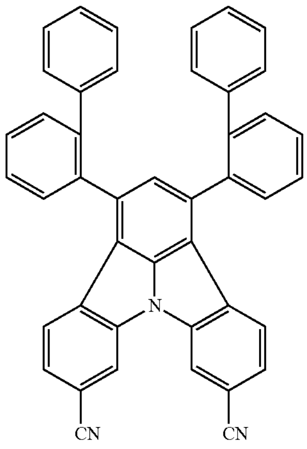 [SMILES: N#Cc1ccc2c3c(-c4ccccc4-c4ccccc4)cc(-c4ccccc4-c4ccccc4)c4c5ccc(C#N)cc5n(c2c1)c34]

-continued
99
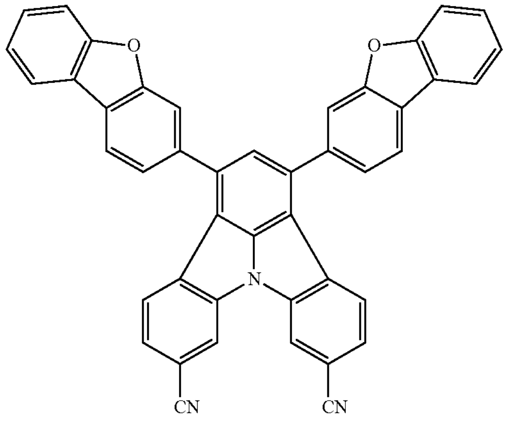 [SMILES: N#Cc1ccc2c3c(-c4ccc5c(c4)oc4ccccc45)cc(-c4ccc5c(c4)oc4ccccc45)c4c5ccc(C#N)cc5n(c2c1)c34]
100
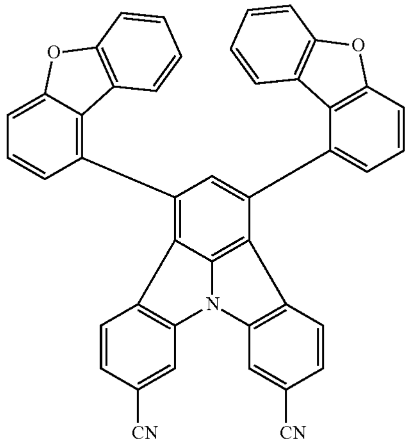 [SMILES: N#Cc1ccc2c3c(-c4cccc5oc6ccccc6c45)cc(-c4cccc5oc6ccccc6c45)c4c5ccc(C#N)cc5n(c2c1)c34]
101
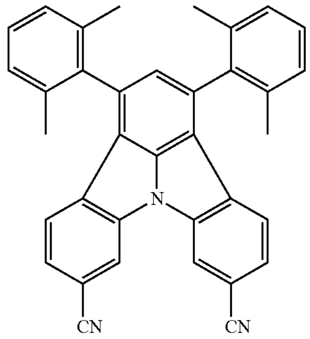 [SMILES: Cc1cccc(C)c1-c1cc(-c2c(C)cccc2C)c2c3ccc(C#N)cc3n3c4cc(C#N)ccc4c1c23]
102
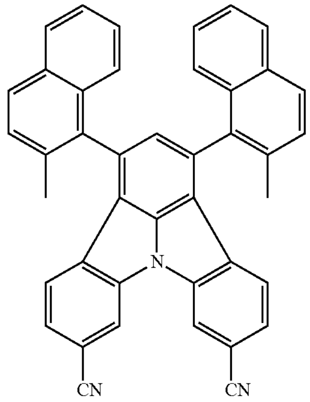 [SMILES: Cc1ccc2ccccc2c1-c1cc(-c2c(C)ccc3ccccc23)c2c3ccc(C#N)cc3n3c4cc(C#N)ccc4c1c23]

-continued
103
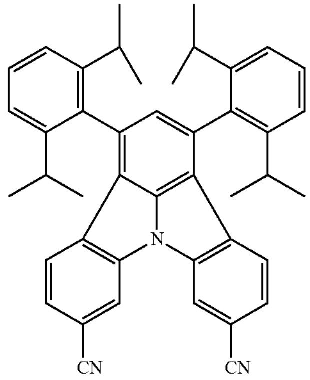 [SMILES: CC(C)c1cccc(C(C)C)c1-c1cc(-c2c(C(C)C)cccc2C(C)C)c2c3ccc(C#N)cc3n3c4cc(C#N)ccc4c1c23]
104
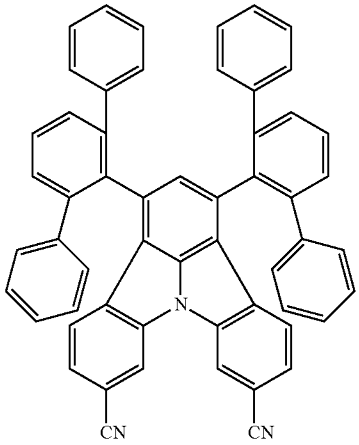 [SMILES: N#Cc1ccc2c3c(-c4c(-c5ccccc5)cccc4-c4ccccc4)cc(-c4c(-c5ccccc5)cccc4-c4ccccc4)c4c5ccc(C#N)cc5n(c2c1)c34]
105
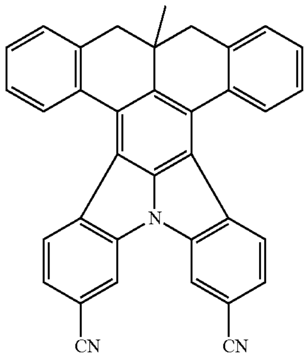 [SMILES: CC12Cc3ccccc3-c3c1c(c1c4ccc(C#N)cc4n4c5cc(C#N)ccc5c3c14)-c1ccccc1C2]
106
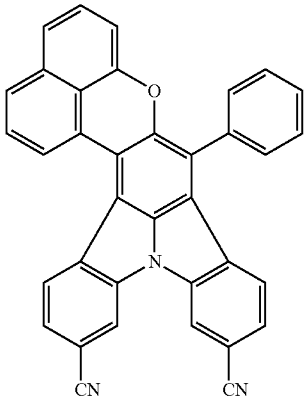 [SMILES: N#Cc1ccc2c3c(-c4ccccc4)c4oc5cccc6cccc(c65)c4c4c5ccc(C#N)cc5n(c2c1)c34]

-continued
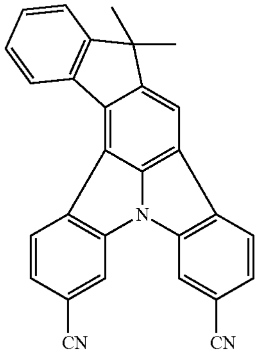 [SMILES: CC1(C)c2ccccc2-c2c1cc1c3ccc(C#N)cc3n3c4cc(C#N)ccc4c2c13]
107
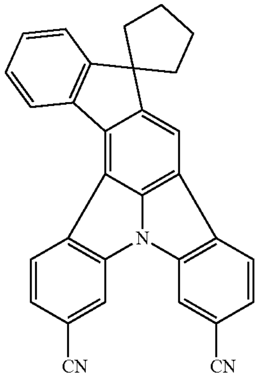 [SMILES: N#Cc1ccc2c3cc4c(c5c6ccc(C#N)cc6n(c2c1)c35)-c1ccccc1C41CCCC1]
108
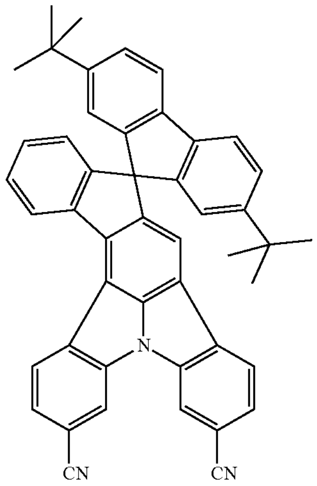 [SMILES: CC(C)(C)c1ccc2c(c1)C1(c3cc(C(C)(C)C)ccc3-2)c2ccccc2-c2c1cc1c3ccc(C#N)cc3n3c4cc(C#N)ccc4c2c13]
109
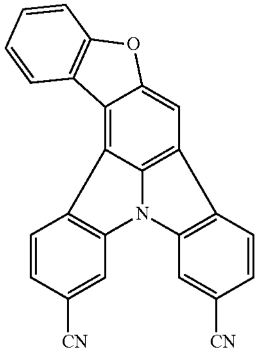 [SMILES: N#Cc1ccc2c3cc4oc5ccccc5c4c4c5ccc(C#N)cc5n(c2c1)c34]
110

-continued
111
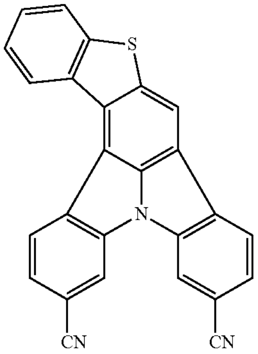 [SMILES: N#Cc1ccc2c3cc4sc5ccccc5c4c4c5ccc(C#N)cc5n(c2c1)c34]
112
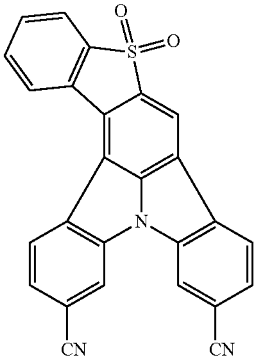 [SMILES: N#Cc1ccc2c3cc4c(c5c6ccc(C#N)cc6n(c2c1)c35)-c1ccccc1S4(=O)=O]
113
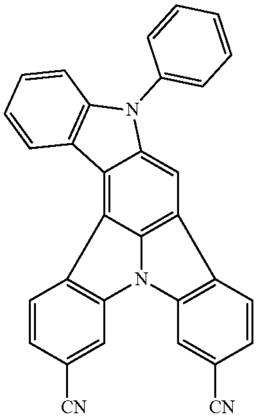 [SMILES: N#Cc1ccc2c3cc4c(c5ccccc5n4-c4ccccc4)c4c5ccc(C#N)cc5n(c2c1)c34]
114
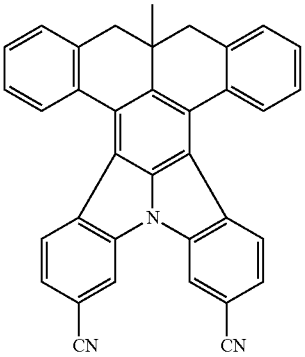 [SMILES: CC12Cc3ccccc3-c3c1c(c1c4ccc(C#N)cc4n4c5cc(C#N)ccc5c3c14)-c1ccccc1C2]

-continued
115
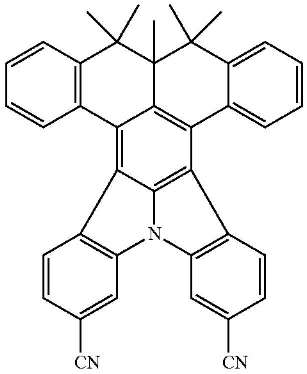 [SMILES: CC1(C)c2ccccc2-c2c3c(c4c5ccc(C#N)cc5n5c6cc(C#N)ccc6c2c45)-c2ccccc2C(C)(C)C31C]
116
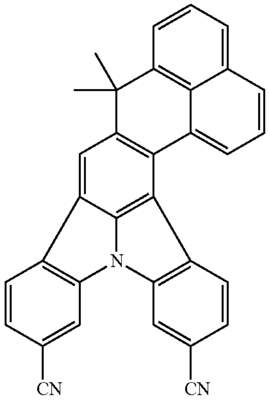 [SMILES: CC1(C)c2cc3c4ccc(C#N)cc4n4c5cc(C#N)ccc5c(c2-c2cccc5cccc1c25)c34]
117
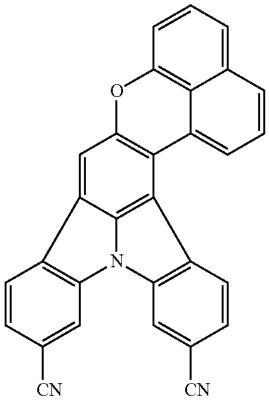 [SMILES: N#Cc1ccc2c3cc4oc5cccc6cccc(c65)c4c4c5ccc(C#N)cc5n(c2c1)c34]
118
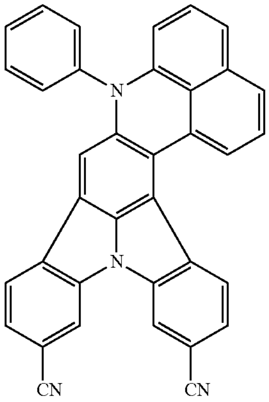 [SMILES: N#Cc1ccc2c3cc4c(c5cccc6cccc(c65)n4-c4ccccc4)c4c5ccc(C#N)cc5n(c2c1)c34]

-continued
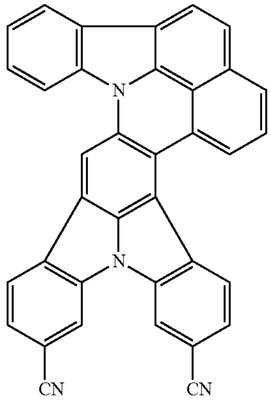 [SMILES: N#Cc1ccc2c3cc4c(c5cccc6ccc7c8ccccc8n4c7c65)c4c5ccc(C#N)cc5n(c2c1)c34]
119
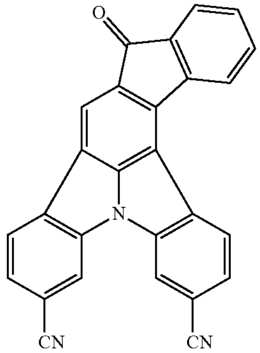 [SMILES: N#Cc1ccc2c3cc4c(c5c6ccc(C#N)cc6n(c2c1)c35)-c1ccccc1C4=O]
120
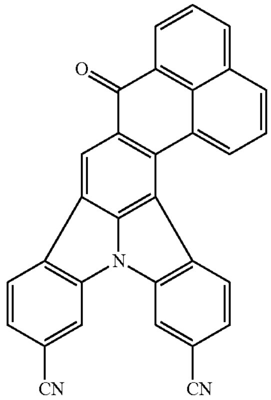 [SMILES: N#Cc1ccc2c3cc4c(=O)c5cccc6cccc(c65)c4c4c5ccc(C#N)cc5n(c2c1)c34]
121
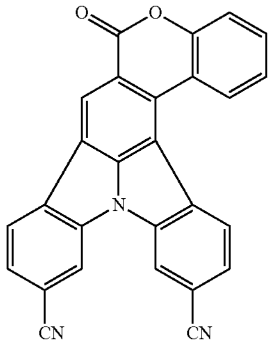 [SMILES: N#Cc1ccc2c3cc4c(=O)oc5ccccc5c4c4c5ccc(C#N)cc5n(c2c1)c34]
122

-continued
123
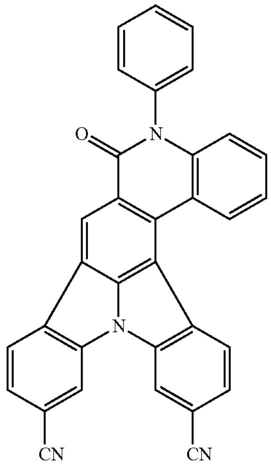 [SMILES: N#Cc1ccc2c3cc4c(=O)n(-c5ccccc5)c5ccccc5c4c4c5ccc(C#N)cc5n(c2c1)c34]
124
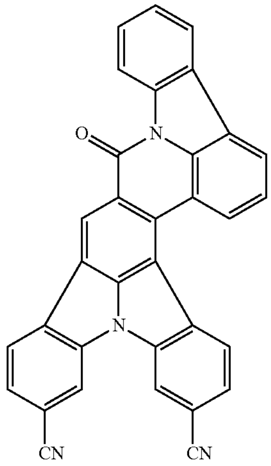 [SMILES: N#Cc1ccc2c3cc4c(=O)n5c6ccccc6c6cccc(c4c4c7ccc(C#N)cc7n(c2c1)c34)c65]
125
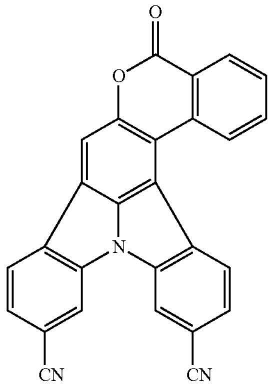 [SMILES: N#Cc1ccc2c3cc4oc(=O)c5ccccc5c4c4c5ccc(C#N)cc5n(c2c1)c34]

-continued
126
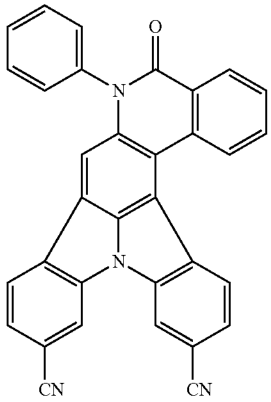 [SMILES: N#Cc1ccc2c3cc4c(c5ccccc5c(=O)n4-c4ccccc4)c4c5ccc(C#N)cc5n(c2c1)c34]
127
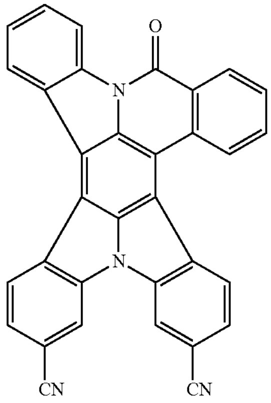 [SMILES: N#Cc1ccc2c3c4c5ccccc5c(=O)n5c6ccccc6c(c6c7ccc(C#N)cc7n(c2c1)c36)c45]
128
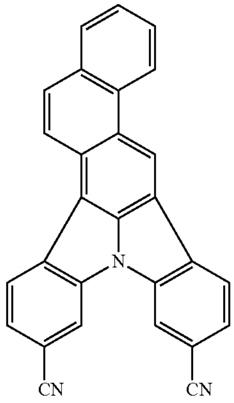 [SMILES: N#Cc1ccc2c3cc4c5ccccc5ccc4c4c5ccc(C#N)cc5n(c2c1)c34]
129
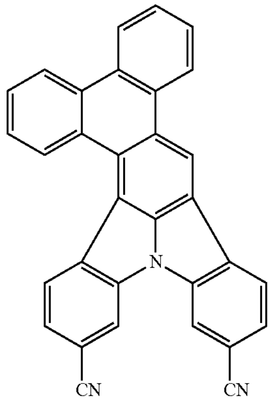 [SMILES: N#Cc1ccc2c3cc4c5ccccc5c5ccccc5c4c4c5ccc(C#N)cc5n(c2c1)c34]

-continued
130
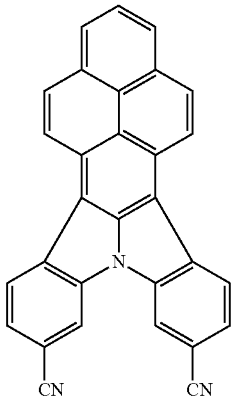 [SMILES: N#Cc1ccc2c3c4ccc5cccc6ccc(c4c56)c4c5ccc(C#N)cc5n(c2c1)c34]
131
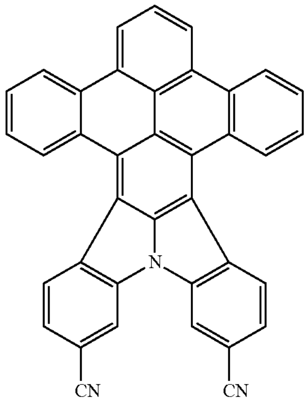 [SMILES: N#Cc1ccc2c3c4c5ccccc5c5cccc6c7ccccc7c(c4c56)c4c5ccc(C#N)cc5n(c2c1)c34]
132
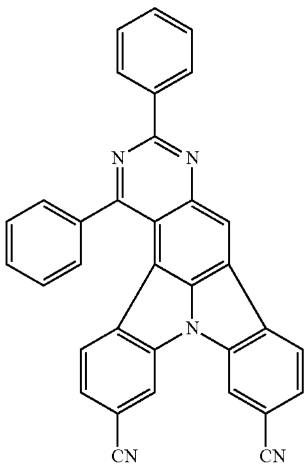 [SMILES: N#Cc1ccc2c3cc4nc(-c5ccccc5)nc(-c5ccccc5)c4c4c5ccc(C#N)cc5n(c2c1)c34]

-continued
133
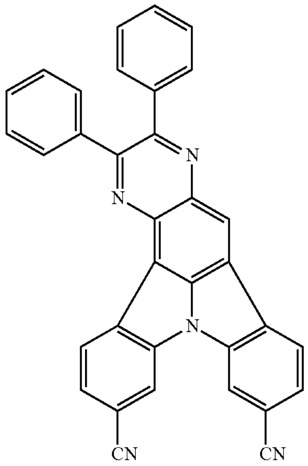 [SMILES: N#Cc1ccc2c3cc4nc(-c5ccccc5)c(-c5ccccc5)nc4c4c5ccc(C#N)cc5n(c2c1)c34]
134
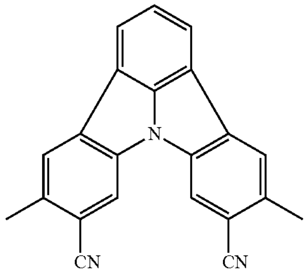
135
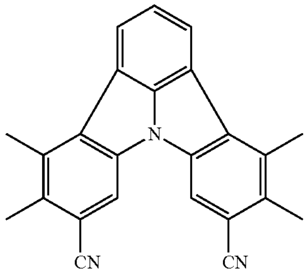
136
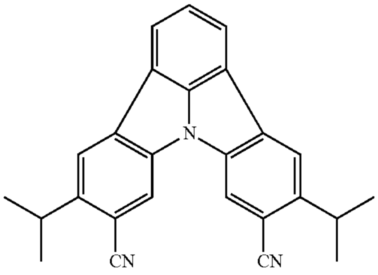 [SMILES: CC(C)c1cc2c3cccc4c5cc(C(C)C)c(C#N)cc5n(c2cc1C#N)c34]
137
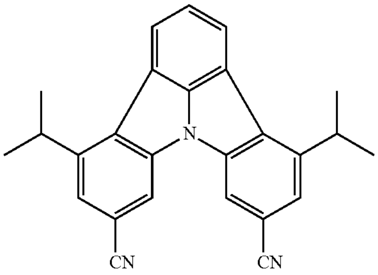 [SMILES: CC(C)c1cc(C#N)cc2c1c1cccc3c4c(C(C)C)cc(C#N)cc4n2c13]

-continued
138
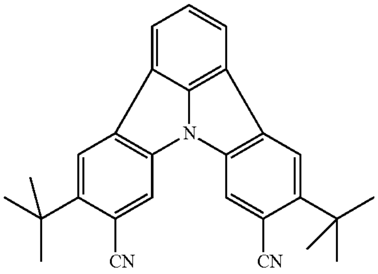 [SMILES: CC(C)(C)c1cc2c3cccc4c5cc(C(C)(C)C)c(C#N)cc5n(c2cc1C#N)c34]
139
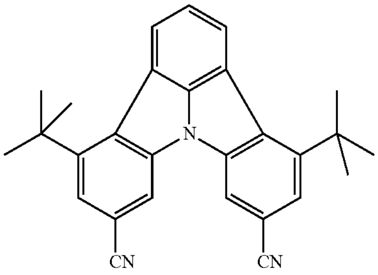 [SMILES: CC(C)(C)c1cc(C#N)cc2c1c1cccc3c4c(C(C)(C)C)cc(C#N)cc4n2c13]
140
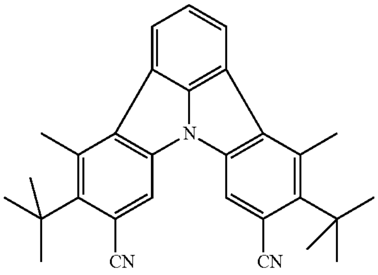 [SMILES: Cc1c(C(C)(C)C)c(C#N)cc2c1c1cccc3c4c(C)c(C(C)(C)C)c(C#N)cc4n2c13]
141
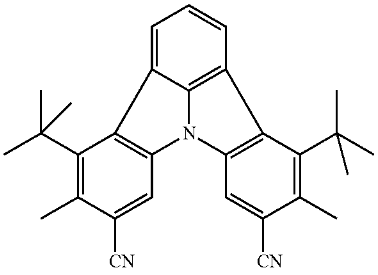 [SMILES: Cc1c(C#N)cc2c(c1C(C)(C)C)c1cccc3c4c(C(C)(C)C)c(C)c(C#N)cc4n2c13]
142
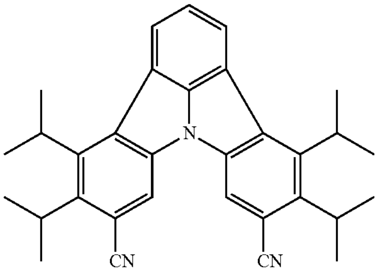 [SMILES: CC(C)c1c(C#N)cc2c(c1C(C)C)c1cccc3c4c(C(C)C)c(C(C)C)c(C#N)cc4n2c13]

-continued
143
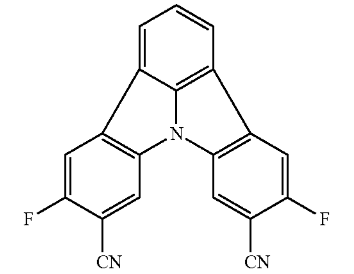 [SMILES: N#Cc1cc2c(cc1F)c1cccc3c4cc(F)c(C#N)cc4n2c13]
144
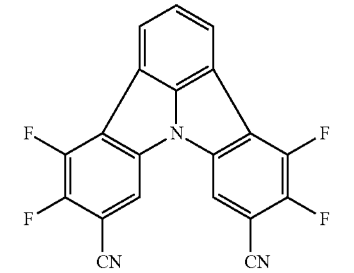 [SMILES: N#Cc1cc2c(c(F)c1F)c1cccc3c4c(F)c(F)c(C#N)cc4n2c13]
145
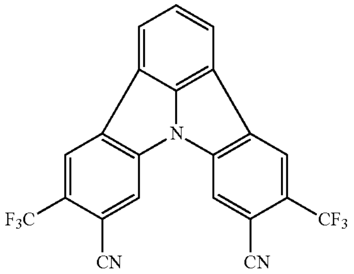 [SMILES: N#Cc1cc2c(cc1C(F)(F)F)c1cccc3c4cc(C(F)(F)F)c(C#N)cc4n2c13]
146
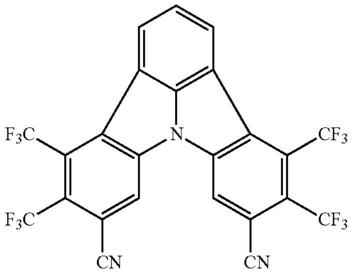 [SMILES: N#Cc1cc2c(c(C(F)(F)F)c1C(F)(F)F)c1cccc3c4c(C(F)(F)F)c(C(F)(F)F)c(C#N)cc4n2c13]
147
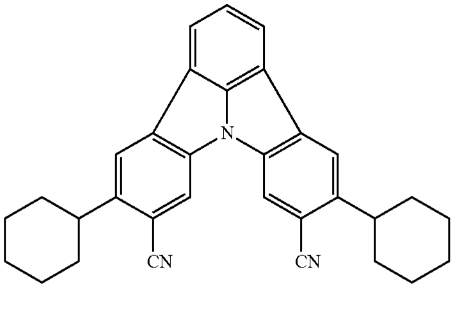 [SMILES: N#Cc1cc2c(cc1C1CCCCC1)c1cccc3c4cc(C5CCCCC5)c(C#N)cc4n2c13]

-continued
148
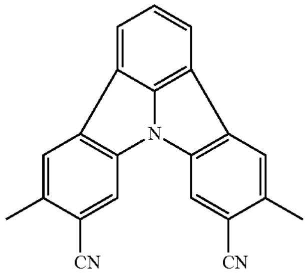
149
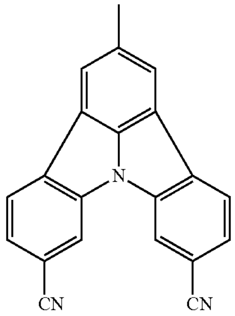 [SMILES: Cc1cc2c3ccc(C#N)cc3n3c4cc(C#N)ccc4c(c1)c23]
150
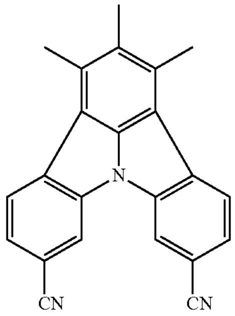 [SMILES: Cc1c(C)c2c3ccc(C#N)cc3n3c4cc(C#N)ccc4c(c1C)c23]
151
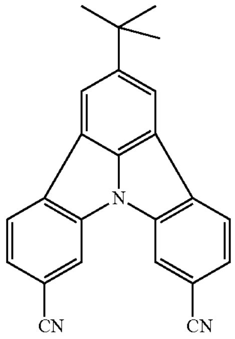 [SMILES: CC(C)(C)c1cc2c3ccc(C#N)cc3n3c4cc(C#N)ccc4c(c1)c23]
152
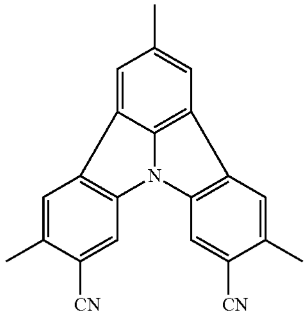

-continued
153
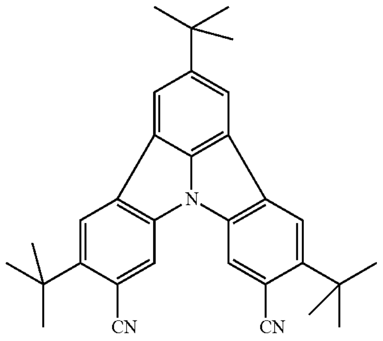 [SMILES: CC(C)(C)c1cc2c3cc(C(C)(C)C)c(C#N)cc3n3c4cc(C#N)c(C(C)(C)C)cc4c(c1)c23]
154
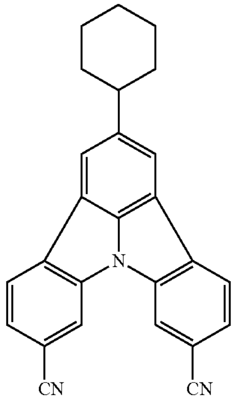 [SMILES: N#Cc1ccc2c3cc(C4CCCCC4)cc4c5ccc(C#N)cc5n(c2c1)c34]
155
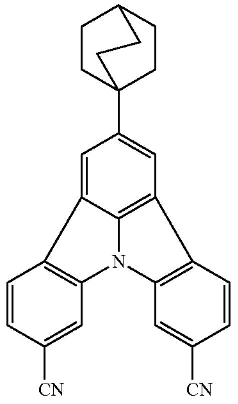 [SMILES: N#Cc1ccc2c3cc(C45CCC(CC4)CC5)cc4c5ccc(C#N)cc5n(c2c1)c34]
156
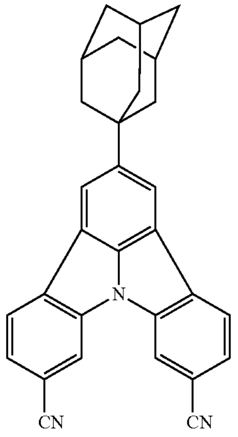 [SMILES: N#Cc1ccc2c3cc(C45CC6CC(CC(C6)C4)C5)cc4c5ccc(C#N)cc5n(c2c1)c34]

-continued
157
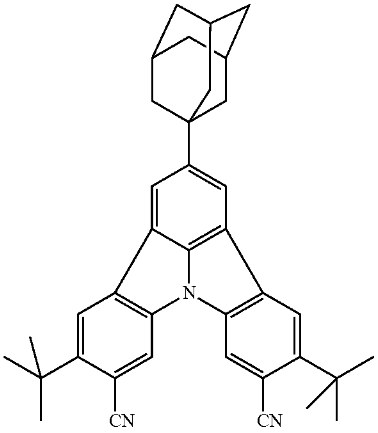 [SMILES: CC(C)(C)c1cc2c3cc(C45CC6CC(CC(C6)C4)C5)cc4c5cc(C(C)(C)C)c(C#N)cc5n(c2cc1C#N)c34]
158
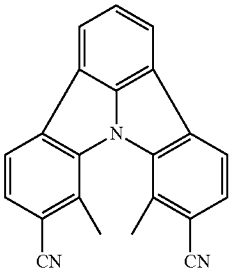 [SMILES: Cc1c(C#N)ccc2c3cccc4c5ccc(C#N)c(C)c5n(c12)c34]
159
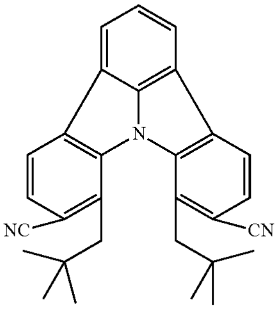 [SMILES: CC(C)(C)Cc1c(C#N)ccc2c3cccc4c5ccc(C#N)c(CC(C)(C)C)c5n(c12)c34]
160
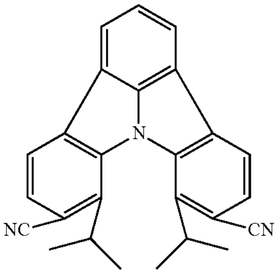 [SMILES: CC(C)c1c(C#N)ccc2c3cccc4c5ccc(C#N)c(C(C)C)c5n(c12)c34]
161
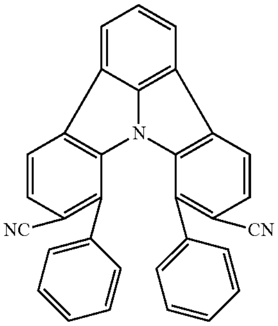 [SMILES: N#Cc1ccc2c3cccc4c5ccc(C#N)c(-c6ccccc6)c5n(c2c1-c1ccccc1)c34]

-continued
162
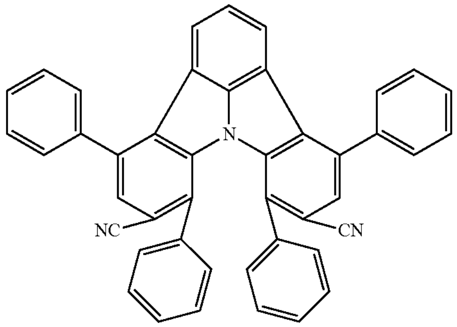 [SMILES: N#Cc1cc(-c2ccccc2)c2c3cccc4c5c(-c6ccccc6)cc(C#N)c(-c6ccccc6)c5n(c2c1-c1ccccc1)c34]
163
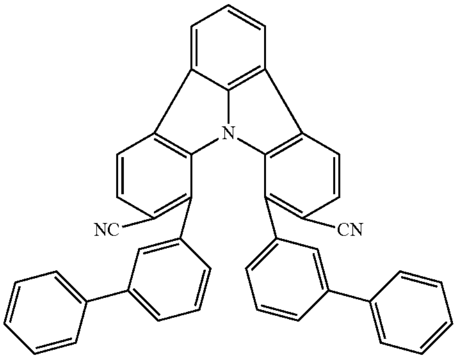 [SMILES: N#Cc1ccc2c3cccc4c5ccc(C#N)c(-c6cccc(-c7ccccc7)c6)c5n(c2c1-c1cccc(-c2ccccc2)c1)c34]
164
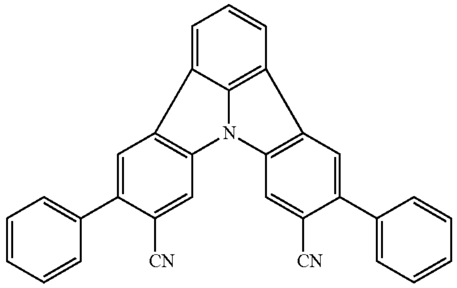 [SMILES: N#Cc1cc2c(cc1-c1ccccc1)c1cccc3c4cc(-c5ccccc5)c(C#N)cc4n2c13]
165
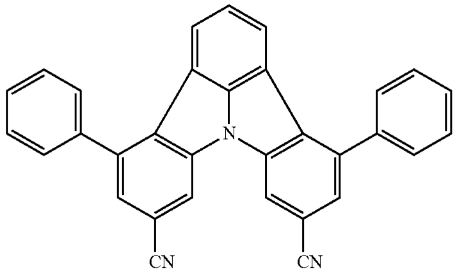 [SMILES: N#Cc1cc(-c2ccccc2)c2c3cccc4c5c(-c6ccccc6)cc(C#N)cc5n(c2c1)c34]
166
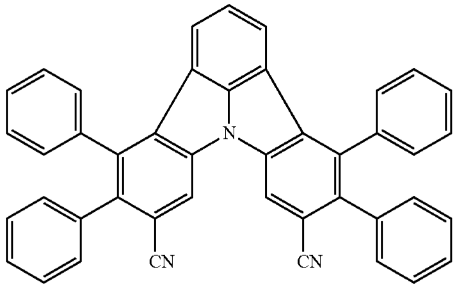 [SMILES: N#Cc1cc2c(c(-c3ccccc3)c1-c1ccccc1)c1cccc3c4c(-c5ccccc5)c(-c5ccccc5)c(C#N)cc4n2c13]

-continued
167
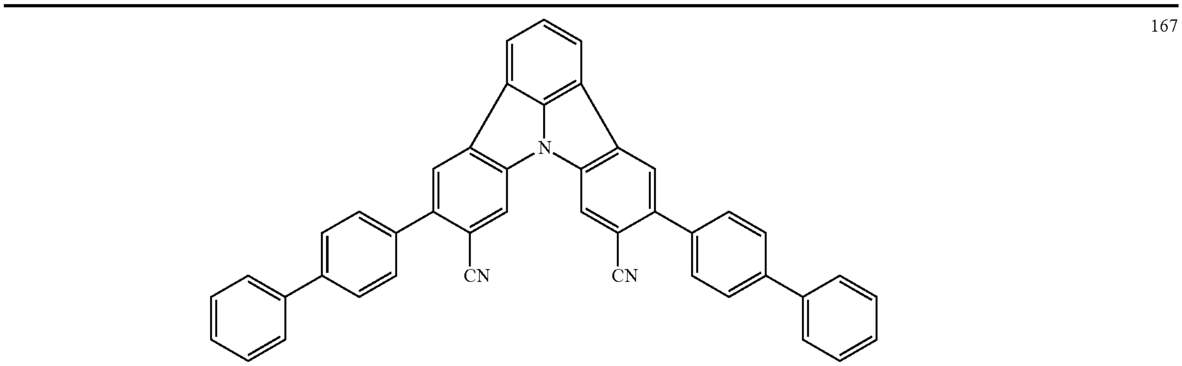
168
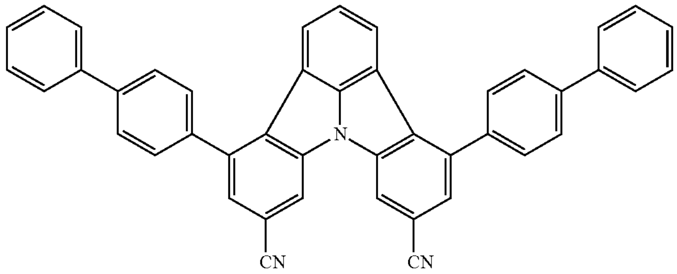 [SMILES: N#Cc1cc(-c2ccc(-c3ccccc3)cc2)c2c3cccc4c5c(-c6ccc(-c7ccccc7)cc6)cc(C#N)cc5n(c2c1)c34]
169
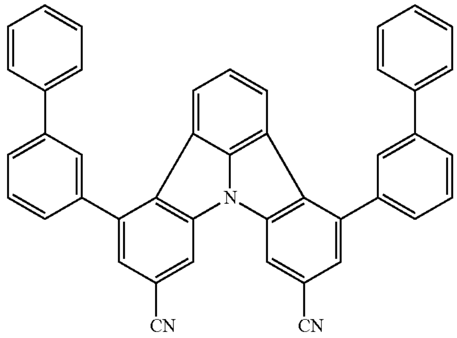 [SMILES: N#Cc1cc(-c2cccc(-c3ccccc3)c2)c2c3cccc4c5c(-c6cccc(-c7ccccc7)c6)cc(C#N)cc5n(c2c1)c34]
170
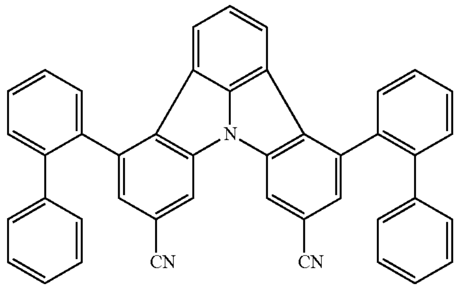 [SMILES: N#Cc1cc(-c2ccccc2-c2ccccc2)c2c3cccc4c5c(-c6ccccc6-c6ccccc6)cc(C#N)cc5n(c2c1)c34]
171
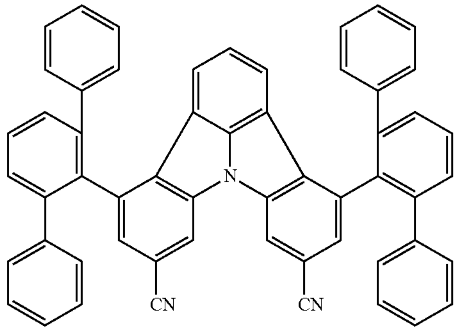 [SMILES: N#Cc1cc(-c2c(-c3ccccc3)cccc2-c2ccccc2)c2c3cccc4c5c(-c6c(-c7ccccc7)cccc6-c6ccccc6)cc(C#N)cc5n(c2c1)c34]

-continued
172
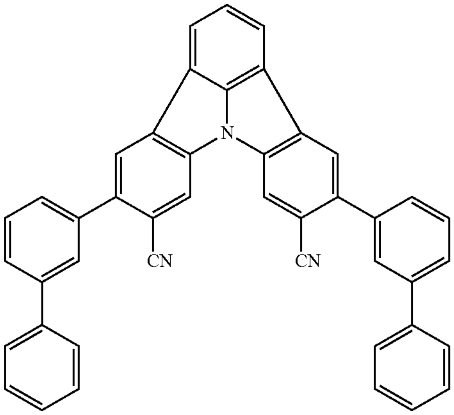 [SMILES: N#Cc1cc2c(cc1-c1cccc(-c3ccccc3)c1)c1cccc3c4cc(-c5cccc(-c6ccccc6)c5)c(C#N)cc4n2c13]
173
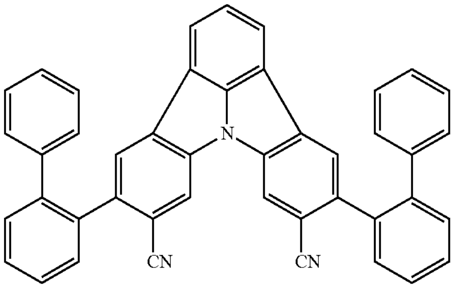 [SMILES: N#Cc1cc2c(cc1-c1ccccc1-c1ccccc1)c1cccc3c4cc(-c5ccccc5-c5ccccc5)c(C#N)cc4n2c13]
174
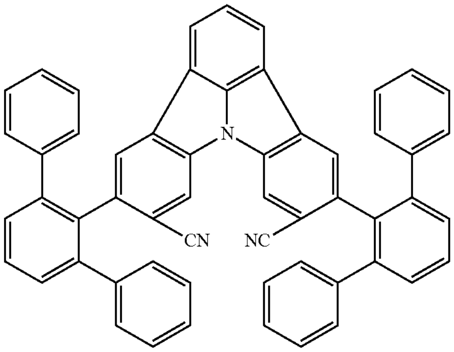 [SMILES: N#Cc1cc2c(cc1-c1c(-c3ccccc3)cccc1-c1ccccc1)c1cccc3c4cc(-c5c(-c6ccccc6)cccc5-c5ccccc5)c(C#N)cc4n2c13]
175
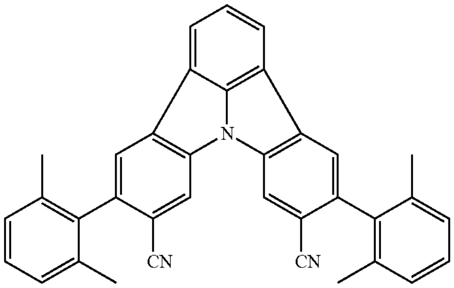 [SMILES: Cc1cccc(C)c1-c1cc2c3cccc4c5cc(-c6c(C)cccc6C)c(C#N)cc5n(c2cc1C#N)c34]

-continued
176
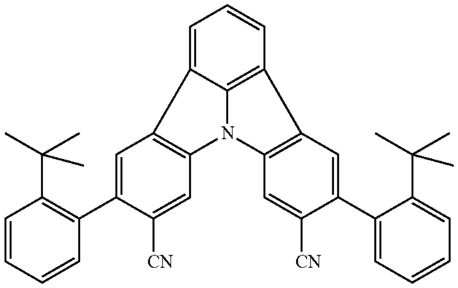 [SMILES: CC(C)(C)c1ccccc1-c1cc2c3cccc4c5cc(-c6ccccc6C(C)(C)C)c(C#N)cc5n(c2cc1C#N)c34]
177
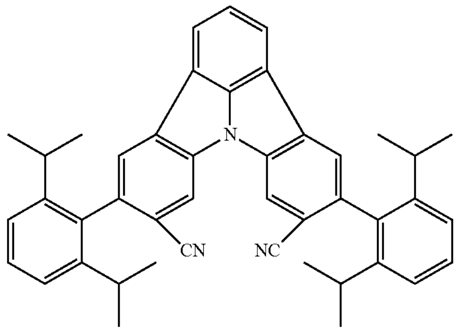 [SMILES: CC(C)c1cccc(C(C)C)c1-c1cc2c3cccc4c5cc(-c6c(C(C)C)cccc6C(C)C)c(C#N)cc5n(c2cc1C#N)c34]
178
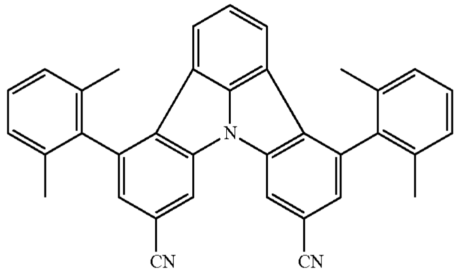 [SMILES: Cc1cccc(C)c1-c1cc(C#N)cc2c1c1cccc3c4c(-c5c(C)cccc5C)cc(C#N)cc4n2c13]
179
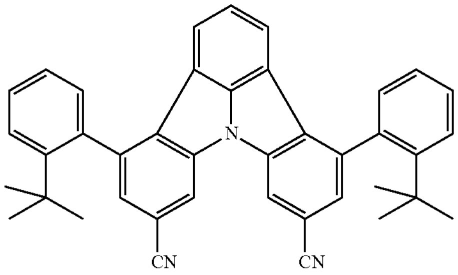 [SMILES: CC(C)(C)c1ccccc1-c1cc(C#N)cc2c1c1cccc3c4c(-c5ccccc5C(C)(C)C)cc(C#N)cc4n2c13]
180
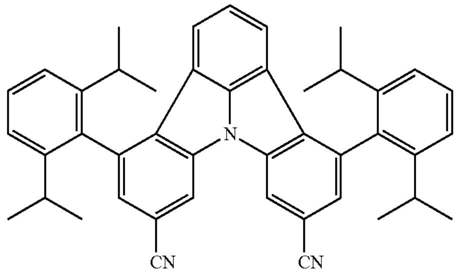 [SMILES: CC(C)c1cccc(C(C)C)c1-c1cc(C#N)cc2c1c1cccc3c4c(-c5c(C(C)C)cccc5C(C)C)cc(C#N)cc4n2c13]

-continued
181
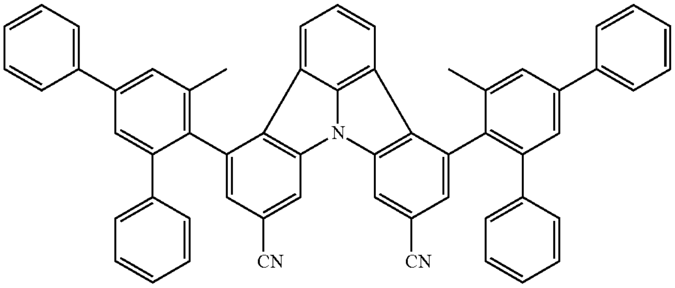 [SMILES: Cc1cc(-c2ccccc2)cc(-c2ccccc2)c1-c1cc(C#N)cc2c1c1cccc3c4c(-c5c(C)cc(-c6ccccc6)cc5-c5ccccc5)cc(C#N)cc4n2c13]
182
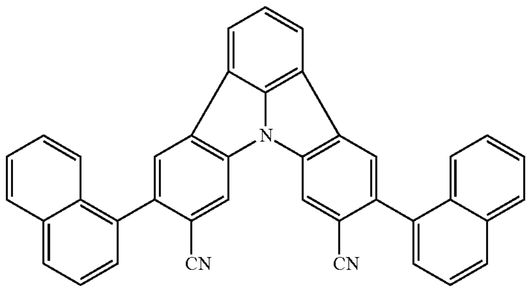 [SMILES: N#Cc1cc2c(cc1-c1cccc3ccccc13)c1cccc3c4cc(-c5cccc6ccccc56)c(C#N)cc4n2c13]
183
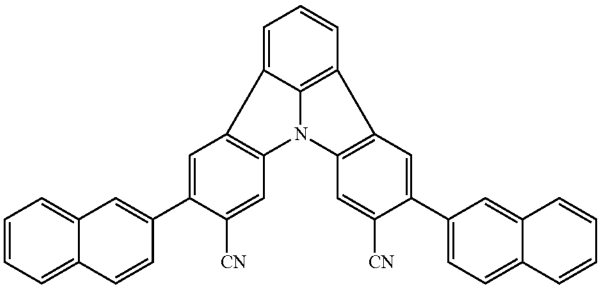 [SMILES: N#Cc1cc2c(cc1-c1ccc3ccccc3c1)c1cccc3c4cc(-c5ccc6ccccc6c5)c(C#N)cc4n2c13]
184
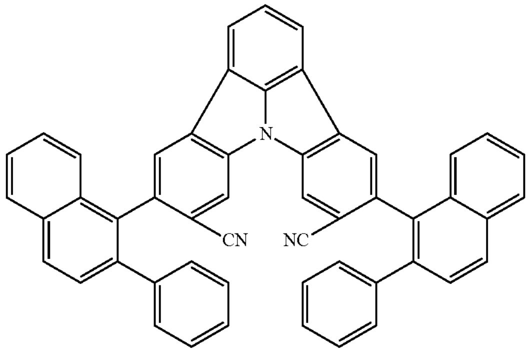 [SMILES: N#Cc1cc2c(cc1-c1c(-c3ccccc3)ccc3ccccc13)c1cccc3c4cc(-c5c(-c6ccccc6)ccc6ccccc56)c(C#N)cc4n2c13]
185
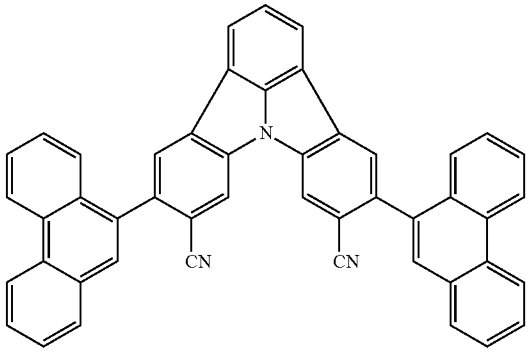 [SMILES: N#Cc1cc2c(cc1-c1cc3ccccc3c3ccccc13)c1cccc3c4cc(-c5cc6ccccc6c6ccccc56)c(C#N)cc4n2c13]

-continued
186
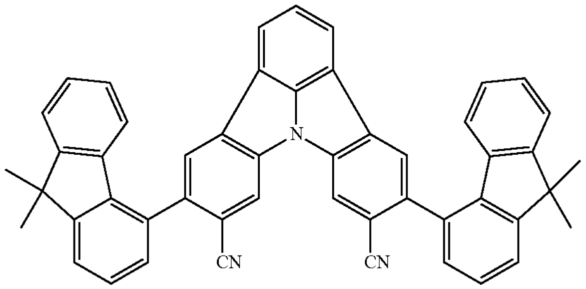
187
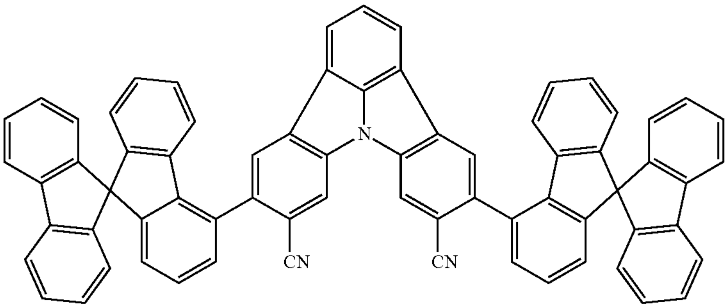 [SMILES: N#Cc1cc2c(cc1-c1cccc3c1-c1ccccc1C31c3ccccc3-c3ccccc31)c1cccc3c4cc(-c5cccc6c5-c5ccccc5C65c6ccccc6-c6ccccc65)c(C#N)cc4n2c13]
188
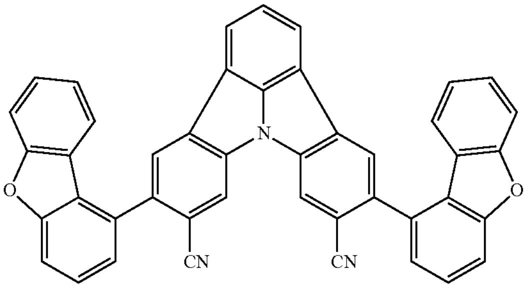 [SMILES: N#Cc1cc2c(cc1-c1cccc3oc4ccccc4c13)c1cccc3c4cc(-c5cccc6oc7ccccc7c56)c(C#N)cc4n2c13]
189
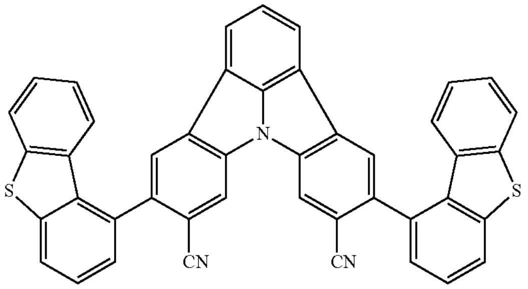 [SMILES: N#Cc1cc2c(cc1-c1cccc3sc4ccccc4c13)c1cccc3c4cc(-c5cccc6sc7ccccc7c56)c(C#N)cc4n2c13]
190
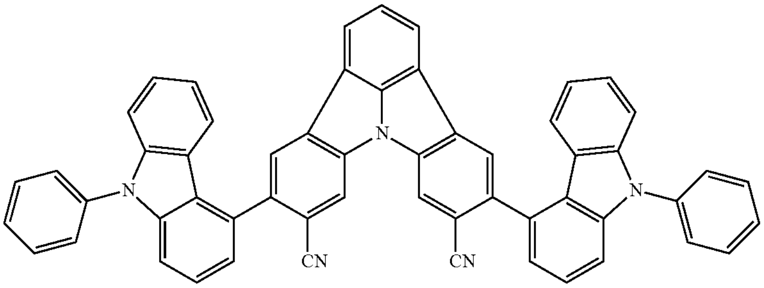 [SMILES: N#Cc1cc2c(cc1-c1cccc3c1c1ccccc1n3-c1ccccc1)c1cccc3c4cc(-c5cccc6c5c5ccccc5n6-c5ccccc5)c(C#N)cc4n2c13]

-continued
191
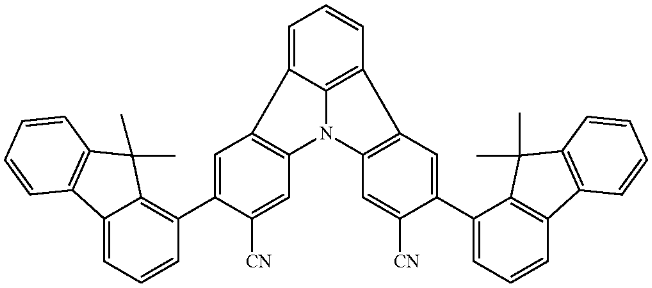 [SMILES: CC1(C)c2ccccc2-c2cccc(-c3cc4c5cccc6c7cc(-c8cccc9c8C(C)(C)c8ccccc8-9)c(C#N)cc7n(c4cc3C#N)c56)c21]
192
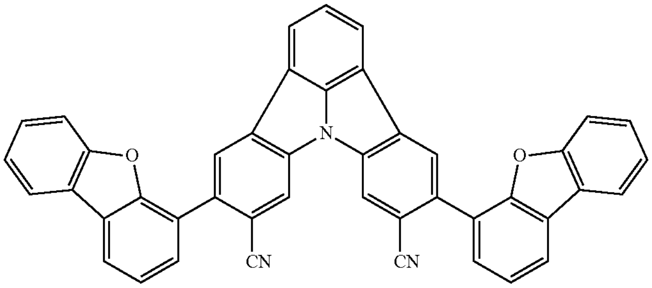
192
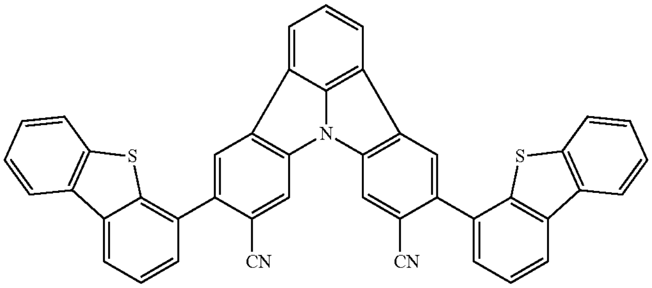 [SMILES: N#Cc1cc2c(cc1-c1cccc3c1oc1ccccc13)c1cccc3c4cc(-c5cccc6c5oc5ccccc56)c(C#N)cc4n2c13]
193
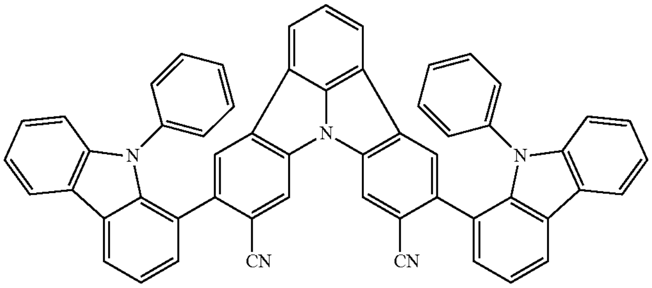 [SMILES: N#Cc1cc2c(cc1-c1cccc3c4ccccc4n(-c4ccccc4)c13)c1cccc3c4cc(-c5cccc6c7ccccc7n(-c7ccccc7)c56)c(C#N)cc4n2c13]
194
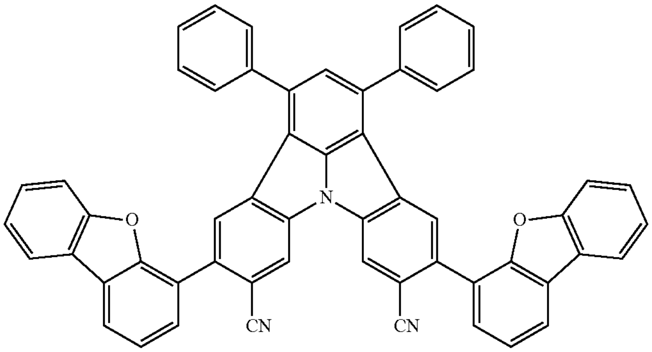 [SMILES: N#Cc1cc2c(cc1-c1cccc3c1oc1ccccc13)c1c(-c3ccccc3)cc(-c3ccccc3)c3c4cc(-c5cccc6c5oc5ccccc56)c(C#N)cc4n2c13]

-continued
195
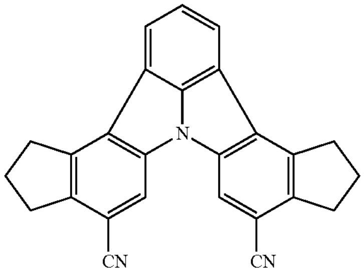 [SMILES: N#Cc1cc2c(c3c1CCC3)c1cccc3c4c5c(c(C#N)cc4n2c13)CCC5]
196
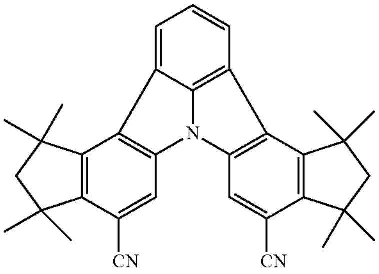
197
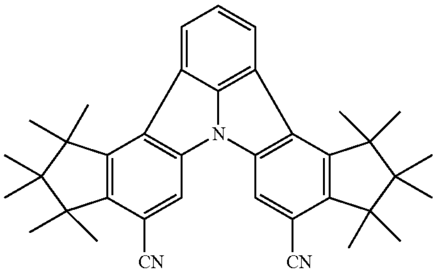
198
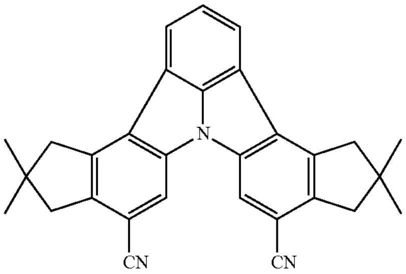
199
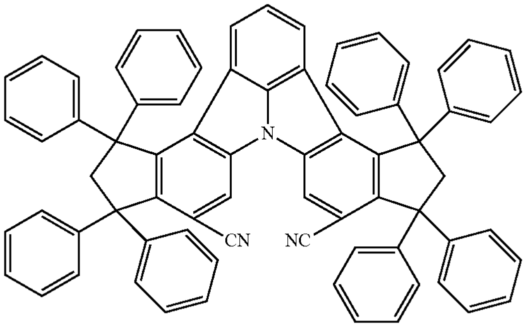 [SMILES: N#Cc1cc2c(c3c1C(c1ccccc1)(c1ccccc1)CC3(c1ccccc1)c1ccccc1)c1cccc3c4c5c(c(C#N)cc4n2c13)C(c1ccccc1)(c1ccccc1)CC5(c1ccccc1)c1ccccc1]

-continued
200
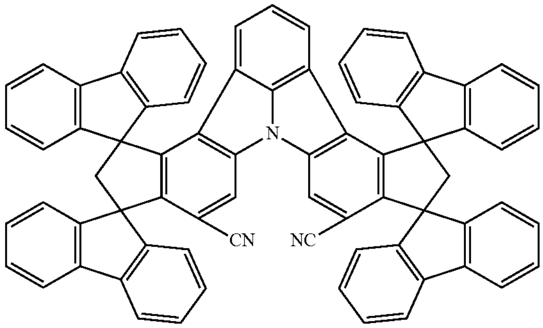 [SMILES: N#Cc1cc2c(c3c1C1(CC34c3ccccc3-c3ccccc34)c3ccccc3-c3ccccc31)c1cccc3c4c5c(c(C#N)cc4n2c13)C1(CC52c3ccccc3-c3ccccc32)c2ccccc2-c2ccccc21]
201
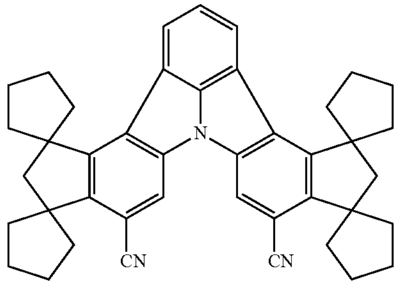 [SMILES: N#Cc1cc2c(c3c1C1(CCCC1)CC31CCCC1)c1cccc3c4c5c(c(C#N)cc4n2c13)C1(CCCC1)CC51CCCC1]
202
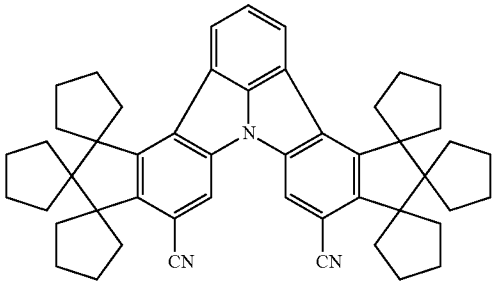 [SMILES: N#Cc1cc2c(c3c1C1(CCCC1)C1(CCCC1)C31CCCC1)c1cccc3c4c5c(c(C#N)cc4n2c13)C1(CCCC1)C1(CCCC1)C51CCCC1]
203
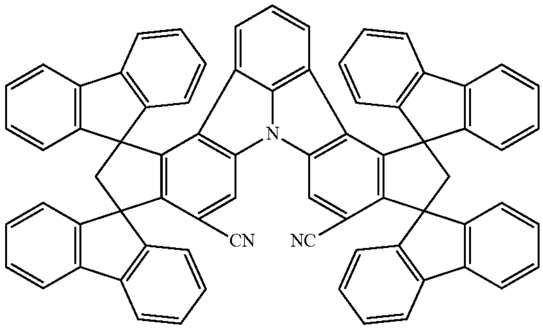 [SMILES: N#Cc1cc2c(c3c1C1(CC34c3ccccc3-c3ccccc34)c3ccccc3-c3ccccc31)c1cccc3c4c5c(c(C#N)cc4n2c13)C1(CC52c3ccccc3-c3ccccc32)c2ccccc2-c2ccccc21]
204
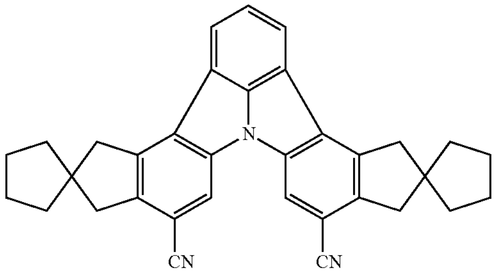 [SMILES: N#Cc1cc2c(c3c1CC1(CCCC1)C3)c1cccc3c4c5c(c(C#N)cc4n2c13)CC1(CCCC1)C5]

-continued
205
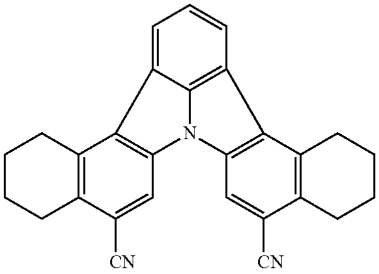 [SMILES: N#Cc1cc2c(c3c1CCCC3)c1cccc3c4c5c(c(C#N)cc4n2c13)CCCC5]
206
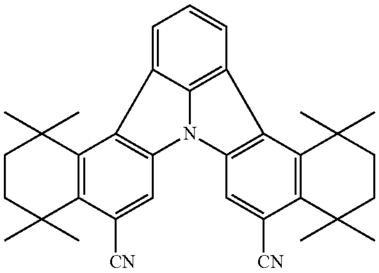 [SMILES: CC1(C)CCC(C)(C)c2c1c(C#N)cc1c2c2cccc3c4c5c(c(C#N)cc4n1c23)C(C)(C)CCC5(C)C]
207
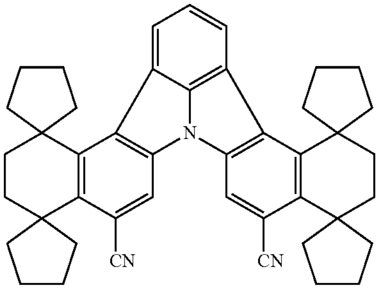 [SMILES: N#Cc1cc2c(c3c1C1(CCCC1)CCC31CCCC1)c1cccc3c4c5c(c(C#N)cc4n2c13)C1(CCCC1)CCC51CCCC1]
208
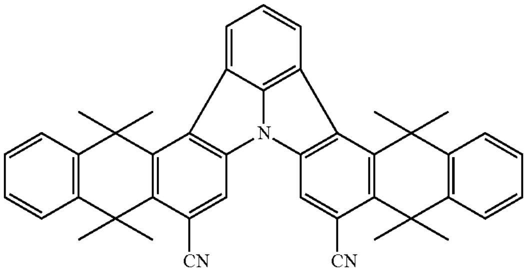 [SMILES: CC1(C)c2ccccc2C(C)(C)c2c1c(C#N)cc1c2c2cccc3c4c5c(c(C#N)cc4n1c23)C(C)(C)c1ccccc1C5(C)C]
209
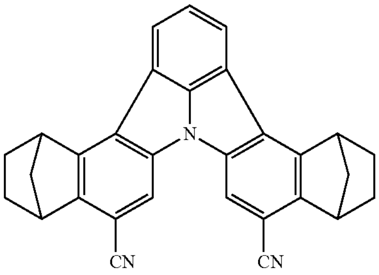
$C_2$ & $C_s$ -continued
210
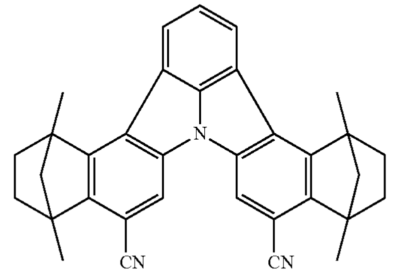 [SMILES: CC12CCC(C)(C1)c1c2c(C#N)cc2c1c1cccc3c4c5c(c(C#N)cc4n2c13)C1(C)CCC5(C)C1]
211
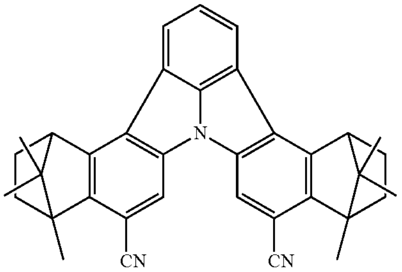
212
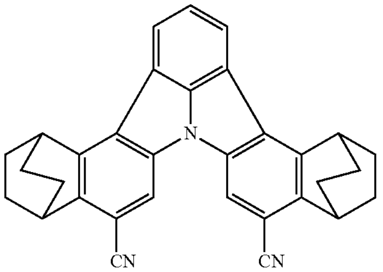 [SMILES: N#Cc1cc2c(c3c1C1CCC3CC1)c1cccc3c4c5c(c(C#N)cc4n2c13)C1CCC5CC1]
213
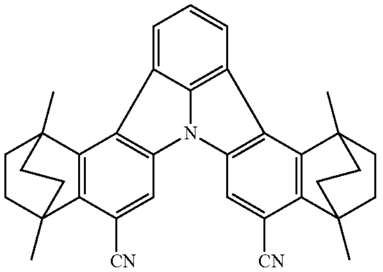 [SMILES: CC12CCC(C)(CC1)c1c2c(C#N)cc2c1c1cccc3c4c5c(c(C#N)cc4n2c13)C1(C)CCC5(C)CC1]
214
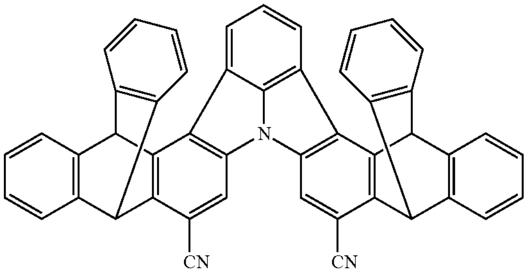 [SMILES: N#Cc1cc2c(c3c1C1c4ccccc4C3c3ccccc31)c1cccc3c4c5c(c(C#N)cc4n2c13)C1c2ccccc2C5c2ccccc21]

-continued
215
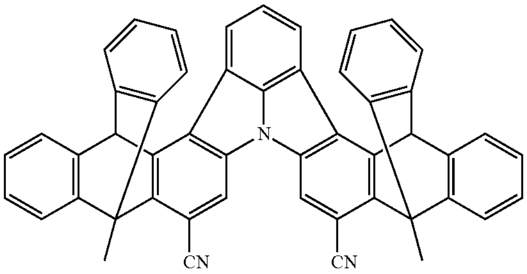 [SMILES: CC12c3ccccc3C(c3ccccc31)c1c2c(C#N)cc2c1c1cccc3c4c5c(c(C#N)cc4n2c13)C1(C)c2ccccc2C5c2ccccc21]
216
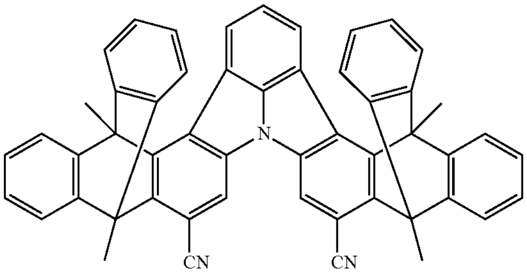 [SMILES: CC12c3ccccc3C(C)(c3ccccc31)c1c2c(C#N)cc2c1c1cccc3c4c5c(c(C#N)cc4n2c13)C1(C)c2ccccc2C5(C)c2ccccc21]
217
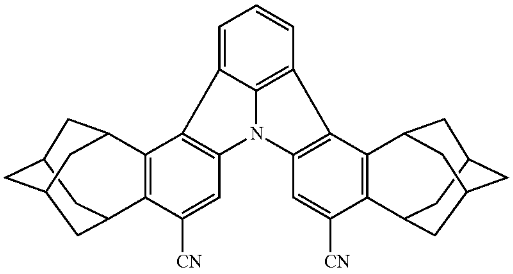 [SMILES: N#Cc1cc2c(c3c1C1CC4CC(C1)CC3C4)c1cccc3c4c5c(c(C#N)cc4n2c13)C1CC2CC(C1)CC5C2]
218
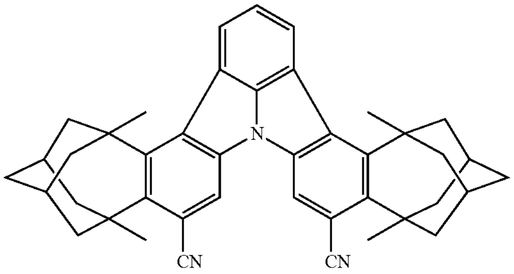 [SMILES: CC12CC3CC(C1)CC(C)(C3)c1c2c(C#N)cc2c1c1cccc3c4c5c(c(C#N)cc4n2c13)C1(C)CC2CC(C1)CC5(C)C2]
219
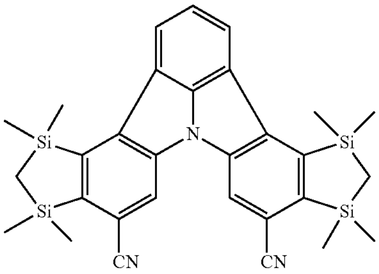

-continued
220
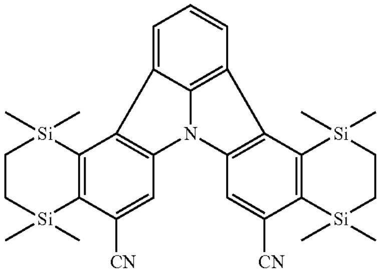 [SMILES: C[Si]1(C)CC[Si](C)(C)c2c1c(C#N)cc1c2c2cccc3c4c5c(c(C#N)cc4n1c23)[Si](C)(C)CC[Si]5(C)C]
221
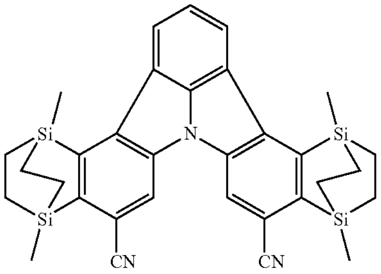 [SMILES: C[Si]12CC[Si](C)(CC1)c1c2c(C#N)cc2c1c1cccc3c4c5c(c(C#N)cc4n2c13)[Si]1(C)CC[Si]5(C)CC1]
222
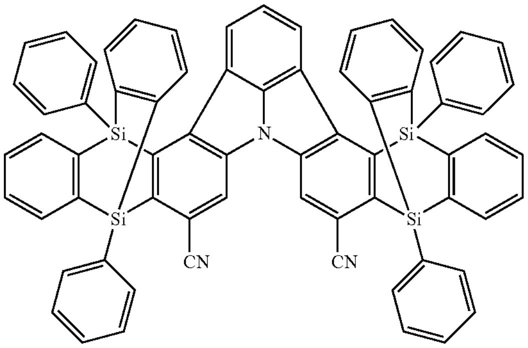 [SMILES: N#Cc1cc2c(c3c1[Si]1(c4ccccc4)c4ccccc4[Si]3(c3ccccc3)c3ccccc31)c1cccc3c4c5c(c(C#N)cc4n2c13)[Si]1(c2ccccc2)c2ccccc2[Si]5(c2ccccc2)c2ccccc21]
223
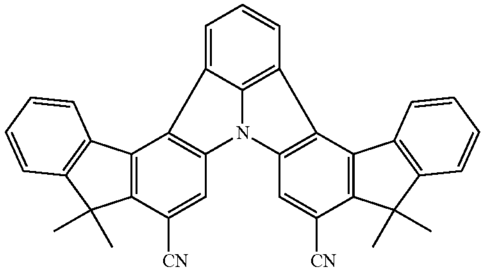 [SMILES: CC1(C)c2ccccc2-c2c1c(C#N)cc1c2c2cccc3c4c5c(c(C#N)cc4n1c23)C(C)(C)c1ccccc1-5]
224
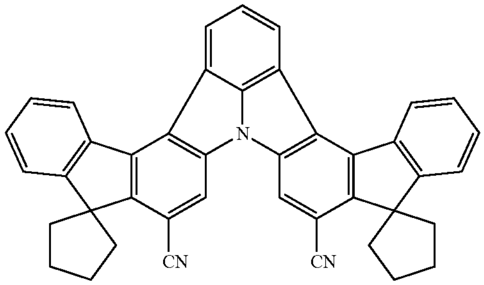 [SMILES: N#Cc1cc2c(c3c1C1(CCCC1)c1ccccc1-3)c1cccc3c4c5c(c(C#N)cc4n2c13)C1(CCCC1)c1ccccc1-5]

-continued
225
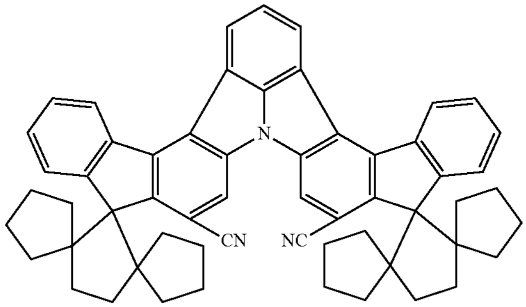 [SMILES: N#Cc1cc2c(c3c1C1(c4ccccc4-3)C3(CCCC3)CCC13CCCC3)c1cccc3c4c5c(c(C#N)cc4n2c13)C1(c2ccccc2-5)C2(CCCC2)CCC12CCCC2]
226
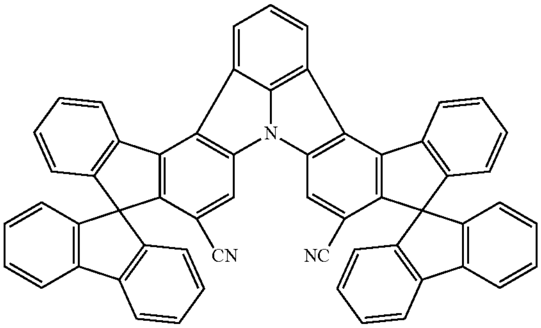 [SMILES: N#Cc1cc2c(c3c1C1(c4ccccc4-c4ccccc41)c1ccccc1-3)c1cccc3c4c5c(c(C#N)cc4n2c13)C1(c2ccccc2-c2ccccc21)c1ccccc1-5]
227
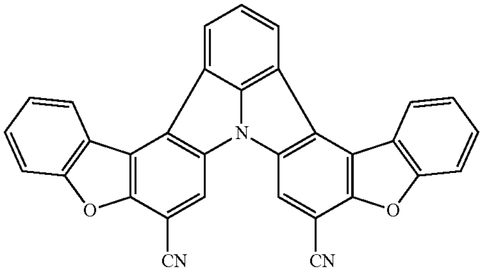 [SMILES: N#Cc1cc2c(c3cccc4c5c6c(oc7ccccc76)c(C#N)cc5n2c34)c2c1oc1ccccc12]
228
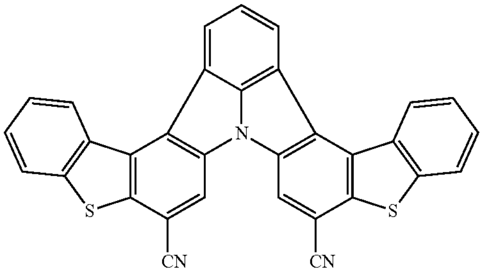
229
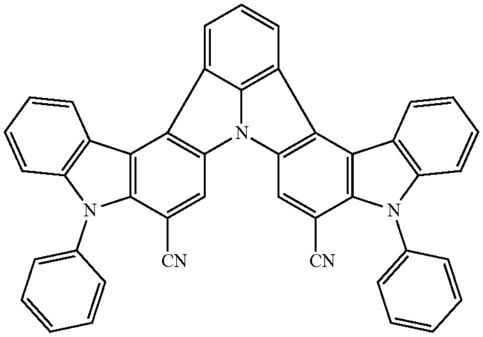 [SMILES: N#Cc1cc2c(c3cccc4c5c6c7ccccc7n(-c7ccccc7)c6c(C#N)cc5n2c34)c2c3ccccc3n(-c3ccccc3)c12]

-continued
230
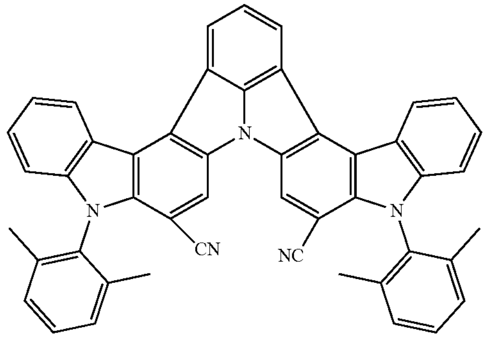 [SMILES: Cc1cccc(C)c1-n1c2ccccc2c2c3c4cccc5c6c7c8ccccc8n(-c8c(C)cccc8C)c7c(C#N)cc6n(c3cc(C#N)c21)c45]
231
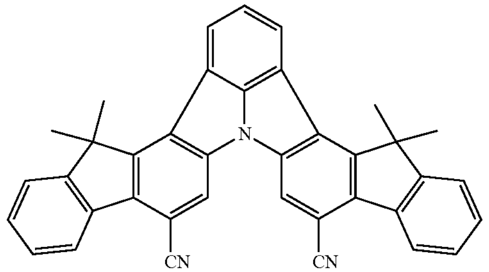 [SMILES: CC1(C)c2ccccc2-c2c(C#N)cc3c(c21)c1cccc2c4c5c(c(C#N)cc4n3c12)-c1ccccc1C5(C)C]
232
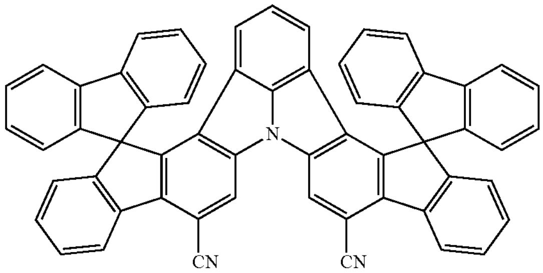 [SMILES: N#Cc1cc2c(c3c1-c1ccccc1C31c3ccccc3-c3ccccc31)c1cccc3c4c5c(c(C#N)cc4n2c13)-c1ccccc1C51c2ccccc2-c2ccccc21]
233
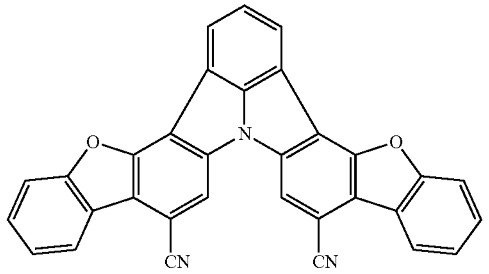 [SMILES: N#Cc1cc2c(c3cccc4c5c6oc7ccccc7c6c(C#N)cc5n2c34)c2oc3ccccc3c12]
234
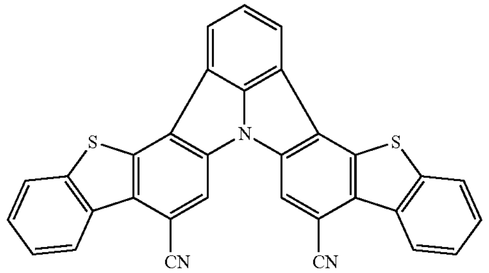

-continued
235
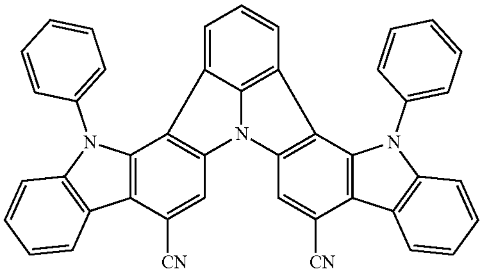 [SMILES: N#Cc1cc2c(c3cccc4c5c6c(c(C#N)cc5n2c34)c2ccccc2n6-c2ccccc2)c2c1c1ccccc1n2-c1ccccc1]
236
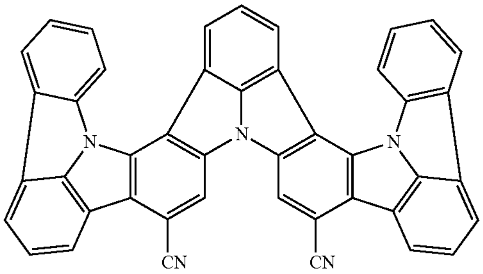 [SMILES: N#Cc1cc2c(c3cccc4c5c(cc(C#N)c6c7cccc8c9ccccc9n(c87)c65)n2c34)c2c1c1cccc3c4ccccc4n2c31]
237
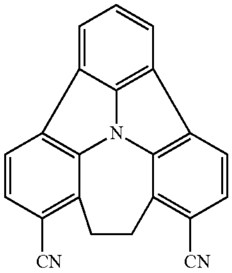 [SMILES: N#Cc1ccc2c3cccc4c5ccc(C#N)c6c5n(c2c1CC6)c34]
238
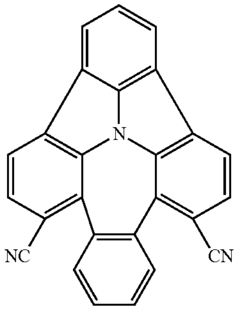 [SMILES: N#Cc1ccc2c3cccc4c5ccc(C#N)c6c5n(c2c1-c1ccccc1-6)c34]
239
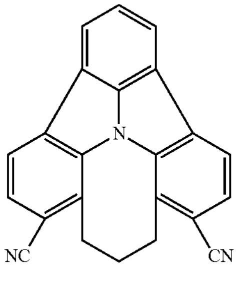 [SMILES: N#Cc1ccc2c3cccc4c5ccc(C#N)c6c5n(c2c1CCC6)c34]

-continued
240
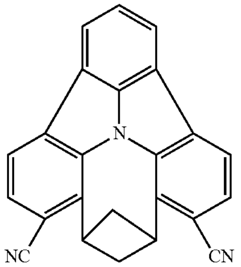 [SMILES: N#Cc1ccc2c3cccc4c5ccc(C#N)c6c5n(c2c1C1CC6C1)c34]
241
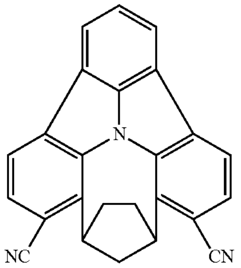 [SMILES: N#Cc1ccc2c3cccc4c5ccc(C#N)c6c5n(c2c1C1CCC6C1)c34]
242
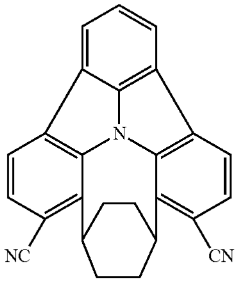 [SMILES: N#Cc1ccc2c3cccc4c5ccc(C#N)c6c5n(c2c1C1CCC6CC1)c34]
243
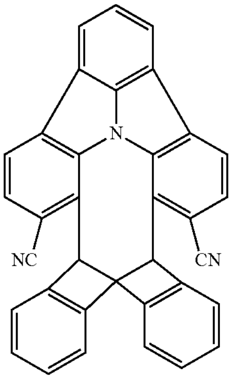 [SMILES: N#Cc1ccc2c3cccc4c5ccc(C#N)c6c5n(c2c1C1c2ccccc2C12c1ccccc1C62)c34]
244
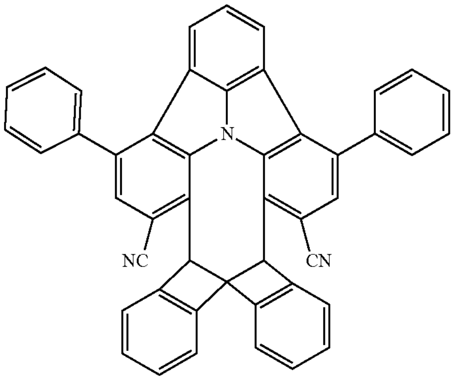 [SMILES: N#Cc1cc(-c2ccccc2)c2c3cccc4c5c(-c6ccccc6)cc(C#N)c6c5n(c2c1C1c2ccccc2C12c1ccccc1C62)c34]

-continued
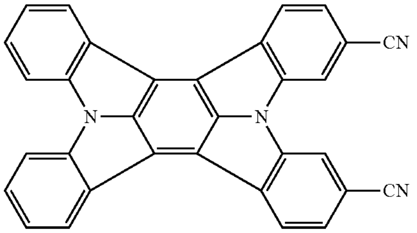 [SMILES: N#Cc1ccc2c3c4c5ccccc5n5c6ccccc6c(c6c7ccc(C#N)cc7n(c2c1)c36)c45]
245
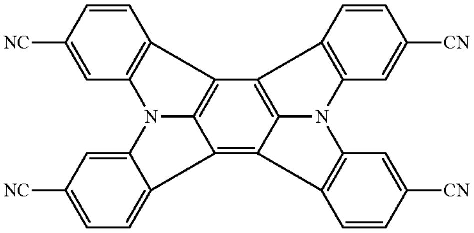 [SMILES: N#Cc1ccc2c3c4c5ccc(C#N)cc5n5c6cc(C#N)ccc6c(c6c7ccc(C#N)cc7n(c2c1)c36)c45]
246
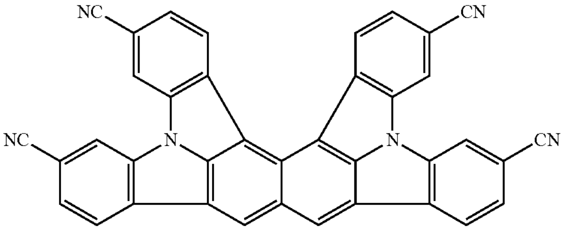 [SMILES: N#Cc1ccc2c3cc4cc5c6ccc(C#N)cc6n6c7cc(C#N)ccc7c(c4c4c7ccc(C#N)cc7n(c2c1)c34)c56]
247
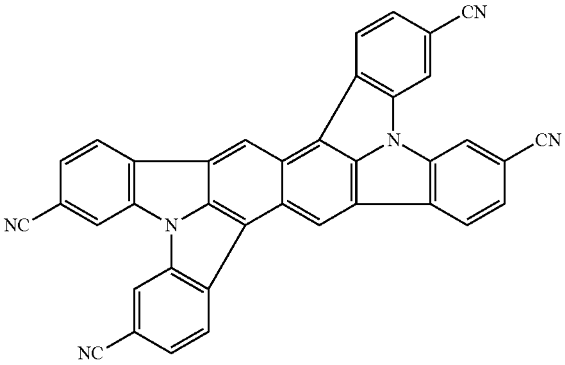 [SMILES: N#Cc1ccc2c3cc4c(cc5c6ccc(C#N)cc6n6c7cc(C#N)ccc7c4c56)c4c5ccc(C#N)cc5n(c2c1)c34]
248
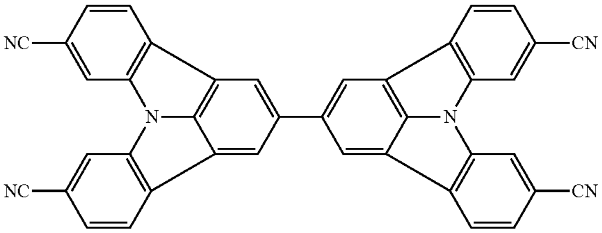 [SMILES: N#Cc1ccc2c3cc(-c4cc5c6ccc(C#N)cc6n6c7cc(C#N)ccc7c(c4)c56)cc4c5ccc(C#N)cc5n(c2c1)c34]
249
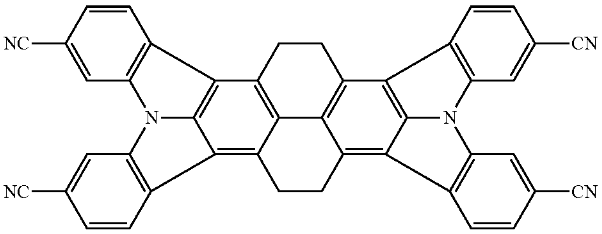 [SMILES: N#Cc1ccc2c3c4c5c(c6c7ccc(C#N)cc7n(c2c1)c36)CCc1c-5c(c2c3ccc(C#N)cc3n3c5cc(C#N)ccc5c1c23)CC4]
250

-continued
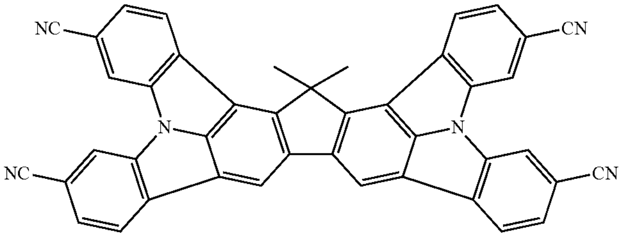 [SMILES: CC1(C)c2c(cc3c4ccc(C#N)cc4n4c5cc(C#N)ccc5c2c34)-c2cc3c4ccc(C#N)cc4n4c5cc(C#N)ccc5c(c21)c34]
251
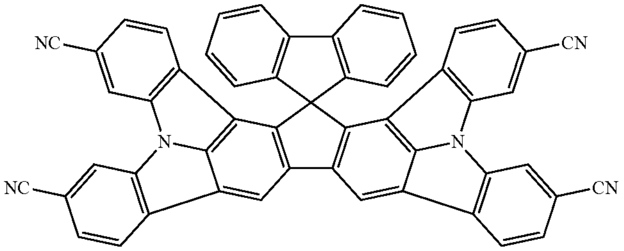 [SMILES: N#Cc1ccc2c3cc4c(c5c6ccc(C#N)cc6n(c2c1)c35)C1(c2ccccc2-c2ccccc21)c1c-4cc2c3ccc(C#N)cc3n3c4cc(C#N)ccc4c1c23]
252
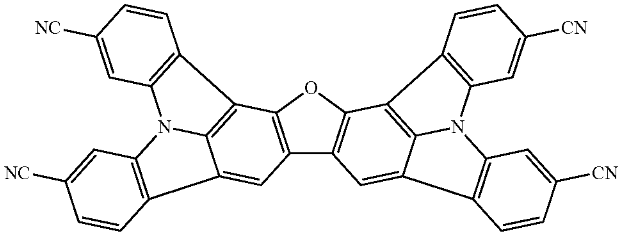 [SMILES: N#Cc1ccc2c3cc4c5cc6c7ccc(C#N)cc7n7c8cc(C#N)ccc8c(c5oc4c4c5ccc(C#N)cc5n(c2c1)c34)c67]
253
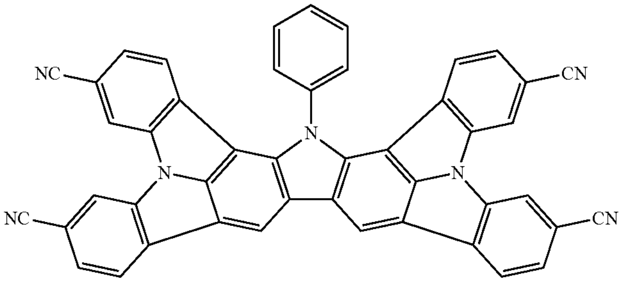 [SMILES: N#Cc1ccc2c3cc4c5cc6c7ccc(C#N)cc7n7c8cc(C#N)ccc8c(c5n(-c5ccccc5)c4c4c5ccc(C#N)cc5n(c2c1)c34)c67]
254
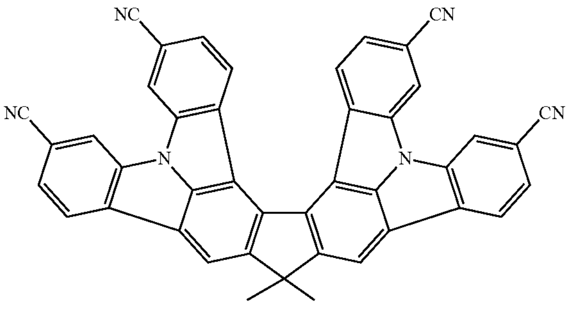 [SMILES: CC1(C)c2cc3c4ccc(C#N)cc4n4c5cc(C#N)ccc5c(c2-c2c1cc1c5ccc(C#N)cc5n5c6cc(C#N)ccc6c2c15)c34]
255

-continued
256
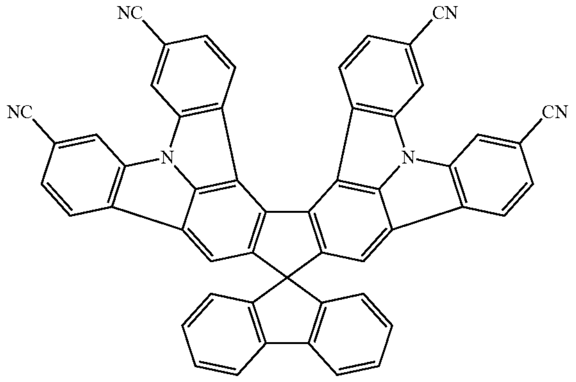 [SMILES: N#Cc1ccc2c3cc4c(c5c6ccc(C#N)cc6n(c2c1)c35)-c1c(cc2c3ccc(C#N)cc3n3c5cc(C#N)ccc5c1c23)C41c2ccccc2-c2ccccc21]
257
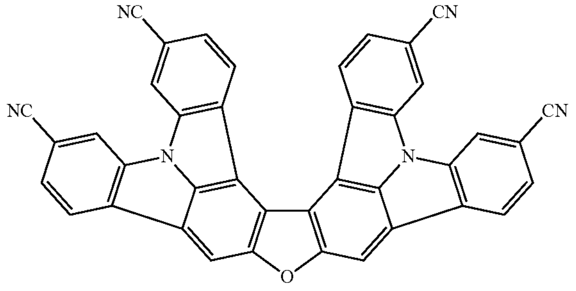 [SMILES: N#Cc1ccc2c3cc4oc5cc6c7ccc(C#N)cc7n7c8cc(C#N)ccc8c(c5c4c4c5ccc(C#N)cc5n(c2c1)c34)c67]
258
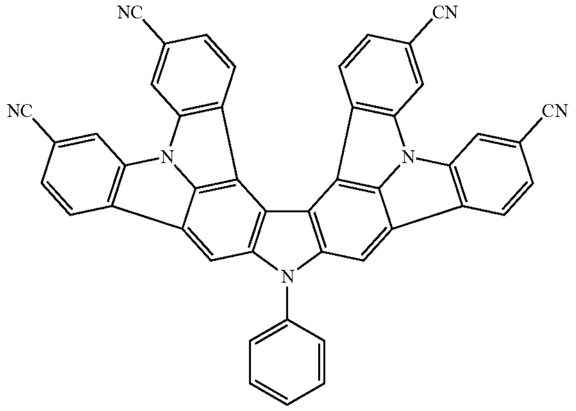 [SMILES: N#Cc1ccc2c3cc4c(c5c6c7ccc(C#N)cc7n7c8cc(C#N)ccc8c(cc5n4-c4ccccc4)c67)c4c5ccc(C#N)cc5n(c2c1)c34]
258
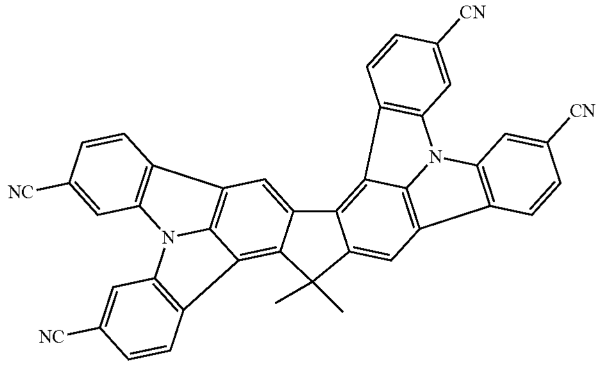 [SMILES: CC1(C)c2cc3c4ccc(C#N)cc4n4c5cc(C#N)ccc5c(c2-c2cc5c6ccc(C#N)cc6n6c7cc(C#N)ccc7c(c21)c56)c34]

-continued
259
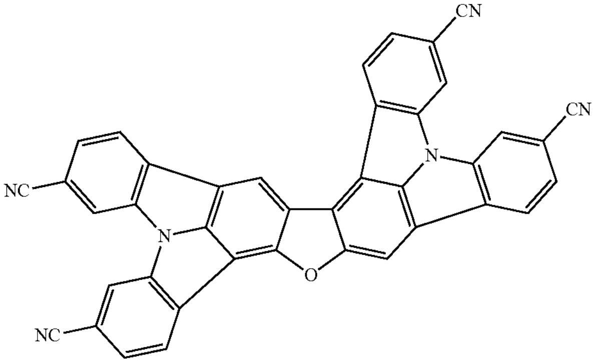 [SMILES: N#Cc1ccc2c3cc4c(oc5cc6c7ccc(C#N)cc7n7c8cc(C#N)ccc8c(c54)c67)c4c5ccc(C#N)cc5n(c2c1)c34]
260
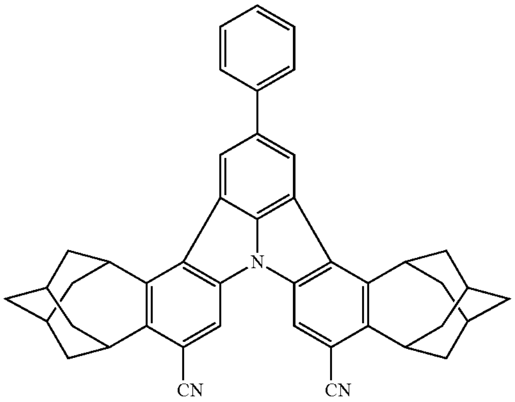 [SMILES: N#Cc1cc2c(c3c1C1CC4CC(C1)CC3C4)c1cc(-c3ccccc3)cc3c4c5c(c(C#N)cc4n2c13)C1CC2CC(C1)CC5C2]
261
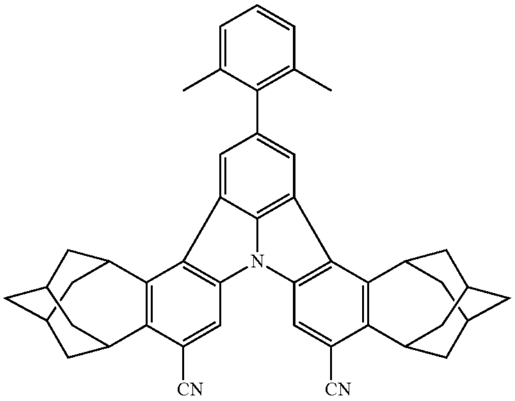 [SMILES: Cc1cccc(C)c1-c1cc2c3c4c(c(C#N)cc3n3c5cc(C#N)c6c(c5c(c1)c23)C1CC2CC(CC6C2)C1)C1CC2CC(C1)CC4C2]
262
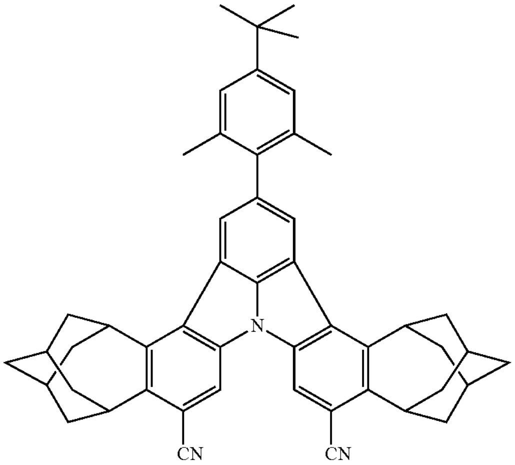 [SMILES: Cc1cc(C(C)(C)C)cc(C)c1-c1cc2c3c4c(c(C#N)cc3n3c5cc(C#N)c6c(c5c(c1)c23)C1CC2CC(CC6C2)C1)C1CC2CC(C1)CC4C2]

-continued
263
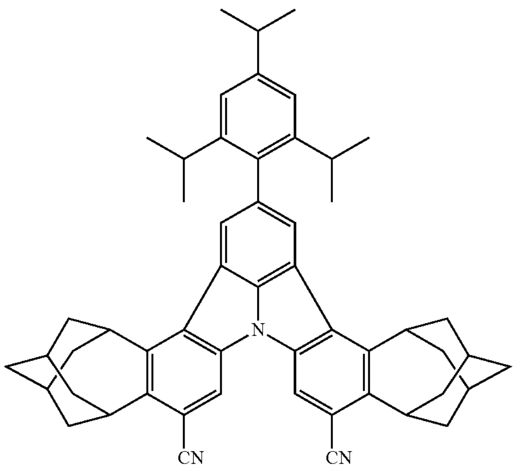 [SMILES: CC(C)c1cc(C(C)C)c(-c2cc3c4c5c(c(C#N)cc4n4c6cc(C#N)c7c(c6c(c2)c34)C2CC3CC(CC7C3)C2)C2CC3CC(C2)CC5C3)c(C(C)C)c1]
264
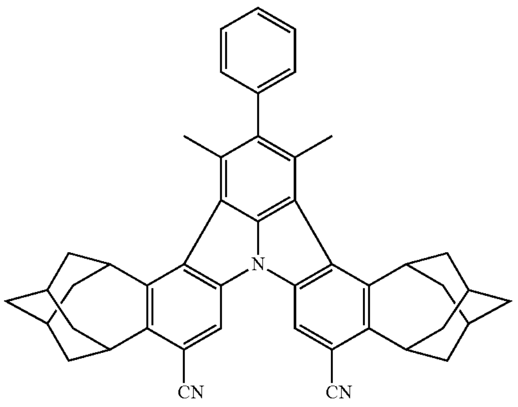 [SMILES: Cc1c(-c2ccccc2)c(C)c2c3c4c(c(C#N)cc3n3c5cc(C#N)c6c(c5c1c23)C1CC2CC(CC6C2)C1)C1CC2CC(C1)CC4C2]
265
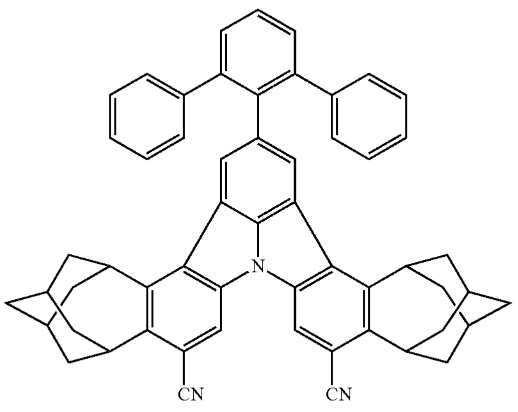 [SMILES: N#Cc1cc2c(c3c1C1CC4CC(C1)CC3C4)c1cc(-c3c(-c4ccccc4)cccc3-c3ccccc3)cc3c4c5c(c(C#N)cc4n2c13)C1CC2CC(C1)CC5C2]

-continued
266
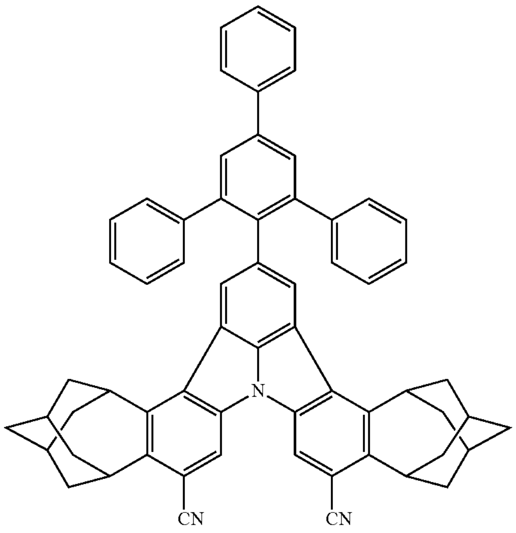 [SMILES: N#Cc1cc2c(c3c1C1CC4CC(C1)CC3C4)c1cc(-c3c(-c4ccccc4)cc(-c4ccccc4)cc3-c3ccccc3)cc3c4c5c(c(C#N)cc4n2c13)C1CC2CC(C1)CC5C2]
267
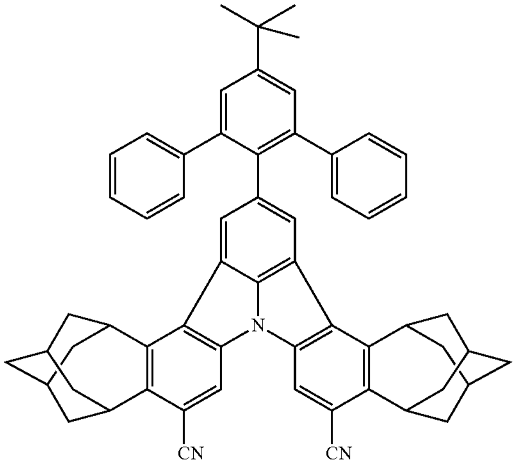 [SMILES: CC(C)(C)c1cc(-c2ccccc2)c(-c2cc3c4c5c(c(C#N)cc4n4c6cc(C#N)c7c(c6c(c2)c34)C2CC3CC(CC7C3)C2)C2CC3CC(C2)CC5C3)c(-c2ccccc2)c1]
268
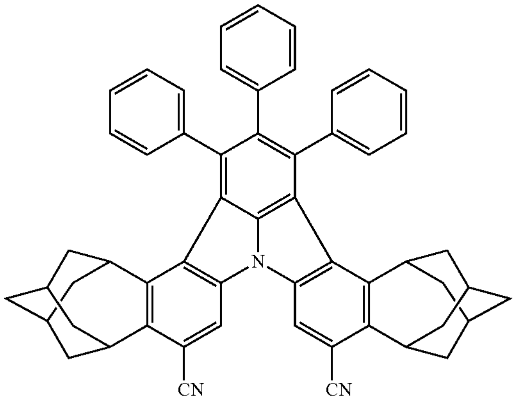 [SMILES: N#Cc1cc2c(c3c1C1CC4CC(C1)CC3C4)c1c(-c3ccccc3)c(-c3ccccc3)c(-c3ccccc3)c3c4c5c(c(C#N)cc4n2c13)C1CC2CC(C1)CC5C2]

-continued
269
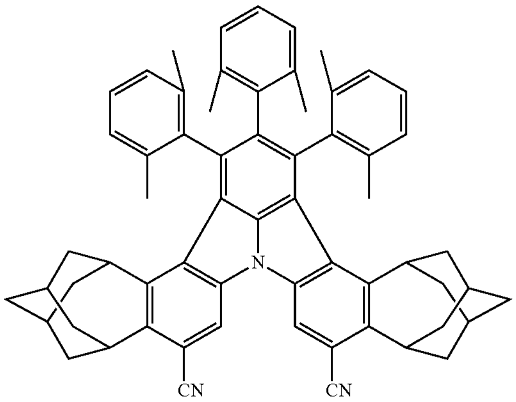 [SMILES: Cc1cccc(C)c1-c1c(-c2c(C)cccc2C)c2c3c4c(c(C#N)cc3n3c5cc(C#N)c6c(c5c(c1-c1c(C)cccc1C)c23)C1CC2CC(CC6C2)C1)C1CC2CC(C1)CC4C2]
270
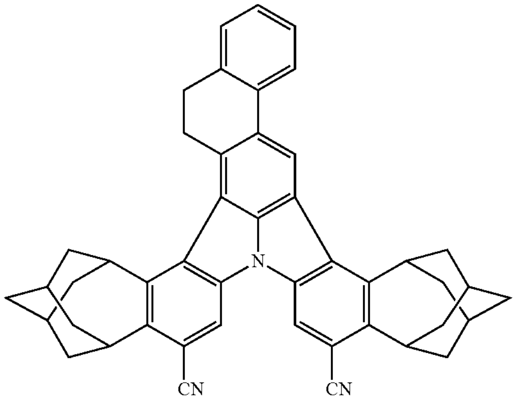 [SMILES: N#Cc1cc2c(c3c1C1CC4CC(C1)CC3C4)c1cc3c(c4c5c6c(c(C#N)cc5n2c14)C1CC2CC(C1)CC6C2)CCc1ccccc1-3]
271
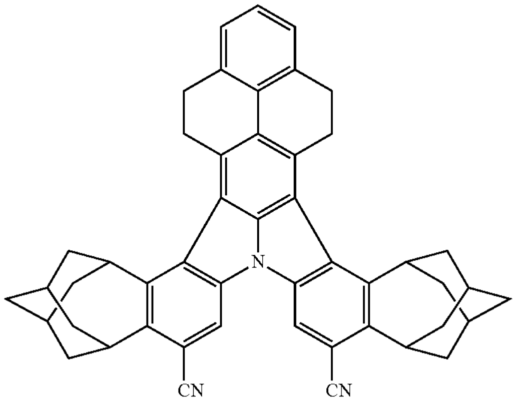 [SMILES: N#Cc1cc2c(c3c1C1CC4CC(C1)CC3C4)c1c3c4c(c5c6c7c(c(C#N)cc6n2c15)C1CC2CC(C1)CC7C2)CCc1cccc(c1-4)CC3]

-continued
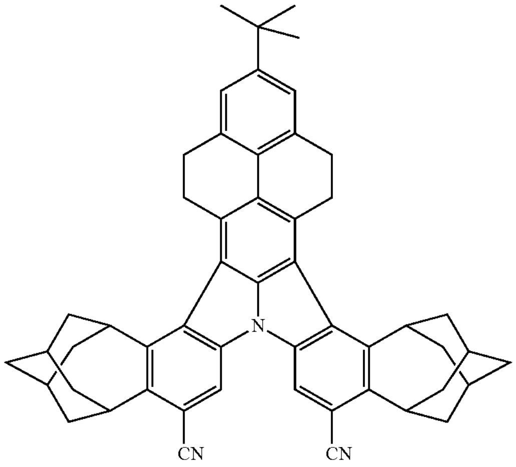 [SMILES: CC(C)(C)c1cc2c3c(c1)CCc1c-3c(c3c4c5c(c(C#N)cc4n4c6cc(C#N)c7c(c6c1c34)C1CC3CC(CC7C3)C1)C1CC3CC(C1)CC5C3)CC2]
272
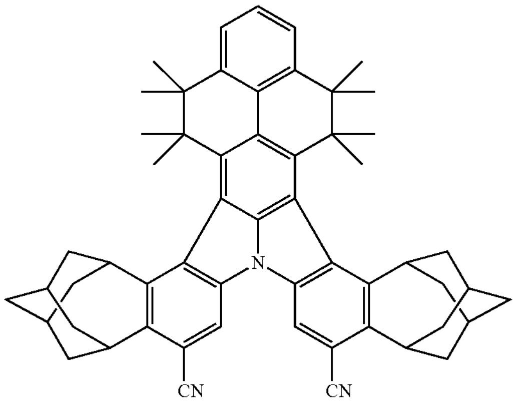 [SMILES: CC1(C)c2cccc3c2-c2c(c4c5c6c(c(C#N)cc5n5c7cc(C#N)c8c(c7c(c2C(C)(C)C3(C)C)c45)C2CC3CC(CC8C3)C2)C2CC3CC(C2)CC6C3)C1(C)C]
272
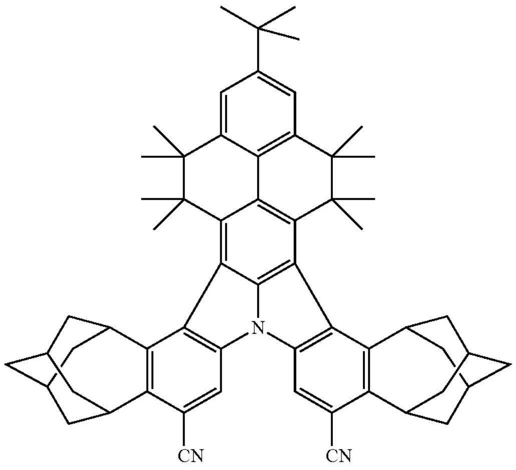 [SMILES: CC(C)(C)c1cc2c3c(c1)C(C)(C)C(C)(C)c1c-3c(c3c4c5c(c(C#N)cc4n4c6cc(C#N)c7c(c6c1c34)C1CC3CC(CC7C3)C1)C1CC3CC(C1)CC5C3)C(C)(C)C2(C)C]
273

-continued
274
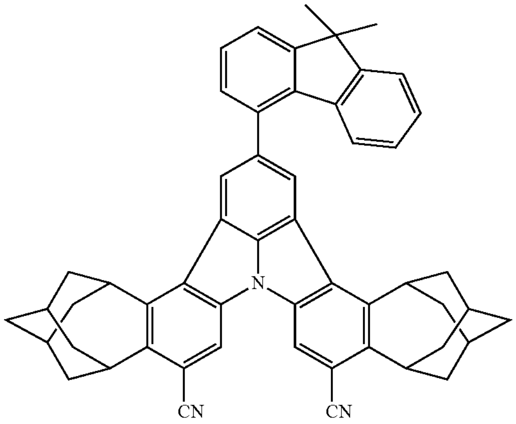 [SMILES: CC1(C)c2ccccc2-c2c(-c3cc4c5c6c(c(C#N)cc5n5c7cc(C#N)c8c(c7c(c3)c45)C3CC4CC(CC8C4)C3)C3CC4CC(C3)CC6C4)cccc21]
275
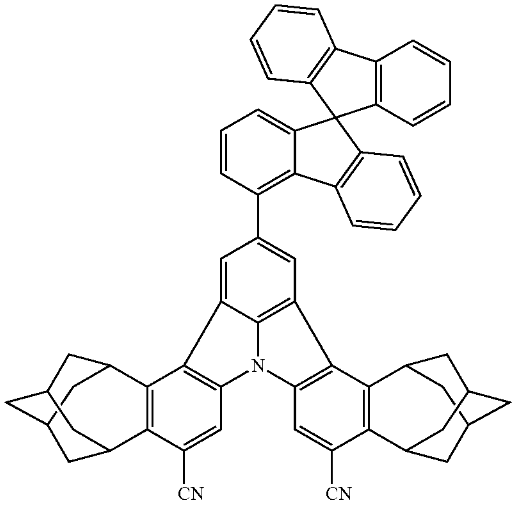 [SMILES: N#Cc1cc2c(c3c1C1CC4CC(C1)CC3C4)c1cc(-c3cccc4c3-c3ccccc3C43c4ccccc4-c4ccccc43)cc3c4c5c(c(C#N)cc4n2c13)C1CC2CC(C1)CC5C2]
276
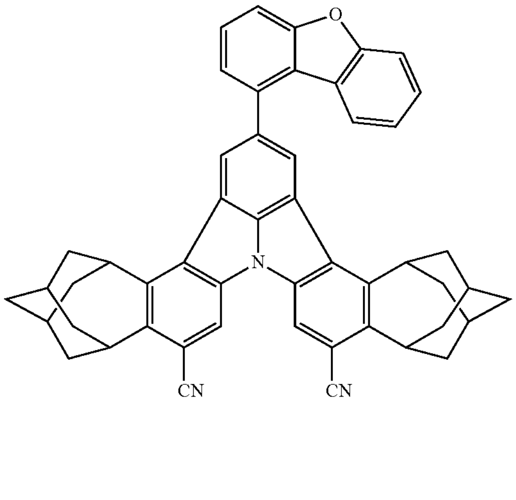 [SMILES: N#Cc1cc2c(c3c1C1CC4CC(C1)CC3C4)c1cc(-c3cccc4oc5ccccc5c34)cc3c4c5c(c(C#N)cc4n2c13)C1CC2CC(C1)CC5C2]

-continued
277
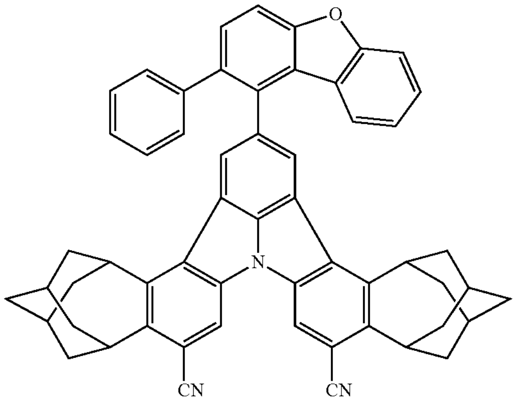 [SMILES: N#Cc1cc2c(c3c1C1CC4CC(C1)CC3C4)c1cc(-c3c(-c4ccccc4)ccc4oc5ccccc5c34)cc3c4c5c(c(C#N)cc4n2c13)C1CC2CC(C1)CC5C2]
278
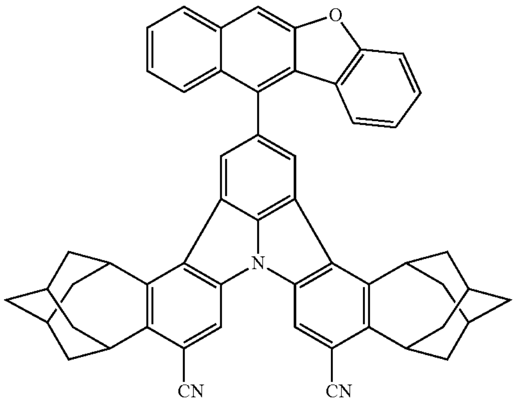 [SMILES: N#Cc1cc2c(c3c1C1CC4CC(C1)CC3C4)c1cc(-c3c4ccccc4cc4oc5ccccc5c34)cc3c4c5c(c(C#N)cc4n2c13)C1CC2CC(C1)CC5C2]
279
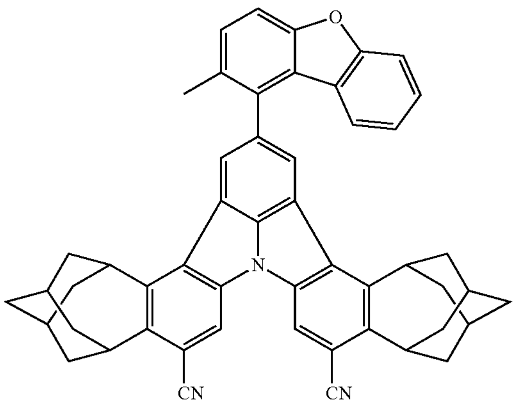 [SMILES: Cc1ccc2oc3ccccc3c2c1-c1cc2c3c4c(c(C#N)cc3n3c5cc(C#N)c6c(c5c(c1)c23)C1CC2CC(CC6C2)C1)C1CC2CC(C1)CC4C2]

-continued
280
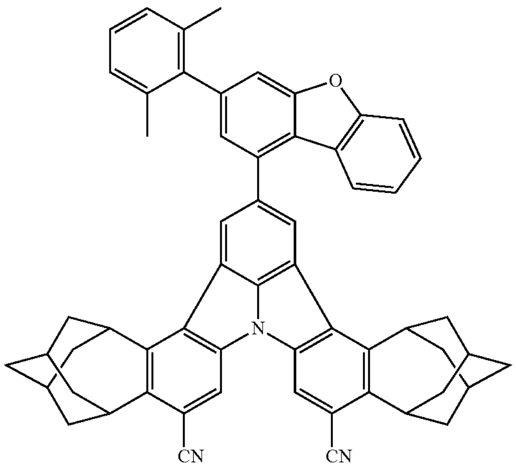 [SMILES: Cc1cccc(C)c1-c1cc(-c2cc3c4c5c(c(C#N)cc4n4c6cc(C#N)c7c(c6c(c2)c34)C2CC3CC(CC7C3)C2)C2CC3CC(C2)CC5C3)c2c(c1)oc1ccccc12]
282
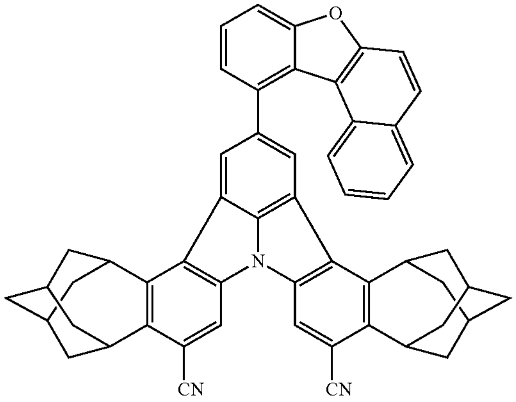 [SMILES: N#Cc1cc2c(c3c1C1CC4CC(C1)CC3C4)c1cc(-c3cccc4oc5ccc6ccccc6c5c34)cc3c4c5c(c(C#N)cc4n2c13)C1CC2CC(C1)CC5C2]
283
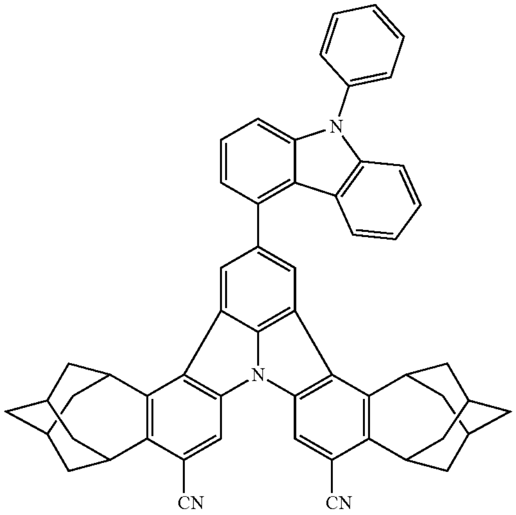 [SMILES: N#Cc1cc2c(c3c1C1CC4CC(C1)CC3C4)c1cc(-c3cccc4c3c3ccccc3n4-c3ccccc3)cc3c4c5c(c(C#N)cc4n2c13)C1CC2CC(C1)CC5C2]

-continued
284
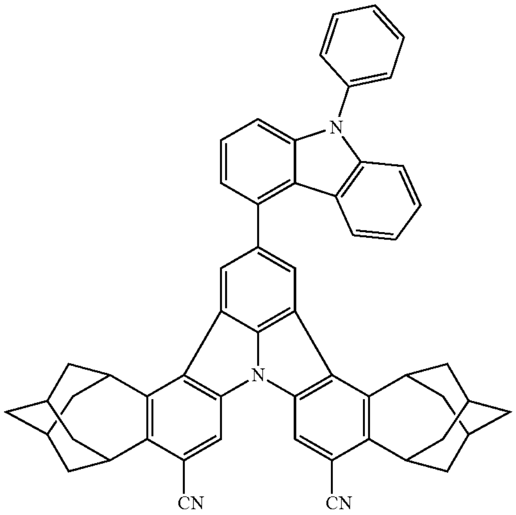 [SMILES: N#Cc1cc2c(c3c1C1CC4CC(C1)CC3C4)c1cc(-c3cccc4c3c3ccccc3n4-c3ccccc3)cc3c4c5c(c(C#N)cc4n2c13)C1CC2CC(C1)CC5C2]
285
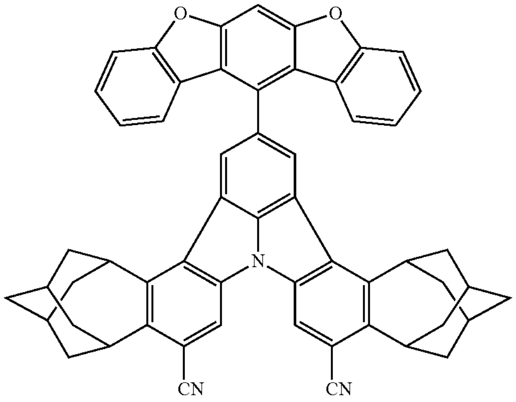 [SMILES: N#Cc1cc2c(c3c1C1CC4CC(C1)CC3C4)c1cc(-c3c4c(cc5oc6ccccc6c35)oc3ccccc34)cc3c4c5c(c(C#N)cc4n2c13)C1CC2CC(C1)CC5C2]
286
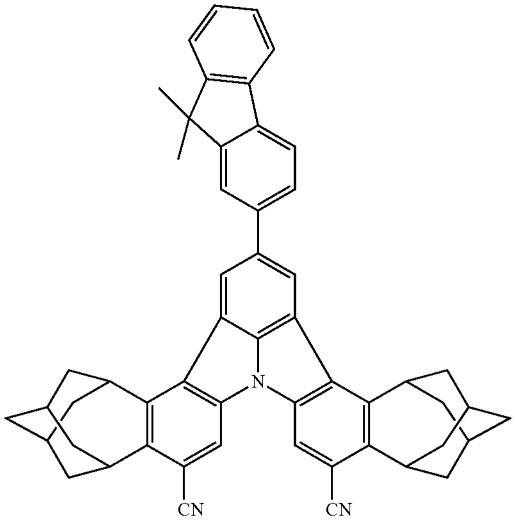 [SMILES: CC1(C)c2ccccc2-c2ccc(-c3cc4c5c6c(c(C#N)cc5n5c7cc(C#N)c8c(c7c(c3)c45)C3CC4CC(CC8C4)C3)C3CC4CC(C3)CC6C4)cc21]

-continued
287
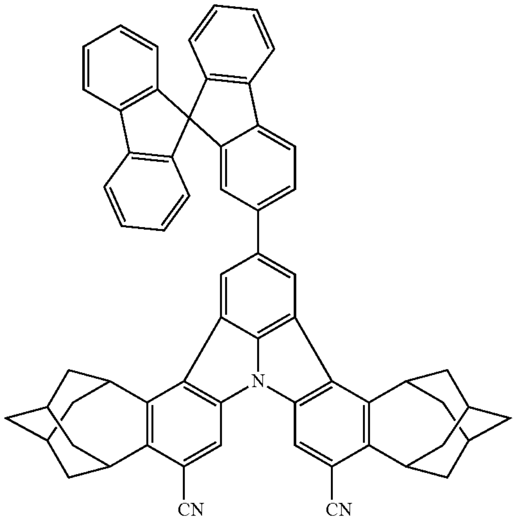 [SMILES: N#Cc1cc2c(c3c1C1CC4CC(C1)CC3C4)c1cc(-c3ccc4c(c3)C3(c5ccccc5-c5ccccc53)c3ccccc3-4)cc3c4c5c(c(C#N)cc4n2c13)C1CC2CC(C1)CC5C2]
288
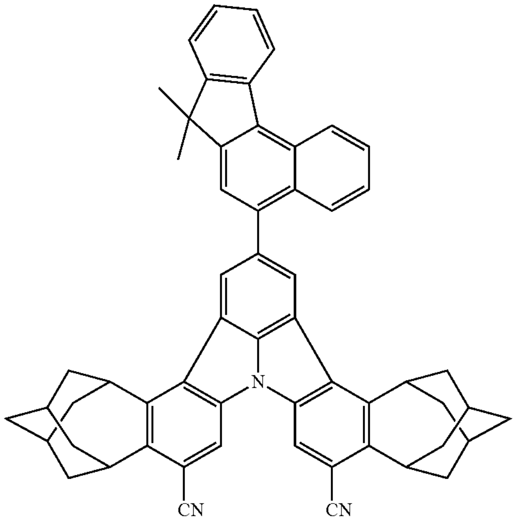 [SMILES: CC1(C)c2ccccc2-c2c1cc(-c1cc3c4c5c(c(C#N)cc4n4c6cc(C#N)c7c(c6c(c1)c34)C1CC3CC(CC7C3)C1)C1CC3CC(C1)CC5C3)c1ccccc21]
289
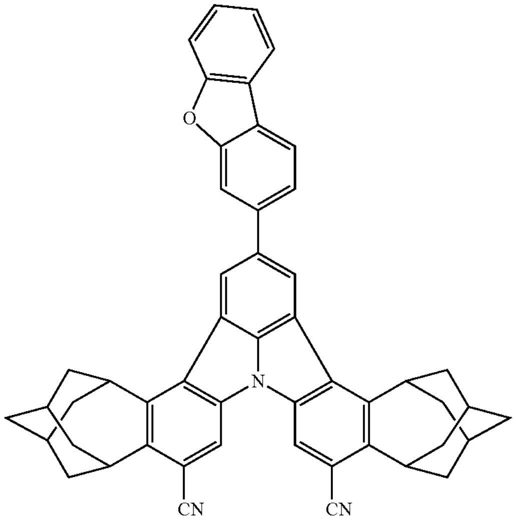 [SMILES: N#Cc1cc2c(c3c1C1CC4CC(C1)CC3C4)c1cc(-c3ccc4c(c3)oc3ccccc34)cc3c4c5c(c(C#N)cc4n2c13)C1CC2CC(C1)CC5C2]

-continued
290
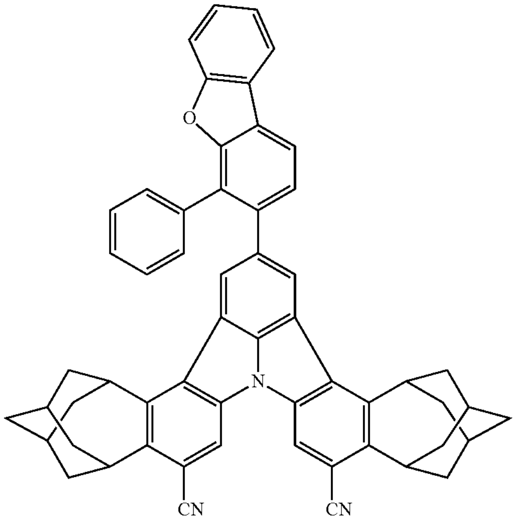 [SMILES: N#Cc1cc2c(c3c1C1CC4CC(C1)CC3C4)c1cc(-c3ccc4c(oc5ccccc54)c3-c3ccccc3)cc3c4c5c(c(C#N)cc4n2c13)C1CC2CC(C1)CC5C2]
291
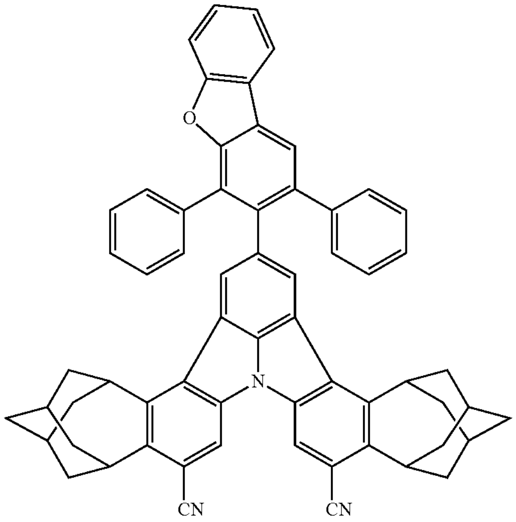 [SMILES: N#Cc1cc2c(c3c1C1CC4CC(C1)CC3C4)c1cc(-c3c(-c4ccccc4)cc4c(oc5ccccc54)c3-c3ccccc3)cc3c4c5c(c(C#N)cc4n2c13)C1CC2CC(C1)CC5C2]
292
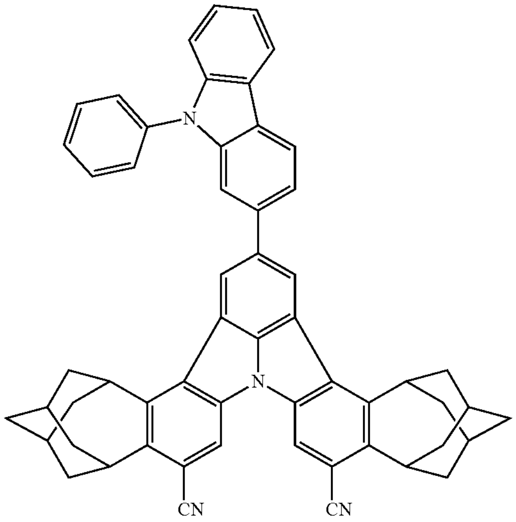 [SMILES: N#Cc1cc2c(c3c1C1CC4CC(C1)CC3C4)c1cc(-c3ccc4c5ccccc5n(-c5ccccc5)c4c3)cc3c4c5c(c(C#N)cc4n2c13)C1CC2CC(C1)CC5C2]

-continued
293
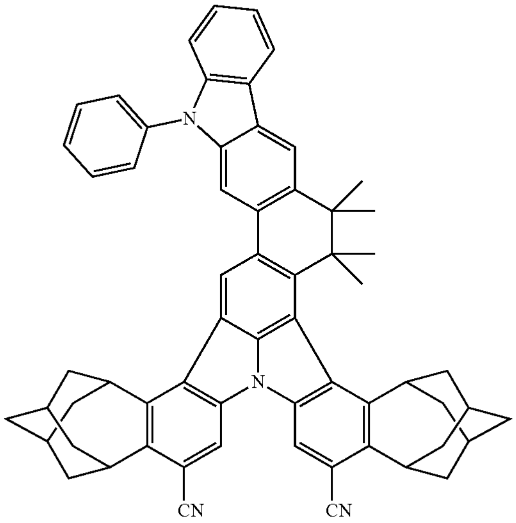 [SMILES: CC1(C)c2cc3c4ccccc4n(-c4ccccc4)c3cc2-c2cc3c4c5c(c(C#N)cc4n4c6cc(C#N)c7c(c6c(c2C1(C)C)c34)C1CC2CC(CC7C2)C1)C1CC2CC(C1)CC5C2]
294
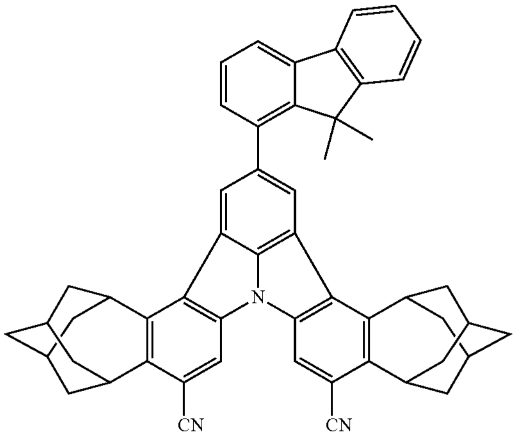 [SMILES: CC1(C)c2ccccc2-c2cccc(-c3cc4c5c6c(c(C#N)cc5n5c7cc(C#N)c8c(c7c(c3)c45)C3CC4CC(CC8C4)C3)C3CC4CC(C3)CC6C4)c21]
295
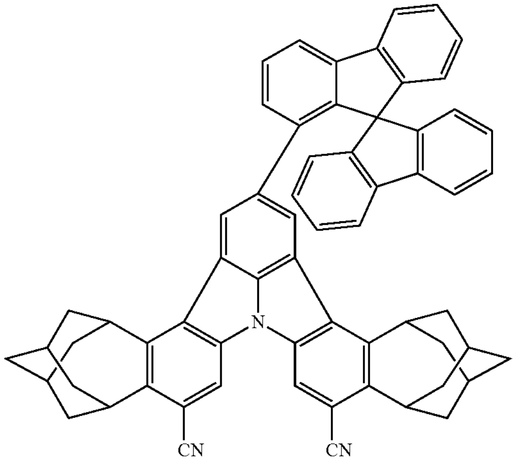 [SMILES: N#Cc1cc2c(c3c1C1CC4CC(C1)CC3C4)c1cc(-c3cccc4c3C3(c5ccccc5-c5ccccc53)c3ccccc3-4)cc3c4c5c(c(C#N)cc4n2c13)C1CC2CC(C1)CC5C2]

-continued
296
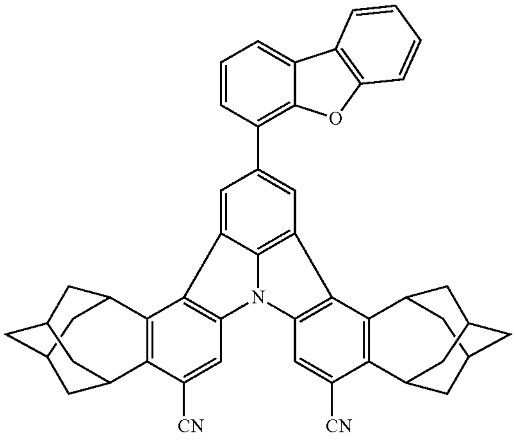 [SMILES: N#Cc1cc2c(c3c1C1CC4CC(C1)CC3C4)c1cc(-c3cccc4c3oc3ccccc34)cc3c4c5c(c(C#N)cc4n2c13)C1CC2CC(C1)CC5C2]
297
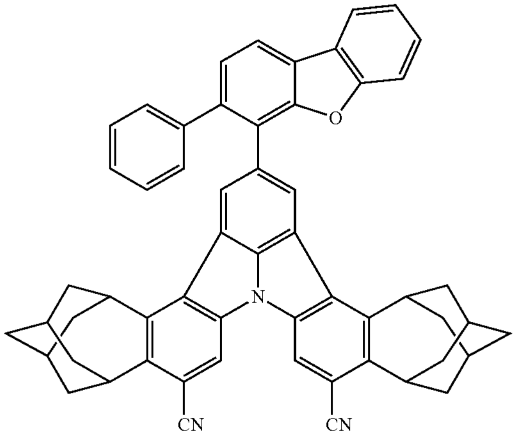 [SMILES: N#Cc1cc2c(c3c1C1CC4CC(C1)CC3C4)c1cc(-c3c(-c4ccccc4)ccc4c3oc3ccccc34)cc3c4c5c(c(C#N)cc4n2c13)C1CC2CC(C1)CC5C2]
298
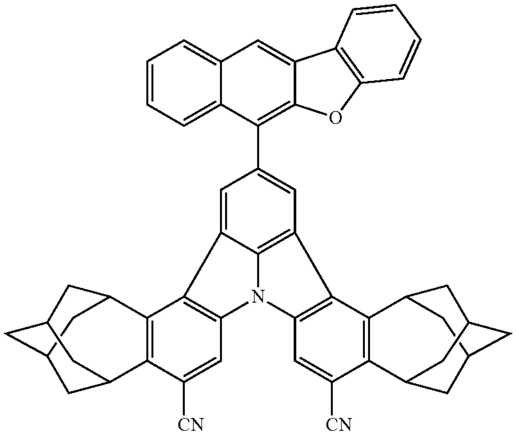 [SMILES: N#Cc1cc2c(c3c1C1CC4CC(C1)CC3C4)c1cc(-c3c4ccccc4cc4c3oc3ccccc34)cc3c4c5c(c(C#N)cc4n2c13)C1CC2CC(C1)CC5C2]

-continued
299
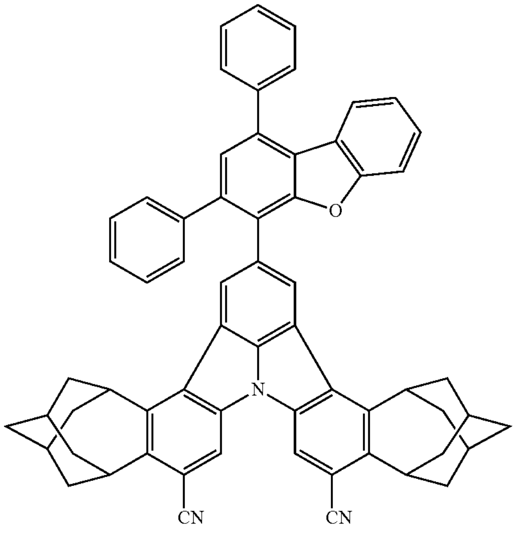 [SMILES: N#Cc1cc2c(c3c1C1CC4CC(C1)CC3C4)c1cc(-c3c(-c4ccccc4)cc(-c4ccccc4)c4c3oc3ccccc34)cc3c4c5c(c(C#N)cc4n2c13)C1CC2CC(C1)CC5C2]
300
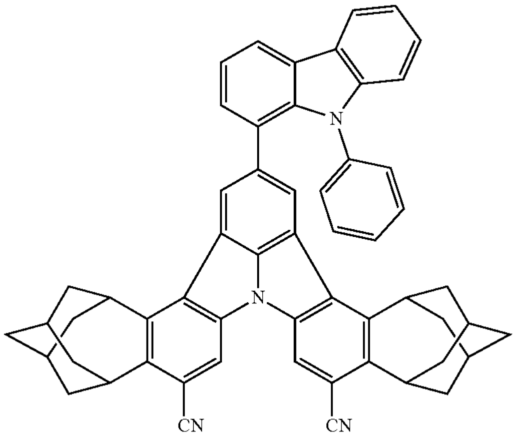 [SMILES: N#Cc1cc2c(c3c1C1CC4CC(C1)CC3C4)c1cc(-c3cccc4c5ccccc5n(-c5ccccc5)c34)cc3c4c5c(c(C#N)cc4n2c13)C1CC2CC(C1)CC5C2]
301
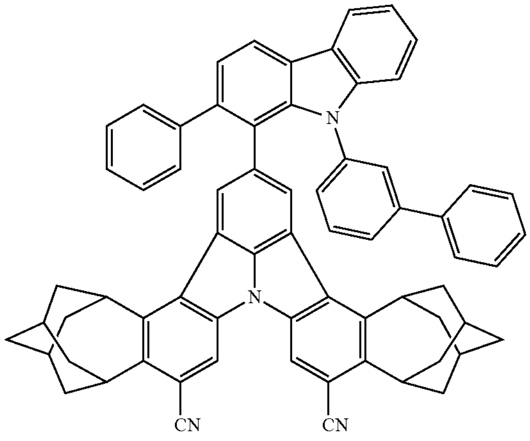 [SMILES: N#Cc1cc2c(c3c1C1CC4CC(C1)CC3C4)c1cc(-c3c(-c4ccccc4)ccc4c5ccccc5n(-c5cccc(-c6ccccc6)c5)c34)cc3c4c5c(c(C#N)cc4n2c13)C1CC2CC(C1)CC5C2]

-continued
302
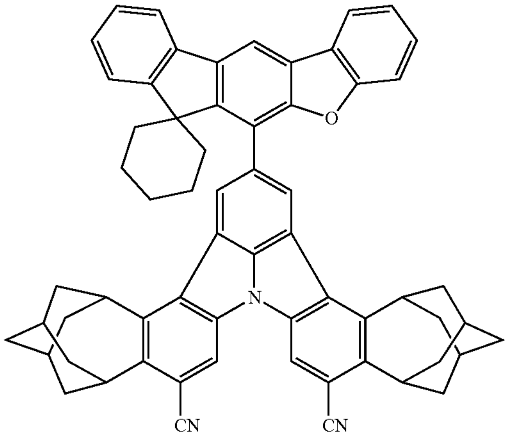 [SMILES: N#Cc1cc2c(c3c1C1CC4CC(C1)CC3C4)c1cc(-c3c4c(cc5c3oc3ccccc35)-c3ccccc3C43CCCCC3)cc3c4c5c(c(C#N)cc4n2c13)C1CC2CC(C1)CC5C2]
303
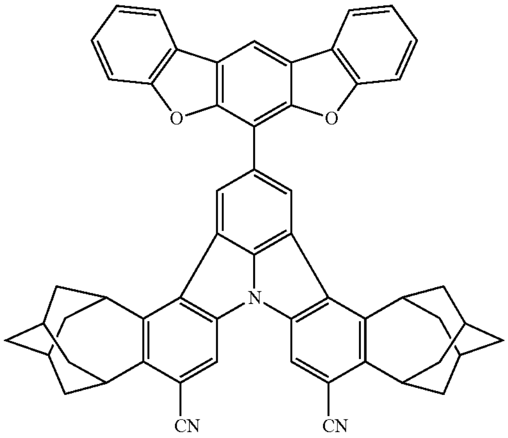 [SMILES: N#Cc1cc2c(c3c1C1CC4CC(C1)CC3C4)c1cc(-c3c4oc5ccccc5c4cc4c3oc3ccccc34)cc3c4c5c(c(C#N)cc4n2c13)C1CC2CC(C1)CC5C2]
304
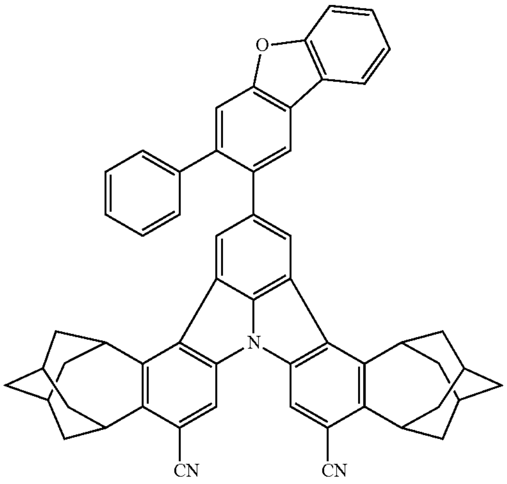 [SMILES: N#Cc1cc2c(c3c1C1CC4CC(C1)CC3C4)c1cc(-c3cc4c(cc3-c3ccccc3)oc3ccccc34)cc3c4c5c(c(C#N)cc4n2c13)C1CC2CC(C1)CC5C2]

-continued
305
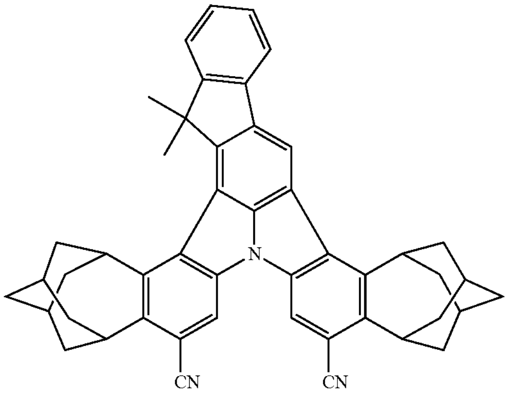 [SMILES: CC1(C)c2ccccc2-c2cc3c4c5c(c(C#N)cc4n4c6cc(C#N)c7c(c6c(c21)c34)C1CC2CC(CC7C2)C1)C1CC2CC(C1)CC5C2]
306
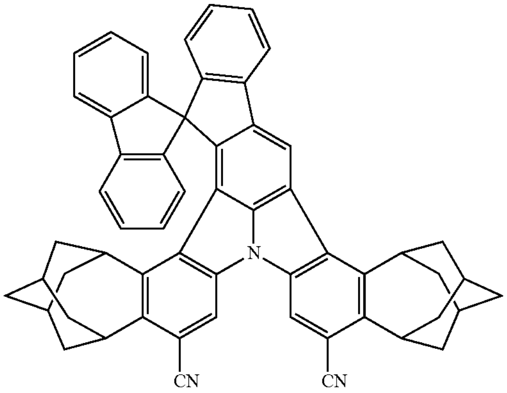 [SMILES: N#Cc1cc2c(c3c1C1CC4CC(C1)CC3C4)c1cc3c(c4c5c6c(c(C#N)cc5n2c14)C1CC2CC(C1)CC6C2)C1(c2ccccc2-c2ccccc21)c1ccccc1-3]
307
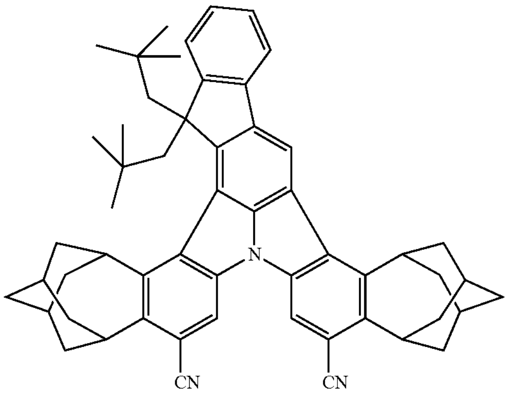 [SMILES: CC(C)(C)CC1(CC(C)(C)C)c2ccccc2-c2cc3c4c5c(c(C#N)cc4n4c6cc(C#N)c7c(c6c(c21)c34)C1CC2CC(CC7C2)C1)C1CC2CC(C1)CC5C2]
308
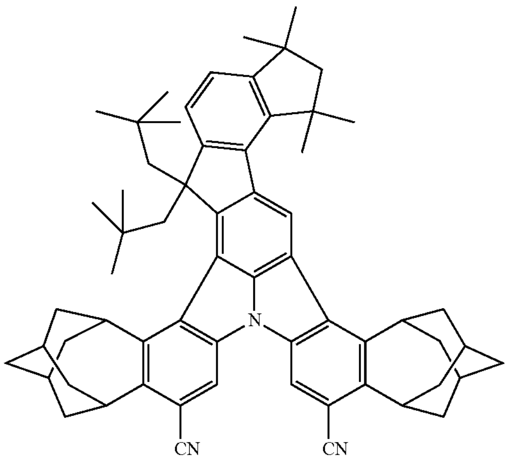 [SMILES: CC(C)(C)CC1(CC(C)(C)C)c2ccc3c(c2-c2cc4c5c6c(c(C#N)cc5n5c7cc(C#N)c8c(c7c(c21)c45)C1CC2CC(CC8C2)C1)C1CC2CC(C1)CC6C2)C(C)(C)CC3(C)C]

-continued
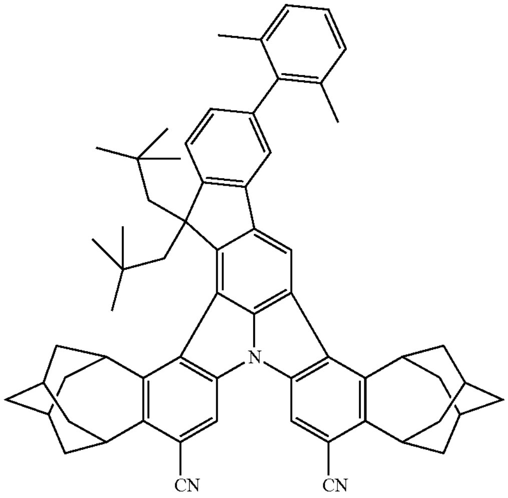 [SMILES: Cc1cccc(C)c1-c1ccc2c(c1)-c1cc3c4c5c(c(C#N)cc4n4c6cc(C#N)c7c(c6c(c1C2(CC(C)(C)C)CC(C)(C)C)c34)C1CC2CC(CC7C2)C1)C1CC2CC(C1)CC5C2]
309
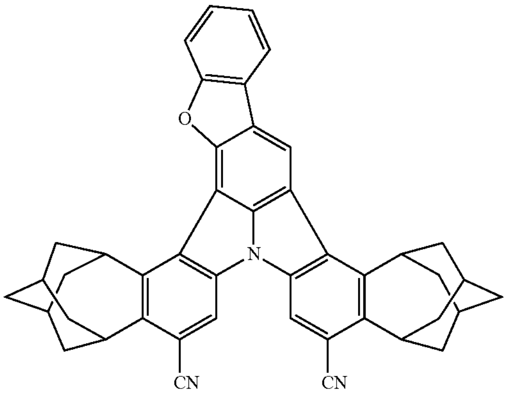 [SMILES: N#Cc1cc2c(c3c1C1CC4CC(C1)CC3C4)c1cc3c4ccccc4oc3c3c4c5c(c(C#N)cc4n2c13)C1CC2CC(C1)CC5C2]
310
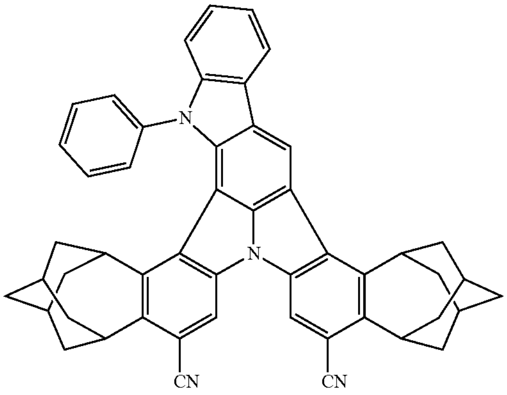 [SMILES: N#Cc1cc2c(c3c1C1CC4CC(C1)CC3C4)c1cc3c4ccccc4n(-c4ccccc4)c3c3c4c5c(c(C#N)cc4n2c13)C1CC2CC(C1)CC5C2]
311

-continued
312
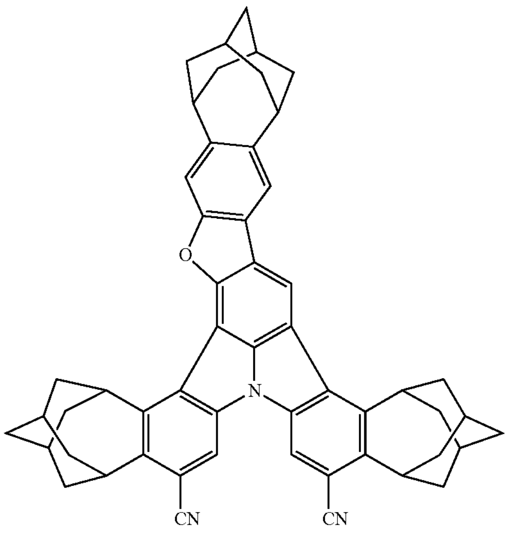 [SMILES: N#Cc1cc2c(c3c1C1CC4CC(C1)CC3C4)c1cc3c4cc5c(cc4oc3c3c4c6c(c(C#N)cc4n2c13)C1CC2CC(C1)CC6C2)C1CC2CC(C1)CC5C2]
313
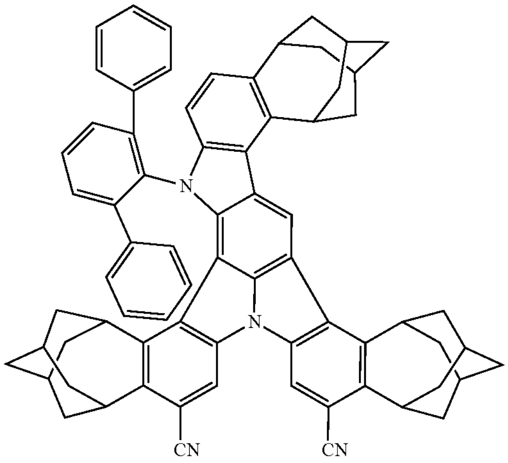 [SMILES: N#Cc1cc2c(c3c1C1CC4CC(C1)CC3C4)c1cc3c4c5c(ccc4n(-c4c(-c6ccccc6)cccc4-c4ccccc4)c3c3c4c6c(c(C#N)cc4n2c13)C1CC2CC(C1)CC6C2)C1CC2CC(C1)CC5C2]
314
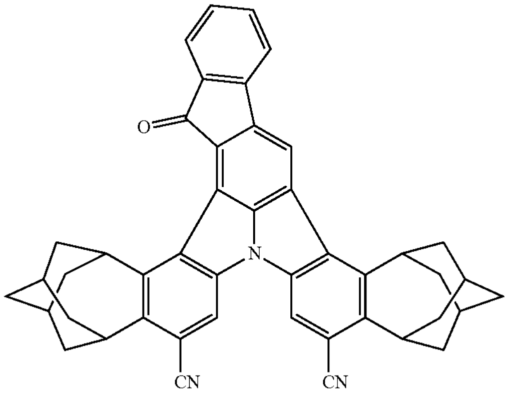 [SMILES: N#Cc1cc2c(c3c1C1CC4CC(C1)CC3C4)c1cc3c(c4c5c6c(c(C#N)cc5n2c14)C1CC2CC(C1)CC6C2)C(=O)c1ccccc1-3]

-continued
315
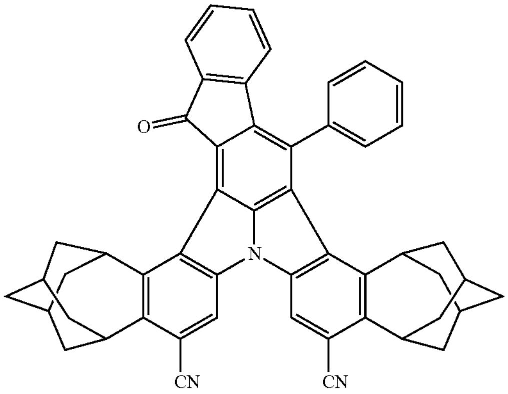 [SMILES: N#Cc1cc2c(c3c1C1CC4CC(C1)CC3C4)c1c3c(c(-c4ccccc4)c4c5c6c(c(C#N)cc5n2c14)C1CC2CC(C1)CC6C2)-c1ccccc1C3=O]
316
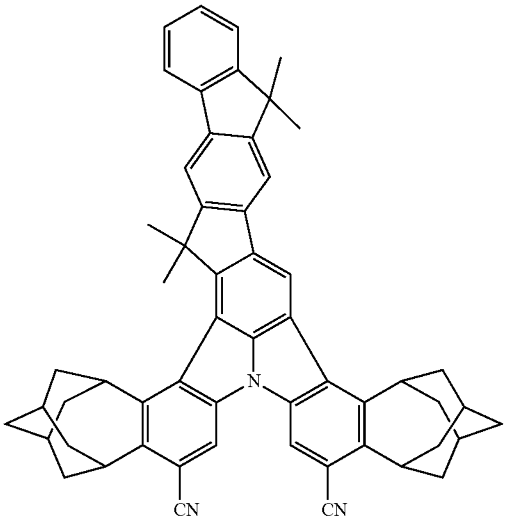 [SMILES: CC1(C)c2ccccc2-c2cc3c(cc21)-c1cc2c4c5c(c(C#N)cc4n4c6cc(C#N)c7c(c6c(c1C3(C)C)c24)C1CC2CC(CC7C2)C1)C1CC2CC(C1)CC5C2]
317
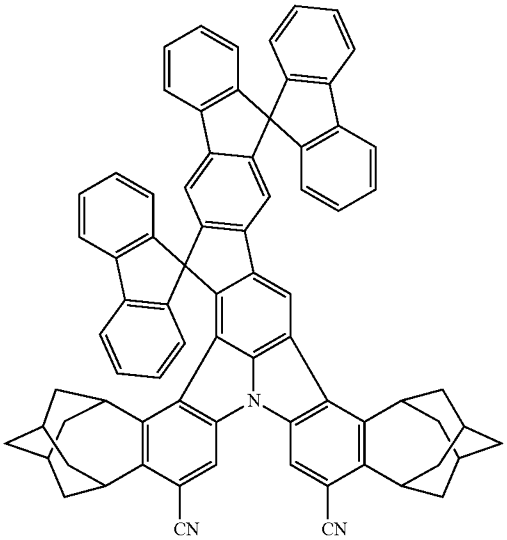 [SMILES: N#Cc1cc2c(c3c1C1CC4CC(C1)CC3C4)c1cc3c(c4c5c6c(c(C#N)cc5n2c14)C1CC2CC(C1)CC6C2)C1(c2ccccc2-c2ccccc21)c1cc2c(cc1-3)C1(c3ccccc3-c3ccccc31)c1ccccc1-2]

-continued
318
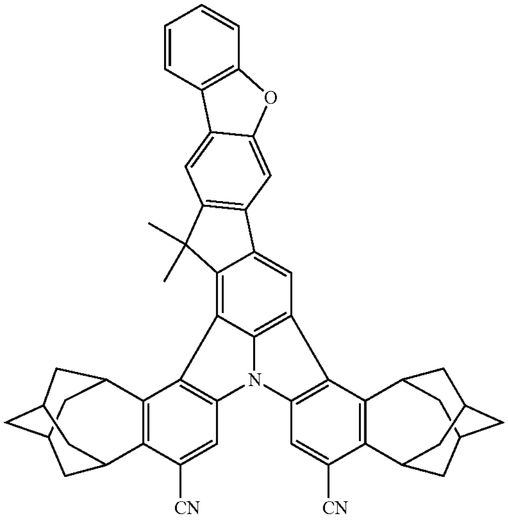 [SMILES: CC1(C)c2cc3c(cc2-c2cc4c5c6c(c(C#N)cc5n5c7cc(C#N)c8c(c7c(c21)c45)C1CC2CC(CC8C2)C1)C1CC2CC(C1)CC6C2)oc1ccccc13]
319
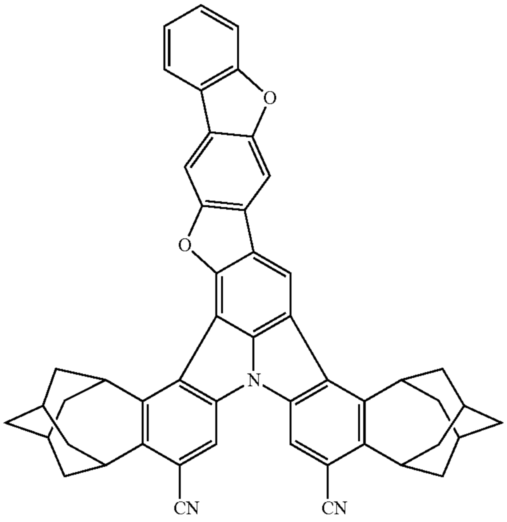 [SMILES: N#Cc1cc2c(c3c1C1CC4CC(C1)CC3C4)c1cc3c4cc5oc6ccccc6c5cc4oc3c3c4c5c(c(C#N)cc4n2c13)C1CC2CC(C1)CC5C2]
320
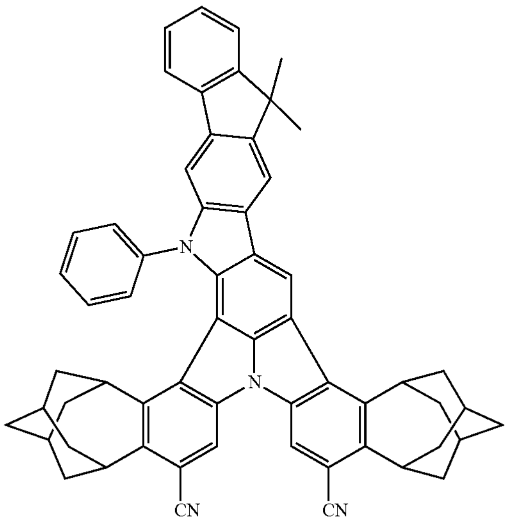 [SMILES: CC1(C)c2ccccc2-c2cc3c(cc21)c1cc2c4c5c(c(C#N)cc4n4c6cc(C#N)c7c(c6c(c1n3-c1ccccc1)c24)C1CC2CC(CC7C2)C1)C1CC2CC(C1)CC5C2]

-continued
321
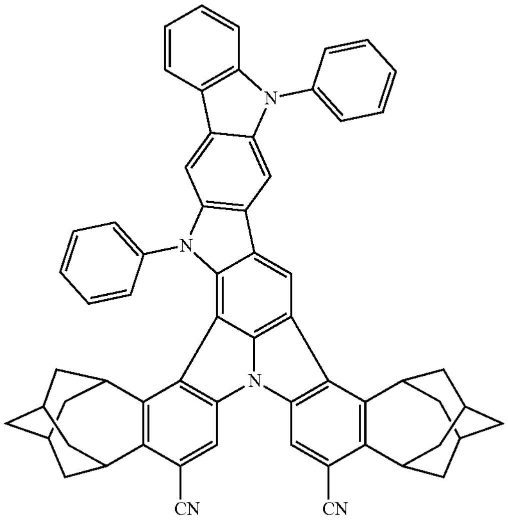 [SMILES: N#Cc1cc2c(c3c1C1CC4CC(C1)CC3C4)c1cc3c4cc5c(cc4n(-c4ccccc4)c3c3c4c6c(c(C#N)cc4n2c13)C1CC2CC(C1)CC6C2)c1ccccc1n5-c1ccccc1]
322
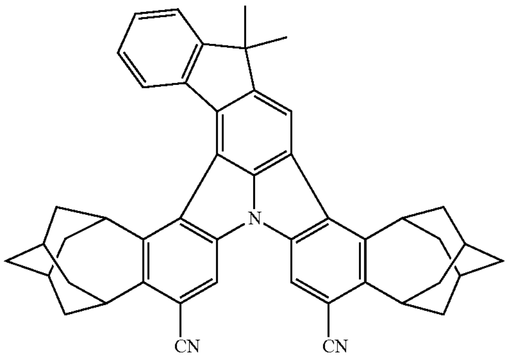 [SMILES: CC1(C)c2ccccc2-c2c1cc1c3c4c(c(C#N)cc3n3c5cc(C#N)c6c(c5c2c13)C1CC2CC(CC6C2)C1)C1CC2CC(C1)CC4C2]
323
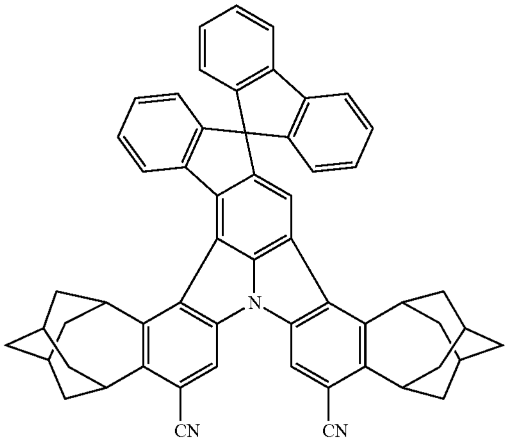 [SMILES: N#Cc1cc2c(c3c1C1CC4CC(C1)CC3C4)c1cc3c(c4c5c6c(c(C#N)cc5n2c14)C1CC2CC(C1)CC6C2)-c1ccccc1C31c2ccccc2-c2ccccc21]

-continued
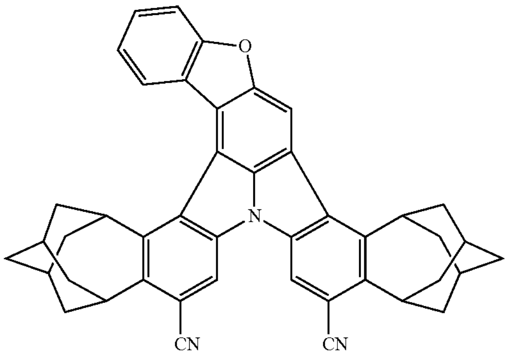 [SMILES: N#Cc1cc2c(c3c1C1CC4CC(C1)CC3C4)c1cc3oc4ccccc4c3c3c4c5c(c(C#N)cc4n2c13)C1CC2CC(C1)CC5C2]
324
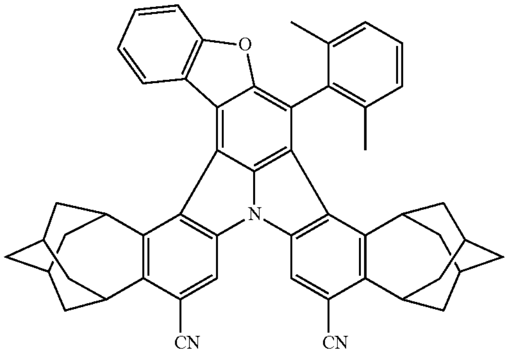 [SMILES: Cc1cccc(C)c1-c1c2oc3ccccc3c2c2c3c4c(c(C#N)cc3n3c5cc(C#N)c6c(c5c1c23)C1CC2CC(CC6C2)C1)C1CC2CC(C1)CC4C2]
325
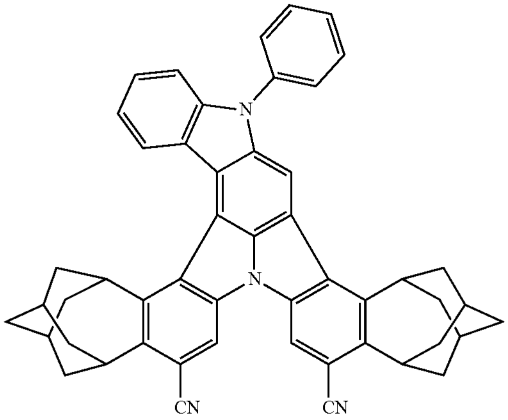 [SMILES: N#Cc1cc2c(c3c1C1CC4CC(C1)CC3C4)c1cc3c(c4ccccc4n3-c3ccccc3)c3c4c5c(c(C#N)cc4n2c13)C1CC2CC(C1)CC5C2]
326
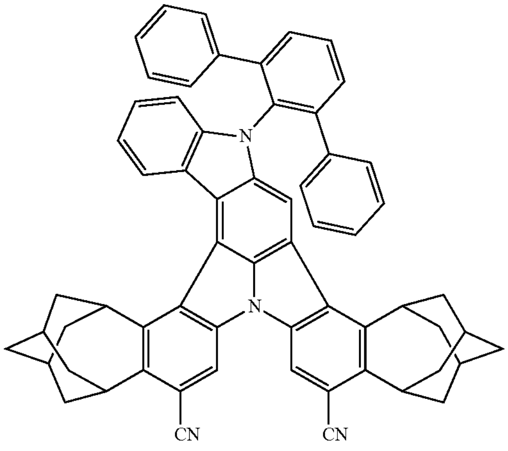 [SMILES: N#Cc1cc2c(c3c1C1CC4CC(C1)CC3C4)c1cc3c(c4ccccc4n3-c3c(-c4ccccc4)cccc3-c3ccccc3)c3c4c5c(c(C#N)cc4n2c13)C1CC2CC(C1)CC5C2]
327

-continued
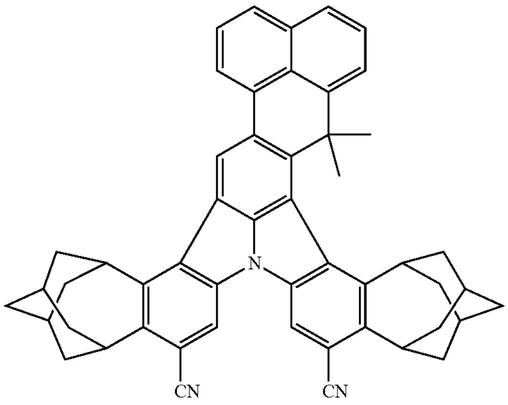 [SMILES: CC1(C)c2cccc3cccc(c23)-c2cc3c4c5c(c(C#N)cc4n4c6cc(C#N)c7c(c6c(c21)c34)C1CC2CC(CC7C2)C1)C1CC2CC(C1)CC5C2]
328
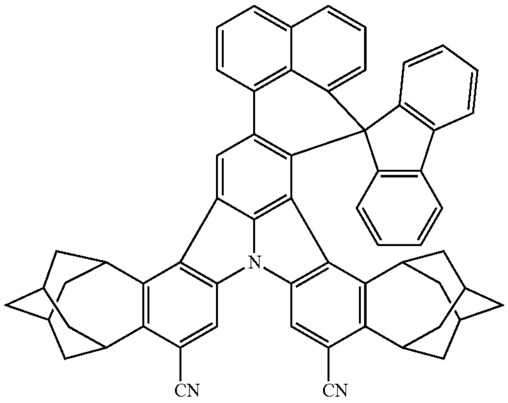 [SMILES: N#Cc1cc2c(c3c1C1CC4CC(C1)CC3C4)c1cc3c(c4c5c6c(c(C#N)cc5n2c14)C1CC2CC(C1)CC6C2)C1(c2ccccc2-c2ccccc21)c1cccc2cccc-3c12]
329
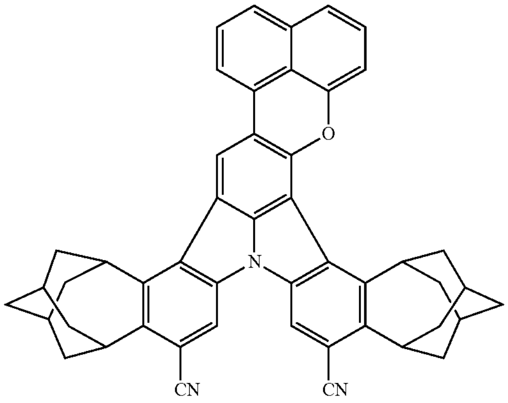 [SMILES: N#Cc1cc2c(c3c1C1CC4CC(C1)CC3C4)c1cc3c4cccc5cccc(oc3c3c6c7c(c(C#N)cc6n2c13)C1CC2CC(C1)CC7C2)c54]
330

-continued
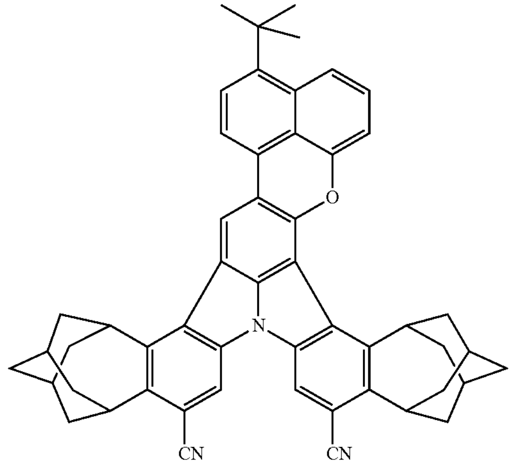 [SMILES: CC(C)(C)c1ccc2c3cc4c5c6c(c(C#N)cc5n5c7cc(C#N)c8c(c7c(c3oc3cccc1c32)c45)C1CC2CC(CC8C2)C1)C1CC2CC(C1)CC6C2]
331
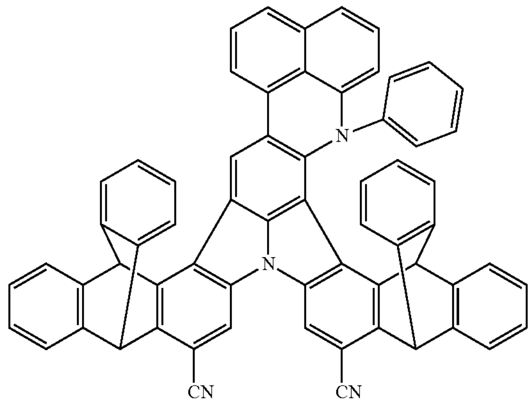 [SMILES: N#Cc1cc2c(c3c1C1c4ccccc4C3c3ccccc31)c1cc3c4cccc5cccc(c54)n(-c4ccccc4)c3c3c4c5c(c(C#N)cc4n2c13)C1c2ccccc2C5c2ccccc21]
332
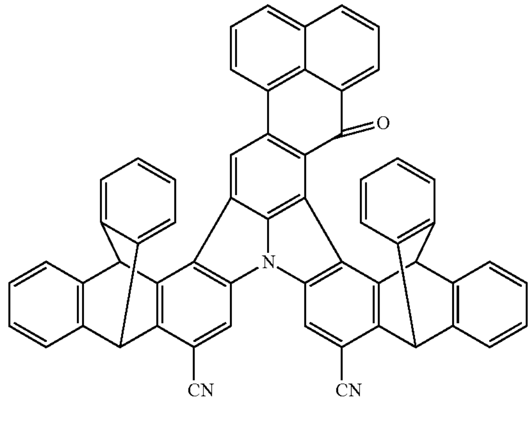 [SMILES: N#Cc1cc2c(c3c1C1c4ccccc4C3c3ccccc31)c1cc3c4cccc5cccc(c(=O)c3c3c6c7c(c(C#N)cc6n2c13)C1c2ccccc2C7c2ccccc21)c54]
333

-continued
334
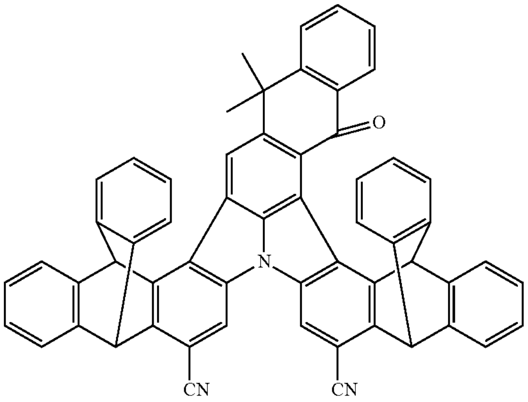 [SMILES: CC1(C)c2ccccc2C(=O)c2c1cc1c3c4c(c(C#N)cc3n3c5cc(C#N)c6c(c5c2c13)C1c2ccccc2C6c2ccccc21)C1c2ccccc2C4c2ccccc21]
335
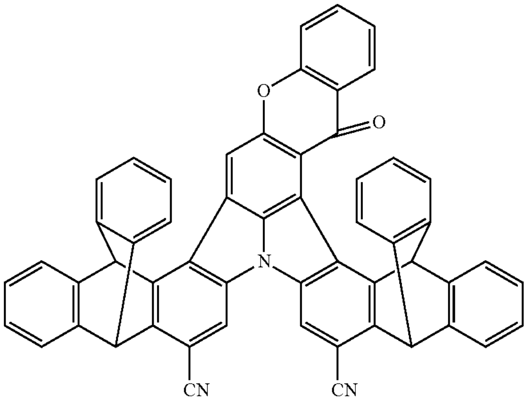 [SMILES: N#Cc1cc2c(c3c1C1c4ccccc4C3c3ccccc31)c1cc3oc4ccccc4c(=O)c3c3c4c5c(c(C#N)cc4n2c13)C1c2ccccc2C5c2ccccc21]
336
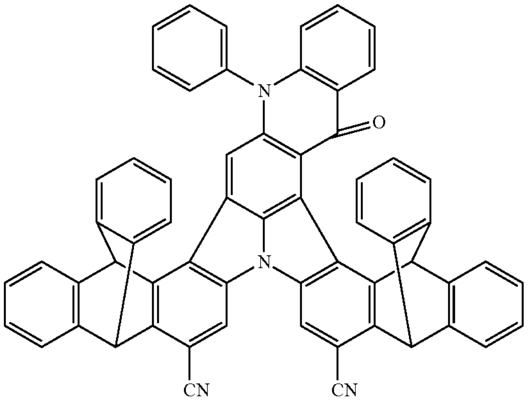 [SMILES: N#Cc1cc2c(c3c1C1c4ccccc4C3c3ccccc31)c1cc3c(c(=O)c4ccccc4n3-c3ccccc3)c3c4c5c(c(C#N)cc4n2c13)C1c2ccccc2C5c2ccccc21]
337
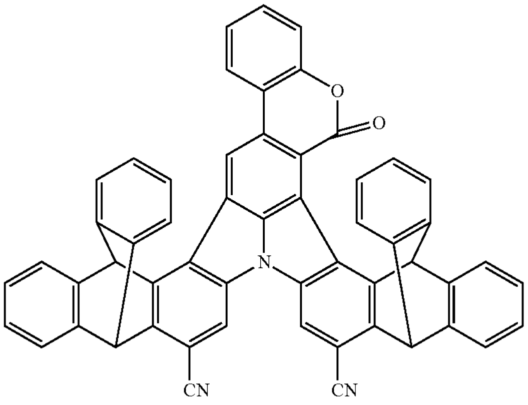 [SMILES: N#Cc1cc2c(c3c1C1c4ccccc4C3c3ccccc31)c1cc3c4ccccc4oc(=O)c3c3c4c5c(c(C#N)cc4n2c13)C1c2ccccc2C5c2ccccc21]

-continued
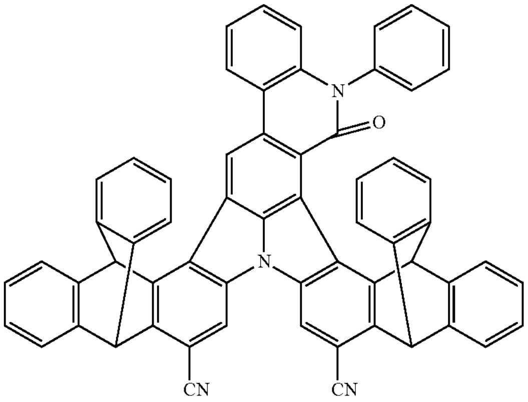 [SMILES: N#Cc1cc2c(c3c1C1c4ccccc4C3c3ccccc31)c1cc3c4ccccc4n(-c4ccccc4)c(=O)c3c3c4c5c(c(C#N)cc4n2c13)C1c2ccccc2C5c2ccccc21]
338
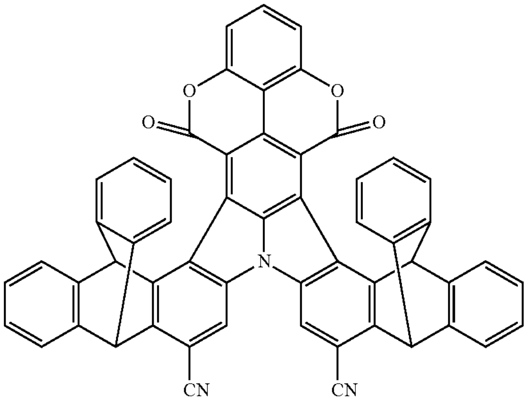 [SMILES: N#Cc1cc2c(c3c1C1c4ccccc4C3c3ccccc31)c1c3c(=O)oc4cccc5oc(=O)c(c3c45)c3c4c5c(c(C#N)cc4n2c13)C1c2ccccc2C5c2ccccc21]
339
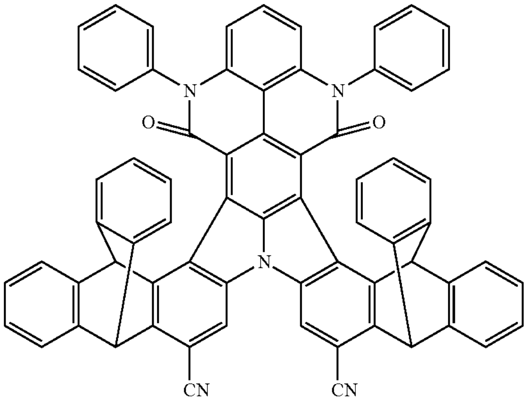 [SMILES: N#Cc1cc2c(c3c1C1c4ccccc4C3c3ccccc31)c1c3c(=O)n(-c4ccccc4)c4cccc5c4c3c(c(=O)n5-c3ccccc3)c3c4c5c(c(C#N)cc4n2c13)C1c2ccccc2C5c2ccccc21]
340
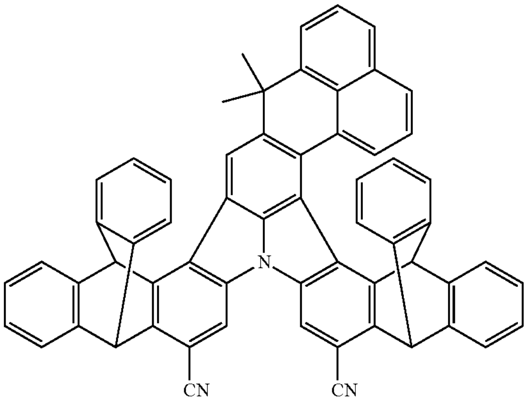 [SMILES: CC1(C)c2cc3c4c5c(c(C#N)cc4n4c6cc(C#N)c7c(c6c(c2-c2cccc6cccc1c26)c34)C1c2ccccc2C7c2ccccc21)C1c2ccccc2C5c2ccccc21]
341

-continued
342
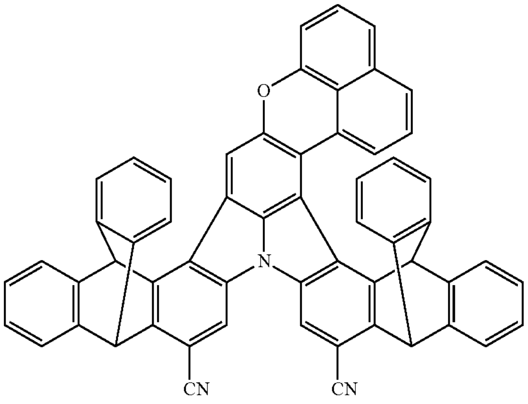 [SMILES: N#Cc1cc2c(c3c1C1c4ccccc4C3c3ccccc31)c1cc3oc4cccc5cccc(c54)c3c3c4c5c(c(C#N)cc4n2c13)C1c2ccccc2C5c2ccccc21]
343
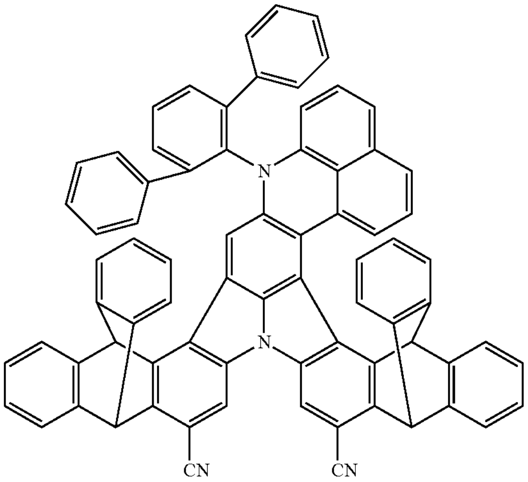 [SMILES: N#Cc1cc2c(c3c1C1c4ccccc4C3c3ccccc31)c1cc3c(c4cccc5cccc(c54)n3-c3c(-c4ccccc4)cccc3-c3ccccc3)c3c4c5c(c(C#N)cc4n2c13)C1c2ccccc2C5c2ccccc21]
344
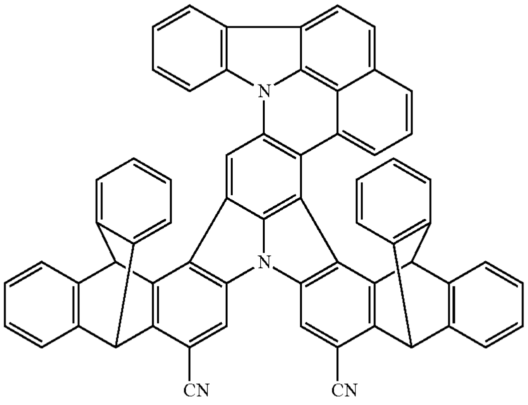 [SMILES: N#Cc1cc2c(c3c1C1c4ccccc4C3c3ccccc31)c1cc3c(c4cccc5ccc6c7ccccc7n3c6c54)c3c4c5c(c(C#N)cc4n2c13)C1c2ccccc2C5c2ccccc21]

-continued
345
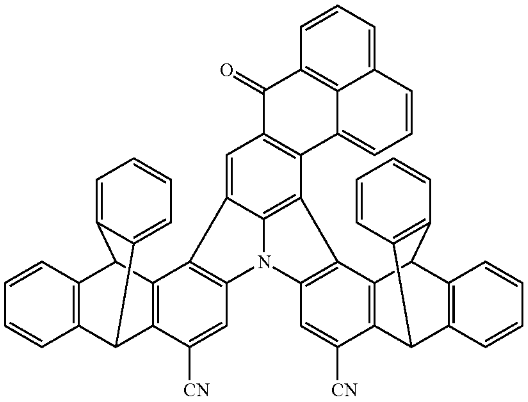 [SMILES: N#Cc1cc2c(c3c1C1c4ccccc4C3c3ccccc31)c1cc3c(=O)c4cccc5cccc(c54)c3c3c4c5c(c(C#N)cc4n2c13)C1c2ccccc2C5c2ccccc21]
346
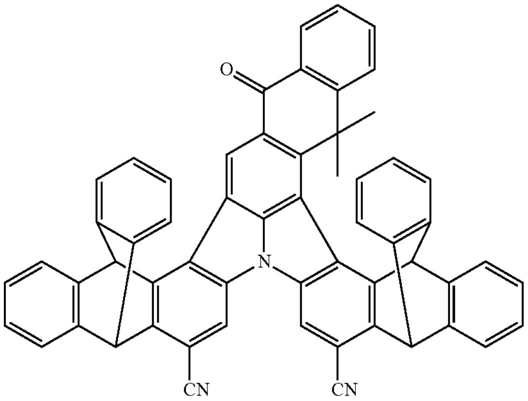 [SMILES: CC1(C)c2ccccc2C(=O)c2cc3c4c5c(c(C#N)cc4n4c6cc(C#N)c7c(c6c(c21)c34)C1c2ccccc2C7c2ccccc21)C1c2ccccc2C5c2ccccc21]
347
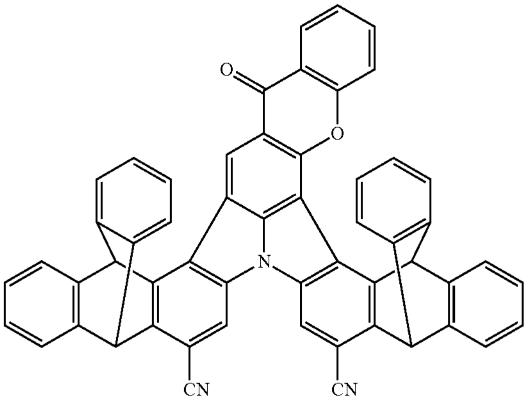 [SMILES: N#Cc1cc2c(c3c1C1c4ccccc4C3c3ccccc31)c1cc3c(=O)c4ccccc4oc3c3c4c5c(c(C#N)cc4n2c13)C1c2ccccc2C5c2ccccc21]
348
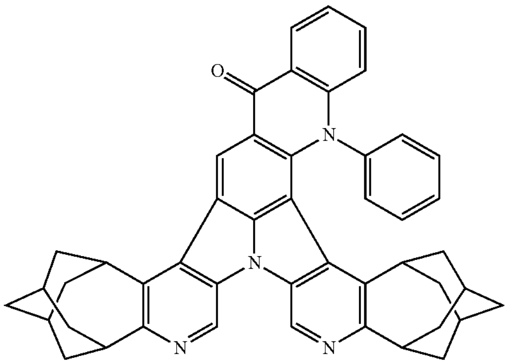 [SMILES: O=c1c2ccccc2n(-c2ccccc2)c2c1cc1c3c4c(ncc3n3c5cnc6c(c5c2c13)C1CC2CC(CC6C2)C1)C1CC2CC(C1)CC4C2]

-continued
349
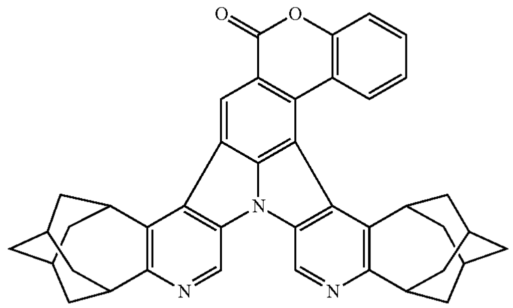 [SMILES: O=c1oc2ccccc2c2c1cc1c3c4c(ncc3n3c5cnc6c(c5c2c13)C1CC2CC(CC6C2)C1)C1CC2CC(C1)CC4C2]
350
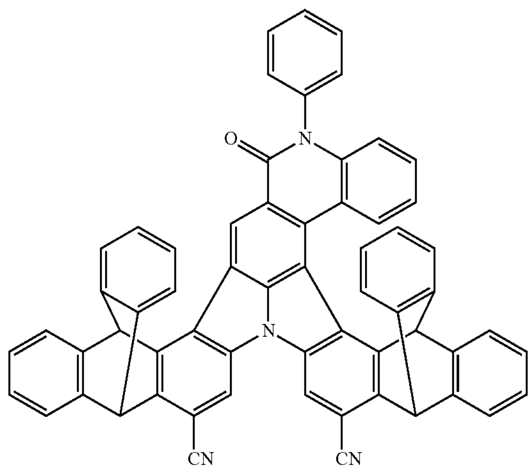 [SMILES: N#Cc1cc2c(c3c1C1c4ccccc4C3c3ccccc31)c1cc3c(=O)n(-c4ccccc4)c4ccccc4c3c3c4c5c(c(C#N)cc4n2c13)C1c2ccccc2C5c2ccccc21]
351
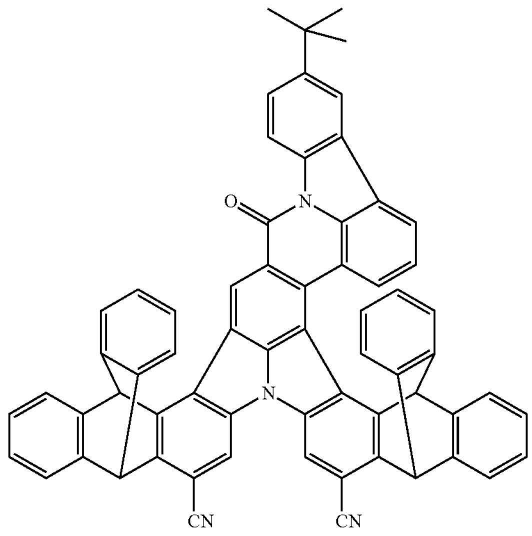 [SMILES: CC(C)(C)c1ccc2c(c1)c1cccc3c4c(cc5c6c7c(c(C#N)cc6n6c8cc(C#N)c9c(c8c4c56)C4c5ccccc5C9c5ccccc54)C4c5ccccc5C7c5ccccc54)c(=O)n2c13]

-continued
352
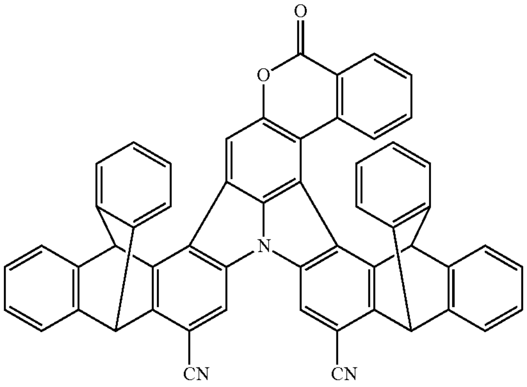 [SMILES: N#Cc1cc2c(c3c1C1c4ccccc4C3c3ccccc31)c1cc3oc(=O)c4ccccc4c3c3c4c5c(c(C#N)cc4n2c13)C1c2ccccc2C5c2ccccc21]
353
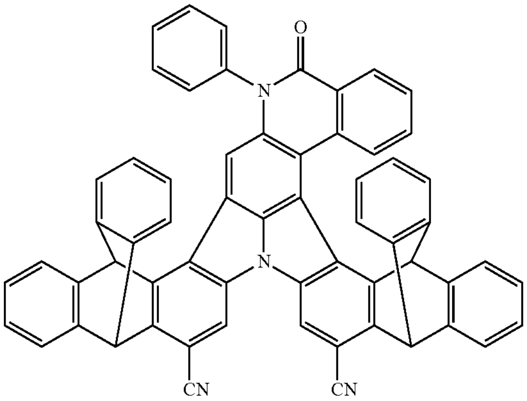 [SMILES: N#Cc1cc2c(c3c1C1c4ccccc4C3c3ccccc31)c1cc3c(c4ccccc4c(=O)n3-c3ccccc3)c3c4c5c(c(C#N)cc4n2c13)C1c2ccccc2C5c2ccccc21]
354
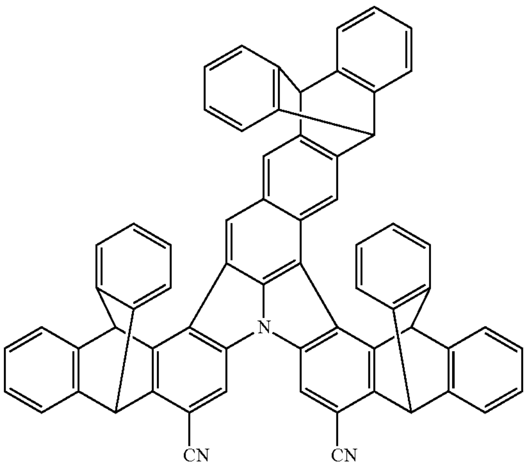 [SMILES: N#Cc1cc2c(c3c1C1c4ccccc4C3c3ccccc31)c1cc3cc4c(cc3c3c5c6c(c(C#N)cc5n2c13)C1c2ccccc2C6c2ccccc21)C1c2ccccc2C4c2ccccc21]

-continued
355
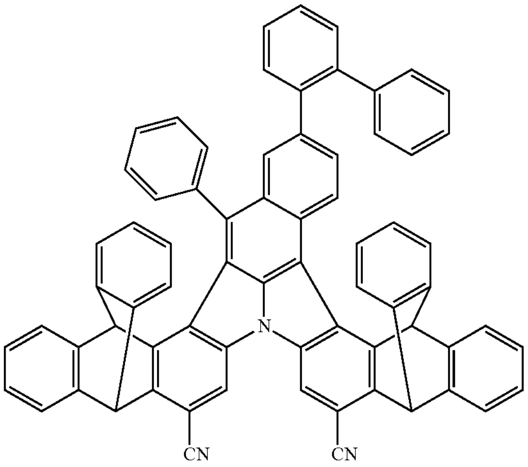 [SMILES: N#Cc1cc2c(c3c1C1c4ccccc4C3c3ccccc31)c1c(-c3ccccc3)c3cc(-c4ccccc4-c4ccccc4)ccc3c3c4c5c(c(C#N)cc4n2c13)C1c2ccccc2C5c2ccccc21]
356
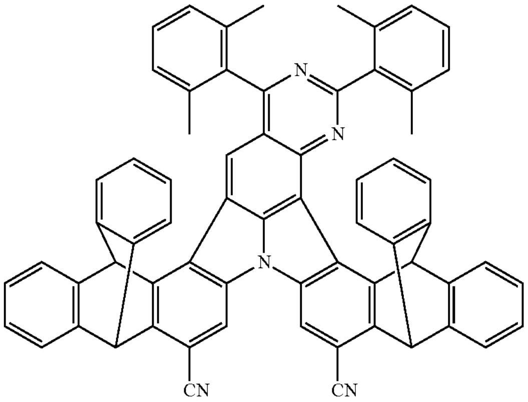 [SMILES: Cc1cccc(C)c1-c1nc(-c2c(C)cccc2C)c2cc3c4c5c(c(C#N)cc4n4c6cc(C#N)c7c(c6c(c2n1)c34)C1c2ccccc2C7c2ccccc21)C1c2ccccc2C5c2ccccc21]
357
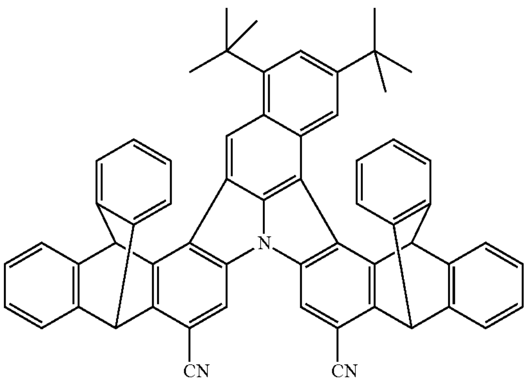 [SMILES: CC(C)(C)c1cc(C(C)(C)C)c2cc3c4c5c(c(C#N)cc4n4c6cc(C#N)c7c(c6c(c2c1)c34)C1c2ccccc2C7c2ccccc21)C1c2ccccc2C5c2ccccc21]

-continued
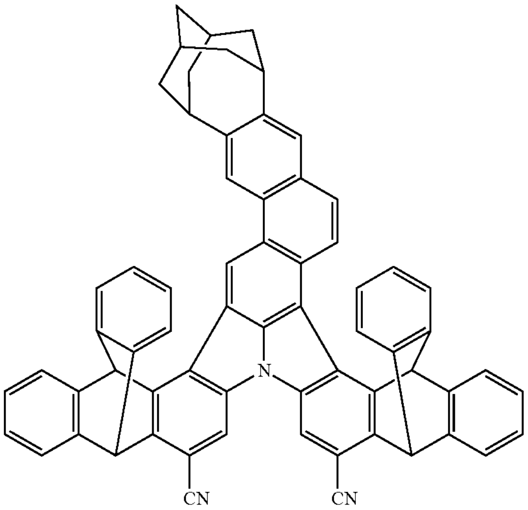 [SMILES: N#Cc1cc2c(c3c1C1c4ccccc4C3c3ccccc31)c1cc3c4cc5c(cc4ccc3c3c4c6c(c(C#N)cc4n2c13)C1c2ccccc2C6c2ccccc21)C1CC2CC(C1)CC5C2]
358
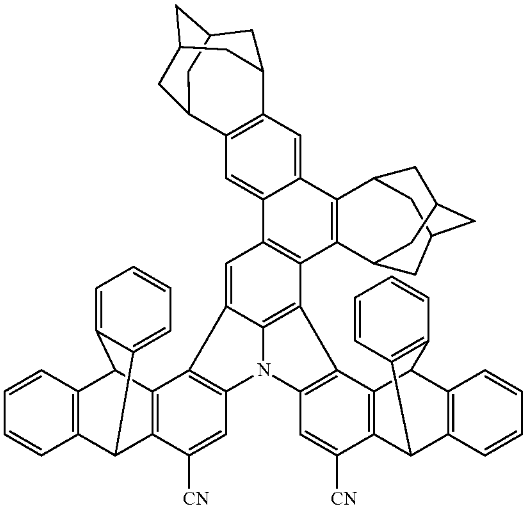 [SMILES: N#Cc1cc2c(c3c1C1c4ccccc4C3c3ccccc31)c1cc3c4cc5c(cc4c4c(c3c3c6c7c(c(C#N)cc6n2c13)C1c2ccccc2C7c2ccccc21)C1CC2CC(CC4C2)C1)C1CC2CC(C1)CC5C2]
359
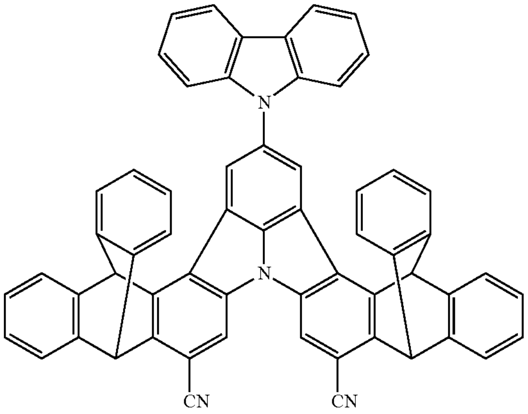 [SMILES: N#Cc1cc2c(c3c1C1c4ccccc4C3c3ccccc31)c1cc(-n3c4ccccc4c4ccccc43)cc3c4c5c(c(C#N)cc4n2c13)C1c2ccccc2C5c2ccccc21]
360

-continued
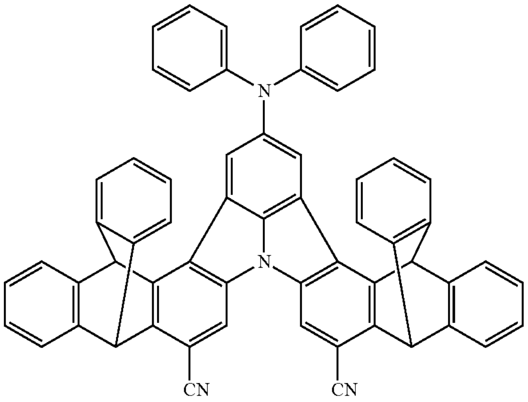 [SMILES: N#Cc1cc2c(c3c1C1c4ccccc4C3c3ccccc31)c1cc(N(c3ccccc3)c3ccccc3)cc3c4c5c(c(C#N)cc4n2c13)C1c2ccccc2C5c2ccccc21]
361
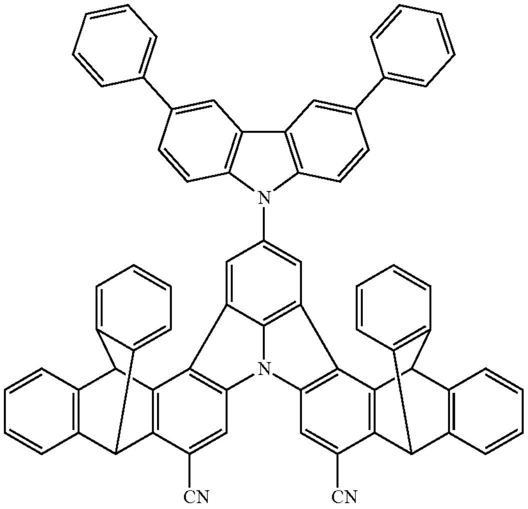 [SMILES: N#Cc1cc2c(c3c1C1c4ccccc4C3c3ccccc31)c1cc(-n3c4ccc(-c5ccccc5)cc4c4cc(-c5ccccc5)ccc43)cc3c4c5c(c(C#N)cc4n2c13)C1c2ccccc2C5c2ccccc21]
362
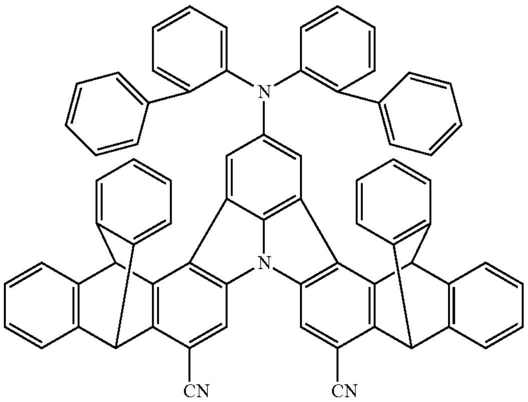 [SMILES: N#Cc1cc2c(c3c1C1c4ccccc4C3c3ccccc31)c1cc(N(c3ccccc3-c3ccccc3)c3ccccc3-c3ccccc3)cc3c4c5c(c(C#N)cc4n2c13)C1c2ccccc2C5c2ccccc21]
363

-continued
364
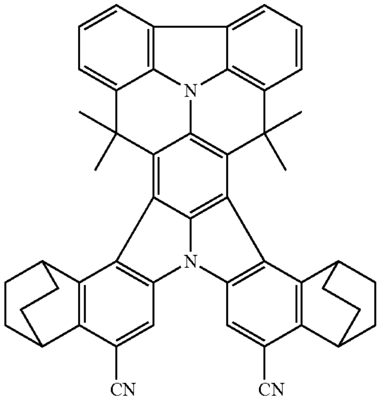 [SMILES: CC1(C)c2c3c(c4c5c6c(c(C#N)cc5n5c7cc(C#N)c8c(c7c2c45)C2CCC8CC2)C2CCC6CC2)C(C)(C)c2cccc4c5cccc1c5n-3c24]
365
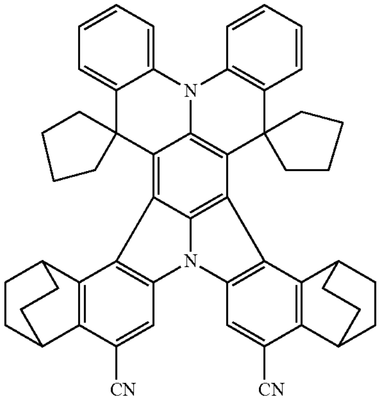 [SMILES: N#Cc1cc2c(c3c1C1CCC3CC1)c1c3c4c(c5c6c7c(c(C#N)cc6n2c15)C1CCC7CC1)C1(CCCC1)c1ccccc1N4c1ccccc1C31CCCC1]
366
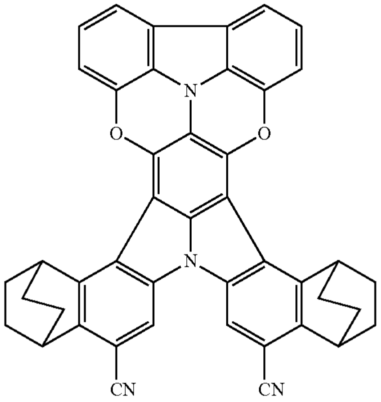 [SMILES: N#Cc1cc2c(c3c1C1CCC3CC1)c1c3oc4cccc5c6cccc7oc(c8c9c%10c(c(C#N)cc9n2c18)C1CCC%10CC1)c3n(c45)c76]
367
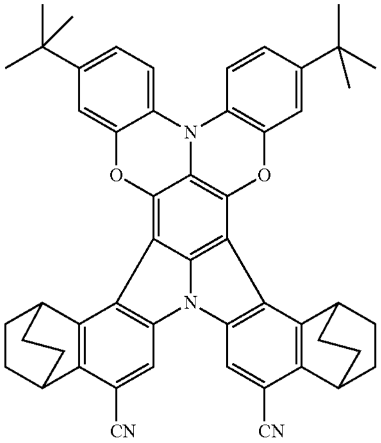 [SMILES: CC(C)(C)c1ccc2c(c1)Oc1c3c(c4c5c6c(c(C#N)cc5n5c7cc(C#N)c8c(c7c1c45)C1CCC8CC1)C1CCC6CC1)Oc1cc(C(C)(C)C)ccc1N23]

-continued
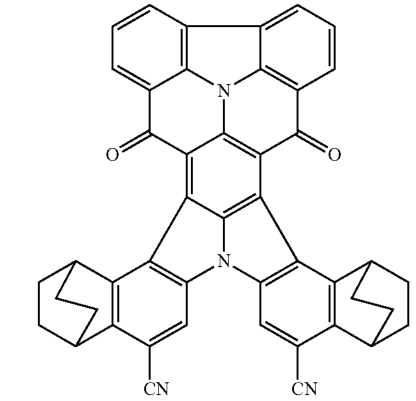 [SMILES: N#Cc1cc2c(c3c1C1CCC3CC1)c1c3c(=O)c4cccc5c6cccc7c(=O)c(c8c9c%10c(c(C#N)cc9n2c18)C1CCC%10CC1)c3n(c45)c76]
368
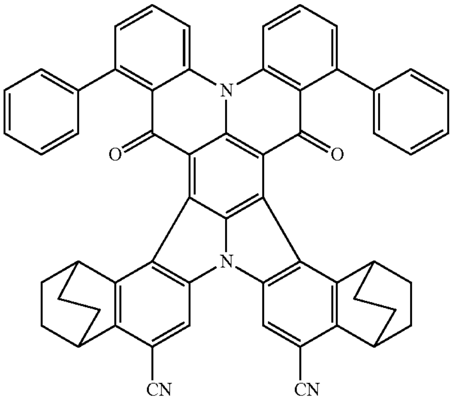 [SMILES: N#Cc1cc2c(c3c1C1CCC3CC1)c1c3c(=O)c4c(-c5ccccc5)cccc4n4c5cccc(-c6ccccc6)c5c(=O)c(c5c6c7c(c(C#N)cc6n2c15)C1CCC7CC1)c34]
369
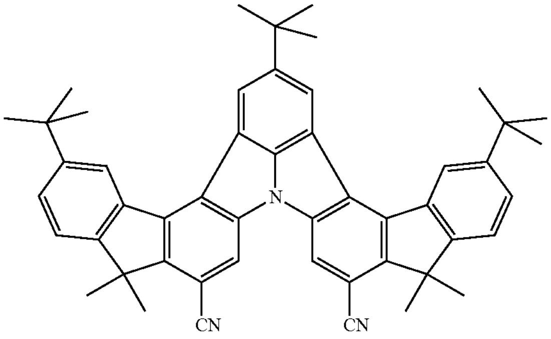 [SMILES: CC(C)(C)c1ccc2c(c1)-c1c(c(C#N)cc3c1c1cc(C(C)(C)C)cc4c5c6c(c(C#N)cc5n3c14)C(C)(C)c1ccc(C(C)(C)C)cc1-6)C2(C)C]
370
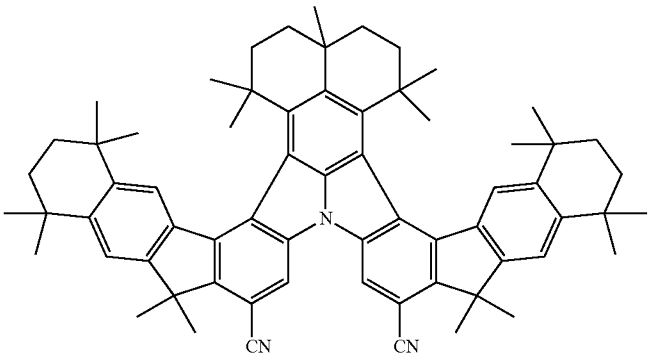
371

-continued
372
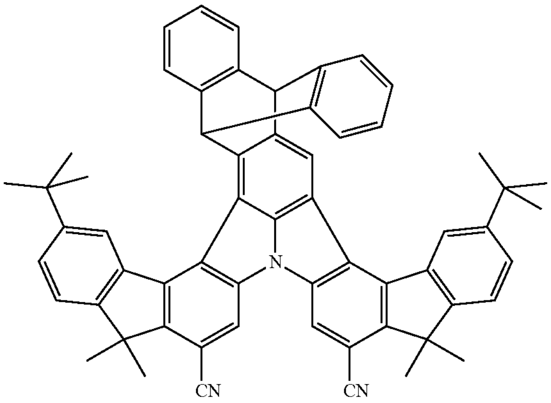 [SMILES: CC(C)(C)c1ccc2c(c1)-c1c(c(C#N)cc3c1c1cc4c(c5c6c7c(c(C#N)cc6n3c15)C(C)(C)c1ccc(C(C)(C)C)cc1-7)C1c3ccccc3C4c3ccccc31)C2(C)C]
373
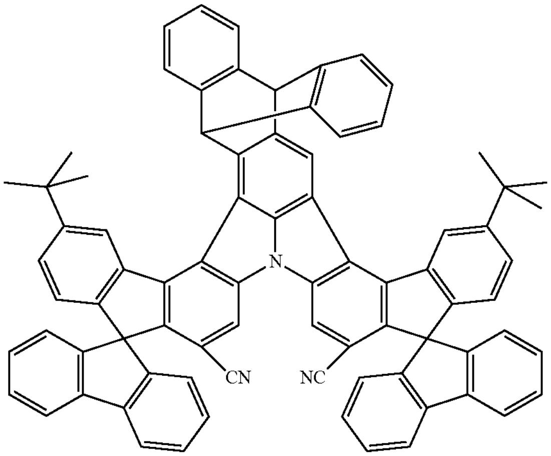 [SMILES: CC(C)(C)c1ccc2c(c1)-c1c(c(C#N)cc3c1c1cc4c(c5c6c7c(c(C#N)cc6n3c15)C1(c3ccccc3-c3ccccc31)c1ccc(C(C)(C)C)cc1-7)C1c3ccccc3C4c3ccccc31)C21c2ccccc2-c2ccccc21]
374
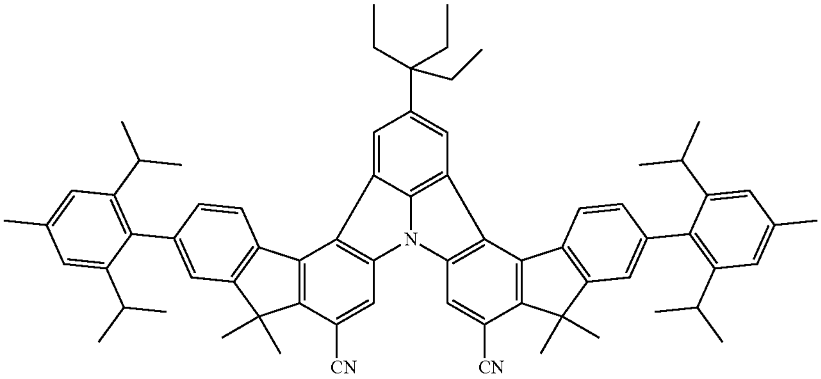
375
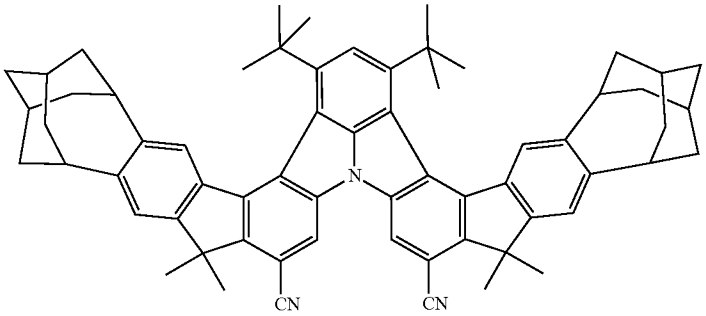 [SMILES: CC(C)(C)c1cc(C(C)(C)C)c2c3c4c(c(C#N)cc3n3c5cc(C#N)c6c(c5c1c23)-c1cc2c(cc1C6(C)C)C1CC3CC(CC2C3)C1)C(C)(C)c1cc2c(cc1-4)C1CC3CC(C1)CC2C3]

-continued
376
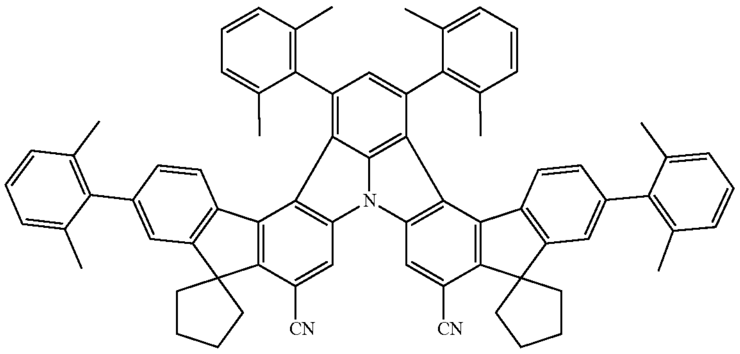 [SMILES: Cc1cccc(C)c1-c1ccc2c(c1)C1(CCCC1)c1c(C#N)cc3c(c1-2)c1c(-c2c(C)cccc2C)cc(-c2c(C)cccc2C)c2c4c5c(c(C#N)cc4n3c12)C1(CCCC1)c1cc(-c2c(C)cccc2C)ccc1-5]
377
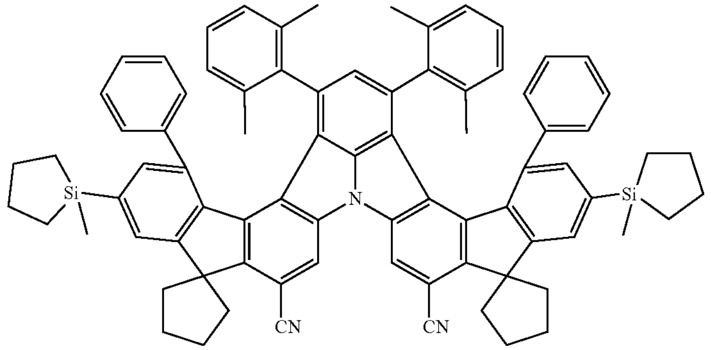 [SMILES: Cc1cccc(C)c1-c1cc(-c2c(C)cccc2C)c2c3c4c(c(C#N)cc3n3c5cc(C#N)c6c(c5c1c23)-c1c(-c2ccccc2)cc([Si]2(C)CCCC2)cc1C61CCCC1)C1(CCCC1)c1cc([Si]2(C)CCCC2)cc(-c2ccccc2)c1-4]
378
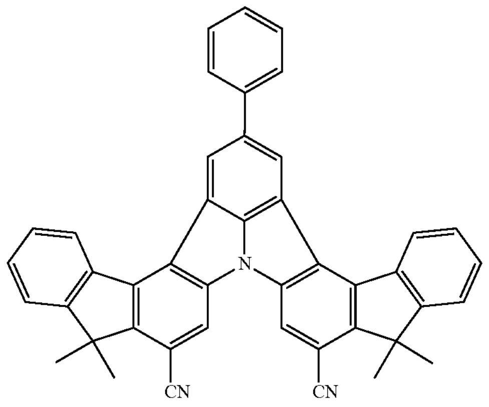 [SMILES: CC1(C)c2ccccc2-c2c1c(C#N)cc1c2c2cc(-c3ccccc3)cc3c4c5c(c(C#N)cc4n1c23)C(C)(C)c1ccccc1-5]
379
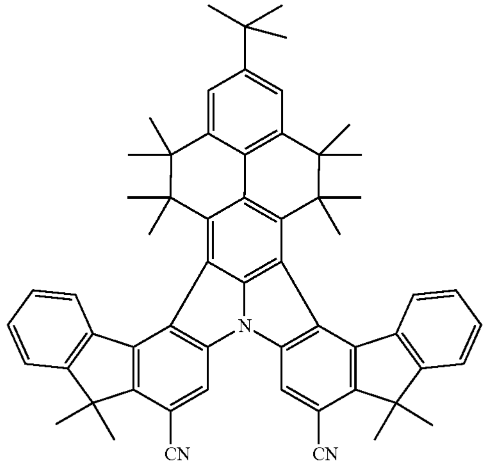 [SMILES: CC(C)(C)c1cc2c3c(c1)C(C)(C)C(C)(C)c1c-3c(c3c4c5c(c(C#N)cc4n4c6cc(C#N)c7c(c6c1c34)-c1ccccc1C7(C)C)C(C)(C)c1ccccc1-5)C(C)(C)C2(C)C]

-continued
380
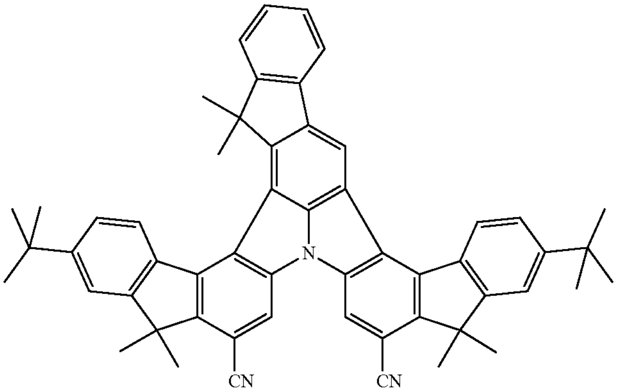 [SMILES: CC(C)(C)c1ccc2c(c1)C(C)(C)c1c(C#N)cc3c(c1-2)c1cc2c(c4c5c6c(c(C#N)cc5n3c14)C(C)(C)c1cc(C(C)(C)C)ccc1-6)C(C)(C)c1ccccc1-2]
381
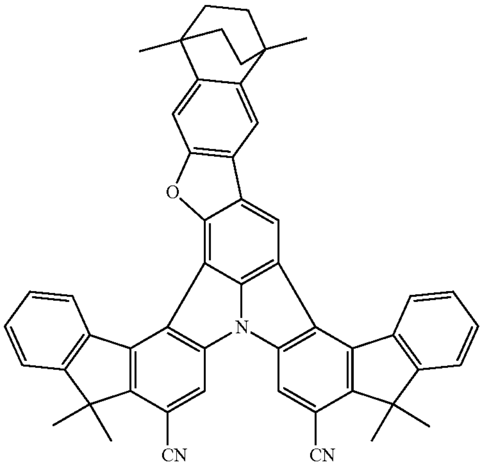 [SMILES: CC12CCC(C)(CC1)c1cc3c(cc12)oc1c3cc2c3c4c(c(C#N)cc3n3c5cc(C#N)c6c(c5c1c23)-c1ccccc1C6(C)C)C(C)(C)c1ccccc1-4]
382
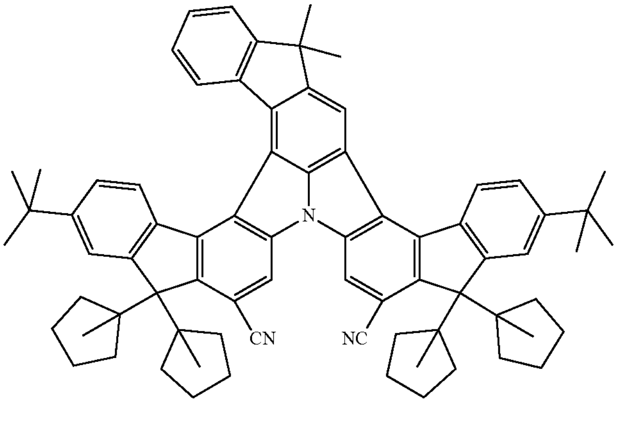

-continued
383
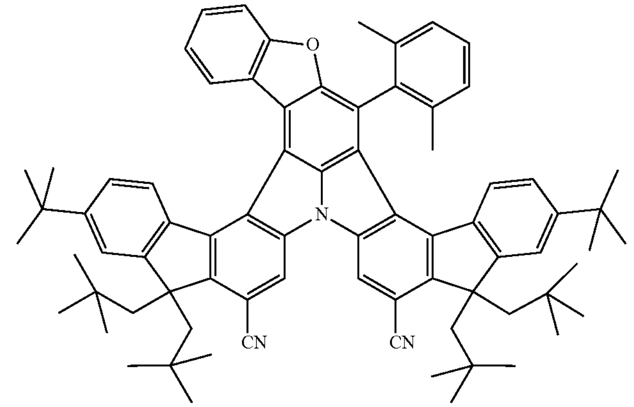 [SMILES: Cc1cccc(C)c1-c1c2oc3ccccc3c2c2c3c4c(c(C#N)cc3n3c5cc(C#N)c6c(c5c1c23)-c1ccc(C(C)(C)C)cc1C6(CC(C)(C)C)CC(C)(C)C)C(CC(C)(C)C)(CC(C)(C)C)c1cc(C(C)(C)C)ccc1-4]
384
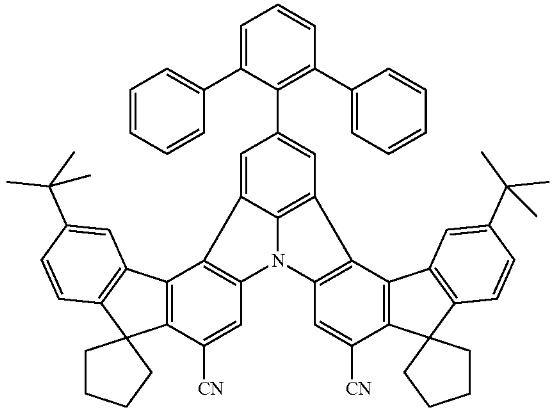 [SMILES: CC(C)(C)c1ccc2c(c1)-c1c(c(C#N)cc3c1c1cc(-c4c(-c5ccccc5)cccc4-c4ccccc4)cc4c5c6c(c(C#N)cc5n3c14)C1(CCCC1)c1ccc(C(C)(C)C)cc1-6)C21CCCC1]
385
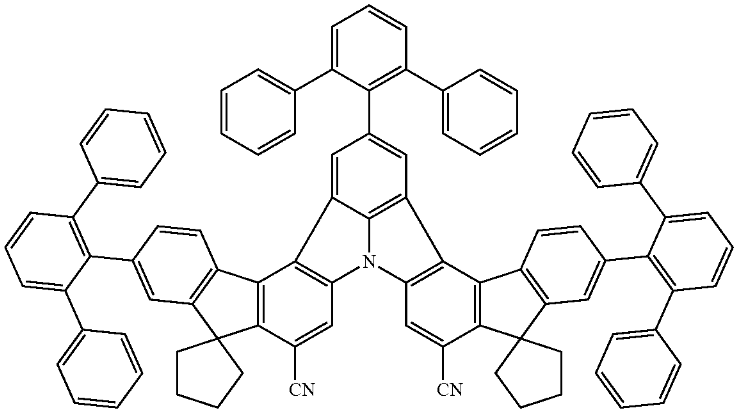 [SMILES: N#Cc1cc2c(c3c1C1(CCCC1)c1cc(-c4c(-c5ccccc5)cccc4-c4ccccc4)ccc1-3)c1cc(-c3c(-c4ccccc4)cccc3-c3ccccc3)cc3c4c5c(c(C#N)cc4n2c13)C1(CCCC1)c1cc(-c2c(-c3ccccc3)cccc2-c2ccccc2)ccc1-5]
386
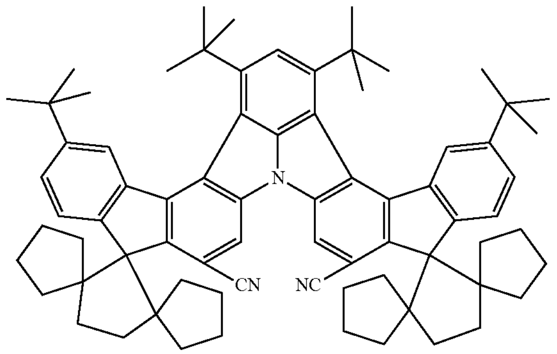 [SMILES: CC(C)(C)c1ccc2c(c1)-c1c(c(C#N)cc3c1c1c(C(C)(C)C)cc(C(C)(C)C)c4c5c6c(c(C#N)cc5n3c14)C1(c3ccc(C(C)(C)C)cc3-6)C3(CCCC3)CCC13CCCC3)C21C2(CCCC2)CCC12CCCC2]

-continued
387
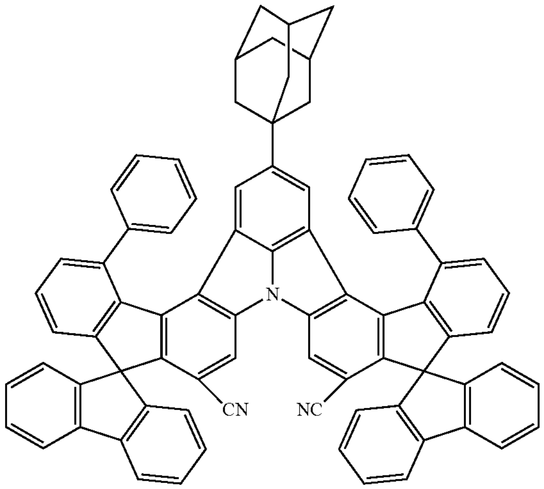 [SMILES: N#Cc1cc2c(c3c1C1(c4ccccc4-c4ccccc41)c1cccc(-c4ccccc4)c1-3)c1cc(C34CC5CC(CC(C5)C3)C4)cc3c4c5c(c(C#N)cc4n2c13)C1(c2ccccc2-c2ccccc21)c1cccc(-c2ccccc2)c1-5]
388
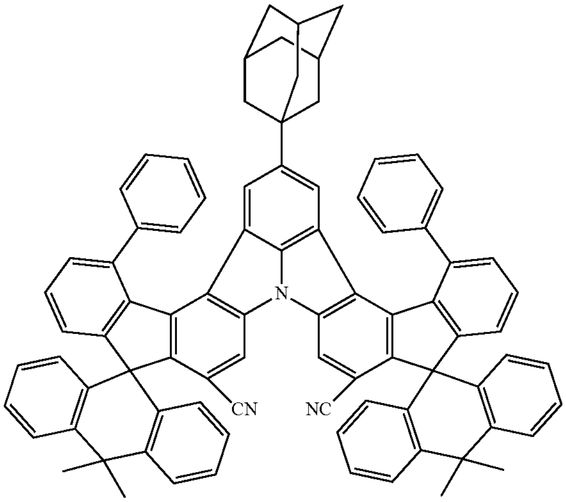 [SMILES: CC1(C)c2ccccc2C2(c3ccccc31)c1cccc(-c3ccccc3)c1-c1c2c(C#N)cc2c1c1cc(C34CC5CC(CC(C5)C3)C4)cc3c4c5c(c(C#N)cc4n2c13)C1(c2ccccc2C(C)(C)c2ccccc21)c1cccc(-c2ccccc2)c1-5]
389
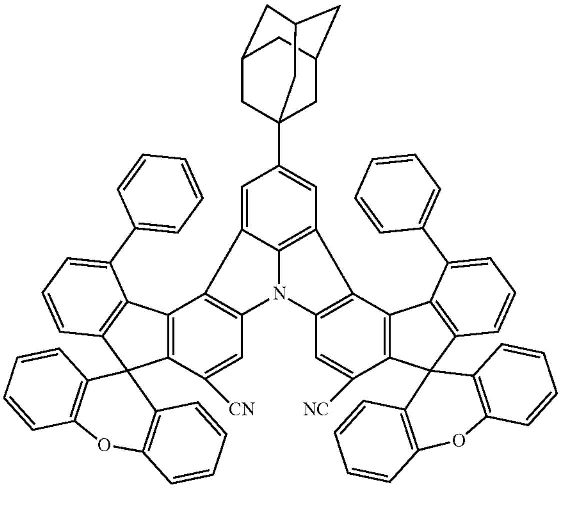 [SMILES: N#Cc1cc2c(c3c1C1(c4ccccc4Oc4ccccc41)c1cccc(-c4ccccc4)c1-3)c1cc(C34CC5CC(CC(C5)C3)C4)cc3c4c5c(c(C#N)cc4n2c13)C1(c2ccccc2Oc2ccccc21)c1cccc(-c2ccccc2)c1-5]

-continued
390
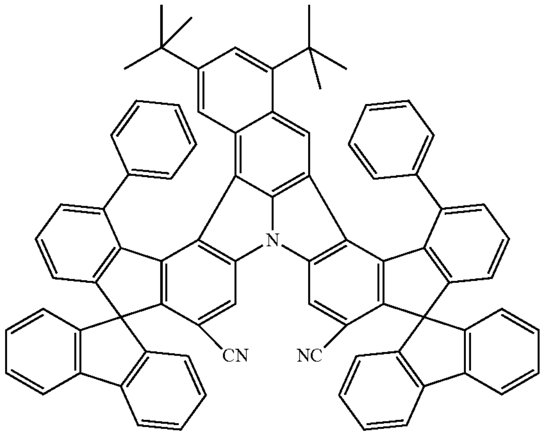 [SMILES: CC(C)(C)c1cc(C(C)(C)C)c2cc3c4c5c(c(C#N)cc4n4c6cc(C#N)c7c(c6c(c2c1)c34)-c1c(-c2ccccc2)cccc1C71c2ccccc2-c2ccccc21)C1(c2ccccc2-c2ccccc21)c1cccc(-c2ccccc2)c1-5]
391
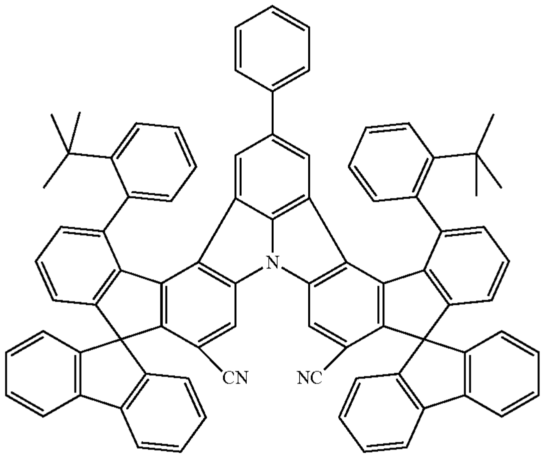 [SMILES: CC(C)(C)c1ccccc1-c1cccc2c1-c1c(c(C#N)cc3c1c1cc(-c4ccccc4)cc4c5c6c(c(C#N)cc5n3c14)C1(c3ccccc3-c3ccccc31)c1cccc(-c3ccccc3C(C)(C)C)c1-6)C21c2ccccc2-c2ccccc21]
=0
392
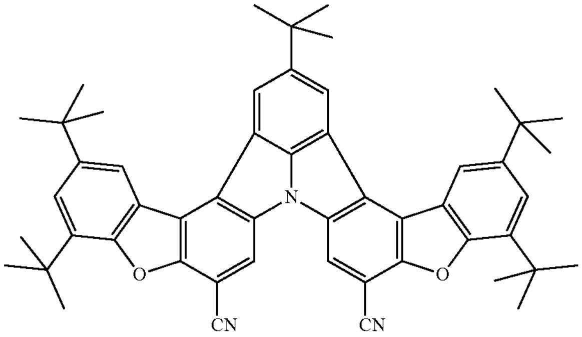 [SMILES: CC(C)(C)c1cc(C(C)(C)C)c2oc3c(C#N)cc4c(c5cc(C(C)(C)C)cc6c7c8c(oc9c(C(C)(C)C)cc(C(C)(C)C)cc98)c(C#N)cc7n4c56)c3c2c1]
393
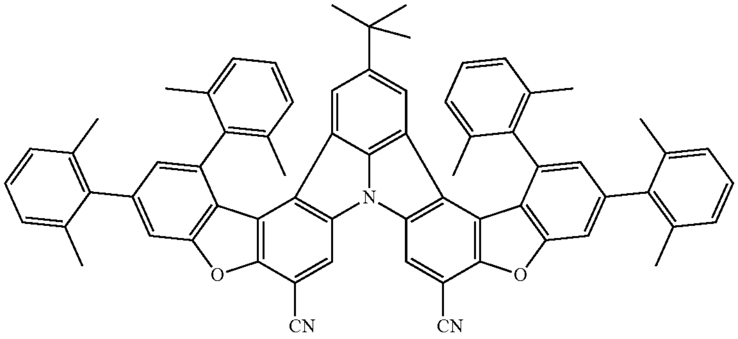 [SMILES: Cc1cccc(C)c1-c1cc(-c2c(C)cccc2C)c2c(c1)oc1c(C#N)cc3c(c4cc(C(C)(C)C)cc5c6c7c(oc8cc(-c9c(C)cccc9C)cc(-c9c(C)cccc9C)c87)c(C#N)cc6n3c45)c12]

-continued
394
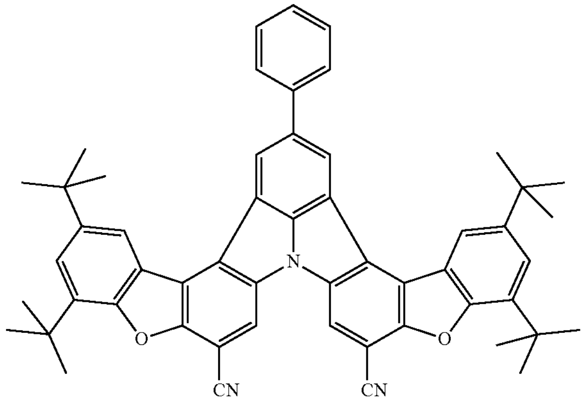 [SMILES: CC(C)(C)c1cc(C(C)(C)C)c2oc3c(C#N)cc4c(c5cc(-c6ccccc6)cc6c7c8c(oc9c(C(C)(C)C)cc(C(C)(C)C)cc98)c(C#N)cc7n4c56)c3c2c1]
395
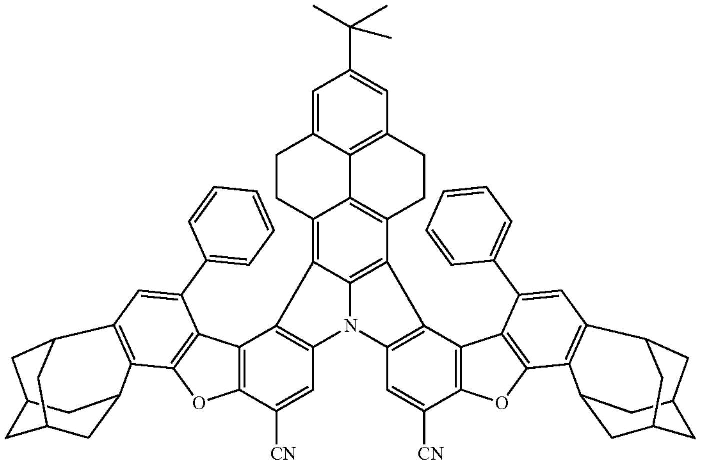 [SMILES: CC(C)(C)c1cc2c3c(c1)CCc1c-3c(c3c4c5c(oc6c7c(cc(-c8ccccc8)c65)C5CC6CC(C5)CC7C6)c(C#N)cc4n4c5cc(C#N)c6oc7c8c(cc(-c9ccccc9)c7c6c5c1c34)C1CC3CC(C1)CC8C3)CC2]
396
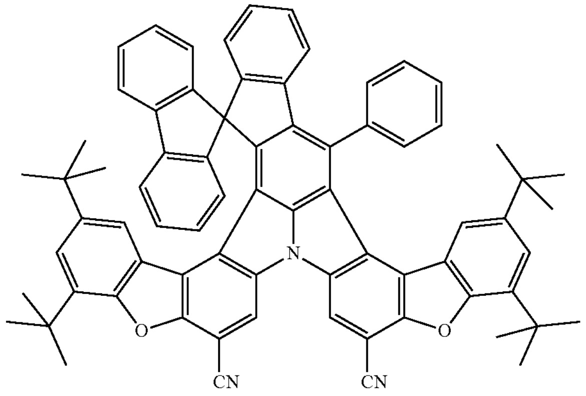 [SMILES: CC(C)(C)c1cc(C(C)(C)C)c2oc3c(C#N)cc4c(c5c(-c6ccccc6)c6c(c7c8c9c(oc%10c(C(C)(C)C)cc(C(C)(C)C)cc%109)c(C#N)cc8n4c57)C4(c5ccccc5-c5ccccc54)c4ccccc4-6)c3c2c1]

-continued
397
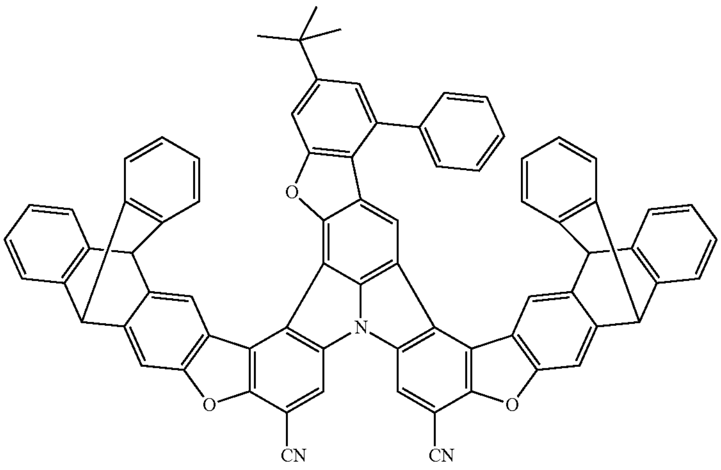 [SMILES: CC(C)(C)c1cc(-c2ccccc2)c2c(c1)oc1c2cc2c3c4c(oc5cc6c(cc54)C4c5ccccc5C6c5ccccc54)c(C#N)cc3n3c4cc(C#N)c5oc6cc7c(cc6c5c4c1c23)C1c2ccccc2C7c2ccccc21]
398
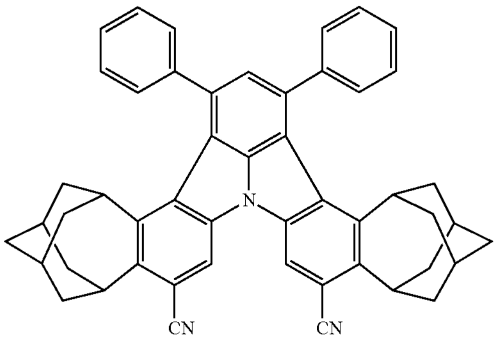 [SMILES: N#Cc1cc2c(c3c1C1CC4CC(C1)CC3C4)c1c(-c3ccccc3)cc(-c3ccccc3)c3c4c5c(c(C#N)cc4n2c13)C1CC2CC(C1)CC5C2]
399
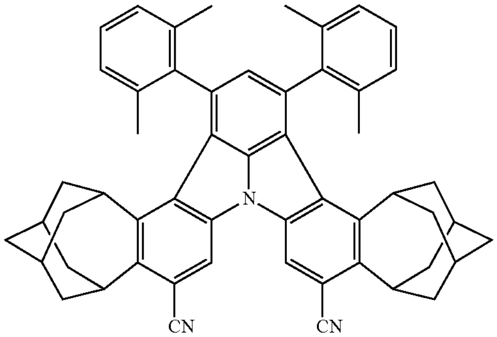 [SMILES: Cc1cccc(C)c1-c1cc(-c2c(C)cccc2C)c2c3c4c(c(C#N)cc3n3c5cc(C#N)c6c(c5c1c23)C1CC2CC(CC6C2)C1)C1CC2CC(C1)CC4C2]
400
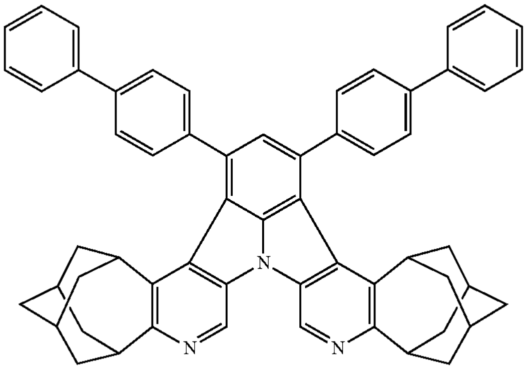 [SMILES: c1ccc(-c2ccc(-c3cc(-c4ccc(-c5ccccc5)cc4)c4c5c6c(ncc5n5c7cnc8c(c7c3c45)C3CC4CC(CC8C4)C3)C3CC4CC(C3)CC6C4)cc2)cc1]

-continued
401
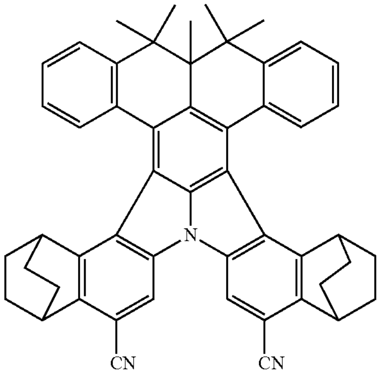 [SMILES: CC1(C)c2ccccc2-c2c3c(c4c5c6c(c(C#N)cc5n5c7cc(C#N)c8c(c7c2c45)C2CCC8CC2)C2CCC6CC2)-c2ccccc2C(C)(C)C31C]
C2, Cs
402
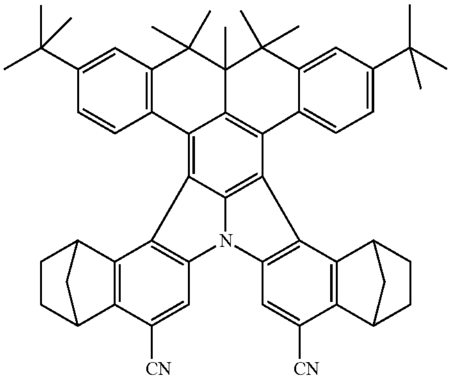
403
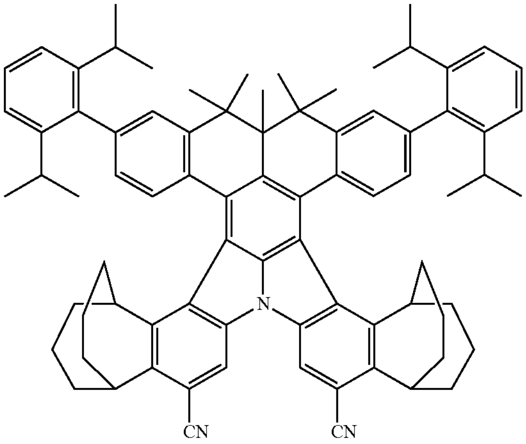 [SMILES: CC(C)c1cccc(C(C)C)c1-c1ccc2c(c1)C(C)(C)C1(C)c3c-2c2c4c5c(c(C#N)cc4n4c6cc(C#N)c7c(c6c(c3-c3ccc(-c6c(C(C)C)cccc6C(C)C)cc3C1(C)C)c24)C1CCCC7CCC1)C1CCCC5CCC1]

-continued
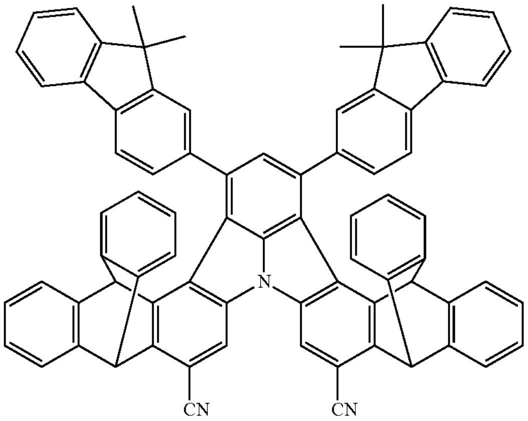 [SMILES: CC1(C)c2ccccc2-c2ccc(-c3cc(-c4ccc5c(c4)C(C)(C)c4ccccc4-5)c4c5c6c(c(C#N)cc5n5c7cc(C#N)c8c(c7c3c45)C3c4ccccc4C8c4ccccc43)C3c4ccccc4C6c4ccccc43)cc21]
404
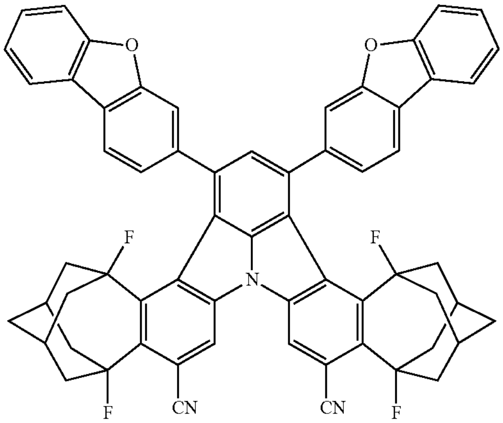 [SMILES: N#Cc1cc2c(c3c1C1(F)CC4CC(C1)CC3(F)C4)c1c(-c3ccc4c(c3)oc3ccccc34)cc(-c3ccc4c(c3)oc3ccccc34)c3c4c5c(c(C#N)cc4n2c13)C1(F)CC2CC(C1)CC5(F)C2]
405
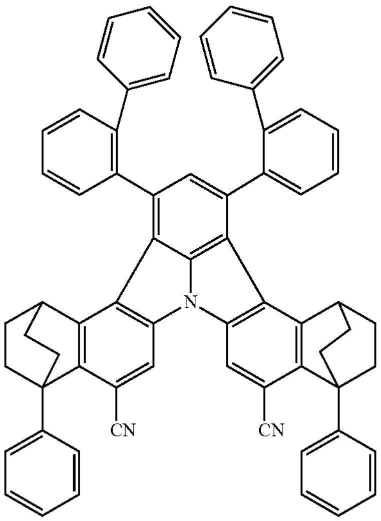 [SMILES: N#Cc1cc2c(c3c1C1(c4ccccc4)CCC3CC1)c1c(-c3ccccc3-c3ccccc3)cc(-c3ccccc3-c3ccccc3)c3c4c5c(c(C#N)cc4n2c13)C1(c2ccccc2)CCC5CC1]
406

-continued
407
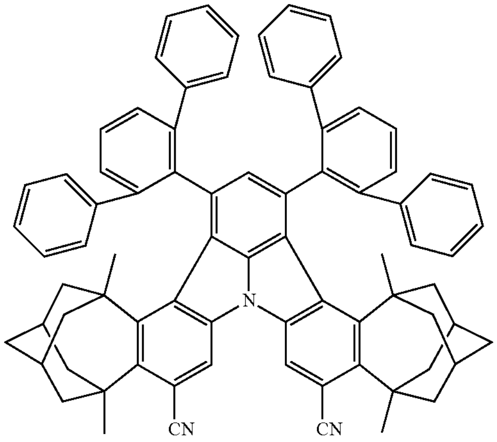 [SMILES: CC12CC3CC(C1)CC(C)(C3)c1c2c(C#N)cc2c1c1c(-c3c(-c4ccccc4)cccc3-c3ccccc3)cc(-c3c(-c4ccccc4)cccc3-c3ccccc3)c3c4c5c(c(C#N)cc4n2c13)C1(C)CC2CC(C1)CC5(C)C2]
408
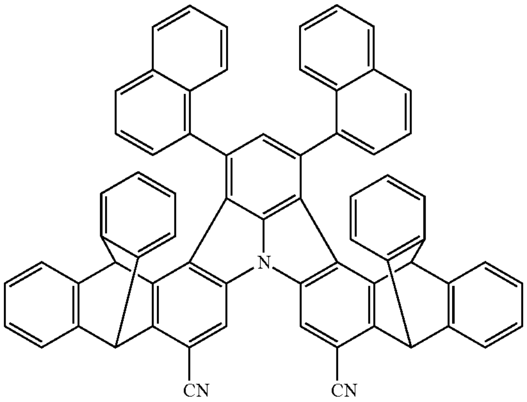 [SMILES: N#Cc1cc2c(c3c1C1c4ccccc4C3c3ccccc31)c1c(-c3cccc4ccccc34)cc(-c3cccc4ccccc34)c3c4c5c(c(C#N)cc4n2c13)C1c2ccccc2C5c2ccccc21]
409
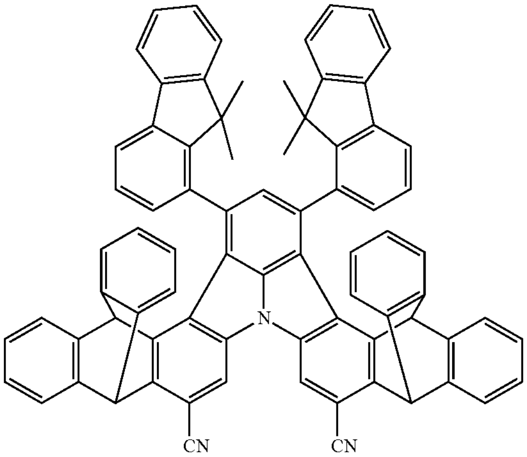 [SMILES: CC1(C)c2ccccc2-c2cccc(-c3cc(-c4cccc5c4C(C)(C)c4ccccc4-5)c4c5c6c(c(C#N)cc5n5c7cc(C#N)c8c(c7c3c45)C3c4ccccc4C8c4ccccc43)C3c4ccccc4C6c4ccccc43)c21]

-continued
410
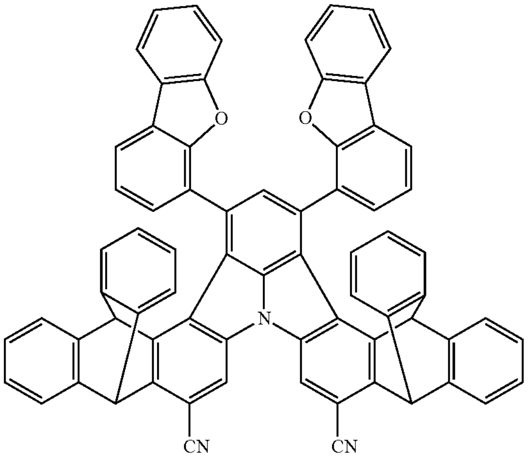 [SMILES: N#Cc1cc2c(c3c1C1c4ccccc4C3c3ccccc31)c1c(-c3cccc4c3oc3ccccc34)cc(-c3cccc4c3oc3ccccc34)c3c4c5c(c(C#N)cc4n2c13)C1c2ccccc2C5c2ccccc21]
411
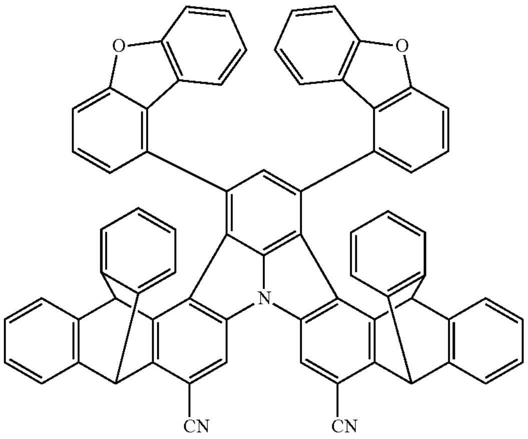 [SMILES: N#Cc1cc2c(c3c1C1c4ccccc4C3c3ccccc31)c1c(-c3cccc4oc5ccccc5c34)cc(-c3cccc4oc5ccccc5c34)c3c4c5c(c(C#N)cc4n2c13)C1c2ccccc2C5c2ccccc21]
412
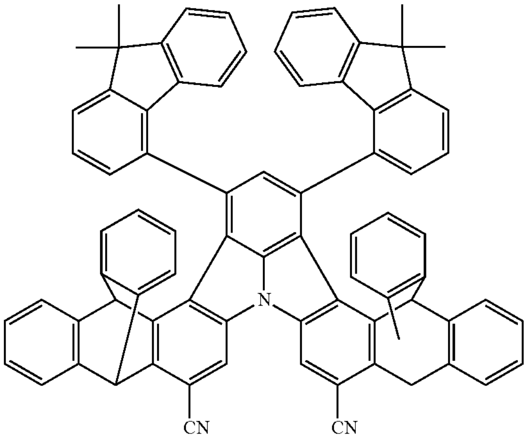

-continued
413
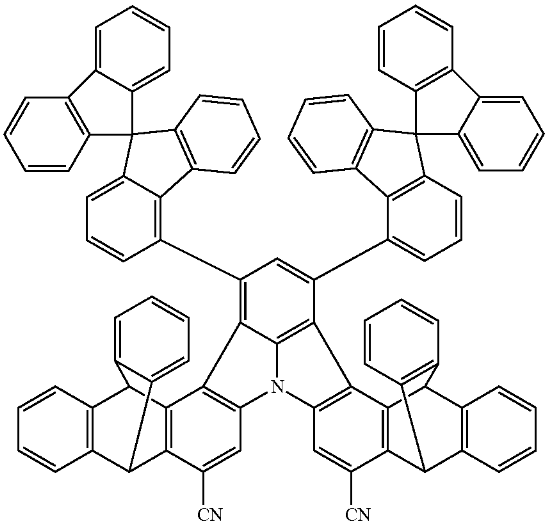 [SMILES: N#Cc1cc2c(c3c1C1c4ccccc4C3c3ccccc31)c1c(-c3cccc4c3-c3ccccc3C43c4ccccc4-c4ccccc43)cc(-c3cccc4c3-c3ccccc3C43c4ccccc4-c4ccccc43)c3c4c5c(c(C#N)cc4n2c13)C1c2ccccc2C5c2ccccc21]
414
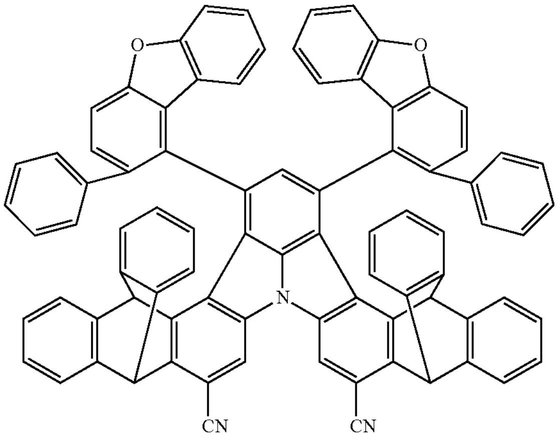 [SMILES: N#Cc1cc2c(c3c1C1c4ccccc4C3c3ccccc31)c1c(-c3c(-c4ccccc4)ccc4oc5ccccc5c34)cc(-c3c(-c4ccccc4)ccc4oc5ccccc5c34)c3c4c5c(c(C#N)cc4n2c13)C1c2ccccc2C5c2ccccc21]
415
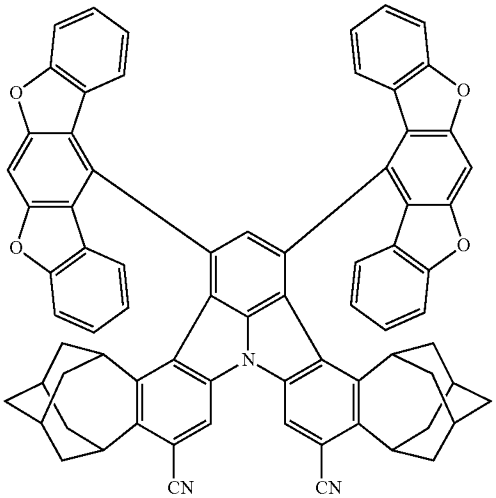 [SMILES: N#Cc1cc2c(c3c1C1CC4CC(C1)CC3C4)c1c(-c3c4c(cc5oc6ccccc6c35)oc3ccccc34)cc(-c3c4c(cc5oc6ccccc6c35)oc3ccccc34)c3c4c5c(c(C#N)cc4n2c13)C1CC2CC(C1)CC5C2]

-continued
416
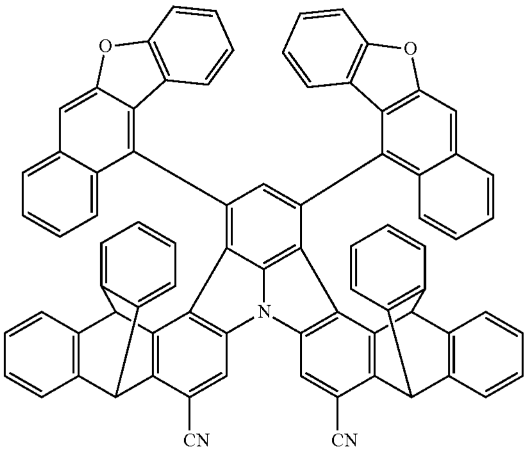 [SMILES: N#Cc1cc2c(c3c1C1c4ccccc4C3c3ccccc31)c1c(-c3c4ccccc4cc4oc5ccccc5c34)cc(-c3c4ccccc4cc4oc5ccccc5c34)c3c4c5c(c(C#N)cc4n2c13)C1c2ccccc2C5c2ccccc21]
417
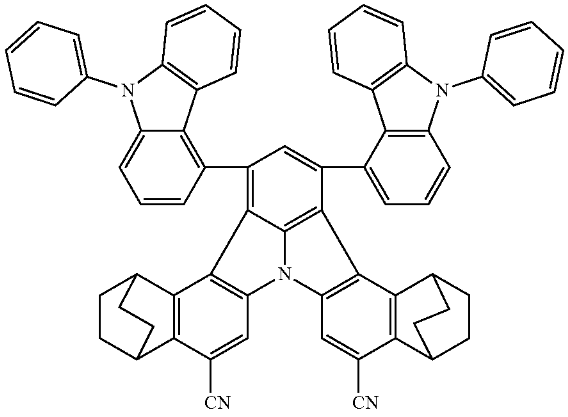 [SMILES: N#Cc1cc2c(c3c1C1CCC3CC1)c1c(-c3cccc4c3c3ccccc3n4-c3ccccc3)cc(-c3cccc4c3c3ccccc3n4-c3ccccc3)c3c4c5c(c(C#N)cc4n2c13)C1CCC5CC1]
418
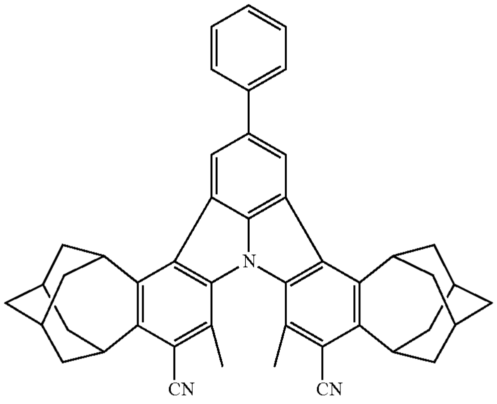 [SMILES: Cc1c(C#N)c2c(c3c4cc(-c5ccccc5)cc5c6c7c(c(C#N)c(C)c6n(c13)c45)C1CC3CC(C1)CC7C3)C1CC3CC(CC2C3)C1]

-continued
419
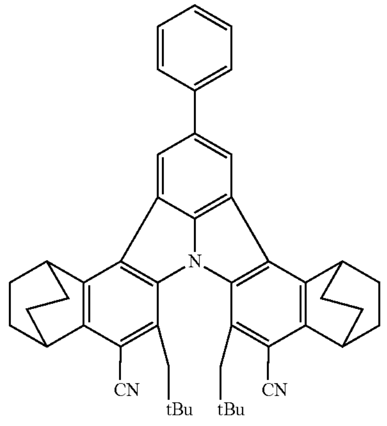 [SMILES: CC(C)(C)Cc1c(C#N)c2c(c3c4cc(-c5ccccc5)cc5c6c7c(c(C#N)c(CC(C)(C)C)c6n(c13)c45)C1CCC7CC1)C1CCC2CC1]
420
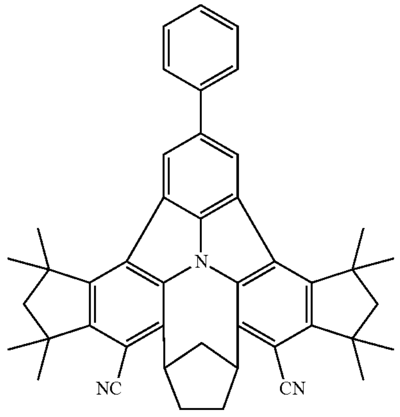
421
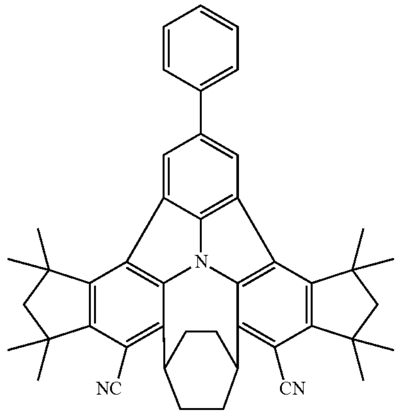

-continued
422
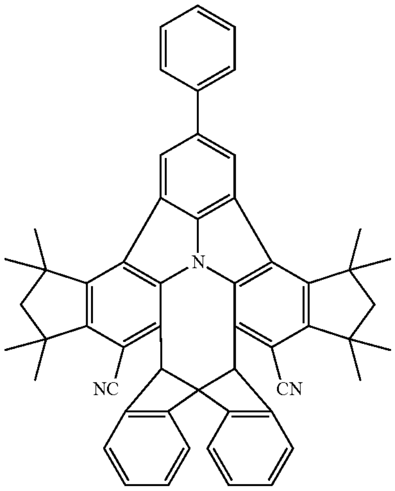
423
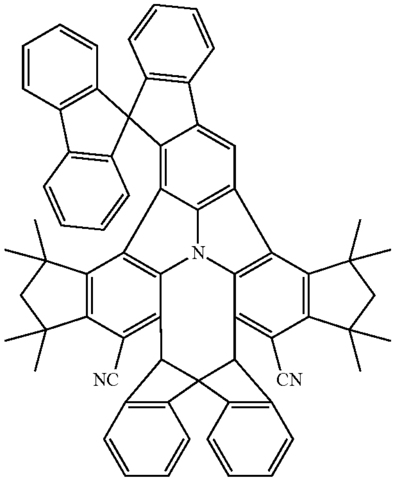
424
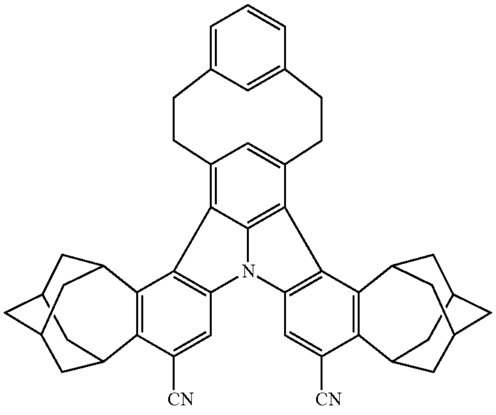 [SMILES: N#Cc1cc2c(c3c1C1CC4CC(C1)CC3C4)c1c3cc(c4c5c6c(c(C#N)cc5n2c14)C1CC2CC(C1)CC6C2)CCc1cccc(c1)CC3]

-continued
425
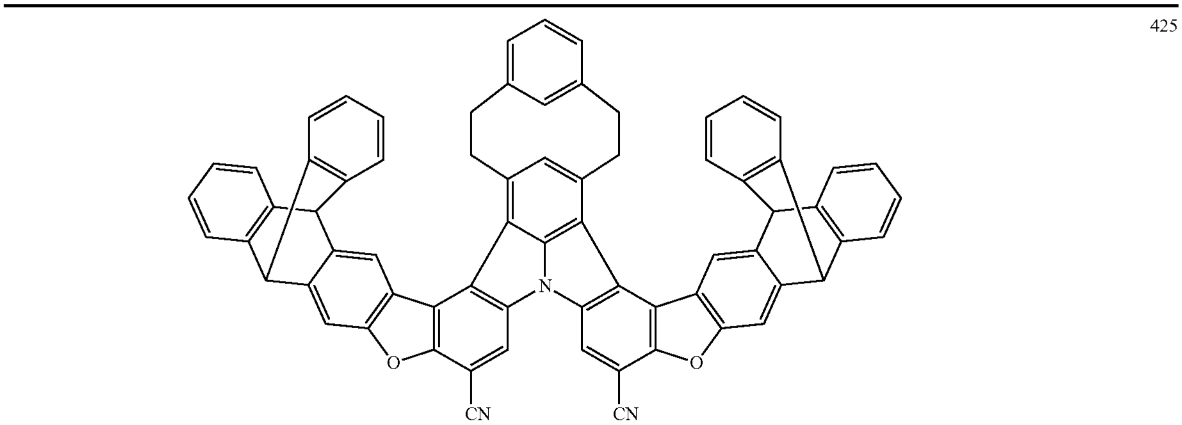
426
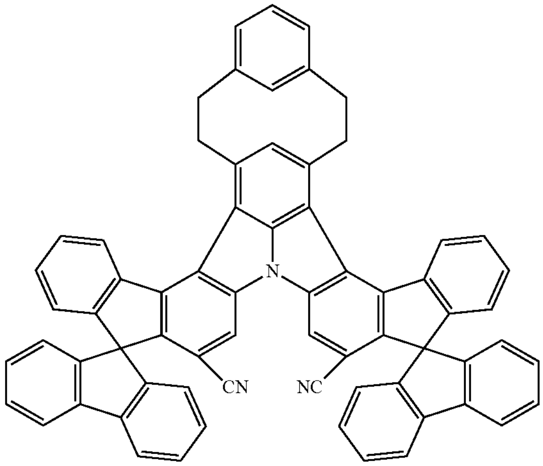 [SMILES: N#Cc1cc2c(c3c1C1(c4ccccc4-c4ccccc41)c1ccccc1-3)c1c3cc(c4c5c6c(c(C#N)cc5n2c14)C1(c2ccccc2-c2ccccc21)c1ccccc1-6)CCc1cccc(c1)CC3]
427
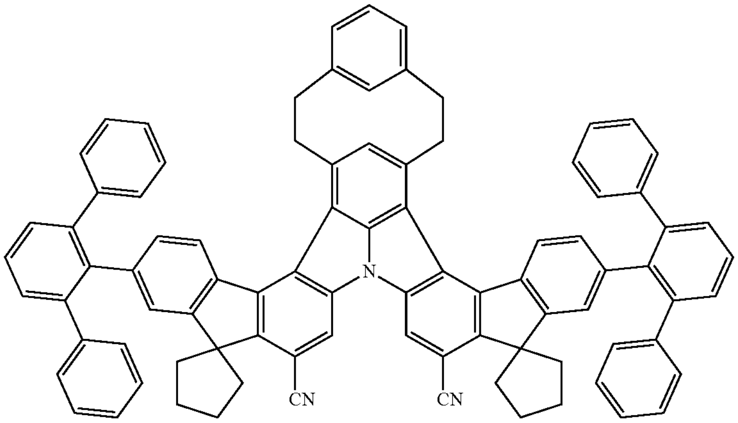 [SMILES: N#Cc1cc2c(c3c1C1(CCCC1)c1cc(-c4c(-c5ccccc5)cccc4-c4ccccc4)ccc1-3)c1c3cc(c4c5c6c(c(C#N)cc5n2c14)C1(CCCC1)c1cc(-c2c(-c4ccccc4)cccc2-c2ccccc2)ccc1-6)CCc1cccc(c1)CC3]

-continued
428
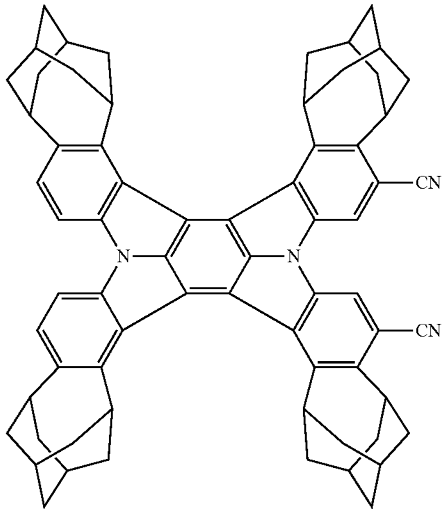 [SMILES: N#Cc1cc2c(c3c1C1CC4CC(C1)CC3C4)c1c3c4c5c(ccc4n4c6ccc7c(c6c(c6c8c9c(c(C#N)cc8n2c16)C1CC2CC(C1)CC9C2)c34)C1CC2CC(CC7C2)C1)C1CC2CC(C1)CC5C2]
429
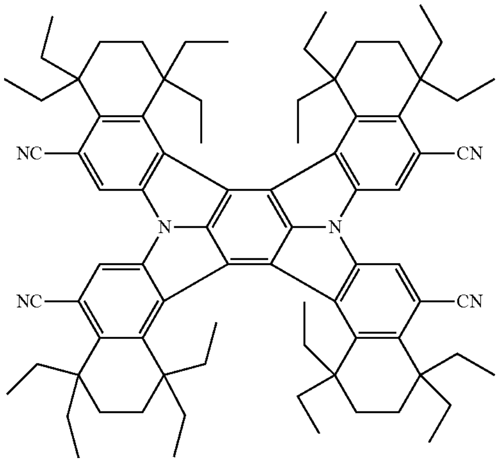 [SMILES: CCC1(CC)CCC(CC)(CC)c2c1c(C#N)cc1c2c2c3c4c5c(c(C#N)cc4n4c6cc(C#N)c7c(c6c(c6c8c9c(c(C#N)cc8n1c26)C(CC)(CC)CCC9(CC)CC)c34)C(CC)(CC)CCC7(CC)CC)C(CC)(CC)CCC5(CC)CC]
430
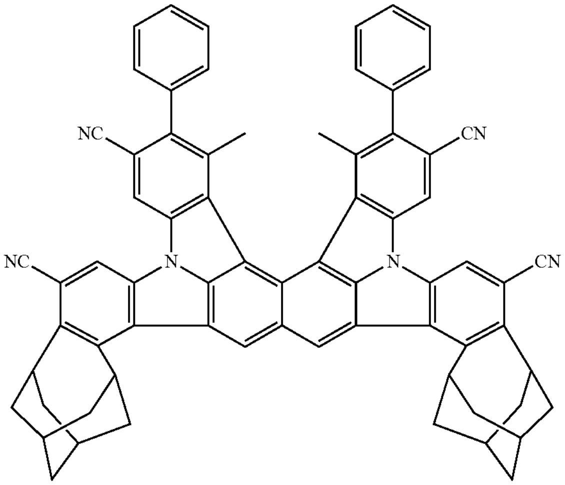 [SMILES: Cc1c(-c2ccccc2)c(C#N)cc2c1c1c3c(cc4c5c6c(c(C#N)cc5n2c41)C1CC2CC(C1)CC6C2)cc1c2c4c(c(C#N)cc2n2c5cc(C#N)c(-c6ccccc6)c(C)c5c3c12)C1CC2CC(C1)CC4C2]

-continued
431
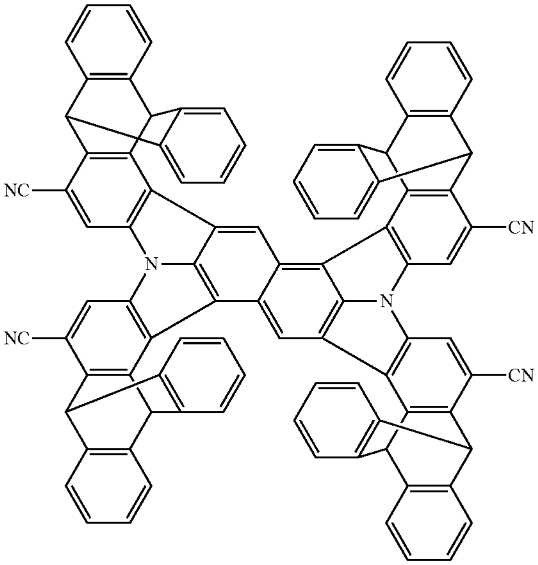 [SMILES: N#Cc1cc2c(c3c1C1c4ccccc4C3c3ccccc31)c1cc3c(cc4c5c6c(c(C#N)cc5n5c7cc(C#N)c8c(c7c3c45)C3c4ccccc4C8c4ccccc43)C3c4ccccc4C6c4ccccc43)c3c4c5c(c(C#N)cc4n2c13)C1c2ccccc2C5c2ccccc21]
432
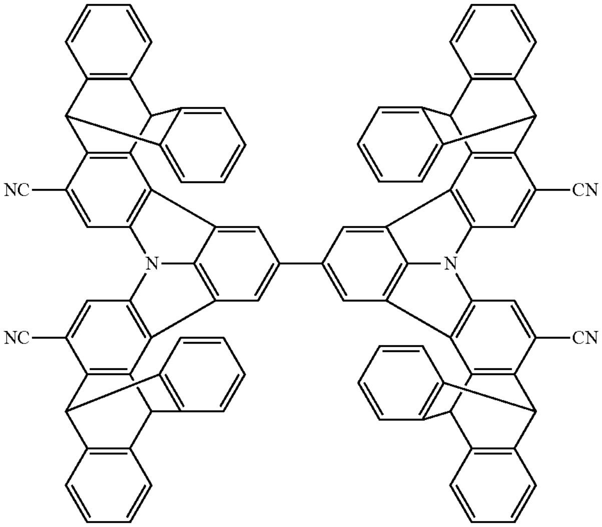 [SMILES: N#Cc1cc2c(c3c1C1c4ccccc4C3c3ccccc31)c1cc(-c3cc4c5c6c(c(C#N)cc5n5c7cc(C#N)c8c(c7c(c3)c45)C3c4ccccc4C8c4ccccc43)C3c4ccccc4C6c4ccccc43)cc3c4c5c(c(C#N)cc4n2c13)C1c2ccccc2C5c2ccccc21]
433
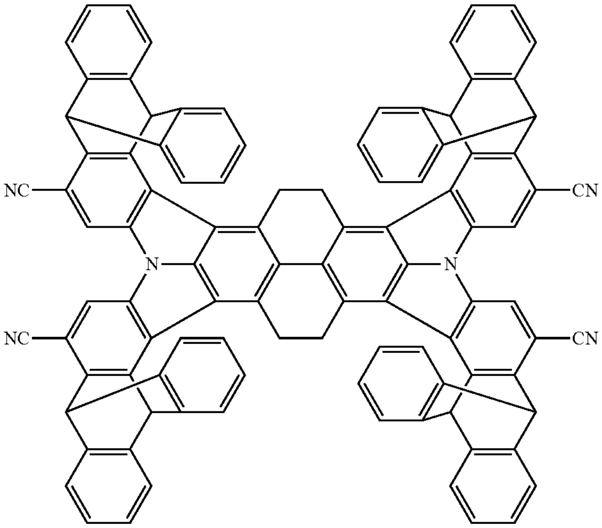 [SMILES: N#Cc1cc2c(c3c1C1c4ccccc4C3c3ccccc31)c1c3c4c(c5c6c7c(c(C#N)cc6n2c15)C1c2ccccc2C7c2ccccc21)CCc1c-4c(c2c4c5c(c(C#N)cc4n4c6cc(C#N)c7c(c6c1c24)C1c2ccccc2C7c2ccccc21)C1c2ccccc2C5c2ccccc21)CC3]

-continued
434
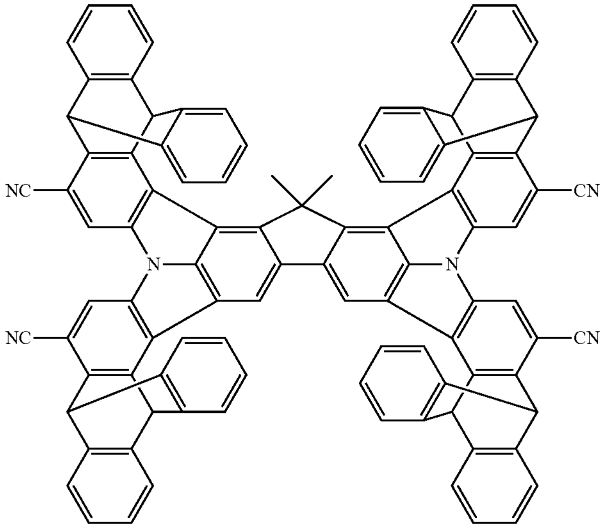 [SMILES: CC1(C)c2c(cc3c4c5c(c(C#N)cc4n4c6cc(C#N)c7c(c6c2c34)C2c3ccccc3C7c3ccccc32)C2c3ccccc3C5c3ccccc32)-c2cc3c4c5c(c(C#N)cc4n4c6cc(C#N)c7c(c6c(c21)c34)C1c2ccccc2C7c2ccccc21)C1c2ccccc2C5c2ccccc21]
435
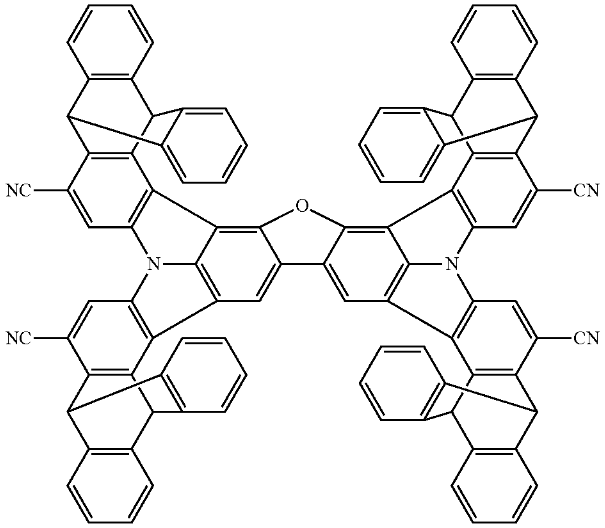 [SMILES: N#Cc1cc2c(c3c1C1c4ccccc4C3c3ccccc31)c1cc3c4cc5c6c7c(c(C#N)cc6n6c8cc(C#N)c9c(c8c(c4oc3c3c4c8c(c(C#N)cc4n2c13)C1c2ccccc2C8c2ccccc21)c56)C1c2ccccc2C9c2ccccc21)C1c2ccccc2C7c2ccccc21]
436
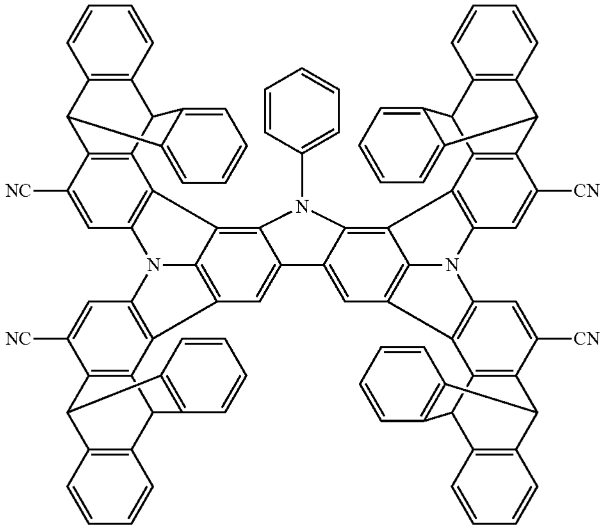 [SMILES: N#Cc1cc2c(c3c1C1c4ccccc4C3c3ccccc31)c1cc3c4cc5c6c7c(c(C#N)cc6n6c8cc(C#N)c9c(c8c(c4n(-c4ccccc4)c3c3c4c8c(c(C#N)cc4n2c13)C1c2ccccc2C8c2ccccc21)c56)C1c2ccccc2C9c2ccccc21)C1c2ccccc2C7c2ccccc21]

-continued
437
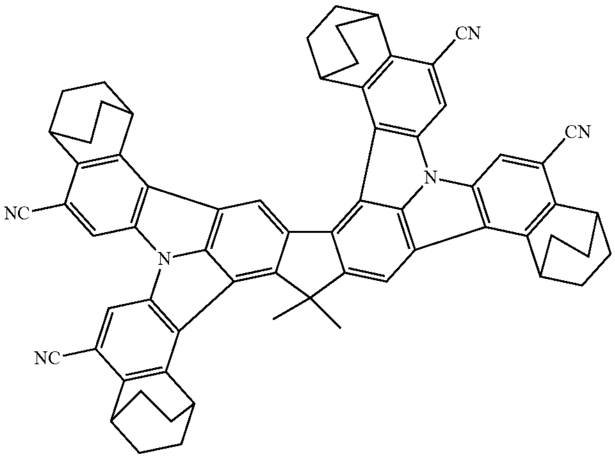 [SMILES: CC1(C)c2cc3c4c5c(c(C#N)cc4n4c6cc(C#N)c7c(c6c(c2-c2cc6c8c9c(c(C#N)cc8n8c%10cc(C#N)c%11c(c%10c(c21)c68)C1CCC%11CC1)C1CCC9CC1)c34)C1CCC7CC1)C1CCC5CC1]
438
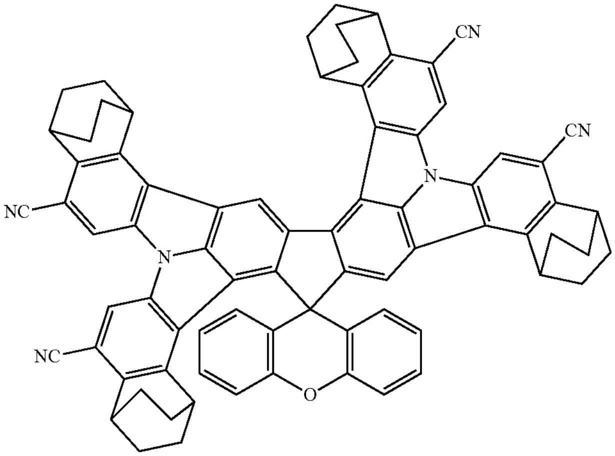 [SMILES: N#Cc1cc2c(c3c1C1CCC3CC1)c1cc3c(c4c5c6c(c(C#N)cc5n2c14)C1CCC6CC1)-c1cc2c4c5c(c(C#N)cc4n4c6cc(C#N)c7c(c6c(c1C31c3ccccc3Oc3ccccc31)c24)C1CCC7CC1)C1CCC5CC1]
439
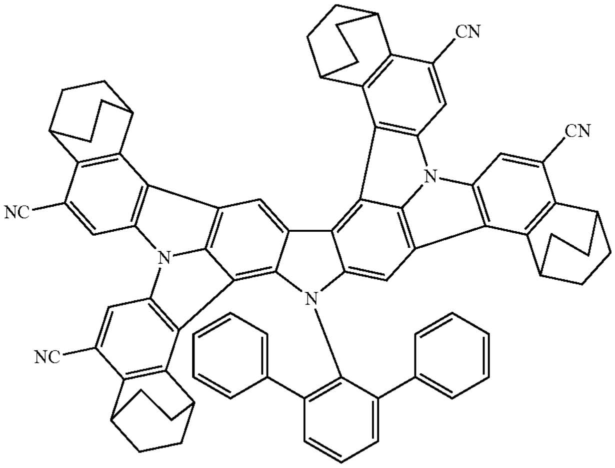 [SMILES: N#Cc1cc2c(c3c1C1CCC3CC1)c1cc3c(c4cc5c6c7c(c(C#N)cc6n6c8cc(C#N)c9c(c8c(c4n3-c3c(-c4ccccc4)cccc3-c3ccccc3)c56)C3CCC9CC3)C3CCC7CC3)c3c4c5c(c(C#N)cc4n2c13)C1CCC5CC1]

-continued
440
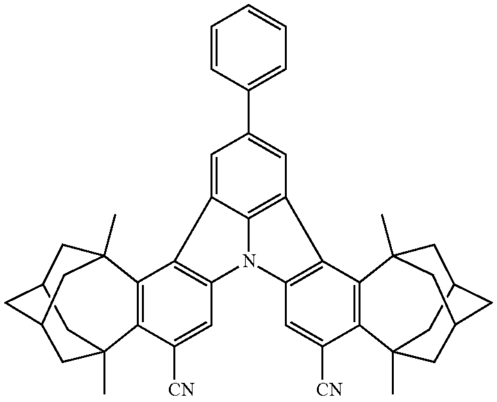 [SMILES: CC12CC3CC(C1)CC(C)(C3)c1c2c(C#N)cc2c1c1cc(-c3ccccc3)cc3c4c5c(c(C#N)cc4n2c13)C1(C)CC2CC(C1)CC5(C)C2]
441
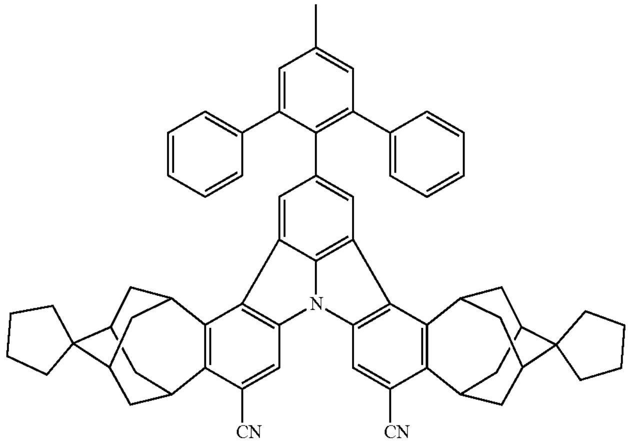 [SMILES: Cc1cc(-c2ccccc2)c(-c2cc3c4c5c(c(C#N)cc4n4c6cc(C#N)c7c(c6c(c2)c34)C2CC3CC7CC(C2)C32CCCC2)C2CC3CC5CC(C2)C32CCCC2)c(-c2ccccc2)c1]
442
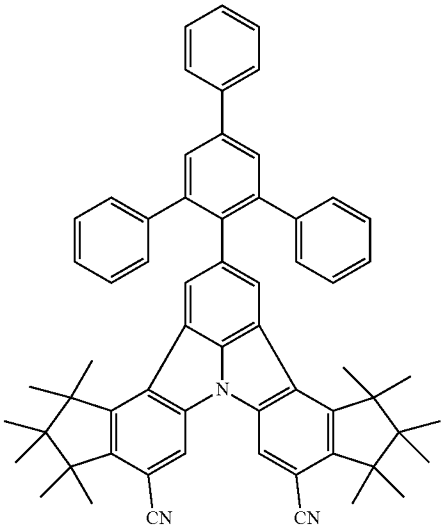

-continued
443
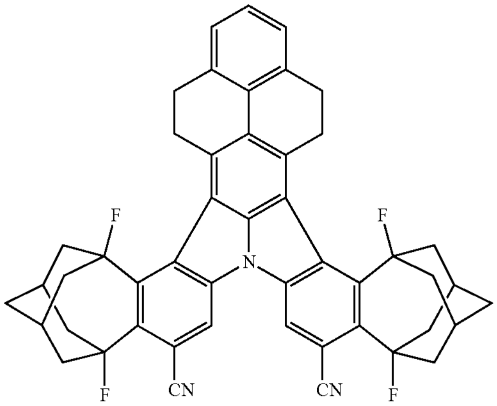 [SMILES: N#Cc1cc2c(c3c1C1(F)CC4CC(C1)CC3(F)C4)c1c3c4c(c5c6c7c(c(C#N)cc6n2c15)C1(F)CC2CC(C1)CC7(F)C2)CCc1cccc(c1-4)CC3]
444
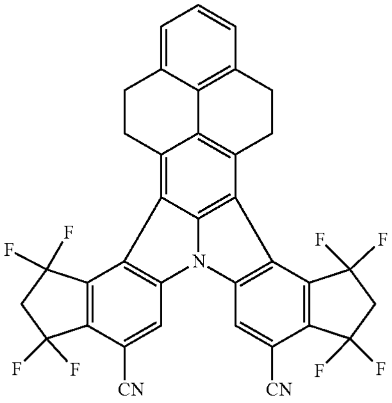 [SMILES: N#Cc1cc2c(c3c1C(F)(F)CC3(F)F)c1c3c4c(c5c6c7c(c(C#N)cc6n2c15)C(F)(F)CC7(F)F)CCc1cccc(c1-4)CC3]
445
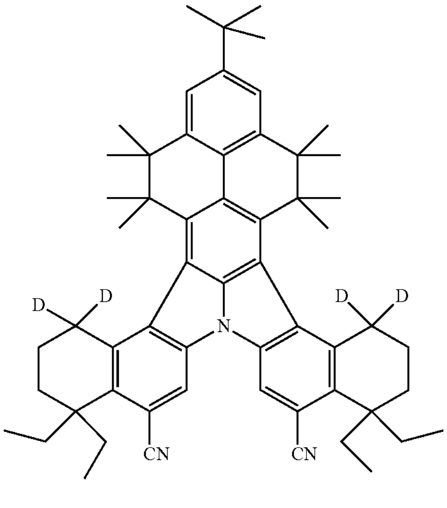 [SMILES: [2H]C1([2H])CCC(CC)(CC)c2c(C#N)cc3c(c21)c1c2c4c(c5c6c7c(c(C#N)cc6n3c15)C(CC)(CC)CCC7([2H])[2H])C(C)(C)C(C)(C)c1cc(C(C)(C)C)cc(c1-4)C(C)(C)C2(C)C]

-continued
446
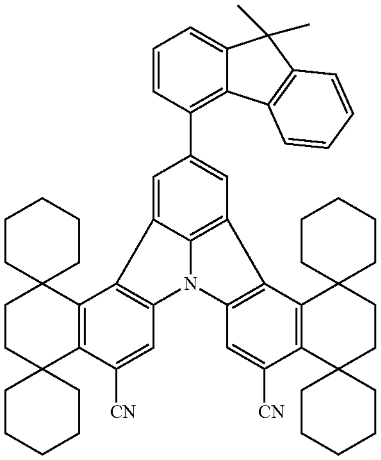 [SMILES: CC1(C)c2ccccc2-c2c(-c3cc4c5c6c(c(C#N)cc5n5c7cc(C#N)c8c(c7c(c3)c45)C3(CCCCC3)CCC83CCCCC3)C3(CCCCC3)CCC63CCCCC3)cccc21]
447
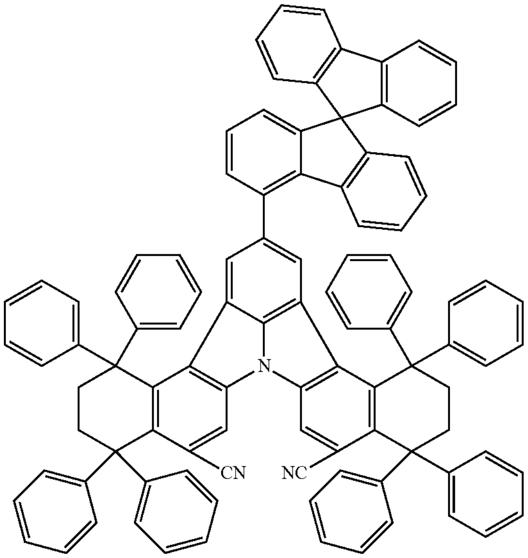 [SMILES: N#Cc1cc2c(c3c1C(c1ccccc1)(c1ccccc1)CCC3(c1ccccc1)c1ccccc1)c1cc(-c3cccc4c3-c3ccccc3C43c4ccccc4-c4ccccc43)cc3c4c5c(c(C#N)cc4n2c13)C(c1ccccc1)(c1ccccc1)CCC5(c1ccccc1)c1ccccc1]
448
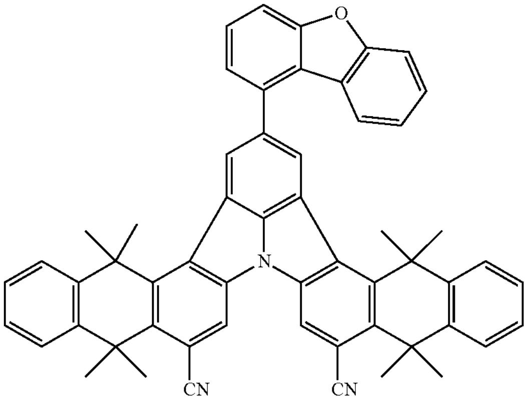 [SMILES: CC1(C)c2ccccc2C(C)(C)c2c1c(C#N)cc1c2c2cc(-c3cccc4oc5ccccc5c34)cc3c4c5c(c(C#N)cc4n1c23)C(C)(C)c1ccccc1C5(C)C]

-continued
449
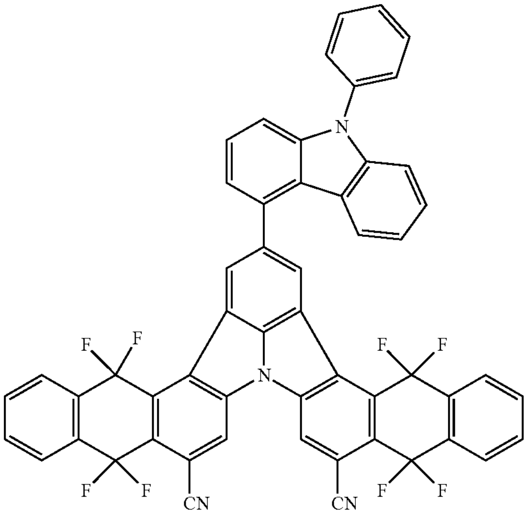 [SMILES: N#Cc1cc2c(c3c1C(F)(F)c1ccccc1C3(F)F)c1cc(-c3cccc4c3c3ccccc3n4-c3ccccc3)cc3c4c5c(c(C#N)cc4n2c13)C(F)(F)c1ccccc1C5(F)F]
450
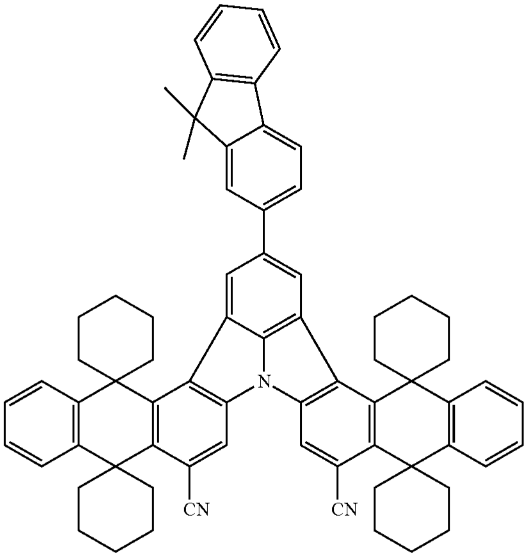 [SMILES: CC1(C)c2ccccc2-c2ccc(-c3cc4c5c6c(c(C#N)cc5n5c7cc(C#N)c8c(c7c(c3)c45)C3(CCCCC3)c3ccccc3C83CCCCC3)C3(CCCCC3)c3ccccc3C63CCCCC3)cc21]
451
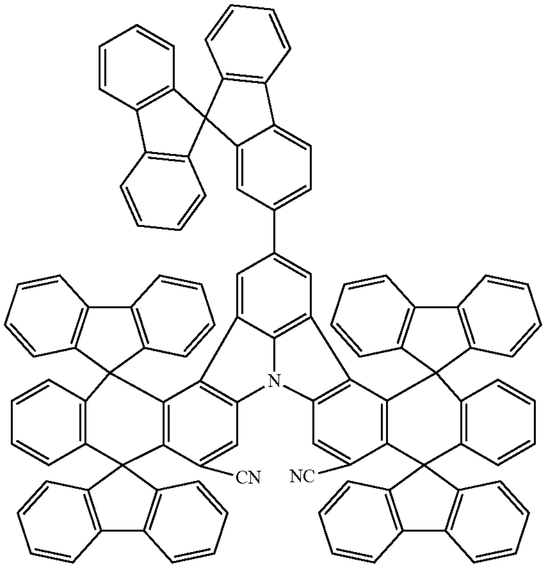 [SMILES: N#Cc1cc2c(c3c1C1(c4ccccc4-c4ccccc41)c1ccccc1C31c3ccccc3-c3ccccc31)c1cc(-c3ccc4c(c3)C3(c5ccccc5-c5ccccc53)c3ccccc3-4)cc3c4c5c(c(C#N)cc4n2c13)C1(c2ccccc2-c2ccccc21)c1ccccc1C51c2ccccc2-c2ccccc21]

-continued
452
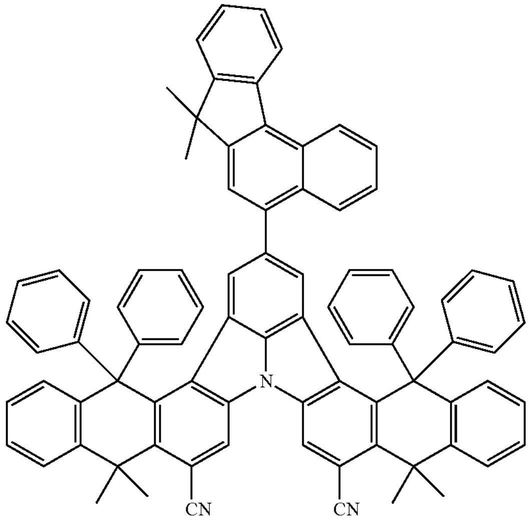 [SMILES: CC1(C)c2ccccc2-c2c1cc(-c1cc3c4c5c(c(C#N)cc4n4c6cc(C#N)c7c(c6c(c1)c34)C(c1ccccc1)(c1ccccc1)c1ccccc1C7(C)C)C(C)(C)c1ccccc1C5(c1ccccc1)c1ccccc1)c1ccccc21]
453
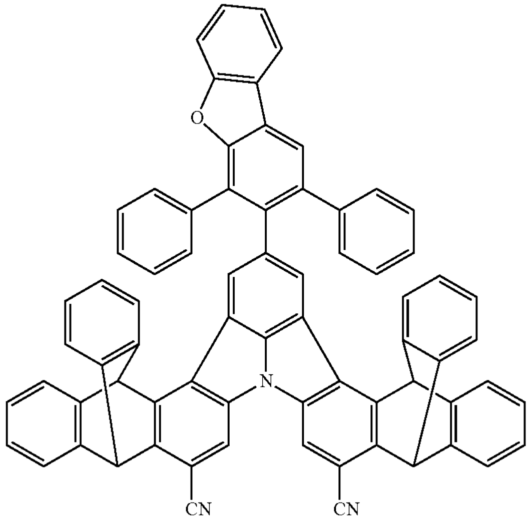 [SMILES: N#Cc1cc2c(c3c1C1c4ccccc4C3c3ccccc31)c1cc(-c3c(-c4ccccc4)cc4c(oc5ccccc54)c3-c3ccccc3)cc3c4c5c(c(C#N)cc4n2c13)C1c2ccccc2C5c2ccccc21]
454
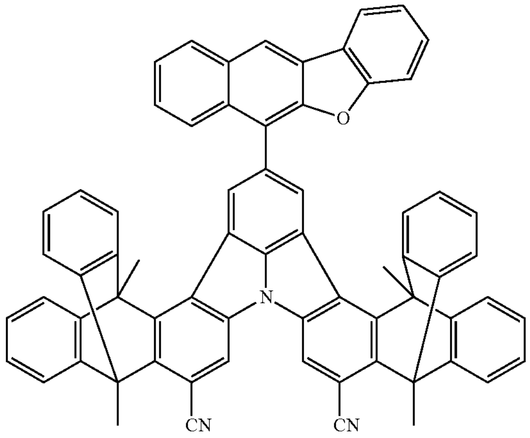 [SMILES: CC12c3ccccc3C(C)(c3ccccc31)c1c2c(C#N)cc2c1c1cc(-c3c4ccccc4cc4c3oc3ccccc34)cc3c4c5c(c(C#N)cc4n2c13)C1(C)c2ccccc2C5(C)c2ccccc21]

-continued
455
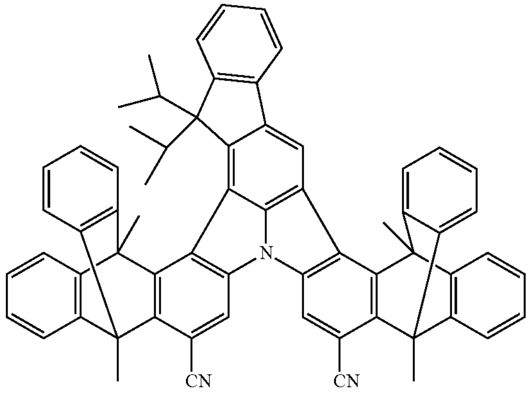 [SMILES: CC(C)C1(C(C)C)c2ccccc2-c2cc3c4c5c(c(C#N)cc4n4c6cc(C#N)c7c(c6c(c21)c34)C1(C)c2ccccc2C7(C)c2ccccc21)C1(C)c2ccccc2C5(C)c2ccccc21]
456
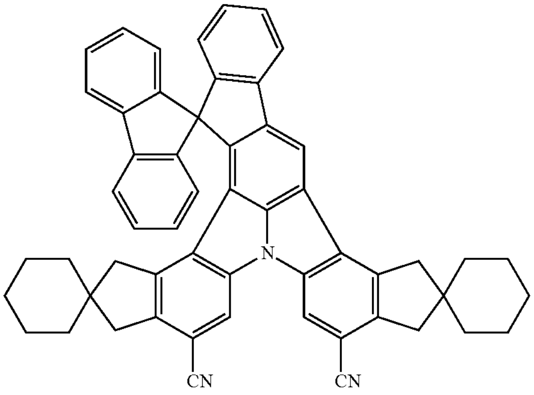 [SMILES: N#Cc1cc2c(c3c1CC1(CCCCC1)C3)c1cc3c(c4c5c6c(c(C#N)cc5n2c14)CC1(CCCCC1)C6)C1(c2ccccc2-c2ccccc21)c1ccccc1-3]
457
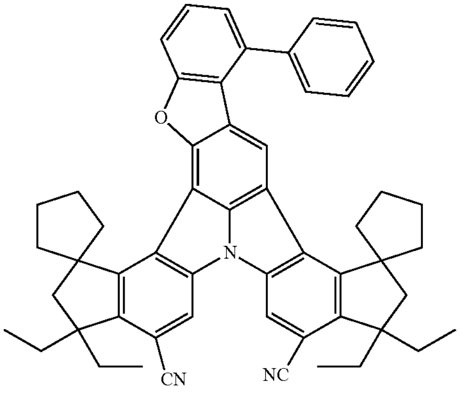 [SMILES: CCC1(CC)CC2(CCCC2)c2c1c(C#N)cc1c2c2cc3c(oc4cccc(-c5ccccc5)c43)c3c4c5c(c(C#N)cc4n1c23)C(CC)(CC)CC51CCCC1]

-continued
458
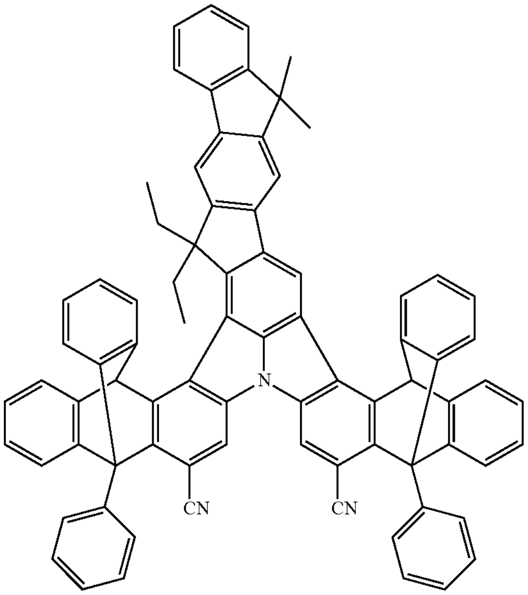 [SMILES: CCC1(CC)c2cc3c(cc2-c2cc4c5c6c(c(C#N)cc5n5c7cc(C#N)c8c(c7c(c21)c45)C1c2ccccc2C8(c2ccccc2)c2ccccc21)C1(c2ccccc2)c2ccccc2C6c2ccccc21)C(C)(C)c1ccccc1-3]
459
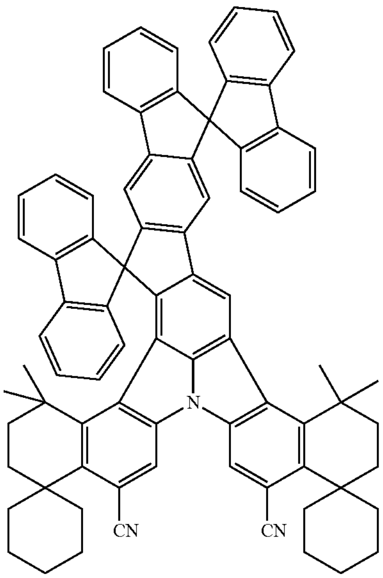

-continued
460
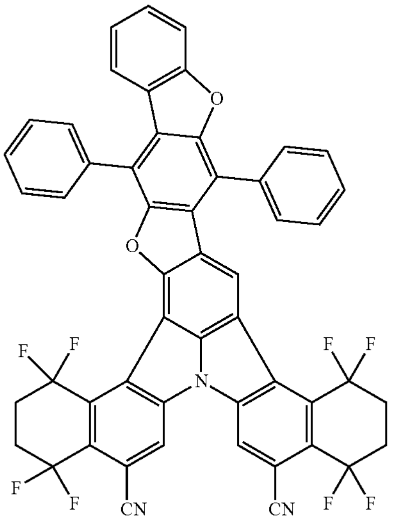 [SMILES: N#Cc1cc2c(c3c1C(F)(F)CCC3(F)F)c1cc3c(oc4c(-c5ccccc5)c5c(oc6ccccc65)c(-c5ccccc5)c43)c3c4c5c(c(C#N)cc4n2c13)C(F)(F)CCC5(F)F]
461
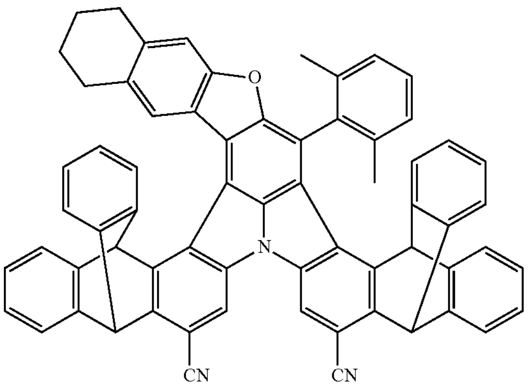 [SMILES: Cc1cccc(C)c1-c1c2oc3cc4c(cc3c2c2c3c5c(c(C#N)cc3n3c6cc(C#N)c7c(c6c1c23)C1c2ccccc2C7c2ccccc21)C1c2ccccc2C5c2ccccc21)CCCC4]
462
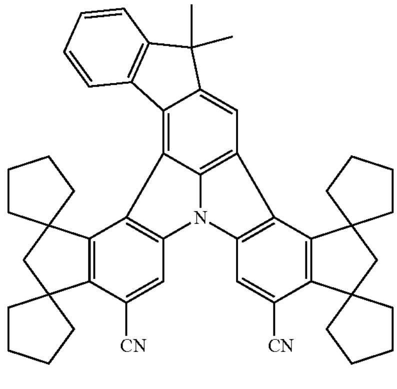 [SMILES: CC1(C)c2ccccc2-c2c1cc1c3c4c(c(C#N)cc3n3c5cc(C#N)c6c(c5c2c13)C1(CCCC1)CC61CCCC1)C1(CCCC1)CC41CCCC1]

-continued
463
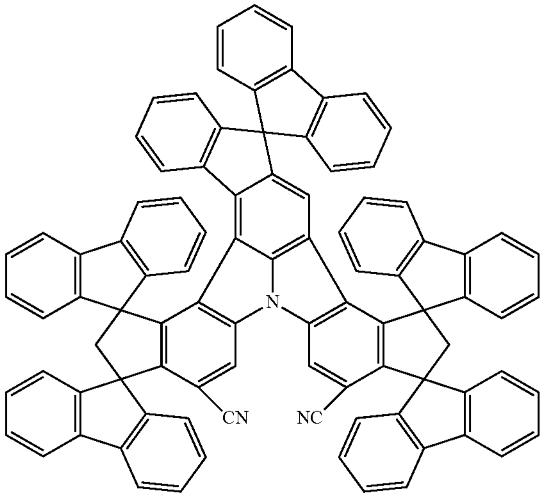 [SMILES: N#Cc1cc2c(c3c1C1(CC34c3ccccc3-c3ccccc34)c3ccccc3-c3ccccc31)c1cc3c(c4c5c6c(c(C#N)cc5n2c14)C1(CC62c4ccccc4-c4ccccc42)c2ccccc2-c2ccccc21)-c1ccccc1C31c2ccccc2-c2ccccc21]
464
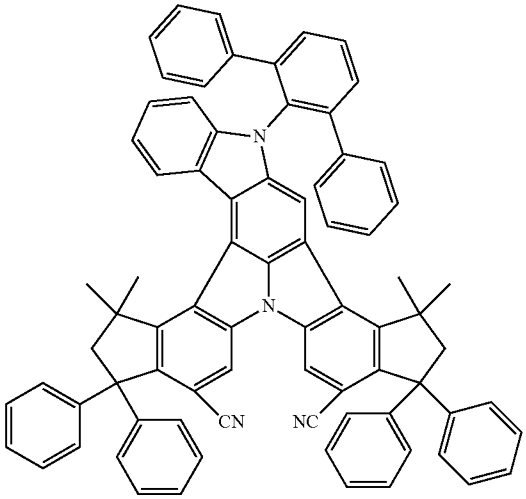 [SMILES: CC1(C)CC(c2ccccc2)(c2ccccc2)c2c(C#N)cc3c(c21)c1cc2c(c4ccccc4n2-c2c(-c4ccccc4)cccc2-c2ccccc2)c2c4c5c(c(C#N)cc4n3c12)C(c1ccccc1)(c1ccccc1)CC5(C)C]
465
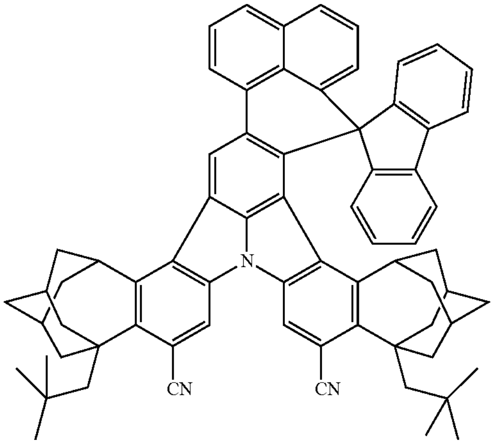 [SMILES: CC(C)(C)CC12CC3CC(CC(C3)c3c1c(C#N)cc1c3c3cc4c(c5c6c7c(c(C#N)cc6n1c35)C1(CC(C)(C)C)CC3CC(CC7C3)C1)C1(c3ccccc3-c3ccccc31)c1cccc3cccc-4c13)C2]

-continued
466
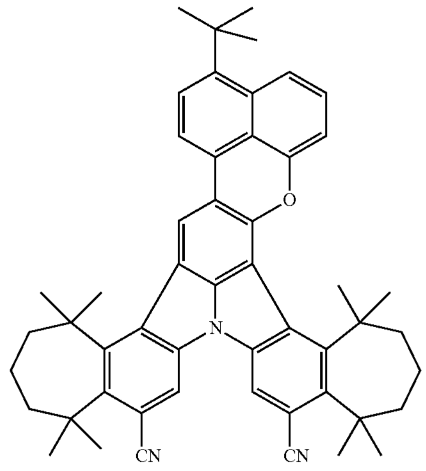 [SMILES: CC(C)(C)c1ccc2c3cc4c5c6c(c(C#N)cc5n5c7cc(C#N)c8c(c7c(c3oc3cccc1c32)c45)C(C)(C)CCCC8(C)C)C(C)(C)CCCC6(C)C]
467
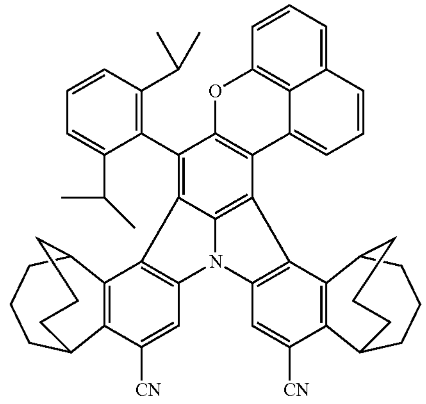 [SMILES: CC(C)c1cccc(C(C)C)c1-c1c2oc3cccc4cccc(c43)c2c2c3c4c(c(C#N)cc3n3c5cc(C#N)c6c(c5c1c23)C1CCCC6CCC1)C1CCCC4CCC1]
468
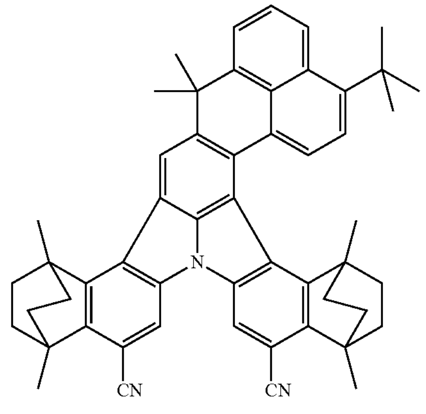 [SMILES: CC(C)(C)c1ccc2c3c(cccc13)C(C)(C)c1cc3c4c5c(c(C#N)cc4n4c6cc(C#N)c7c(c6c(c1-2)c34)C1(C)CCC7(C)CC1)C1(C)CCC5(C)CC1]

-continued
469
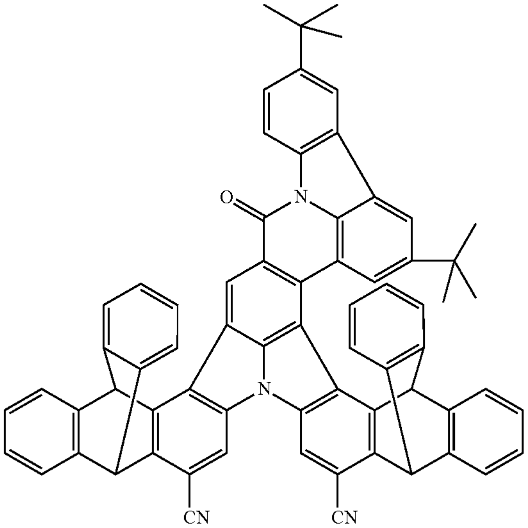 [SMILES: CC(C)(C)c1ccc2c(c1)c1cc(C(C)(C)C)cc3c4c(cc5c6c7c(c(C#N)cc6n6c8cc(C#N)c9c(c8c4c56)C4c5ccccc5C9c5ccccc54)C4c5ccccc5C7c5ccccc54)c(=O)n2c13]
470
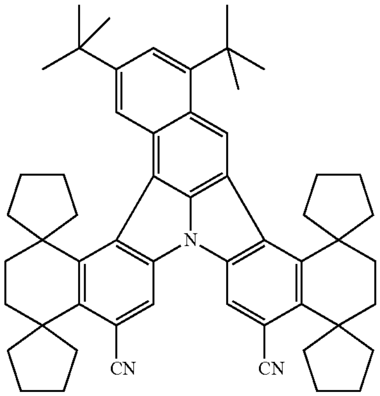 [SMILES: CC(C)(C)c1cc(C(C)(C)C)c2cc3c4c5c(c(C#N)cc4n4c6cc(C#N)c7c(c6c(c2c1)c34)C1(CCCC1)CCC71CCCC1)C1(CCCC1)CCC51CCCC1]
471
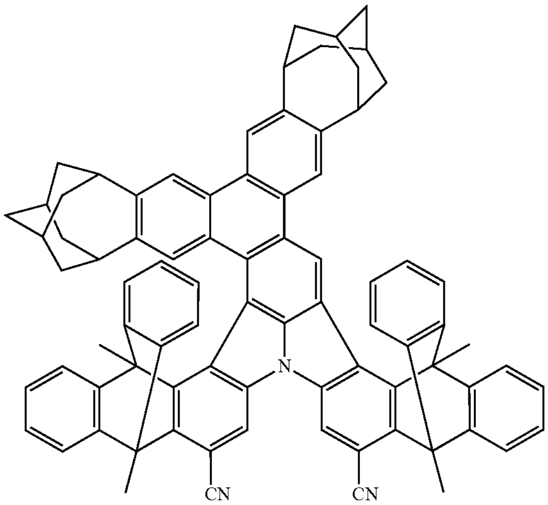 [SMILES: CC12c3ccccc3C(C)(c3ccccc31)c1c2c(C#N)cc2c1c1cc3c4cc5c(cc4c4cc6c(cc4c3c3c4c7c(c(C#N)cc4n2c13)C1(C)c2ccccc2C7(C)c2ccccc21)C1CC2CC(CC6C2)C1)C1CC2CC(C1)CC5C2]

-continued
472
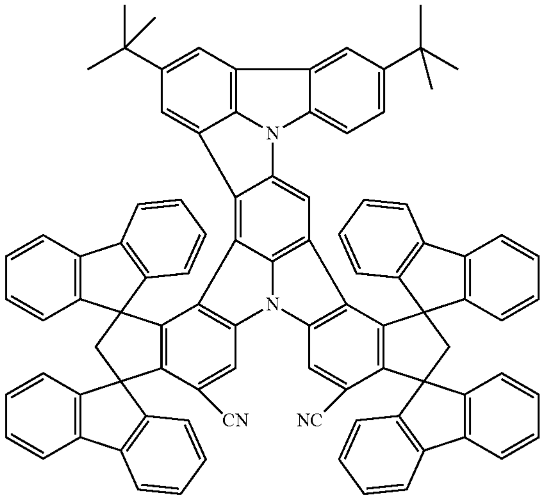 [SMILES: CC(C)(C)c1ccc2c(c1)c1cc(C(C)(C)C)cc3c4c5c6c7c(c(C#N)cc6n6c8cc(C#N)c9c(c8c(cc4n2c13)c56)C1(CC92c3ccccc3-c3ccccc32)c2ccccc2-c2ccccc21)C1(CC72c3ccccc3-c3ccccc32)c2ccccc2-c2ccccc21]
473
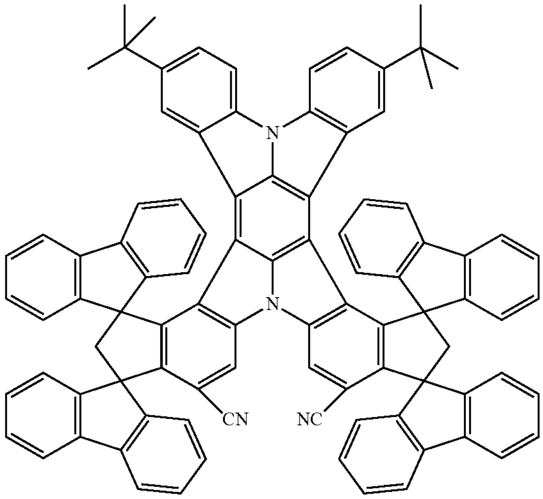 [SMILES: CC(C)(C)c1ccc2c(c1)c1c3c4c5c(c(C#N)cc4n4c6cc(C#N)c7c(c6c(c6c8cc(C(C)(C)C)ccc8n2c16)c34)C1(CC72c3ccccc3-c3ccccc32)c2ccccc2-c2ccccc21)C1(CC52c3ccccc3-c3ccccc32)c2ccccc2-c2ccccc21]
474
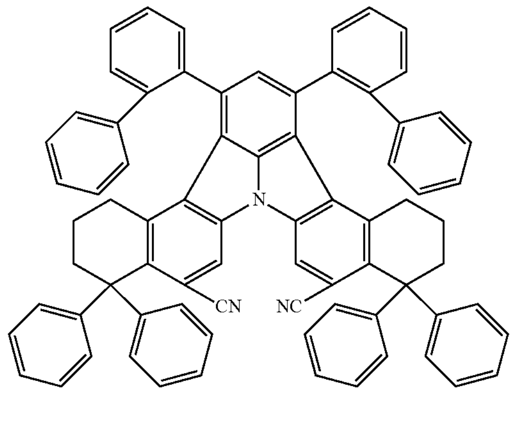 [SMILES: N#Cc1cc2c(c3c1C(c1ccccc1)(c1ccccc1)CCC3)c1c(-c3ccccc3-c3ccccc3)cc(-c3ccccc3-c3ccccc3)c3c4c5c(c(C#N)cc4n2c13)C(c1ccccc1)(c1ccccc1)CCC5]

-continued
475
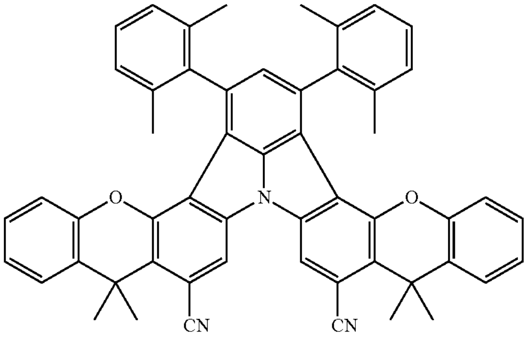 [SMILES: Cc1cccc(C)c1-c1cc(-c2c(C)cccc2C)c2c3c4c(c(C#N)cc3n3c5cc(C#N)c6c(c5c1c23)Oc1ccccc1C6(C)C)C(C)(C)c1ccccc1O4]
476
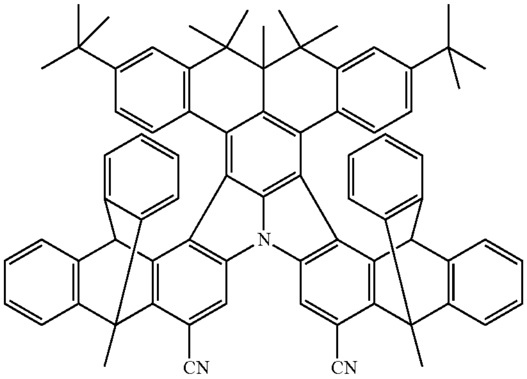 [SMILES: CC(C)(C)c1ccc2c(c1)C(C)(C)C1(C)c3c-2c2c4c5c(c(C#N)cc4n4c6cc(C#N)c7c(c6c(c3-c3ccc(C(C)(C)C)cc3C1(C)C)c24)C1c2ccccc2C7(C)c2ccccc21)C1(C)c2ccccc2C5c2ccccc21]
477
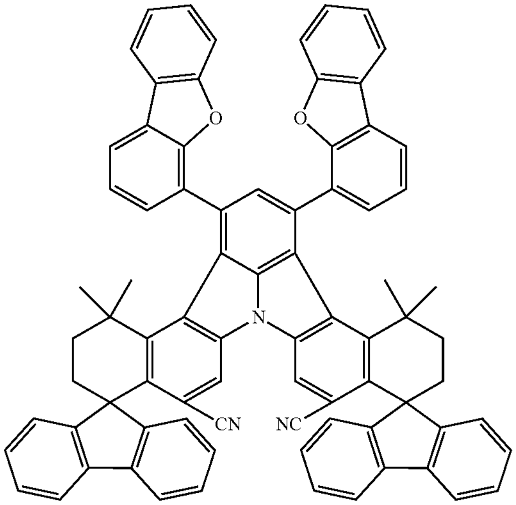 [SMILES: CC1(C)CCC2(c3ccccc3-c3ccccc32)c2c(C#N)cc3c(c21)c1c(-c2cccc4c2oc2ccccc24)cc(-c2cccc4c2oc2ccccc24)c2c4c5c(c(C#N)cc4n3c12)C1(CCC5(C)C)c2ccccc2-c2ccccc21]

-continued
478
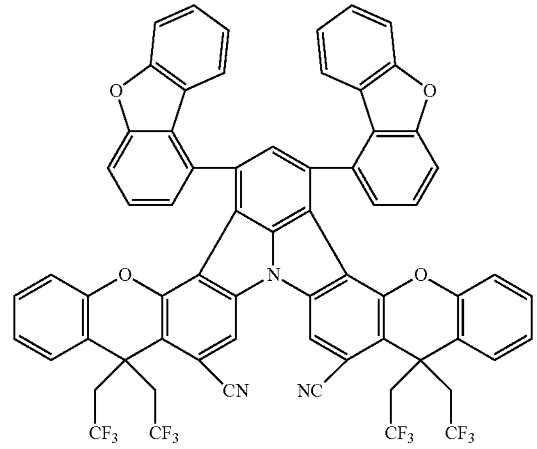 [SMILES: N#Cc1cc2c(c3c1C(CC(F)(F)F)(CC(F)(F)F)c1ccccc1O3)c1c(-c3cccc4oc5ccccc5c34)cc(-c3cccc4oc5ccccc5c34)c3c4c5c(c(C#N)cc4n2c13)C(CC(F)(F)F)(CC(F)(F)F)c1ccccc1O5]
479
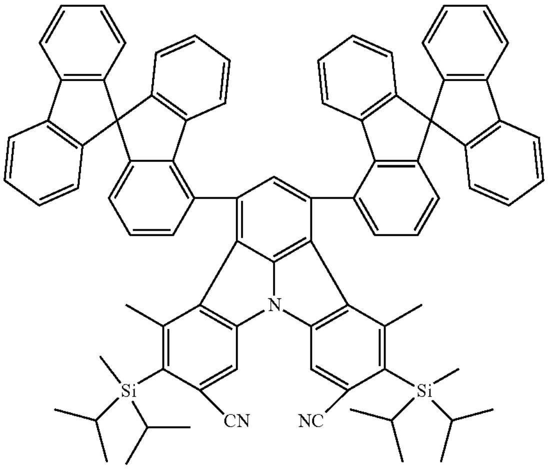 [SMILES: Cc1c([Si](C)(C(C)C)C(C)C)c(C#N)cc2c1c1c(-c3cccc4c3-c3ccccc3C43c4ccccc4-c4ccccc43)cc(-c3cccc4c3-c3ccccc3C43c4ccccc4-c4ccccc43)c3c4c(C)c([Si](C)(C(C)C)C(C)C)c(C#N)cc4n2c13]
480
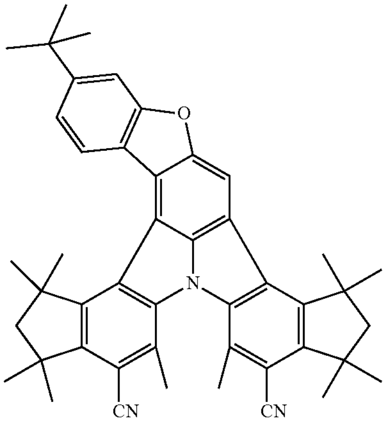

-continued
481
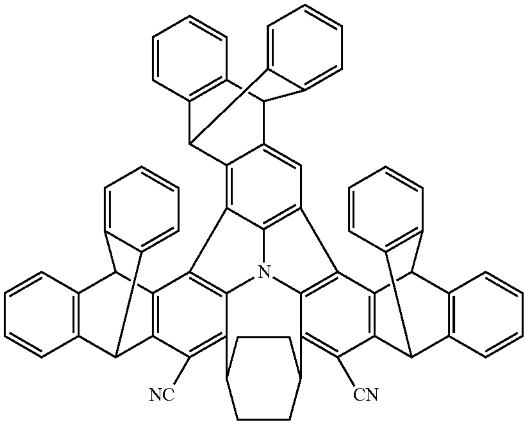 [SMILES: N#Cc1c2c(c3c4cc5c(c6c7c8c(c(C#N)c9c7n(c3c1C1CCC9CC1)c46)C1c3ccccc3C8c3ccccc31)C1c3ccccc3C5c3ccccc31)C1c3ccccc3C2c2ccccc21]
482
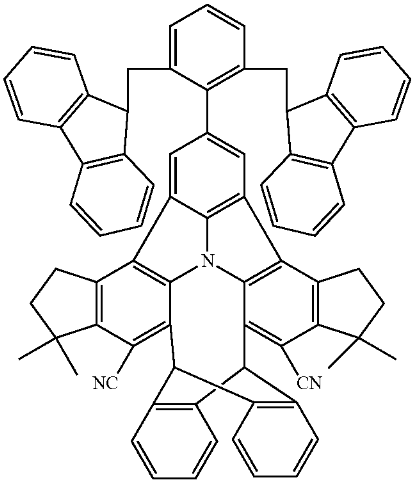 [SMILES: CC1(C)CCc2c1c(C#N)c1c3c2c2cc(-c4c(CC5c6ccccc6-c6ccccc65)cccc4CC4c5ccccc5-c5ccccc54)cc4c5c6c(c(C#N)c(c5n3c24)C2c3ccccc3C1c1ccccc12)C(C)(C)CC6]
483
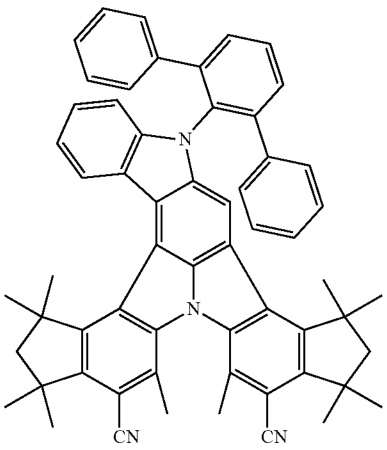

-continued
484
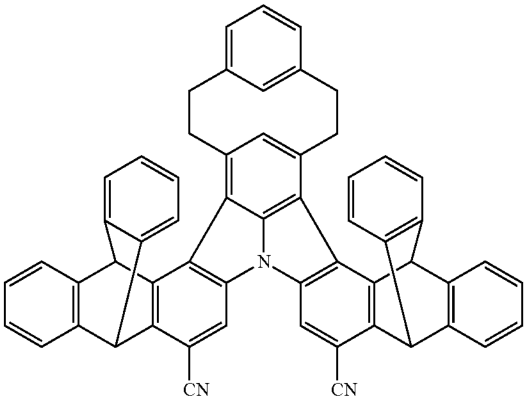 [SMILES: N#Cc1cc2c(c3c1C1c4ccccc4C3c3ccccc31)c1c3cc(c4c5c6c(c(C#N)cc5n2c14)C1c2ccccc2C6c2ccccc21)CCc1cccc(c1)CC3]
485
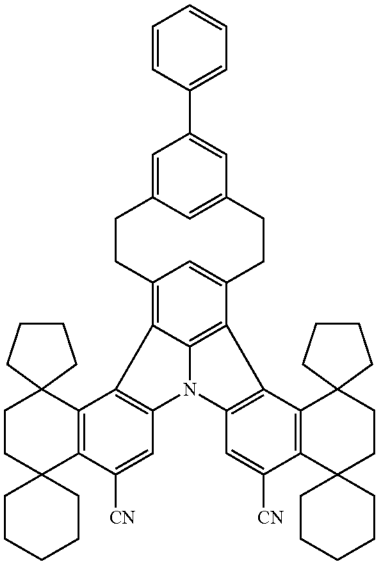 [SMILES: N#Cc1cc2c(c3c1C1(CCCCC1)CCC31CCCC1)c1c3cc(c4c5c6c(c(C#N)cc5n2c14)C1(CCCCC1)CCC61CCCC1)CCc1cc(cc(-c2ccccc2)c1)CC3]
486
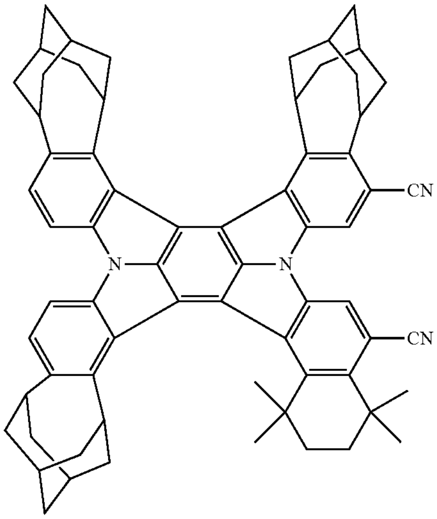 [SMILES: CC1(C)CCC(C)(C)c2c1c(C#N)cc1c2c2c3c4c5c(ccc4n4c6ccc7c(c6c(c6c8c9c(c(C#N)cc8n1c62)C1CC2CC(C1)CC9C2)c34)C1CC2CC(CC7C2)C1)C1CC2CC(C1)CC5C2]

-continued
487
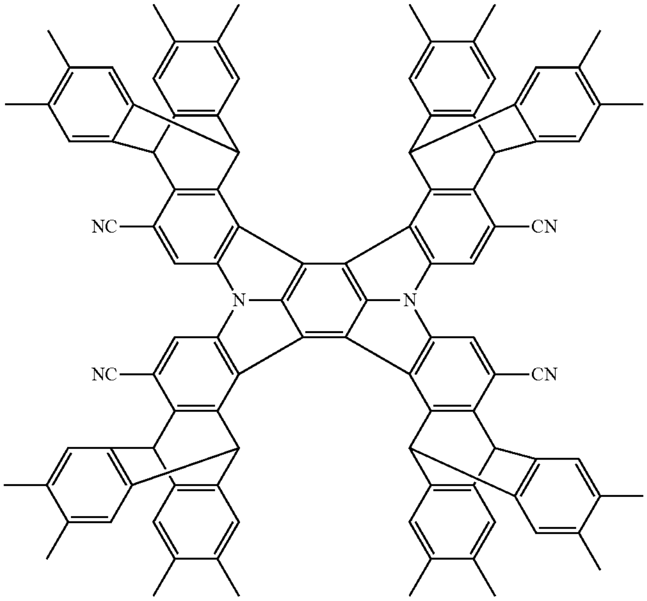
488
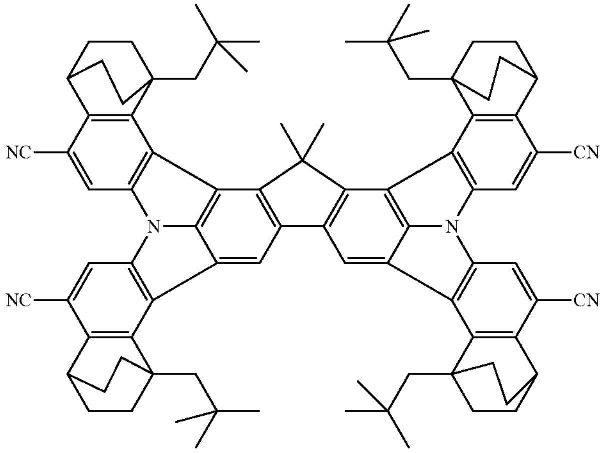 [SMILES: CC(C)(C)CC12CCC(CC1)c1c(C#N)cc3c(c12)c1cc2c(c4c5c6c(c(C#N)cc5n3c14)C1CCC6(CC(C)(C)C)CC1)C(C)(C)c1c-2cc2c3c4c(c(C#N)cc3n3c5cc(C#N)c6c(c5c1c23)C1(CC(C)(C)C)CCC6CC1)C1CCC4(CC(C)(C)C)CC1]
489
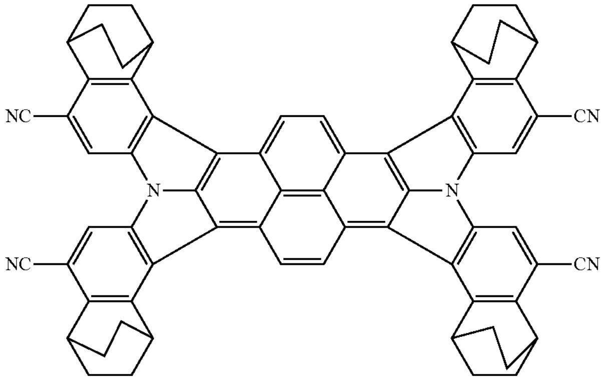 [SMILES: N#Cc1cc2c(c3c1C1CCC3CC1)c1c3ccc4c5c(ccc(c35)c3c5c6c(c(C#N)cc5n2c13)C1CCC6CC1)c1c2c3c(c(C#N)cc2n2c5cc(C#N)c6c(c5c4c12)C1CCC6CC1)C1CCC3CC1]

-continued
490
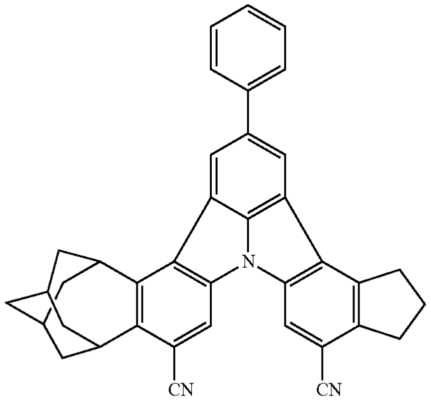 [SMILES: N#Cc1cc2c(c3c1CCC3)c1cc(-c3ccccc3)cc3c4c5c(c(C#N)cc4n2c13)C1CC2CC(C1)CC5C2]
491
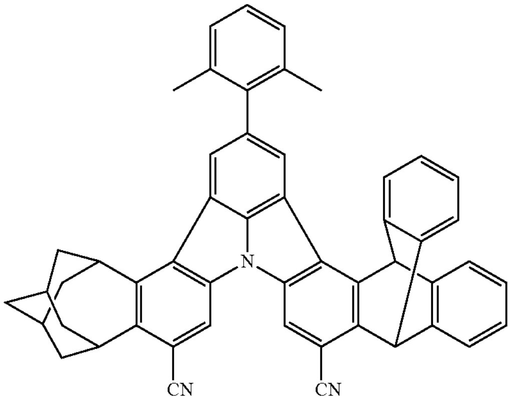 [SMILES: Cc1cccc(C)c1-c1cc2c3c4c(c(C#N)cc3n3c5cc(C#N)c6c(c5c(c1)c23)C1c2ccccc2C6c2ccccc21)C1CC2CC(C1)CC4C2]
492
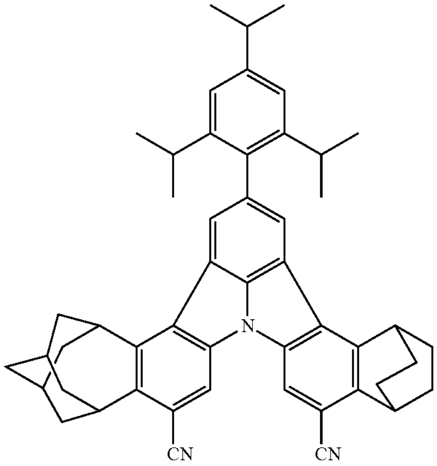 [SMILES: CC(C)c1cc(C(C)C)c(-c2cc3c4c5c(c(C#N)cc4n4c6cc(C#N)c7c(c6c(c2)c34)C2CC3CC(CC7C3)C2)C2CCC5CC2)c(C(C)C)c1]

-continued
493
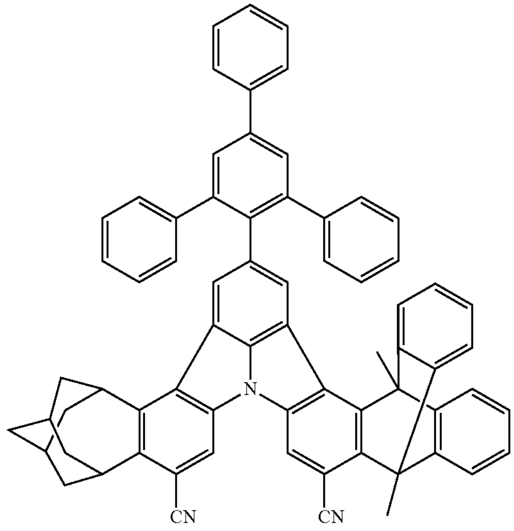 [SMILES: CC12c3ccccc3C(C)(c3ccccc31)c1c2c(C#N)cc2c1c1cc(-c3c(-c4ccccc4)cc(-c4ccccc4)cc3-c3ccccc3)cc3c4c5c(c(C#N)cc4n2c31)C1CC2CC(C1)CC5C2]
494
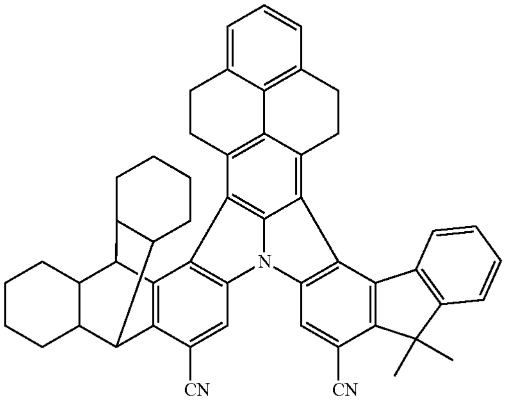 [SMILES: CC1(C)c2ccccc2-c2c1c(C#N)cc1c2c2c3c4c(c5c6c7c(c(C#N)cc6n1c25)C1C2CCCCC2C7C2CCCCC21)CCc1cccc(c1-4)CC3]
495
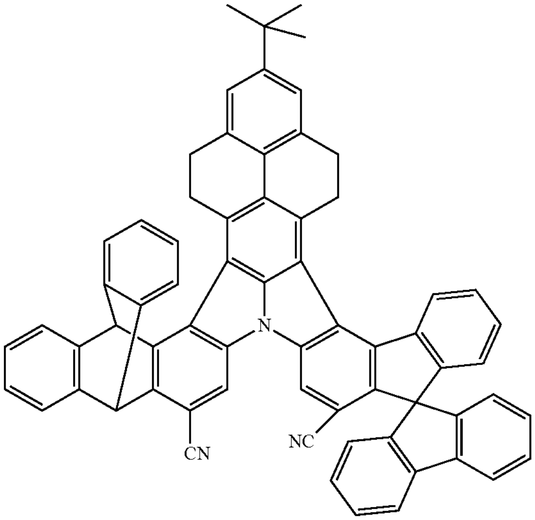 [SMILES: CC(C)(C)c1cc2c3c(c1)CCc1c-3c(c3c4c5c(c(C#N)cc4n4c6cc(C#N)c7c(c6c1c34)C1c3ccccc3C7c3ccccc31)C1(c3ccccc3-c3ccccc31)c1ccccc1-5)CC2]

-continued
496
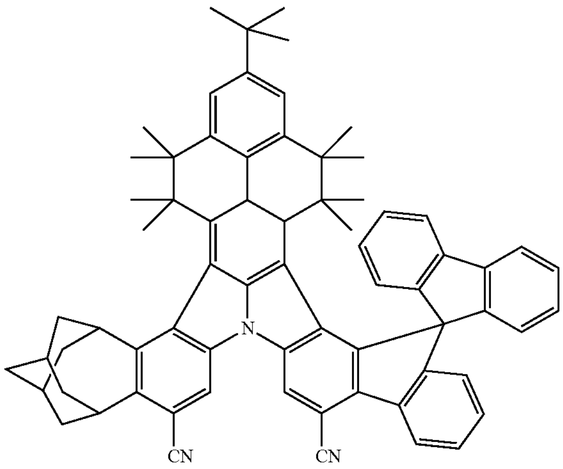 [SMILES: CC(C)(C)c1cc2c3c(c1)C(C)(C)C(C)(C)C1c4c5c6c(c(C#N)cc5n5c4c(c4c7c(c(C#N)cc45)C4CC5CC(C4)CC7C5)=C(C31)C(C)(C)C2(C)C)-c1ccccc1C61c2ccccc2-c2ccccc21]
497
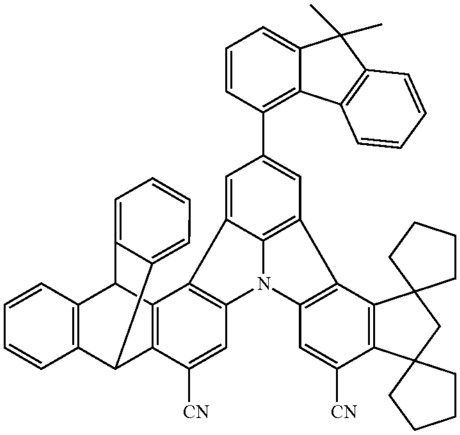 [SMILES: CC1(C)c2ccccc2-c2c(-c3cc4c5c6c(c(C#N)cc5n5c7cc(C#N)c8c(c7c(c3)c45)C3(CCCC3)CC83CCCC3)C3c4ccccc4C6c4ccccc43)cccc21]
498
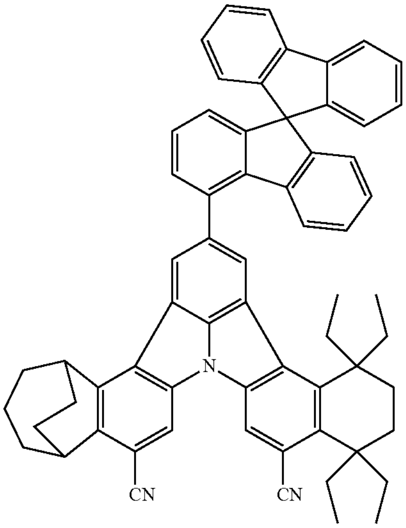 [SMILES: CCC1(CC)CCC(CC)(CC)c2c1c(C#N)cc1c2c2cc(-c3cccc4c3-c3ccccc3C43c4ccccc4-c4ccccc43)cc3c4c5c(c(C#N)cc4n1c32)C1CCCC5CC1]

-continued
499
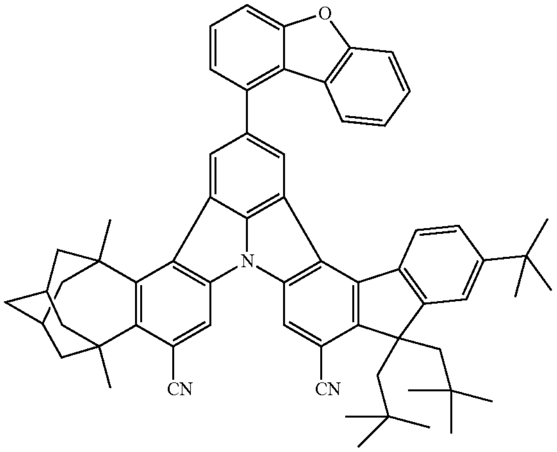 [SMILES: CC(C)(C)CC1(CC(C)(C)C)c2cc(C(C)(C)C)ccc2-c2c1c(C#N)cc1c2c2cc(-c3cccc4oc5ccccc5c34)cc3c4c5c(c(C#N)cc4n1c23)C1(C)CC2CC(C1)CC5(C)C2]
500
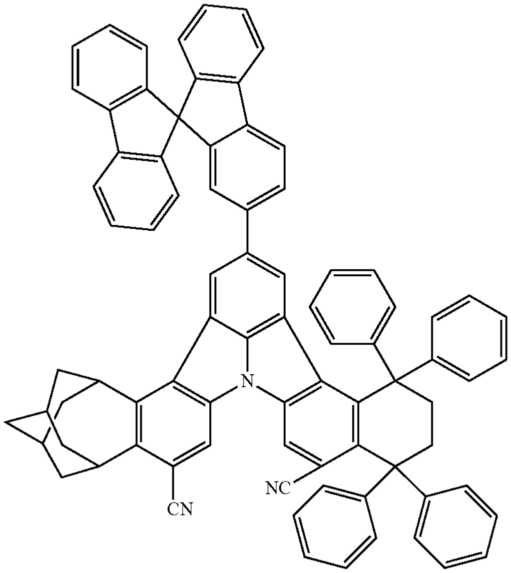 [SMILES: N#Cc1cc2c(c3c1C1CC4CC(C1)CC3C4)c1cc(-c3ccc4c(c3)C3(c5ccccc5-c5ccccc53)c3ccccc3-4)cc3c4c5c(c(C#N)cc4n2c13)C(c1ccccc1)(c1ccccc1)CCC5(c1ccccc1)c1ccccc1]
501
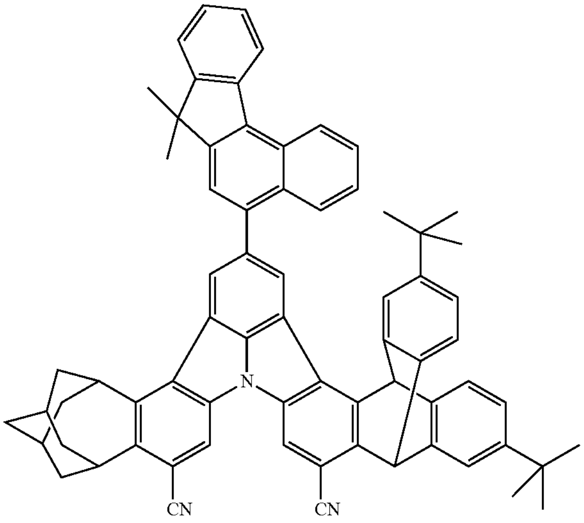 [SMILES: CC(C)(C)c1ccc2c(c1)C1c3ccc(C(C)(C)C)cc3C2c2c1c(C#N)cc1c2c2cc(-c3cc4c(c5ccccc35)-c3ccccc3C4(C)C)cc3c4c5c(c(C#N)cc4n1c32)C1CC2CC(C1)CC5C2]

-continued
502
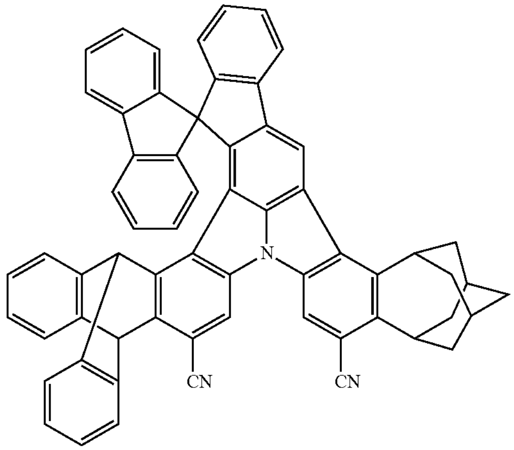 [SMILES: N#Cc1cc2c(c3c1C1CC4CC(C1)CC3C4)c1cc3c(c4c5c6c(c(C#N)cc5n2c14)C1c2ccccc2C6c2ccccc21)C1(c2ccccc2-c2ccccc21)c1ccccc1-3]
503
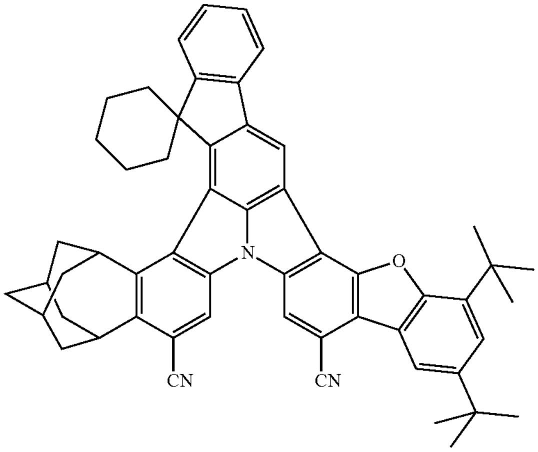 [SMILES: CC(C)(C)c1cc(C(C)(C)C)c2oc3c(c(C#N)cc4c3c3cc5c(c6c7c8c(c(C#N)cc7n4c36)C3CC4CC(C3)CC8C4)C3(CCCCC3)c3ccccc3-5)c2c1]
504
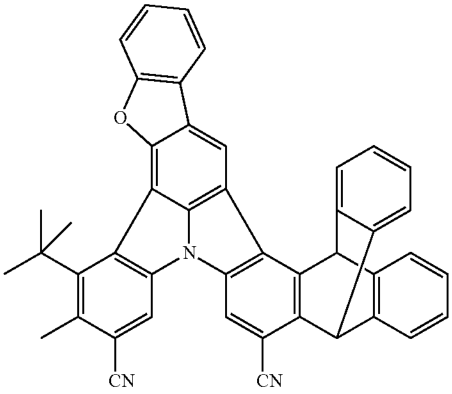

-continued
505
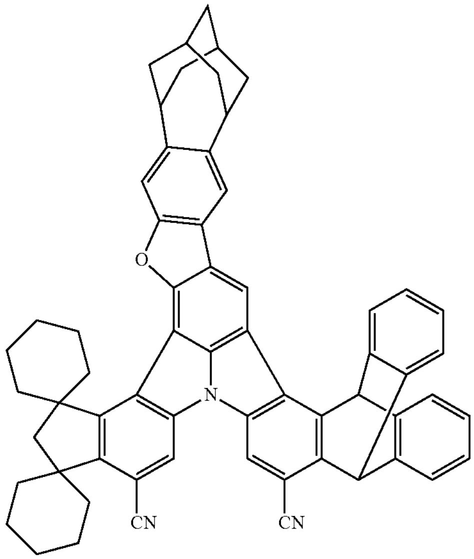
506
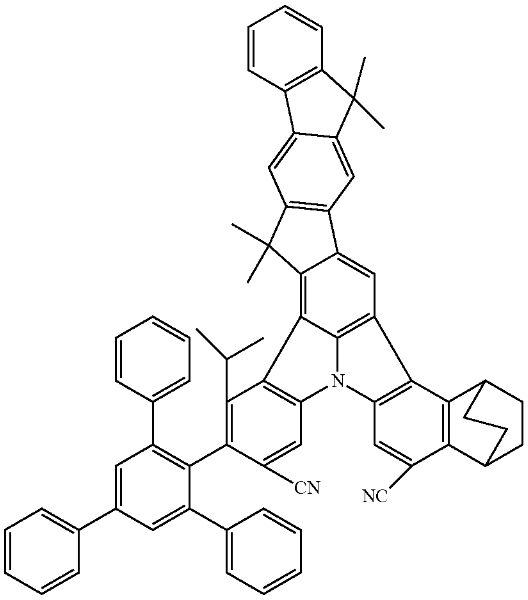
507
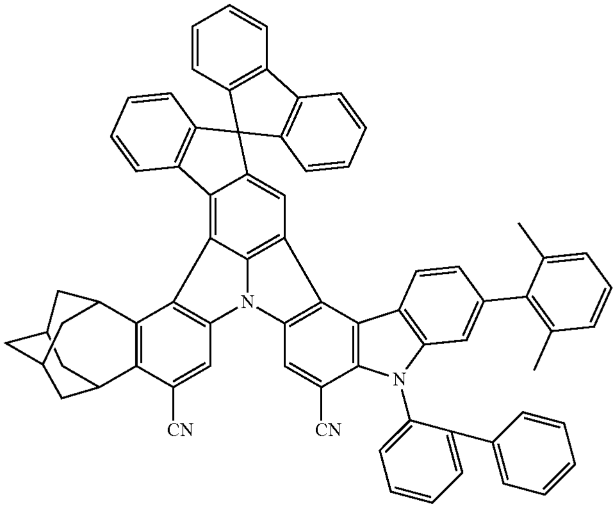 [SMILES: Cc1cccc(C)c1-c1ccc2c3c4c5cc6c(c7c8c9c(c(C#N)cc8n(c4cc(C#N)c3n(-c3ccccc3-c3ccccc3)c2c1)c57)C1CC2CC(C1)CC9C2)-c1ccccc1C61c2ccccc2-c2ccccc21]

-continued
508
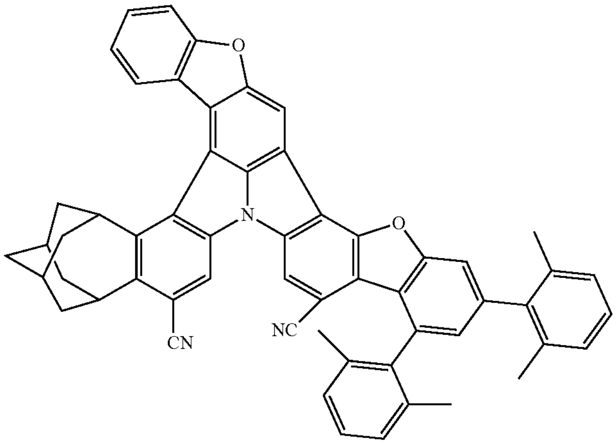 [SMILES: Cc1cccc(C)c1-c1cc(-c2c(C)cccc2C)c2c(c1)oc1c2c(C#N)cc2c1c1cc3oc4ccccc4c3c3c4c5c(c(C#N)cc4n2c13)C1CC2CC(C1)CC5C2]
509
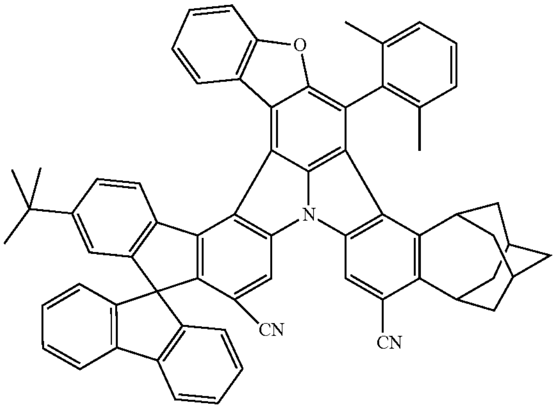 [SMILES: Cc1cccc(C)c1-c1c2oc3ccccc3c2c2c3c4c(c(C#N)cc3n3c5cc(C#N)c6c(c5c1c23)C1CC2CC(CC6C2)C1)C1(c2ccccc2-c2ccccc21)c1cc(C(C)(C)C)ccc1-4]
510
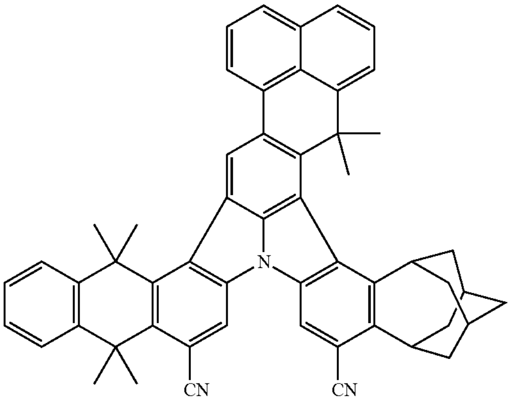 [SMILES: CC1(C)c2ccccc2C(C)(C)c2c1c(C#N)cc1c2c2cc3c(c4c5c6c(c(C#N)cc5n1c24)C1CC2CC(C1)CC6C2)C(C)(C)c1cccc2cccc-3c12]

-continued
511
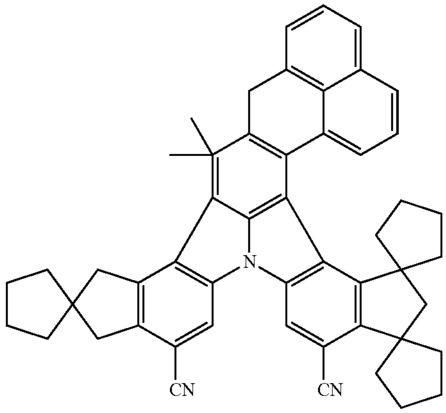
512
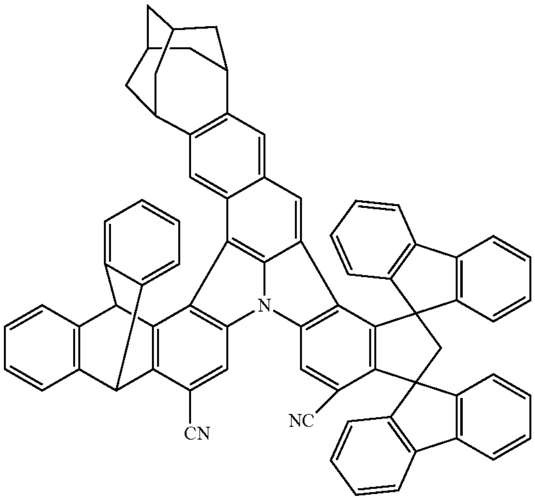 [SMILES: N#Cc1cc2c(c3c1C1c4ccccc4C3c3ccccc31)c1c3cc4c(cc3cc3c5c6c(c(C#N)cc5n2c31)C1(CC62c3ccccc3-c3ccccc32)c2ccccc2-c2ccccc21)C1CC2CC(C1)CC4C2]
513
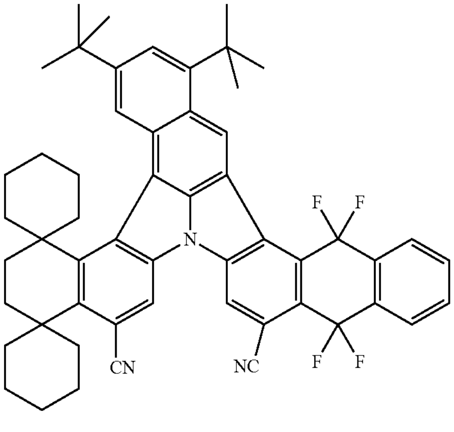 [SMILES: CC(C)(C)c1cc(C(C)(C)C)c2cc3c4c5c(c(C#N)cc4n4c6cc(C#N)c7c(c6c(c2c1)c34)C1(CCCCC1)CCC71CCCCC1)C(F)(F)c1ccccc1C5(F)F]

-continued
514
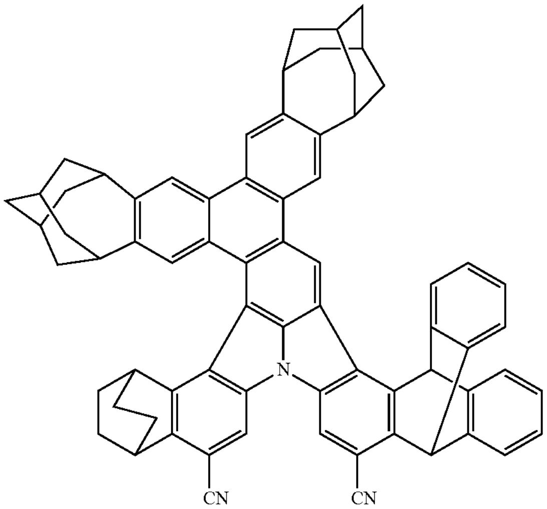 [SMILES: N#Cc1cc2c(c3c1C1CCC3CC1)c1c3c4cc5c(cc4c4cc6c(cc4c3cc3c4c7c(c(C#N)cc4n2c31)C1c2ccccc2C7c2ccccc21)C1CC2CC(CC6C2)C1)C1CC2CC(C1)CC5C2]
515
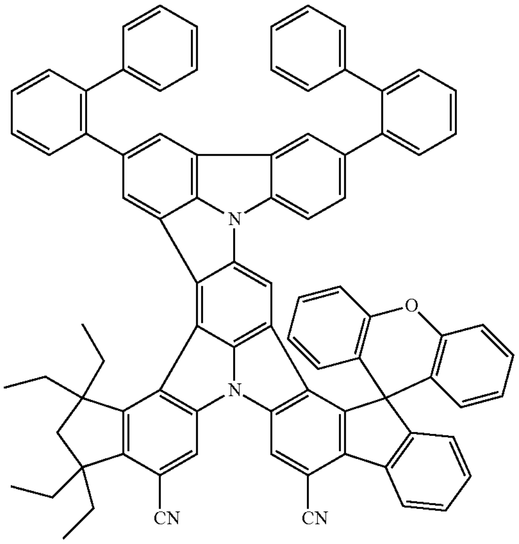 [SMILES: CCC1(CC)CC(CC)(CC)c2c1c(C#N)cc1c2c2c3c4cc(-c5ccccc5-c5ccccc5)cc5c6cc(-c7ccccc7-c7ccccc7)ccc6n(c3cc3c6c7c(c(C#N)cc6n1c32)-c1ccccc1C71c2ccccc2Oc2ccccc21)c54]
516
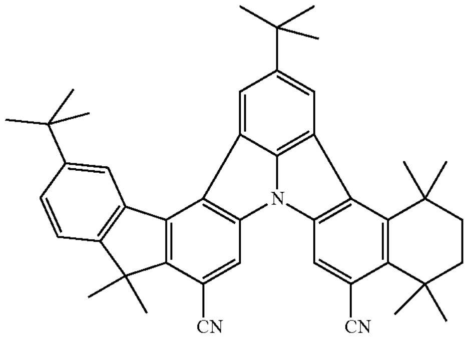 [SMILES: CC(C)(C)c1ccc2c(c1)-c1c(c(C#N)cc3c1c1cc(C(C)(C)C)cc4c5c6c(c(C#N)cc5n3c14)C(C)(C)CCC6(C)C)C2(C)C]

-continued
517
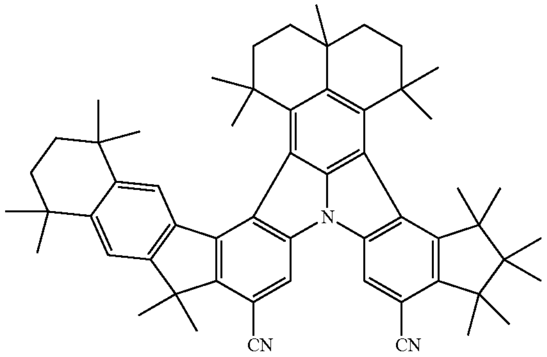
518
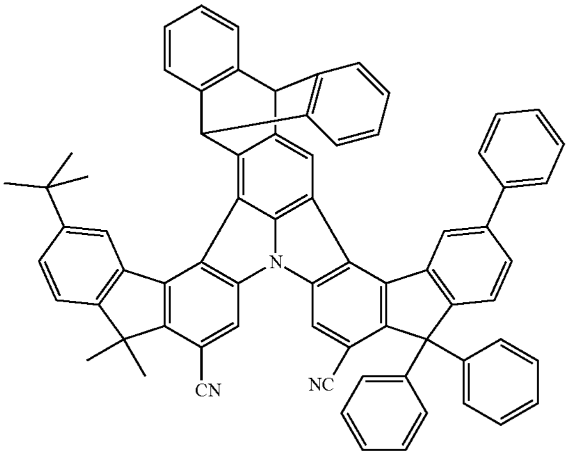 [SMILES: CC(C)(C)c1ccc2c(c1)-c1c(c(C#N)cc3c1c1c4c(cc5c6c7c(c(C#N)cc6n3c51)C(c1ccccc1)(c1ccccc1)c1ccc(-c3ccccc3)cc1-7)C1c3ccccc3C4c3ccccc31)C2(C)C]
519
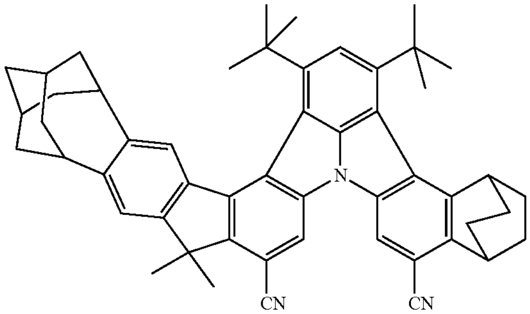 [SMILES: CC(C)(C)c1cc(C(C)(C)C)c2c3c4c(c(C#N)cc3n3c5cc(C#N)c6c(c5c1c23)-c1cc2c(cc1C6(C)C)C1CC3CC(CC2C3)C1)C1CCC4CC1]
520
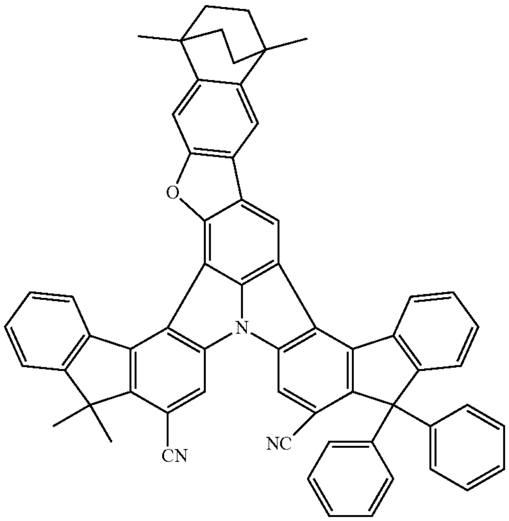 [SMILES: CC12CCC(C)(CC1)c1cc3c(cc12)oc1c3cc2c3c4c(c(C#N)cc3n3c5cc(C#N)c6c(c5c1c23)-c1ccccc1C6(C)C)C(c1ccccc1)(c1ccccc1)c1ccccc1-4]

-continued
521
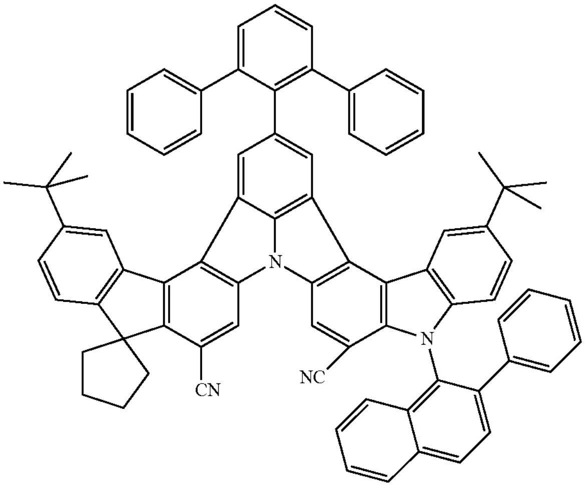 [SMILES: CC(C)(C)c1ccc2c(c1)-c1c(c(C#N)cc3c1c1cc(-c4c(-c5ccccc5)cccc4-c4ccccc4)cc4c5c6c7cc(C(C)(C)C)ccc7n(-c7c(-c8ccccc8)ccc8ccccc78)c6c(C#N)cc5n3c14)C21CCCC1]
522
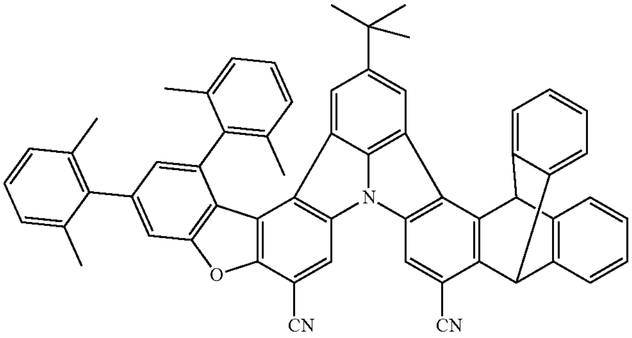 [SMILES: Cc1cccc(C)c1-c1cc(-c2c(C)cccc2C)c2c(c1)oc1c(C#N)cc3c(c4cc(C(C)(C)C)cc5c6c7c(c(C#N)cc6n3c54)C3c4ccccc4C7c4ccccc43)c12]
523
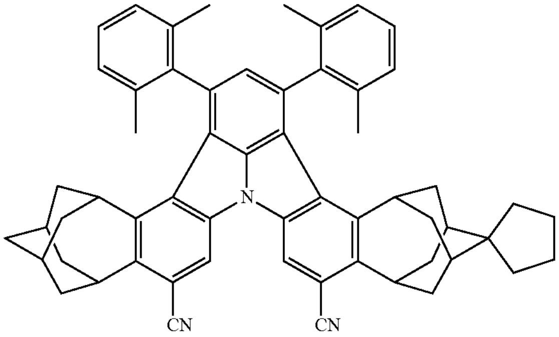 [SMILES: Cc1cccc(C)c1-c1cc(-c2c(C)cccc2C)c2c3c4c(c(C#N)cc3n3c5cc(C#N)c6c(c5c1c23)C1CC2CC(CC6C2)C1)C1CC2CC4CC(C1)C21CCCC1]

-continued
524
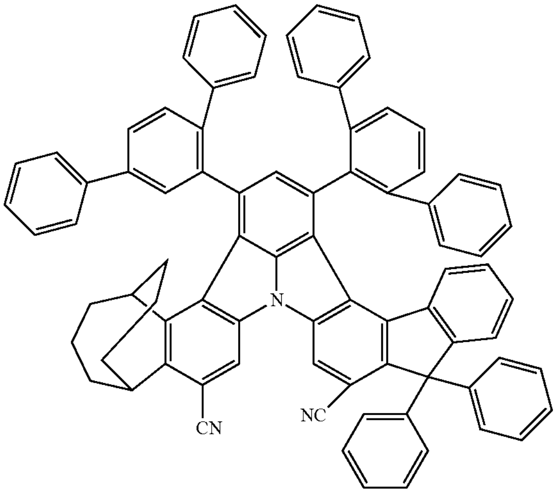 [SMILES: N#Cc1cc2c(c3c1C1CCCC3CCC1)c1c(-c3cc(-c4ccccc4)ccc3-c3ccccc3)cc(-c3c(-c4ccccc4)cccc3-c3ccccc3)c3c4c5c(c(C#N)cc4n2c31)C(c1ccccc1)(c1ccccc1)c1ccccc1-5]
525
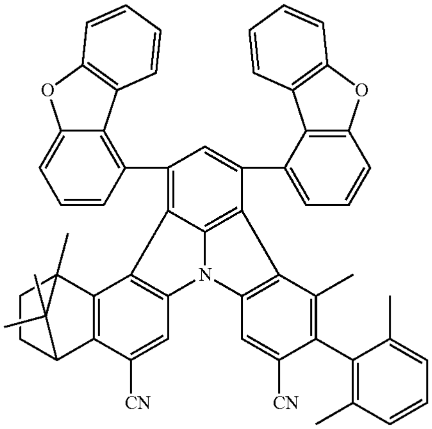 [SMILES: Cc1cccc(C)c1-c1c(C#N)cc2c(c1C)c1c(-c3cccc4oc5ccccc5c34)cc(-c3cccc4oc5ccccc5c34)c3c4c5c(c(C#N)cc4n2c13)C1CCC5(C)C1(C)C]
526
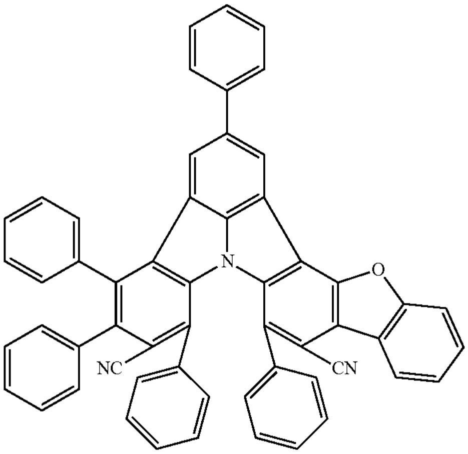 [SMILES: N#Cc1c(-c2ccccc2)c(-c2ccccc2)c2c3cc(-c4ccccc4)cc4c5c6oc7ccccc7c6c(C#N)c(-c6ccccc6)c5n(c2c1-c1ccccc1)c34]

-continued
527
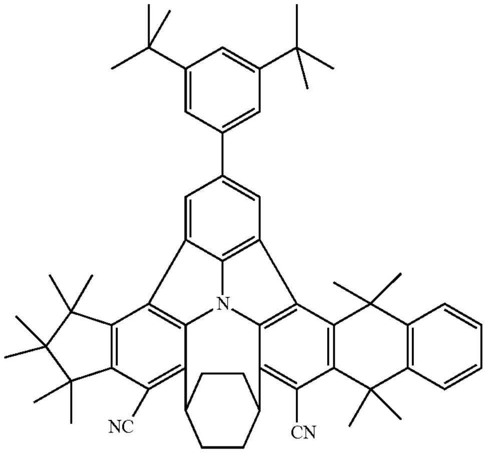 [SMILES: CC(C)(C)c1cc(-c2cc3c4c5c(c(C#N)c6c4n4c7c(c(C#N)c8c(c7c(c2)c34)C(C)(C)C(C)(C)C8(C)C)C2CCC6CC2)C(C)(C)c2ccccc2C5(C)C)cc(C(C)(C)C)c1]
528
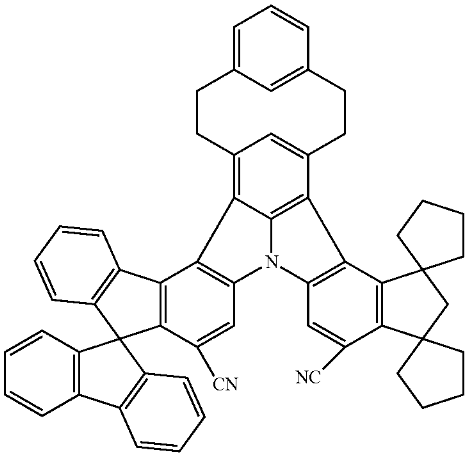 [SMILES: N#Cc1cc2c(c3c1C1(CCCC1)CC31CCCC1)c1c3cc(c4c5c6c(c(C#N)cc5n2c41)C1(c2ccccc2-c2ccccc21)c1ccccc1-6)CCc1cccc(c1)CC3]
529
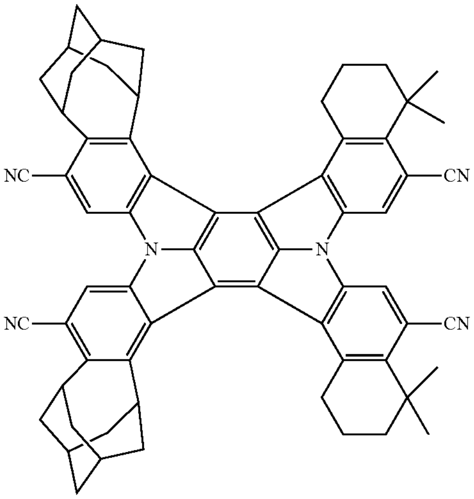 [SMILES: CC1(C)CCCc2c1c(C#N)cc1c2c2c3c4c5c(c(C#N)cc4n4c6cc(C#N)c7c(c6c(c6c8c9c(c(C#N)cc8n1c26)C(C)(C)CCC9)c34)C1CC2CC(CC7C2)C1)C1CC2CC(C1)CC5C2]

-continued
530
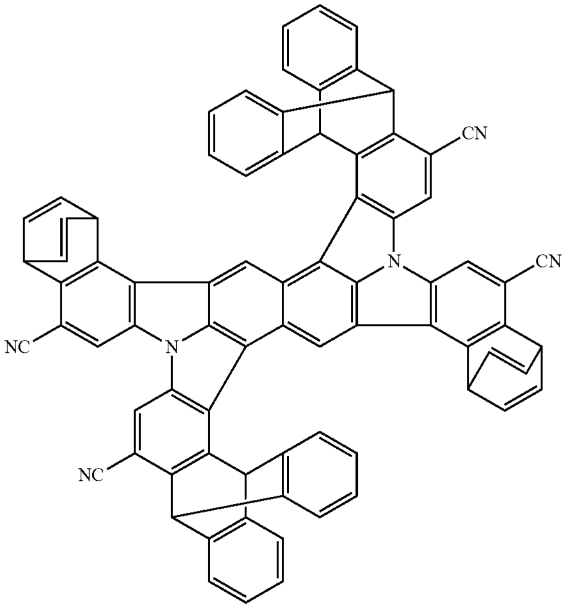 [SMILES: N#Cc1cc2c(c3c1C1C=CC3C=C1)c1cc3c(cc4c5c6c(c(C#N)cc5n5c7cc(C#N)c8c(c7c3c45)C3c4ccccc4C8c4ccccc43)C3C=CC6C=C3)c3c4c5c(c(C#N)cc4n2c13)C1c2ccccc2C5c2ccccc21]
531
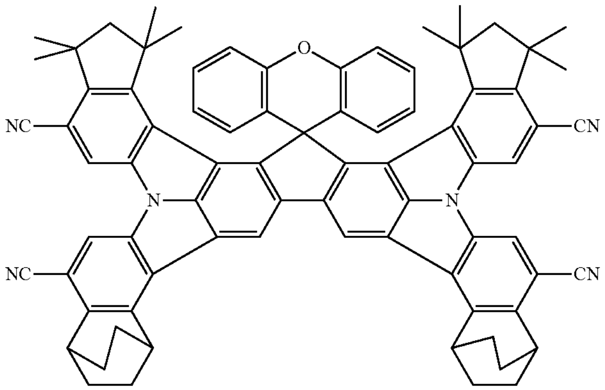 [SMILES: CC1(C)CC(C)(C)c2c1c(C#N)cc1c2c2c3c(cc4c5c6c(c(C#N)cc5n1c42)C1CCC6CC1)-c1cc2c4c5c(c(C#N)cc4n4c6cc(C#N)c7c(c6c(c1C31c3ccccc3Oc3ccccc31)c24)C(C)(C)CC7(C)C)C1CCC5CC1]
532
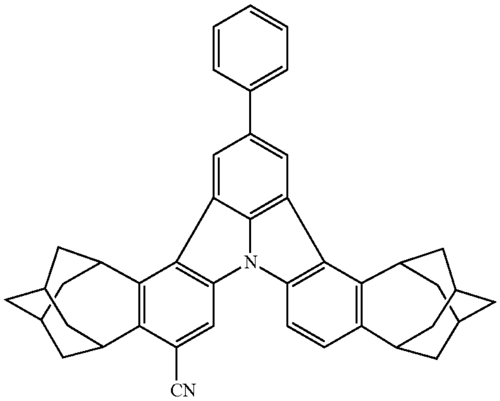 [SMILES: N#Cc1cc2c(c3c1C1CC4CC(C1)CC3C4)c1cc(-c3ccccc3)cc3c4c5c(ccc4n2c31)C1CC2CC(C1)CC5C2]

-continued
533
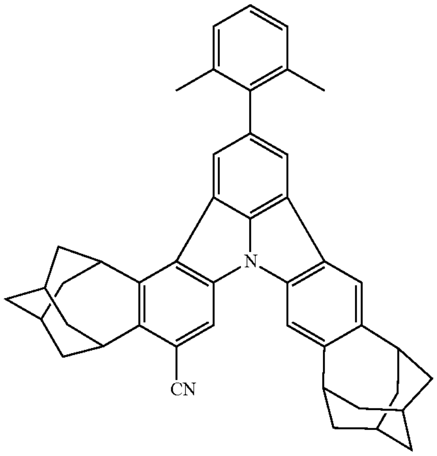 [SMILES: Cc1cccc(C)c1-c1cc2c3cc4c(cc3n3c5cc(C#N)c6c(c5c(c1)c23)C1CC2CC(CC6C2)C1)C1CC2CC(CC4C2)C1]
534
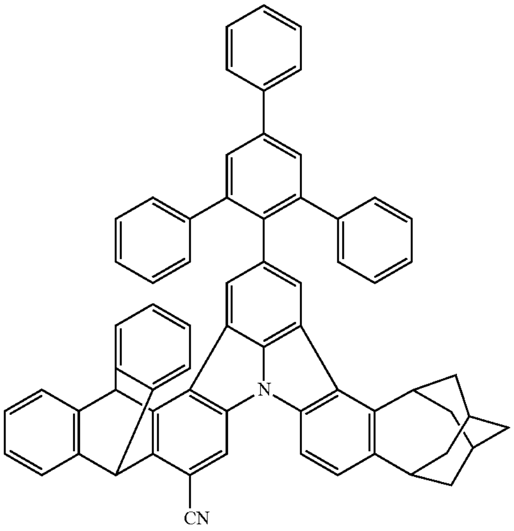 [SMILES: N#Cc1cc2c(c3c1C1c4ccccc4C3c3ccccc31)c1cc(-c3c(-c4ccccc4)cc(-c4ccccc4)cc3-c3ccccc3)cc3c4c5c(ccc4n2c31)C1CC2CC(C1)CC5C2]
535
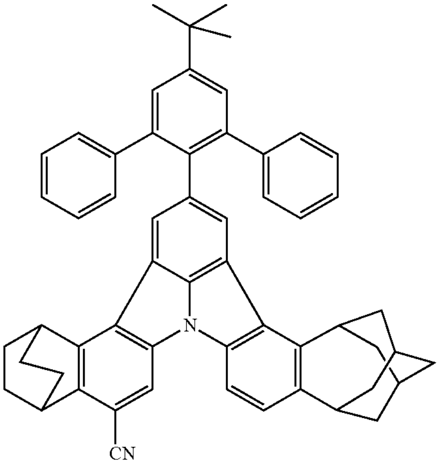 [SMILES: CC(C)(C)c1cc(-c2ccccc2)c(-c2cc3c4c5c(ccc4n4c6cc(C#N)c7c(c6c(c2)c34)C2CCC7CC2)C2CC3CC(C2)CC5C3)c(-c2ccccc2)c1]

-continued
536
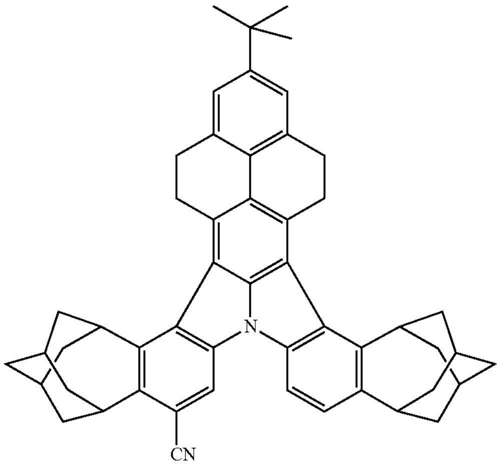 [SMILES: CC(C)(C)c1cc2c3c(c1)CCc1c-3c(c3c4c5c(ccc4n4c6cc(C#N)c7c(c6c1c34)C1CC3CC(CC7C3)C1)C1CC3CC(C1)CC5C3)CC2]
537
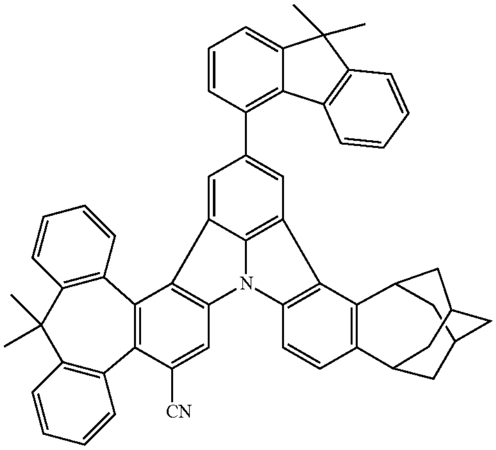 [SMILES: CC1(C)c2ccccc2-c2c(C#N)cc3c(c2-c2ccccc21)c1cc(-c2cccc4c2-c2ccccc2C4(C)C)cc2c4c5c(ccc4n3c12)C1CC2CC(C1)CC5C2]
538
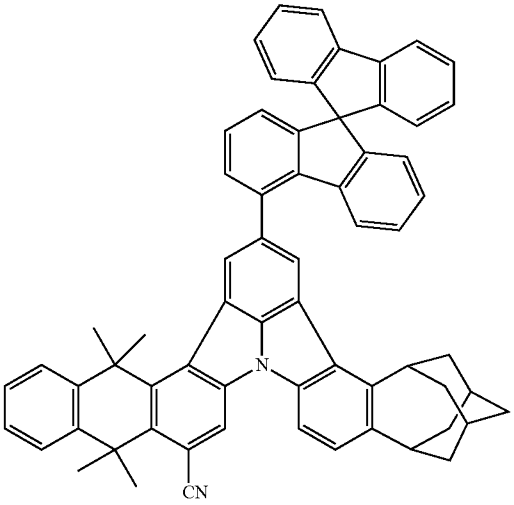 [SMILES: CC1(C)c2ccccc2C(C)(C)c2c1c(C#N)cc1c2c2cc(-c3cccc4c3-c3ccccc3C43c4ccccc4-c4ccccc43)cc3c4c5c(ccc4n1c32)C1CC2CC(C1)CC5C2]

-continued
539
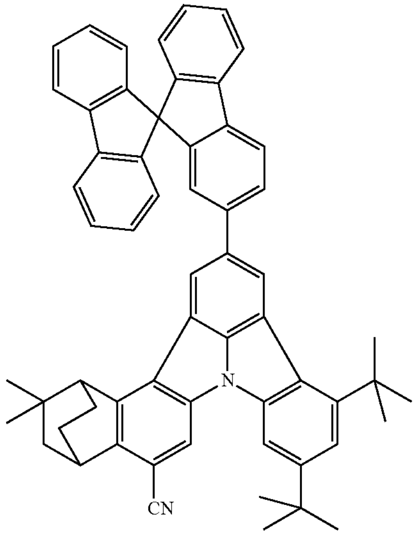 [SMILES: CC(C)(C)c1cc(C(C)(C)C)c2c3cc(-c4ccc5c(c4)C4(c6ccccc6-c6ccccc64)c4ccccc4-5)cc4c5c6c(c(C#N)cc5n(c2c1)c34)C1CCC6C(C)(C)C1]
540
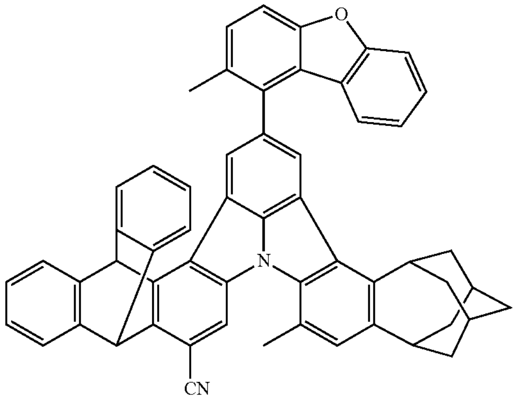 [SMILES: Cc1ccc2oc3ccccc3c2c1-c1cc2c3c4c(c(C#N)cc3n3c5c(C)cc6c(c5c(c1)c23)C1CC2CC(CC6C2)C1)C1c2ccccc2C4c2ccccc21]
541
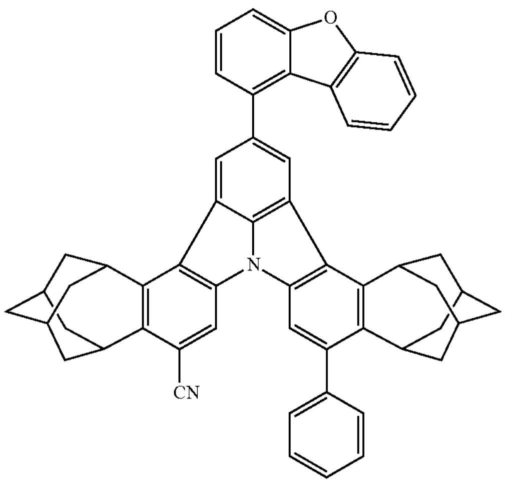 [SMILES: N#Cc1cc2c(c3c1C1CC4CC(C1)CC3C4)c1cc(-c3cccc4oc5ccccc5c34)cc3c4c5c(c(-c6ccccc6)cc4n2c13)C1CC2CC(C1)CC5C2]

-continued
542
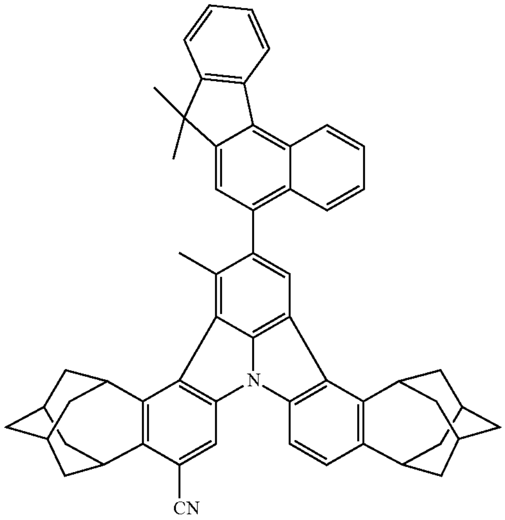 [SMILES: Cc1c(-c2cc3c(c4ccccc24)-c2ccccc2C3(C)C)cc2c3c4c(ccc3n3c5cc(C#N)c6c(c5c1c23)C1CC2CC(CC6C2)C1)C1CC2CC(C1)CC4C2]
543
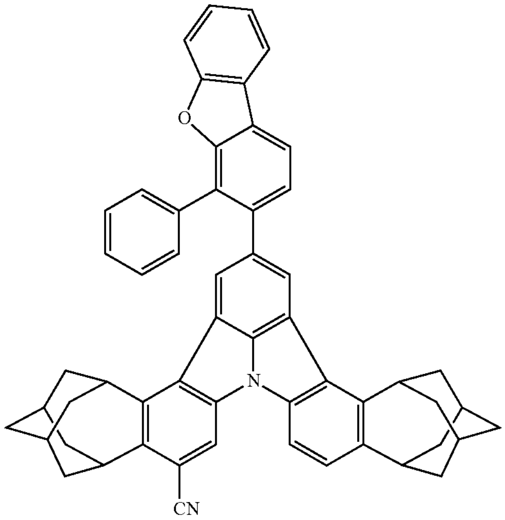 [SMILES: N#Cc1cc2c(c3c1C1CC4CC(C1)CC3C4)c1cc(-c3ccc4c(oc5ccccc54)c3-c3ccccc3)cc3c4c5c(ccc4n2c31)C1CC2CC(C1)CC5C2]
544
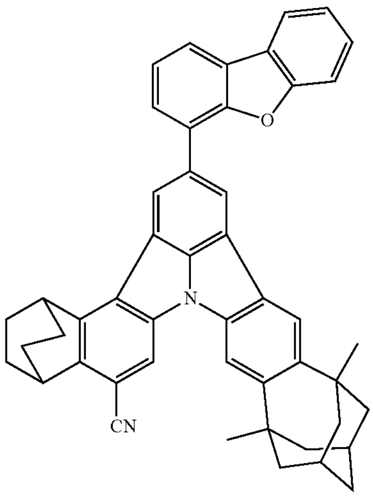 [SMILES: CC12CC3CC(C1)CC(C)(C3)c1cc3c(cc12)c1cc(-c2cccc4c2oc2ccccc24)cc2c4c5c(c(C#N)cc4n3c12)C1CCC5CC1]

-continued
545
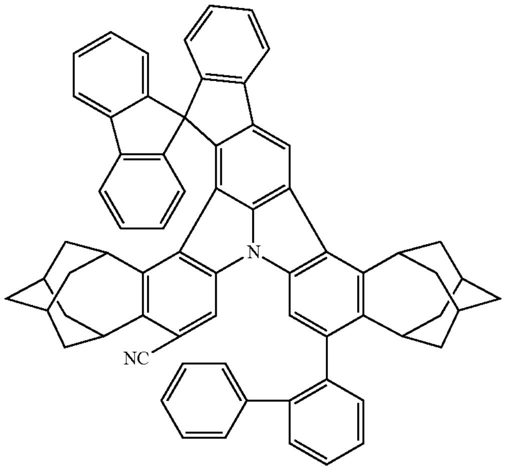 [SMILES: N#Cc1cc2c(c3c1C1CC4CC(C1)CC3C4)c1c3c(cc4c5c6c(c(-c7ccccc7-c7ccccc7)cc5n2c41)C1CC2CC(C1)CC6C2)-c1ccccc1C31c2ccccc2-c2ccccc21]
546
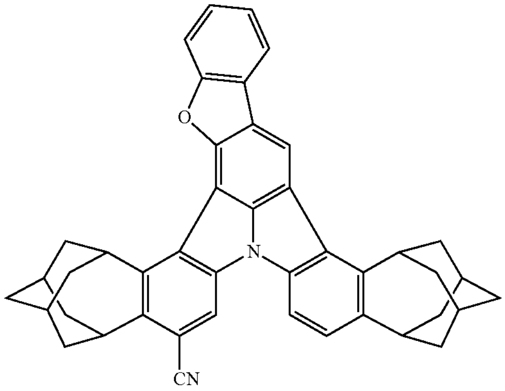 [SMILES: N#Cc1cc2c(c3c1C1CC4CC(C1)CC3C4)c1c3oc4ccccc4c3cc3c4c5c(ccc4n2c31)C1CC2CC(C1)CC5C2]
547
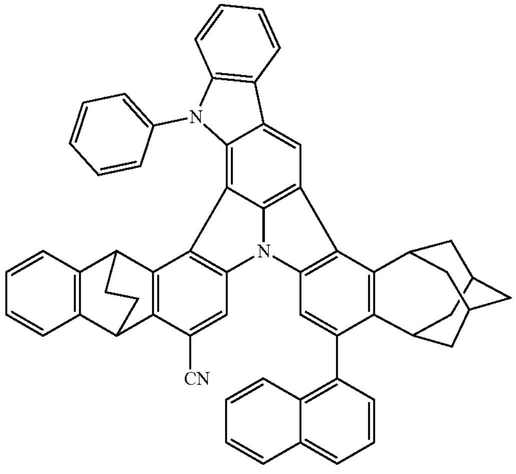 [SMILES: N#Cc1cc2c(c3c1C1CCC3c3ccccc31)c1c3c(cc4c5c6c(c(-c7cccc8ccccc78)cc5n2c41)C1CC2CC(C1)CC6C2)c1ccccc1n3-c1ccccc1]

-continued
548
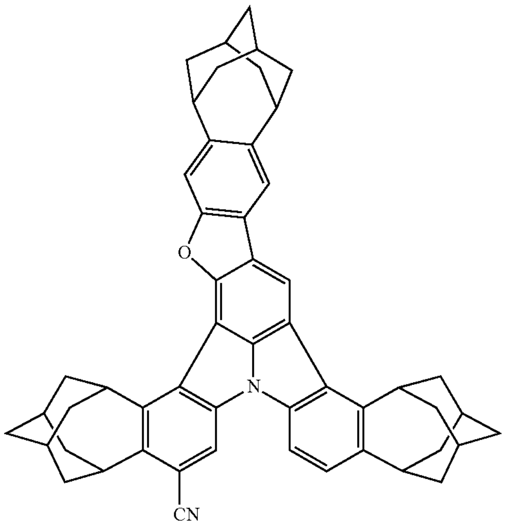 [SMILES: N#Cc1cc2c(c3c1C1CC4CC(C1)CC3C4)c1c3oc4cc5c(cc4c3cc3c4c6c(ccc4n2c31)C1CC2CC(C1)CC6C2)C1CC2CC(CC5C2)C1]
549
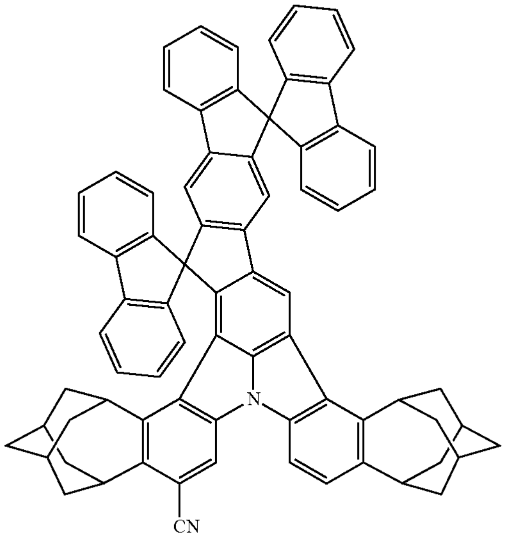 [SMILES: N#Cc1cc2c(c3c1C1CC4CC(C1)CC3C4)c1c3c(cc4c5c6c(ccc5n2c41)C1CC2CC(C1)CC6C2)-c1cc2c(cc1C31c3ccccc3-c3ccccc31)-c1ccccc1C21c2ccccc2-c2ccccc21]
550
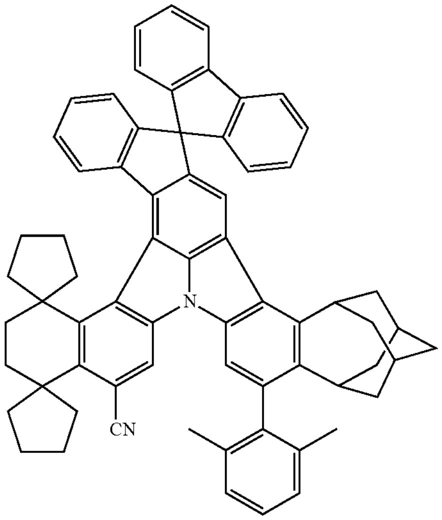 [SMILES: Cc1cccc(C)c1-c1cc2c(c3c1C1CC4CC(C1)CC3C4)c1cc3c(c4c5c6c(c(C#N)cc5n2c14)C1(CCCC1)CCC61CCCC1)-c1ccccc1C31c2ccccc2-c2ccccc21]

-continued
551
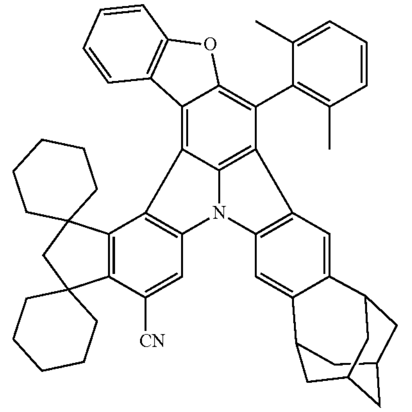 [SMILES: Cc1cccc(C)c1-c1c2oc3ccccc3c2c2c3c4c(c(C#N)cc3n3c5cc6c(cc5c1c23)C1CC2CC(C1)CC6C2)C1(CCCCC1)CC41CCCCC1]
552
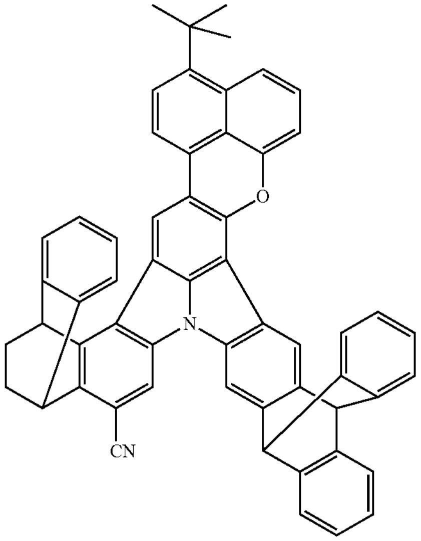 [SMILES: CC(C)(C)c1ccc2c3cc4c5c6c(c(C#N)cc5n5c7cc8c(cc7c(c3oc3cccc1c32)c45)C1c2ccccc2C8c2ccccc21)C1CCC6c2ccccc21]
553
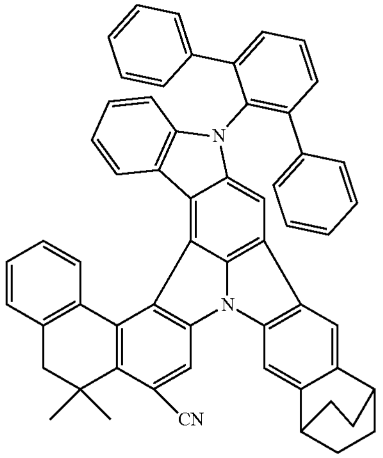 [SMILES: CC1(C)Cc2ccccc2-c2c1c(C#N)cc1c2c2c3c4ccccc4n(-c4c(-c5ccccc5)cccc4-c4ccccc4)c3cc3c4cc5c(cc4n1c32)C1CCC5CC1]

-continued
554
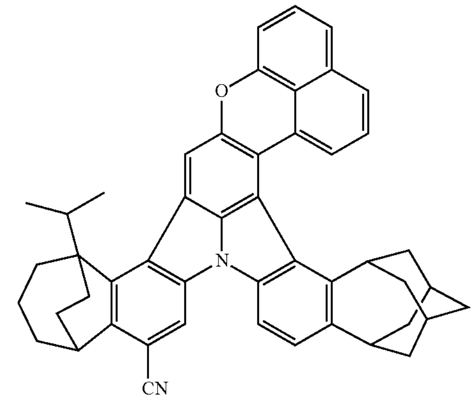 [SMILES: CC(C)C12CCCC(CC1)c1c(C#N)cc3c(c12)c1cc2oc4cccc5cccc(c54)c2c2c4c5c(ccc4n3c12)C1CC2CC(C1)CC5C2]
555
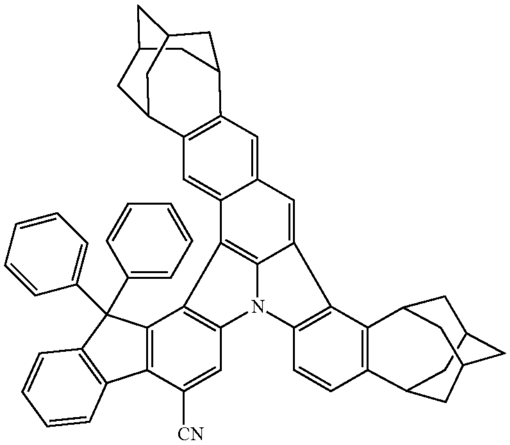 [SMILES: N#Cc1cc2c(c3c1-c1ccccc1C3(c1ccccc1)c1ccccc1)c1c3cc4c(cc3cc3c5c6c(ccc5n2c31)C1CC2CC(C1)CC6C2)C1CC2CC(C1)CC4C2]
556
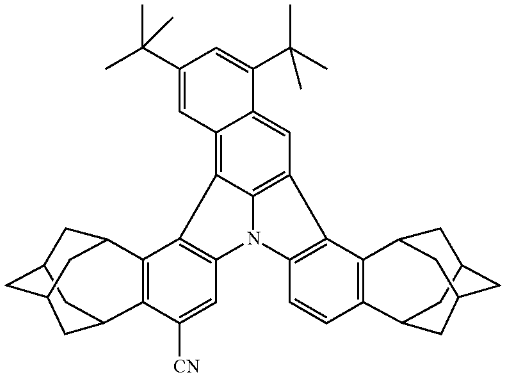 [SMILES: CC(C)(C)c1cc(C(C)(C)C)c2cc3c4c5c(ccc4n4c6cc(C#N)c7c(c6c(c2c1)c34)C1CC2CC(CC7C2)C1)C1CC2CC(C1)CC5C2]

-continued
557
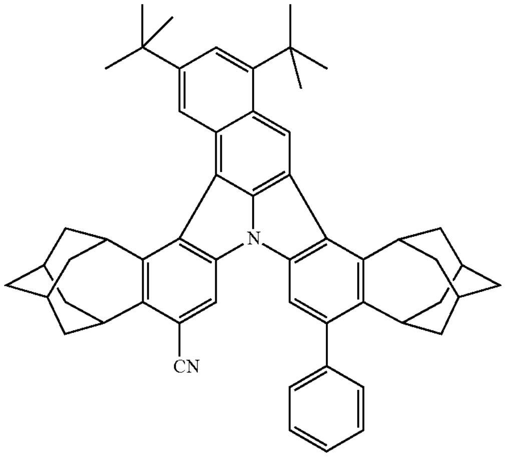 [SMILES: CC(C)(C)c1cc(C(C)(C)C)c2cc3c4c5c(c(-c6ccccc6)cc4n4c6cc(C#N)c7c(c6c(c2c1)c34)C1CC2CC(CC7C2)C1)C1CC2CC(C1)CC5C2]
558
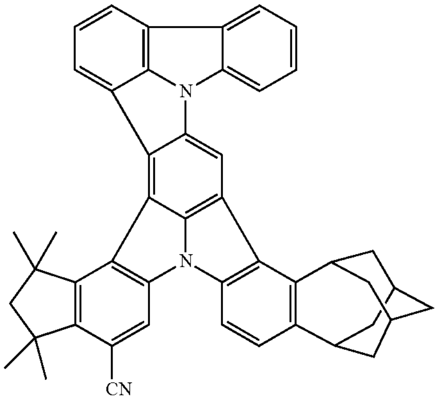 [SMILES: CC1(C)CC(C)(C)c2c1c(C#N)cc1c2c2c3c4cccc5c6ccccc6n(c3cc3c6c7c(ccc6n1c32)C1CC2CC(C1)CC7C2)c54]
559
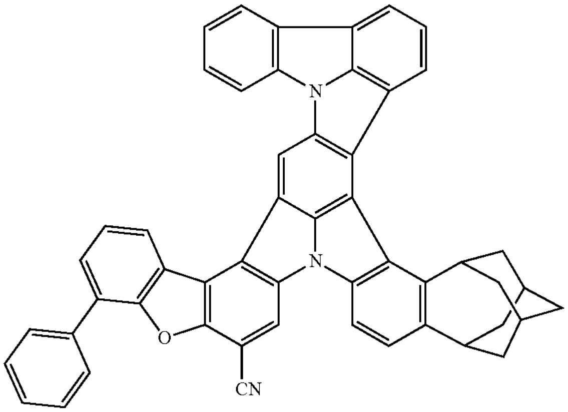 [SMILES: N#Cc1cc2c(c3cc4c(c5cccc6c7ccccc7n4c65)c4c5c6c(ccc5n2c34)C2CC3CC(C2)CC6C3)c2c1oc1c(-c3ccccc3)cccc12]
560
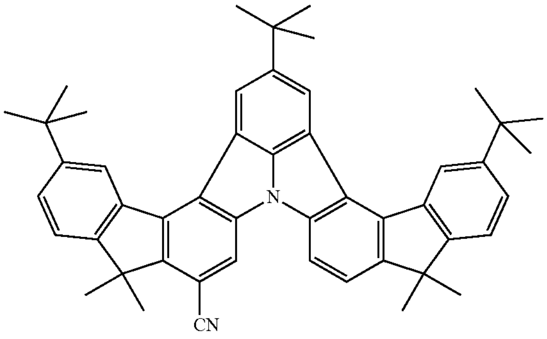 [SMILES: CC(C)(C)c1ccc2c(c1)-c1c(ccc3c1c1cc(C(C)(C)C)cc4c5c6c(c(C#N)cc5n3c14)C(C)(C)c1ccc(C(C)(C)C)cc1-6)C2(C)C]

-continued
561
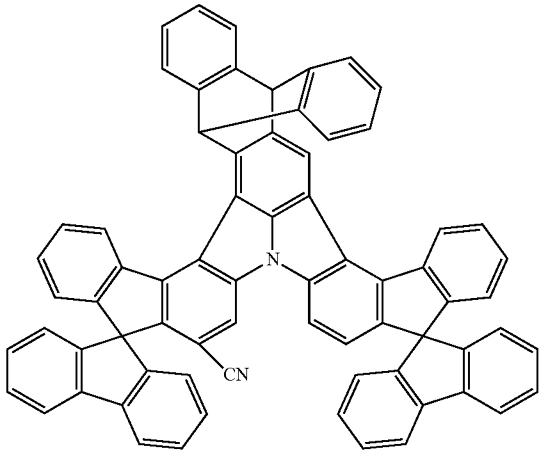 [SMILES: N#Cc1cc2c(c3c1C1(c4ccccc4-c4ccccc41)c1ccccc1-3)c1c3c(cc4c5c6c(ccc5n2c41)C1(c2ccccc2-c2ccccc21)c1ccccc1-6)C1c2ccccc2C3c2ccccc21]
562
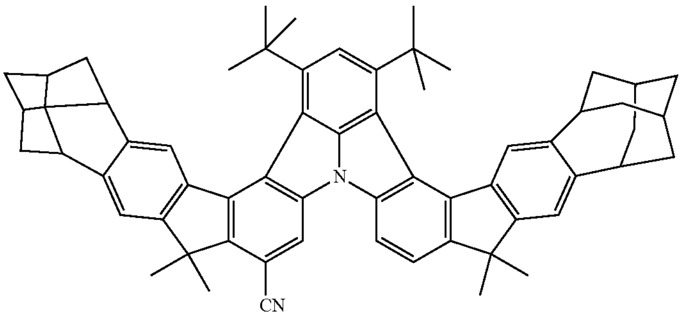 [SMILES: CC(C)(C)c1cc(C(C)(C)C)c2c3c4c(c(C#N)cc3n3c5ccc6c(c5c1c23)-c1cc2c(cc1C6(C)C)C1CC3CC(CC2C3)C1)C(C)(C)c1cc2c(cc1-4)C1CC3CC4CC2C341]
563
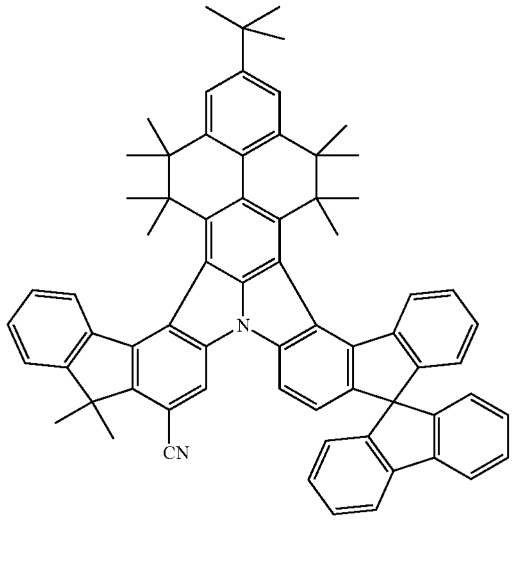 [SMILES: CC(C)(C)c1cc2c3c(c1)C(C)(C)C(C)(C)c1c-3c(c3c4c5c(ccc4n4c6cc(C#N)c7c(c6c1c34)-c1ccccc1C7(C)C)C1(c3ccccc3-c3ccccc31)c1ccccc1-5)C(C)(C)C2(C)C]

-continued
564
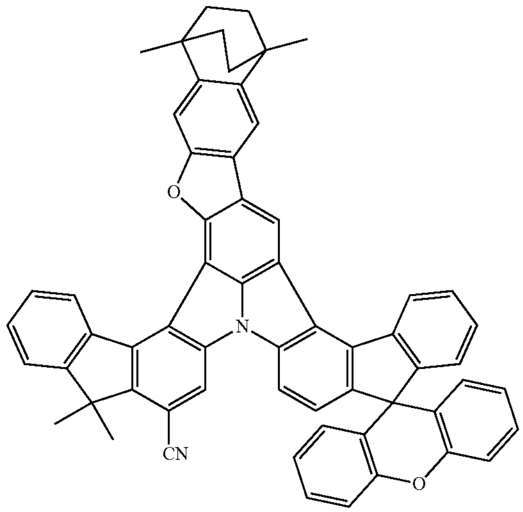 [SMILES: CC12CCC(C)(CC1)c1cc3c(cc12)oc1c3cc2c3c4c(ccc3n3c5cc(C#N)c6c(c5c1c23)-c1ccccc1C6(C)C)C1(c2ccccc2Oc2ccccc21)c1ccccc1-4]
565
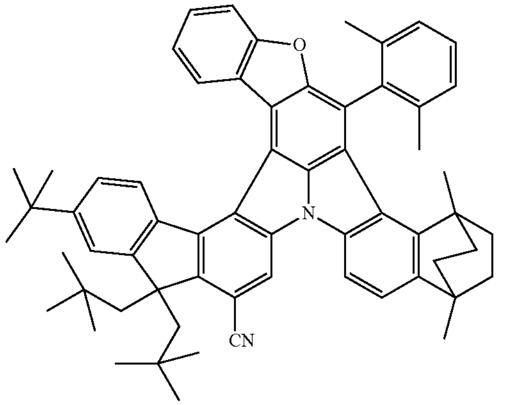 [SMILES: Cc1cccc(C)c1-c1c2oc3ccccc3c2c2c3c4c(c(C#N)cc3n3c5ccc6c(c5c1c23)C1(C)CCC6(C)CC1)C(CC(C)(C)C)(CC(C)(C)C)c1cc(C(C)(C)C)ccc1-4]
566
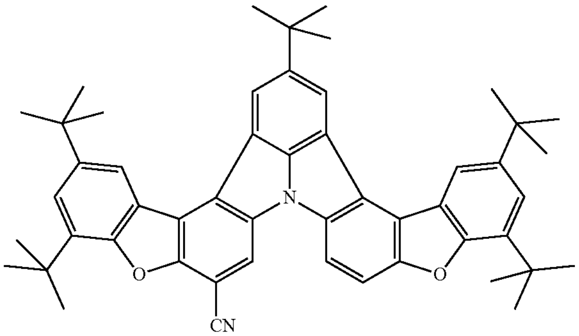 [SMILES: CC(C)(C)c1cc(C(C)(C)C)c2oc3ccc4c(c5cc(C(C)(C)C)cc6c7c8c(oc9c(C(C)(C)C)cc(C(C)(C)C)cc98)c(C#N)cc7n4c56)c3c2c1]
567
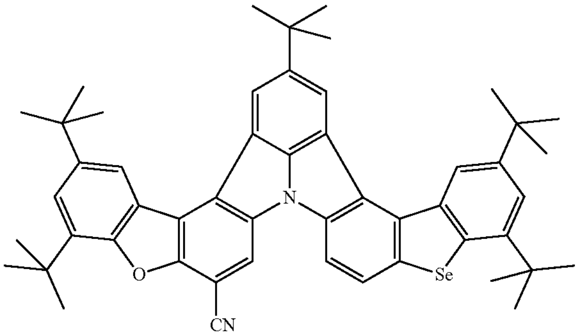 [SMILES: CC(C)(C)c1cc(C(C)(C)C)c2[se]c3ccc4c(c5cc(C(C)(C)C)cc6c7c8c(oc9c(C(C)(C)C)cc(C(C)(C)C)cc98)c(C#N)cc7n4c56)c3c2c1]

-continued
568
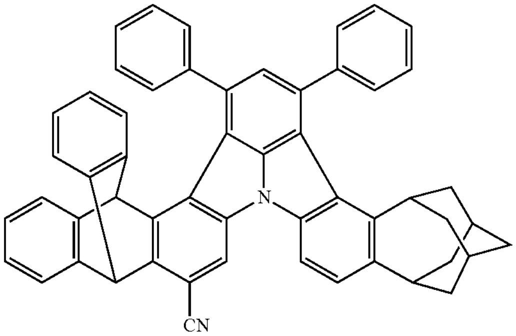 [SMILES: N#Cc1cc2c(c3c1C1c4ccccc4C3c3ccccc31)c1c(-c3ccccc3)cc(-c3ccccc3)c3c4c5c(ccc4n2c31)C1CC2CC(C1)CC5C2]
569
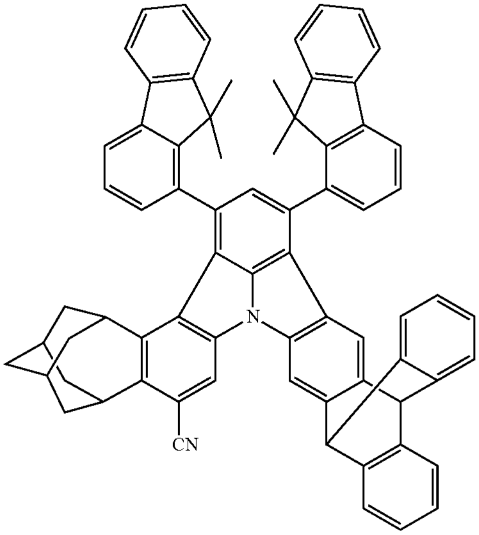 [SMILES: CC1(C)c2ccccc2-c2cccc(-c3cc(-c4cccc5c4C(C)(C)c4ccccc4-5)c4c5c6c(c(C#N)cc5n5c7cc8c(cc7c3c45)C3c4ccccc4C8c4ccccc43)C3CC4CC(C3)CC6C4)c21]
570
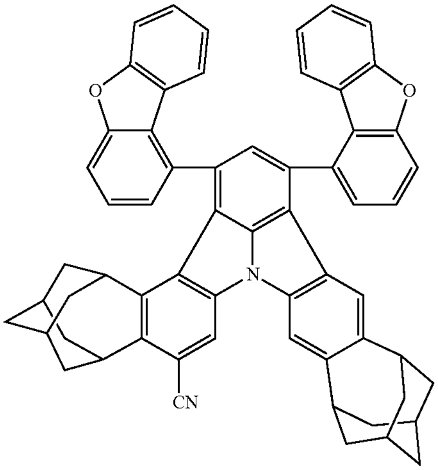 [SMILES: N#Cc1cc2c(c3c1C1CC4CC(C1)CC3C4)c1c(-c3cccc4oc5ccccc5c34)cc(-c3cccc4oc5ccccc5c34)c3c4cc5c(cc4n2c31)C1CC2CC(CC5C2)C1]

-continued
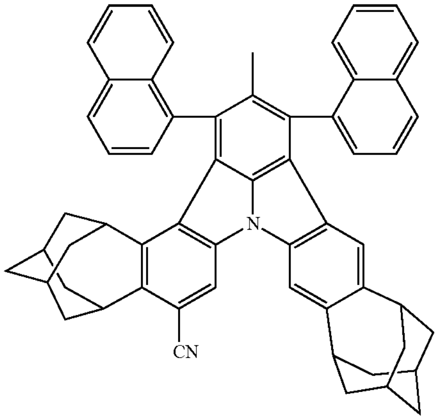 [SMILES: Cc1c(-c2cccc3ccccc23)c2c3cc4c(cc3n3c5cc(C#N)c6c(c5c(c1-c1cccc5ccccc15)c23)C1CC2CC(CC6C2)C1)C1CC2CC(CC4C2)C1]
571
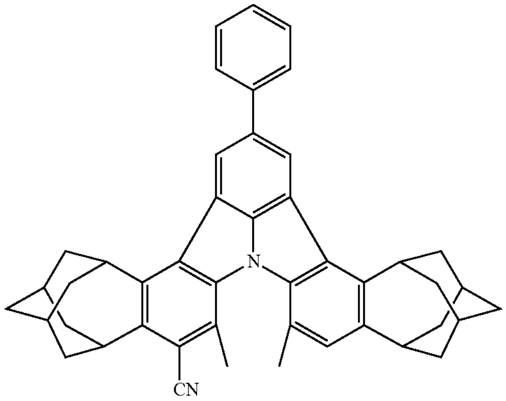 [SMILES: Cc1cc2c(c3c4cc(-c5ccccc5)cc5c6c7c(c(C#N)c(C)c6n(c13)c45)C1CC3CC(C1)CC7C3)C1CC3CC(CC2C3)C1]
572
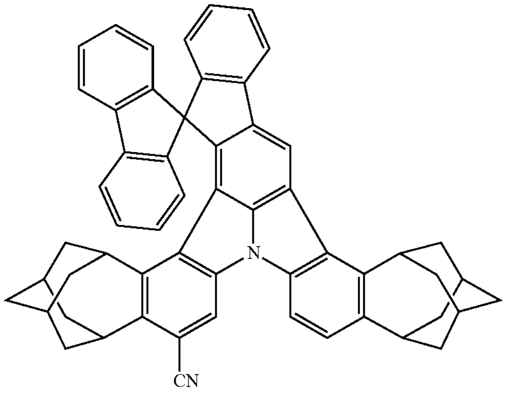 [SMILES: N#Cc1cc2c(c3c1C1CC4CC(C1)CC3C4)c1c3c(cc4c5c6c(ccc5n2c41)C1CC2CC(C1)CC6C2)-c1ccccc1C31c2ccccc2-c2ccccc21]
573

-continued
574
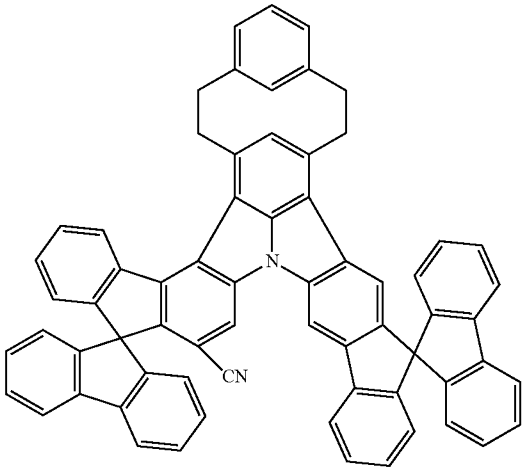 [SMILES: N#Cc1cc2c(c3c1C1(c4ccccc4-c4ccccc41)c1ccccc1-3)c1c3cc(c4c5cc6c(cc5n2c41)-c1ccccc1C61c2ccccc2-c2ccccc21)CCc1cccc(c1)CC3]
575
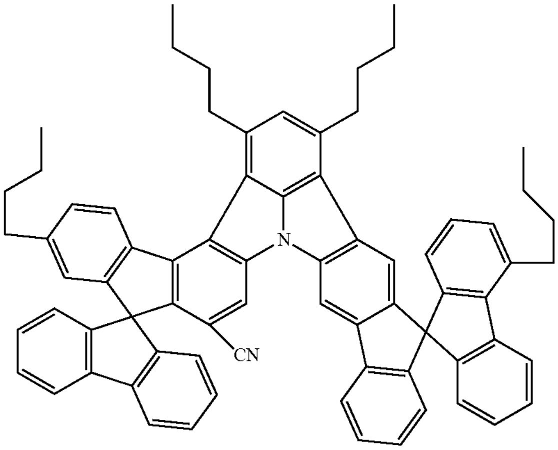 [SMILES: CCCCc1ccc2c(c1)C1(c3ccccc3-c3ccccc31)c1c(C#N)cc3c(c1-2)c1c(CCCC)cc(CCCC)c2c4cc5c(cc4n3c21)-c1ccccc1C51c2ccccc2-c2c(CCCC)cccc21]
576
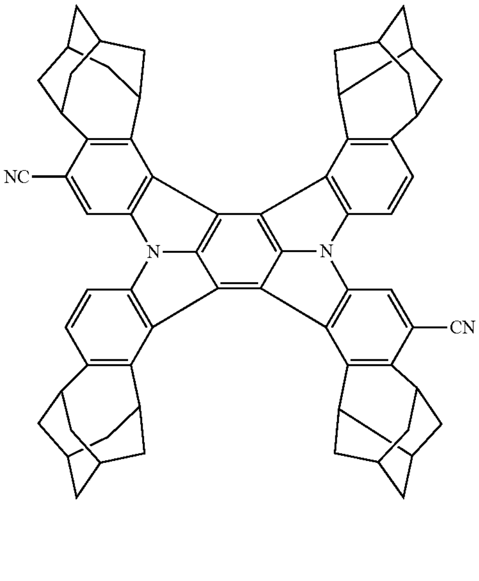 [SMILES: Cc1c(-n2c3ccc4c(c3c3c5c6c7c(c(C#N)cc6n6c8ccc9c(c8c(cc32)c56)C2CC3CC(CC9C3)C2)C2CC3CC(C2)CC7C3)C2CC3CC4CC2C3)cc(C#N)c2c1C1CC3CC2CC1C3]

-continued
577
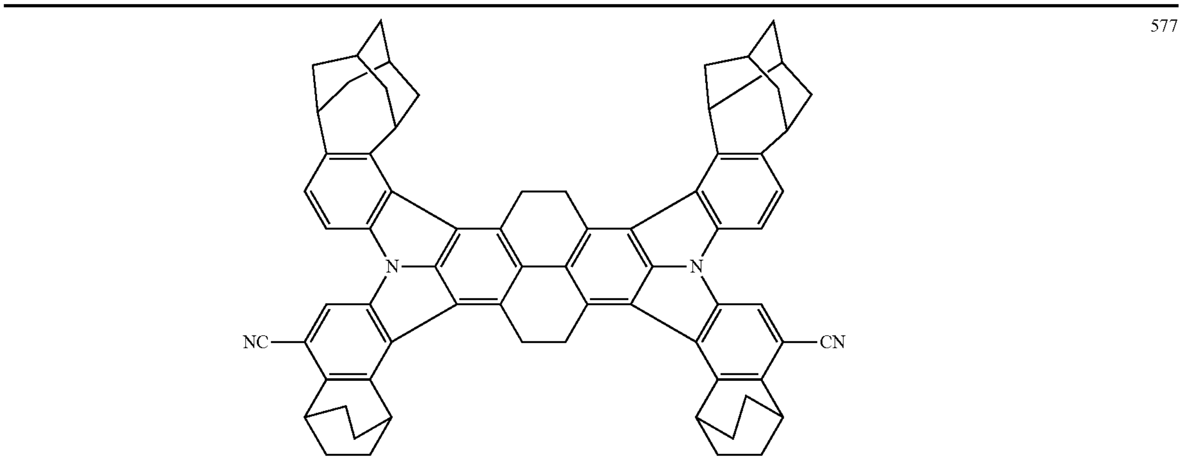
578
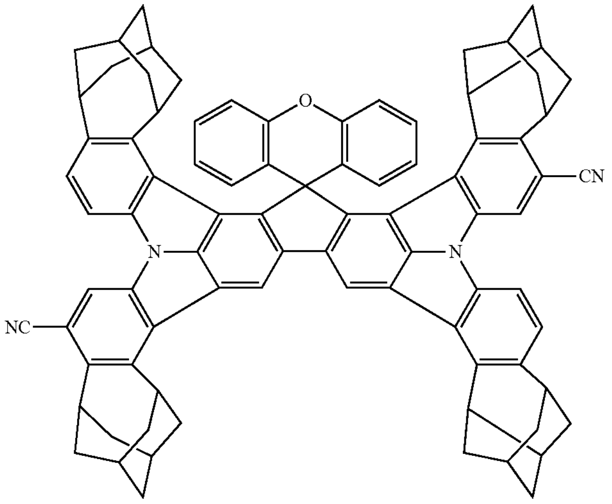 [SMILES: N#Cc1cc2c(c3c1C1CC4CC(C1)CC3C4)c1cc3c(c4c5c6c(ccc5n2c14)C1CC2CC(C1)CC6C2)C1(c2ccccc2Oc2ccccc21)c1c-3cc2c3c4c(ccc3n3c5cc(C#N)c6c(c5c1c23)C1CC2CC6CC1C2)C1CC2CC(C1)C4C2]
579
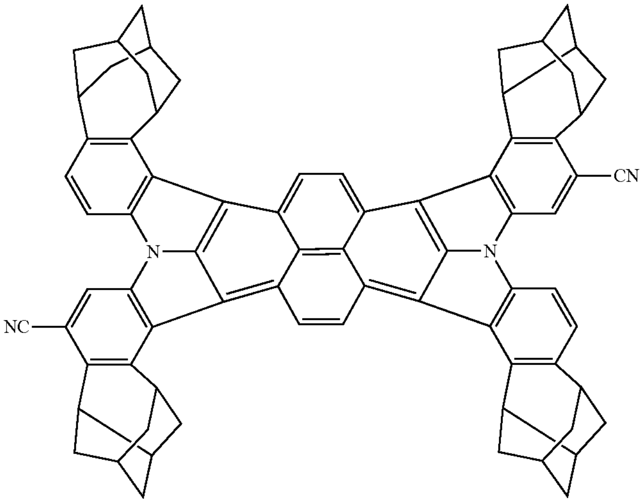 [SMILES: N#Cc1cc2c(c3c1C1CC4CC(C1)C3C4)c1c3ccc4c5c(ccc(c35)c3c5c6c(ccc5n2c31)C1CC2CC(C1)C6C2)c1c2c3c(c(C#N)cc2n2c5ccc6c(c5c4c12)C1CC2CC(CC6C2)C1)C1CC2CC3CC1C2]

-continued
580
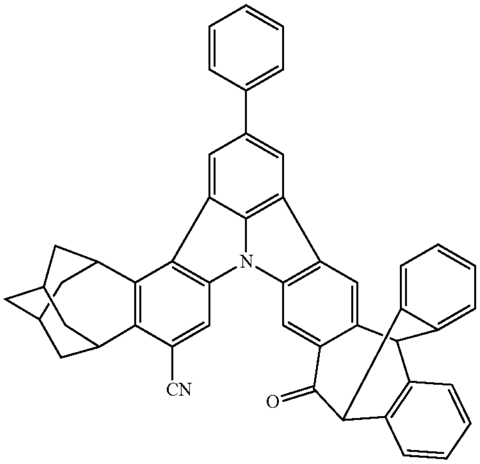 [SMILES: N#Cc1cc2c(c3c1C1CC4CC(C1)CC3C4)c1cc(-c3ccccc3)cc3c4cc5c(cc4n2c31)C(=O)C1c2ccccc2C5c2ccccc21]
581
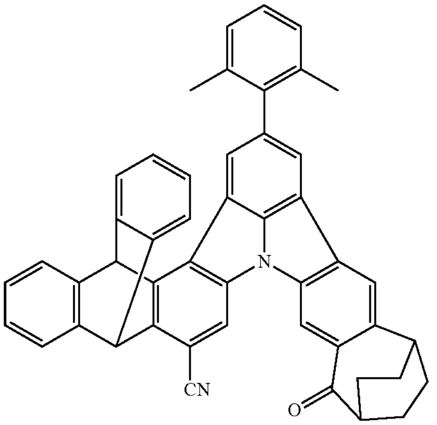 [SMILES: Cc1cccc(C)c1-c1cc2c3cc4c(cc3n3c5cc(C#N)c6c(c5c(c1)c23)C1c2ccccc2C6c2ccccc21)C(=O)C1CCC4CC1]
582
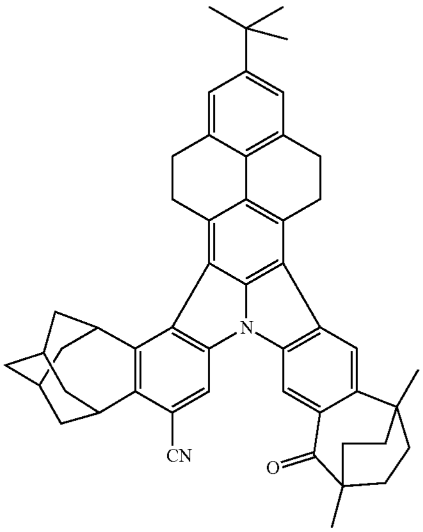 [SMILES: CC12CCC(C)(CC1)c1cc3c4c5c6c(c7c8c9c(c(C#N)cc8n(c3cc1C2=O)c47)C1CC2CC(C1)CC9C2)CCc1cc(C(C)(C)C)cc(c1-6)CC5]

-continued
583
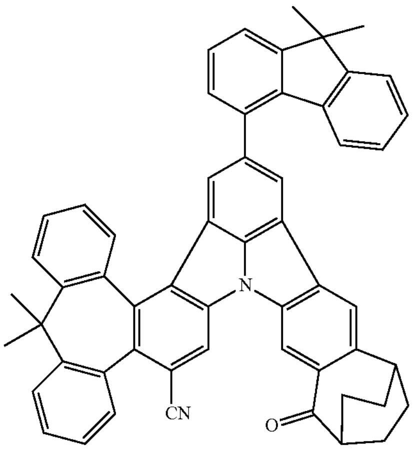 [SMILES: CC1(C)c2ccccc2-c2c(C#N)cc3c(c2-c2ccccc21)c1cc(-c2cccc4c2-c2ccccc2C4(C)C)cc2c4cc5c(cc4n3c21)C(=O)C1CCC5CC1]
584
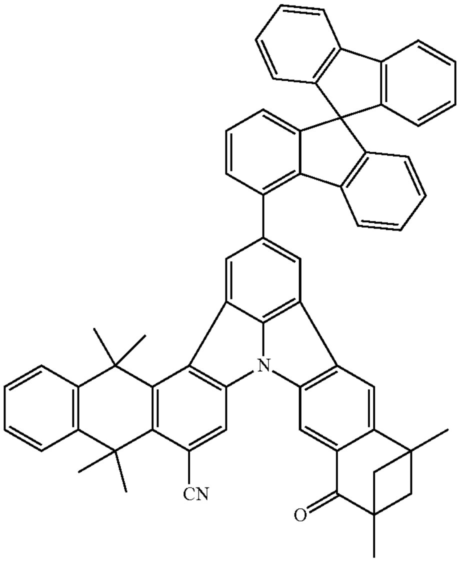 [SMILES: CC12CC(C)(C1)c1cc3c4cc(-c5cccc6c5-c5ccccc5C65c6ccccc6-c6ccccc65)cc5c6c7c(c(C#N)cc6n(c3cc1C2=O)c45)C(C)(C)c1ccccc1C7(C)C]
585
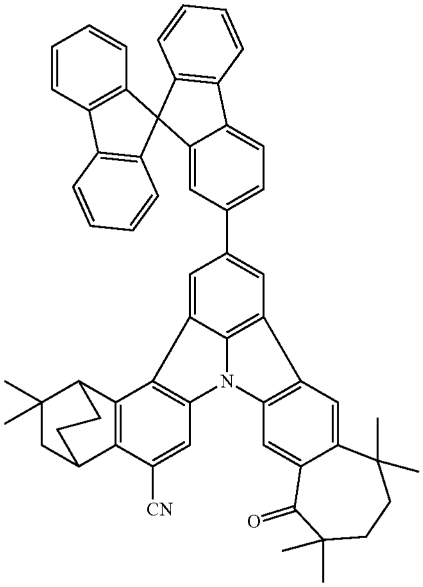

-continued
586
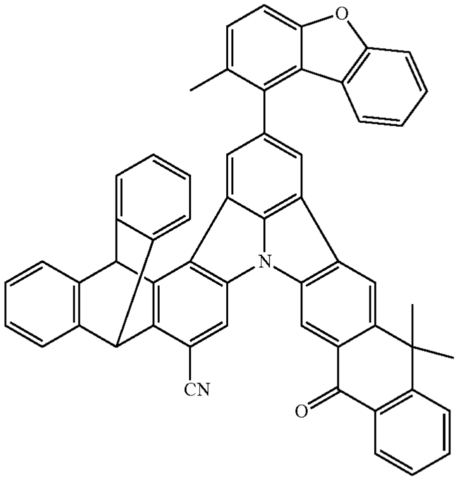 [SMILES: Cc1ccc2oc3ccccc3c2c1-c1cc2c3cc4c(cc3n3c5cc(C#N)c6c(c5c(c1)c23)C1c2ccccc2C6c2ccccc21)C(=O)c1ccccc1C4(C)C]
587
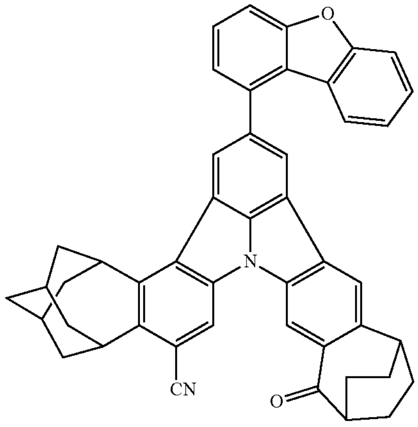 [SMILES: N#Cc1cc2c(c3c1C1CC4CC(C1)CC3C4)c1cc(-c3cccc4oc5ccccc5c34)cc3c4cc5c(cc4n2c31)C(=O)C1CCC5CC1]
588
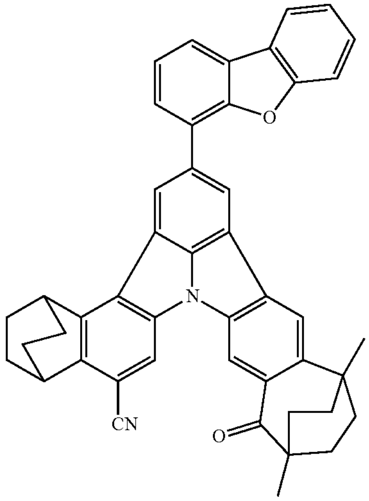 [SMILES: CC12CCC(C)(CC1)c1cc3c4cc(-c5cccc6c5oc5ccccc56)cc5c6c7c(c(C#N)cc6n(c3cc1C2=O)c45)C1CCC7CC1]

-continued
589
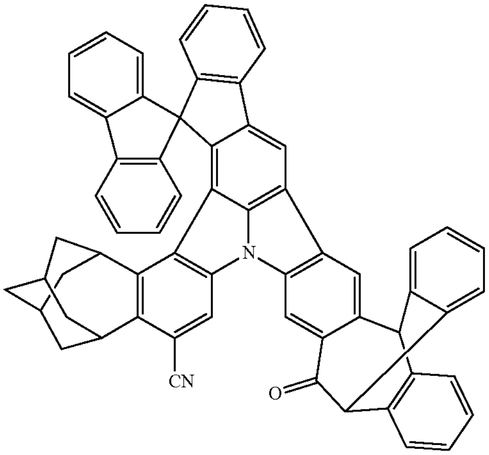 [SMILES: N#Cc1cc2c(c3c1C1CC4CC(C1)CC3C4)c1c3c(cc4c5cc6c(cc5n2c41)C(=O)C1c2ccccc2C6c2ccccc21)-c1ccccc1C31c2ccccc2-c2ccccc21]
590
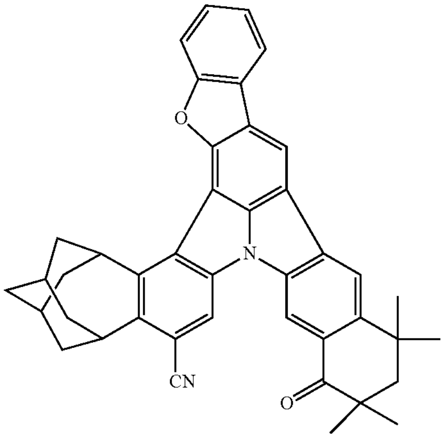 [SMILES: CC1(C)CC(C)(C)c2cc3c4cc5c6ccccc6oc5c5c6c7c(c(C#N)cc6n(c3cc2C1=O)c45)C1CC2CC(C1)CC7C2]
591
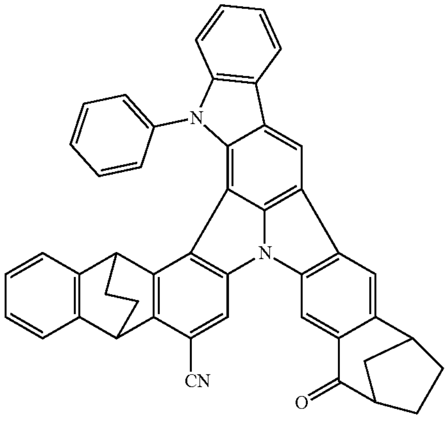 [SMILES: N#Cc1cc2c(c3c1C1CCC3c3ccccc31)c1c3c(cc4c5cc6c(cc5n2c41)C(=O)C1CCC6C1)c1ccccc1n3-c1ccccc1]

-continued
592
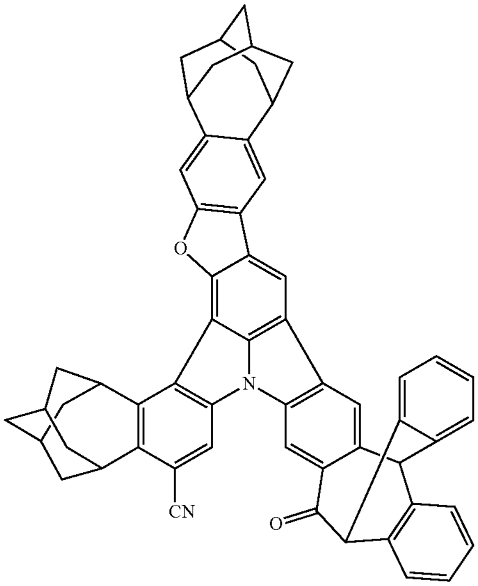 [SMILES: N#Cc1cc2c(c3c1C1CC4CC(C1)CC3C4)c1c3oc4cc5c(cc4c3cc3c4cc6c(cc4n2c31)C(=O)C1c2ccccc2C6c2ccccc21)C1CC2CC(CC5C2)C1]
593
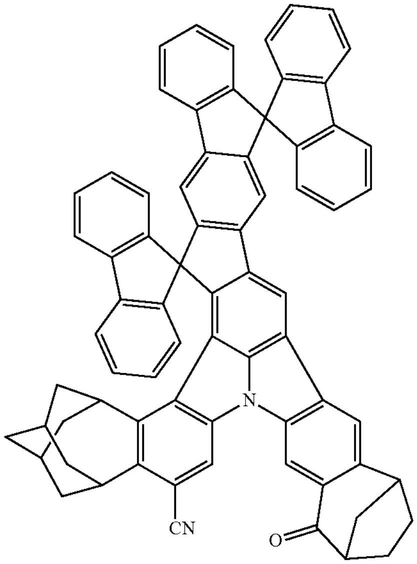 [SMILES: N#Cc1cc2c(c3c1C1CC4CC(C1)CC3C4)c1c3c(cc4c5cc6c(cc5n2c41)C(=O)C1CCC6C1)-c1cc2c(cc1C31c3ccccc3-c3ccccc31)-c1ccccc1C21c2ccccc2-c2ccccc21]
594
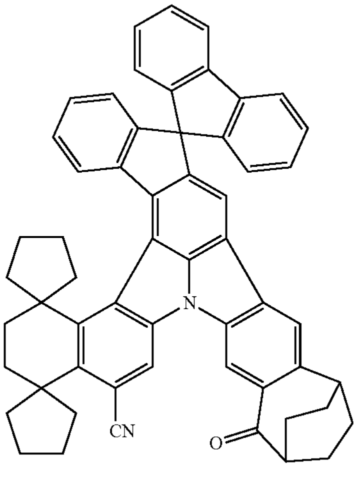 [SMILES: N#Cc1cc2c(c3c1C1(CCCC1)CCC31CCCC1)c1c3c(cc4c5cc6c(cc5n2c41)C(=O)C1CCC6CC1)C1(c2ccccc2-c2ccccc21)c1ccccc1-3]

-continued
595
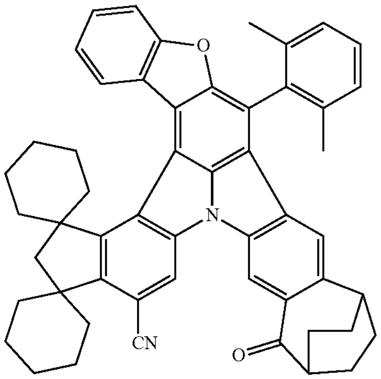 [SMILES: Cc1cccc(C)c1-c1c2oc3ccccc3c2c2c3c4c(c(C#N)cc3n3c5cc6c(cc5c1c23)C1CCC(CC1)C6=O)C1(CCCCC1)CC41CCCCC1]
596
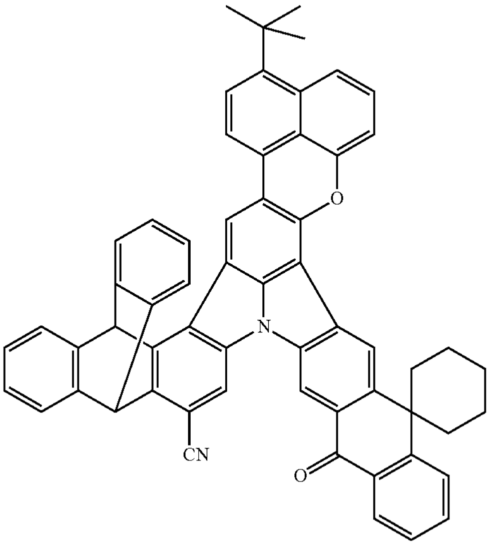 [SMILES: CC(C)(C)c1ccc2c3cc4c5c6c(c(C#N)cc5n5c7cc8c(cc7c(c3oc3cccc1c32)c45)C1(CCCCC1)c1ccccc1C8=O)C1c2ccccc2C6c2ccccc21]
597
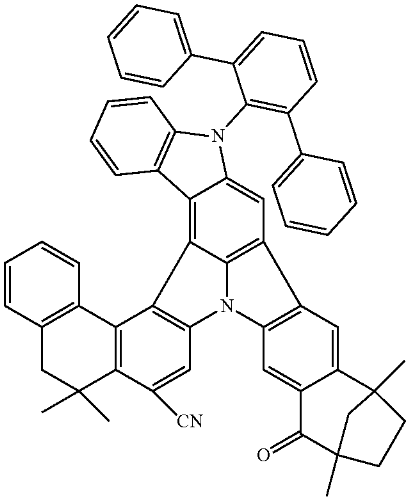 [SMILES: CC12CCC(C)(C1)c1cc3c4cc5c(c6ccccc6n5-c5c(-c6ccccc6)cccc5-c5ccccc5)c5c6c7c(c(C#N)cc6n(c3cc1C2=O)c45)C(C)(C)Cc1ccccc1-7]

-continued
598
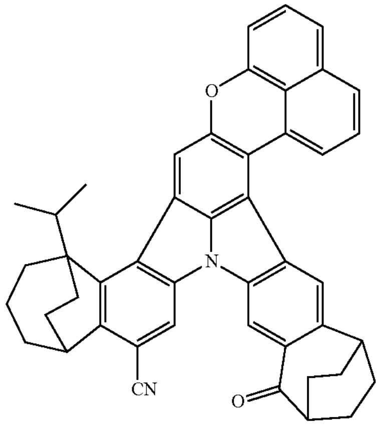 [SMILES: CC(C)C12CCCC(CC1)c1c(C#N)cc3c(c12)c1cc2oc4cccc5cccc(c54)c2c2c4cc5c(cc4n3c12)C(=O)C1CCC5CC1]
599
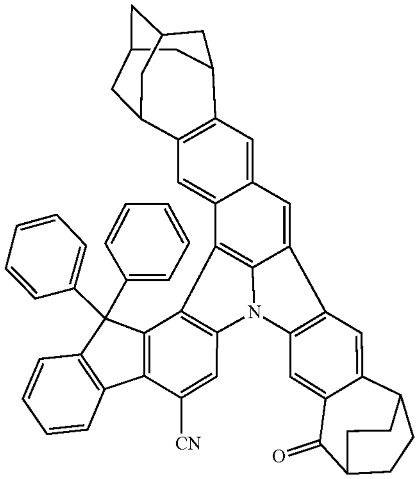 [SMILES: N#Cc1cc2c(c3c1-c1ccccc1C3(c1ccccc1)c1ccccc1)c1c3cc4c(cc3cc3c5cc6c(cc5n2c31)C(=O)C1CCC6CC1)C1CC2CC(C1)CC4C2]
600
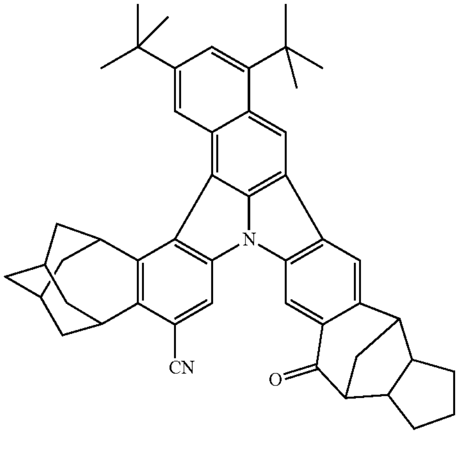 [SMILES: CC(C)(C)c1cc(C(C)(C)C)c2cc3c4cc5c(cc4n4c6cc(C#N)c7c(c6c(c2c1)c34)C1CC2CC(CC7C2)C1)C(=O)C1CC5C2CCCC12]

-continued
601
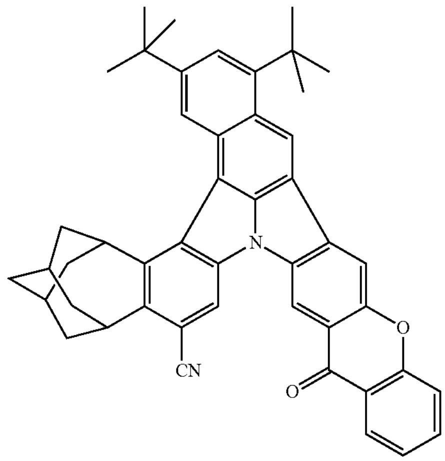 [SMILES: CC(C)(C)c1cc(C(C)(C)C)c2cc3c4cc5oc6ccccc6c(=O)c5cc4n4c5cc(C#N)c6c(c5c(c2c1)c34)C1CC2CC(CC6C2)C1]
602
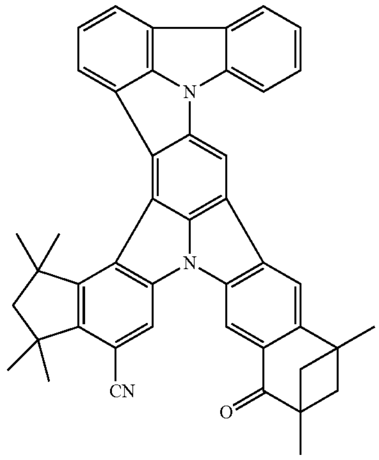
603
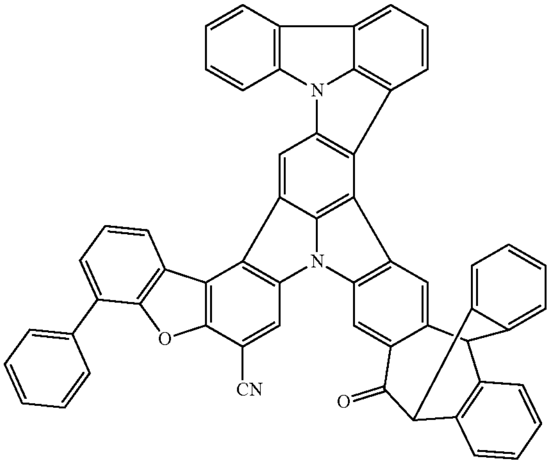 [SMILES: N#Cc1cc2c(c3cc4c(c5cccc6c7ccccc7n4c65)c4c5cc6c(cc5n2c34)C(=O)C2c3ccccc3C6c3ccccc32)c2c1oc1c(-c3ccccc3)cccc12]

-continued
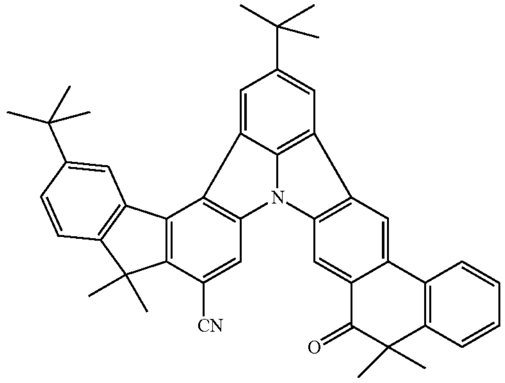 [SMILES: CC(C)(C)c1ccc2c(c1)-c1c(c(C#N)cc3c1c1cc(C(C)(C)C)cc4c5cc6c(cc5n3c41)C(=O)C(C)(C)c1ccccc1-6)C2(C)C]
604
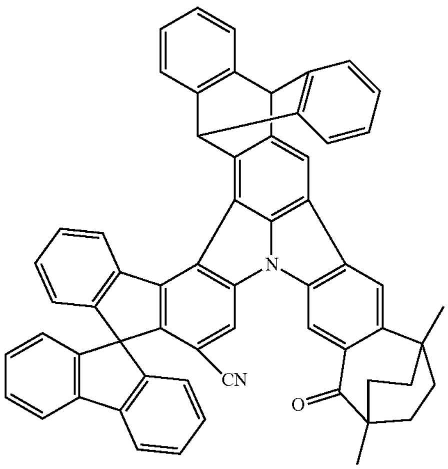 [SMILES: CC12CCC(C)(CC1)c1cc3c4cc5c(c6c7c8c(c(C#N)cc7n(c3cc1C2=O)c46)C1(c2ccccc2-c2ccccc21)c1ccccc1-8)C1c2ccccc2C5c2ccccc21]
605
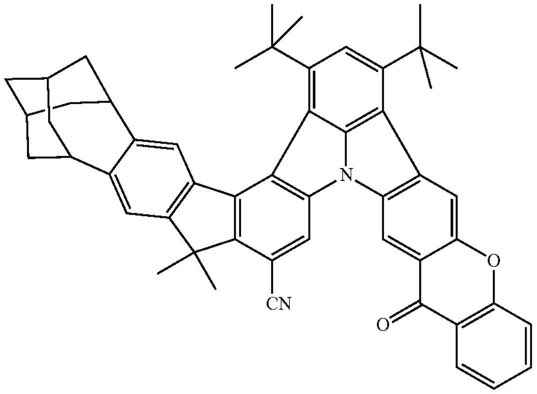 [SMILES: CC(C)(C)c1cc(C(C)(C)C)c2c3c4c(c(C#N)cc3n3c5cc6c(=O)c7ccccc7oc6cc5c1c23)C(C)(C)c1cc2c(cc1-4)C1CC3CC(C1)CC2C3]
606

-continued
607
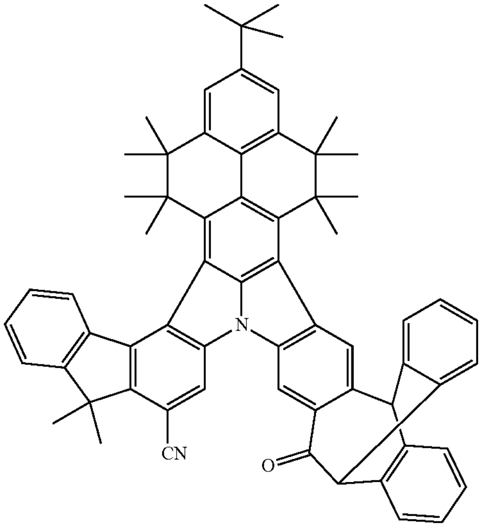 [SMILES: CC(C)(C)c1cc2c3c(c1)C(C)(C)C(C)(C)c1c-3c(c3c4cc5c(cc4n4c6cc(C#N)c7c(c6c1c34)-c1ccccc1C7(C)C)C(=O)C1c3ccccc3C5c3ccccc31)C(C)(C)C2(C)C]
608
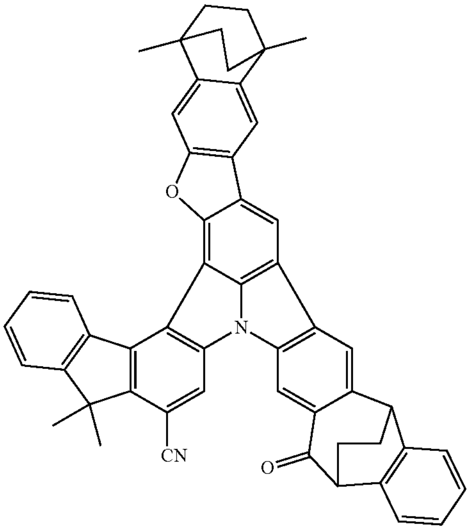 [SMILES: CC12CCC(C)(CC1)c1cc3c(cc12)oc1c3cc2c3cc4c(cc3n3c5cc(C#N)c6c(c5c1c23)-c1ccccc1C6(C)C)C(=O)C1CCC4c2ccccc21]
609
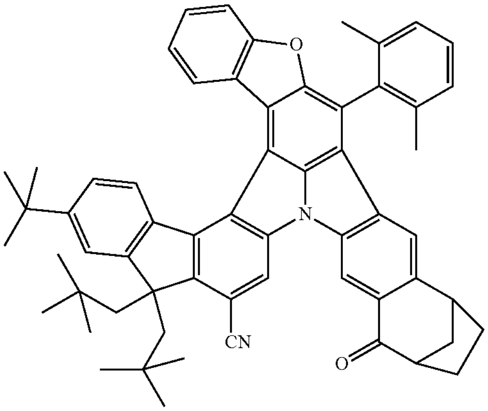 [SMILES: Cc1cccc(C)c1-c1c2oc3ccccc3c2c2c3c4c(c(C#N)cc3n3c5cc6c(cc5c1c23)C1CCC(C1)C6=O)C(CC(C)(C)C)(CC(C)(C)C)c1cc(C(C)(C)C)ccc1-4]

-continued
610
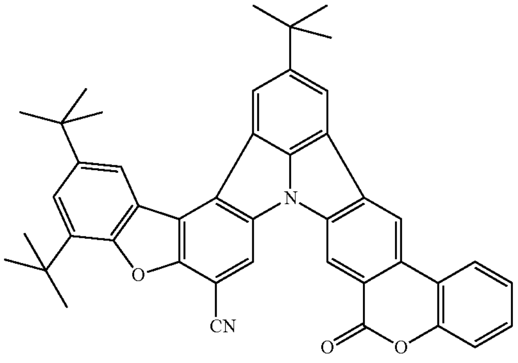 [SMILES: CC(C)(C)c1cc(C(C)(C)C)c2oc3c(C#N)cc4c(c5cc(C(C)(C)C)cc6c7cc8c(cc7n4c65)c(=O)oc4ccccc48)c3c2c1]
611
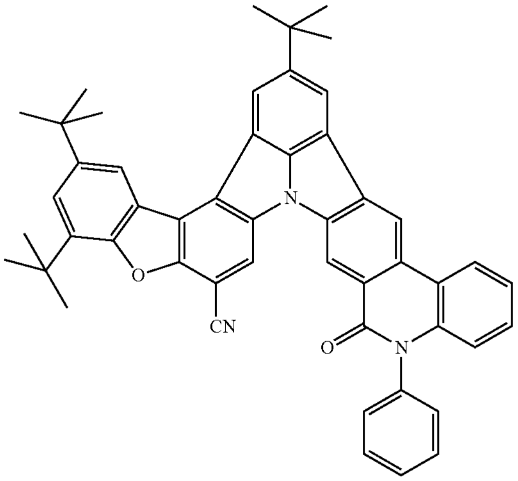 [SMILES: CC(C)(C)c1cc(C(C)(C)C)c2oc3c(C#N)cc4c(c5cc(C(C)(C)C)cc6c7cc8c(cc7n4c65)c(=O)n(-c4ccccc4)c4ccccc84)c3c2c1]
612
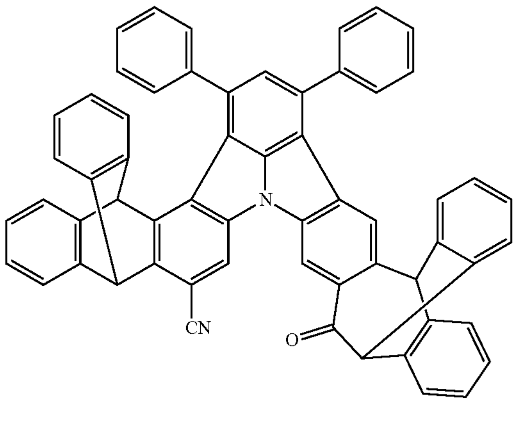 [SMILES: N#Cc1cc2c(c3c1C1c4ccccc4C3c3ccccc31)c1c(-c3ccccc3)cc(-c3ccccc3)c3c4cc5c(cc4n2c31)C(=O)C1c2ccccc2C5c2ccccc21]

-continued
613
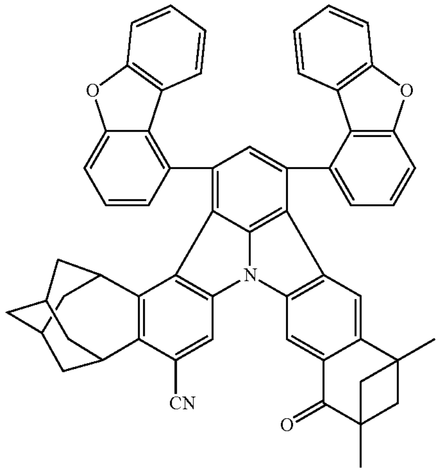 [SMILES: CC12CC(C)(C1)c1cc3c4c(-c5cccc6oc7ccccc7c56)cc(-c5cccc6oc7ccccc7c56)c5c6c7c(c(C#N)cc6n(c3cc1C2=O)c45)C1CC2CC(C1)CC7C2]
614
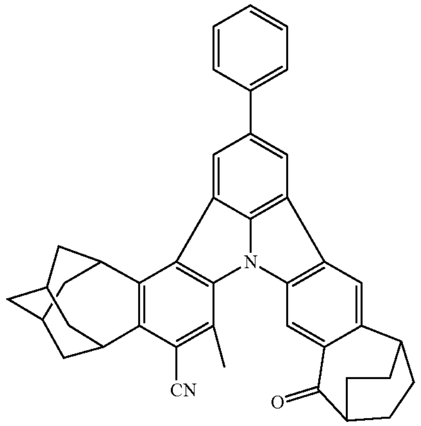 [SMILES: Cc1c(C#N)c2c(c3c4cc(-c5ccccc5)cc5c6cc7c(cc6n(c13)c54)C(=O)C1CCC7CC1)C1CC3CC(CC2C3)C1]
615
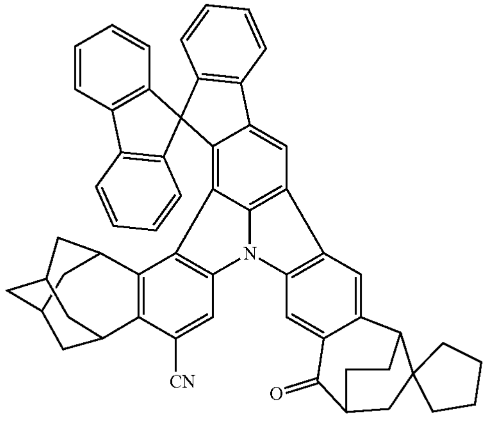 [SMILES: N#Cc1cc2c(c3c1C1CC4CC(C1)CC3C4)c1c3c(cc4c5cc6c(cc5n2c41)C(=O)C1CCC6C2(CCCC2)C1)-c1ccccc1C31c2ccccc2-c2ccccc21]

-continued
616
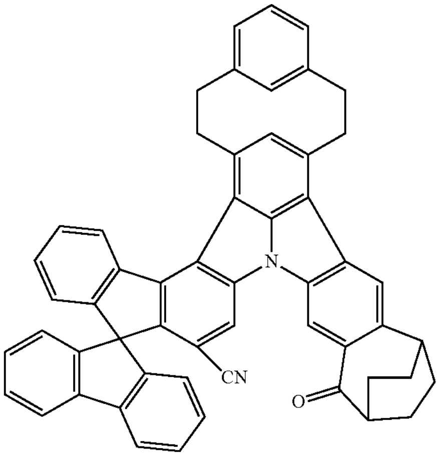 [SMILES: N#Cc1cc2c(c3c1C1(c4ccccc4-c4ccccc41)c1ccccc1-3)c1c3cc(c4c5cc6c(cc5n2c41)C(=O)C1CCC6CC1)CCc1cccc(c1)CC3]
617
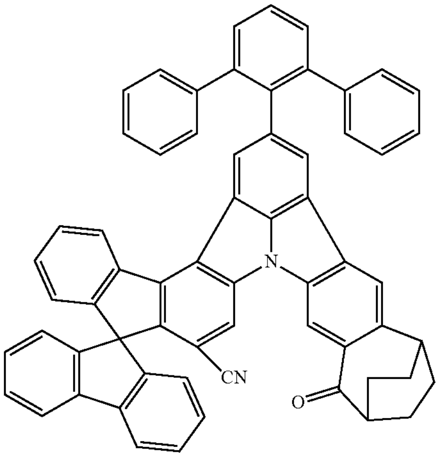 [SMILES: N#Cc1cc2c(c3c1C1(c4ccccc4-c4ccccc41)c1ccccc1-3)c1cc(-c3c(-c4ccccc4)cccc3-c3ccccc3)cc3c4cc5c(cc4n2c31)C(=O)C1CCC5CC1]
618
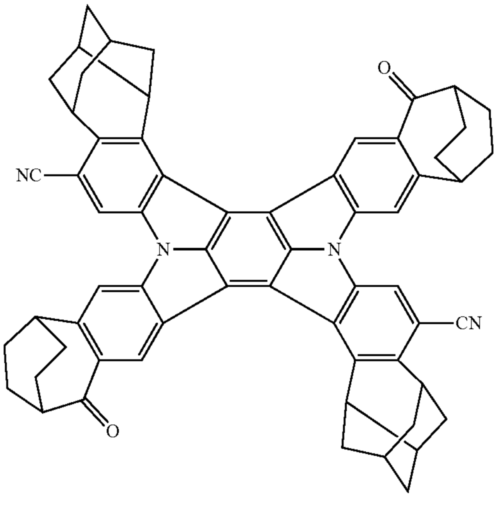 [SMILES: N#Cc1cc2c(c3c1C1CC4CC(C1)C3C4)c1c3c4cc5c(cc4n4c6cc(C#N)c7c(c6c(c6c8cc9c(cc8n2c61)C1CCC(CC1)C9=O)c34)C1CC2CC7CC1C2)C1CCC(CC1)C5=O]

-continued
619
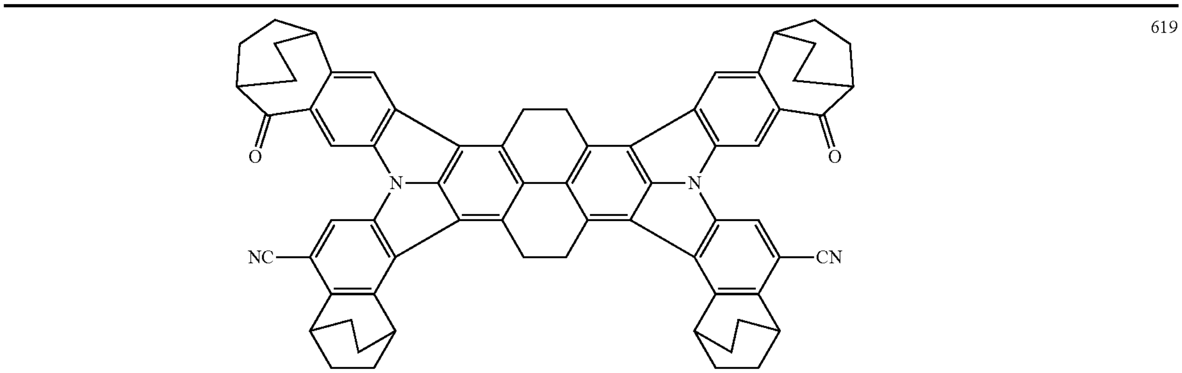
620
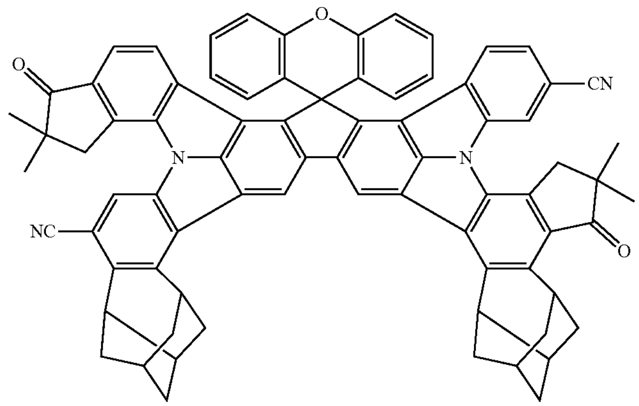
621
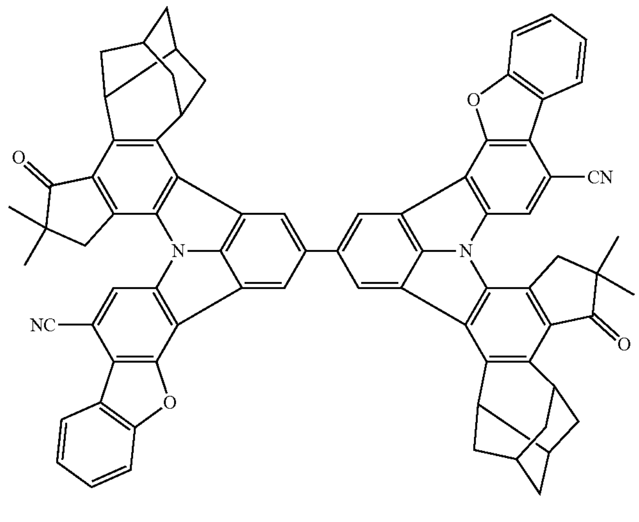

-continued
622
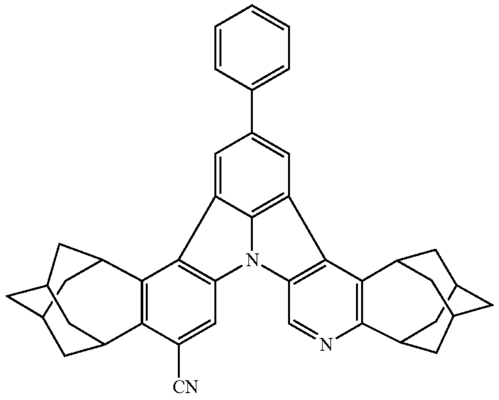 [SMILES: N#Cc1cc2c(c3c1C1CC4CC(C1)CC3C4)c1cc(-c3ccccc3)cc3c4c5c(ncc4n2c31)C1CC2CC(C1)CC5C2]
623
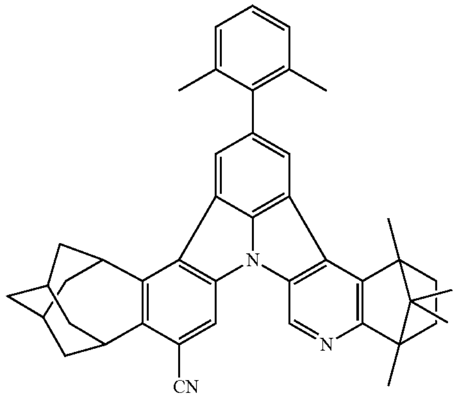 [SMILES: Cc1cccc(C)c1-c1cc2c3c4c(c(C#N)cc3n3c5cnc6c(c5c(c1)c23)C1(C)CCC6(C)C1(C)C)C1CC2CC(C1)CC4C2]
624
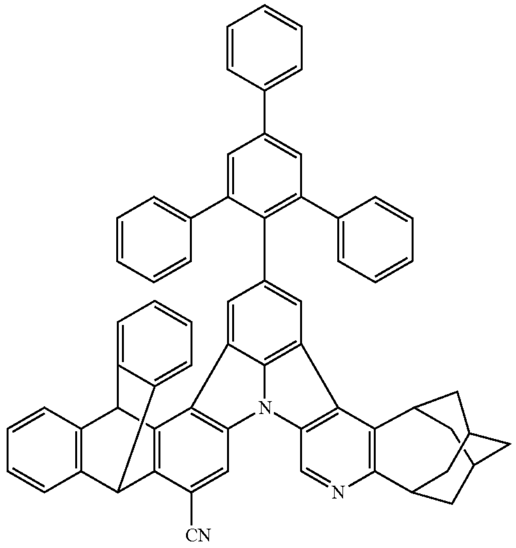 [SMILES: N#Cc1cc2c(c3c1C1c4ccccc4C3c3ccccc31)c1cc(-c3c(-c4ccccc4)cc(-c4ccccc4)cc3-c3ccccc3)cc3c4c5c(ncc4n2c31)C1CC2CC(C1)CC5C2]

-continued
625
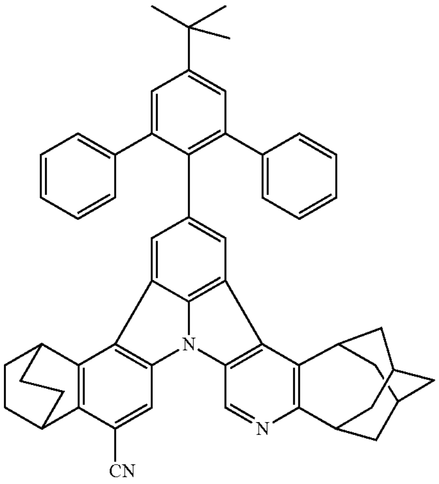 [SMILES: CC(C)(C)c1cc(-c2ccccc2)c(-c2cc3c4c5c(ncc4n4c6cc(C#N)c7c(c6c(c2)c34)C2CCC7CC2)C2CC3CC(C2)CC5C3)c(-c2ccccc2)c1]
626
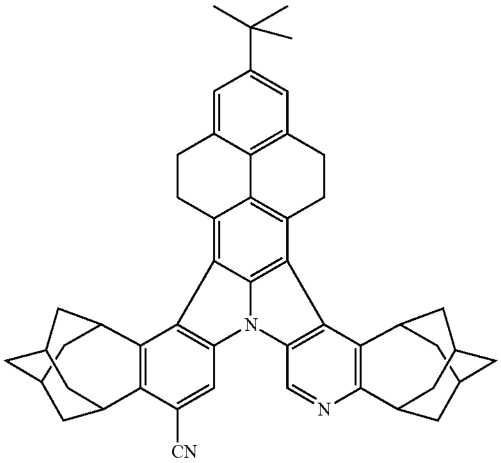 [SMILES: CC(C)(C)c1cc2c3c(c1)CCc1c-3c(c3c4c5c(ncc4n4c6cc(C#N)c7c(c6c1c34)C1CC3CC(CC7C3)C1)C1CC3CC(C1)CC5C3)CC2]
627
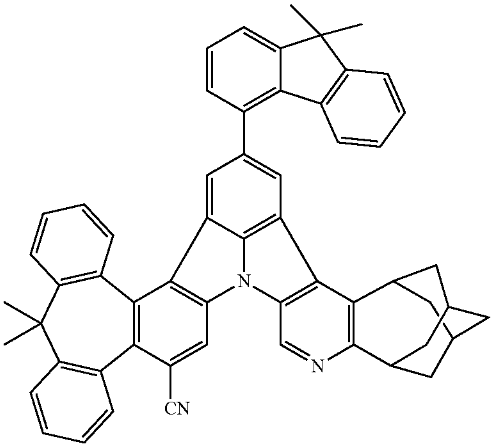 [SMILES: CC1(C)c2ccccc2-c2c(C#N)cc3c(c2-c2ccccc21)c1cc(-c2cccc4c2-c2ccccc2C4(C)C)cc2c4c5c(ncc4n3c12)C1CC2CC(C1)CC5C2]

-continued
628
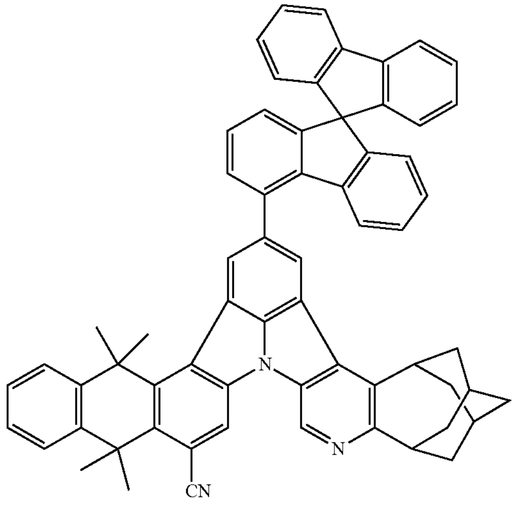 [SMILES: CC1(C)c2ccccc2C(C)(C)c2c1c(C#N)cc1c2c2cc(-c3cccc4c3-c3ccccc3C43c4ccccc4-c4ccccc43)cc3c4c5c(ncc4n1c32)C1CC2CC(C1)CC5C2]
629
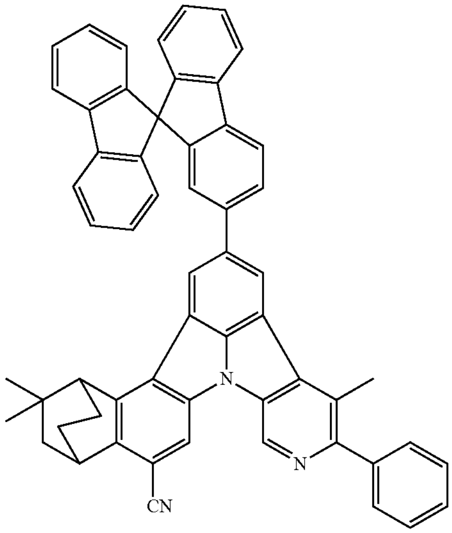 [SMILES: Cc1c(-c2ccccc2)ncc2c1c1cc(-c3ccc4c(c3)C3(c5ccccc5-c5ccccc53)c3ccccc3-4)cc3c4c5c(c(C#N)cc4n2c13)C1CCC5C(C)(C)C1]
630
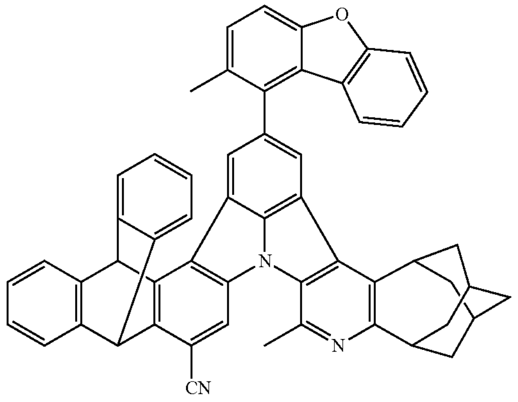 [SMILES: Cc1ccc2oc3ccccc3c2c1-c1cc2c3c4c(c(C#N)cc3n3c5c(C)nc6c(c5c(c1)c23)C1CC2CC(CC6C2)C1)C1c2ccccc2C4c2ccccc21]

-continued
631
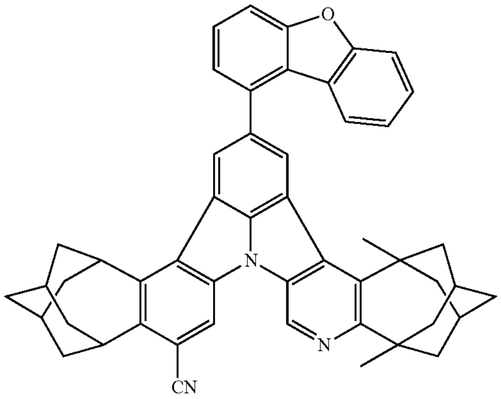 [SMILES: CC12CC3CC(C1)CC(C)(C3)c1c2ncc2c1c1cc(-c3cccc4oc5ccccc5c34)cc3c4c5c(c(C#N)cc4n2c31)C1CC2CC(C1)CC5C2]
632
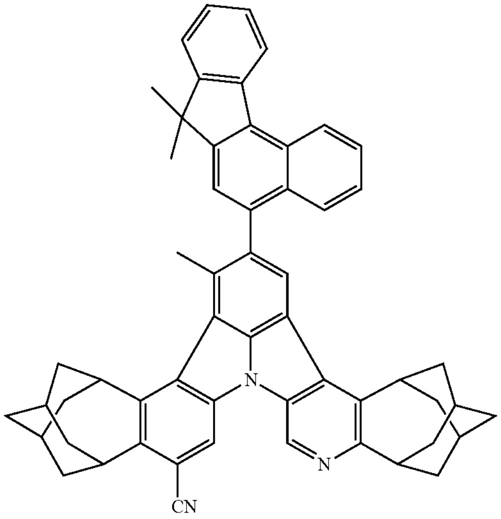 [SMILES: Cc1c(-c2cc3c(c4ccccc24)-c2ccccc2C3(C)C)cc2c3c4c(ncc3n3c5cc(C#N)c6c(c5c1c23)C1CC2CC(CC6C2)C1)C1CC2CC(C1)CC4C2]
633
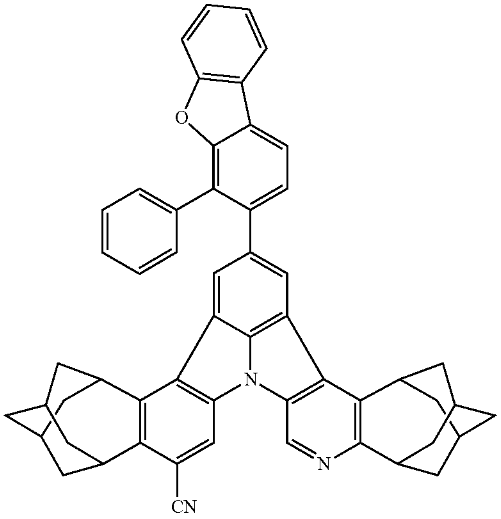 [SMILES: N#Cc1cc2c(c3c1C1CC4CC(C1)CC3C4)c1cc(-c3ccc4c(oc5ccccc54)c3-c3ccccc3)cc3c4c5c(ncc4n2c31)C1CC2CC(C1)CC5C2]

-continued
634
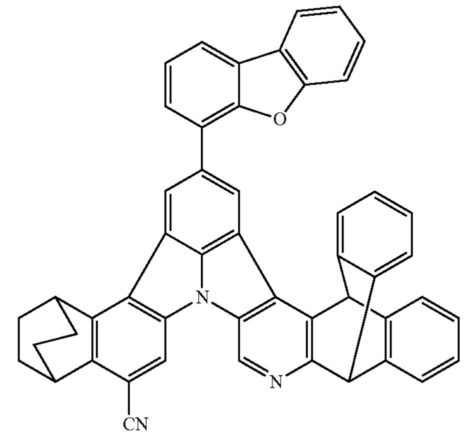 [SMILES: N#Cc1cc2c(c3c1C1CCC3CC1)c1cc(-c3cccc4c3oc3ccccc34)cc3c4c5c(ncc4n2c13)C1c2ccccc2C5c2ccccc21]
635
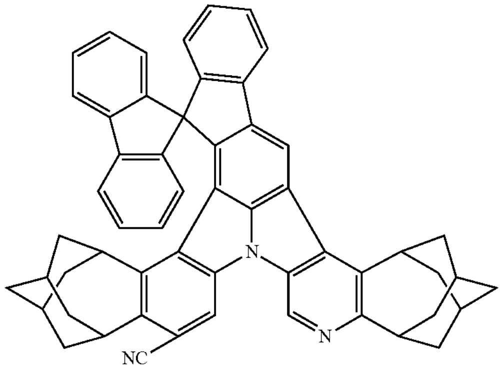 [SMILES: N#Cc1cc2c(c3c1C1CC4CC(C1)CC3C4)c1c3c(cc4c5c6c(ncc5n2c41)C1CC2CC(C1)CC6C2)-c1ccccc1C31c2ccccc2-c2ccccc21]
636
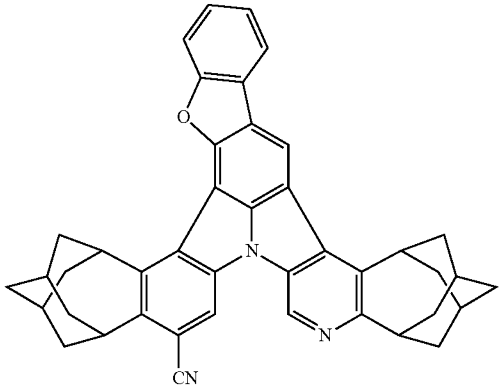 [SMILES: N#Cc1cc2c(c3c1C1CC4CC(C1)CC3C4)c1c3oc4ccccc4c3cc3c4c5c(ncc4n2c31)C1CC2CC(C1)CC5C2]
637
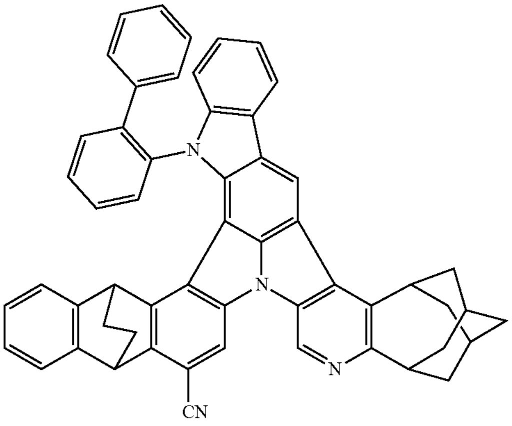 [SMILES: N#Cc1cc2c(c3c1C1CCC3c3ccccc31)c1c3c(cc4c5c6c(ncc5n2c41)C1CC2CC(C1)CC6C2)c1ccccc1n3-c1ccccc1-c1ccccc1]

-continued
638
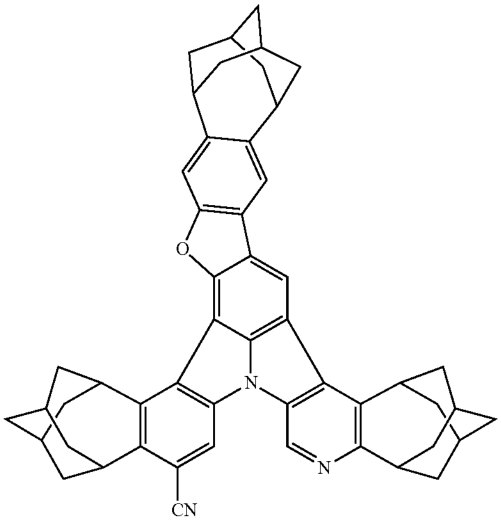 [SMILES: N#Cc1cc2c(c3c1C1CC4CC(C1)CC3C4)c1c3oc4cc5c(cc4c3cc3c4c6c(ncc4n2c31)C1CC2CC(C1)CC6C2)C1CC2CC(CC5C2)C1]
639
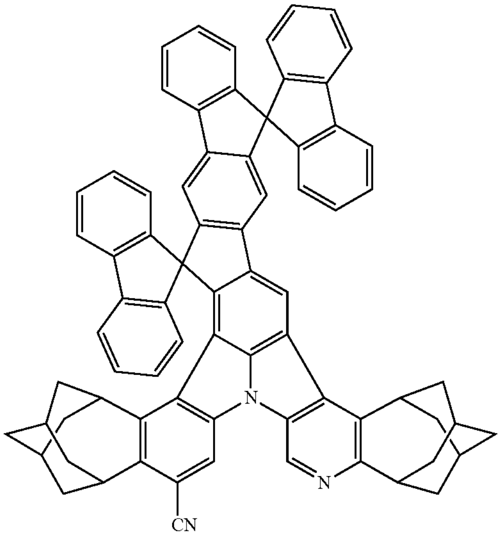 [SMILES: N#Cc1cc2c(c3c1C1CC4CC(C1)CC3C4)c1c3c(cc4c5c6c(ncc5n2c41)C1CC2CC(C1)CC6C2)-c1cc2c(cc1C31c3ccccc3-c3ccccc31)-c1ccccc1C21c2ccccc2-c2ccccc21]
640
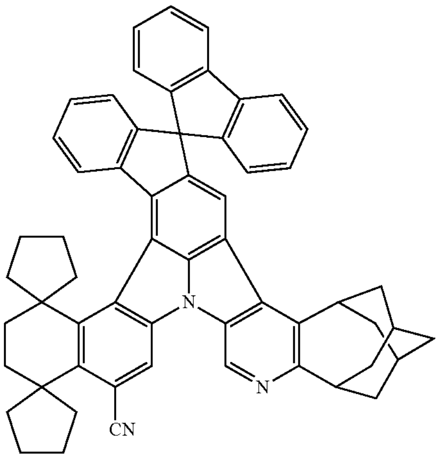 [SMILES: N#Cc1cc2c(c3c1C1(CCCC1)CCC31CCCC1)c1c3c(cc4c5c6c(ncc5n2c41)C1CC2CC(C1)CC6C2)C1(c2ccccc2-c2ccccc21)c1ccccc1-3]

-continued
640
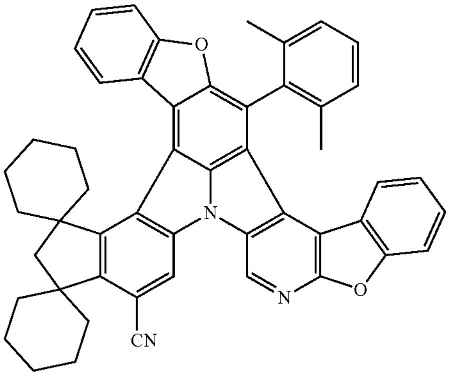 [SMILES: Cc1cccc(C)c1-c1c2oc3ccccc3c2c2c3c4c(c(C#N)cc3n3c5cnc6oc7ccccc7c6c5c1c23)C1(CCCCC1)CC41CCCCC1]
642
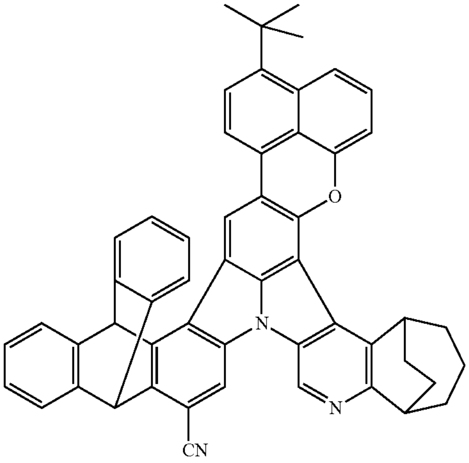 [SMILES: CC(C)(C)c1ccc2c3cc4c5c6c(c(C#N)cc5n5c7cnc8c(c7c(c3oc3cccc1c32)c45)C1CCCC8CC1)C1c2ccccc2C6c2ccccc21]
643
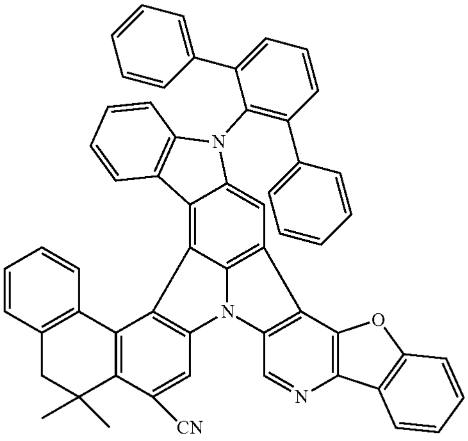 [SMILES: CC1(C)Cc2ccccc2-c2c1c(C#N)cc1c2c2c3c4ccccc4n(-c4c(-c5ccccc5)cccc4-c4ccccc4)c3cc3c4c5oc6ccccc6c5ncc4n1c32]

-continued
644
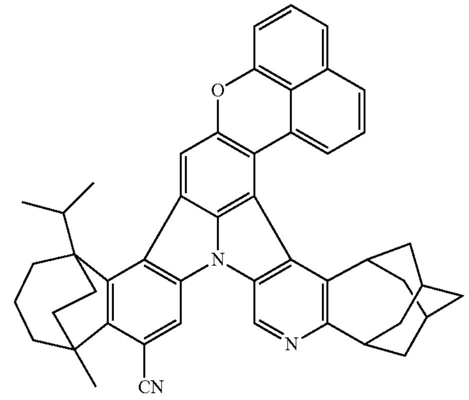 [SMILES: CC(C)C12CCCC(C)(CC1)c1c(C#N)cc3c(c12)c1cc2oc4cccc5cccc(c54)c2c2c4c5c(ncc4n3c12)C1CC2CC(C1)CC5C2]
645
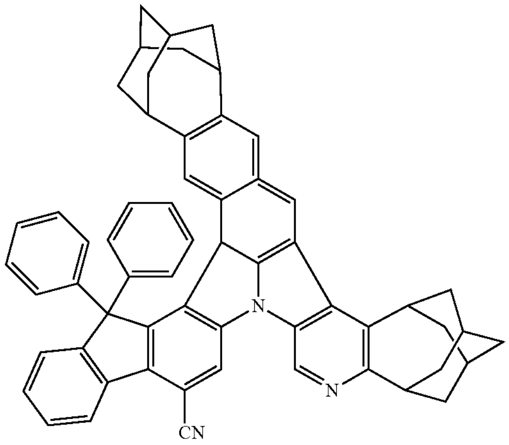
646
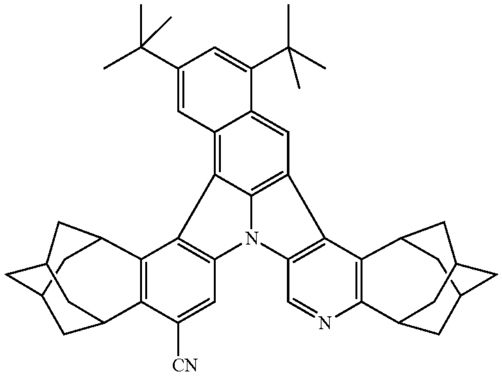 [SMILES: CC(C)(C)c1cc(C(C)(C)C)c2cc3c4c5c(ncc4n4c6cc(C#N)c7c(c6c(c2c1)c34)C1CC2CC(CC7C2)C1)C1CC2CC(C1)CC5C2]
647
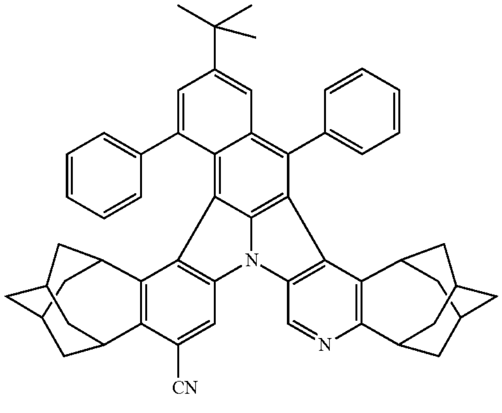 [SMILES: CC(C)(C)c1cc(-c2ccccc2)c2c(c1)c(-c1ccccc1)c1c3c4c(ncc3n3c5cc(C#N)c6c(c5c2c13)C1CC2CC(CC6C2)C1)C1CC2CC(C1)CC4C2]

-continued
648
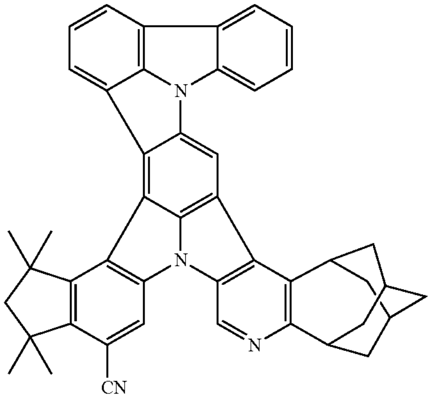 [SMILES: CC1(C)CC(C)(C)c2c1c(C#N)cc1c2c2c3c4cccc5c6ccccc6n(c3cc3c6c7c(ncc6n1c32)C1CC2CC(C1)CC7C2)c54]
649
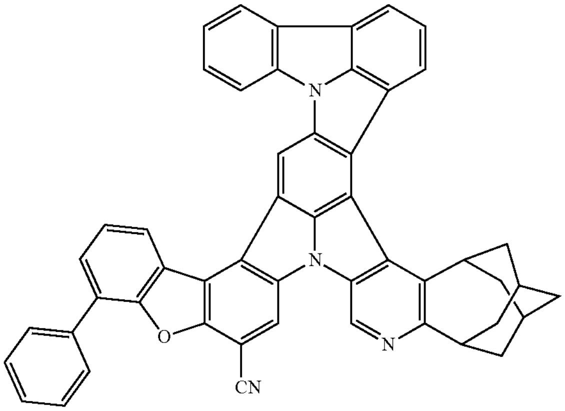 [SMILES: N#Cc1cc2c(c3cc4c(c5cccc6c7ccccc7n4c65)c4c5c6c(ncc5n2c34)C2CC3CC(C2)CC6C3)c2c1oc1c(-c3ccccc3)cccc12]
650
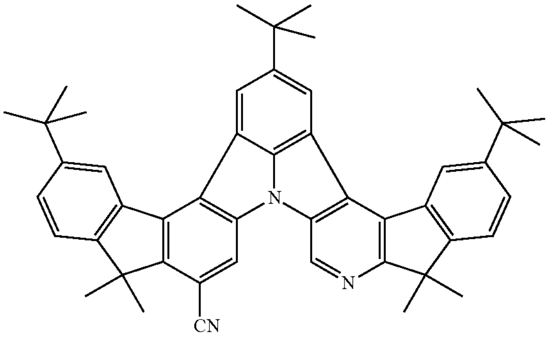 [SMILES: CC(C)(C)c1ccc2c(c1)-c1c(ncc3c1c1cc(C(C)(C)C)cc4c5c6c(c(C#N)cc5n3c14)C(C)(C)c1ccc(C(C)(C)C)cc1-6)C2(C)C]
651
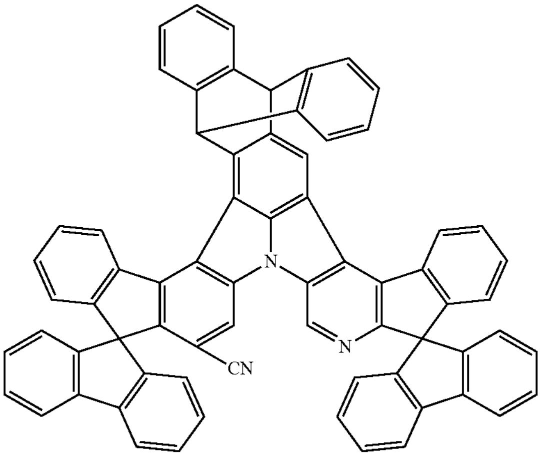 [SMILES: N#Cc1cc2c(c3c1C1(c4ccccc4-c4ccccc41)c1ccccc1-3)c1c3c(cc4c5c6c(ncc5n2c41)C1(c2ccccc2-c2ccccc21)c1ccccc1-6)C1c2ccccc2C3c2ccccc21]

-continued
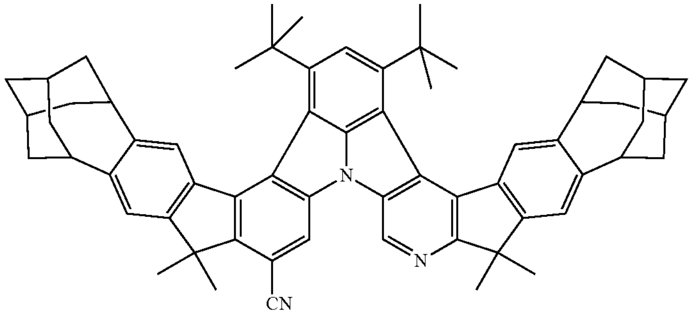 [SMILES: CC(C)(C)c1cc(C(C)(C)C)c2c3c4c(c(C#N)cc3n3c5cnc6c(c5c1c23)-c1cc2c(cc1C6(C)C)C1CC3CC(CC2C3)C1)C(C)(C)c1cc2c(cc1-4)C1CC3CC(C1)CC2C3]
652
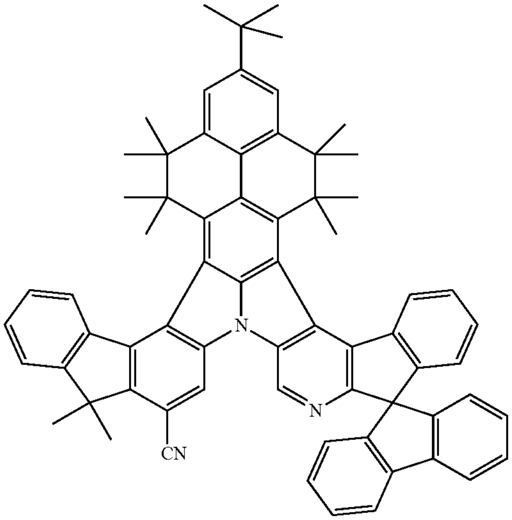 [SMILES: CC(C)(C)c1cc2c3c(c1)C(C)(C)C(C)(C)c1c-3c(c3c4c5c(ncc4n4c6cc(C#N)c7c(c6c1c34)-c1ccccc1C7(C)C)C1(c3ccccc3-c3ccccc31)c1ccccc1-5)C(C)(C)C2(C)C]
653
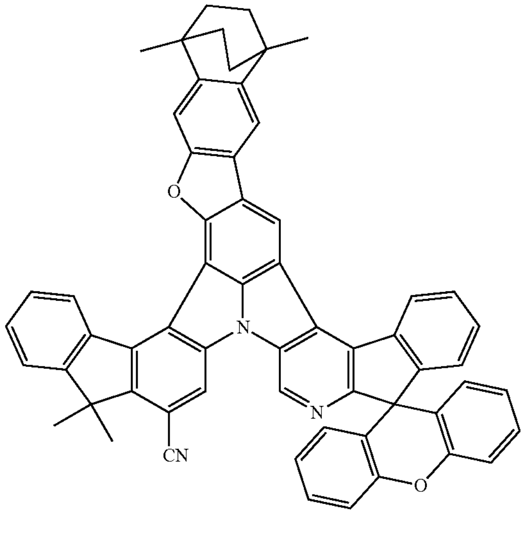 [SMILES: CC12CCC(C)(CC1)c1cc3c(cc12)oc1c3cc2c3c4c(ncc3n3c5cc(C#N)c6c(c5c1c23)-c1ccccc1C6(C)C)C1(c2ccccc2Oc2ccccc21)c1ccccc1-4]
654

-continued
655
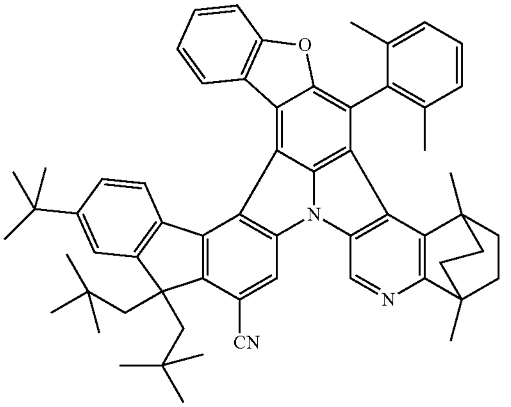 [SMILES: Cc1cccc(C)c1-c1c2oc3ccccc3c2c2c3c4c(c(C#N)cc3n3c5cnc6c(c5c1c23)C1(C)CCC6(C)CC1)C(CC(C)(C)C)(CC(C)(C)C)c1cc(C(C)(C)C)ccc1-4]
656
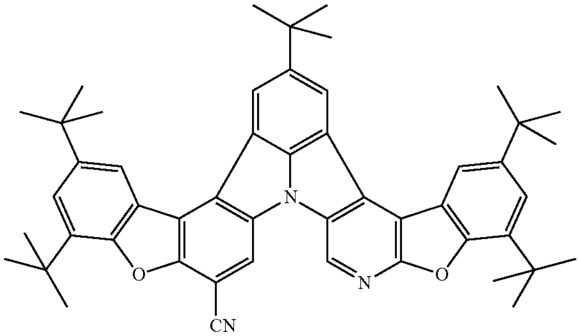 [SMILES: CC(C)(C)c1cc(C(C)(C)C)c2oc3ncc4c(c5cc(C(C)(C)C)cc6c7c8c(oc9c(C(C)(C)C)cc(C(C)(C)C)cc98)c(C#N)cc7n4c56)c3c2c1]
657
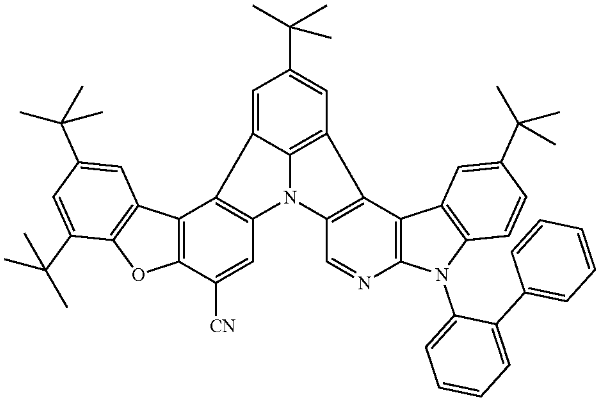 [SMILES: CC(C)(C)c1cc(C(C)(C)C)c2oc3c(C#N)cc4c(c5cc(C(C)(C)C)cc6c7c8c9cc(C(C)(C)C)ccc9n(-c9ccccc9-c9ccccc9)c8ncc7n4c56)c3c2c1]
658
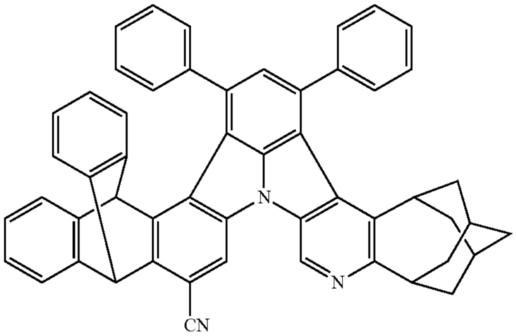 [SMILES: N#Cc1cc2c(c3c1C1c4ccccc4C3c3ccccc31)c1c(-c3ccccc3)cc(-c3ccccc3)c3c4c5c(ncc4n2c31)C1CC2CC(C1)CC5C2]

-continued
659
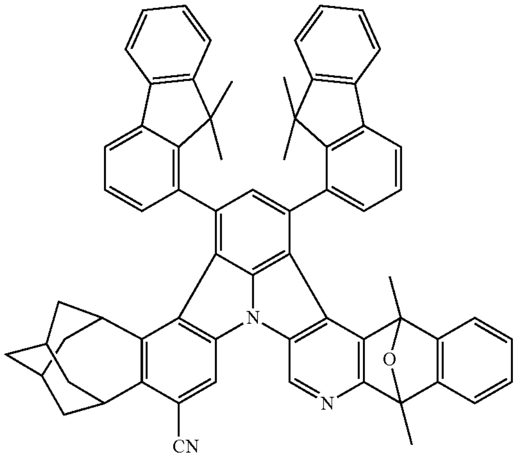 [SMILES: CC1(C)c2ccccc2-c2cccc(-c3cc(-c4cccc5c4C(C)(C)c4ccccc4-5)c4c5c6c(ncc5n5c7cc(C#N)c8c(c7c3c45)C3CC4CC(CC8C4)C3)C3(C)OC6(C)c4ccccc43)c21]
660
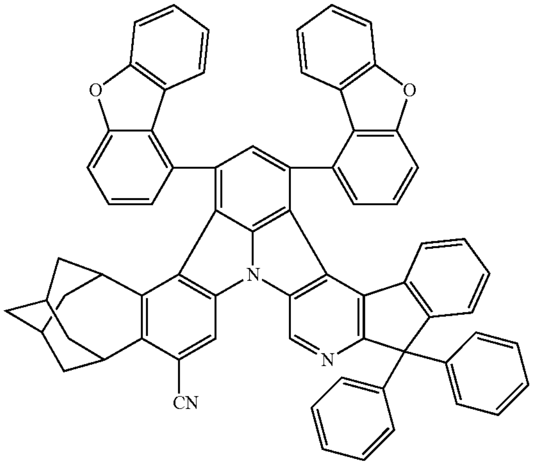 [SMILES: N#Cc1cc2c(c3c1C1CC4CC(C1)CC3C4)c1c(-c3cccc4oc5ccccc5c34)cc(-c3cccc4oc5ccccc5c34)c3c4c5c(ncc4n2c31)C(c1ccccc1)(c1ccccc1)c1ccccc1-5]
661
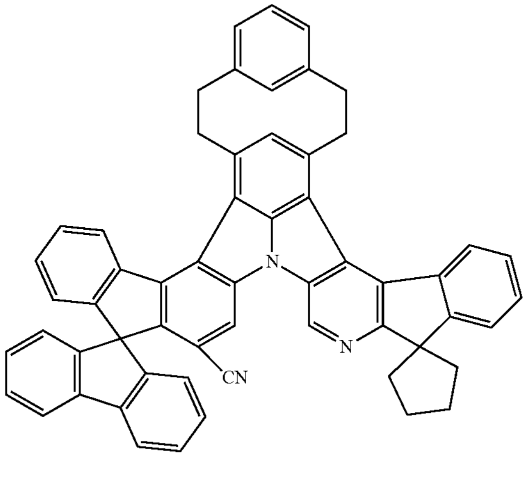 [SMILES: N#Cc1cc2c(c3c1C1(c4ccccc4-c4ccccc41)c1ccccc1-3)c1c3cc(c4c5c6c(ncc5n2c41)C1(CCCC1)c1ccccc1-6)CCc1cccc(c1)CC3]

-continued
662
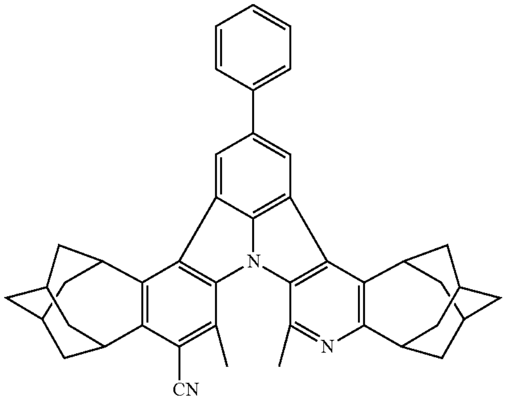 [SMILES: Cc1nc2c(c3c4cc(-c5ccccc5)cc5c6c7c(c(C#N)c(C)c6n(c13)c45)C1CC3CC(C1)CC7C3)C1CC3CC(CC2C3)C1]
663
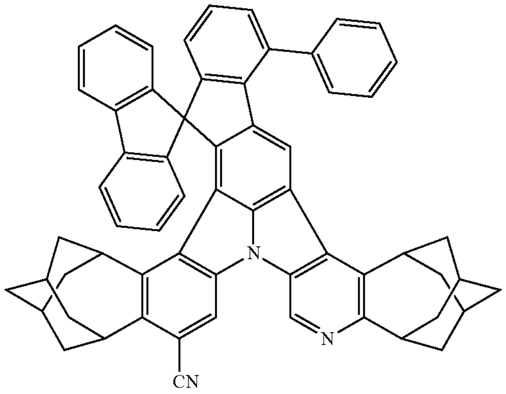 [SMILES: N#Cc1cc2c(c3c1C1CC4CC(C1)CC3C4)c1c3c(cc4c5c6c(ncc5n2c41)C1CC2CC(C1)CC6C2)-c1c(-c2ccccc2)cccc1C31c2ccccc2-c2ccccc21]
664
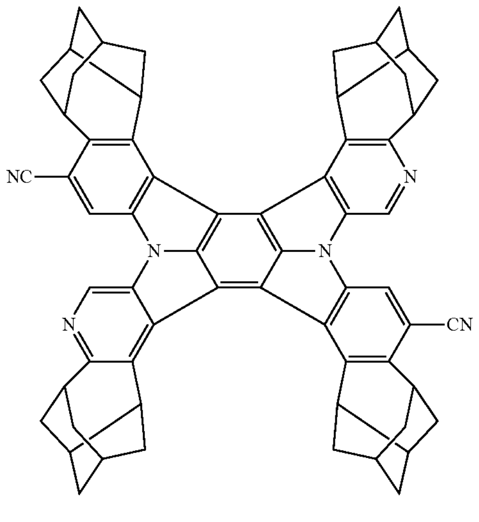 [SMILES: N#Cc1cc2c(c3c1C1CC4CC(C1)C3C4)c1c3c4c5c(ncc4n4c6cc(C#N)c7c(c6c(c6c8c9c(ncc8n2c61)C1CC2CC(C1)C9C2)c34)C1CC2CC7CC1C2)C1CC2CC(C1)C5C2]

-continued
665
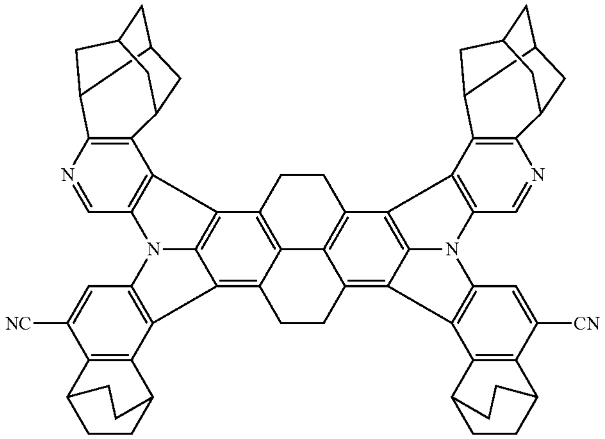 [SMILES: N#Cc1cc2c(c3c1C1CCC3CC1)c1c3c4c(c5c6c7c(ncc6n2c51)C1CC2CC7CC1C2)CCc1c-4c(c2c4c5c(c(C#N)cc4n4c6cnc7c(c6c1c24)C1CC2CC7CC1C2)C1CCC5CC1)CC3]
666
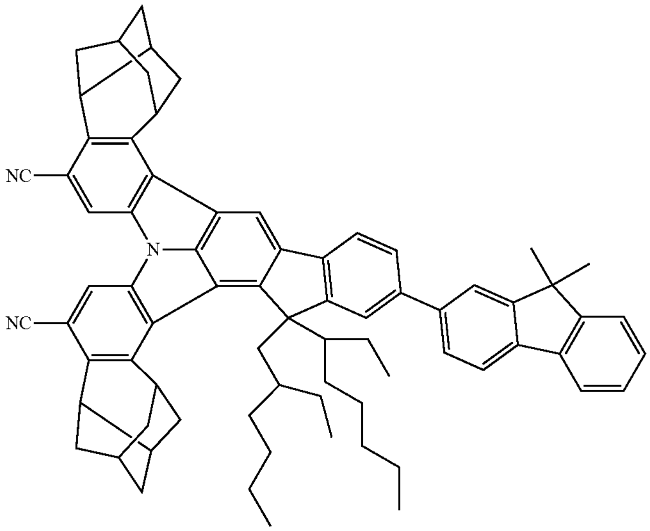 [SMILES: CCCCCC(CC)C1(CC(CC)CCCC)c2cc(-c3ccc4c(c3)C(C)(C)c3ccccc3-4)ccc2-c2cc3c4c5c(c(C#N)cc4n4c6cc(C#N)c7c(c6c(c21)c34)C1CC2CC(C1)C7C2)C1CC2CC5CC1C2]
667
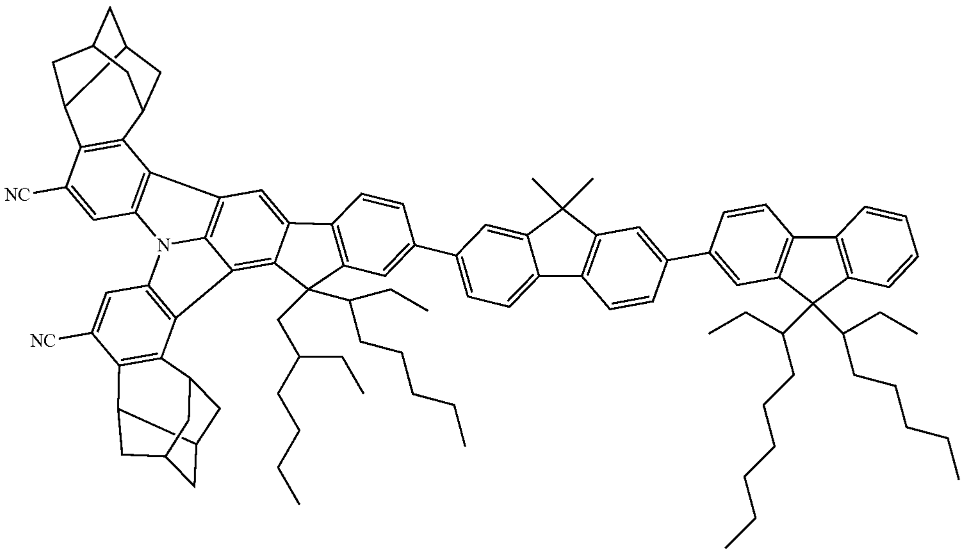 [SMILES: CCCCCCC(CC)C1(C(CC)CCCCC)c2ccccc2-c2ccc(-c3ccc4c(c3)C(C)(C)c3cc(-c5ccc6c(c5)C(CC(CC)CCCC)(C(CC)CCCCC)c5c-6cc6c7c8c(c(C#N)cc7n7c9cc(C#N)c%10c(c9c5c67)C5CC6CC(C5)C%10C6)C5CC6CC8CC5C6)ccc3-4)cc21]

-continued
668
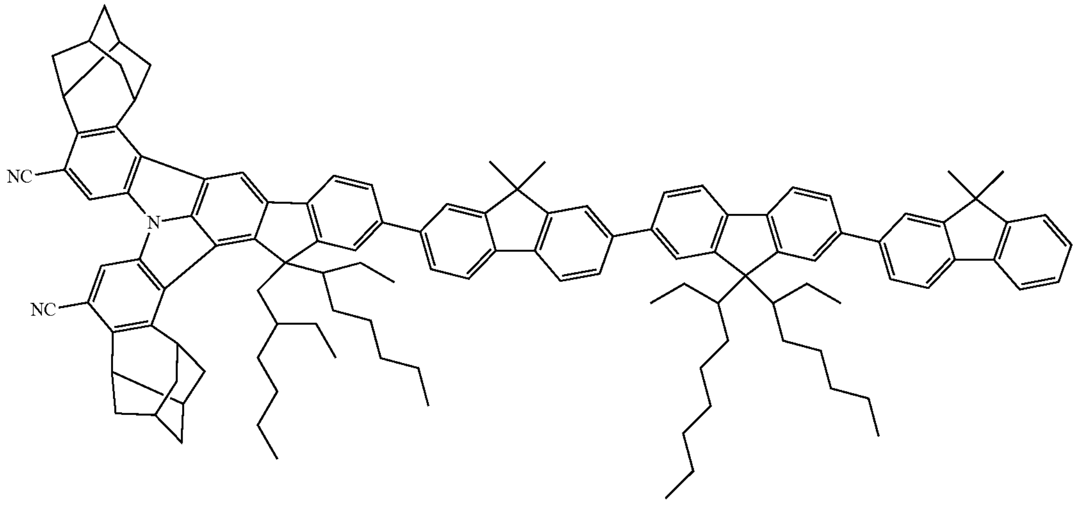 [SMILES: CCCCCCC(CC)C1(C(CC)CCCCC)c2cc(-c3ccc4c(c3)C(C)(C)c3ccccc3-4)ccc2-c2ccc(-c3ccc4c(c3)C(C)(C)c3cc(-c5ccc6c(c5)C(CC(CC)CCCC)(C(CC)CCCCC)c5c-6cc6c7c8c(c(C#N)cc7n7c9cc(C#N)c%10c(c9c5c67)C5CC6CC(C5)C%10C6)C5CC6CC8CC5C6)ccc3-4)cc21]
669
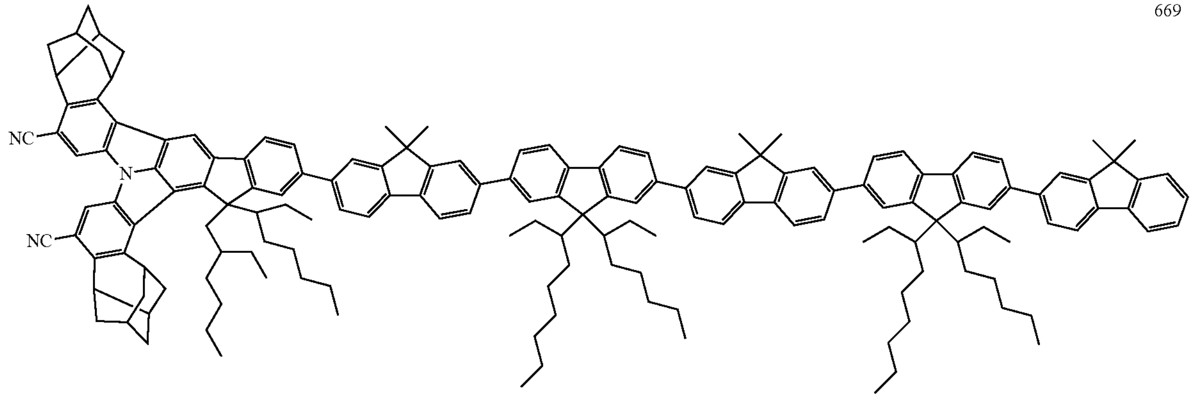 [SMILES: CCCCCCC(CC)C1(C(CC)CCCCC)c2cc(-c3ccc4c(c3)C(C)(C)c3ccccc3-4)ccc2-c2ccc(-c3ccc4c(c3)C(C)(C)c3cc(-c5ccc6c(c5)C(C(CC)CCCCC)(C(CC)CCCCCC)c5cc(-c7ccc8c(c7)C(C)(C)c7cc(-c9ccc%10c(c9)C(CC(CC)CCCC)(C(CC)CCCCC)c9c-%10cc%10c%11c%12c(c(C#N)cc%11n%11c%13cc(C#N)c%14c(c%13c9c%10%11)C9CC%10CC(C9)C%14C%10)C9CC%10CC%12CC9C%10)ccc7-8)ccc5-6)ccc3-4)cc21]
670
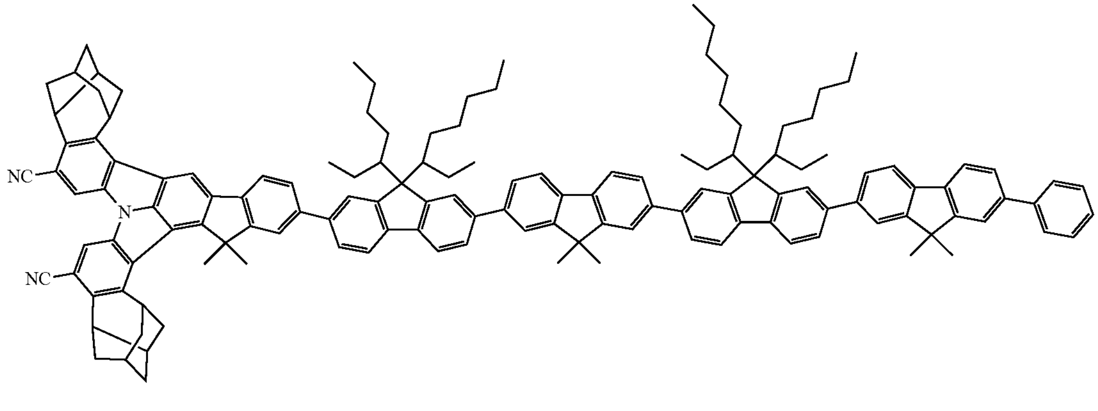 [SMILES: CCCCCCC(CC)C1(C(CC)CCCCC)c2cc(-c3ccc4c(c3)C(C)(C)c3cc(-c5ccccc5)ccc3-4)ccc2-c2ccc(-c3ccc4c(c3)C(C)(C)c3cc(-c5ccc6c(c5)C(C(CC)CCCC)(C(CC)CCCCC)c5cc(-c7ccc8c(c7)C(C)(C)c7c-8cc8c9c%10c(c(C#N)cc9n9c%11cc(C#N)c%12c(c%11c7c89)C7CC8CC(C7)C%12C8)C7CC8CC%10CC7C8)ccc5-6)ccc3-4)cc21]

-continued
671
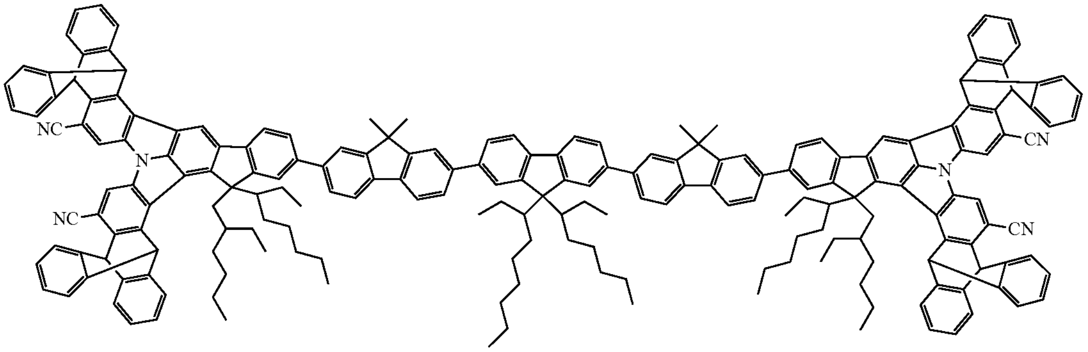 [SMILES: CCCCCCC(CC)C1(C(CC)CCCCC)c2cc(-c3ccc4c(c3)C(C)(C)c3cc(-c5ccc6c(c5)C(CC(CC)CCCC)(C(CC)CCCCC)c5c-6cc6c7c8c(c(C#N)cc7n7c9cc(C#N)c%10c(c9c5c67)C5c6ccccc6C%10c6ccccc65)C5c6ccccc6C8c6ccccc65)ccc3-4)ccc2-c2ccc(-c3ccc4c(c3)C(C)(C)c3cc(-c5ccc6c(c5)C(CC(CC)CCCC)(C(CC)CCCCC)c5c-6cc6c7c8c(c(C#N)cc7n7c9cc(C#N)c%10c(c9c5c67)C5c6ccccc6C%10c6ccccc65)C5c6ccccc6C8c6ccccc65)ccc3-4)cc21]
672
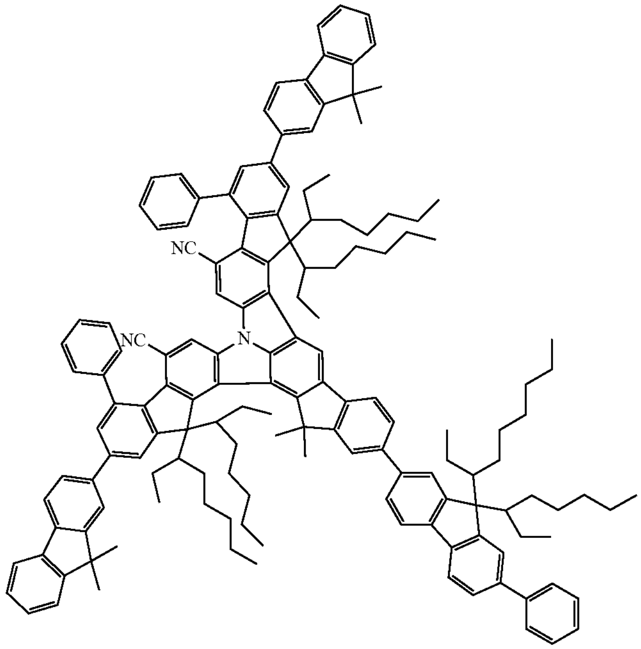 [SMILES: CCCCCCC(CC)C1(C(CC)CCCCC)c2cc(-c3ccccc3)ccc2-c2ccc(-c3ccc4c(c3)C(C)(C)c3c-4cc4c5c6c(c(C#N)cc5n5c7cc(C#N)c8c(c7c3c45)C(C(CC)CCCCC)(C(CC)CCCCC)c3cc(-c4ccc5c(c4)C(C)(C)c4ccccc4-5)cc(-c4ccccc4)c3-8)-c3c(-c4ccccc4)cc(-c4ccc5c(c4)C(C)(C)c4ccccc4-5)cc3C6(C(CC)CCCCC)C(CC)CCCCC)cc21]
$R = nC_8H_{17}$
673
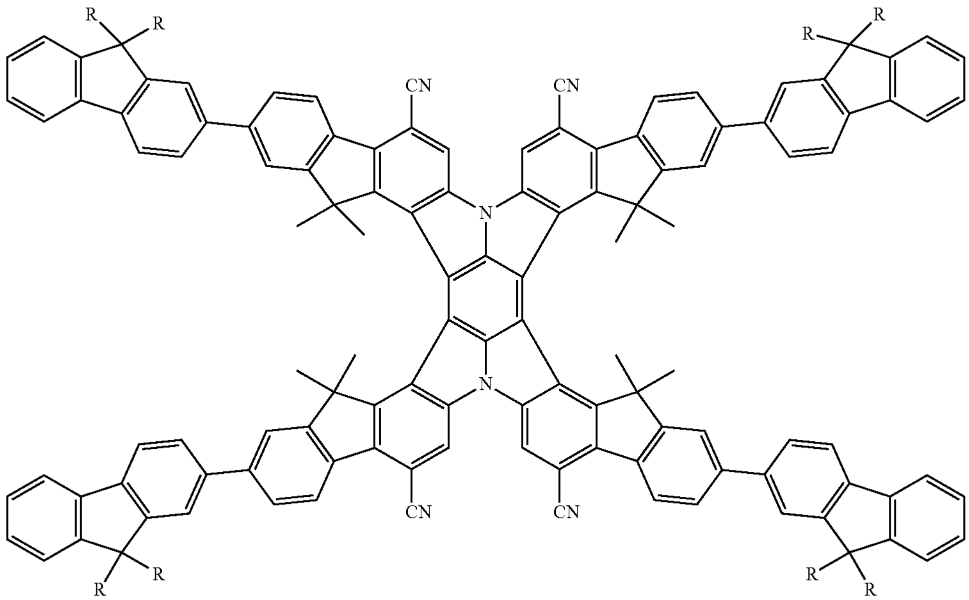

-continued

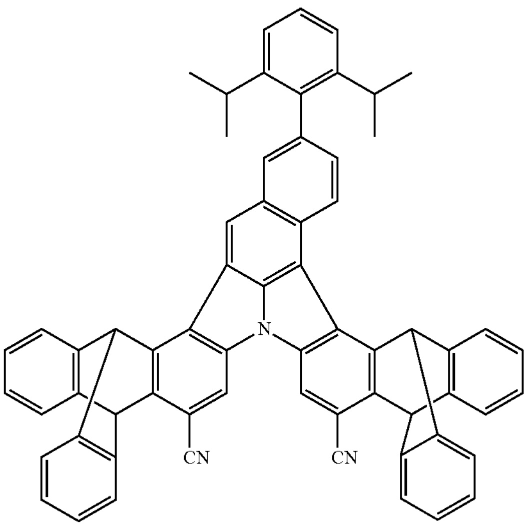 [SMILES: CC(C)c1cccc(C(C)C)c1-c1ccc2c(c1)cc1c3c4c(c(C#N)cc3n3c5cc(C#N)c6c(c5c2c13)C1c2ccccc2C6c2ccccc21)C1c2ccccc2C4c2ccccc21]

674

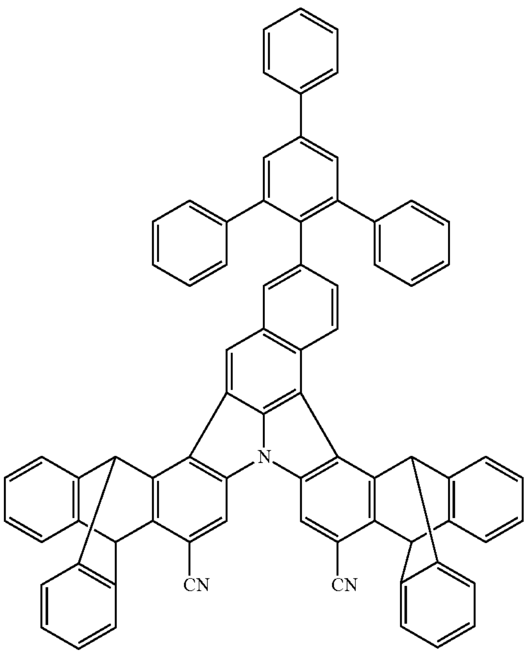 [SMILES: N#Cc1cc2c(c3c1C1c4ccccc4C3c3ccccc31)c1cc3cc(-c4c(-c5ccccc5)cc(-c5ccccc5)cc4-c4ccccc4)ccc3c3c4c5c(c(C#N)cc4n2c13)C1c2ccccc2C5c2ccccc21]

675

Preferred embodiments of compounds of the invention are recited in detail in the examples, these compounds being usable alone or in combination with further compounds for all purposes of the invention.

Provided that the conditions specified in claim 1 are met, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds of the invention, in which a base skeleton having an aromatic amino group is synthesized and at least one aromatic or heteroaromatic radical is introduced, preferably by means of a nucleophilic aromatic substitution reaction or a coupling reaction.

Suitable compounds comprising a base skeleton having an aromatic amino group are in many cases commercially available, and the starting compounds detailed in the examples are obtainable by known processes, and so reference is made thereto.

These compounds can be reacted with further compounds by known coupling reactions, the necessary conditions for this purpose being known to the person skilled in the art, and detailed specifications in the examples giving support to the person skilled in the art in conducting these reactions.

Particularly suitable and preferred coupling reactions which all lead to C—C bond formations and/or C—N bond formations are those according to BUCHWALD, SUZUKI, YAMAMOTO, STILLE, HECK, NEGISHI, SONO- GASHIRA and HIYAMA. These reactions are widely known, and the examples will provide the person skilled in the art with further pointers.

The principles of the preparation processes detailed above are known in principle from the literature for similar compounds and can be adapted easily by the person skilled in the art for the preparation of the compounds of the invention. Further information can be found in the examples.

It is possible by these methods, if necessary followed by purification, for example recrystallization or sublimation, to obtain the compounds of the invention in high purity, preferably more than 99% (determined by means of $^1$H NMR and/or HPLC).

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formula (I) and preferred embodiments of this formula or compounds of the invention, wherein one or more bonds of the compounds of the invention or of the structures of the formula (I) and preferred embodiments of that formula to the polymer, oligomer or dendrimer are present. According to the linkage of the structures of the formula (I) and preferred embodiments of this formula or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the formula (I) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation or a composition comprising at least one compound of the invention and at least one further compound. The further compound may, for example, be a solvent, especially one of the abovementioned solvents or a mixture of these solvents. If the further compound comprises a solvent, this mixture is referred to herein as formulation. The further compound may alternatively be at least one further organic or inorganic compound which is likewise used in the electronic device, for example an emitter and/or a matrix material, where these compounds differ from the compounds of the invention. Suitable emitters and matrix materials are listed at the back in connection with the organic electroluminescent device. The further compound may also be polymeric.

The present invention therefore still further provides a composition comprising a compound of the invention and at least one further organofunctional material. Functional materials are generally the organic or inorganic materials introduced between the anode and cathode. Preferably, the organically functional material is selected from the group consisting of fluorescent emitters, phosphorescent emitters, emitters that exhibit TADF (thermally activated delayed fluorescence), host materials, electron transport materials, electron injection materials, hole conductor materials, hole injection materials, electron blocker materials, hole blocker materials, wide bandgap materials and n-dopants, preferably host materials.

The present invention further provides for the use of a compound of the invention in an electronic device, especially in an organic electroluminescent device, preferably as emitter, more preferably as green, red or blue emitter, especially preferably as blue emitter. In this case, compounds of the invention preferably exhibit fluorescent properties and thus provide preferentially fluorescent emitters.

The present invention still further provides an electronic device comprising at least one compound of the invention. An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs, sOLED, PLEDs, LECs, etc.), preferably organic light-emitting diodes (OLEDs), organic light-emitting diodes based on small molecules (sOLEDs), organic light-emitting diodes based on polymers (PLEDs), light-emitting electrochemical cells (LECs), organic laser diodes (0-laser), organic plasmon-emitting devices (D. M. Koller et al., *Nature Photonics* 2008, 1-4), organic integrated circuits (0-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs) and organic electrical sensors, preferably organic electroluminescent devices (OLEDs, sOLED, PLEDs, LECs, etc.), more preferably organic light-emitting diodes (OLEDs), organic light-emitting diodes based on small molecules (sOLEDs), organic light-emitting diodes based on polymers (PLEDs), especially phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem electroluminescent device, especially for white-emitting OLEDs.

The compound of the invention may be used in different layers, according to the exact structure. Preference is given to an organic electroluminescent device comprising a compound of formula (I) or the above-detailed preferred embodiments in an emitting layer as emitter, preferably red, green or blue emitter, more preferably as blue emitter.

When the compound of the invention is used as emitter in an emitting layer, preference is given to using a suitable matrix material which is known as such.

A preferred mixture of the compound of the invention and a matrix material contains between 99% and 1% by volume, preferably between 98% and 10% by volume, more preferably between 97% and 60% by volume and especially between 95% and 80% by volume of matrix material, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, dibenzofuran derivatives, for example according to WO 2015/169412, WO 2016/015810, WO 2016/023608, WO 2017/148564 or WO 2017/148565, or biscarbazoles, for example according to JP 3139321 B2.

In addition, the co-host used may be a compound that does not take part in charge transport to a significant degree, if at all, as described, for example, in WO 2010/108579. Especially suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2009/124627 or in WO 2010/006680.

In a preferred configuration, a compound of the invention which is used as emitter is preferably used in combination with one or more phosphorescent materials (triplet emitters) and/or a compound which is a TADF (thermally activated delayed fluorescence) host material. Preference is given here to forming a hyperfluorescence and/or hyperphosphorescence system.

WO 2015/091716 A1 and WO 2016/193243 A1 disclose OLEDs containing both a phosphorescent compound and a fluorescent emitter in the emission layer, where the energy is transferred from the phosphorescent compound to the fluorescent emitter (hyperphosphorescence). In this context, the phosphorescent compound accordingly behaves as a host material. As the person skilled in the art knows, host materials have higher singlet and triplet energies as compared to the emitters in order that the energy from the host material can also be transferred to the emitter with maximum efficiency. The systems disclosed in the prior art have exactly such an energy relation.

Phosphorescence in the context of this invention is understood to mean luminescence from an excited state having higher spin multiplicity, i.e. a spin state>1, especially from an excited triplet state. In the context of this application, all luminescent complexes with transition metals or lanthanides, especially all iridium, platinum and copper complexes, shall be regarded as phosphorescent compounds.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186, WO 2018/001990, WO 2018/019687, WO 2018/019688, WO 2018/041769, WO 2018/054798, WO 2018/069196, WO 2018/069197, WO 2018/069273, WO 2018/178001, WO 2018/177981, WO 2019/020538, WO 2019/115423, WO 2019/158453 and WO 2019/179909. In general, all phosphorescent complexes as used for phosphorescent electroluminescent devices according to the prior art and as known to those skilled in the art in the field of organic electroluminescence are suitable, and the person skilled in the art will be able to use further phosphorescent complexes without exercising inventive skill.

A compound of the invention may preferably be used in combination with a TADF host material and/or a TADF emitter, as set out above.

The process referred to as thermally activated delayed fluorescence (TADF) is described, for example, by B. H. Uoyama et al., Nature 2012, Vol. 492, 234. In order to enable this process, a comparatively small singlet-triplet separation $\Delta E(S_1-T_1)$ of less than about 2000 $cm^{-1}$, for example, is needed in the emitter. In order to open up the $T_1 \rightarrow S_1$ transition which is spin-forbidden in principle, as well as the emitter, it is possible to provide a further compound in the matrix that has strong spin-orbit coupling, such that intersystem crossing is enabled via the spatial proximity and the interaction which is thus possible between the molecules, or the spin-orbit coupling is generated by means of a metal atom present in the emitter.

Sources of further valuable information relating to hyperfluorescence systems include WO2012/133188 (Idemitsu), WO2015/022974 (Kyushu Univ.), WO2015/098975 (Idemitsu), WO2020/053150 (Merck) and DE202019005189 (Merck).

Sources of further valuable information relating to hyperphosphorescence systems include WO2015/091716 A1, WO2016/193243 A1 (BASF), WO01/08230 A1 (Princeton Univ. (Mark Thompson)), US2005/0214575A1 (Fuji), WO2012/079673 (Merck), WO2020/053314 (Merck) and WO2020/053315 (Merck).

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (I) or the above-recited preferred embodiments.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

Formulations for applying a compound of formula (I) or the preferred embodiments thereof detailed above are novel. The present invention therefore further provides formulations containing at least one solvent and a compound according to formula (I) or the preferred embodiments thereof detailed above.

In addition, hybrid methods are possible, in which, for example, one or more layers are applied from solution and one or more further layers are applied by vapour deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention have the particular feature of an improved lifetime and higher colour purity with respect to the prior art. At the same time, the further electronic properties of the electroluminescent devices, such as efficiency or operating voltage, remain at least equally good. In a further variant, the compounds of the invention and the organic electroluminescent devices of the invention especially feature improved efficiency and/or operating voltage and higher lifetime compared to the prior art.

The compounds of the invention may also be used for colour conversion. They can preferably be used for colour conversion in light-emitting displays. Preferred fields of use are pixels in displays, areal elements in displays (signage) and lighting elements.

The light-emitting device here may be selected from the multitude of known devices. Two selected examples of light-emitting devices are LEDs and organic electroluminescent devices.

For the purpose of colour conversion, the compounds are incorporated into a composition which is then processed by known methods (spin-coating, slit-coating, bar coating, screenprinting, nozzle printing, inkjet printing, etc.) to give pixels or two-dimensional layers.

As well as one or more compounds of the invention, the compositions typically comprise crosslinkable components (monomers, oligomers, polymers), for example based on acrylates, acrylamides, polyesters, silicones etc., and one or more thermally or photochemically activatable starter components. It is additionally possible to introduce further components such as organic auxiliaries (antioxidants, stabilizers, levelling aids, viscosity moderators, etc.) or inorganic fillers ($SiO_2$, $TiO_2$, $Al_2O_3$, etc.). It may additionally be preferable when the composition contains one or more further fluorescent materials other than the compounds of the invention. Useful materials here include all fluorescent materials known to the person skilled in the art. It is possible to use inorganic or organic fluorescent materials.

The principle of colour conversion and of colour conversion films and the production and components thereof are well known to the person skilled in the art (e.g. WO 2017/054898 A1, WO2019/002239 A1, X. Bai et al., 30, SID DIGEST 2019, J. E. Kwon, J. A. Chem. Soc., 135, 0.30, 11239, 2013, W. H. Kim et al., Appl. Sci, 10, 2112, 2020).

The present invention therefore also relates to a composition comprising one or more compounds of the invention and a crosslinkable component. The crosslinkable component may be any desired components that the person skilled in the art would consider for this purpose. The crosslinkable component is preferably an acrylate, acrylamide, polyester or silicone, acrylates are very preferred. Very preferably, the composition, as well as one or more compounds of the invention and the crosslinkable component, also contains a starter component, and it is more preferable when the composition additionally contains one or more auxiliaries, which may include the abovementioned auxiliaries.

The present invention also further relates to a colour conversion film containing one or more of the compounds of the invention. Use of the colour conversion films enables achievement of efficient and pure emission colours with narrow emission bands. The colour conversion films may, for example, be applied to a blue-emitting organic electroluminescent device. The compounds of the invention absorb at least some of the light emitted by the organic electroluminescent device and re-emit light of longer wavelength (colour downconversion). According to which compounds of the invention are used, it is possible in this way to obtain efficient, pure-colour and narrow-band blue, green, yellow, red or infrared emissions. The compound of the invention is used in this case not as an electroluminescent component but as a photoluminescent component.

In addition, the present invention relates to a light-emitting device comprising an organic electroluminescent device and a colour conversion film. The colour conversion film is preferably disposed in the light exit region of the organic electroluminescent device.

The present invention further relates to colour conversion with the aid of the compounds of the invention in the agricultural industry, in order to alter the radiation emitted by a source, for example solar radiation or radiation from an artificial light source, such that biological material, preferably plants, algae or fungi, experiences tailored conditions. It is thus possible to optimize and influence the condition and growth of the biological material. For this purpose, the compounds of the invention are preferably introduced into a film. The compounds of the invention may alternatively be incorporated into roofs of greenhouses. A further possibility is the processing of the compounds of the invention in a solution or dispersion that can be sprayed directly onto the biological material.

The electronic devices of the invention, especially organic electroluminescent devices, are notable for one or more of the following surprising advantages over the prior art:

1. Electronic devices, especially organic electroluminescent devices comprising compounds of formula (I) or the preferred embodiments as emitters that have been recited above and hereinafter have very narrow emission bands having very low FWHM (Full Width Half Maximum) values, and lead to particularly pure-colour emission, recognizable by the low CIE y values. What is particularly surprising here is that both blue emitters having low FWHM values and emitters having low FWHM that emit in the green, yellow or red region of the colour spectrum are provided.
2. The emission bands, in the long-wave emission flank, often have a shoulder or secondary maximum respectively having less than 40%, often less than 30%, of the intensity of the main maximum. In top-emission OLED components, this leads to a favourably low viewing angle dependence of the colour impression, compared to prior art narrowband boron-containing emitters that often have no such shoulders or secondary maxima and show greater viewing angle dependence of the colour impression.
3. Electronic devices, especially organic electroluminescent devices, comprising compounds of formula (I) or the preferred embodiments recited above and hereinafter, especially as emitters, have a very good lifetime. In this context, these compounds especially bring about low roll-off, i.e. a small drop in power efficiency of the device at high luminances.
4. Electronic devices, especially organic electroluminescent devices, comprising compounds of formula (I) or the preferred embodiments as emitters that have been recited above and hereinafter, have excellent efficiency. In this context, compounds of the invention of formula (I) or the preferred embodiments recited above and hereinafter bring about a low operating voltage when used in electronic devices.

5. The inventive compounds of formula (I) or the preferred embodiments recited above and hereinafter exhibit very high stability and lifetime.
6. With compounds of formula (I) or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
   Exciton energy is transmitted from a matrix or host in the emission layer to the emitter, typically either via what is called Dexter transfer or via Förster transfer. Förster energy transfer (FRET) from a host or matrix to the emitter of the invention is particularly preferred here, since it is particularly efficient, which leads to electronic devices having particularly good performance data (for example efficiency, voltage and lifetime). It is found that energy is preferably transferred from a host or matrix to the compounds of the invention via Förster transfer.
7. Compounds of formula (I) or the preferred embodiments recited above and hereinafter have excellent glass film formation.
8. Compounds of formula (I) or the preferred embodiments recited above and hereinafter form very good films from solutions and show excellent solubility.

FIGURE

FIG. 1 shows the photoluminescence spectra (PL spectra) of compounds ES1, ES94 and 675, measured with a Hitachi F-4500 PL spectrometer in about $10^{-5}$ molar degassed toluene solution at room temperature (about 25° C.).

These abovementioned advantages are not accompanied by an inordinately high deterioration in the further electronic properties.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or stages are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in more detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere in dried solvents. The solvents and reagents can be purchased, for example, from Sigma-ALDRICH or ABCR. The respective figures in square brackets or the numbers quoted for individual compounds relate to the CAS numbers of the compounds known from the literature. In the case of compounds that can show multiple configurational isomers, enantiomers, diastereomers or tautomeric forms, one form is shown in a representative manner.

1) Preparation of the Synthons

1.1) Nitriles: Example S1

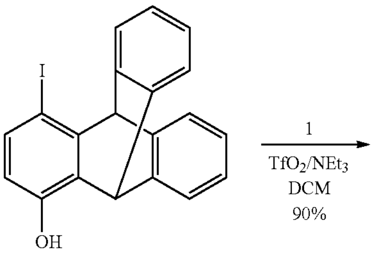

[1370032-70-4]

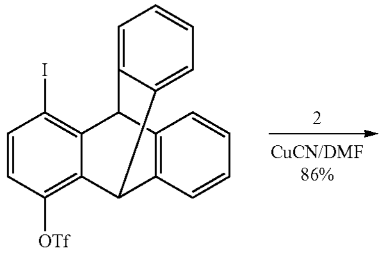

[1370032-72-6]

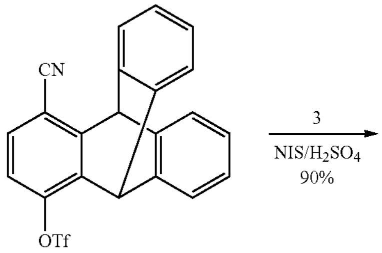

[1370032-64-6]

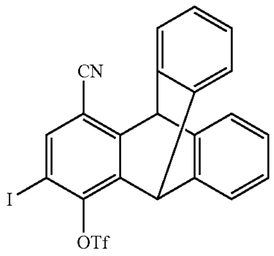

S1 can be prepared in 69% yield by the above route, according to the following literature:

Stages 1 and 2: W. S. Tan et al., J. Chin. Chem. Soc., 2012, 59, 399.

Stage 3: J. M. Herbert et al., J. Label. Compd. Radiopharm., 2007, 50, 440.

Purification is effected by flash chromatography using an automated column system (Combi-Flash Torrent, from Axel Semrau).

The following synthons can be prepared analogously:

| Ex. | Reactant | Product | Yield |
|---|---|---|---|
| S2 | 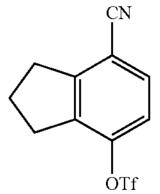 1403327-05-8, stage 3 | 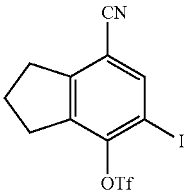 [SMILES: N#Cc1cc(I)c(OS(=O)(=O)C(F)(F)F)c2c1CCC2] | 85% |
| S3 | 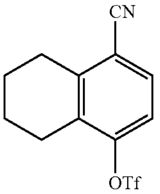 664364-61-8, stage 3 | 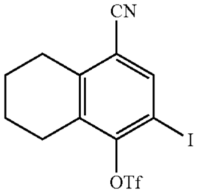 [SMILES: N#Cc1cc(I)c(OS(=O)(=O)C(F)(F)F)c2c1CCCC2] | 83% |
| S4 | 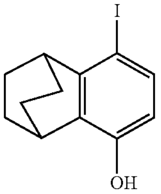 1560647-41-7, stages 1-3 | 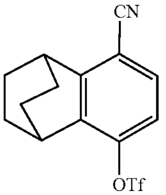 [SMILES: N#Cc1ccc(OS(=O)(=O)C(F)(F)F)c2c1C1CCC2CC1] | 64% |

Alternative Mode of Preparation:

Alternatively, S1 to S4 can be prepared in improved yield by the following route:

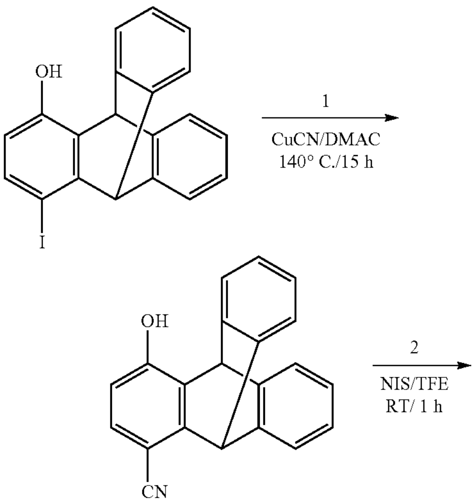

-continued

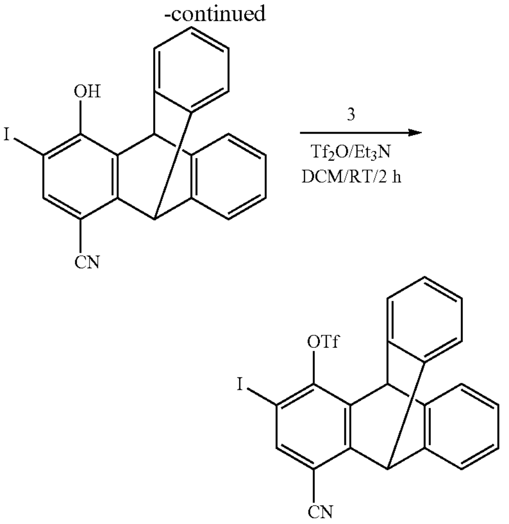

Stages 1 and 3: Analogously to W. S. Tan et al., J. Chin. Chem. Soc., 2012, 59, 399. Stage 1 yield ~95%; stage 3 yield quantitative.

Stage 2: Iodination with N-iodosuccinimide in trifluoroethanol (TFE) or hexafluoroisopropanol analogously to R.-J. Tang et al. J. Org. Chem., 2018, 83, 930. Yield 93%.

Example S1b

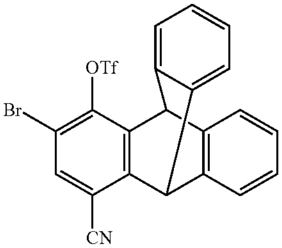 [SMILES: N#Cc1cc(Cl)c(OS(=O)(=O)C(F)(F)F)c2c1C1c3ccccc3C2c2ccccc21]

Analogously, the corresponding bromo triflates can be obtained by using N-bromosuccinimide. Yield over 3 stages 87%.

Example S1c

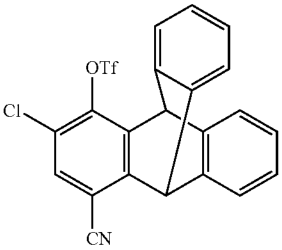

Analogously, the corresponding chloro triflates can be obtained by using N-chlorosuccinimide. Yield over 3 stages 69%.

Example S1d

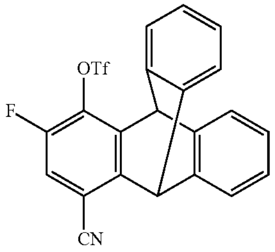 [SMILES: N#Cc1cc(F)c(OS(=O)(=O)C(F)(F)F)c2c1C1c3ccccc3C2c2ccccc21]

Analogously, the corresponding fluoro triflates can be obtained by fluorination in stage 2 analogously to R. D. Chambers et al., J. Fluor. Chem., 2000, 102, 169. Yield over 3 stages 30%.

Example S1e

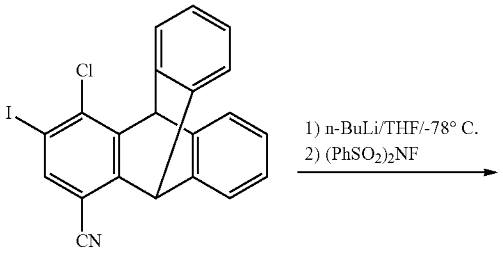

S10

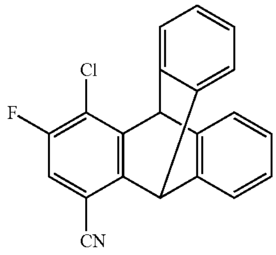

S1e

I-F exchange analogously to C. S. Hartley et al., Chem. Mater. 2004, 16, 5297. Yield 28%.

Alternatively, stage S1e can be prepared as follows:

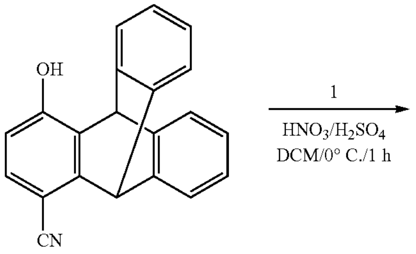

-continued

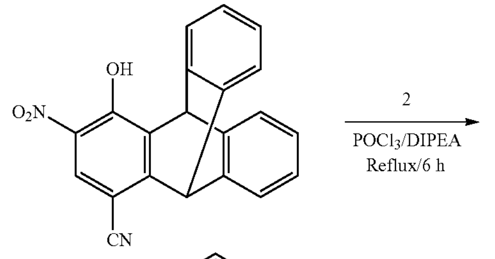

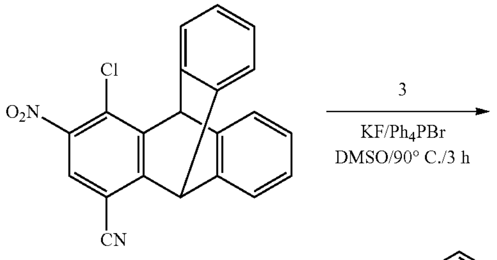

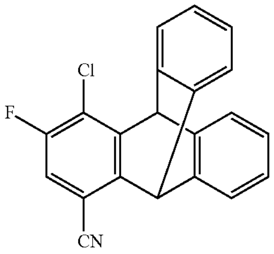

S1e

Stage 1: Analogously to M. A. Zolfigol et al., Molecules 2001, 6, 614. Yield: 93%.

Stage 2: G. Ralf et al. Journal fuer Praktische Chemie 1987, 329(6), 945. Yield 89%.

Stage 3: Analogously to J. H. Clark et al., Chem. & Ind. 1991, 436. Yield: 38%.

Optimized Synthesis of S1e

Stage 1

To a solution, cooled to 0° C., of 29.5 g (100 mmol) of 1-cyano-4-hydroxytriptycene is added dropwise a mixture of 19.0 g of 65% by weight nitric acid and 20.0 g of 96% by weight nitric acid over the course of 1 h. The mixture is stirred for a further 30 min and then poured cautiously (foaming!) with very good stirring onto a mixture of 37.8 g (450 mmol) of sodium hydrogencarbonate and 3 l of ice-water. The organic phase is separated off, the aqueous phase is extracted three times with 200 ml each time of DCM, and the combined organic phases are dried with saturated sodium chloride solution and over magnesium sulfate. The desiccant is filtered off, the DCM is removed under reduced pressure and the residue is chromatographed (silica gel, n-heptane/EA 5:1). Yield: 31.5 g (93 mmol), 93%; purity: about 98% by $^1$H NMR.

Stage 2

To a well-stirred mixture of 34.0 g (100 mmol) of 1-cyano-3-nitro-4-hydroxytriptycene and 93.5 ml (1 mol) of phosphoryl chloride is added 21.0 ml (120 mmol) of diisopropylethylamine (DIPEA), and the mixture is stirred under reflux for 4 h. The reaction mixture is poured gradually (exothermic, induction period!) onto 2 l of ice-water with very good stirring and stirred for a further 30 min. The aqueous phase is extracted five times with 200 ml each time of DCM, and the combined organic phases are dried with saturated sodium chloride solution and over magnesium sulfate. The desiccant is filtered off, the DCM is removed under reduced pressure and the residue is chromatographed (silica gel, n-heptane/EA 5:1). Yield: 40.1 g (89 mmol), 89%; purity: about 97% by $^{1}H$ NMR.

Stage 3

Analogously to J. H. Clark et al., Chem. & Ind. 1991, 436. Yield: 38%.

Alternatively, stage S1e can be prepared in improved yield as follows:

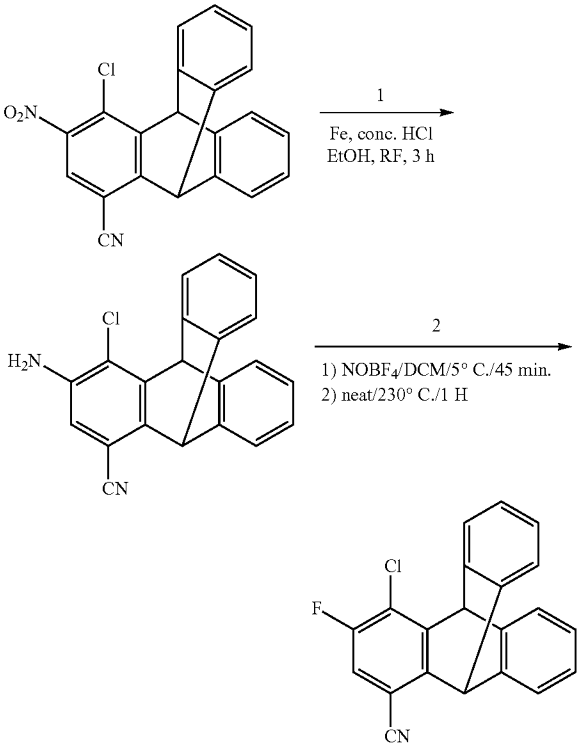

S1e

Stage 1: Analogously to S. Chandrappa et al., Synlett 2010, 3019. Yield: 87%.

Stage 2: D. J. Milner et al., Synth. Commun., 1992, 22(1), 73. Yield: 77%.

Optimized Synthesis of S1e:

Stage 1

To a well-stirred suspension of 35.9 g (100 mmol) of 1-cyano-3-nitro-4-chlorotriptycene and 25.1 g (450 mmol) of iron powder in 700 ml EtOH is added dropwise, under reflux over 30 minutes, 75.0 ml of 37% by weight aqueous hydrochloric acid (caution: evolution of hydrogen!). The mixture is stirred at reflux for another 3 h, allowed to cool, diluted with 2 l of water and 2 l of DCM, and alkalized with cautious addition (foaming!) of solid sodium carbonate (pH~9). The mixture is filtered with suction through Celite, the organic phase of the filtrate is separated off, the aqueous phase is extracted five times with 100 ml each time of DCM, and the combined organic phases are dried by washing twice with 300 ml each time of saturated sodium chloride solution and over magnesium sulfate. The desiccant is filtered off, the DCM is removed under reduced pressure, and the crude product is applied to Isolute and chromatographed (silica gel, n-heptane/DCM 1:1>1:2). Another chromatography step is performed if necessary until the product is obtained in white to pale beige form. Yield: 3-28.5 g (87 mmol), 87%; purity: about 98% by $^{1}H$ NMR.

Stage 2

To a well-stirred solution, cooled to 0° C., of 12.9 g (110 mmol) of nitrosyl tetrafluoroborate $[NO][BF_4]$ in 500 ml of DCM is added 32.9 g (100 mmol) of 1-cyano-3-amino-4-chlorotriptycene in portions over the course of 10 min. The mixture is stirred for a further 30 min, and the diazonium salt is filtered off, washed once with 100 ml of DCM/n-heptane (1:2, vv) and once with 100 ml of n-heptane and dried briefly under reduced pressure at RT. Yield: 40.6 g (97%).

The diazonium salt thus obtained is quenched in a rotating flask in a gentle argon stream at 220-230° C. until the evolution of nitrogen has ended (about 1 h). The cooled residue is extracted with 500 ml of DCM. The insoluble fractions are filtered off, the filtrate is concentrated to dryness and the residue is chromatographed (silica gel, n-heptane/DCM 2:1). Yield: 25.4 g (77 mmol); purity: about 98% by $^{1}H$ NMR.

The following synthons can be prepared analogously: Yield over 4 or 5 stages

| Ex. | Reactant | Product | Yield |
|---|---|---|---|
| S2e | 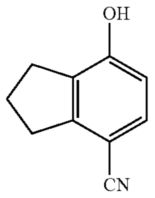 1403327-04-7 | 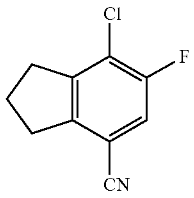 [SMILES: N#Cc1cc(F)c(Cl)c2c1CCC2] | 42% |
| S3e | 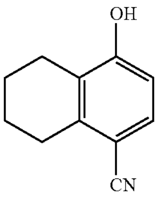 89682-91-7 | 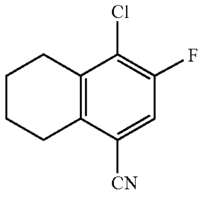 [SMILES: N#Cc1cc(F)c(Cl)c2c1CCCC2] | 44% |
| S4e | 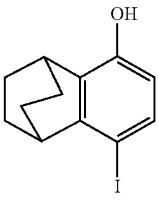 1560647-41-7 | 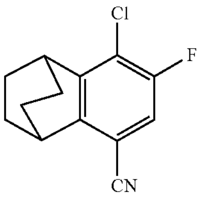 [SMILES: N#Cc1cc(F)c(Cl)c2c1C1CCC2CC1] | 35% |

Example S10

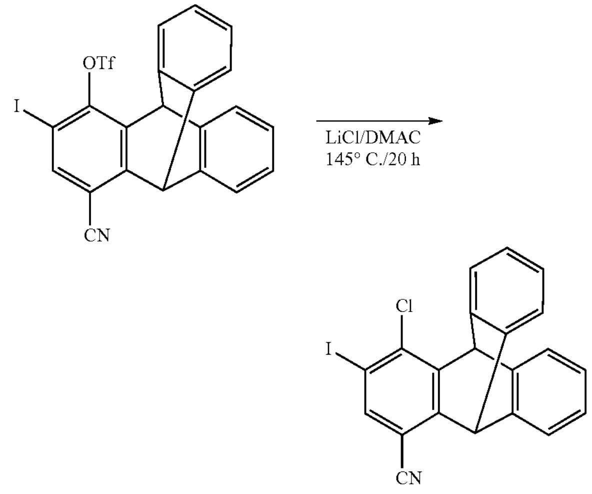

Procedure analogous to W. S. Tan et al., J. Chin. Chem. Soc., 2012, 59, 399. Rather than DMF, dimethylacetamide (DMAC) is used, which leads to improved yields. Yield: 66%.

Analogously to S1 (alternative mode of preparation) and S10, it is possible to prepare the following synthons:

| Ex. | Reactant | Product | Yield |
|---|---|---|---|
| S10b | S1b | 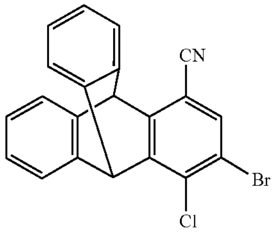 [SMILES: N#Cc1cc(Br)c(Cl)c2c1C1c3ccccc3C2c2ccccc21] | 68% |
| S11 | S2 | 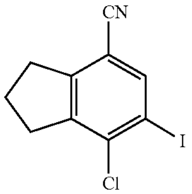 [SMILES: N#Cc1cc(I)c(Cl)c2c1CCC2] | 57% |
| S12 | S3 | 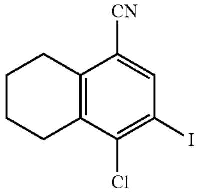 [SMILES: N#Cc1cc(I)c(Cl)c2c1CCCC2] | 64% |
| S13 | S4 | 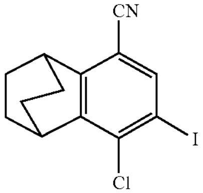 [SMILES: N#Cc1cc(I)c(Cl)c2c1C1CCC2CC1] | 57% |

-continued

| Ex. | Reactant | Product | Yield |
|---|---|---|---|
| S14 | 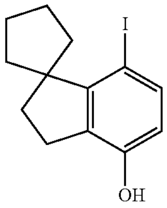 1588404-75-4 | 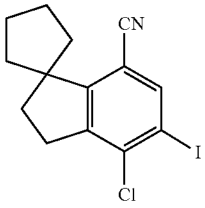 [SMILES: N#Cc1cc(I)c(Cl)c2c1C1(CCCC1)CC2] | 48% |
| S15 | 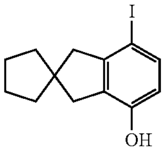 1419387-01-1 | 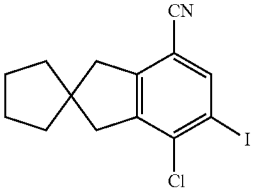 [SMILES: N#Cc1cc(I)c(Cl)c2c1CC1(CCCC1)C2] | 49% |
| S16 | 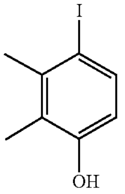 17938-69-1 | 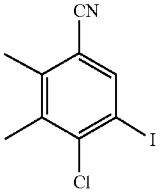 | 50% |
| S17 | 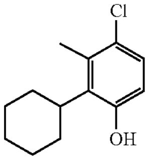 93257-53-5 | 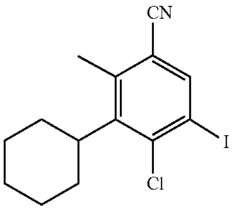 [SMILES: Cc1c(C#N)cc(I)c(Cl)c1C1CCCCC1] | 43% |

1.2) Bicyclic Ketones

Example S50

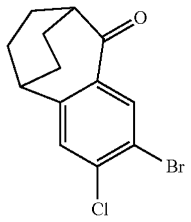 [SMILES: O=C1c2cc(Br)c(Cl)cc2C2CCC1CC2]

A) Via Grignard Route

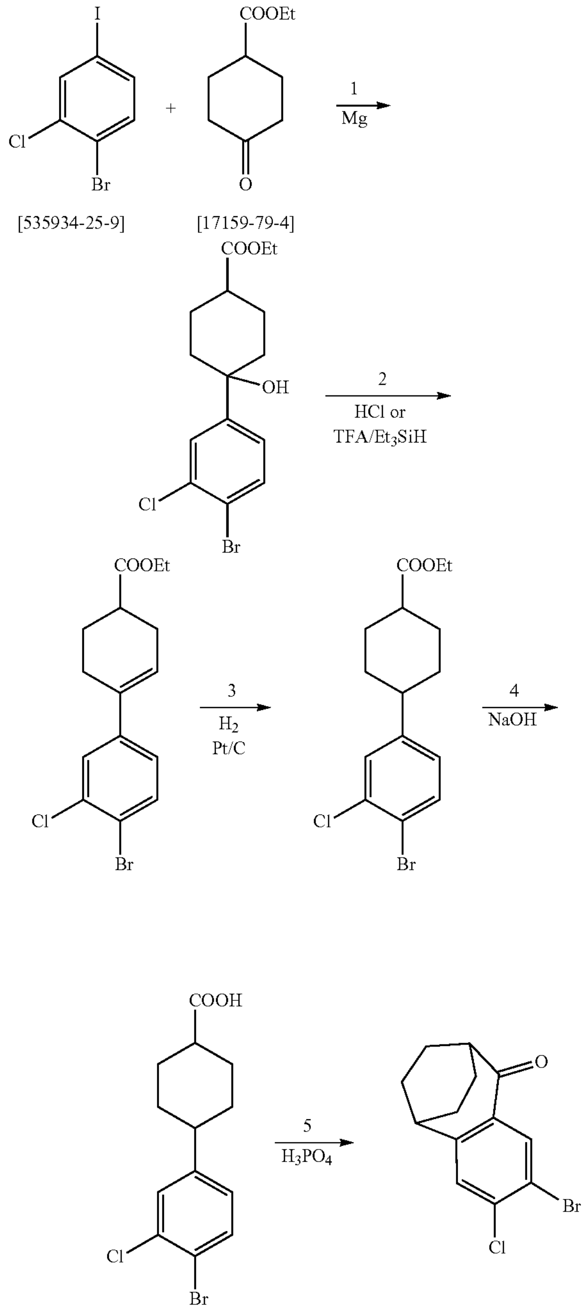

S50 can be prepared in 34% yield by the abovementioned Grignard route proceeding from the abovementioned reactants, according to the following literature:

Stages 1-4: B. M. Fox et al., J. Med. Chem., 2014, 52, 3464.

Stage 5: 1. Dragutan et al., Org. Prep. Proced., Int., 1975, 7, 2, 75.

The purification, especially the removal of regioisomers from the cyclization in stage 5, is effected via flash chromatography on an automated column system (Combi-Flash Torrent, from Axel Semrau).

B) Via Suzuki Route

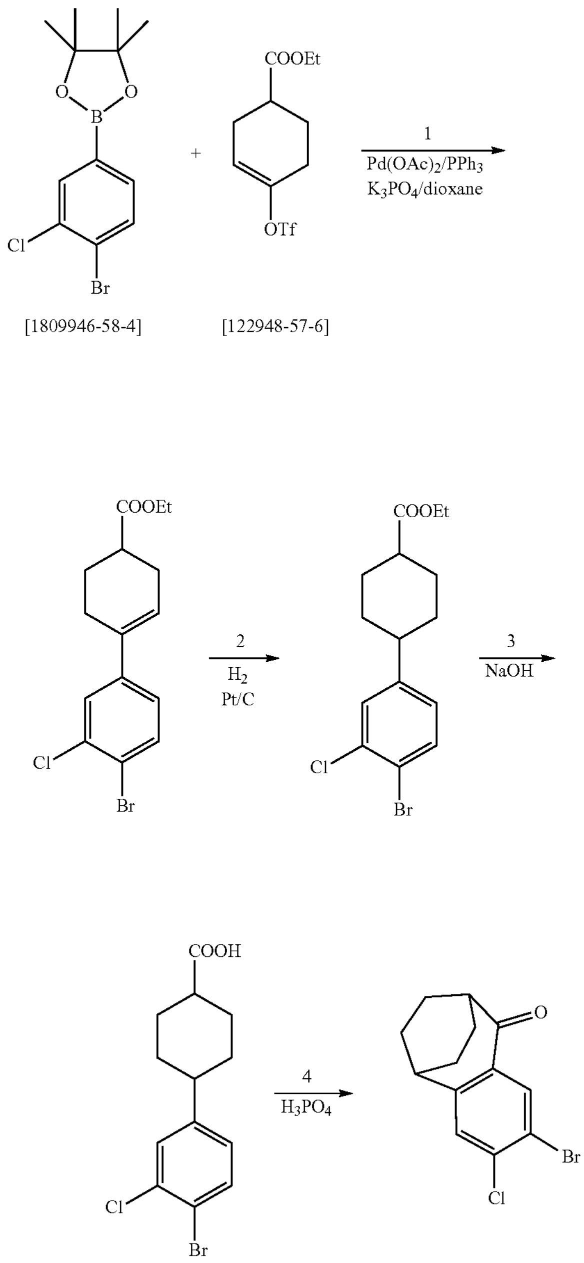

S50 can also be prepared in 41% yield by the abovementioned Suzuki route proceeding from the abovementioned reactants, according to the following literature:

Stages 1 to 3: C. Dolente et al., WO 2011/120877

Stage 4: 1. Dragutan et al., Org. Prep. Proced., Int., 1975, 7, 2, 75.

The purification, especially the removal of regioisomers from the cyclization in stage 4, is effected via flash chromatography on an automated column system (Combi-Flash Torrent, from Axel Semrau).

Example S51

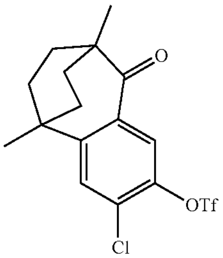 [SMILES: CC12CCC(C)(CC1)c1cc(Cl)c(OS(=O)(=O)C(F)(F)F)cc1C2=O]

C) Via Friedel-Crafts Alkylation and Acylation

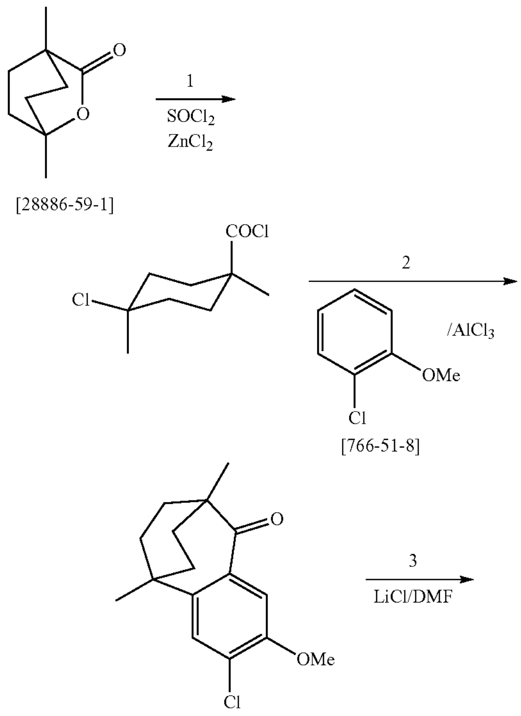

-continued

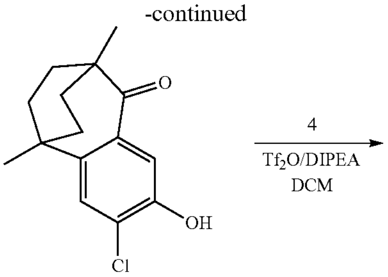

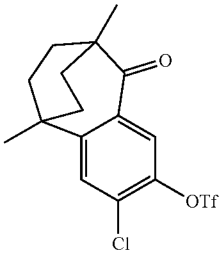

S51 can be prepared in 28% yield by the abovementioned Friedel-Crafts route, according to the following literature data, except using 2-chloroanisole rather than anisole:

Stage 1: Ismailov, A. G. et al, Nauch. Tr. Azerb. Un-t. Ser. Khim. N, 1979, (4), 47.

Stage 2: Ismailov, A. G. et al., Zhurnal Organicheskoi Khimii, 1978, 14(4), 811.

Stages 3 and 4: M. L. Maddess et al., Org. Process Res. Dev. 2014, 18, 528-538.

The purification, especially the removal of regioisomers from the cyclization in stage 2, is effected via flash chromatography on an automated column system (Combi-Flash Torrent, from Axel Semrau).

The following synthons can be prepared analogously:

| Ex. | Reactant | Product | Yield |
|---|---|---|---|
| S52 | 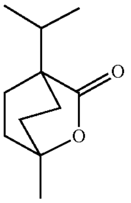 1222103-23-2 | 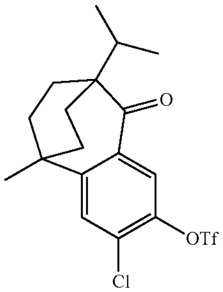 [SMILES: CC(C)C12CCC(C)(CC1)c1cc(Cl)c(OS(=O)(=O)C(F)(F)F)cc1C2=O] | 30% |

-continued
| Ex. | Reactant | Product | Yield |
|---|---|---|---|
| S53 | 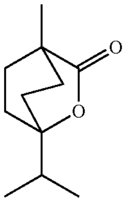 1222103-24-3 | 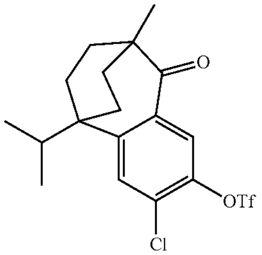 [SMILES: CC(C)C12CCC(C)(CC1)C(=O)c1cc(OS(=O)(=O)C(F)(F)F)c(Cl)cc12] | 23% |
| S54 | 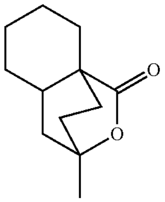 108793-30-2 | 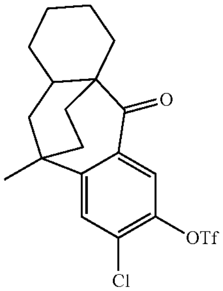 [SMILES: CC12CCC3(CCCCC3C1)C(=O)c1cc(OS(=O)(=O)C(F)(F)F)c(Cl)cc12] | 27% |
| S55 | 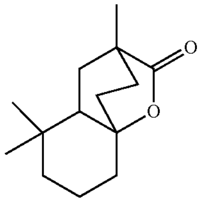 21280-29-5 | 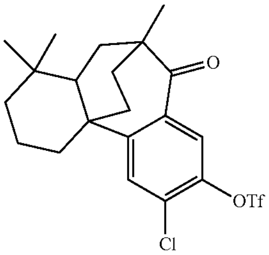 [SMILES: CC12CCC3(CCCC(C)(C)C3C1)c1cc(Cl)c(OS(=O)(=O)C(F)(F)F)cc1C2=O] | 25% |
| S56 | 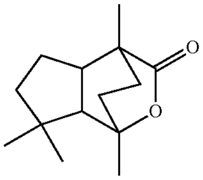 64390-25-6 | 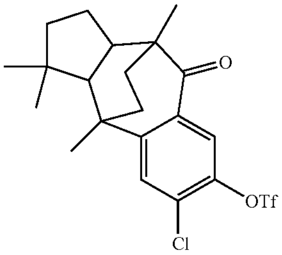 [SMILES: CC1(C)CCC2C1C1(C)CCC2(C)C(=O)c2cc(OS(=O)(=O)C(F)(F)F)c(Cl)cc21] | 22% |
| S57 | 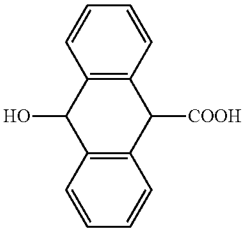 1076197-47-1 | 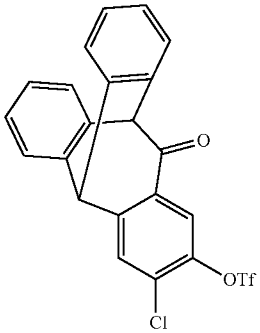 [SMILES: O=C1c2cc(OS(=O)(=O)C(F)(F)F)c(Cl)cc2C2c3ccccc3C1c1ccccc12] | 30% |

Example S58

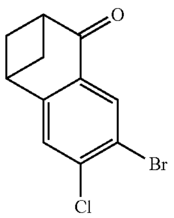 [SMILES: O=C1c2cc(Br)c(Cl)cc2C2CC1C2]

S58 can be prepared in 55% yield by the abovementioned Grignard route A) in accordance with the above-cited literature or by the Grignard route described by G. M. Castanedo et al., J. Med. Chem., 2017, 60, 627, by using 1-bromo-2-chloro-4-iodobenzene rather than 1-bromo-2-fluoro-4-iodobenzene.

1.3) Synthesis of the Substituted Iodochloropyridines

Synthesis Scheme Using the Example of a Homoadamantane Enamine

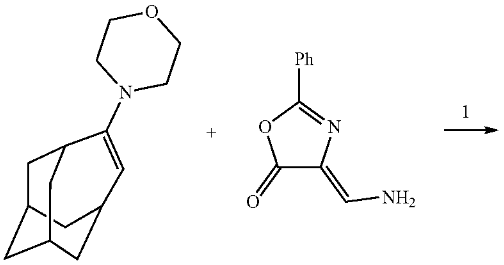

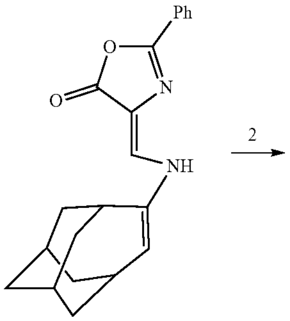

-continued

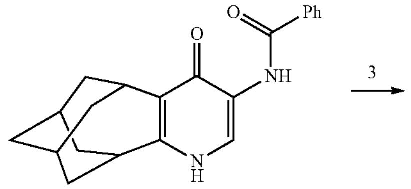

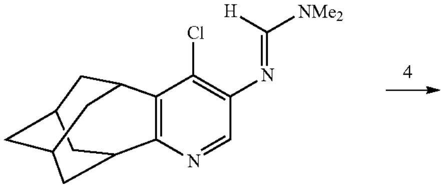

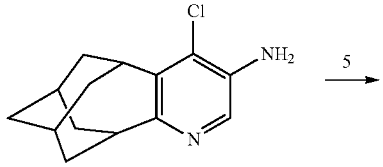

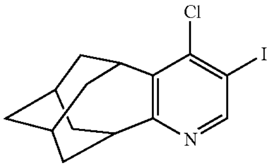

Stages 1 to 5 are conducted analogously to syntheses known from the literature:

Stages 1 to 4: M. Adachi et al., Tetrahedron Letters, 37 (49), 8871, 1996; EP 0 556 008 B1.

Stage 5: J. D. Eckelbarger et al., U.S. Pat. No. 8,835,409; E. A. Krasnokutskaya et al., Synthesis, 2007, 1, 81.

A) Synthesis of Enamines

The enamines can be prepared by the process detailed in WO 2020/06466, page 108, from the ketones shown and morpholine in yields of about 60-80%, or are known from the literature.

| Ex. | Reactant<br>Ketone / morpholine | Product<br>Enamine |
|---|---|---|
| S100 | 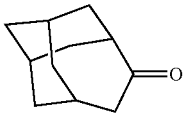<br>24669-56-5 | 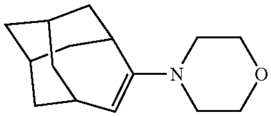 [SMILES: C1=C(N2CCOCC2)C2CC3CC1CC(C3)C2] |
| S101 | 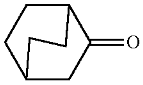<br>2716-23-6 | 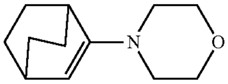 [SMILES: C1=C(N2CCOCC2)C2CCC1CC2] |
| S102 | 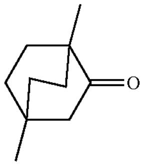<br>59117-09-8 | 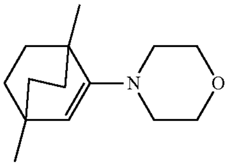 [SMILES: CC12C=C(N3CCOCC3)C(C)(CC1)CC2] |
| S103 | 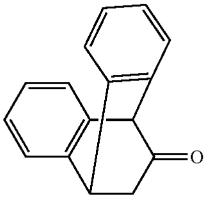<br>6372-63-0 | 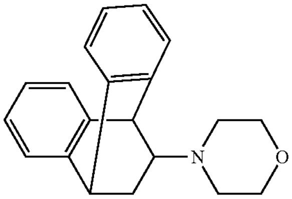 [SMILES: c1ccc2c(c1)C1CC(N3CCOCC3)C2c2ccccc21] |
| S104 | 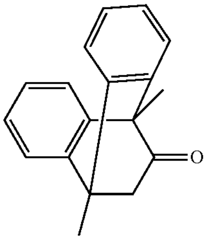<br>73164-06-4 | 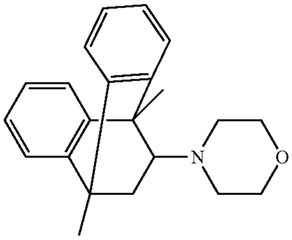 [SMILES: CC12CC(N3CCOCC3)C(C)(c3ccccc31)c1ccccc12] |
| S105 | 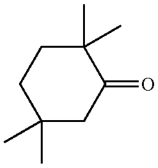<br>15189-14-7 | 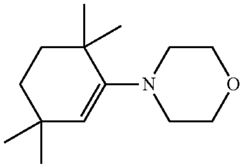 [SMILES: CC1(C)C=C(N2CCOCC2)C(C)(C)CC1] |
| S106 | 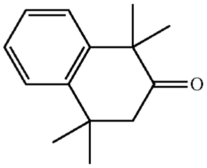<br>6308-02-7 | 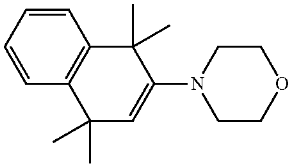 [SMILES: CC1(C)C=C(N2CCOCC2)C(C)(C)c2ccccc21] |

-continued
| Ex. | Reactant<br>Ketone / morpholine | Product<br>Enamine |
|---|---|---|
| S107 | 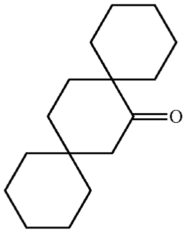<br>1781-82-4 | 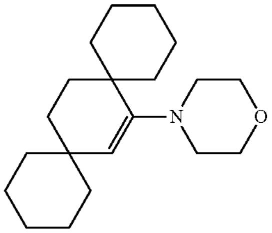 [SMILES: C1=C(N2CCOCC2)C2(CCCCC2)CCC12CCCCC2] |
| S108 | 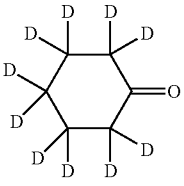<br>51209-49-5 | 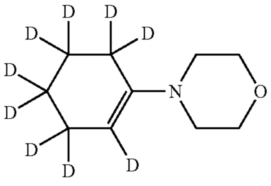 [SMILES: [2H]C1=C(N2CCOCC2)C([2H])([2H])C([2H])([2H])C([2H])([2H])C1([2H])[2H]] |
| S109 | 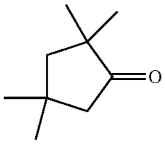<br>4694-115 | 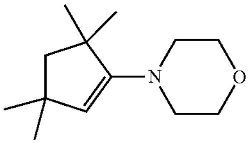 |
| S110 | 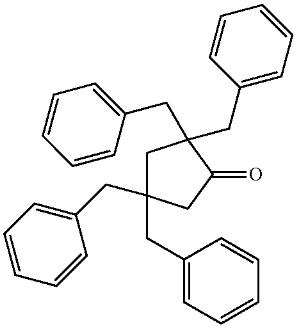<br>96676-35-6 | 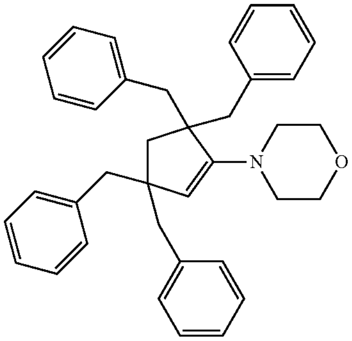 [SMILES: C1=C(N2CCOCC2)C(Cc2ccccc2)(Cc2ccccc2)CC1(Cc1ccccc1)Cc1ccccc1] |
| S111 | 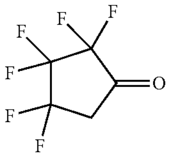<br>180690-80-6 | 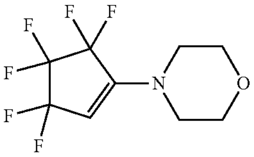 [SMILES: FC1(F)C=C(N2CCOCC2)C(F)(F)C1(F)F] |
| S112 | — | 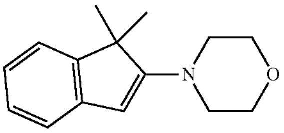<br>124032-58-2 |

-continued
| Ex. | Reactant<br>Ketone / morpholine | Product<br>Enamine |
|---|---|---|
| S113 | 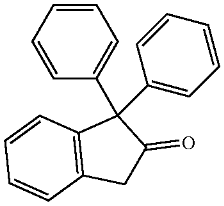<br>54193-73-6 | 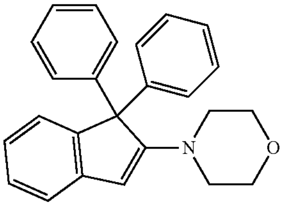 [SMILES: C1=C(N2CCOCC2)C(c2ccccc2)(c2ccccc2)c2ccccc21] |
| S114 | 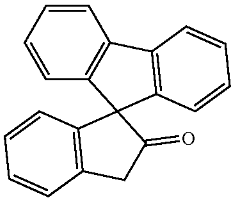<br>126495-32-7 | 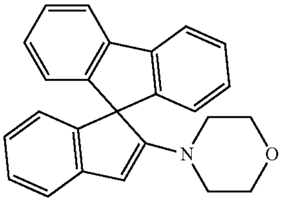 [SMILES: C1=C(N2CCOCC2)C2(c3ccccc31)c1ccccc1-c1ccccc12] |
| S115 | — | 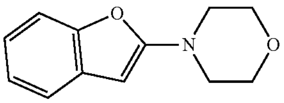<br>1195901-19-9 |
| S116 | — | 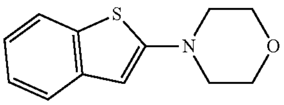<br>73129-56-3 |
| S117 | 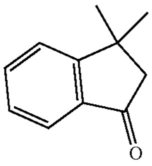<br>26465-81-6 | 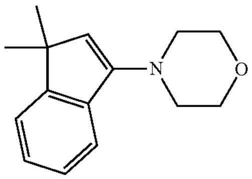 [SMILES: CC1(C)C=C(N2CCOCC2)c2ccccc21] |
| S118 | 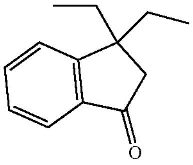<br>26465-81-6 | 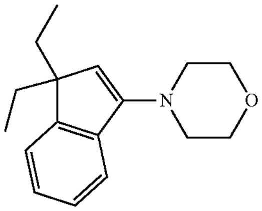 [SMILES: CCC1(CC)C=C(N2CCOCC2)c2ccccc21] |
| S119 | 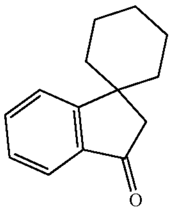<br>36449-72-6 | 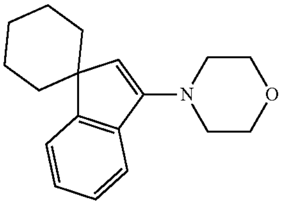 [SMILES: C1=C(N2CCOCC2)c2ccccc2C12CCCCC2] |

-continued

| Ex. | Reactant Ketone / morpholine | Product Enamine |
|---|---|---|
| S120 | 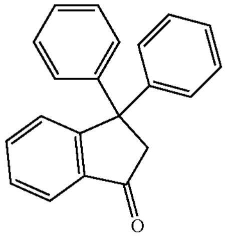 55010-17-8 | 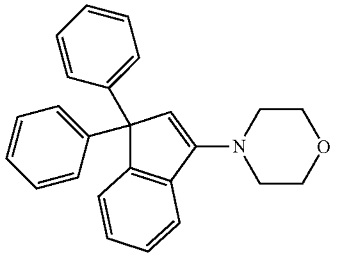 [SMILES: C1=C(N2CCOCC2)c2ccccc2C1(c1ccccc1)c1ccccc1] |
| S121 | 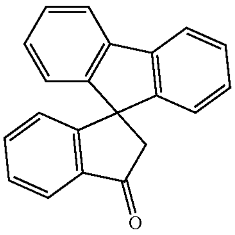 866762-72-3 | 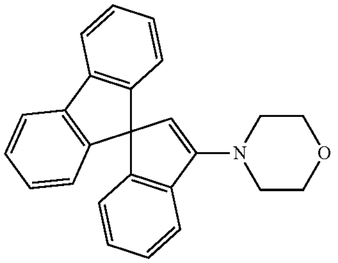 [SMILES: C1=C(N2CCOCC2)c2ccccc2C12c1ccccc1-c1ccccc12] |
| S122 | — | 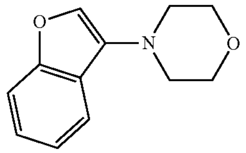 56639-83-9 |

B) Synthesis of the Substituted Pyridines

Stage 1: Example S200

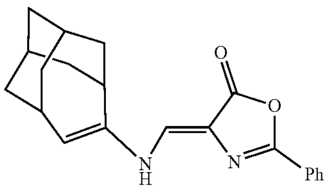 [SMILES: O=C1OC(c2ccccc2)=N/C1=C\NC1=CC2CC3CC(C2)CC1C3]

A mixture of 23.3 g (100 mmol) of S100 (analogously for the other 6- and 7-membered enamines), 22.6 g (120 mmol) of 4-(aminomethylene)-2-phenyl-5(4H)-oxazolone [3674-51-9], 47.3 ml (500 mmol) of acetic anhydride [108-24-7] and 150 ml of toluene is stirred at 100° C. for 4 h (5-membered enamines are converted in o-xylene at 130° C./4 h in an autoclave). The mixture is concentrated completely under reduced pressure, 70 ml of methanol is added to the oil, the mixture is stirred for a further 3 h, and the crystallized product is filtered off with suction, washed once with 25 ml of ice-cold methanol and dried under reduced pressure. The crude product thus obtained is converted further without purification. Yield: 26.2 g (78 mmol), 78% E,Z isomer mixture; purity: about 95% by $^1H$ NMR.

Stage 2: Example S300

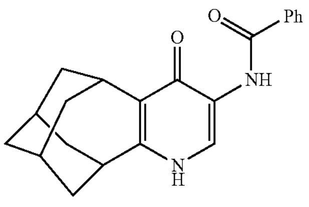 [SMILES: O=C(Nc1c[nH]c2c(c1=O)C1CC3CC(CC2C3)C1)c1ccccc1]

A mixture of 33.4 g (100 mmol) S200 and 200 ml of 1-methyl-2-pyrrolidinone (NMP) is stirred at 200-205° C. for 1.5 h. The mixture is allowed to cool to about 100° C., the NMP is largely removed under reduced pressure, the glassy, viscous residue is taken up in 100 ml of warm acetonitrile, stirred at room temperature for a further 12 h, and the crystallite product is filtered off and dried under reduced pressure. Yield: 25.1 g (75 mmol), 75%; purity: about 95% by $^1H$ NMR.

Stage 3: Example S400

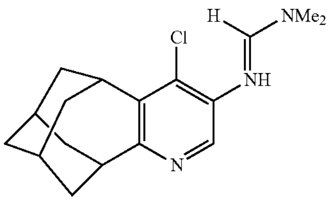 [SMILES: CN(C)/C=N/c1cnc2c(c1Cl)C1CC3CC(CC2C3)C1]

To a suspension of 33.4 g (100 mmol) of S300 in a mixture of 150 ml of N,N-dimethylformamide (DMF), under ice-salt cooling (about −10° C.), is added dropwise 14.0 ml (150 mmol) of phosphoryl chloride in 50 ml of DMF, and then the mixture is stirred at room temperature for a further 16 h. The reaction mixture is poured cautiously onto 1000 ml of ice-water and stirred for a further 10 min, 200 ml of dichloromethane (DCM) is added, the mixture is stirred for a further 10 min, and the organic phase is removed. The aqueous phase is basified (pH 8-9) with cautious addition of conc. aqueous ammonia solution, the aqueous phase is extracted three times with 200 ml each time of ethyl acetate, and the combined ethyl acetate extracts are washed twice with 200 ml each time of ice-water, once with 200 ml of saturated sodium hydrogencarbonate solution and twice with 100 ml each time of saturated sodium chloride solution. The mixture is dried over a mixture of magnesium sulfate and sodium carbonate, the desiccant is filtered off, the organic phase is concentrated under reduced pressure and the residue is recrystallized once from acetonitrile with addition of ethyl acetate (EA). Yield: 24.7 g (81 mmol), 81%; purity: about 95% by $^1$H NMR.

Stage 4: Example S500

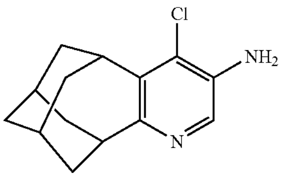 [SMILES: Nc1cnc2c(c1Cl)C1CC3CC(CC2C3)C1]

A mixture of 30.4 g (100 mmol) of S400, 100 ml of 3 N sulfuric acid and 200 ml of dioxane is stirred at 100° C. for 1.5 h. After cooling, the reaction mixture is diluted with 1000 ml of ice-water and then adjusted to pH~7.5 with 3 N NaOH while cooling with ice. The aqueous phase is extracted three times with 200 ml each time of DCM, and the combined organic phases are washed twice with 200 ml of water and once with 200 ml of saturated sodium chloride solution, and dried over magnesium sulfate. The desiccant is filtered off, the filtrate is concentrated to dryness and the solids are recrystallized from methanol. Yield: 23.1 g (93 mmol), 93%; purity: about 95% by $^1$H NMR.

Stage 5: Example S600

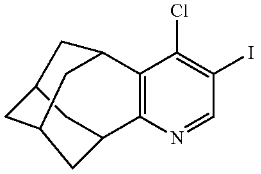 [SMILES: Clc1c(I)cnc2c1C1CC3CC(CC2C3)C1]

Variant 1

24.9 g (100 mmol) of S500 is introduced with good stirring into 500 ml of concentrated hydrochloric acid cooled to 3-5° C. To the suspension is added dropwise, with good stirring over the course of 15 min, a cooled solution of 10.4 g (150 mmol) of sodium nitrite in 50 ml of water, and then the mixture is stirred at 5° C. for about a further 20 min. The diazonium solution thus obtained is poured into a well-stirred solution, cooled to 5° C., of 90.0 g (600 mmol) of potassium iodide in 5000 ml of water to which 1000 ml of DCM has been added (caution: foaming!). After evolution of nitrogen has ended (about 25 min), sodium bisulfite solution is added until decolorization, and the pH is adjusted cautiously to ~7.5 with 5 N NaOH under very good cooling. The mixture is diluted with a further 1500 ml of DCM, the organic phase is removed, the aqueous phase is re-extracted twice with 500 ml each time of DCM, and the combined organic phases are washed twice with 500 ml each time of water and twice with 500 ml each time of saturated sodium chloride solution and then dried over magnesium sulfate. After the DCM has been removed under reduced pressure, the residue is subjected to flash chromatography (Combi-Flash Torrent from A. Semrau). Yield: 22.9 g (63 mmol), 63%; purity: about 97% by $^1$H NMR.

Variant 2

To a solution of 24.9 g (100 mmol) of S500 in 500 ml of acetonitrile is added 57.1 g (300 mmol) of p-toluenesulfonic acid monohydrate [6192-52-5] in portions, and then the mixture is cooled to 10° C. in an ice bath. To the suspension is added in portions, with good stirring and ice cooling, a solution of 13.9 g (200 mmol) of sodium nitrite and 37.5 g (250 mmol) of potassium iodide in 60 ml of water, and the mixture is stirred at 10° C. for 15 min. The mixture is then allowed to warm up to room temperature and stirred for a further 70 min. Then the mixture is diluted with 1500 ml of water, adjusted to pH 9.5 by adding saturated sodium hydrogen carbonate solution and admixed with 200 ml of 2M sodium bisulfite solution. The precipitated crude product is filtered off with suction, washed twice with 50 ml each time of water and briefly dried by suction. The crude product is dissolved in 500 ml of DCM, the solution is dried over sodium sulfate, the desiccant is filtered off with suction and the crude product is applied to Isolute. Purification is effected by flash chromatography (Combi-Flash Torrent from A. Semrau). Yield: 25.0 g (72 mmol), 72%; purity: about 97% by 1H NMR.

The following pyridines can be obtained analogously to stages 1 to 5. Yield over five stages (stages 1-5):
| Ex. | Enamine | Product | Yield |
|---|---|---|---|
| S601 | S101 | 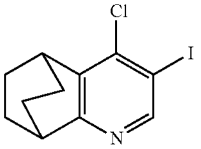 [SMILES: Clc1c(I)cnc2c1C1CCC2CC1] | 28% |
| S602 | S102 | 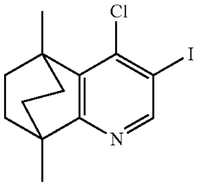 [SMILES: CC12CCC(C)(CC1)c1c2ncc(I)c1Cl] | 25% |
| S603 | S103 | 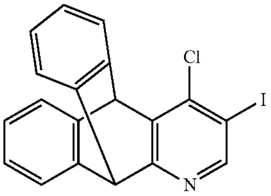 [SMILES: Clc1c(I)cnc2c1C1c3ccccc3C2c2ccccc21] | 30% |
| S604 | S104 | 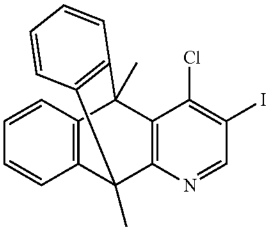 [SMILES: CC12c3ccccc3C(C)(c3ccccc31)c1c2ncc(I)c1Cl] | 23% |
| S605 | S105 | 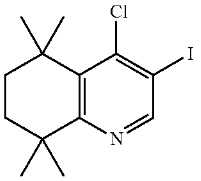 [SMILES: CC1(C)CCC(C)(C)c2c1ncc(I)c2Cl] | 24% |
| S606 | S106 | 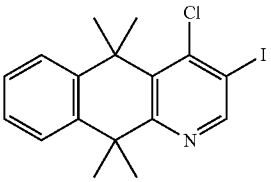 [SMILES: CC1(C)c2ccccc2C(C)(C)c2c1ncc(I)c2Cl] | 26% |
| S607 | S107 | 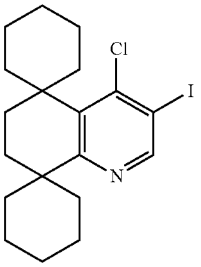 [SMILES: Clc1c(I)cnc2c1C1(CCCCC1)CCC21CCCCC1] | 19% |
-continued
| Ex. | Enamine | Product | Yield |
|---|---|---|---|
| S608 | S108 | 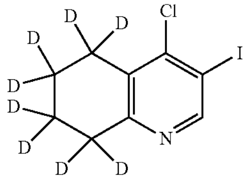 [SMILES: [2H]C1([2H])c2ncc(I)c(Cl)c2C([2H])([2H])C([2H])([2H])C1([2H])[2H]] | 32% |
| S609 | S109 | 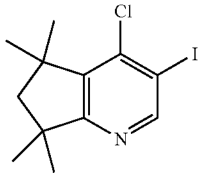 | 19% |
| S610 | S110 | 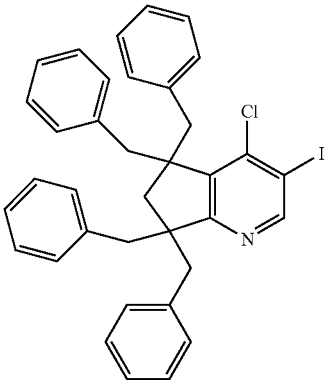 [SMILES: Clc1c(I)cnc2c1C(Cc1ccccc1)(Cc1ccccc1)CC2(Cc1ccccc1)Cc1ccccc1] | 15% |
| S611 | S111 | 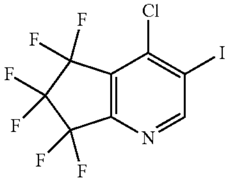 [SMILES: FC1(F)c2ncc(I)c(Cl)c2C(F)(F)C1(F)F] | 23% |
| S612 | S112 | 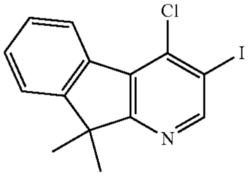 [SMILES: CC1(C)c2ccccc2-c2c1ncc(I)c2Cl] | 21% |
| S613 | S113 | 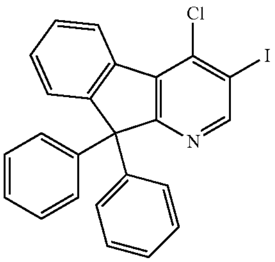 [SMILES: Clc1c(I)cnc2c1-c1ccccc1C2(c1ccccc1)c1ccccc1] | 20% |

-continued
| Ex. | Enamine | Product | Yield |
|---|---|---|---|
| S614 | S114 | 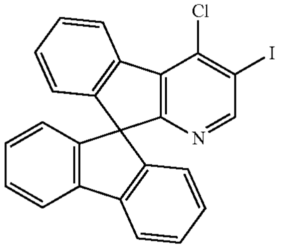 [SMILES: Clc1c(I)cnc2c1-c1ccccc1C21c2ccccc2-c2ccccc21] | 20% |
| S615 | S115 | 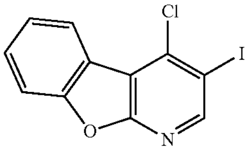 [SMILES: Clc1c(I)cnc2oc3ccccc3c12] | 22% |
| S616 | S116 | 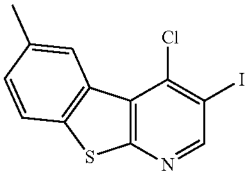 [SMILES: Cc1ccc2sc3ncc(I)c(Cl)c3c2c1] | 18% |
| S617 | S117 | 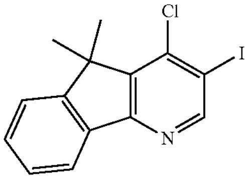 [SMILES: CC1(C)c2ccccc2-c2ncc(I)c(Cl)c21] | 23% |
| S618 | S118 | 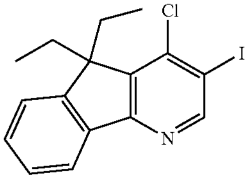 [SMILES: CCC1(CC)c2ccccc2-c2ncc(I)c(Cl)c21] | 21% |
| S619 | S119 | 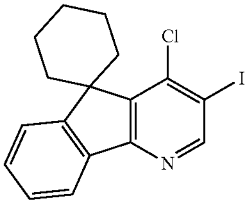 [SMILES: Clc1c(I)cnc2c1C1(CCCCC1)c1ccccc1-2] | 18% |
| S620 | S120 | 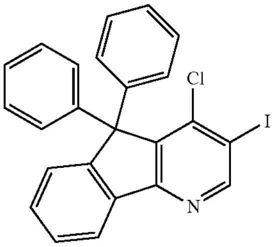 [SMILES: Clc1c(I)cnc2c1C(c1ccccc1)(c1ccccc1)c1ccccc1-2] | 19% |
-continued
| Ex. | Enamine | Product | Yield |
|---|---|---|---|
| S621 | S121 | 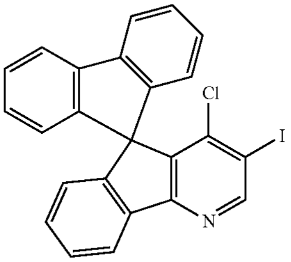 [SMILES: Clc1c(I)cnc2c1C1(c3ccccc3-c3ccccc31)c1ccccc1-2] | 17% |
| S622 | S122 | 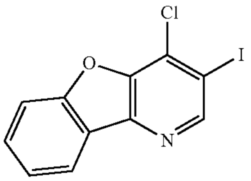 [SMILES: Clc1c(I)cnc2c1oc1ccccc12] | 24% |
1.4) Synthesis of Anilines
Example 700
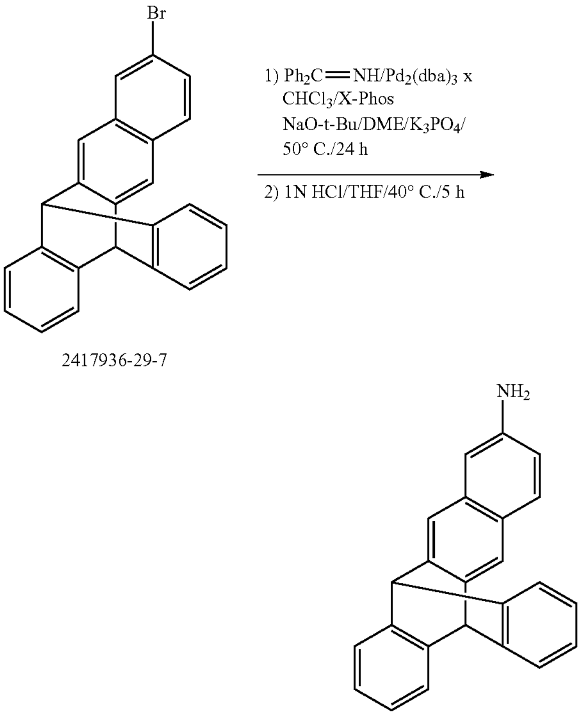
2417936-29-7
Procedure analogous to S. Bhagwanth et al., Tetrahedron Letters 50 (2009) 1582. Starting materials: 38.g (100 mmol) of bromide; glass beads are added to the mechanically stirred reaction mixture. Yield: 21.6 g (67 mmol), 67%; purity: about 97% by 1H NMR.

| Ex. | Reactants | Product | Yield |
|---|---|---|---|
| S701 | 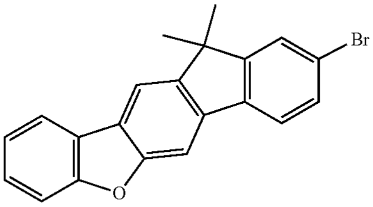 1898280-80-2 | 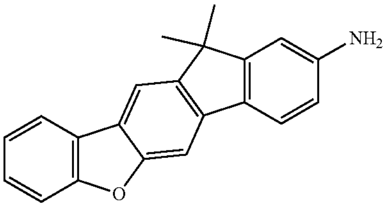 [SMILES: CC1(C)c2cc(N)ccc2-c2cc3oc4ccccc4c3cc21] | 55% |
| S702 | 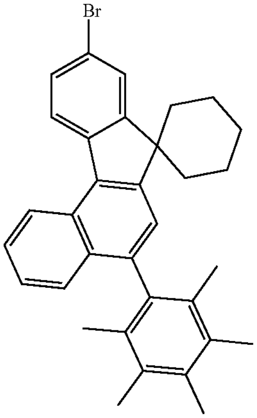 1579280-82-2 | 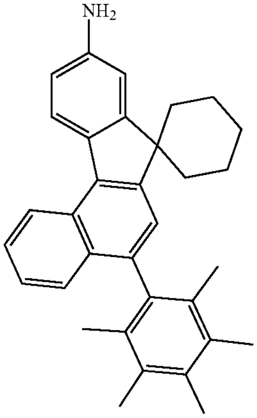 [SMILES: Cc1c(C)c(C)c(-c2cc3c(c4ccccc24)-c2ccc(N)cc2C32CCCCC2)c(C)c1C] | 61% |
| S703 | 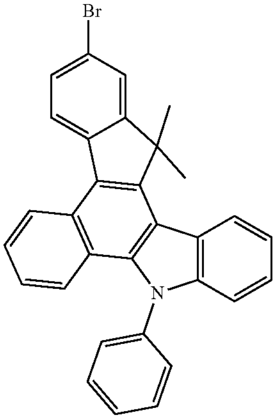 1678504-51-2 | 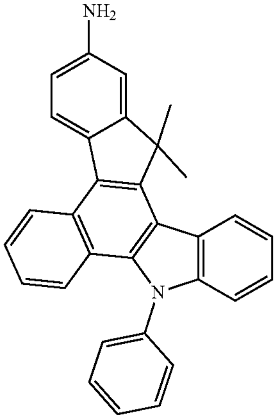 [SMILES: CC1(C)c2cc(N)ccc2-c2c1c1c3ccccc3n(-c3ccccc3)c1c1ccccc21] | 64% |
| S704 | 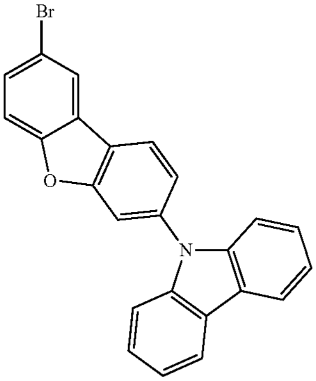 1914081-14-3 | 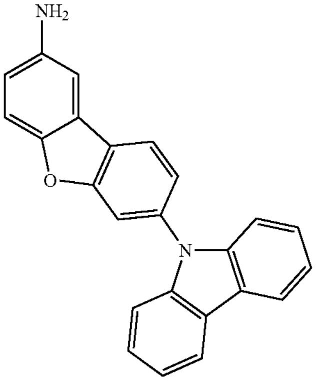 [SMILES: Nc1ccc2oc3cc(-n4c5ccccc5c5ccccc54)ccc3c2c1] | 60% |

-continued

| Ex. | Reactants | Product | Yield |
|---|---|---|---|
| S705 | 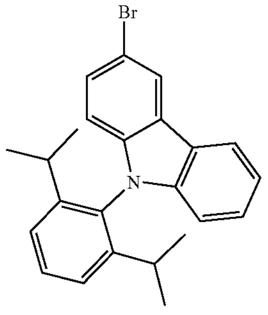 1147894-96-9 | 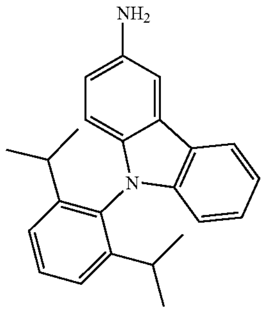 [SMILES: CC(C)c1cccc(C(C)C)c1-n1c2ccccc2c2cc(N)ccc21] | 70% |

1.5) Synthesis of the Symmetrically Substituted Amines

Example A1

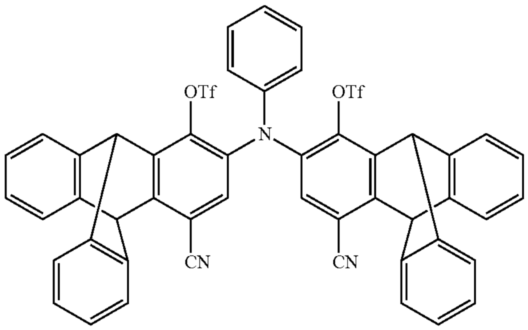 [SMILES: N#Cc1cc(N(c2ccccc2)c2cc(C#N)c3c(c2OS(=O)(=O)C(F)(F)F)C2c4ccccc4C3c3ccccc32)c(OS(=O)(=O)C(F)(F)F)c2c1C1c3ccccc3C2c2ccccc21]

Variant 1: Buchwald Coupling

Procedure analogous to the following literature:

P. B. Tiruveedhula et al., Organic & Biomolecular Chemistry, 13 (43), 10705, 2015. K Revunova et al., Polyhedron, 2013, 52, 1118.

A mixture of 60.9 g (110 mmol) of S1, 4.57 ml (50 mmol) of aniline, 65.2 g (200 mmol) of caesium carbonate, 2.18 g (3.5 mmol) of rac-BINAP [98327-87-8], 561 mg (2.5 mmol) of palladium(II) acetate, 500 ml of toluene and 50 g of glass beads (diameter 3 mm) is stirred first at 60° C. for 4 h and then at 100° C. for 12-16 h. The reaction mixture is allowed to cool to 60° C., and the salts are filtered off through a Celite bed in the form of a toluene slurry. The filtrate is concentrated to dryness, the residue is extracted by boiling with 200 ml of methanol, and the solids are filtered off, washed twice with 50 ml each time of methanol, dried under reduced pressure and subjected to flash chromatography (Combi-Flash Torrent from A. Semrau). Yield: 31.2 g (33 mmol), 66%; purity: about 95% by $^1$H NMR.

Alternatively, it is possible to use other phosphines (e.g. tri-tert-butylphosphine, di-tert-butylmethylphosphine, SPhos, XPhos, AmPhos, etc.) and bases (e.g. alkoxides such as sodium tert-butoxide).

Variant 2: Jourdan-Ullmann Coupling

Procedure analogous to the following literature:

Y.-L-Tasi et al., J. Luminesc., 2007, 127, 41.

A mixture of 60.9 g (110 mmol) of S1, 4.57 ml (50 mmol) of aniline, 27.6 g (200 mmol) of potassium carbonate, 42.7 g (300 mmol) of sodium sulfate, 954 mg (15 mmol) of copper powder, 500 ml of nitrobenzene and 1000 g of glass beads (diameter 3 mm) is stirred first at 160° C. for 12-16 h. The reaction mixture is allowed to cool to 60° C., and the salts are filtered off through a Celite bed in the form of a toluene slurry. The filtrate is concentrated to dryness, the residue is extracted by boiling with 200 ml of methanol, and the solids are filtered off, washed twice with 50 ml each time of methanol, dried under reduced pressure and subjected to flash chromatography (Combi-Flash Torrent from A. Semrau). Yield: 27.9 g (29.5 mmol), 59%; purity: about 95% by $^1$H NMR.

1.6) Synthesis of the Asymmetrically Substituted Amines

Example A500

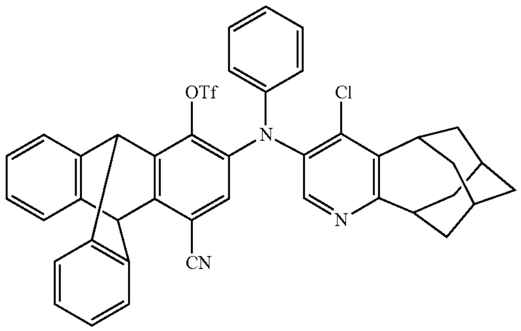 [SMILES: N#Cc1cc(N(c2ccccc2)c2cnc3c(c2Cl)C2CC4CC(CC3C4)C2)c(OS(=O)(=O)C(F)(F)F)c2c1C1c3ccccc3C2c2ccccc21]

A mixture of 27.7 g (50 mmol) of S1, 4.57 ml (50 mmol) of aniline, 65.2 g (200 mmol) of caesium carbonate, 2.18 g (3.5 mmol) of rac-BINAP [98327-97-8], 561 mg (2.5 mmol) of palladium(II) acetate, 500 ml of toluene and 50 g of glass beads (diameter 3 mm) is stirred at 60° C. until conversion is complete (TLC monitoring, typically 2-4 h). Then 18.0 g (50 mmol) of S600 is added; the temperature is increased to 100° C. On completion of conversion (TLC monitoring, typically 12-16 h), the reaction mixture is allowed to cool to 60° C., and the salts are filtered off through a Celite bed in the form of a toluene slurry. The filtrate is concentrated to dryness, the residue is extracted by boiling with 200 ml of methanol, and the solids are filtered off, washed twice with 50 ml each time of methanol, dried under reduced pressure and subjected to flash chromatography (Combi-Flash Torrent from A. Semrau). Yield: 21.0 g (28 mmol), 56%; purity: about 95% by $^1$H NMR.

Asymmetric amines obtained in this way can be converted as described in 2.) to the inventive emitters EAS.

2.) Synthesis of the Inventive Emitters

2.1) Synthesis of the Symmetrically Substituted Emitters

Example ES1

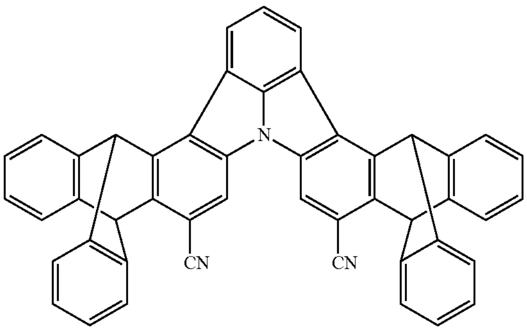 [SMILES: N#Cc1cc2c(c3c1C1c4ccccc4C3c3ccccc31)c1cccc3c4c5c(c(C#N)cc4n2c13)C1c2ccccc2C5c2ccccc21]

Variant 1

Procedure analogous to the following literature: T. Kader et al., Chem. Eur. J., 2019, 25, 4412-4425.

A mixture of 47.2 g (50 mmol) of A1, 27.6 g (200 mmol) of potassium carbonate, 1.72 g (3 mmol) of (NHC)Pd(allyl)Cl [478980-03-9], 50 g of glass beads (diameter 3 mm) and 500 ml of N,N-dimethylacetamide (DMAc) is heated to 150° C. with good stirring for 16 h. After cooling to 80° C., 1000 ml of water is added dropwise, the precipitated solids are filtered off with suction, and these are washed twice with 100 ml each time of water and twice with 50 ml each time of methanol, and dried under reduced pressure. The crude product is subjected to flash chromatography (Combi-Flash Torrent from A. Semrau, DCM: 2% MeOH), and then purified by repeated hot extraction crystallization (DCM: acetonitrile 1:3 to 2:1) and subsequent fractional sublimation or by heat treatment under high vacuum. Yield: 14.9 g (23 mmol), 46%; purity: >99.9% by HPLC.

Rather than (NHC)Pd(allyl)CI, it is also possible to use 4 mmol of $[(tBu)_3PH][BF_4]$ and 2 mmol of $Pd(OAc)_2$.

Variant 2

Procedure analogous to the following literature: A. W. Jones et al., Adv. Synth. Catal. 2015, 357, 945.

A mixture of 47.2 g (50 mmol) A1, 3.1 g (10 mmol) of palladium(II) pivalate [106224-36-6], 27.8 g (120 mmol) of silver(I) oxide [20667-12-3], 9.6 g (120 mmol) of copper(II) oxide [1317-38-0], 50 g of glass beads (diameter 3 mm) and 200 ml of pivalic acid (PivOH) is heated to 130° C. with good stirring for 24 h. After cooling to 80° C., 1000 ml of water is added dropwise, the precipitated solids are filtered off with suction, and these are washed twice with 100 ml each time of water and twice with 50 ml each time of methanol, and dried under reduced pressure. The crude product is subjected to flash chromatography (Combi-Flash Torrent from A. Semrau, DCM: 2% MeOH), then purified by repeated hot extraction crystallization (DCM:acetonitrile 1:3 to 2:1) and subsequent fractional sublimation or by heat treatment under high vacuum. Yield: 12.3 g (19 mmol), 38%; purity: >99.9% by HPLC.

Analogously to stages 1.4 and 2.1, it is possible to prepare the following emitters ES: yield over two stages:

| Ex. | Nitrile Amine | Product | Yield |
|---|---|---|---|
| ES2 | S1 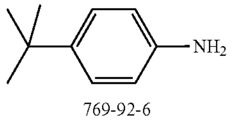 769-92-6 | 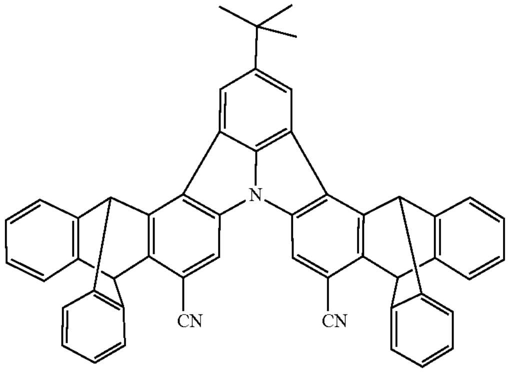 [SMILES: CC(C)(C)c1cc2c3c4c(c(C#N)cc3n3c5cc(C#N)c6c(c5c(c1)c23)C1c2ccccc2C6c2ccccc21)C1c2ccccc2C4c2ccccc21] | 36% |

-continued
| Ex. | Nitrile Amine | Product | Yield |
|---|---|---|---|
| ES3 | S1 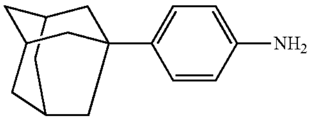 1459-48-9 | 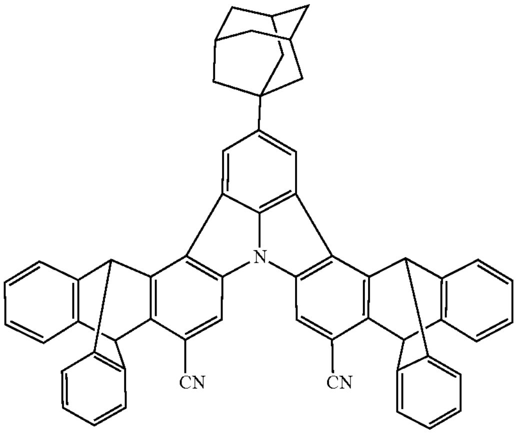 [SMILES: N#Cc1cc2c(c3c1C1c4ccccc4C3c3ccccc31)c1cc(C34CC5CC(CC(C5)C3)C4)cc3c4c5c(c(C#N)cc4n2c13)C1c2ccccc2C5c2ccccc21] | 38% |
| ES4 | S2 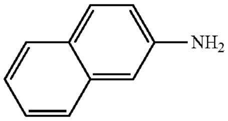 91-59-8 | 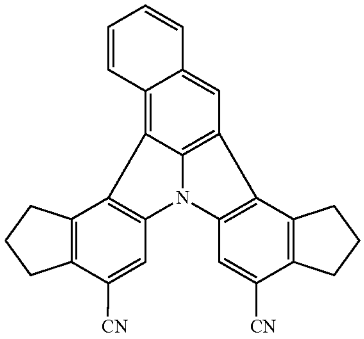 [SMILES: N#Cc1cc2c(c3c1CCC3)c1cc3ccccc3c3c4c5c(c(C#N)cc4n2c13)CCC5] | 35% |
| ES5 | S1 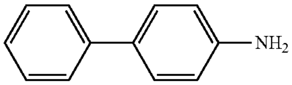 92-67-1 | 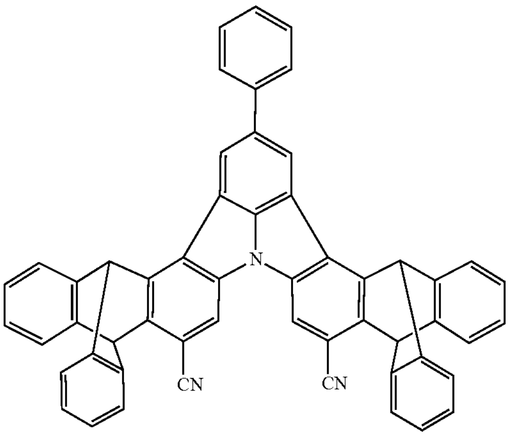 [SMILES: N#Cc1cc2c(c3c1C1c4ccccc4C3c3ccccc31)c1cc(-c3ccccc3)cc3c4c5c(c(C#N)cc4n2c13)C1c2ccccc2C5c2ccccc21] | 33% |

-continued
| Ex. | Nitrile Amine | Product | Yield |
|---|---|---|---|
| ES6 | S1 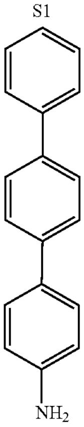 7293-45-0 | 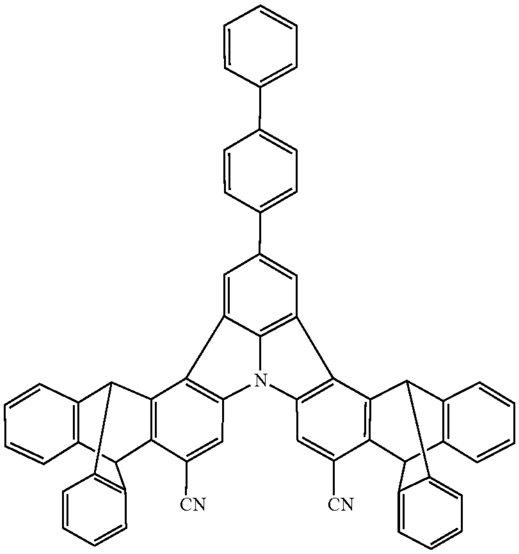 [SMILES: N#Cc1cc2c(c3c1C1c4ccccc4C3c3ccccc31)c1cc(-c3ccc(-c4ccccc4)cc3)cc3c4c5c(c(C#N)cc4n2c13)C1c2ccccc2C5c2ccccc21] | 36% |
| ES7 | S3 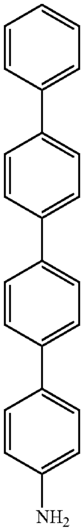 25660-12-2 | 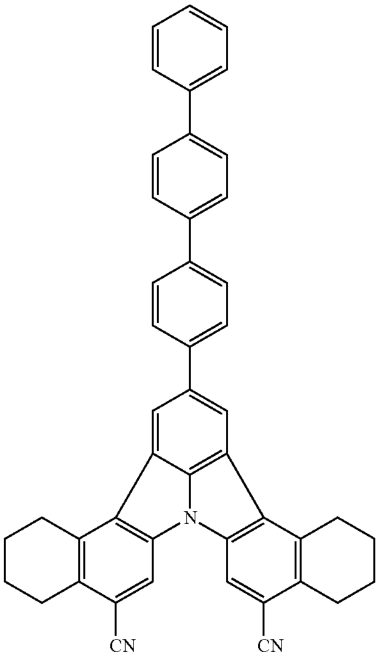 [SMILES: N#Cc1cc2c(c3c1CCCC3)c1cc(-c3ccc(-c4ccc(-c5ccccc5)cc4)cc3)cc3c4c5c(c(C#N)cc4n2c13)CCCC5] | 40% |

-continued
| Ex. | Nitrile Amine | Product | Yield |
|---|---|---|---|
| ES8 | S4 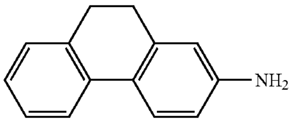 76302-58-4 | 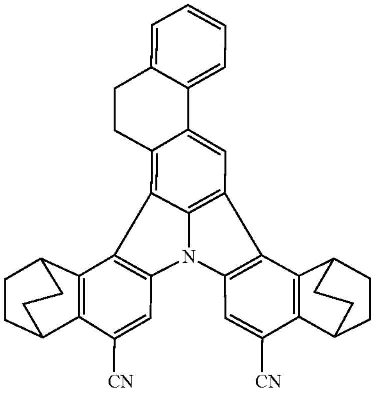 [SMILES: N#Cc1cc2c(c3c1C1CCC3CC1)c1cc3c(c4c5c6c(c(C#N)cc5n2c14)C1CCC6CC1)CCc1ccccc1-3] | 33% |
| ES9 | S1 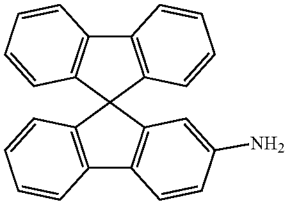 118951-68-1 | 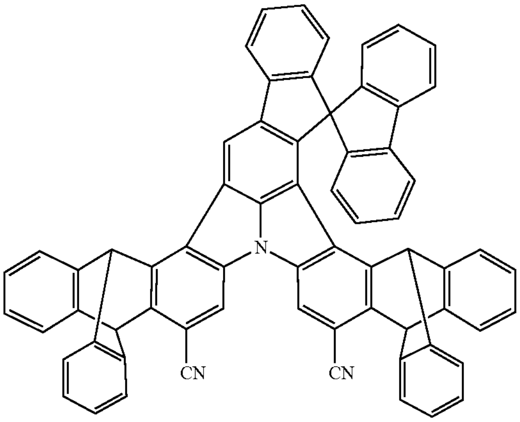 [SMILES: N#Cc1cc2c(c3c1C1c4ccccc4C3c3ccccc31)c1cc3c(c4c5c6c(c(C#N)cc5n2c14)C1c2ccccc2C6c2ccccc21)C1(c2ccccc2-c2ccccc21)c1ccccc1-3] | 3% |
| ES10 | S1 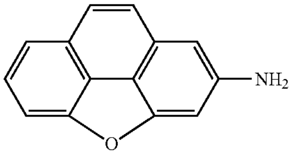 2018346-63-7 | 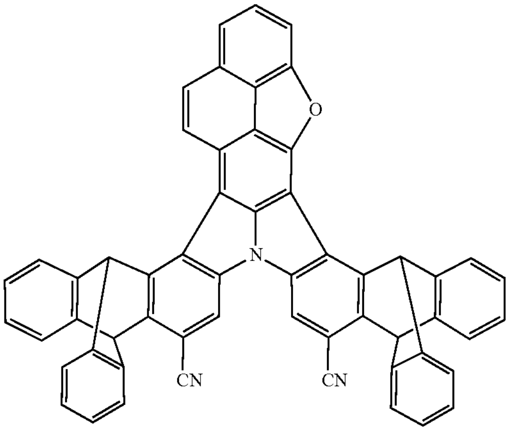 [SMILES: N#Cc1cc2c(c3c1C1c4ccccc4C3c3ccccc31)c1c3ccc4cccc5oc(c3c45)c3c4c5c(c(C#N)cc4n2c13)C1c2ccccc2C5c2ccccc21] | 37% |

-continued
| Ex. | Nitrile Amine | Product | Yield |
|---|---|---|---|
| ES11 | S1 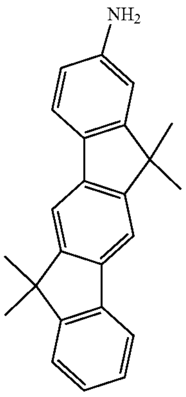 2295808-71-6 | 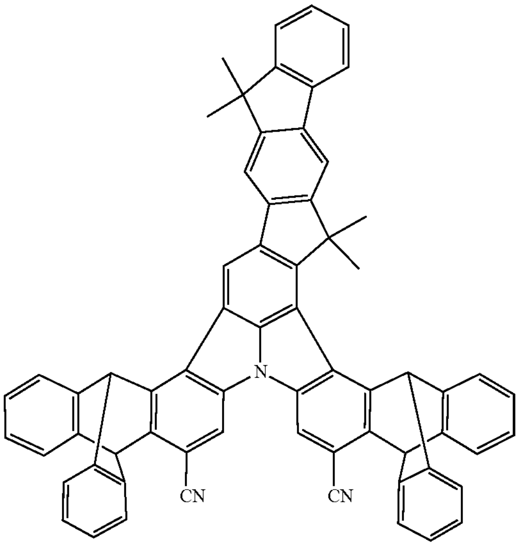 [SMILES: CC1(C)c2ccccc2-c2cc3c(cc21)-c1cc2c4c5c(c(C#N)cc4n4c6cc(C#N)c7c(c6c(c1C3(C)C)c24)C1c2ccccc2C7c2ccccc21)C1c2ccccc2C5c2ccccc21] | 35% |
| ES12 | S4 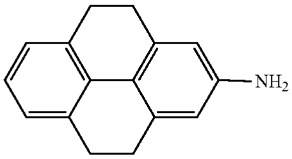 101283-00-5 | 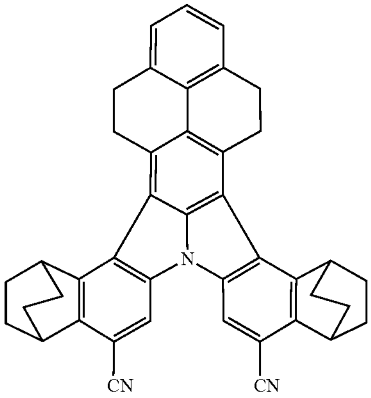 [SMILES: N#Cc1cc2c(c3c1C1CCC3CC1)c1c3c4c(c5c6c7c(c(C#N)cc6n2c15)C1CCC7CC1)CCc1cccc(c1-4)CC3] | 37% |
| ES13 | S1 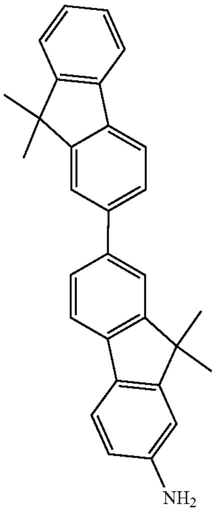 1416158-30-9 | 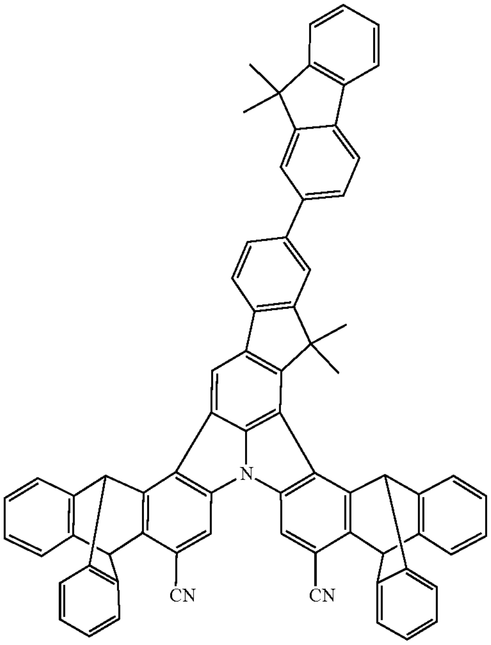 [SMILES: CC1(C)c2ccccc2-c2ccc(-c3ccc4c(c3)C(C)(C)c3c-4cc4c5c6c(c(C#N)cc5n5c7cc(C#N)c8c(c7c3c45)C3c4ccccc4C8c4ccccc43)C3c4ccccc4C6c4ccccc43)cc21] | 39% |

-continued
| Ex. | Nitrile Amine | Product | Yield |
|---|---|---|---|
| ES14 | S1 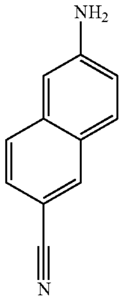 129667-70-5 | 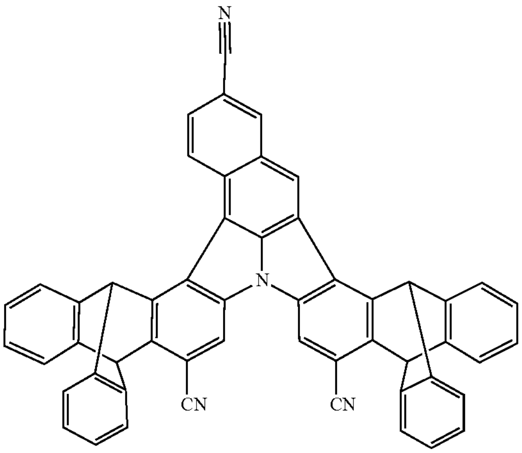 [SMILES: N#Cc1ccc2c(c1)cc1c3c4c(c(C#N)cc3n3c5cc(C#N)c6c(c5c2c13)C1c2ccccc2C6c2ccccc21)C1c2ccccc2C4c2ccccc21] | 30% |
| ES15 | S1 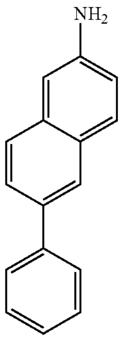 861046-41-5 | 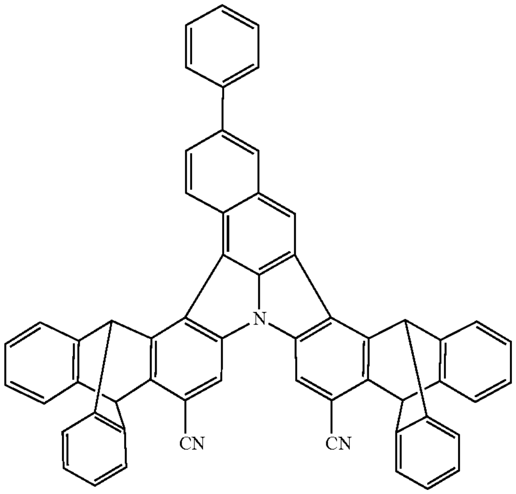 [SMILES: N#Cc1cc2c(c3c1C1c4ccccc4C3c3ccccc31)c1cc3cc(-c4ccccc4)ccc3c3c4c5c(c(C#N)cc4n2c13)C1c2ccccc2C5c2ccccc21] | 32% |
| ES16 | S1 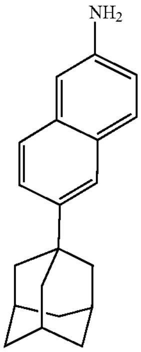 37521-66-7 | 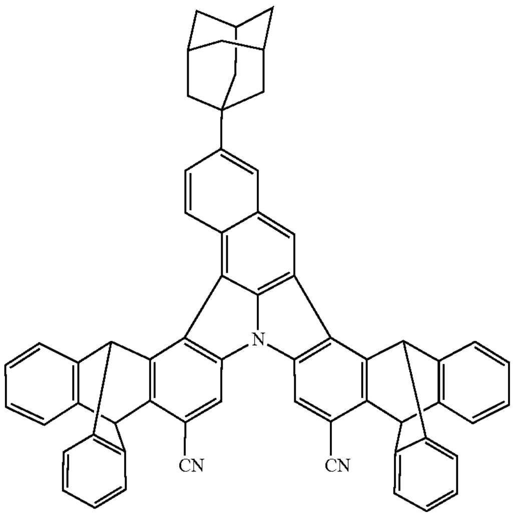 [SMILES: N#Cc1cc2c(c3c1C1c4ccccc4C3c3ccccc31)c1cc3cc(C45CC6CC(CC(C6)C4)C5)ccc3c3c4c5c(c(C#N)cc4n2c13)C1c2ccccc2C5c2ccccc21] | 35% |

-continued
| Ex. | Nitrile Amine | Product | Yield |
|---|---|---|---|
| ES17 | S1 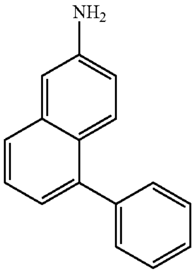 1609130-36-0 | 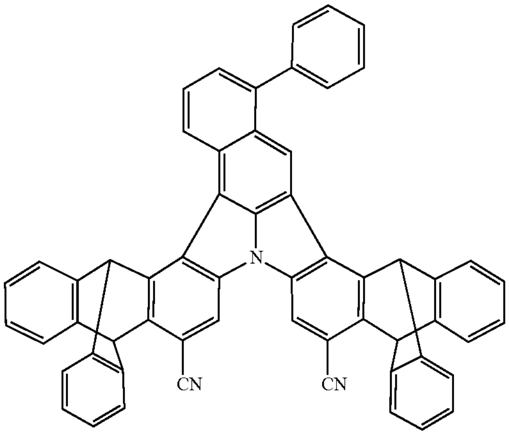 [SMILES: N#Cc1cc2c(c3c1C1c4ccccc4C3c3ccccc31)c1cc3c(-c4ccccc4)cccc3c3c4c5c(c(C#N)cc4n2c13)C1c2ccccc2C5c2ccccc21] | 38% |
| ES18 | S4 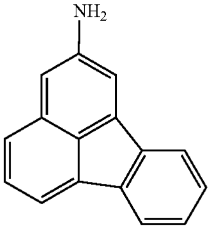 13177-26-9 | 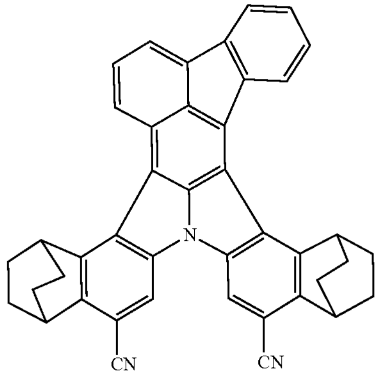 [SMILES: N#Cc1cc2c(c3c1C1CCC3CC1)c1c3cccc4c5ccccc5c(c43)c3c4c5c(c(C#N)cc4n2c13)C1CCC5CC1] | 33% |
| ES19 | S1 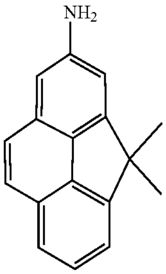 1639349-82-8 | 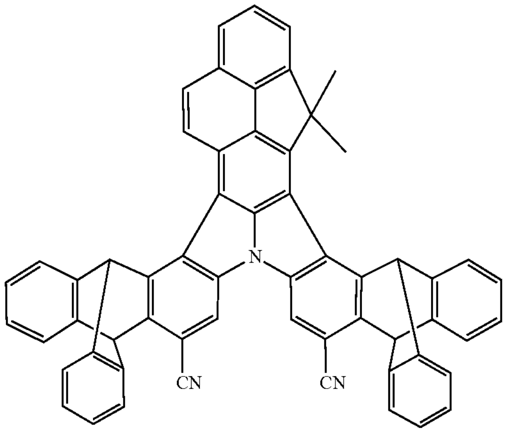 [SMILES: CC1(C)c2cccc3ccc4c(c1c1c5c6c(c(C#N)cc5n5c7cc(C#N)c8c(c7c4c15)C1c4ccccc4C8c4ccccc41)C1c4ccccc4C6c4ccccc41)c23] | 35% |

-continued
| Ex. | Nitrile Amine | Product | Yield |
|---|---|---|---|
| ES20 | S1 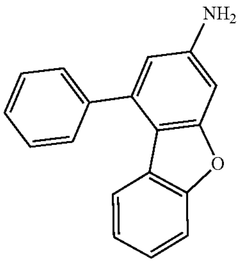 1882060-04-9 | 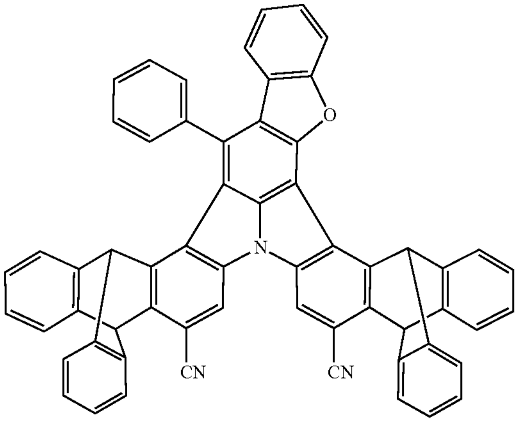 [SMILES: N#Cc1cc2c(c3c1C1c4ccccc4C3c3ccccc31)c1c(-c3ccccc3)c3c4ccccc4oc3c3c4c5c(c(C#N)cc4n2c13)C1c2ccccc2C5c2ccccc21] | 34% |
| ES21 | S1 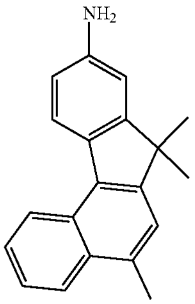 2379812-68-5 | 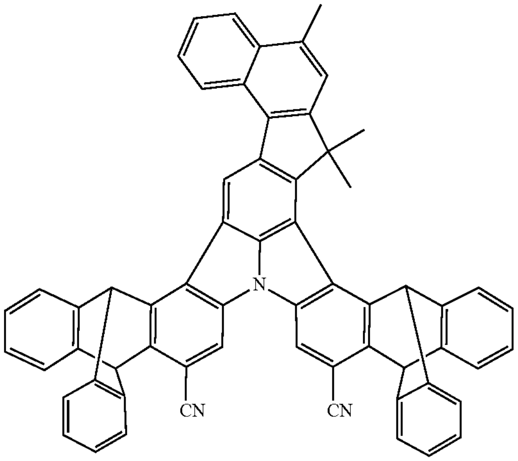 [SMILES: Cc1cc2c(c3ccccc13)-c1cc3c4c5c(c(C#N)cc4n4c6cc(C#N)c7c(c6c(c1C2(C)C)c34)C1c2ccccc2C7c2ccccc21)C1c2ccccc2C5c2ccccc21] | 34% |
| ES22 | S3 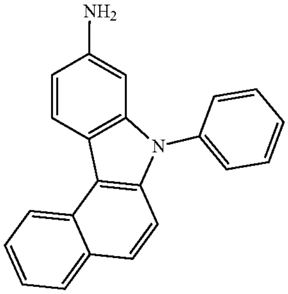 2086712-51-6 | 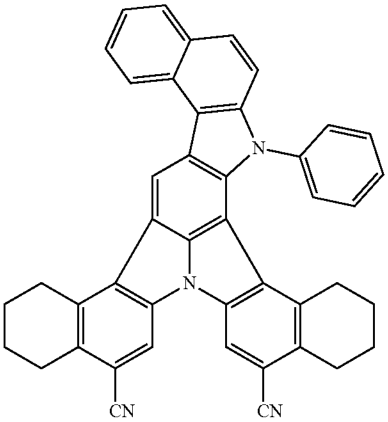 [SMILES: N#Cc1cc2c(c3c1CCCC3)c1cc3c4c5ccccc5ccc4n(-c4ccccc4)c3c3c4c5c(c(C#N)cc4n2c13)CCCC5] | 35% |

-continued
| Ex. | Nitrile Amine | Product | Yield |
|---|---|---|---|
| ES23 | S4 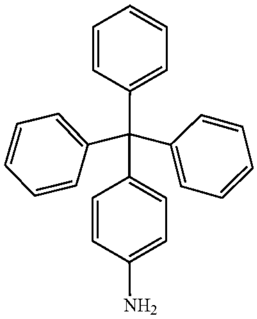 22948-06-7 | 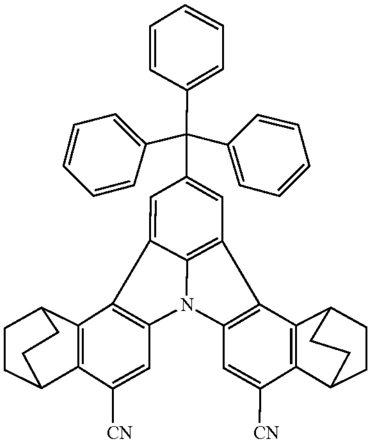 [SMILES: N#Cc1cc2c(c3c1C1CCC3CC1)c1cc(C(c3ccccc3)(c3ccccc3)c3ccccc3)cc3c4c5c(c(C#N)cc4n2c13)C1CCC5CC1] | 32% |
| ES24 | S1 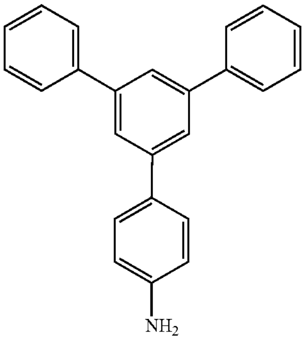 343239-58-7 | 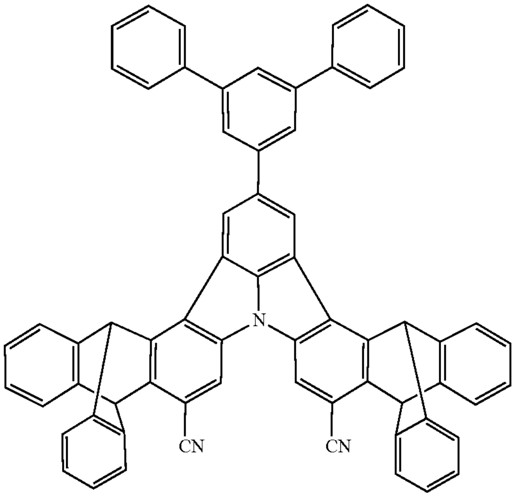 [SMILES: N#Cc1cc2c(c3c1C1c4ccccc4C3c3ccccc31)c1cc(-c3cc(-c4ccccc4)cc(-c4ccccc4)c3)cc3c4c5c(c(C#N)cc4n2c13)C1c2ccccc2C5c2ccccc21] | 33% |
| ES25 | S4 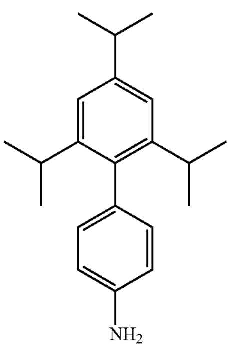 1801716-11-9 | 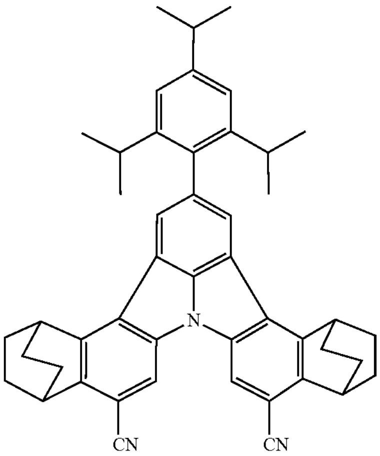 [SMILES: CC(C)c1cc(C(C)C)c(-c2cc3c4c5c(c(C#N)cc4n4c6cc(C#N)c7c(c6c(c2)c34)C2CCC7CC2)C2CCC5CC2)c(C(C)C)c1] | 39% |

-continued
| Ex. | Nitrile Amine | Product | Yield |
|---|---|---|---|
| ES26 | S1 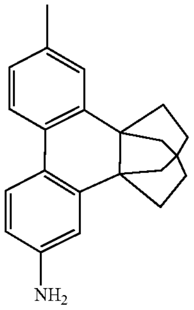 1884138-08-2 | 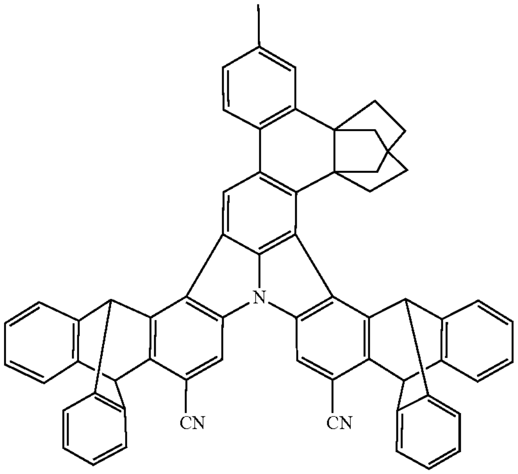 [SMILES: Cc1ccc2c(c1)C13CCC4(CCC1(C4)c1c-2cc2c4c5c(c(C#N)cc4n4c6cc(C#N)c7c(c6c1c24)C1c2ccccc2C7c2ccccc21)C1c2ccccc2C5c2ccccc21)C3] | 34% |
| ES27 | S1 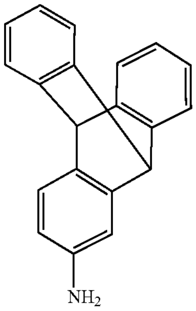 31997-11-2 | 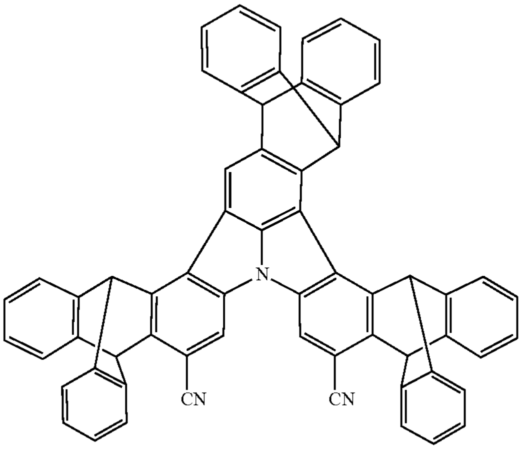 [SMILES: N#Cc1cc2c(c3c1C1c4ccccc4C3c3ccccc31)c1cc3c(c4c5c6c(c(C#N)cc5n2c14)C1c2ccccc2C6c2ccccc21)C1c2ccccc2C12c1ccccc1C32] | 36% |
| ES28 | S1 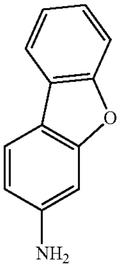 4106-66-5 | 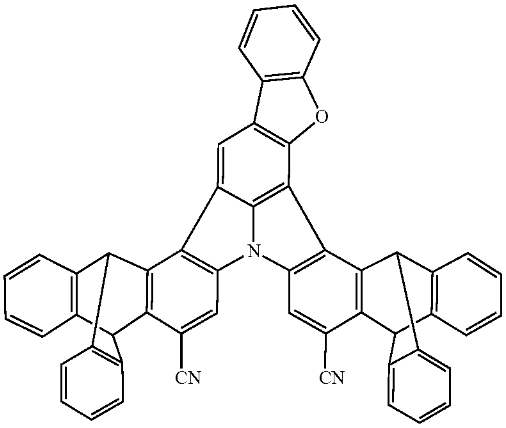 [SMILES: N#Cc1cc2c(c3c1C1c4ccccc4C3c3ccccc31)c1cc3c4ccccc4oc3c3c4c5c(c(C#N)cc4n2c13)C1c2ccccc2C5c2ccccc21] | 37% |

-continued
| Ex. | Nitrile<br>Amine | Product | Yield |
|---|---|---|---|
| ES29 | S1<br>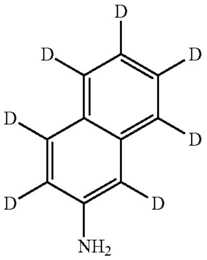<br>93951-94-1 | 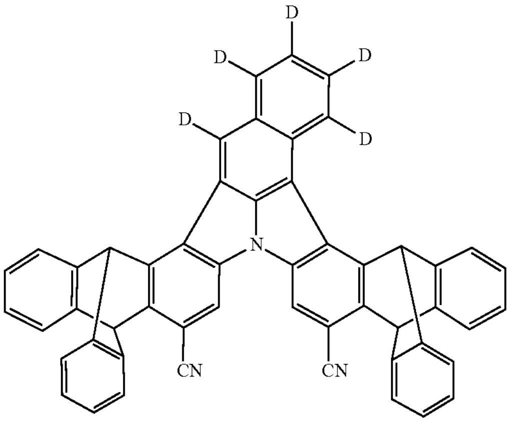 [SMILES: [2H]c1c([2H])c([2H])c2c(c1[2H])c([2H])c1c3c4c(c(C#N)cc3n3c5cc(C#N)c6c(c5c2c13)C1c2ccccc2C6c2ccccc21)C1c2ccccc2C4c2ccccc21] | 31% |
| ES30 | S4<br>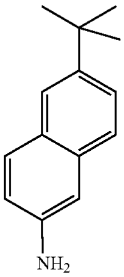<br>37521-64-5 | 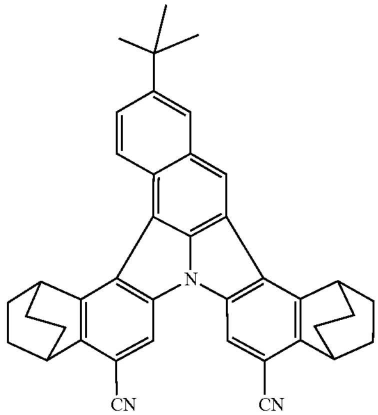 [SMILES: CC(C)(C)c1ccc2c(c1)cc1c3c4c(c(C#N)cc3n3c5cc(C#N)c6c(c5c2c13)C1CCC6CC1)C1CCC4CC1] | 33% |
| ES31 | S1<br>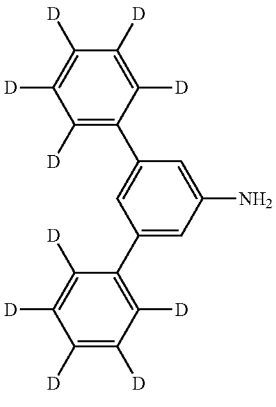<br>1846604-58-7 | 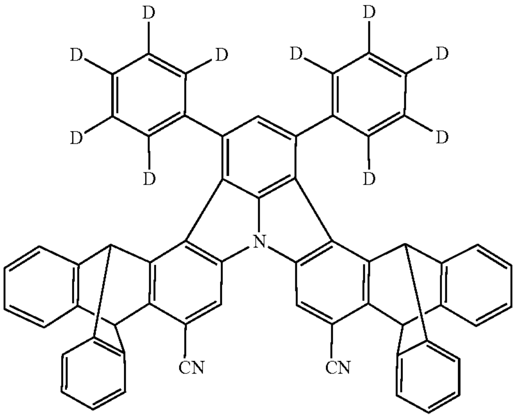 [SMILES: [2H]c1c([2H])c([2H])c(-c2cc(-c3c([2H])c([2H])c([2H])c([2H])c3[2H])c3c4c5c(c(C#N)cc4n4c6cc(C#N)c7c(c6c2c34)C2c3ccccc3C7c3ccccc32)C2c3ccccc3C5c3ccccc32)c([2H])c1[2H]] | 35% |

-continued
| Ex. | Nitrile Amine | Product | Yield |
|---|---|---|---|
| ES32 | S1 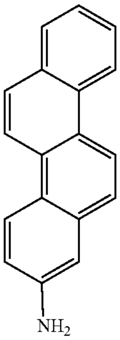 789-47-9 | 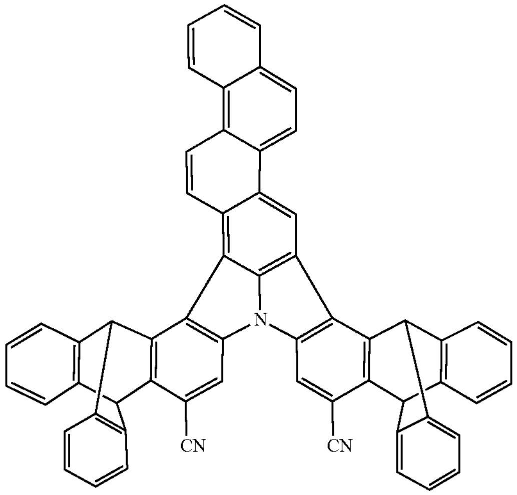 [SMILES: N#Cc1cc2c(c3c1C1c4ccccc4C3c3ccccc31)c1cc3c4ccc5ccccc5c4ccc3c3c4c5c(c(C#N)cc4n2c13)C1c2ccccc2C5c2ccccc21] | 34% |
| ES33 | S1 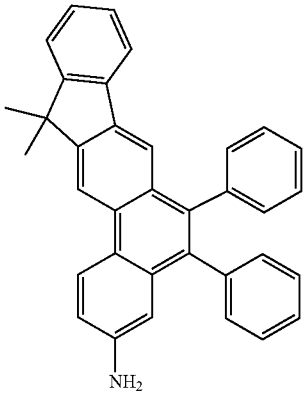 1409971-49-8 | 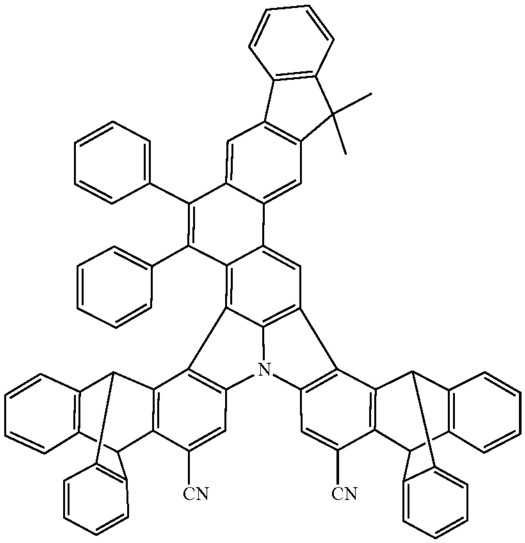 [SMILES: CC1(C)c2ccccc2-c2cc3c(-c4ccccc4)c(-c4ccccc4)c4c(cc5c6c7c(c(C#N)cc6n6c8cc(C#N)c9c(c8c4c56)C4c5ccccc5C9c5ccccc54)C4c5ccccc5C7c5ccccc54)c3cc21] | 29% |
| ES34 | S1 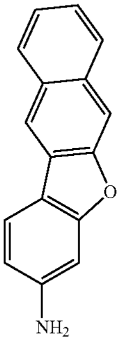 2281888-57-9 | 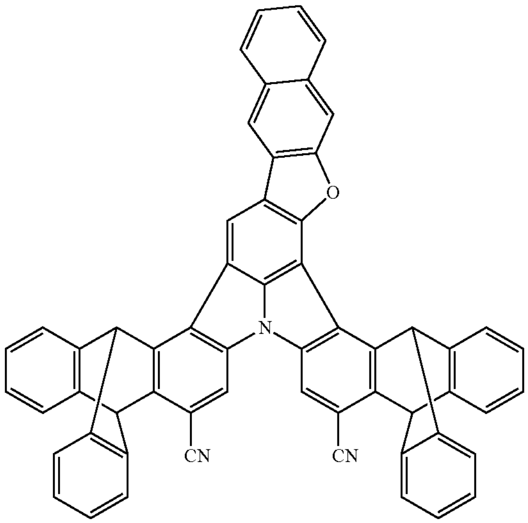 [SMILES: N#Cc1cc2c(c3c1C1c4ccccc4C3c3ccccc31)c1cc3c4cc5ccccc5cc4oc3c3c4c5c(c(C#N)cc4n2c13)C1c2ccccc2C5c2ccccc21] | 40% |

-continued
| Ex. | Nitrile Amine | Product | Yield |
|---|---|---|---|
| ES35 | S1 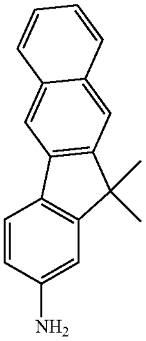 1642327-33-0 | 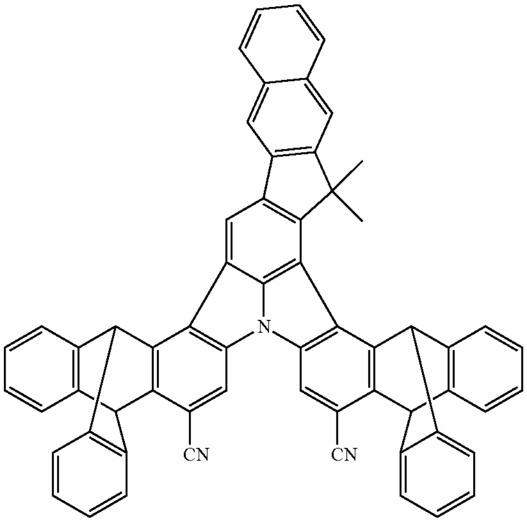 [SMILES: CC1(C)c2cc3ccccc3cc2-c2cc3c4c5c(c(C#N)cc4n4c6cc(C#N)c7c(c6c(c21)c34)C1c2ccccc2C7c2ccccc21)C1c2ccccc2C5c2ccccc21] | 38% |
| ES36 | S1 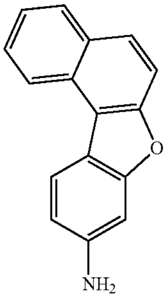 2460139-08-4 | 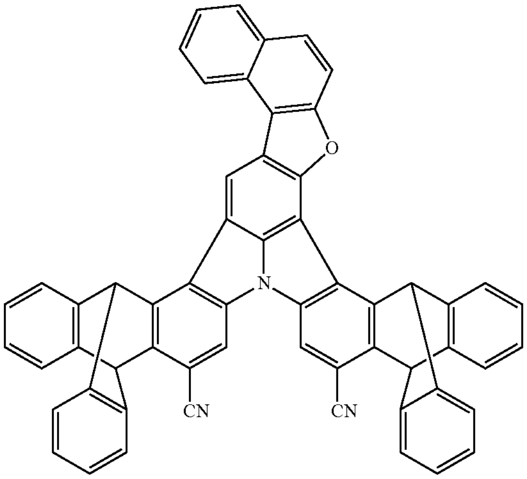 [SMILES: N#Cc1cc2c(c3c1C1c4ccccc4C3c3ccccc31)c1cc3c(oc4ccc5ccccc5c43)c3c4c5c(c(C#N)cc4n2c13)C1c2ccccc2C5c2ccccc21] | 39% |
| ES37 | S1 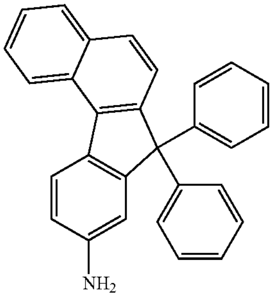 2411114-95-7 | 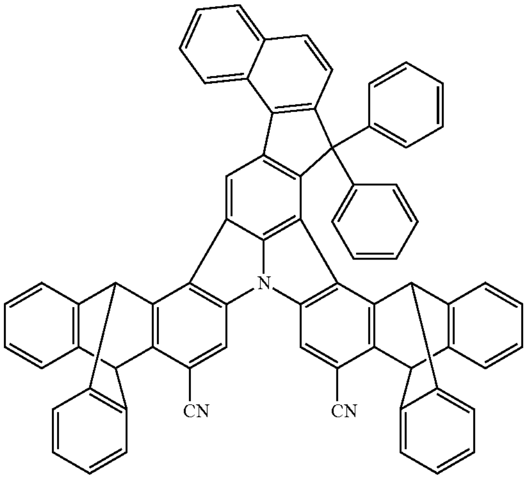 [SMILES: N#Cc1cc2c(c3c1C1c4ccccc4C3c3ccccc31)c1cc3c(c4c5c6c(c(C#N)cc5n2c14)C1c2ccccc2C6c2ccccc21)C(c1ccccc1)(c1ccccc1)c1ccc2ccccc2c1-3] | 34% |

-continued
| Ex. | Nitrile<br>Amine | Product | Yield |
|---|---|---|---|
| ES38 | S1<br>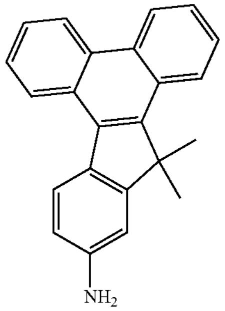<br>2226959-71-1 | 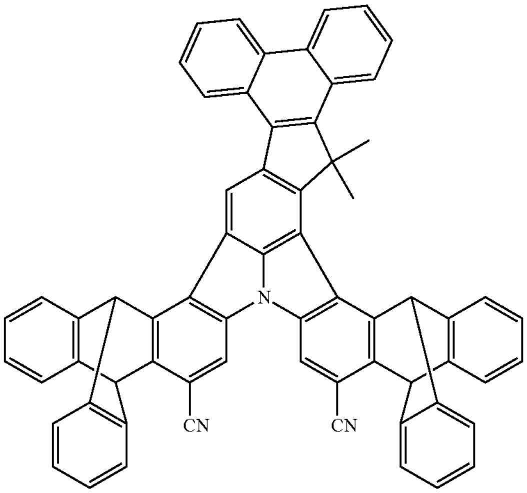 [SMILES: CC1(C)c2c(c3ccccc3c3ccccc23)-c2cc3c4c5c(c(C#N)cc4n4c6cc(C#N)c7c(c6c(c21)c34)C1c2ccccc2C7c2ccccc21)C1c2ccccc2C5c2ccccc21] | 36% |
| ES39 | S1<br>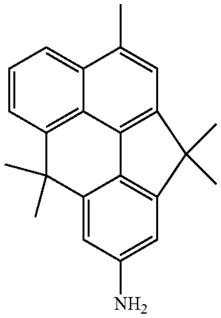<br>1225219-95-3 | 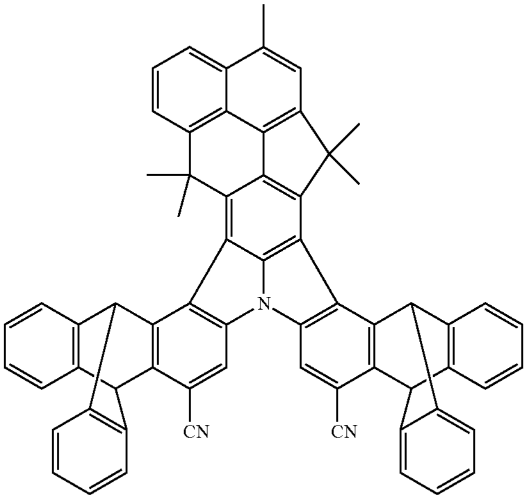 [SMILES: Cc1cc2c3c4c(cccc14)C(C)(C)c1c-3c(c3c4c5c(c(C#N)cc4n4c6cc(C#N)c7c(c6c1c34)C1c3ccccc3C7c3ccccc31)C1c3ccccc3C5c3ccccc31)C2(C)C] | 35% |
| ES40 | S1<br>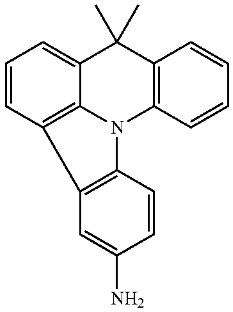<br>1448337-95-8 | 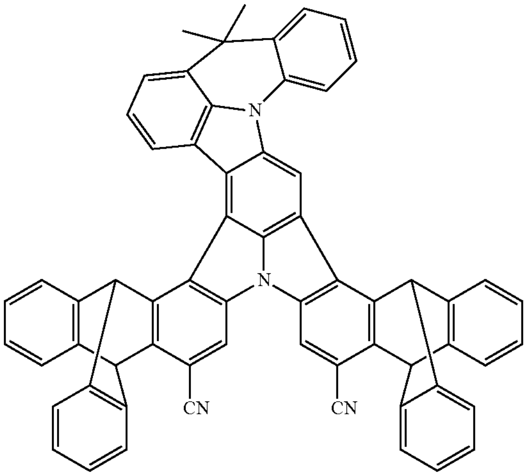 [SMILES: CC1(C)c2ccccc2-n2c3cc4c5c6c(c(C#N)cc5n5c7cc(C#N)c8c(c7c(c3c3cccc1c32)c45)C1c2ccccc2C8c2ccccc21)C1c2ccccc2C6c2ccccc21] | 37% |

-continued
| Ex. | Nitrile<br>Amine | Product | Yield |
|---|---|---|---|
| ES41 | S4<br>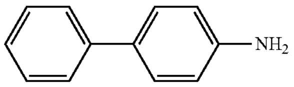<br>92-67-1 | 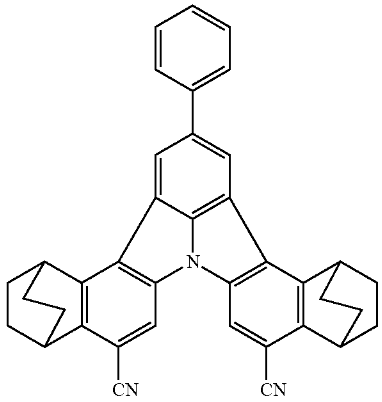 [SMILES: N#Cc1cc2c(c3c1C1CCC3CC1)c1cc(-c3ccccc3)cc3c4c5c(c(C#N)cc4n2c13)C1CCC5CC1] | 38% |
| ES42 | S1<br>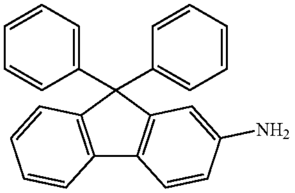<br>1268519-74-9 | 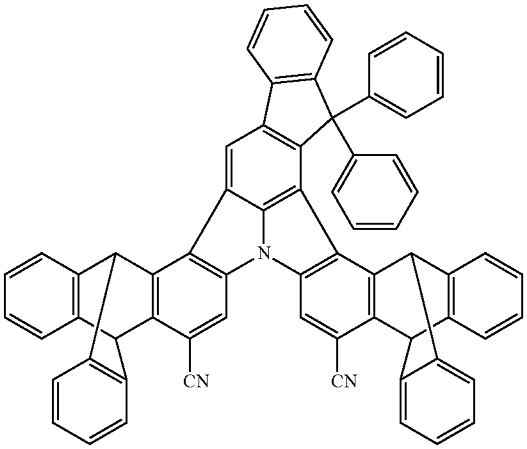 [SMILES: N#Cc1cc2c(c3c1C1c4ccccc4C3c3ccccc31)c1cc3c(c4c5c6c(c(C#N)cc5n2c14)C1c2ccccc2C6c2ccccc21)C(c1ccccc1)(c1ccccc1)c1ccccc1-3] | 37% |
| ES43 | S1<br>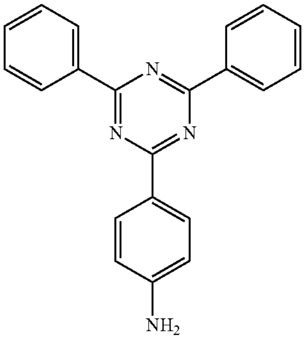<br>174152-47-7 | 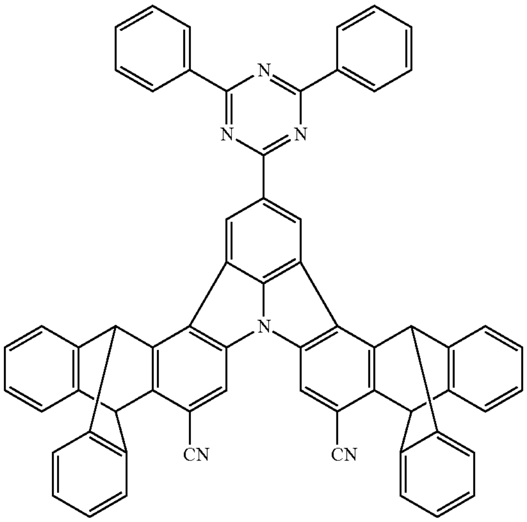 [SMILES: N#Cc1cc2c(c3c1C1c4ccccc4C3c3ccccc31)c1cc(-c3nc(-c4ccccc4)nc(-c4ccccc4)n3)cc3c4c5c(c(C#N)cc4n2c13)C1c2ccccc2C5c2ccccc21] | 28% |

-continued
| Ex. | Nitrile Amine | Product | Yield |
|---|---|---|---|
| ES44 | S1 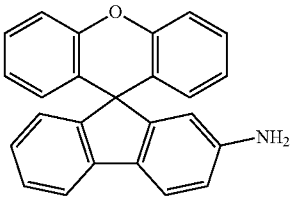 1520097-73-7 | 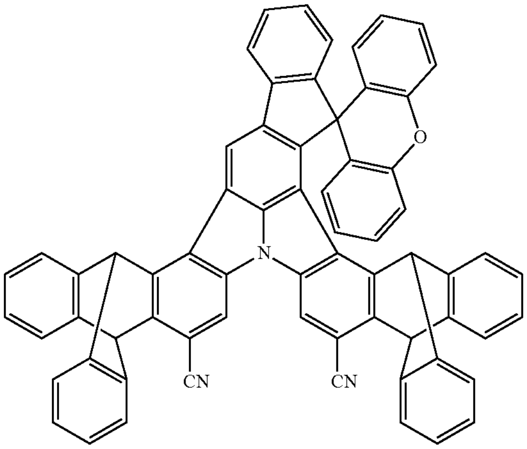 [SMILES: N#Cc1cc2c(c3c1C1c4ccccc4C3c3ccccc31)c1cc3c(c4c5c6c(c(C#N)cc5n2c14)C1c2ccccc2C6c2ccccc21)C1(c2ccccc2Oc2ccccc21)c1ccccc1-3] | 33% |
| ES45 | S1 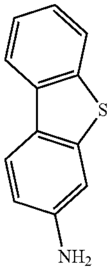 25288-76-0 | 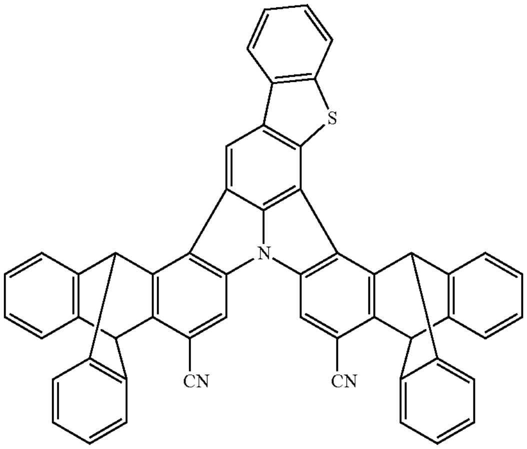 [SMILES: N#Cc1cc2c(c3c1C1c4ccccc4C3c3ccccc31)c1cc3c4ccccc4sc3c3c4c5c(c(C#N)cc4n2c13)C1c2ccccc2C5c2ccccc21] | 35% |
| ES46 | S1 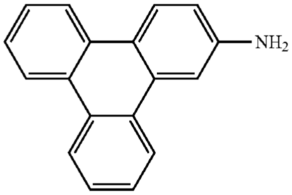 17169-81-2 | 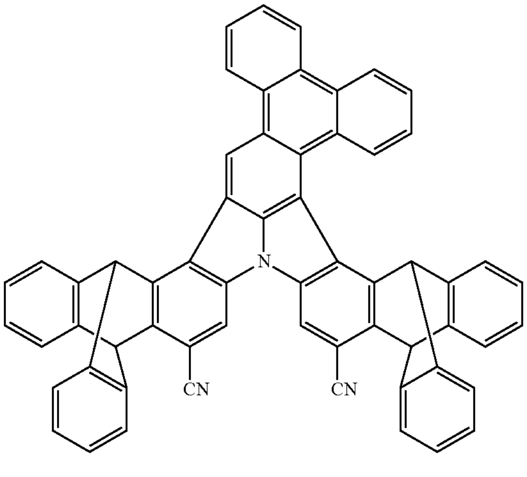 [SMILES: N#Cc1cc2c(c3c1C1c4ccccc4C3c3ccccc31)c1cc3c4ccccc4c4ccccc4c3c3c4c5c(c(C#N)cc4n2c13)C1c2ccccc2C5c2ccccc21] | 38% |

-continued
| Ex. | Nitrile Amine | Product | Yield |
|---|---|---|---|
| ES47 | S1 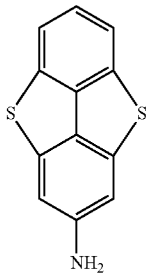 1820037-24-8 | 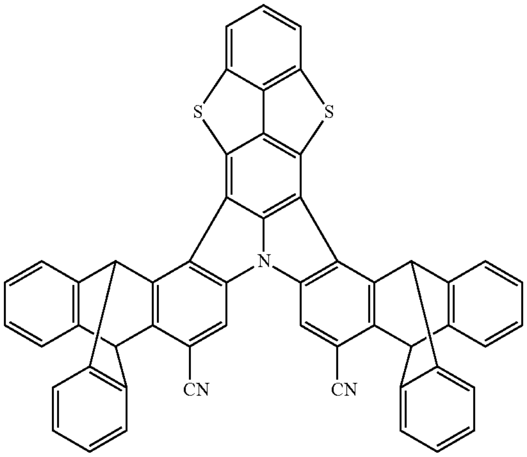 [SMILES: N#Cc1cc2c(c3c1C1c4ccccc4C3c3ccccc31)c1c3sc4cccc5sc(c3c45)c3c4c5c(c(C#N)cc4n2c13)C1c2ccccc2C5c2ccccc21] | 26% |
| ES48 | S1 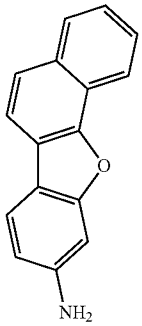 2364548-23-0 | 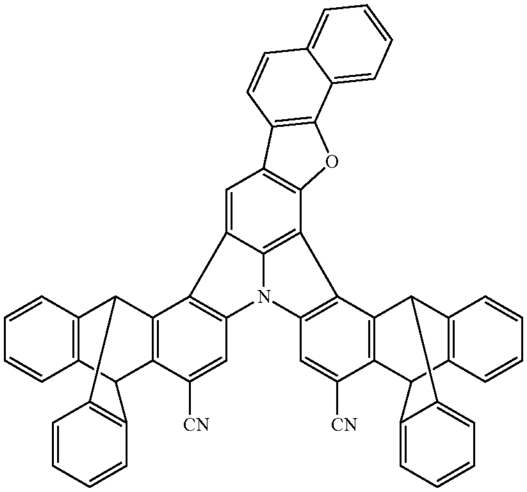 [SMILES: N#Cc1cc2c(c3c1C1c4ccccc4C3c3ccccc31)c1cc3c4ccc5ccccc5c4oc3c3c4c5c(c(C#N)cc4n2c13)C1c2ccccc2C5c2ccccc21] | 39% |
| ES49 | S1 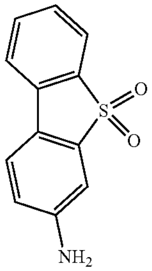 93618-98-5 | 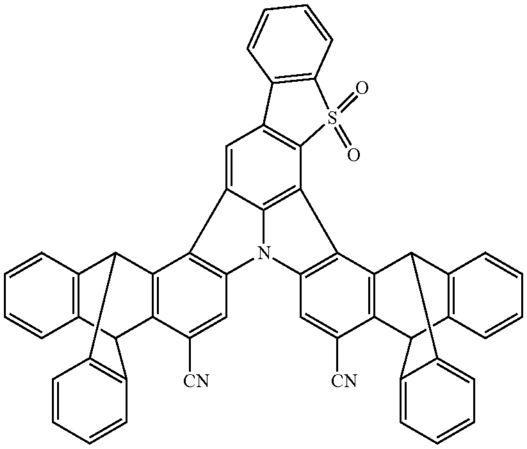 [SMILES: N#Cc1cc2c(c3c1C1c4ccccc4C3c3ccccc31)c1cc3c(c4c5c6c(c(C#N)cc5n2c14)C1c2ccccc2C6c2ccccc21)S(=O)(=O)c1ccccc1-3] | 29% |

-continued
| Ex. | Nitrile Amine | Product | Yield |
|---|---|---|---|
| ES50 | S4 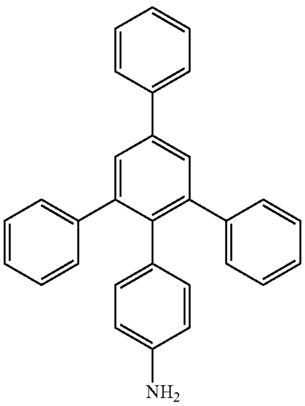 1093882-02-0 | 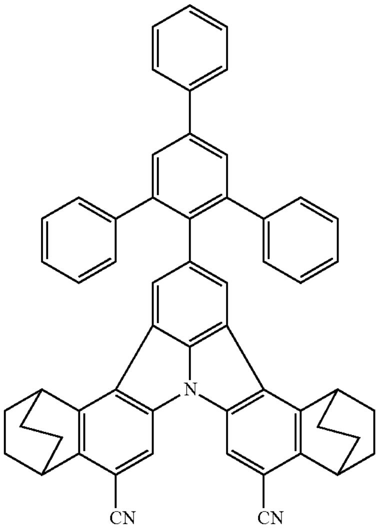 [SMILES: N#Cc1cc2c(c3c1C1CCC3CC1)c1cc(-c3c(-c4ccccc4)cc(-c4ccccc4)cc3-c3ccccc3)cc3c4c5c(c(C#N)cc4n2c13)C1CCC5CC1] | 37% |
| ES51 | S1 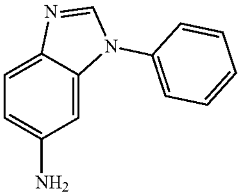 667919-05-3 | 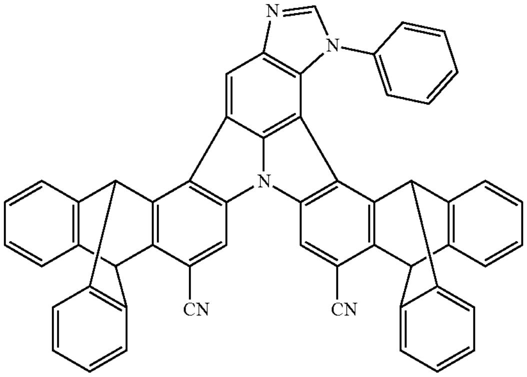 [SMILES: N#Cc1cc2c(c3c1C1c4ccccc4C3c3ccccc31)c1cc3ncn(-c4ccccc4)c3c3c4c5c(c(C#N)cc4n2c13)C1c2ccccc2C5c2ccccc21] | 35% |
| ES52 | S1 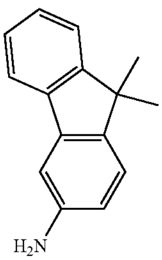 1421789-14-1 | 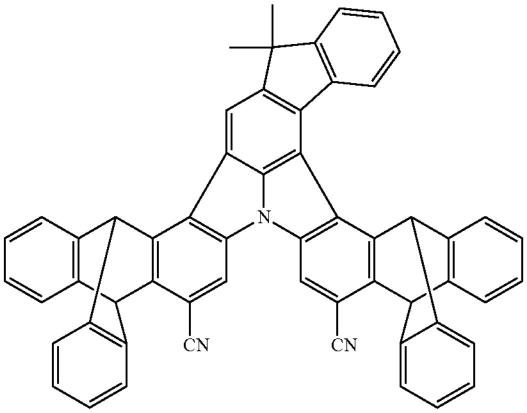 [SMILES: CC1(C)c2ccccc2-c2c1cc1c3c4c(c(C#N)cc3n3c5cc(C#N)c6c(c5c2c13)C1c2ccccc2C6c2ccccc21)C1c2ccccc2C4c2ccccc21] | 33% |

-continued
| Ex. | Nitrile Amine | Product | Yield |
|---|---|---|---|
| ES53 | S1 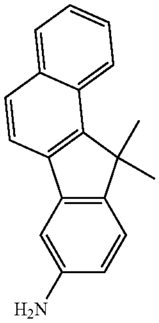 2411114-70-8 | 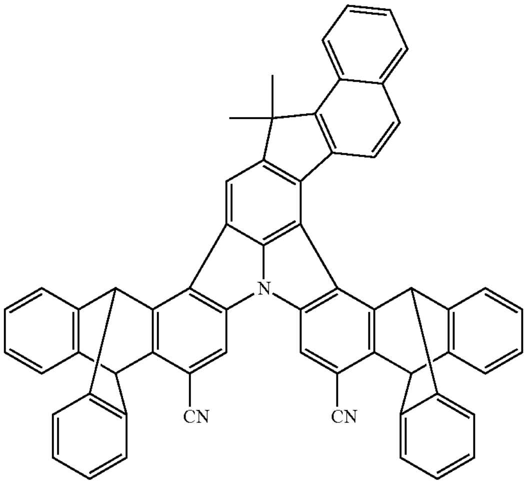 [SMILES: CC1(C)c2cc3c4c5c(c(C#N)cc4n4c6cc(C#N)c7c(c6c(c2-c2ccc6ccccc6c21)c34)C1c2ccccc2C7c2ccccc21)C1c2ccccc2C5c2ccccc21] | 35% |
| ES54 | S1 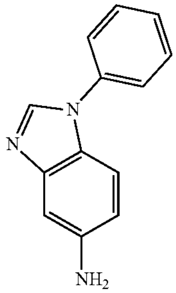 53897-95-3 | 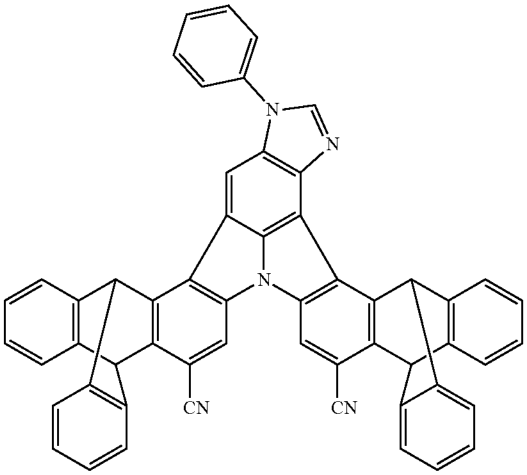 [SMILES: N#Cc1cc2c(c3c1C1c4ccccc4C3c3ccccc31)c1cc3c(ncn3-c3ccccc3)c3c4c5c(c(C#N)cc4n2c13)C1c2ccccc2C5c2ccccc21] | 31% |
| ES55 | S1 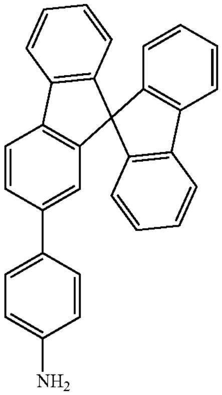 1853250-47-1 | 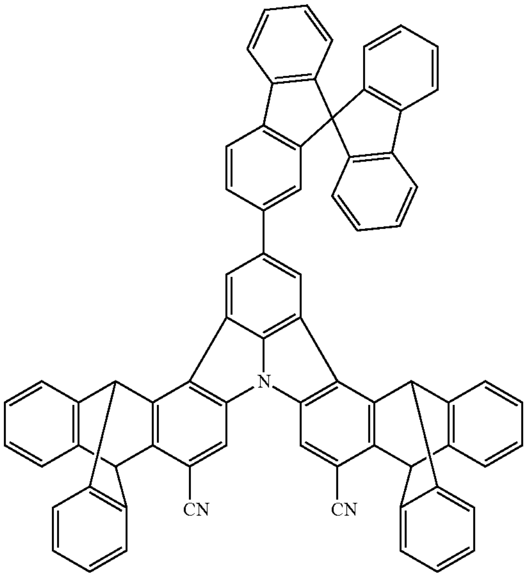 [SMILES: N#Cc1cc2c(c3c1C1c4ccccc4C3c3ccccc31)c1cc(-c3ccc4c(c3)C3(c5ccccc5-c5ccccc53)c3ccccc3-4)cc3c4c5c(c(C#N)cc4n2c13)C1c2ccccc2C5c2ccccc21] | 38% |

-continued
| Ex. | Nitrile Amine | Product | Yield |
|---|---|---|---|
| ES56 | S1 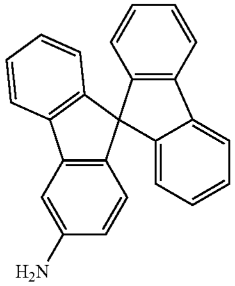 1644466-73-8 | 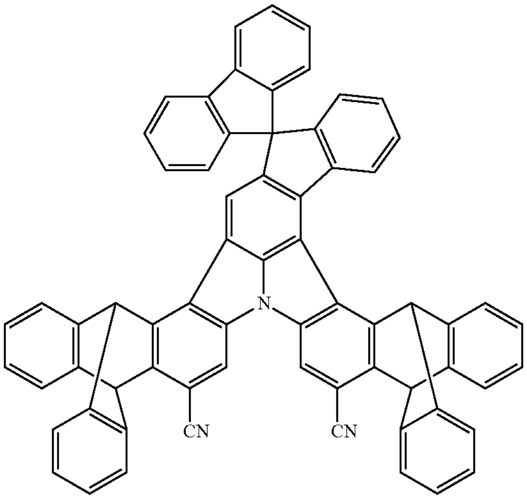 [SMILES: N#Cc1cc2c(c3c1C1c4ccccc4C3c3ccccc31)c1cc3c(c4c5c6c(c(C#N)cc5n2c14)C1c2ccccc2C6c2ccccc21)-c1ccccc1C31c2ccccc2-c2ccccc21] | 36% |
| ES57 | S1 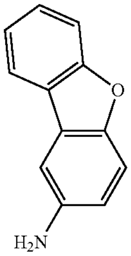 3693-22-9 | 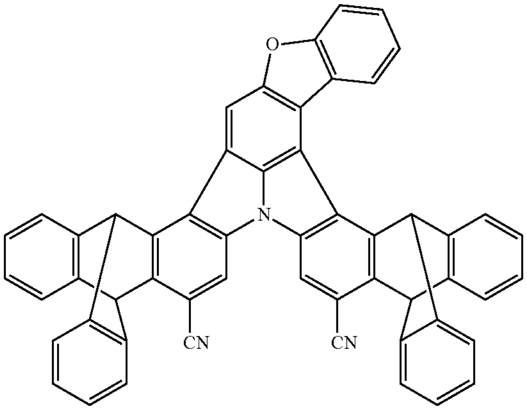 [SMILES: N#Cc1cc2c(c3c1C1c4ccccc4C3c3ccccc31)c1cc3oc4ccccc4c3c3c4c5c(c(C#N)cc4n2c13)C1c2ccccc2C5c2ccccc21] | 37% |
| ES58 | S4 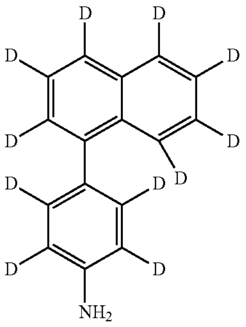 1940112-89-9 | 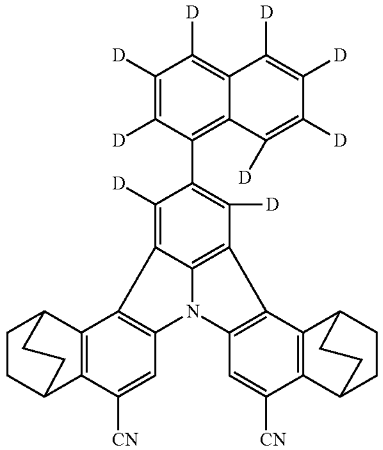 [SMILES: [2H]c1c([2H])c([2H])c2c(-c3c([2H])c4c5c6c(c(C#N)cc5n5c7cc(C#N)c8c(c7c(c3[2H])c45)C3CCC8CC3)C3CCC6CC3)c([2H])c([2H])c([2H])c2c1[2H]] | 35% |

-continued
| Ex. | Nitrile Amine | Product | Yield |
|---|---|---|---|
| ES59 | S1 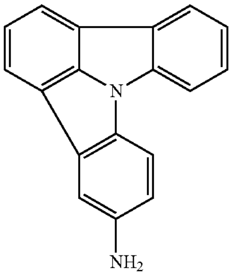 1191512-09-0 | 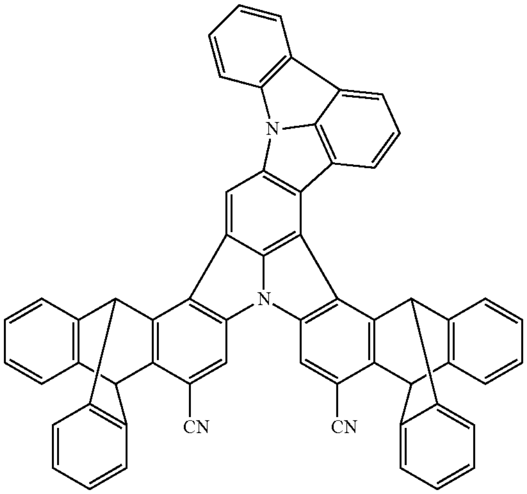 [SMILES: N#Cc1cc2c(c3c1C1c4ccccc4C3c3ccccc31)c1cc3c(c4cccc5c6ccccc6n3c54)c3c4c5c(c(C#N)cc4n2c13)C1c2ccccc2C5c2ccccc21] | 30% |
| ES60 | S4 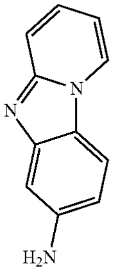 130595-01-6 | 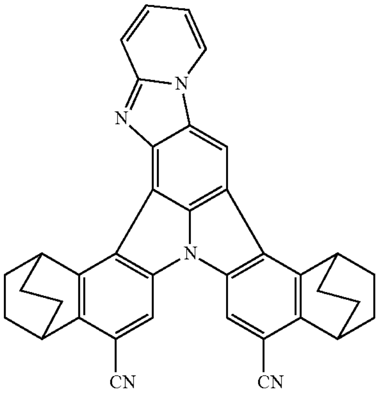 [SMILES: N#Cc1cc2c(c3c1C1CCC3CC1)c1cc3c(nc4ccccn43)c3c4c5c(c(C#N)cc4n2c13)C1CCC5CC1] | 28% |
| ES61 | S1 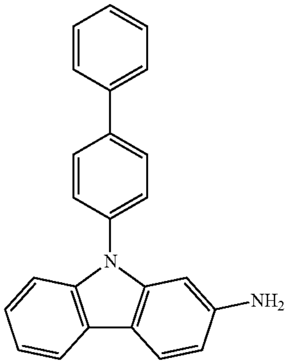 2129673-55-6 | 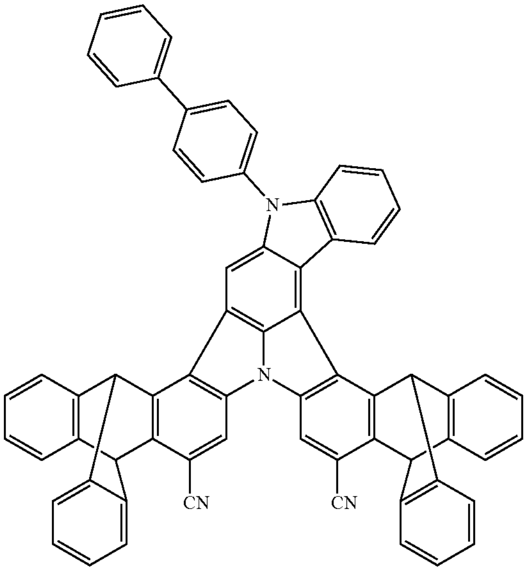 [SMILES: N#Cc1cc2c(c3c1C1c4ccccc4C3c3ccccc31)c1cc3c(c4ccccc4n3-c3ccc(-c4ccccc4)cc3)c3c4c5c(c(C#N)cc4n2c13)C1c2ccccc2C5c2ccccc21] | 36% |

-continued
| Ex. | Nitrile Amine | Product | Yield |
|---|---|---|---|
| ES62 | S1 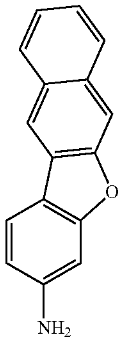 2179038-73-2 | 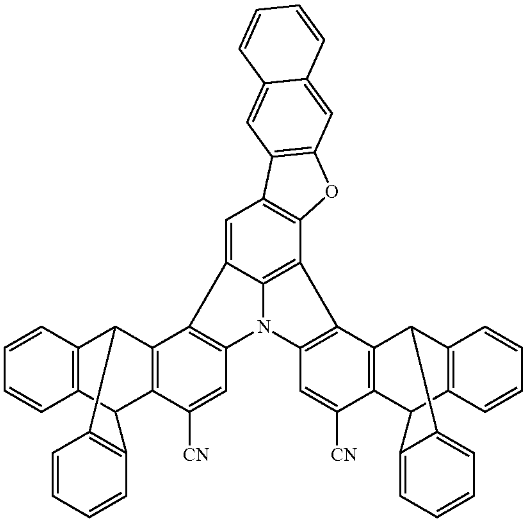 [SMILES: N#Cc1cc2c(c3c1C1c4ccccc4C3c3ccccc31)c1cc3c4cc5ccccc5cc4oc3c3c4c5c(c(C#N)cc4n2c13)C1c2ccccc2C5c2ccccc21] | 38% |
| ES63 | S3 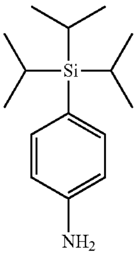 1346517-64-3 | 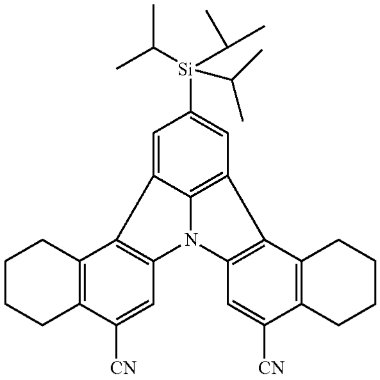 [SMILES: CC(C)[Si](c1cc2c3c4c(c(C#N)cc3n3c5cc(C#N)c6c(c5c(c1)c23)CCCC6)CCCC4)(C(C)C)C(C)C] | 27% |
| ES64 | S1 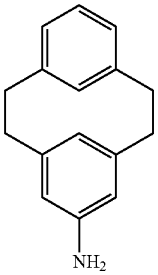 43215-86-7 | 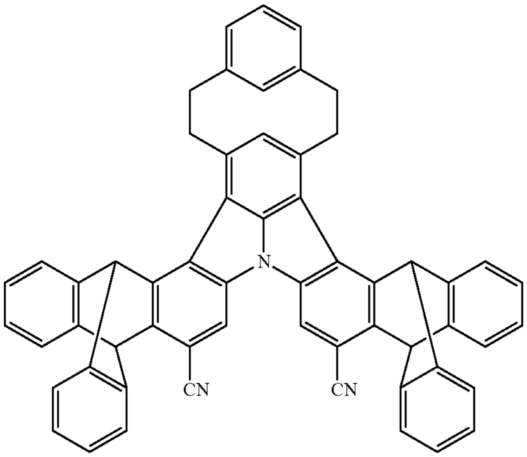 [SMILES: N#Cc1cc2c(c3c1C1c4ccccc4C3c3ccccc31)c1c3cc(c4c5c6c(c(C#N)cc5n2c14)C1c2ccccc2C6c2ccccc21)CCc1cccc(c1)CC3] | 32% |

-continued
| Ex. | Nitrile Amine | Product | Yield |
|---|---|---|---|
| ES65 | S2<br>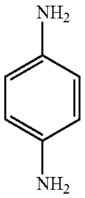<br>106-50-3<br>25 mmol | 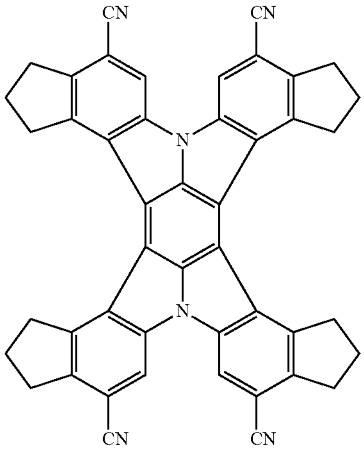 [SMILES: N#Cc1cc2c(c3c1CCC3)c1c3c4c5c(c(C#N)cc4n4c6cc(C#N)c7c(c6c(c6c8c9c(c(C#N)cc8n2c16)CCC9)c34)CCC7)CCC5] | 21% |
| ES66 | S1<br>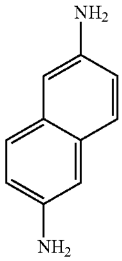<br>2243-67-6<br>25 mmol | 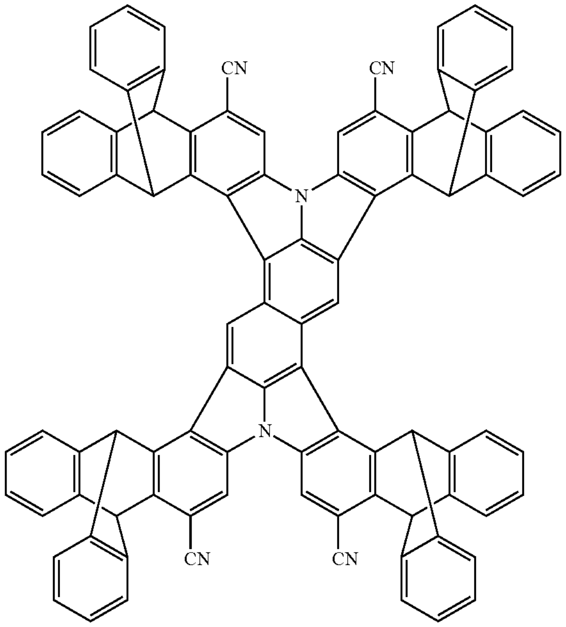 [SMILES: N#Cc1cc2c(c3c1C1c4ccccc4C3c3ccccc31)c1cc3c(cc4c5c6c(c(C#N)cc5n5c7cc(C#N)c8c(c7c3c45)C3c4ccccc4C8c4ccccc43)C3c4ccccc4C6c4ccccc43)c3c4c5c(c(C#N)cc4n2c13)C1c2ccccc2C5c2ccccc21] | 22% |

-continued
| Ex. | Nitrile<br>Amine | Product | Yield |
|---|---|---|---|
| ES67 | S1<br>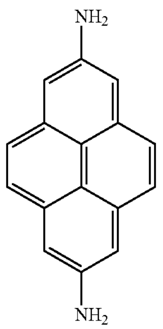<br>64535-41-7<br>25 mmol | 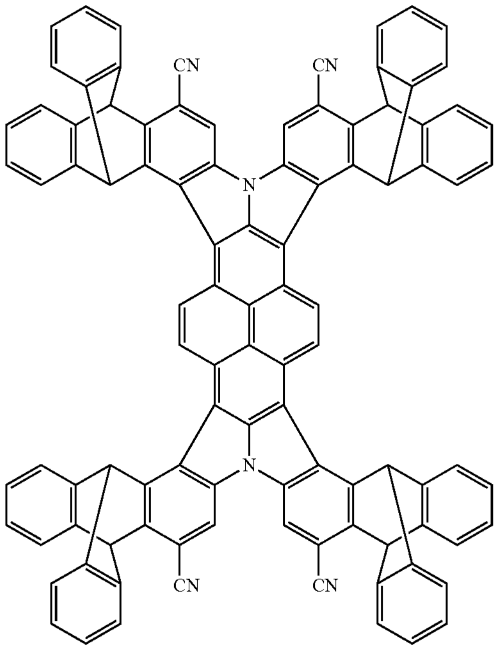 [SMILES: N#Cc1cc2c(c3c1C1c4ccccc4C3c3ccccc31)c1c3ccc4c5c(ccc(c35)c3c5c6c(c(C#N)cc5n2c13)C1c2ccccc2C6c2ccccc21)c1c2c3c(c(C#N)cc2n2c5cc(C#N)c6c(c5c4c12)C1c2ccccc2C6c2ccccc21)C1c2ccccc2C3c2ccccc21] | 19% |
| ES68 | S1<br>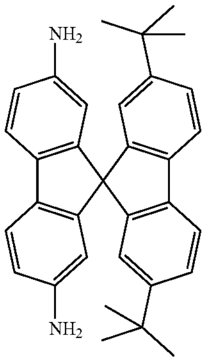<br>866464-33-7<br>25 mmol | 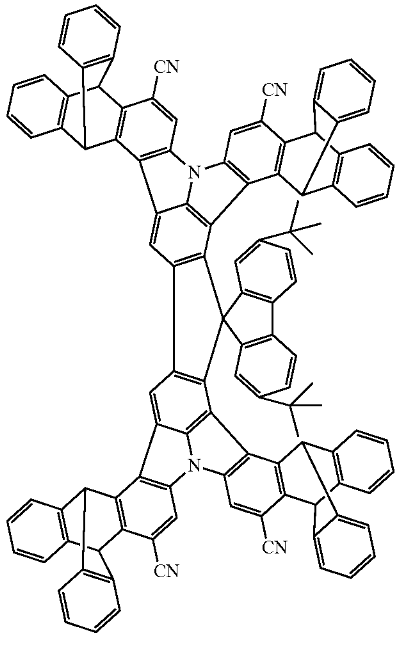 [SMILES: CC(C)(C)c1ccc2c(c1)C1(c3cc(C(C)(C)C)ccc3-2)c2c(cc3c4c5c(c(C#N)cc4n4c6cc(C#N)c7c(c6c2c34)C2c3ccccc3C7c3ccccc32)C2c3ccccc3C5c3ccccc32)-c2cc3c4c5c(c(C#N)cc4n4c6cc(C#N)c7c(c6c(c21)c34)C1c2ccccc2C7c2ccccc21)C1c2ccccc2C5c2ccccc21] | 12% |

-continued
| Ex. | Nitrile Amine | Product | Yield |
|---|---|---|---|
| ES69 | S1 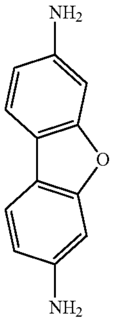 5896-30-0 25 mmol | 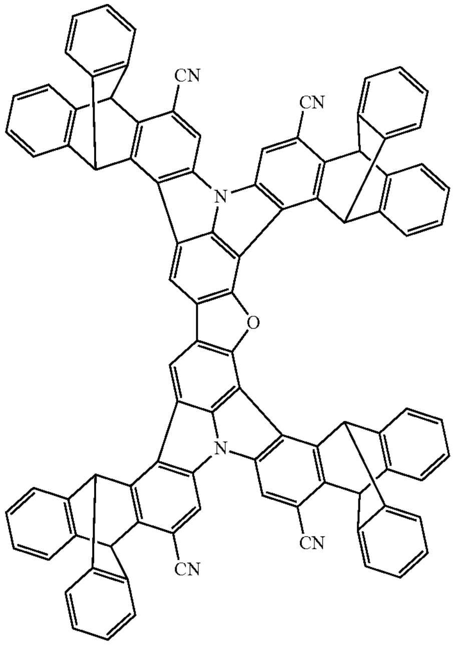 [SMILES: N#Cc1cc2c(c3c1C1c4ccccc4C3c3ccccc31)c1cc3c4cc5c6c7c(c(C#N)cc6n6c8cc(C#N)c9c(c8c(c4oc3c3c4c8c(c(C#N)cc4n2c13)C1c2ccccc2C8c2ccccc21)c56)C1c2ccccc2C9c2ccccc21)C1c2ccccc2C7c2ccccc21] | 21% |
| ES70 | S1 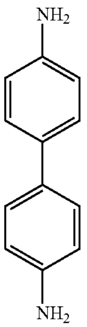 92-87-5 25 mmol | 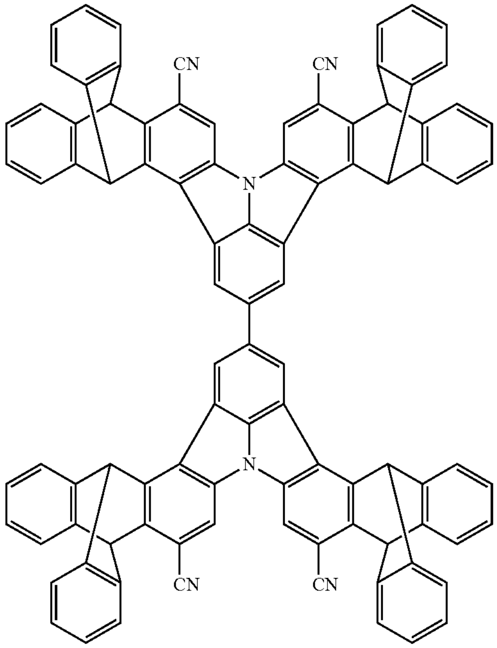 [SMILES: N#Cc1cc2c(c3c1C1c4ccccc4C3c3ccccc31)c1cc(-c3cc4c5c6c(c(C#N)cc5n5c7cc(C#N)c8c(c7c(c3)c45)C3c4ccccc4C8c4ccccc43)C3c4ccccc4C6c4ccccc43)cc3c4c5c(c(C#N)cc4n2c13)C1c2ccccc2C5c2ccccc21] | 20% |

-continued

| Ex. | Nitrile Amine | Product | Yield |
|---|---|---|---|
| ES71 | S4 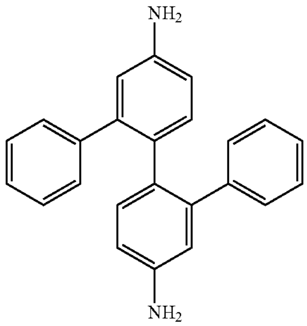 167559-51-5 25 mmol | 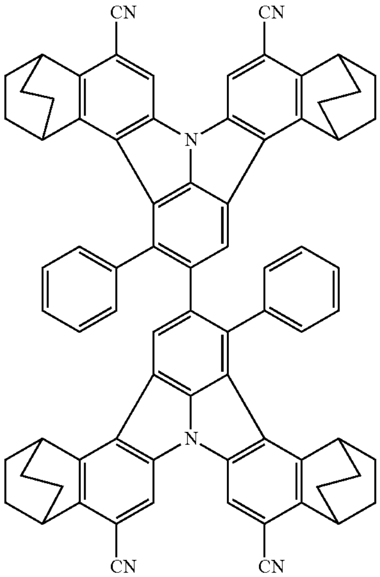 [SMILES: N#Cc1cc2c(c3c1C1CCC3CC1)c1cc(-c3cc4c5c6c(c(C#N)cc5n5c7cc(C#N)c8c(c7c(c3-c3ccccc3)c45)C3CCC8CC3)C3CCC6CC3)c(-c3ccccc3)c3c4c5c(c(C#N)cc4n2c13)C1CCC5CC1] | 18% |

2.2) Synthesis of the Asymmetrically Substituted Emitters EAS

Example EAS1

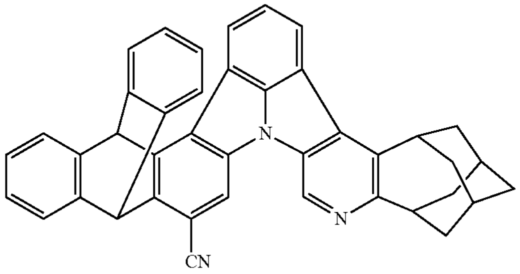 [SMILES: N#Cc1cc2c(c3c1C1c4ccccc4C3c3ccccc31)c1cccc3c4c5c(ncc4n2c31)C1CC2CC(C1)CC5C2]

Variant 1

Procedure analogous to the following literature:

T. Kader et al., Chem. Eur. J., 2019, 25, 4412-4425.

A mixture of 37.5 g (50 mmol) of A500, 27.6 g (200 mmol) of potassium carbonate, 1.72 g (3 mmol) of (NHC)Pd(allyl)Cl [478980-03-9], 50 g of glass beads (diameter 3 mm) and 500 ml of N,N-dimethylacetamide (DMAc) is heated to 140° C. with good stirring for 16 h. After cooling to 80° C., 1000 ml of water is added dropwise, the precipitated solids are filtered off with suction, and these are washed twice with 100 ml each time of water and twice with 50 ml each time of methanol, and dried under reduced pressure. The crude product is subjected to flash chromatography (Combi-Flash Torrent from A. Semrau, DCM: 2% MeOH), which also separates isomers that occur. Finally, the emitters thus obtained are purified by repeated hot extraction crystallization (DCM:acetonitrile 1:3 to 2:1) and subsequent fractional sublimation or by heat treatment under high vacuum. Yield: 14.0 g (25 mmol), 50%; purity: >99.9% by HPLC.

Rather than (NHC)Pd(allyl)Cl, it is also possible to use 4 mmol of $[(tBu)_3PH][BF_4]$ and 2 mmol of $Pd(OAc)_2$.

Analogously to stages 1.5 and 2.2, it is possible to prepare the following emitters EAS; yield over two stages:
| Ex. | Synthons S Amine | Product | Yield |
|---|---|---|---|
| EAS2A | S1 S601 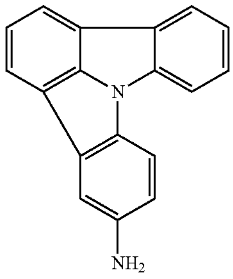 1191512-09-0 | 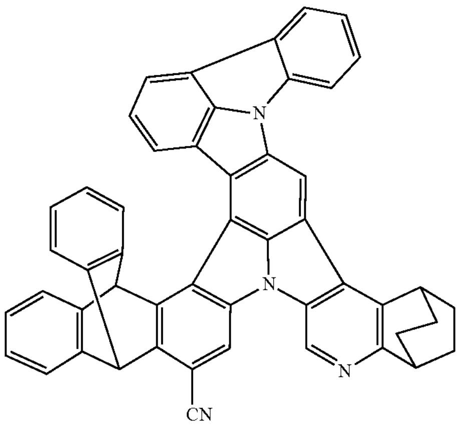 [SMILES: N#Cc1cc2c(c3c1C1c4ccccc4C3c3ccccc31)c1c3c4cccc5c6ccccc6n(c3cc3c6c7c(ncc6n2c31)C1CCC7CC1)c54] | 17% |
| EAS2B | | 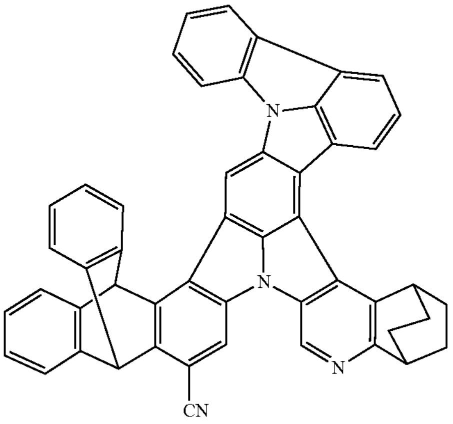 [SMILES: N#Cc1cc2c(c3c1C1c4ccccc4C3c3ccccc31)c1cc3c(c4cccc5c6ccccc6n3c54)c3c4c5c(ncc4n2c13)C1CCC5CC1] | 17% |
| EAS3A | S1 S602 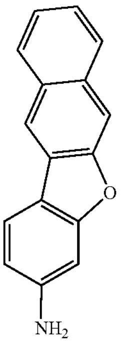 2179038-73-2 | 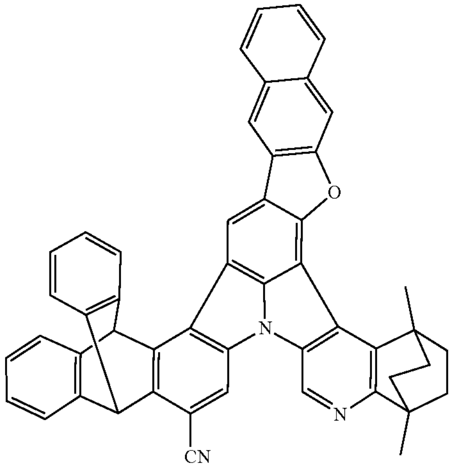 [SMILES: CC12CCC(C)(CC1)c1c2ncc2c1c1c3oc4cc5ccccc5cc4c3cc3c4c5c(c(C#N)cc4n2c31)C1c2ccccc2C5c2ccccc21] | 19% |

-continued
| Ex. | Synthons S Amine | Product | Yield |
|---|---|---|---|
| EAS3B | | 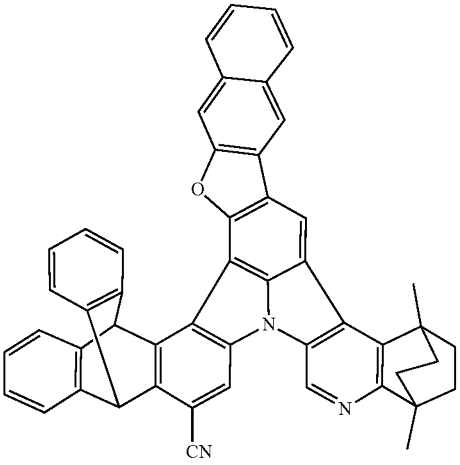 [SMILES: CC12CCC(C)(CC1)c1c2ncc2c1c1cc3c4cc5ccccc5cc4oc3c3c4c5c(c(C#N)cc4n2c13)C1c2ccccc2C5c2ccccc21] | 17% |
| EAS4A | S1<br>S603<br>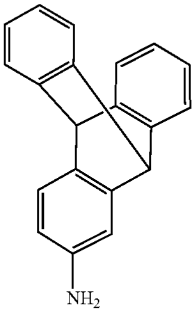<br>31997-11-2 | 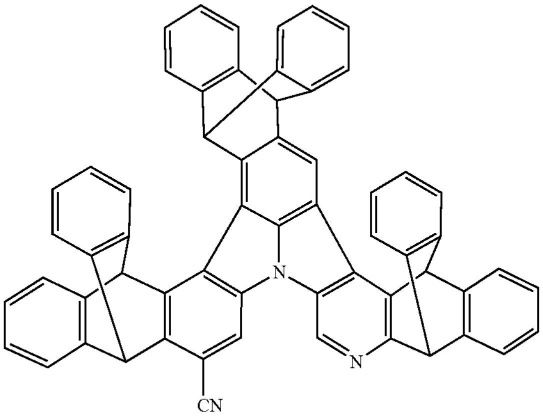 [SMILES: N#Cc1cc2c(c3c1C1c4ccccc4C3c3ccccc31)c1c3c(cc4c5c6c(ncc5n2c41)C1c2ccccc2C6c2ccccc21)C1c2ccccc2C3c2ccccc21] | 19% |
| EAS4B | | 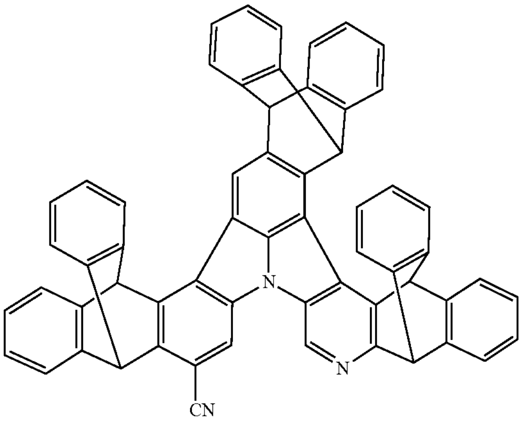 [SMILES: N#Cc1cc2c(c3c1C1c4ccccc4C3c3ccccc31)c1cc3c(c4c5c6c(ncc5n2c14)C1c2ccccc2C6c2ccccc21)C1c2ccccc2C12c1ccccc1C32] | 15% |

-continued
| Ex. | Synthons S Amine | Product | Yield |
|---|---|---|---|
| EAS5 | S1<br>S604<br>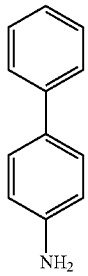<br>92-67-1 | 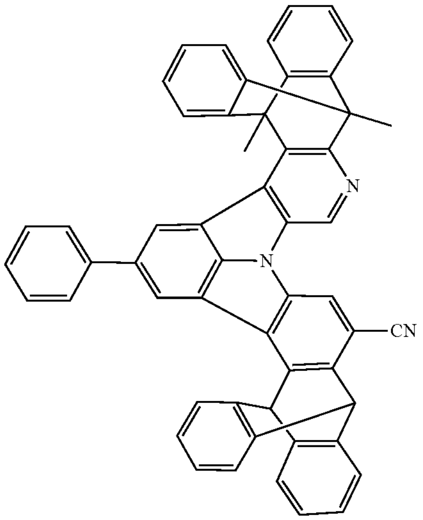 [SMILES: CC12c3ccccc3C(C)(c3ccccc31)c1c2ncc2c1c1cc(-c3ccccc3)cc3c4c5c(c(C#N)cc4n2c31)C1c2ccccc2C5c2ccccc21] | 33% |
| EAS6 | S1<br>S605<br>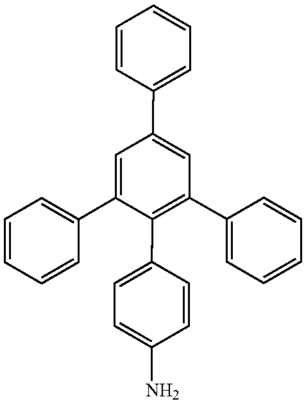<br>1093882-02-0 | 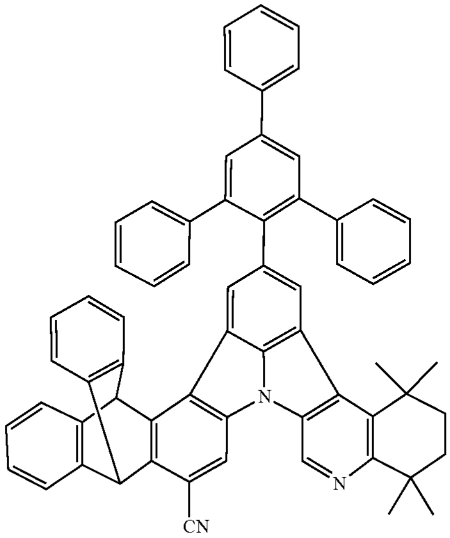 [SMILES: CC1(C)CCC(C)(C)c2c1ncc1c2c2cc(-c3c(-c4ccccc4)cc(-c4ccccc4)cc3-c3ccccc3)cc3c4c5c(c(C#N)cc4n1c32)C1c2ccccc2C5c2ccccc21] | 30% |
| EAS7 | S1<br>S606<br>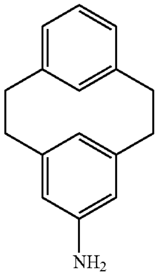<br>43215-86-7 | 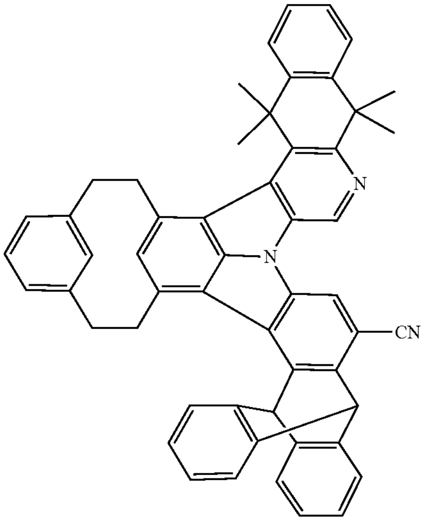 [SMILES: CC1(C)c2ccccc2C(C)(C)c2c1ncc1c2c2c3cc(c4c5c6c(c(C#N)cc5n1c42)C1c2ccccc2C6c2ccccc21)CCc1cccc(c1)CC3] | 35% |

-continued
| Ex. | Synthons S<br>Amine | Product | Yield |
|---|---|---|---|
| EAS8 | S1<br>S607<br>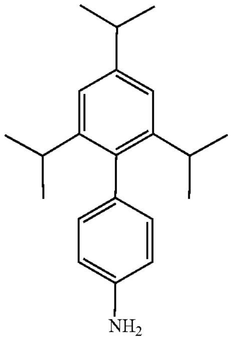<br>1801716-11-9 | 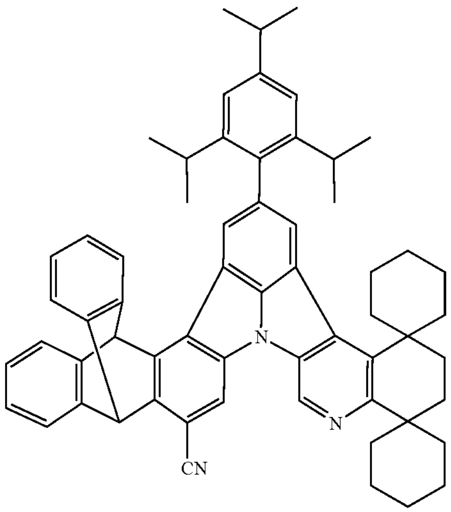 [SMILES: CC(C)c1cc(C(C)C)c(-c2cc3c4c5c(c(C#N)cc4n4c6cnc7c(c6c(c2)c34)C2(CCCCC2)CCC72CCCCC2)C2c3ccccc3C5c3ccccc32)c(C(C)C)c1] | 30% |
| EAS9 | S1<br>S608<br>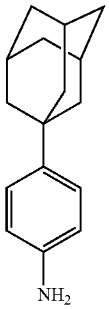<br>1459-48-9 | 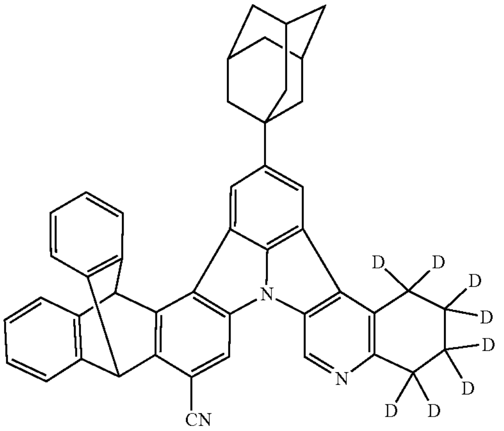 [SMILES: [2H]C1([2H])c2ncc3c(c2C([2H])([2H])C([2H])([2H])C1([2H])[2H])c1cc(C24CC5CC(CC(C5)C2)C4)cc2c4c5c(c(C#N)cc4n3c21)C1c2ccccc2C5c2ccccc21] | 32% |
| EAS10 | S1<br>S609<br>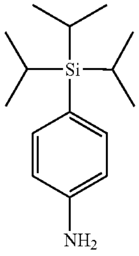<br>1346517-64-3 | 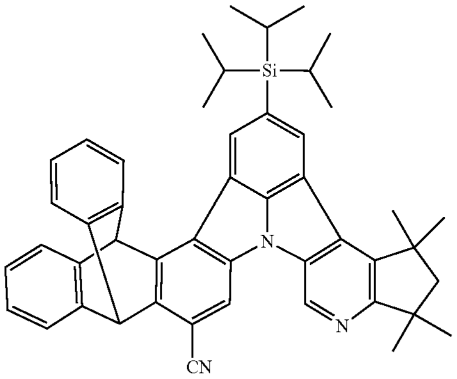 [SMILES: CC(C)[Si](c1cc2c3c4c(c(C#N)cc3n3c5cnc6c(c5c(c1)c23)C(C)(C)CC6(C)C)C1c2ccccc2C4c2ccccc21)(C(C)C)C(C)C] | 22% |

-continued
| Ex. | Synthons S Amine | Product | Yield |
|---|---|---|---|
| EAS11 | S1<br>S610<br>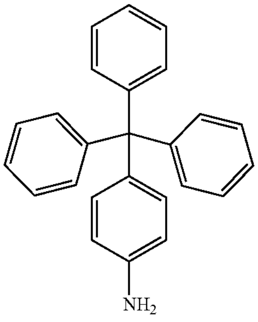<br>22948-06-7 | 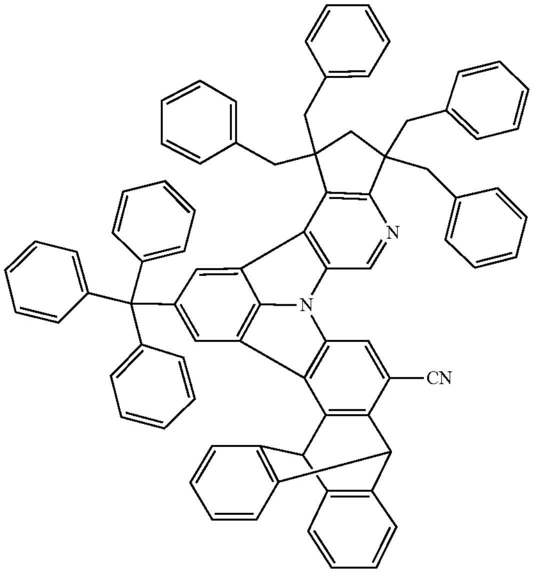 | 33% |
| EAS12 | S1<br>S611<br>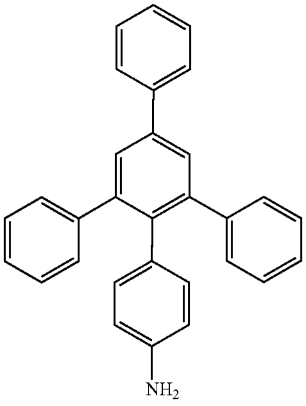<br>1093882-02-0 | 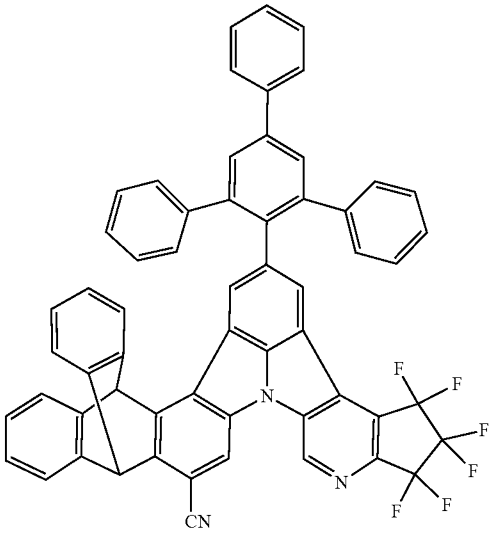 [SMILES: N#Cc1cc2c(c3c1C1c4ccccc4C3c3ccccc31)c1cc(-c3c(-c4ccccc4)cc(-c4ccccc4)cc3-c3ccccc3)cc3c4c5c(ncc4n2c13)C(F)(F)C(F)(F)C5(F)F] | 25% |
| EAS13 | S1<br>S612<br>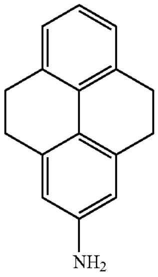<br>101283-00-5 | 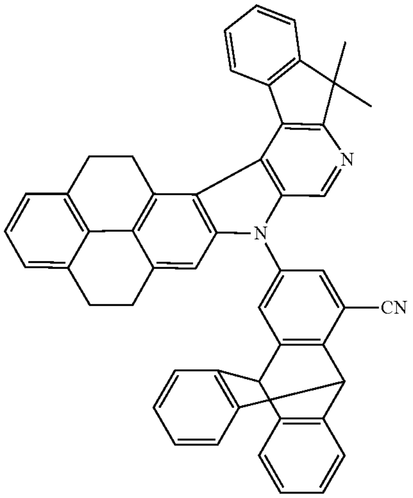 [SMILES: CC1(C)c2ccccc2-c2c1ncc1c2c2c3c4c(cc2n1-c1cc(C#N)c2c(c1)C1c5ccccc5C2c2ccccc21)CCc1cccc(c1-4)CC3] | 39% |

-continued
| Ex. | Synthons S Amine | Product | Yield |
|---|---|---|---|
| EAS14 | S1<br>S613<br>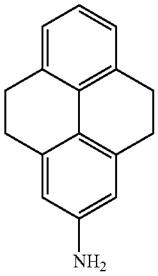<br>101283-00-5 | 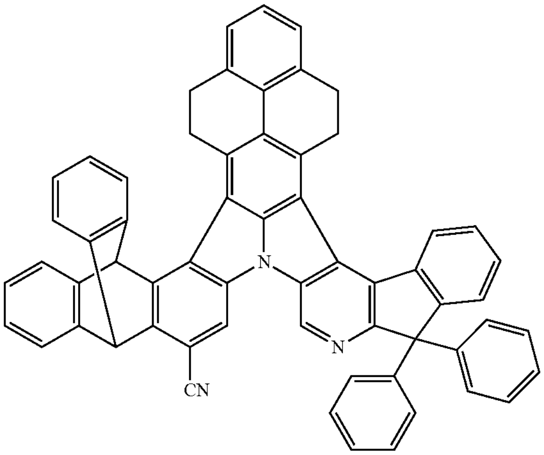 [SMILES: N#Cc1cc2c(c3c1C1c4ccccc4C3c3ccccc31)c1c3c4c(c5c6c7c(ncc6n2c51)C(c1ccccc1)(c1ccccc1)c1ccccc1-7)CCc1cccc(c1-4)CC3] | 38% |
| EAS15A | S1<br>S614<br>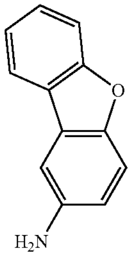<br>3693-22-9 | 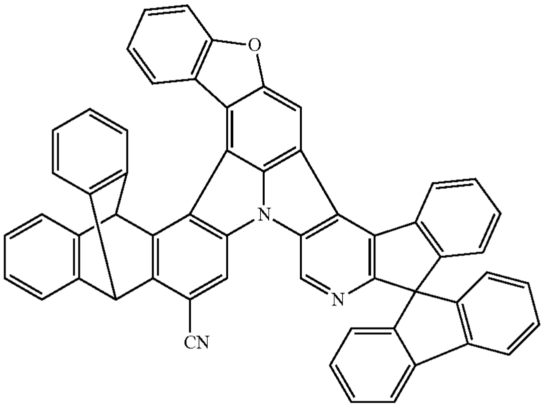 [SMILES: N#Cc1cc2c(c3c1C1c4ccccc4C3c3ccccc31)c1c3c(cc4c5c6c(ncc5n2c41)C1(c2ccccc2-c2ccccc21)c1ccccc1-6)oc1ccccc13] | 17% |
| EAS15B | | 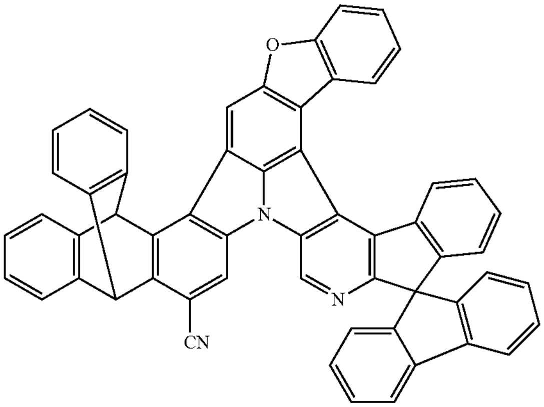 [SMILES: N#Cc1cc2c(c3c1C1c4ccccc4C3c3ccccc31)c1cc3oc4ccccc4c3c3c4c5c(ncc4n2c13)C1(c2ccccc2-c2ccccc21)c1ccccc1-5] | 19% |

-continued
| Ex. | Synthons S Amine | Product | Yield |
|---|---|---|---|
| EAS16 | S1<br>S615<br>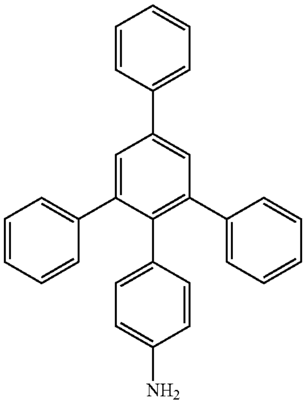<br>1093882-02-0 | 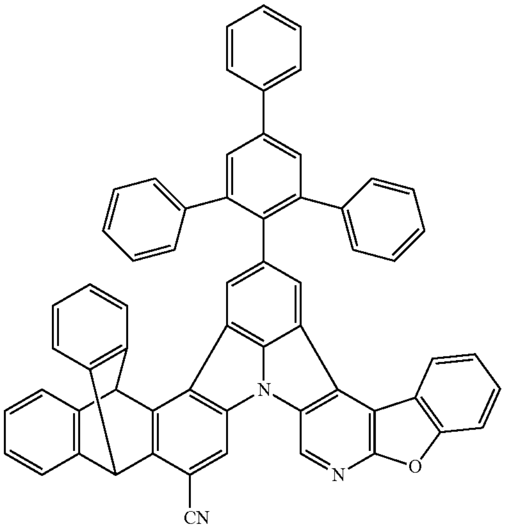 [SMILES: N#Cc1cc2c(c3c1C1c4ccccc4C3c3ccccc31)c1cc(-c3c(-c4ccccc4)cc(-c4ccccc4)cc3-c3ccccc3)cc3c4c5c(ncc4n2c13)oc1ccccc15] | 37% |
| EAS17 | S1<br>S616<br>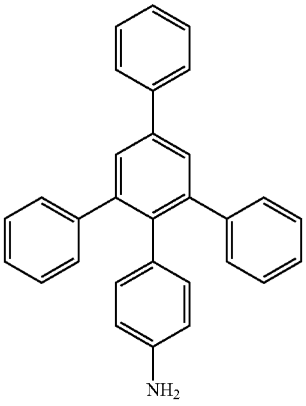<br>1093882-02-0 | 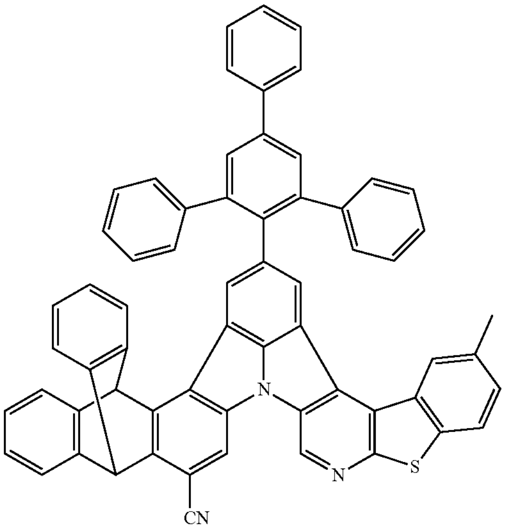 [SMILES: Cc1ccc2sc3ncc4c(c5cc(-c6c(-c7ccccc7)cc(-c7ccccc7)cc6-c6ccccc6)cc6c7c8c(c(C#N)cc7n4c65)C4c5ccccc5C8c5ccccc54)c3c2c1] | 37% |

-continued
| Ex. | Synthons S<br>Amine | Product | Yield |
|---|---|---|---|
| EAS18 | S1<br>S622<br>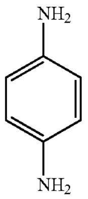<br>106-50-3<br>25 mmol | 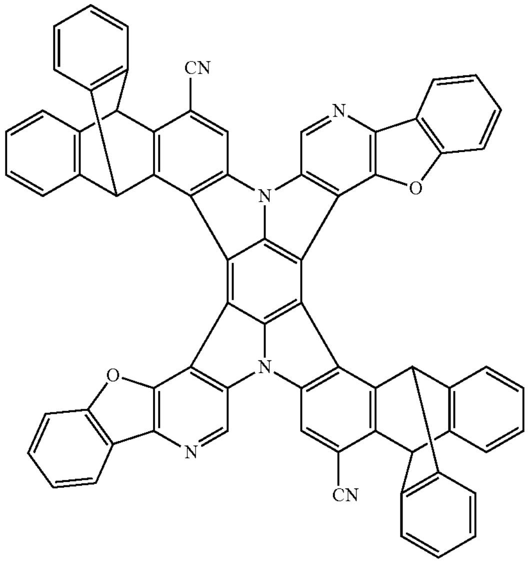 [SMILES: N#Cc1cc2c(c3c1C1c4ccccc4C3c3ccccc31)c1c3c4c5oc6ccccc6c5ncc4n4c5cc(C#N)c6c(c5c(c5c7c8oc9ccccc9c8ncc7n2c15)c34)C1c2ccccc2C6c2ccccc21] | 22% |
| EAS19 | S1<br>S620<br>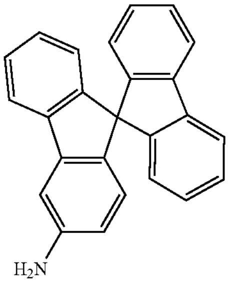<br>1644466-73-8 | 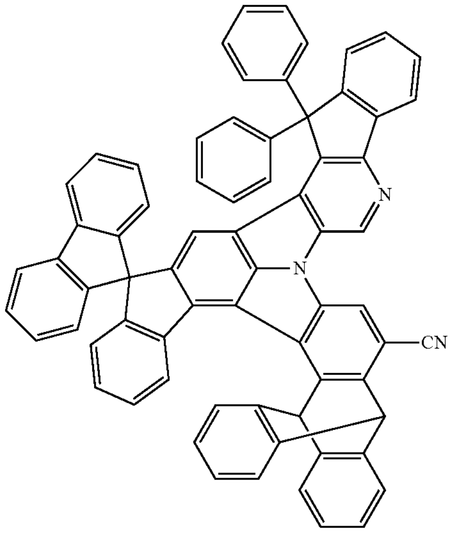 [SMILES: N#Cc1cc2c(c3c1C1c4ccccc4C3c3ccccc31)c1c3c(cc4c5c6c(ncc5n2c41)-c1ccccc1C6(c1ccccc1)c1ccccc1)C1(c2ccccc2-c2ccccc21)c1ccccc1-3] | 20% |

-continued
| Ex. | Synthons S<br>Amine | Product | Yield |
|---|---|---|---|
| EAS20 | S1<br>S622<br>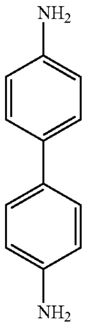<br>92-87-5<br>25 mmol | 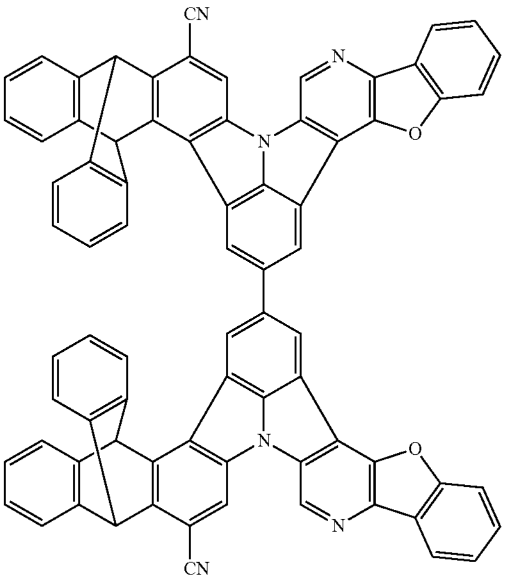 [SMILES: N#Cc1cc2c(c3c1C1c4ccccc4C3c3ccccc31)c1cc(-c3cc4c5c6c(c(C#N)cc5n5c7cnc8c9ccccc9oc8c7c(c3)c45)C3c4ccccc4C6c4ccccc43)cc3c4c5oc6ccccc6c5ncc4n2c13] | 31% |
| EAS21A | S1<br>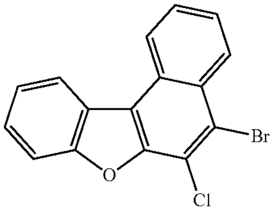<br>2445776-20-3 | 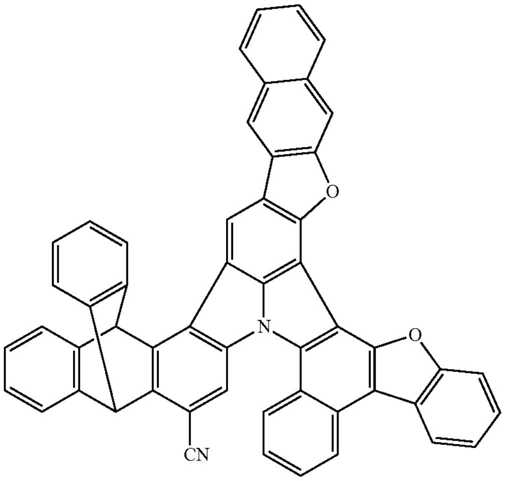 [SMILES: N#Cc1cc2c(c3c1C1c4ccccc4C3c3ccccc31)c1cc3c4cc5ccccc5cc4oc3c3c4c5oc6ccccc6c5c5ccccc5c4n2c13] | 20% |
| EAS21B | 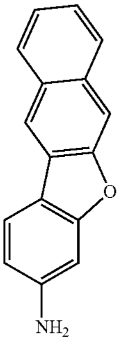<br>2179038-73-2 | 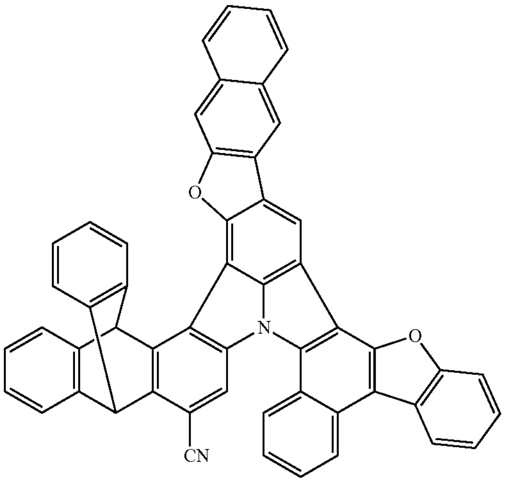 [SMILES: N#Cc1cc2c(c3c1C1c4ccccc4C3c3ccccc31)c1c3oc4cc5ccccc5cc4c3cc3c4c5oc6ccccc6c5c5ccccc5c4n2c31] | 15% |

-continued
| Ex. | Synthons S<br>Amine | Product | Yield |
|---|---|---|---|
| EAS22 | S1<br>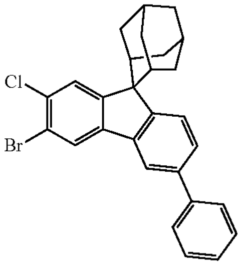<br>2500975-91-5<br>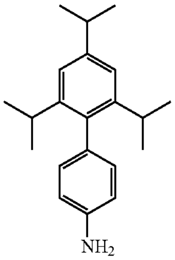<br>1801716-11-9 | 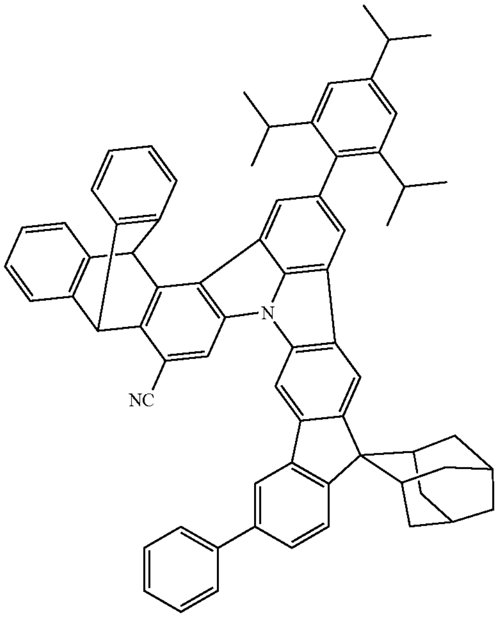 [SMILES: CC(C)c1cc(C(C)C)c(-c2cc3c4cc5c(cc4n4c6cc(C#N)c7c(c6c(c2)c34)C2c3ccccc3C7c3ccccc32)-c2cc(-c3ccccc3)ccc2C52C3CC4CC(C3)CC2C4)c(C(C)C)c1] | 36% |
| EAS23A | S1<br>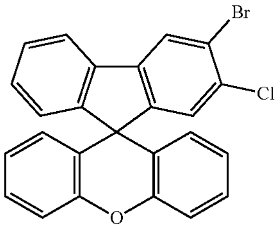<br>2492439-24-2 | 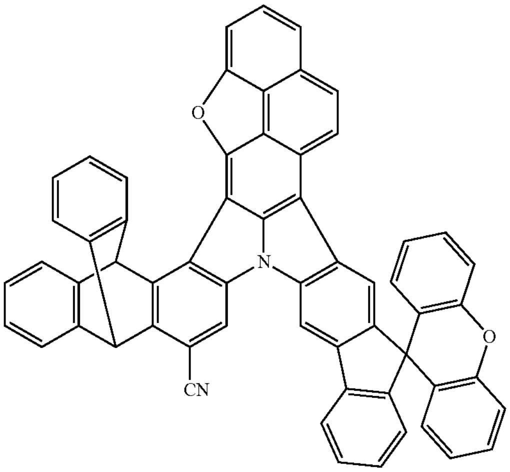 [SMILES: N#Cc1cc2c(c3c1C1c4ccccc4C3c3ccccc31)c1c3oc4cccc5ccc(c3c54)c3c4cc5c(cc4n2c31)-c1ccccc1C51c2ccccc2Oc2ccccc21] | 18% |
| EAS23B | 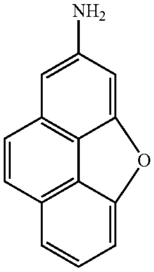<br>2018346-63-7 | 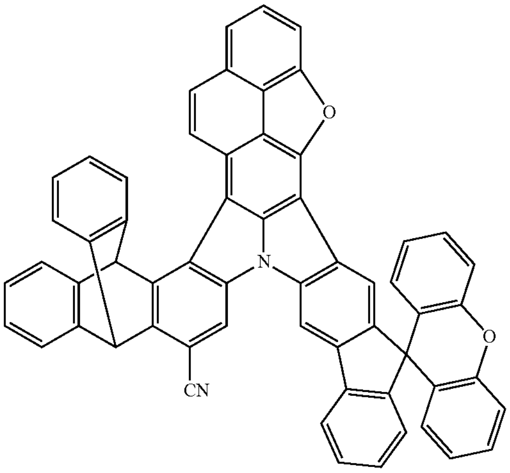 [SMILES: N#Cc1cc2c(c3c1C1c4ccccc4C3c3ccccc31)c1c3ccc4cccc5oc(c3c45)c3c4cc5c(cc4n2c31)-c1ccccc1C51c2ccccc2Oc2ccccc21] | 19% |

-continued
| Ex. | Synthons S<br>Amine | Product | Yield |
| --- | --- | --- | --- |
| EAS24A | S4<br>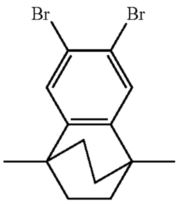<br>1801624-64-5 | 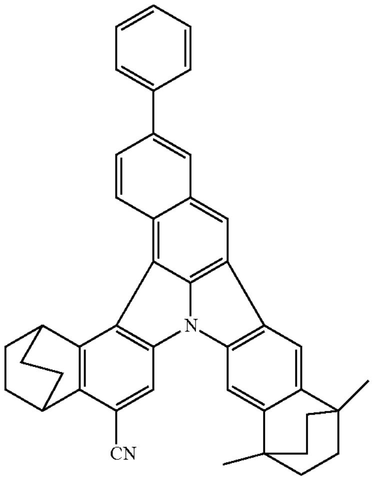 [SMILES: CC12CCC(C)(CC1)c1cc3c(cc12)c1cc2cc(-c4ccccc4)ccc2c2c4c5c(c(C#N)cc4n3c12)C1CCC5CC1] | 19% |
| EAS24B | 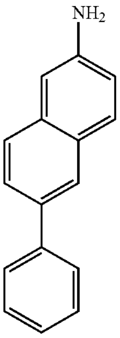<br>861046-41-5 | 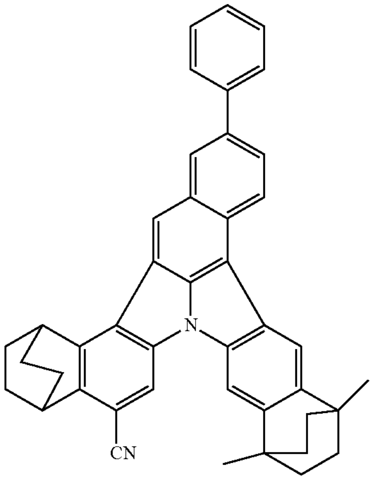 [SMILES: CC12CCC(C)(CC1)c1cc3c(cc12)c1c2ccc(-c4ccccc4)cc2cc2c4c5c(c(C#N)cc4n3c21)C1CCC5CC1] | 20% |
| EAS25 | S4<br>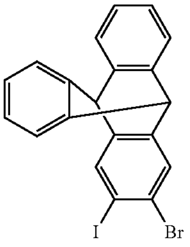<br>52776-04-2<br>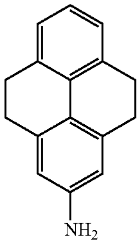<br>101283-00-5 | 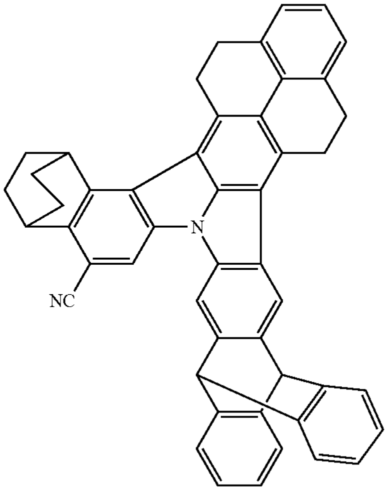 [SMILES: N#Cc1cc2c(c3c1C1CCC3CC1)c1c3c4c(c5c6cc7c(cc6n2c51)C1c2ccccc2C7c2ccccc21)CCc1cccc(c1-4)CC3] | 34% |

-continued
| Ex. | Synthons S<br>Amine | Product | Yield |
|---|---|---|---|
| EAS26 | S3<br>S503<br>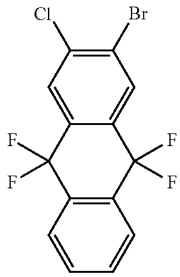<br>2304436-80-2<br>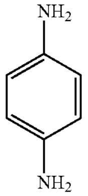<br>106-50-3<br>25 mmol | 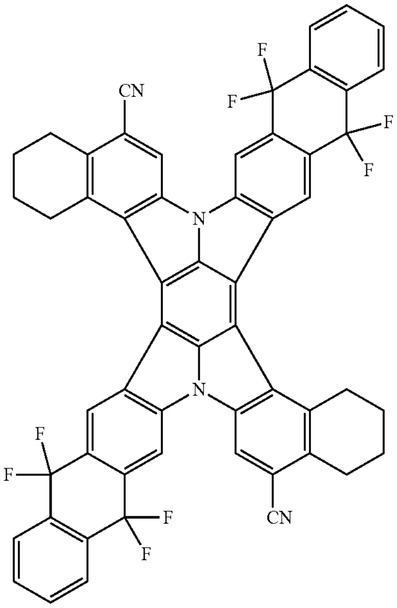 [SMILES: N#Cc1cc2c(c3c1CCCC3)c1c3c4cc5c(cc4n4c6cc(C#N)c7c(c6c(c6c8cc9c(cc8n2c61)C(F)(F)c1ccccc1C9(F)F)c34)CCCC7)C(F)(F)c1ccccc1C5(F)F] | 23% |
| EAS27 | S1<br>S4<br>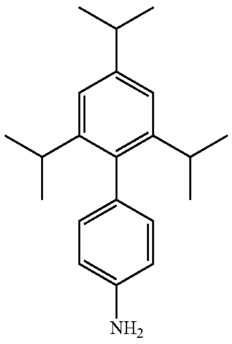<br>1801716-11-9 | 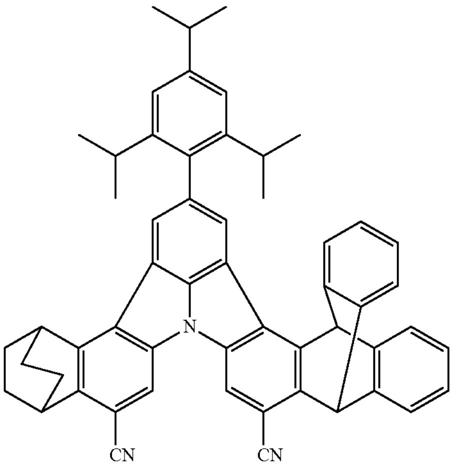 [SMILES: CC(C)c1cc(C(C)C)c(-c2cc3c4c5c(c(C#N)cc4n4c6cc(C#N)c7c(c6c(c2)c34)C2c3ccccc3C7c3ccccc32)C2CCC5CC2)c(C(C)C)c1] | 35% |

-continued
| Ex. | Synthons S<br>Amine | Product | Yield |
|---|---|---|---|
| EAS28 | S1<br>S3<br>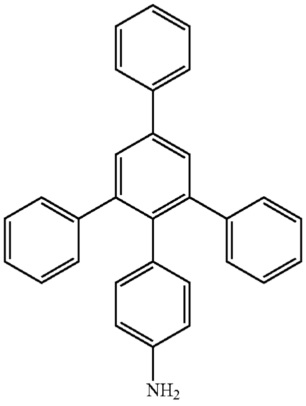<br>1093882-02-0 | 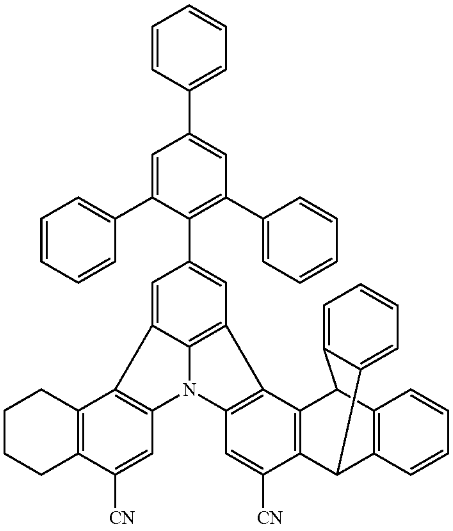 [SMILES: N#Cc1cc2c(c3c1CCCC3)c1cc(-c3c(-c4ccccc4)cc(-c4ccccc4)cc3-c3ccccc3)cc3c4c5c(c(C#N)cc4n2c13)C1c2ccccc2C5c2ccccc21] | 34% |
| EAS29 | S1<br>S4<br>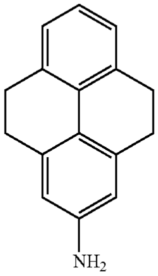<br>101283-00-5 | 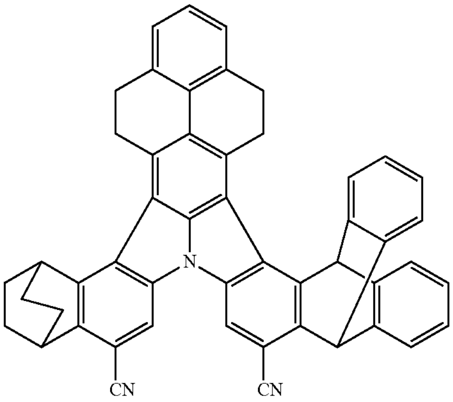 [SMILES: N#Cc1cc2c(c3c1C1CCC3CC1)c1c3c4c(c5c6c7c(c(C#N)cc6n2c15)C1c2ccccc2C7c2ccccc21)CCc1cccc(c1-4)CC3] | 33% |
| EAS30A | S2<br>S3<br>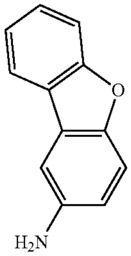<br>3693-22-9 | 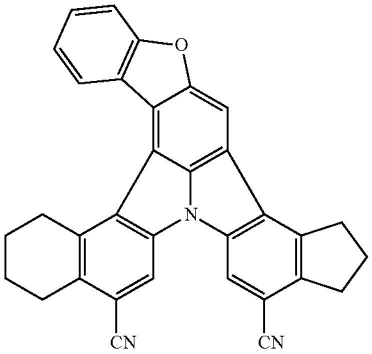 [SMILES: N#Cc1cc2c(c3c1CCC3)c1cc3oc4ccccc4c3c3c4c5c(c(C#N)cc4n2c13)CCCC5] | |

-continued
| Ex. | Synthons S<br>Amine | Product | Yield |
|---|---|---|---|
| EAS30B | | 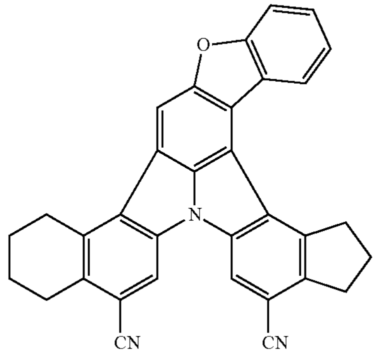<br>Isomer mixture | 34% |
| ESA31 | S1<br>S50<br>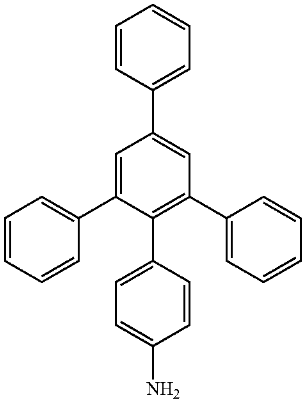<br>1093882-02-0 | 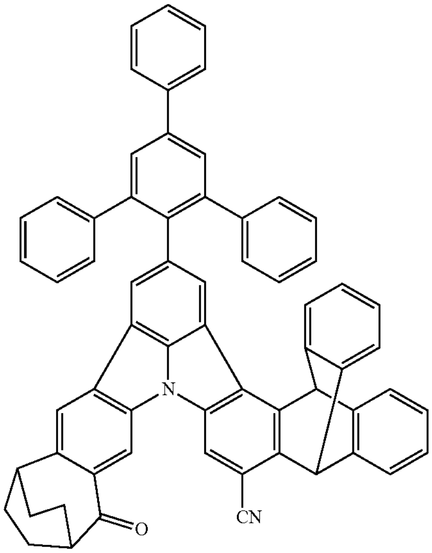 [SMILES: N#Cc1cc2c(c3c1C1c4ccccc4C3c3ccccc31)c1cc(-c3c(-c4ccccc4)cc(-c4ccccc4)cc3-c3ccccc3)cc3c4cc5c(cc4n2c31)C(=O)C1CCC5CC1] | 30% |
| EAS32A | S1<br>S51<br>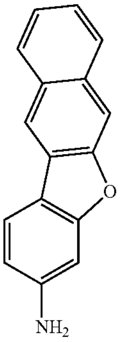<br>2179038-73-2 | 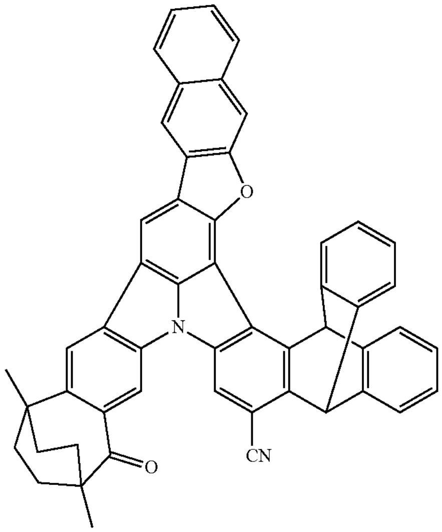 [SMILES: CC12CCC(C)(CC1)c1cc3c4cc5c6cc7ccccc7cc6oc5c5c6c7c(c(C#N)cc6n(c3cc1C2=O)c45)C1c2ccccc2C7c2ccccc21] | 19% |

-continued
| Ex. | Synthons S Amine | Product | Yield |
|---|---|---|---|
| EAS32B | | 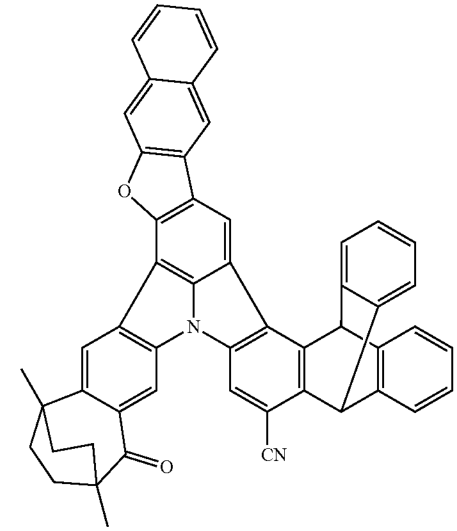 [SMILES: CC12CCC(C)(CC1)c1cc3c4c5oc6cc7ccccc7cc6c5cc5c6c7c(c(C#N)cc6n(c3cc1C2=O)c54)C1c2ccccc2C7c2ccccc21] | 17% |
| EAS33A | S1<br>S57<br>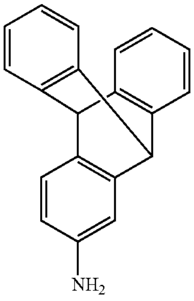<br>31997-11-2 | 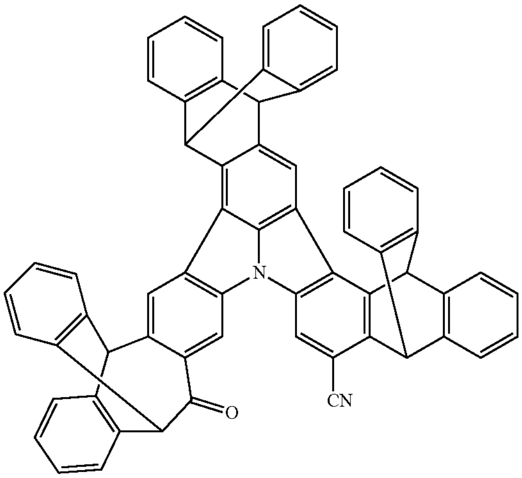 [SMILES: N#Cc1cc2c(c3c1C1c4ccccc4C3c3ccccc31)c1cc3c(c4c5cc6c(cc5n2c14)C(=O)C1c2ccccc2C6c2ccccc21)C1c2ccccc2C3c2ccccc21] | 19% |
| EAS33B | | 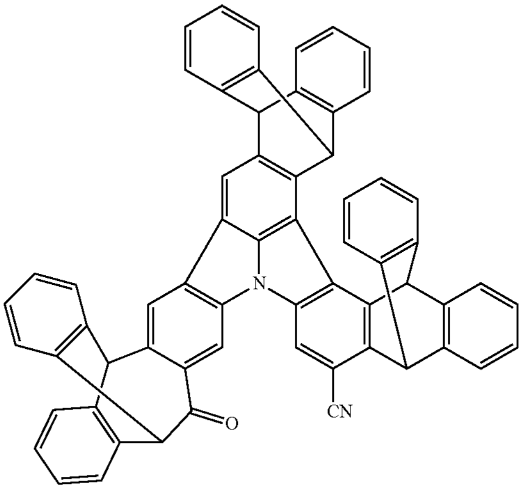 [SMILES: N#Cc1cc2c(c3c1C1c4ccccc4C3c3ccccc31)c1c3c(cc4c5cc6c(cc5n2c41)C(=O)C1c2ccccc2C6c2ccccc21)C1c2ccccc2C3c2ccccc21] | 16% |

-continued
| Ex. | Synthons S Amine | Product | Yield |
|---|---|---|---|
| EAS34 | S4<br>S53<br>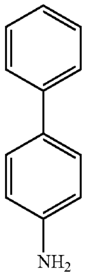<br>92-67-1 | 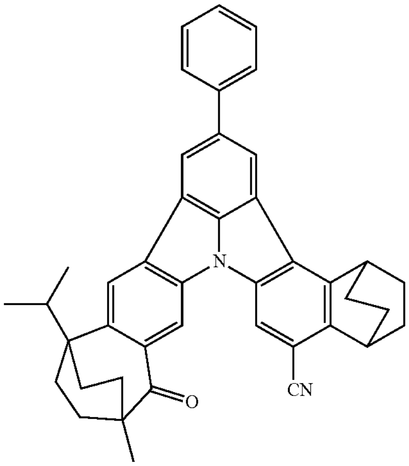 [SMILES: CC(C)C12CCC(C)(CC1)C(=O)c1cc3c(cc12)c1cc(-c2ccccc2)cc2c4c5c(c(C#N)cc4n3c12)C1CCC5CC1] | 35% |
| EAS35 | S3<br>S52<br>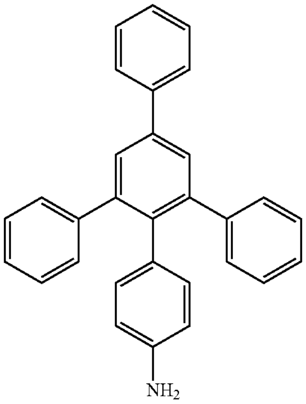<br>1093882-02-0 | 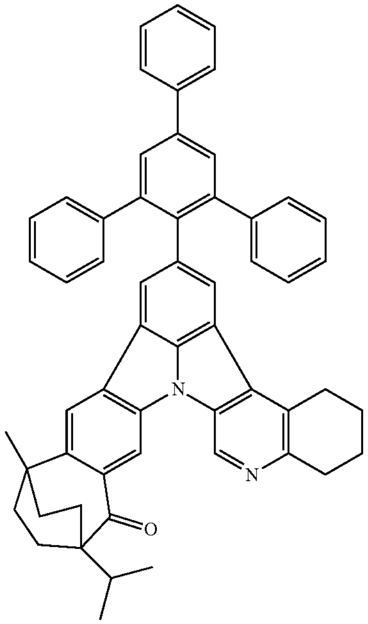 [SMILES: CC(C)C12CCC(C)(CC1)c1cc3c4cc(-c5c(-c6ccccc6)cc(-c6ccccc6)cc5-c5ccccc5)cc5c6c7c(ncc6n(c3cc1C2=O)c45)CCCC7] | 35% |
| EAS36 | S1<br>S54<br>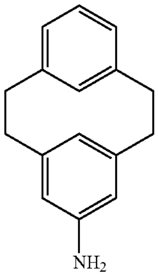<br>43215-86-7 | 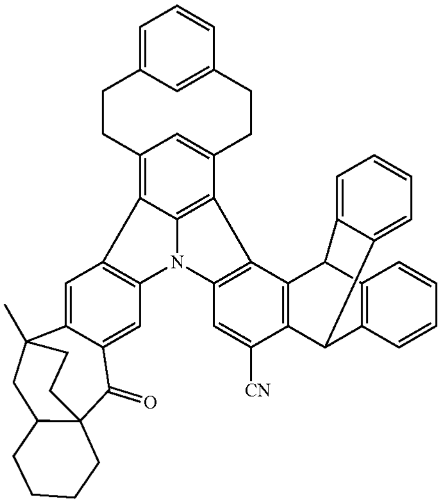 [SMILES: CC12CCC3(CCCCC3C1)C(=O)c1cc3c(cc12)c1c2cc(c4c5c6c(c(C#N)cc5n3c14)C1c3ccccc3C6c3ccccc31)CCc1cccc(c1)CC2] | 30% |

-continued
| Ex. | Synthons S Amine | Product | Yield |
|---|---|---|---|
| EAS37 | S4<br>S51<br>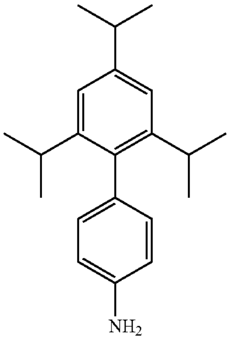<br>1801716-11-9 | 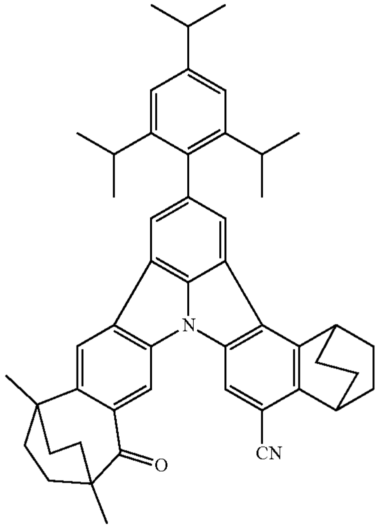 [SMILES: CC(C)c1cc(C(C)C)c(-c2cc3c4cc5c(cc4n4c6cc(C#N)c7c(c6c(c2)c34)C2CCC7CC2)C(=O)C2(C)CCC5(C)CC2)c(C(C)C)c1] | 36% |
| EAS38 | S1<br>S52<br>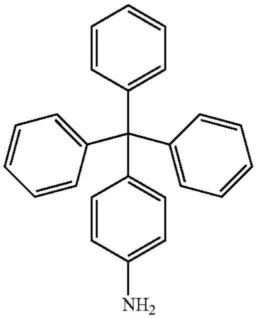<br>22948-06-7 | 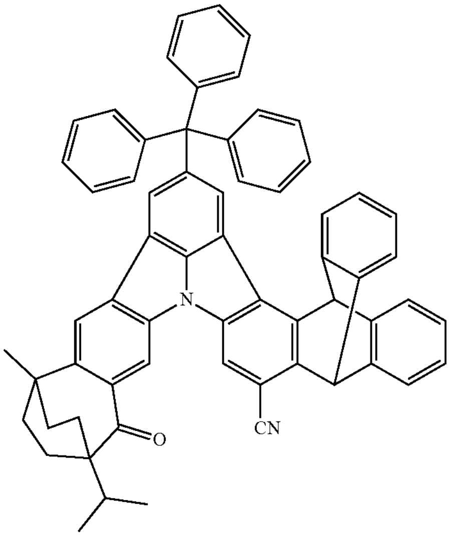 [SMILES: CC(C)C12CCC(C)(CC1)c1cc3c4cc(C(c5ccccc5)(c5ccccc5)c5ccccc5)cc5c6c7c(c(C#N)cc6n(c3cc1C2=O)c45)C1c2ccccc2C7c2ccccc21] | 35% |
| EAS39 | S1<br>S57<br>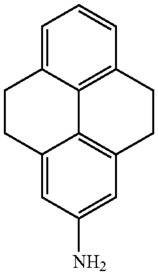<br>101283-00-5 | 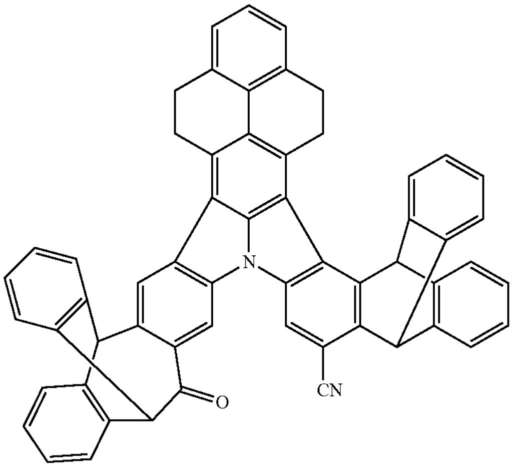 [SMILES: N#Cc1cc2c(c3c1C1c4ccccc4C3c3ccccc31)c1c3c4c(c5c6cc7c(cc6n2c51)C(=O)C1c2ccccc2C7c2ccccc21)CCc1cccc(c1-4)CC3] | 37% |

-continued
| Ex. | Synthons S Amine | Product | Yield |
|---|---|---|---|
| EAS40A | S1<br>S57<br>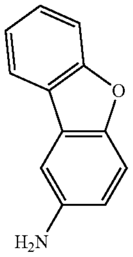<br>3693-22-9 | 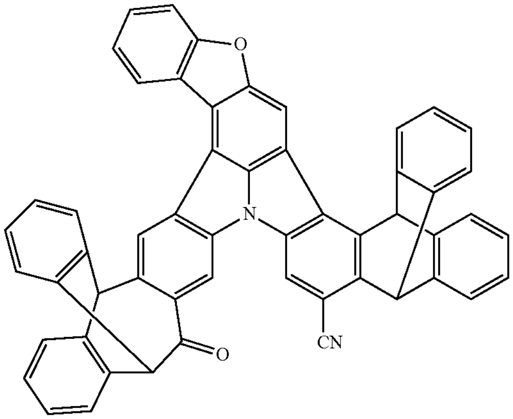 [SMILES: N#Cc1cc2c(c3c1C1c4ccccc4C3c3ccccc31)c1cc3oc4ccccc4c3c3c4cc5c(cc4n2c13)C(=O)C1c2ccccc2C5c2ccccc21] | 19% |
| EAS40B | | 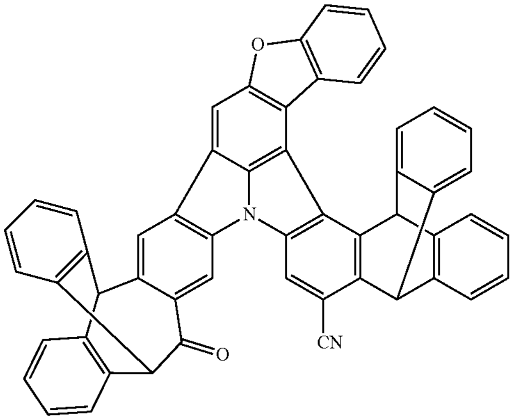 [SMILES: N#Cc1cc2c(c3c1C1c4ccccc4C3c3ccccc31)c1c3c(cc4c5cc6c(cc5n2c41)C(=O)C1c2ccccc2C6c2ccccc21)oc1ccccc13] | 21% |
| EAS41 | S4<br>S58<br>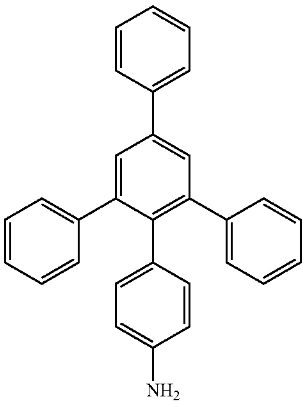<br>1093882-02-0 | 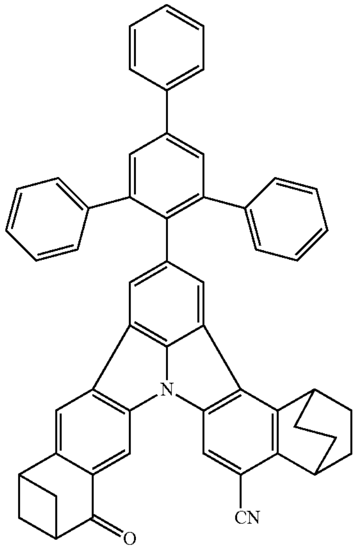 [SMILES: N#Cc1cc2c(c3c1C1CCC3CC1)c1cc(-c3c(-c4ccccc4)cc(-c4ccccc4)cc3-c3ccccc3)cc3c4cc5c(cc4n2c31)C(=O)C1CC5C1] | 35% |

-continued
| Ex. | Synthons S Amine | Product | Yield |
|---|---|---|---|
| EAS42 | S1<br>S57<br>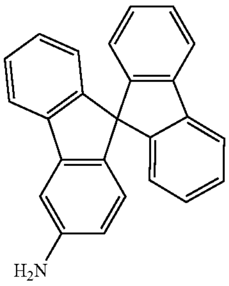<br>1644466-73-8 | 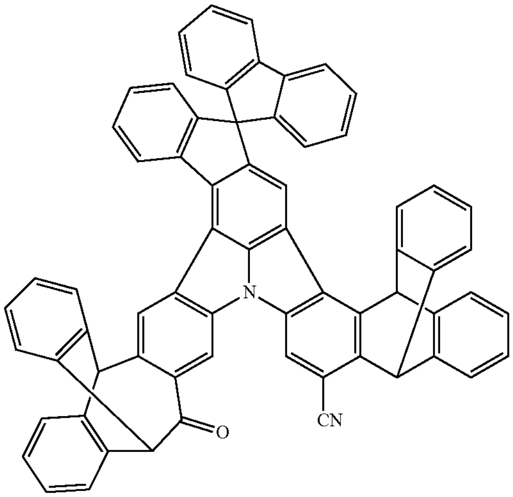 [SMILES: N#Cc1cc2c(c3c1C1c4ccccc4C3c3ccccc31)c1cc3c(c4c5cc6c(cc5n2c14)C(=O)C1c2ccccc2C6c2ccccc21)-c1ccccc1C31c2ccccc2-c2ccccc21] | 20% |
| EAS43 | S1<br>S57<br>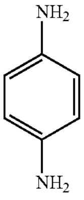<br>106-50-3<br>25 mmol | 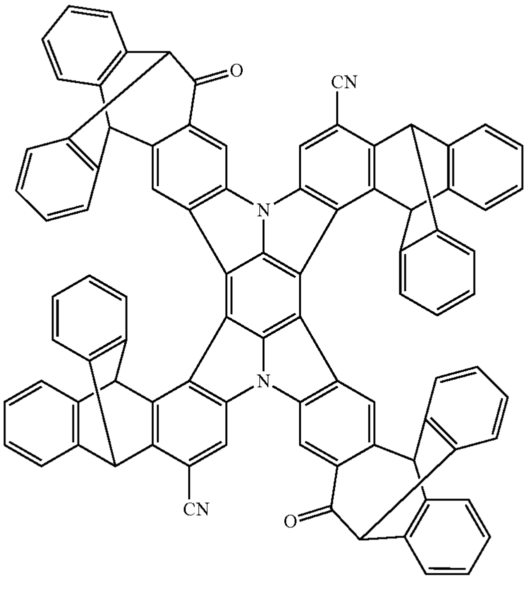 [SMILES: N#Cc1cc2c(c3c1C1c4ccccc4C3c3ccccc31)c1c3c4cc5c(cc4n4c6cc(C#N)c7c(c6c(c6c8cc9c(cc8n2c61)C(=O)C1c2ccccc2C9c2ccccc21)c34)C1c2ccccc2C7c2ccccc21)C(=O)C1c2ccccc2C5c2ccccc21] | 25% |

-continued

| Ex. | Synthons S Amine | Product | Yield |
| --- | --- | --- | --- |
| EAS44 | S4<br>S57<br>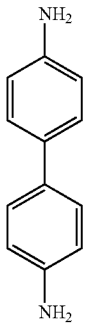<br>92-87-5<br>25 mmol | 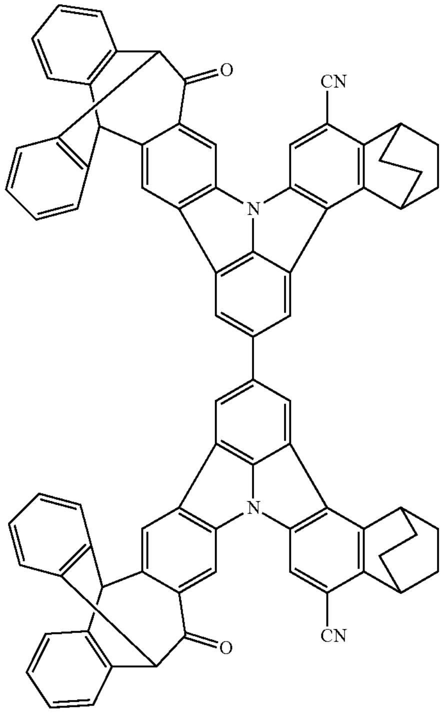 [SMILES: N#Cc1cc2c(c3c1C1CCC3CC1)c1cc(-c3cc4c5cc6c(cc5n5c7cc(C#N)c8c(c7c(c3)c45)C3CCC8CC3)C(=O)C3c4ccccc4C6c4ccccc43)cc3c4cc5c(cc4n2c31)C(=O)C1c2ccccc2C5c2ccccc21] | 28% |

Alternative Synthesis Routes:

The compounds of the invention, in some cases with improved yields, can be prepared by the following alternative synthesis routes:

2.3) Alternative Method A

Stepwise construction by two consecutive Buchwald couplings, followed by a Pd-catalysed intramolecular cyclization using the example of ES1:

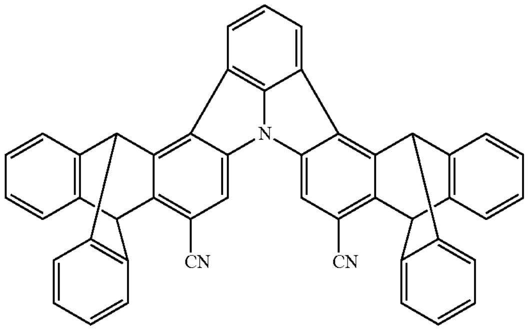 [SMILES: N#Cc1cc2c(c3c1C1c4ccccc4C3c3ccccc31)c1cccc3c4c5c(c(C#N)cc4n2c13)C1c2ccccc2C5c2ccccc21]

Stage 1): Buchwald Coupling 1

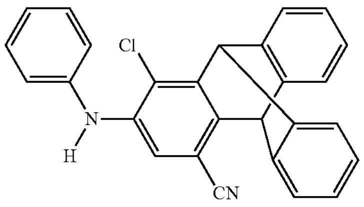 [SMILES: N#Cc1cc(Nc2ccccc2)c(Cl)c2c1C1c3ccccc3C2c2ccccc21]

A mixture of 43.7 g (100 mmol) of S10, 9.13 ml (100 mmol) of aniline [62-53-3], 20.2 g (210 mmol) of sodium tert-butoxide [865-48-5], 1.11 g (2 mmol) of bisdiphenylphosphinoferrocene (dppf) [12150-46-8], 499 mg (2 mmol) of palladium(II) acetate, 500 ml of toluene and 50 g of glass beads (diameter 3 mm) is stirred under gentle reflux until conversion is complete (about 1 h). The reaction mixture is allowed to cool to 60° C., 300 ml of water is added, and the organic phase is removed and washed once with 300 ml of water and once with 300 ml of saturated sodium chloride solution and dried over magnesium sulfate. The mixture is filtered through a silica gel bed in the form of a toluene slurry and washed through with 500 ml of ethyl acetate, and the filtrate is concentrated to dryness. The residue is purified by chromatography (silica gel, cyclohexane/EA, Combi-Flash Torrent from A. Semrau). Yield: 32.7 g (81 mmol), 81%; purity: about 97% by $^{1}H$ NMR.

Stage 2: Buchwald Coupling 2

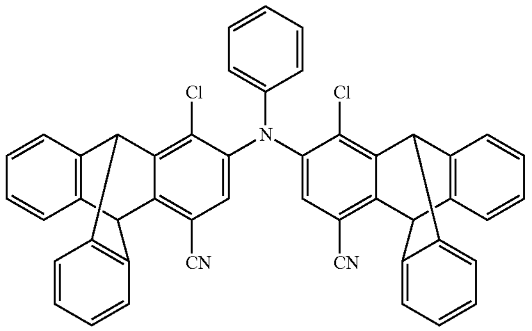 [SMILES: N#Cc1cc(N(c2ccccc2)c2cc(C#N)c3c(c2Cl)C2c4ccccc4C3c3ccccc32)c(Cl)c2c1C1c3ccccc3C2c2ccccc21]

A mixture of 40.4 g (100 mmol) of stage 1), 43.7 g (100 mmol) of S10, 20.2 g (210 mmol) of sodium tert-butoxide [865-48-5], 725 mg (2.5 mmol) of tri-tert-butylphosphonium tetrafluoroborate [131274-22-1], 449 mg (2 mmol) of palladium(II) acetate, 500 ml of toluene and 50 g of glass beads (diameter 3 mm) is stirred under gentle reflux until conversion is complete (about 12 h). The reaction mixture is allowed to cool to 60° C., 300 ml of water is added, and the organic phase is removed and washed once with 300 ml of water and once with 300 ml of saturated sodium chloride solution and dried over magnesium sulfate. The mixture is filtered through a silica gel bed in the form of a toluene slurry and washed through with 500 ml of ethyl acetate, and the filtrate is concentrated to dryness. The residue is purified by chromatography (silica gel, cyclohexane/EA, Combi-Flash Torrent from A. Semrau). Yield: 55.6 g (77 mmol), 77%; purity: about 97% by $^{1}H$ NMR.

Stage 3): Cyclization

A mixture of 71.7 g (100 mmol) of stage 2), 41.5 g (300 mmol) of potassium carbonate, 725 mg (2.5 mmol) of tri-tert-butylphosphonium tetrafluoroborate [131274-22-1], 449 mg (2 mmol) of palladium(II) acetate, 1000 ml of dimethylacetamide and 50 g of glass beads (diameter 3 mm) is stirred at 150° C. until conversion is complete (about 12 h). After cooling to 80° C., 2000 ml of water is added dropwise, the precipitated solids are filtered off with suction, and these are washed twice with 200 ml each time of water and twice with 50 ml each time of methanol, and dried under reduced pressure. The crude product is subjected to flash chromatography (RP silica gel, acetonitrile/THF, Combi-Flash Torrent from A. Semrau), then purified by repeated hot extraction crystallization (DCM:acetonitrile 1:3 to 3:1) and subsequent fractional sublimation or by heat treatment under high vacuum. Yield: 36.5 g (56 mmol), 56%; purity: >99.9% by HPLC.

The alternative method A is suitable not just for construction of symmetrically substituted units, but specifically also for construction of asymmetrically substituted emitters, through use of two different iodochlorobenzonitriles in stage 1) and stage 2).

The following compounds can be prepared analogously:

| Ex. | Reactants | Product | Yield |
| --- | --- | --- | --- |
| ES72 | S13 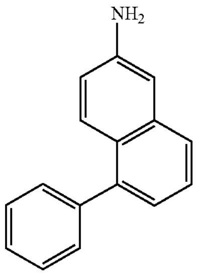 1609130-36-0 | 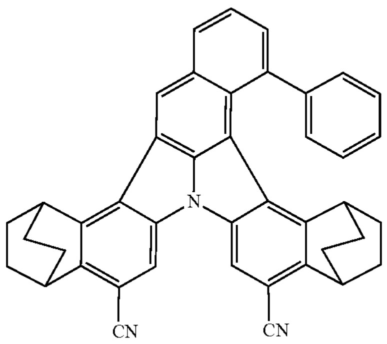 [SMILES: N#Cc1cc2c(c3c1C1CCC3CC1)c1cc3cccc(-c4ccccc4)c3c3c4c5c(c(C#N)cc4n2c13)C1CCC5CC1] | 13% |
| ES73 | S10 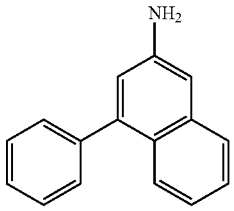 228107-17-3 | 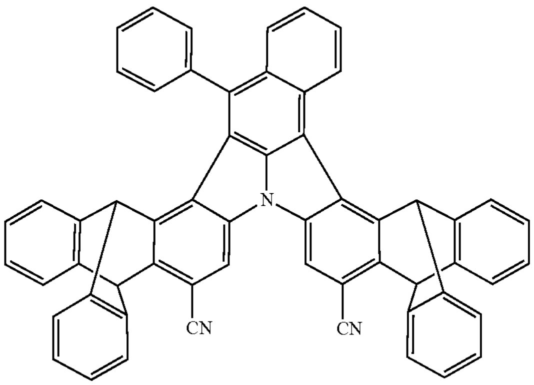 [SMILES: N#Cc1cc2c(c3c1C1c4ccccc4C3c3ccccc31)c1c(-c3ccccc3)c3ccccc3c3c4c5c(c(C#N)cc4n2c13)C1c2ccccc2C5c2ccccc21] | 37% |

-continued
| Ex. | Reactants | Product | Yield |
|---|---|---|---|
| ES74 | S10 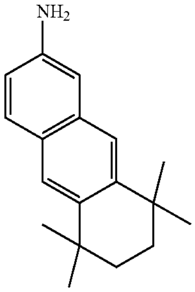 199392-14-8 | 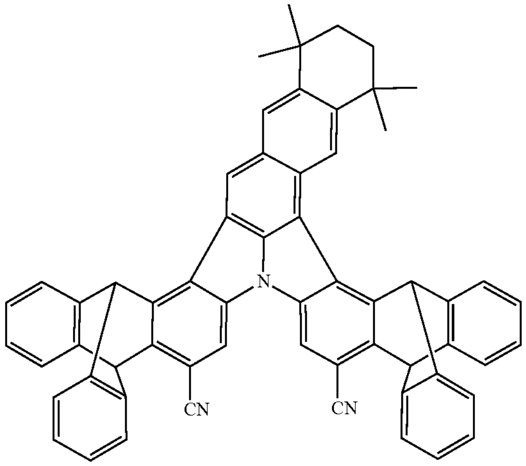 [SMILES: CC1(C)CCC(C)(C)c2cc3c(cc21)cc1c2c4c(c(C#N)cc2n2c5cc(C#N)c6c(c5c3c12)C1c2ccccc2C6c2ccccc21)C1c2ccccc2C4c2ccccc21] | 38% |
| ES75 | S10 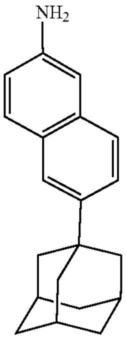 37521-66-7 | 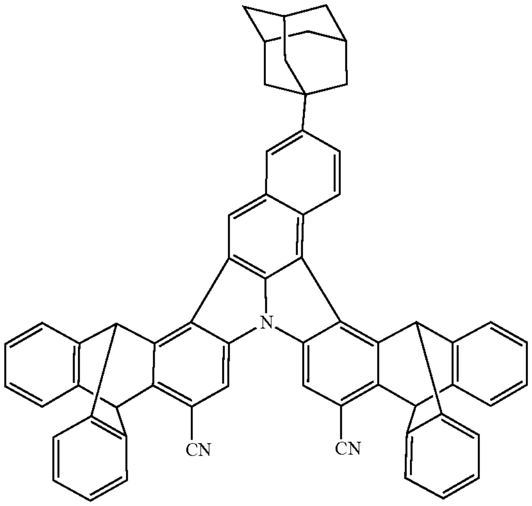 [SMILES: N#Cc1cc2c(c3c1C1c4ccccc4C3c3ccccc31)c1cc3cc(C45CC6CC(CC(C6)C4)C5)ccc3c3c4c5c(c(C#N)cc4n2c13)C1c2ccccc2C5c2ccccc21] | 34% |
| ES76 | S14 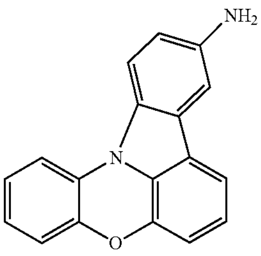 2268818-23-9 | 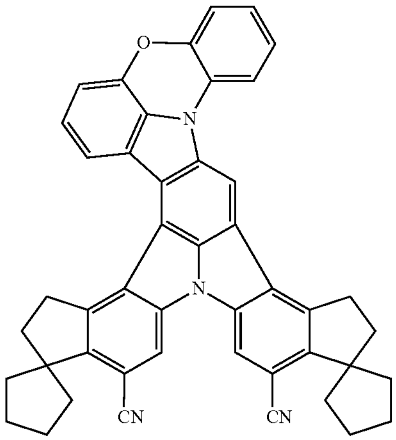 [SMILES: N#Cc1cc2c(c3c1C1(CCCC1)CC3)c1cc3c(c4cccc5oc6ccccc6n3c54)c3c4c5c(c(C#N)cc4n2c13)C1(CCCC1)CC5] | 29% |

-continued
| Ex. | Reactants | Product | Yield |
|---|---|---|---|
| ES77 | S15 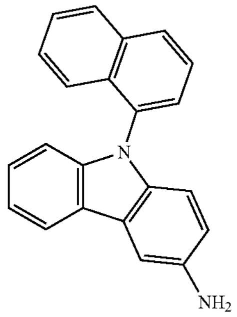 2097255-51-9 | 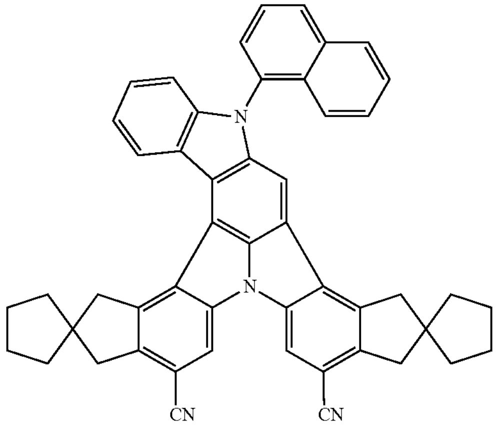 [SMILES: N#Cc1cc2c(c3c1CC1(CCCC1)C3)c1cc3c(c4ccccc4n3-c3cccc4ccccc34)c3c4c5c(c(C#N)cc4n2c13)CC1(CCCC1)C5] | 35% |
| ES78 | S16 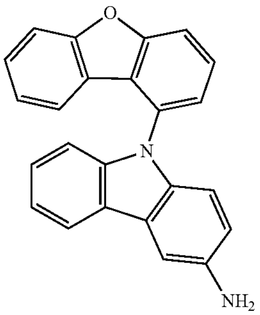 2609787-30-4 | 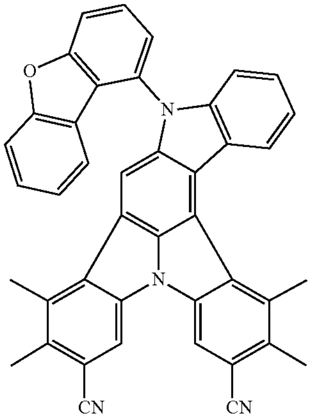 [SMILES: Cc1c(C#N)cc2c(c1C)c1cc3c(c4ccccc4n3-c3cccc4oc5ccccc5c34)c3c4c(C)c(C)c(C#N)cc4n2c13] | 41% |
| ES79 | S17 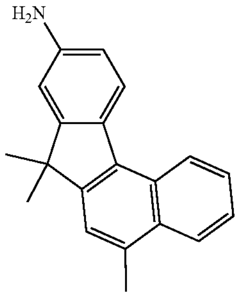 2379812-68-5 | 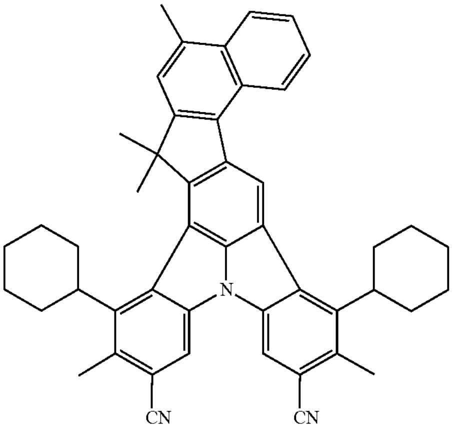 [SMILES: Cc1c(C#N)cc2c(c1C1CCCCC1)c1cc3c(c4c5c(C6CCCCC6)c(C)c(C#N)cc5n2c14)C(C)(C)c1cc(C)c2ccccc2c1-3] | 30% |

-continued
| Ex. | Reactants | Product | Yield |
|---|---|---|---|
| EAS45A | S10 stage 1<br>S14 stage 2<br>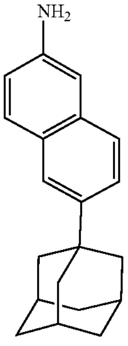<br>37521-66-7 | 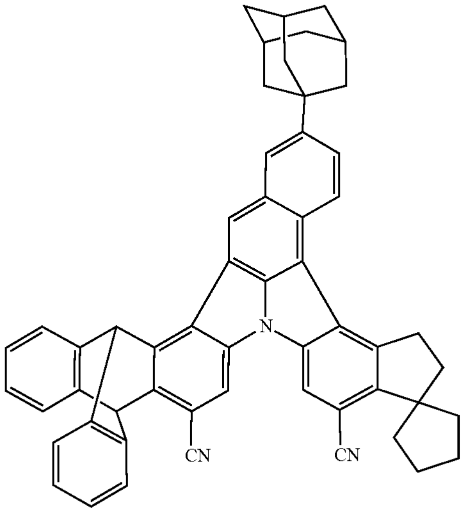 [SMILES: N#Cc1cc2c(c3c1C1c4ccccc4C3c3ccccc31)c1cc3cc(C45CC6CC(CC(C6)C4)C5)ccc3c3c4c5c(c(C#N)cc4n2c13)C1(CCCC1)CC5] | 19% |
| EAS45B | | 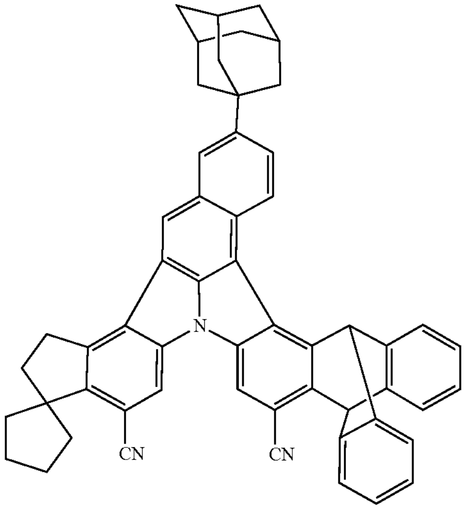 [SMILES: N#Cc1cc2c(c3c1C1c4ccccc4C3c3ccccc31)c1c3ccc(C45CC6CC(CC(C6)C4)C5)cc3cc3c4c5c(c(C#N)cc4n2c31)C1(CCCC1)CC5] | 10% |
2.4) Alternative Method B
Stepwise Amination—Cyclization Via a Carbazole Intermediate
-continued
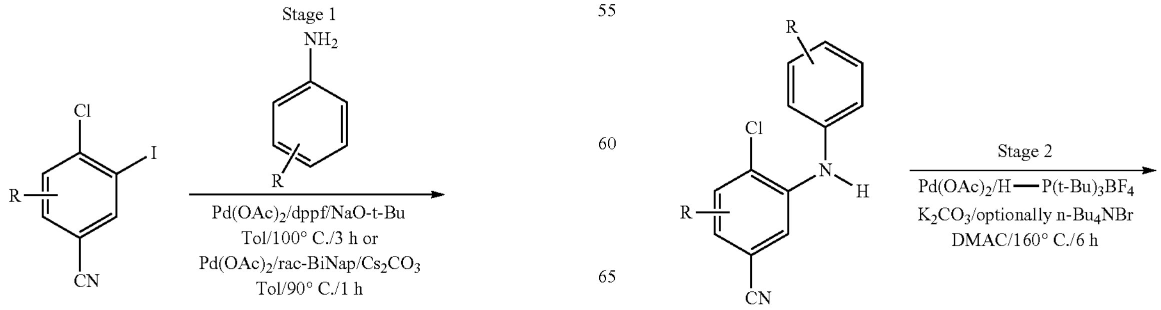

-continued

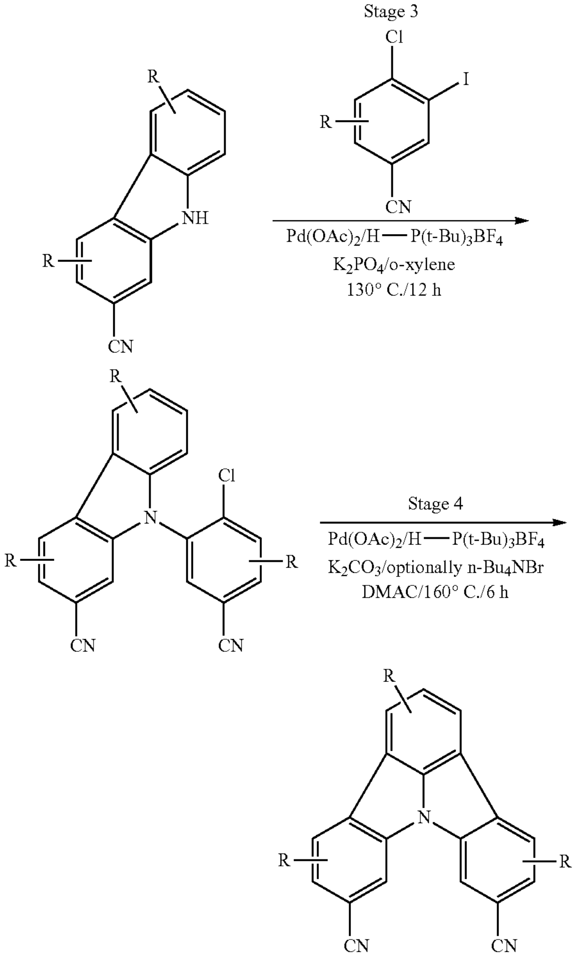

Stage 1: Standard Buchwald coupling method for preparation of secondary amines from an aniline and the iodochlorobenzonitrile, for example analogously to U. Masanobu, et al., J. Am. Chem. Soc., 2004, 126(28), 8755 or P. B. Tiruveedhula, et al., Org. & Biomol. Chem., 2015, 13(43), 10705. Typical yields 70-95%.

Stage 2: Intramolecular cyclization to the carbazole analogously to P. B. Tiruveedhula, et al., Org. & Biomol. Chem., 2015, 13(43), 10705 or F. Chen et al., RSC Adv., 2015, 5, 51512. When asymmetrically substituted anilines are used, the regioisomeric carbazoles are isolated as a mixture and converted further. Typical yields 60-90%.

Stage 3: Standard Buchwald coupling method for preparation of N-arylated carbazoles; alternatively, it is possible to conduct an Ullmann coupling, for example analogously to J. H. Cho et al., Bull. Korean Chem. Soc., (2011), 32(7), 2461. Typical yields 40-80%.

Stage 4: Intramolecular cyclization, analogously to stage 2, for example analogously to T. Kader et al., Chem. Europ. J., 2019, 25(17), 4412 or analogously to U.S. Pat. No. 9,000,421 B1, using tricyclohexylphosphonium tetrafluoroborate or with NHC-Pd complexes, for example allyl[1,3-bis(2,6-diisopropylphenyl)imidazol-2-ylidene]chloropalladium(II). Typical yields 50-80%.

Alternatively, it is possible to construct the carbazole intermediates as follows:

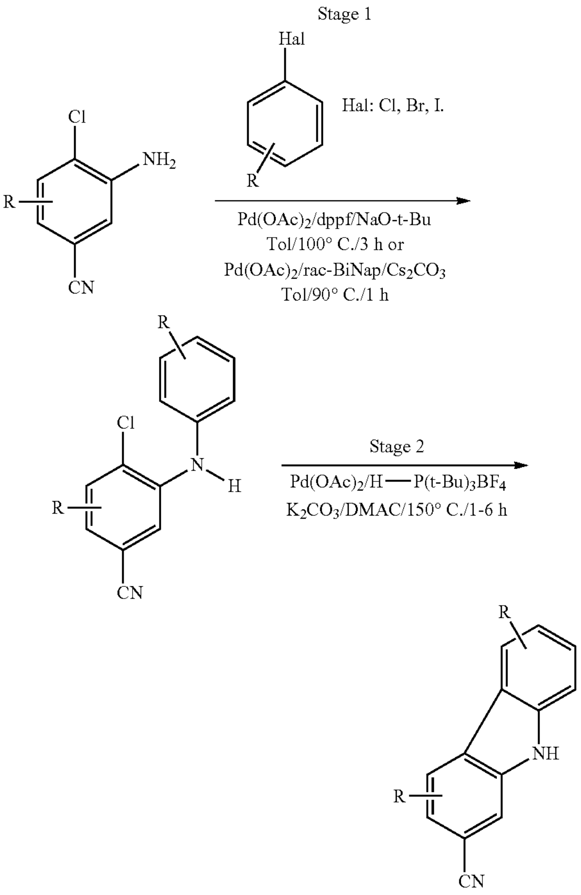

Stage 1: Standard Buchwald coupling method for preparation of secondary amines from an aniline and the iodochlorobenzonitrile, for example analogously to U. Masanobu, et al., J. Am. Chem. Soc., 2004, 126(28), 8755 or P. B. Tiruveedhula, et al., Org. & Biomol. Chem., 2015, 13(43), 10705. Typical yields 70-95%.

Stage 2: see above.

Stage 3 can preferably also be performed with 3-chloro-4-triflate- or 3-fluoro-4-chlorobenzonitriles as follows:

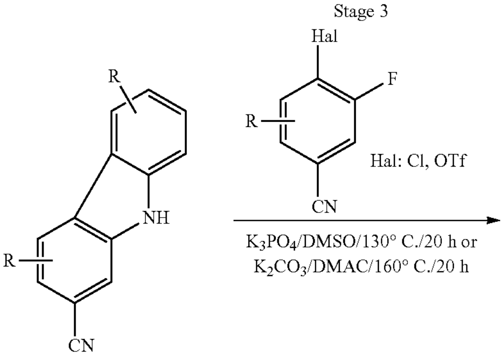

-continued

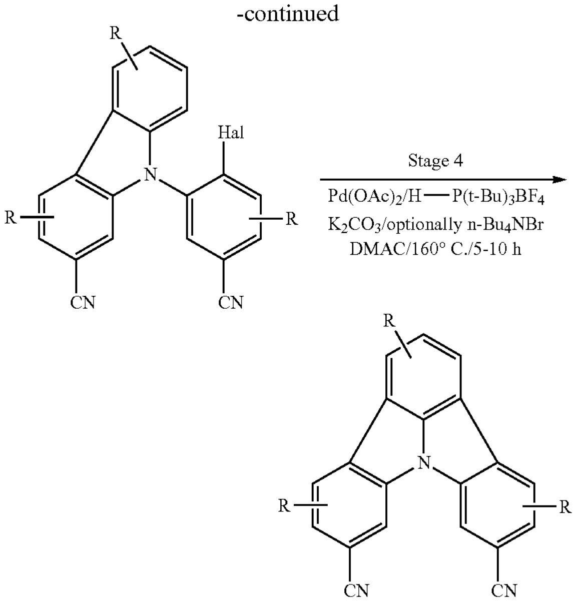

Stage 3: analogously to WO2019063288. Typical yields 60-80%.

Stage 4: see above.

Optimized Synthesis of ES94

Stage 1

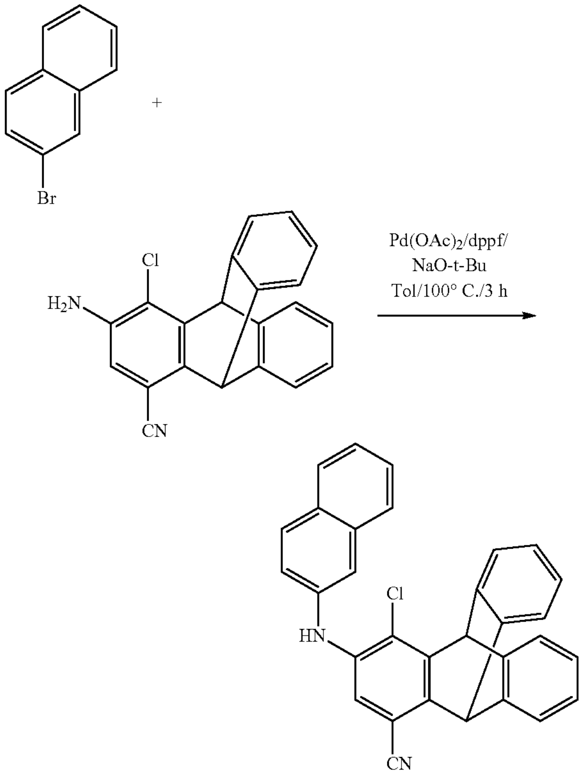

A well-stirred mixture of 32.9 g (100 mmol) of 1-cyano-3-amino-4-chlorotriptycene (see page 228), 20.7 g (100 mmol) of 2-bromonaphthalene, 28.8 g (300 mmol) of sodium tert-butoxide, 1.11 g (2 mmol) of dppf, 225 mg (1 mmol) of palladium(II) acetate in 500 ml of toluene is heated under reflux for 1 h. The mixture is allowed to cool to 70° C., 500 ml of water is added, the mixture is stirred for a further 10 min, and the organic phase is separated off and washed twice with 300 ml each time of water and once with 300 ml of saturated sodium chloride solution and dried over magnesium sulfate. The mixture is filtered through a Celite bed in the form of a toluene slurry, the filtrate is concentrated under reduced pressure, the residue is dissolved in 300 ml of DCM, and the latter is removed under reduced pressure, with replacement of the DCM distilled off by simultaneous addition of EtOH. The crystallized product is filtered off with suction, washed three times with 50 ml each time of EtOH and dried under reduced pressure. Yield: 42.3 g (93 mmol), 93%; purity: about 98% by $^1$H NMR.

Stage 2

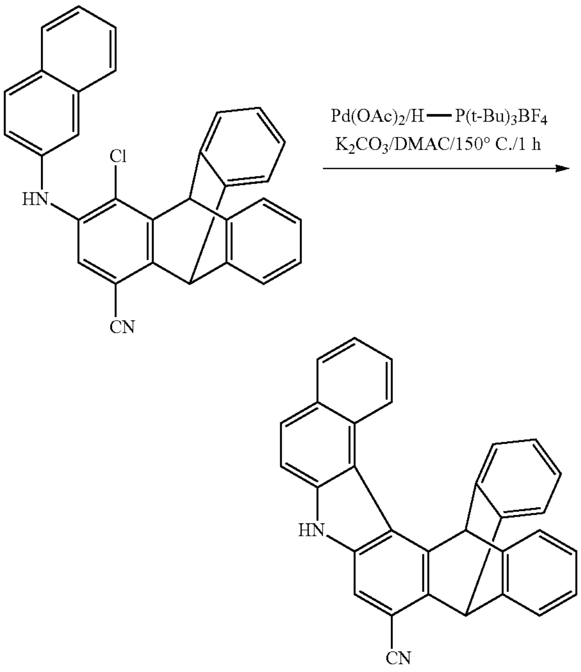

A well-stirred mixture of 45.4 g (100 mmol) of the amine, 500 mmol of potassium carbonate, 1.16 g (4 mmol) of tri-tert-butylphosphonium tetrafluoroborate, 449 mg (2 mmol) of palladium(II) acetate, 100 g of glass beads (diameter 3 mm) and 1000 ml of dimethylacetamide (DMAC) is stirred at 150° C. for 1 h. The mixture is filtered while still hot through a Celite bed in the form of a DMAC slurry, the filtrate is concentrated to dryness, the residue is dissolved in 500 ml of DCM, and the latter is removed under reduced pressure, with replacement of the DCM distilled off by simultaneous addition of 300 ml of EtOH. The crystallized product is filtered off with suction, washed three times with 50 ml each time of EtOH and dried under reduced pressure. Yield: 32.9 g (78 mmol), 78%; purity: about 98% by $^1$H NMR.

Stages 3 and 4: One-Pot Reaction

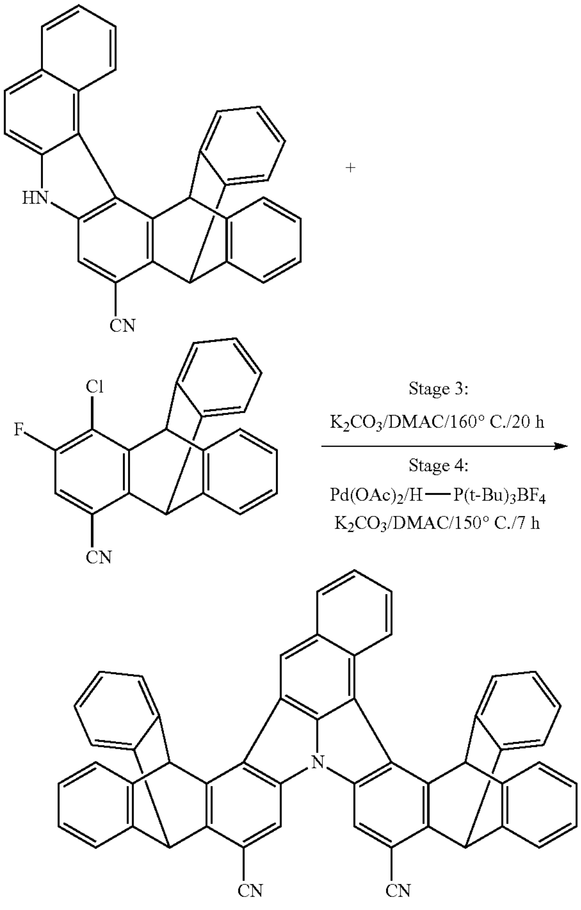

ES94

A well-stirred mixture of 20.9 g (50 mmol) of the carbazole, 19.6 g (50 mmol) of S1e, 34.6 g (250 mmol) of potassium carbonate, 100 g of glass beads (diameter 3 mm) and 500 ml of DMAC is stirred at 150° C. for 20 h. The reaction mixture is allowed to cool to RT, 1.16 g (4 mmol) of tri-tert-butylphosphonium tetrafluoroborate and 449 mg (2 mmol) of palladium(II) acetate are added, and the mixture is stirred at 150° C. for another 7 h. The mixture is filtered while still hot through a Celite bed in the form of a DMAC slurry, the filtrate is concentrated to dryness, the residue is dissolved in 500 ml of DCM, and the latter is removed under reduced pressure, with replacement of the DCM distilled off by simultaneous addition of 300 ml of EtOH. The crystallized crude product is filtered off with suction, washed three times with 50 ml each time of EtOH and dried under reduced pressure. The crude product is purified by hot crystallization extraction five times (DCM:acetonitrile 2:1) and subsequent fractional sublimation under high vacuum (T~300° C., p~$10^{-5}$ mbar). Yield: 20.0 g (29 mmol), 58%; purity: >99.9% by HPLC.

The alternative method B is suitable not just for construction of symmetrically substituted units, but specifically also for regiodirectional construction of asymmetrically substituted emitters, through use of two different iodochlorobenzonitriles in stage 1) and stage 3) or 3-fluoro-4-triflate- or 3-fluorochlorobenzonitrile in stage 3).

The following compounds can be prepared analogously:

| Ex. | Reactants | Product | Yield |
|---|---|---|---|
| ES80 | S10 stages 1 & 3<br>S700 | 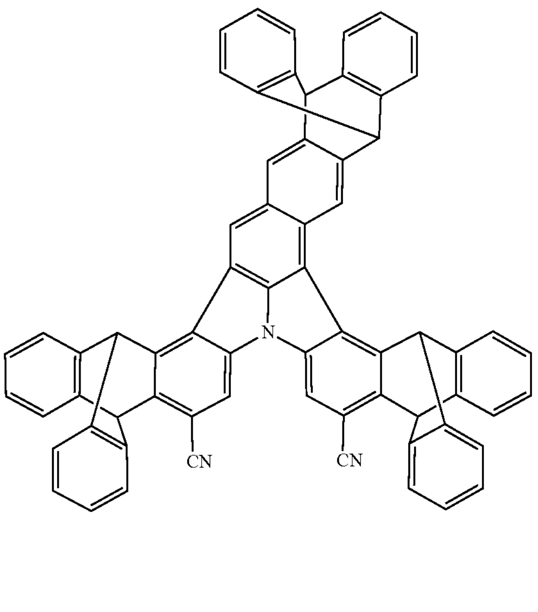 [SMILES: N#Cc1cc2c(c3c1C1c4ccccc4C3c3ccccc31)c1cc3cc4c(cc3c3c5c6c(c(C#N)cc5n2c13)C1c2ccccc2C6c2ccccc21)C1c2ccccc2C4c2ccccc21] | 30% |

-continued
| Ex. | Reactants | Product | Yield |
|---|---|---|---|
| ES80 | S10 stage 1<br>S1d stage 3<br>S700 | ES80 | 37% |
| ES80 | S10 stage 1<br>S1e stage 3<br>S700 | ES80 | 54% |
| ES81 | S14 stages 1 & 3<br>S701 | 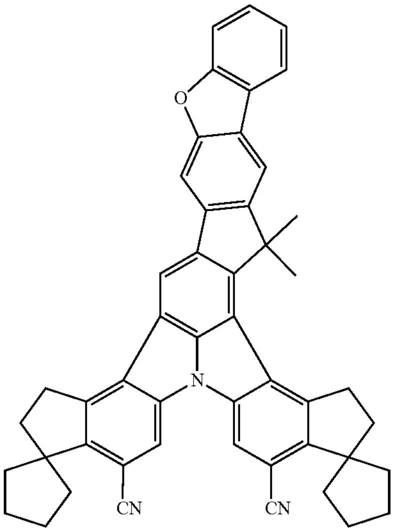 | 28% |
| ES82 | S10 stages 1 & 3<br>S702 | 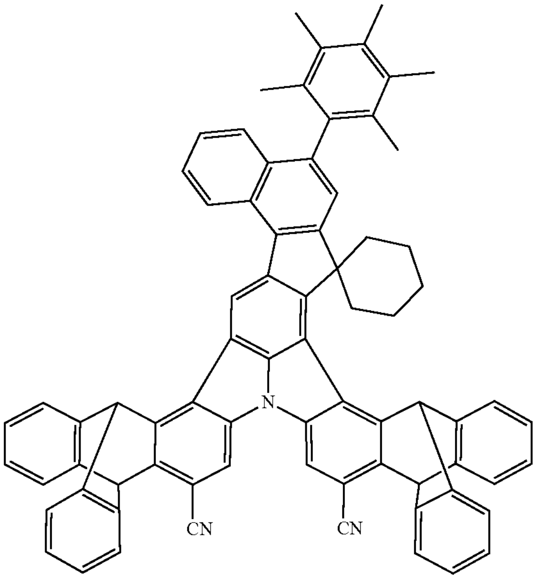 | 20% |

-continued
| Ex. | Reactants | Product | Yield |
|---|---|---|---|
| ES83 | S10 stages 1 & 3<br>S703 | 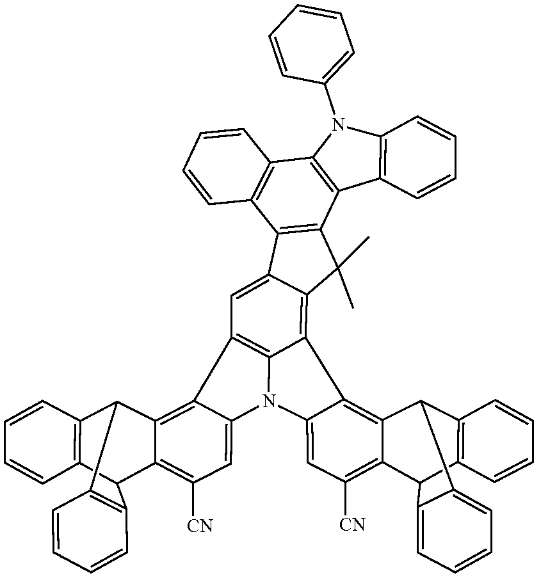 [SMILES: CC1(C)c2c(c3ccccc3c3c2c2ccccc2n3-c2ccccc2)-c2cc3c4c5c(c(C#N)cc4n4c6cc(C#N)c7c(c6c(c21)c34)C1c2ccccc2C7c2ccccc21)C1c2ccccc2C5c2ccccc21] | 27% |
| ES83 | S10 stage 1<br>S1d stage 3<br>S703 | ES83 | 35% |
| ES83 | S10 stage 1<br>S1e stage 3<br><br>S703 | ES83 | 52% |
| ES84 | S13 stages 1 & 3<br>S704 | 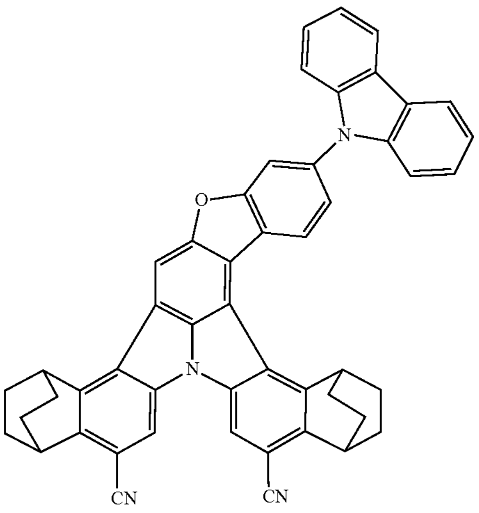 [SMILES: N#Cc1cc2c(c3c1C1CCC3CC1)c1cc3oc4cc(-n5c6ccccc6c6ccccc65)ccc4c3c3c4c5c(c(C#N)cc4n2c13)C1CCC5CC1] | 29% |

-continued
| Ex. | Reactants | Product | Yield |
| --- | --- | --- | --- |
| ES84 | S13 stage 1<br>S4e stage 3<br>S704 | ES84 | 49% |
| EAS46A | S10 stage 1<br>S14 stage 3<br>S705 | 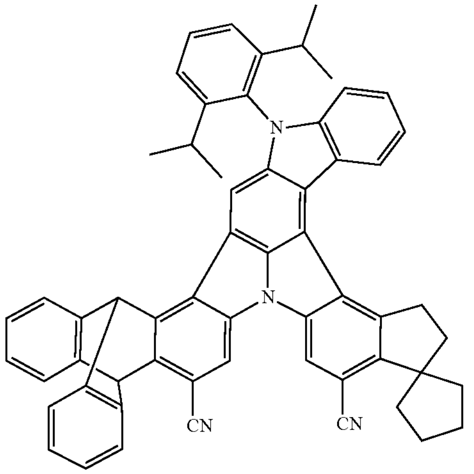 | 19% |
| EAS46B | | 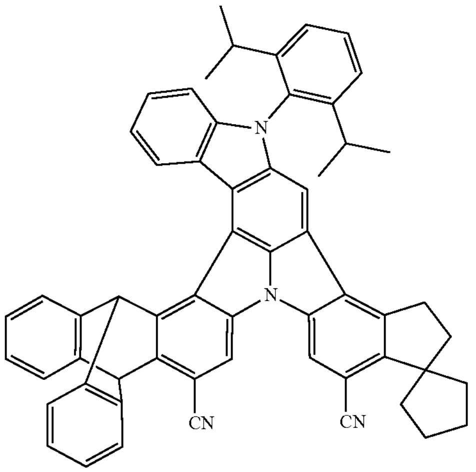 | 6% |
2.5) Alternative Method C
Construction by Suzuki Coupling of 2,6-bisboranylanilines with the Halobenzonitriles and Subsequent Double Cyclizing Buchwald Amination
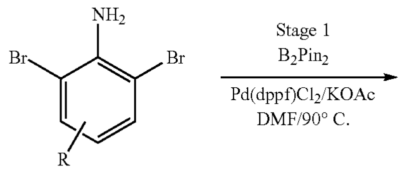
-continued
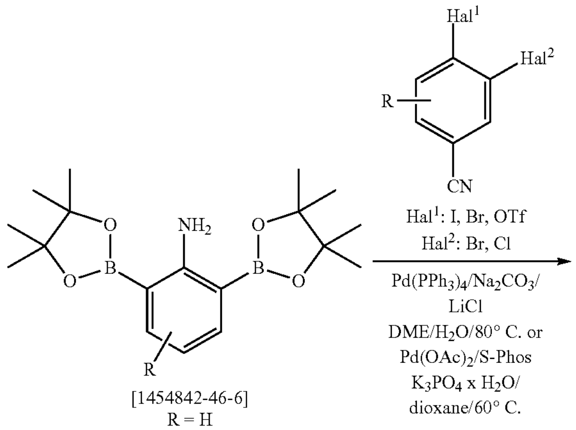
[1454842-46-6]
R = H -continued

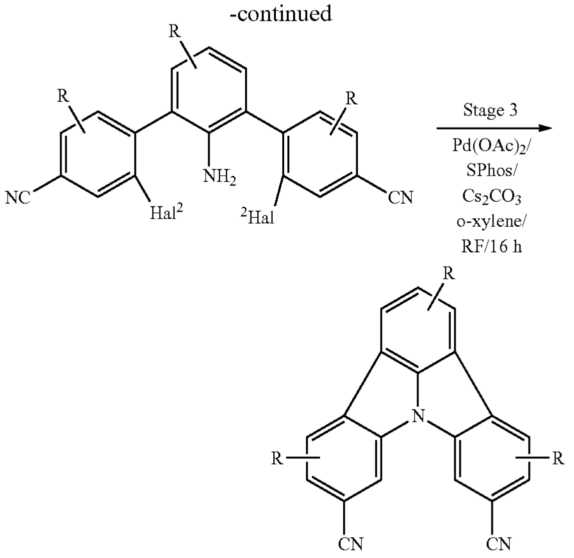

Stage 1: Borylation analogously to A. Osichow et al., Organomet. 2013, 32(18), 5239. Typical yields 60-90%.

Stage 2: Regioselective Suzuki coupling on the chloro triflates or chloro bromides/iodides; preferably used $Hal^1/Hal^2$ combinations are OTf/Cl or I/Cl or Br/Cl analogously to M. 1. Dawson et al., Journal of Medicinal Chemistry, 2007, 50(11), 2622 or WO2021121371. Typical yields 50-80%.

Stage 3: Cyclization analogously to US 2017/0324045. Typical yields 30-60%.

The following compounds can be prepared analogously:

| Ex. | Reactants | Product | Yield |
|---|---|---|---|
| ES85 | S1c<br>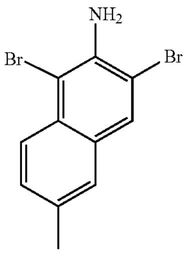<br>1642-18-8 | 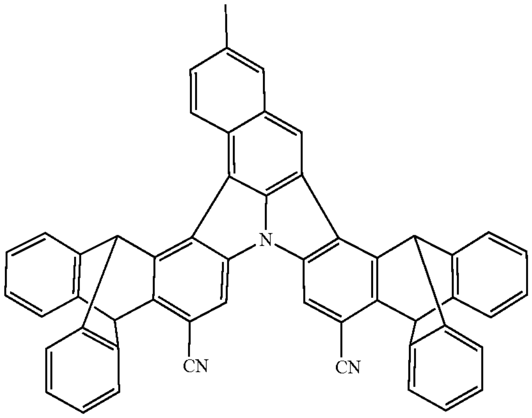 [SMILES: Cc1ccc2c(c1)cc1c3c4c(c(C#N)cc3n3c5cc(C#N)c6c(c5c2c13)C1c2ccccc2C6c2ccccc21)C1c2ccccc2C4c2ccccc21] | 31% |
| ES86 | 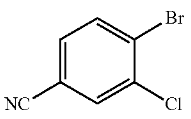<br>57418-97-0<br>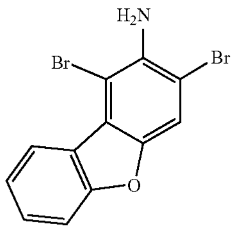<br>667937-52-2 | 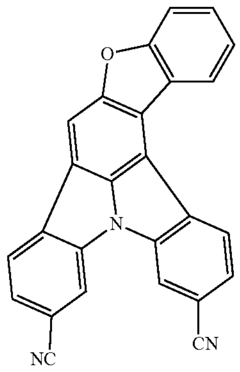 [SMILES: N#Cc1ccc2c3cc4oc5ccccc5c4c4c5ccc(C#N)cc5n(c2c1)c34] | 34% |

-continued

| Ex. | Reactants | Product | Yield |
| --- | --- | --- | --- |
| ES87 | 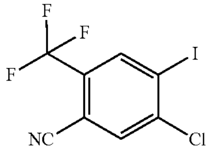 2384544-52-7 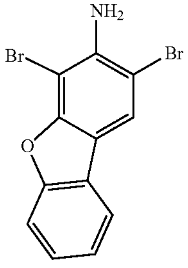 133953-35-2 | 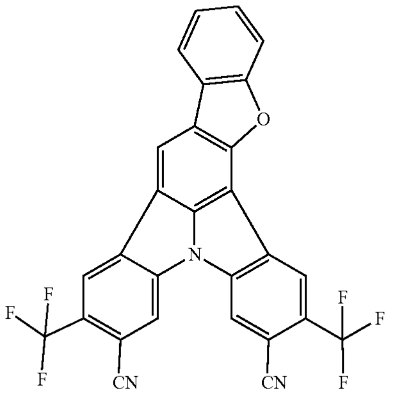 [SMILES: N#Cc1cc2c(cc1C(F)(F)F)c1cc3c4ccccc4oc3c3c4cc(C(F)(F)F)c(C#N)cc4n2c13] | 36% |

2.6) Alternative Method D

Construction from 3-fluoro-4-halobenzonitriles by Suzuki Coupling and Intramolecular Cyclization Via $S_N2Ar$ Reaction

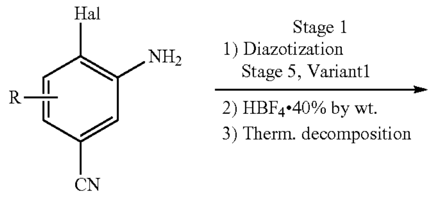

Hal: Cl, Br, I, OTf

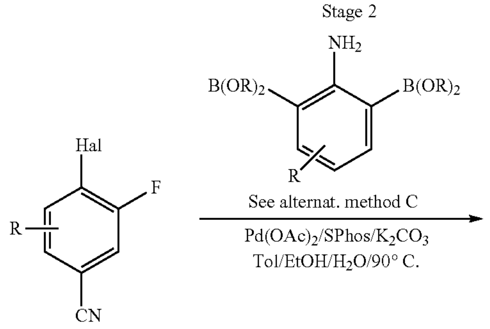

-continued

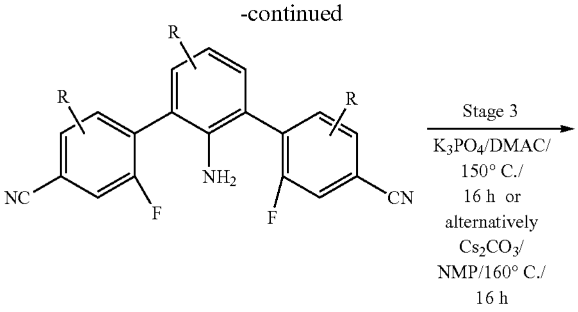

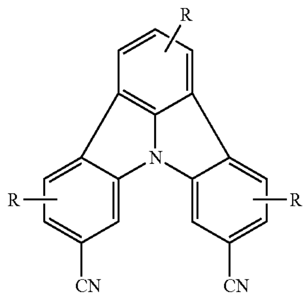

Stage 1: Balz-Schiemann reaction analogously to G. Balz et al., Chem. Ber., 1927, 5, 1186 or via $NOBF_4$ analogously to D. J. Milner et al., Synth. Commun., 1992, 22, 73. See also optimized synthesis of 1e. Typical yields 30-85%.

Stage 2: Suzuki coupling on the 3-fluoro-4-halobenzonitriles. Typical yields 40-80%.

Stage 3: Intramolecular cyclization via $S_{N2}Ar$ reaction, for example analogously to CN108727396. Typical yields 40-80%.

The following compounds can be prepared analogously:
| Ex. | Reactants | Product | Yield |
|---|---|---|---|
| ES88 | 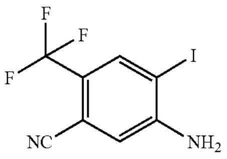<br>2385618-00-6<br>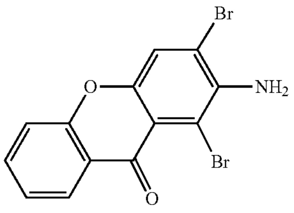<br>840507-06-4 | 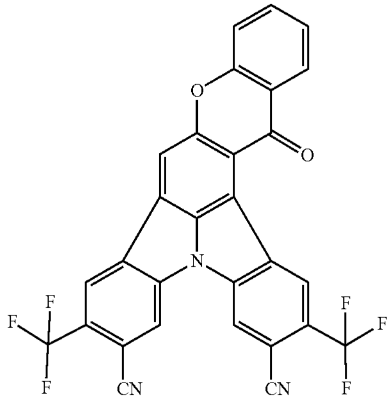 [SMILES: N#Cc1cc2c(cc1C(F)(F)F)c1cc3oc4ccccc4c(=O)c3c3c4cc(C(F)(F)F)c(C#N)cc4n2c13] | 34% |
| ES89 | S1e<br>2385618-00-6<br>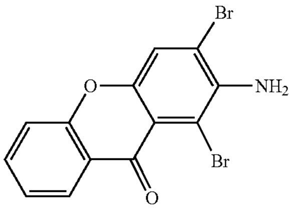 | 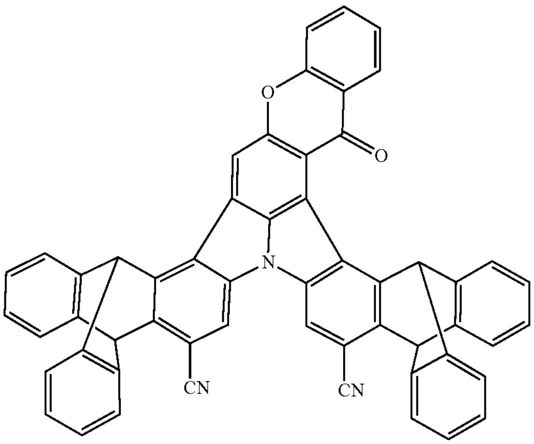 [SMILES: N#Cc1cc2c(c3c1C1c4ccccc4C3c3ccccc31)c1cc3oc4ccccc4c(=O)c3c3c4c5c(c(C#N)cc4n2c13)C1c2ccccc2C5c2ccccc21] | 14% |
| ES90 | 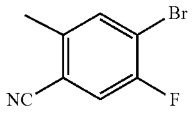<br>916792-15-9<br>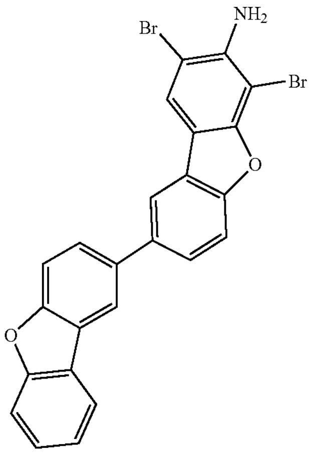<br>1500101-93-8 | 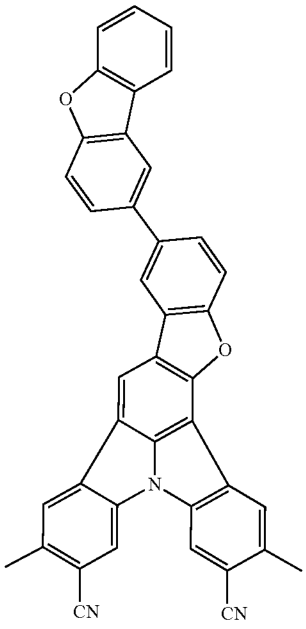 | 32% |

2.7) Alternative Method E
Construction from 2,6-dichloroanilines by Buchwald Coupling and Pd-Catalysed Intramolecular Cyclization
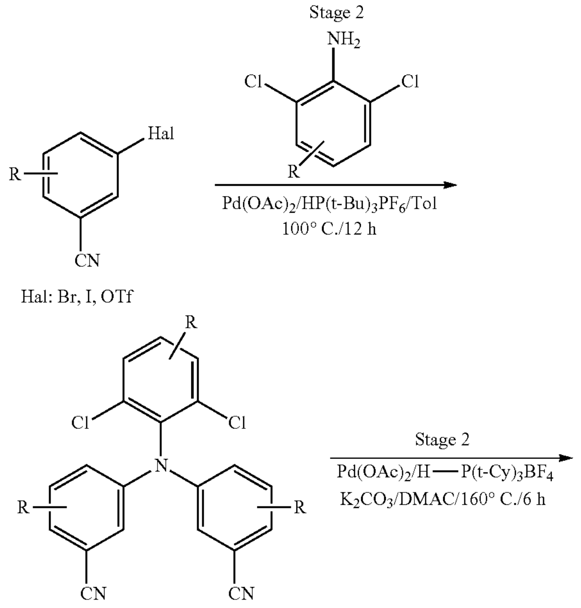
-continued
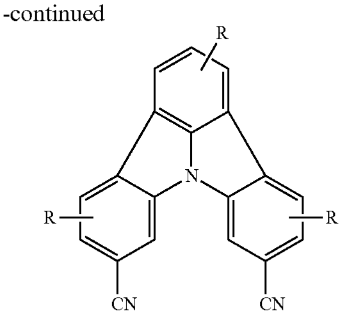
Stage 1 and stage 2: for example analogously to US 2021/0005826.
Typical yields over the two stages 20-50%.
The following compounds can be prepared analogously:
| Ex. | Reactants | Product | Yield |
|---|---|---|---|
| ES91 | 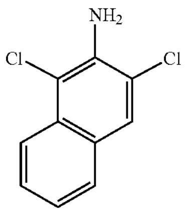 843744-23-0 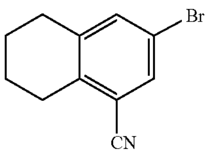 2113577-09-4 | 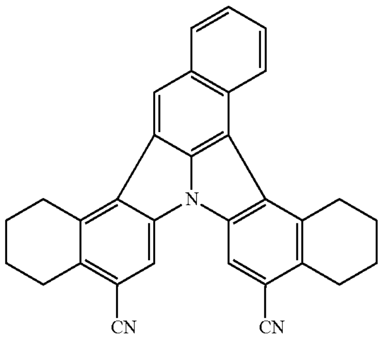 [SMILES: N#Cc1cc2c(c3c1CCCC3)c1cc3ccccc3c3c4c5c(c(C#N)cc4n2c13)CCCC5] | 48% |

-continued

| Ex. | Reactants | Product | Yield |
|---|---|---|---|
| ES92 | 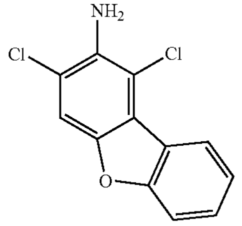 133618-04-9 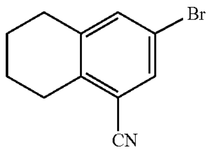 2113577-09-4 | 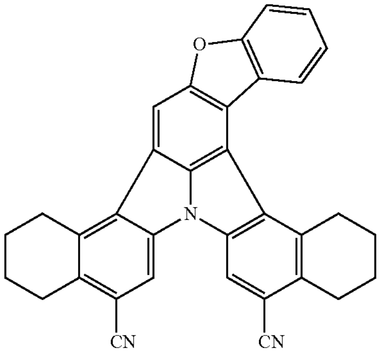 [SMILES: N#Cc1cc2c(c3c1CCCC3)c1cc3oc4ccccc4c3c3c4c5c(c(C#N)cc4n2c13)CCCC5] | 46% |
| ES93 | 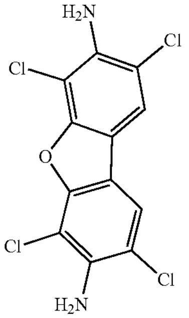 71585-31-4 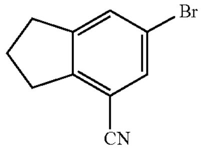 1895095-05-2 | 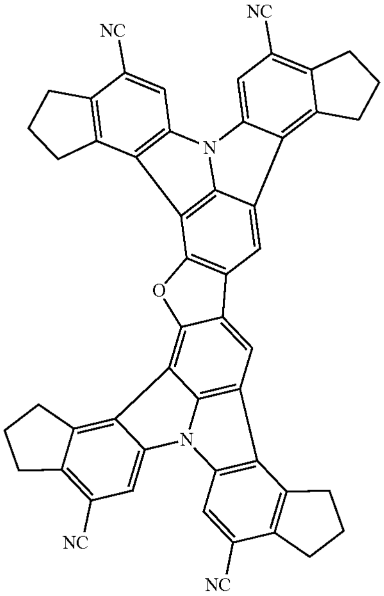 [SMILES: N#Cc1cc2c(c3c1CCC3)c1cc3c4cc5c6c7c(c(C#N)cc6n6c8cc(C#N)c9c(c8c(c4oc3c3c4c8c(c(C#N)cc4n2c13)CCC8)c56)CCC9)CCC7] | 22% |

Measurement of Photoluminescence Spectra (PL Spectra):

FIG. 1 shows PL spectra of inventive compounds ES1, ES94 and comp. 675 (see page 204), measured with a Hitachi F-4500 PL spectrometer in about $10^{-5}$ molar degassed toluene solution at room temperature (about 25° C.).

The PL spectra have very narrow emission bands with low FWHM values (<0.18 eV) and lead to particularly pure-colour emission. Moreover, in the long-wave emission flank, they often have a shoulder or secondary maximum respectively having less than 40% of the intensity of the main maximum. In top-emission OLED components, this leads to a favourably low viewing angle dependence of the colour impression, compared to prior-art narrowband boron-containing emitters that often have no such shoulders or secondary maxima and show greater viewing angle dependence of the colour impression.

Production of OLED Components

1) Vacuum-Processed Components

One use of the compounds of the invention is as dopant in the emission layer in fluorescence and hyperfluorescence OLED components.

OLEDs (organic light emitting diodes) of the invention and OLEDs according to the prior art are produced by a general method according to WO 2004/058911, which is adapted to the circumstances described here (variation in layer thickness, materials used).

In the examples which follow, the results for various OLEDs are presented. Cleaned glass plates (cleaning in Miele laboratory glass washer, Merck Extran detergent) coated with structured ITO (indium tin oxide) of thickness 50 nm are pretreated with UV ozone for 25 minutes (PR-100 UV ozone generator from UVP) and, within 30 min, for improved processing, coated with 20 nm of PEDOT:PSS (poly(3,4-ethylenedioxythiophene) poly(styrenesulfonate), purchased as CLEVIOS™ P VP AI 4083 from Heraeus Precious Metals GmbH Deutschland, spun on from aqueous solution) and then baked at 180° C. for 10 min. These coated glass plates form the substrates to which the OLEDs are applied. After the production, the OLEDs are encapsulated for protection against oxygen and water vapour. The exact layer structure of the electroluminescent OLEDs can be found in the examples. The materials required for production of the OLEDs are shown in table 10.

The OLEDs are characterized in a standard manner. For this purpose, the electroluminescence spectra, the current efficiency (measured in cd/A), the power efficiency (measured in Im/W) and the external quantum efficiency (EQE, measured in percent) are, as a function of luminance, calculated from current-voltage-luminance characteristics (IUL characteristics) assuming Lambertian radiation characteristics. The electroluminescent spectra are recorded at a luminance of 100 or 1000 cd/$m^2$, and these are used to infer the emission colour and the EL-FWHM values (ELectroluminescence-Full Width Half Maximum—width of the EL emission spectra at half the peak height in eV; for better comparability over the entire spectral range).

Fluorescence OLED Components:

All materials are applied by thermal vapour deposition in a vacuum chamber. The emission layer (EML) always consists of at least one matrix material (host material) SMB and an emitting dopant (emitter) ES or EAS which is added to the matrix material(s) in a particular proportion by volume by co-evaporation. Details given in such a form as SMB:ES or EAS (97:3%) mean here that the material SMB is present in the layer in a proportion by volume of 97% and ES or EAS in a proportion of 3%.

Analogously, the electron transport layer may also consist of a mixture of two materials, for example here of ETM1 (50%) and ETM2 (50%); see table 1. The materials used for production of the OLEDs are shown in table 10. The compounds D-Ref.1 (see table 10) are used as a comparison according to the prior art.

Blue Fluorescence OLED Components BF:

The OLEDs basically have the following layer structure:

Substrate

- hole injection layer 1 (HIL1) composed of HTM1 doped with 5% NDP-9 (commercially available from Novaled), 20 nm
- hole transport layer 1 (HTL1) composed of HTM1, 160 nm
- hole transport layer 2 (HTL2), see table 1
- emission layer (EML), see table 1
- electron transport layer (ETL2), see table 1
- electron transport layer (ETL1) composed of ETM1 (50%) and ETM2 (50%), 30 nm electron injection layer (EIL) composed of ETM2, 1 nm
- cathode composed of aluminium, 100 nm

TABLE 1

Structure of blue fluorescence OLED components

| Ex. | HTL2 | EML | ETL2 |
|---|---|---|---|
| Ref-BF1 | HTM2<br>10 nm | SMB1:Ref.- D1 (97:3%)<br>20 nm | ETM1<br>10 nm |
| Ref-BF2 | HTM2<br>10 nm | SMB1:Ref.- D2 (97:3%)<br>20 nm | ETM1<br>10 nm |
| BF1 | HTM2<br>10 nm | SMB1:ES44 (97:3%)<br>20 nm | ETM1<br>10 nm |
| BF2 | HTM2<br>10 nm | SMB2:ES44 (95:5%)<br>20 nm | ETM1<br>10 nm |
| BF3 | HTM2<br>10 nm | SMB3:ES56 (97:3%)<br>20 nm | ETM1<br>10 nm |
| BF4 | HTM2<br>10 nm | SMB1:ES9 (97:3%)<br>20 nm | ETM1<br>10 nm |
| BF5 | HTM2<br>10 nm | SMB1:ES10 (95:5%)<br>20 nm | ETM1<br>10 nm |
| BF6 | HTM2<br>10 nm | SMB1:ES11 (97:3%)<br>20 nm | ETM1<br>10 nm |
| BF7 | HTM2<br>10 nm | SMB1:ES21 (97:3%)<br>20 nm | ETM1<br>10 nm |
| BF8 | HTM2<br>10 nm | SMB1:ES37 (97:3%)<br>20 nm | ETM1<br>10 nm |

TABLE 1-continued

Structure of blue fluorescence OLED components

| Ex. | HTL2 | EML | ETL2 |
|---|---|---|---|
| BF9 | HTM2<br>10 nm | SMB1:ES40 (97:3%)<br>20 nm | ETM1<br>10 nm |
| BF10 | HTM2<br>10 nm | SMB1:ES59 (97:3%)<br>20 nm | ETM1<br>10 nm |
| BF11 | HTM2<br>10 nm | SMB1:61 (97:3%)<br>20 nm | ETM1<br>10 nm |
| BF12 | HTM2<br>10 nm | SMB1:EAS2A (96:4%)<br>20 nm | ETM1<br>10 nm |
| BF13 | HTM2<br>10 nm | SMB1:EAS2B (96:4%)<br>20 nm | ETM1<br>10 nm |
| BF14 | HTM2<br>10 nm | SMB1:EAS3A (97:3%)<br>20 nm | ETM1<br>10 nm |
| BF15 | HTM2<br>10 nm | SMB1:EAS15B (97:3%)<br>20 nm | ETM1<br>10 nm |
| BF16 | HTM2<br>10 nm | SMB1:EAS42 (97:3%)<br>20 nm | ETM1<br>10 nm |
| BF17 | HTM2<br>10 nm | SMB1:ES 73 (97:3%)<br>20 nm | ETM1<br>10 nm |
| BF18 | HTM2<br>10 nm | SMB1:ES78 (95:5%)<br>20 nm | ETM1<br>10 nm |
| BF19 | HTM2<br>10 nm | SMB1:EAS46A (97:3%)<br>20 nm | ETM1<br>10 nm |
| BF20 | HTM2<br>10 nm | SMB1:ES94 (97:3%)<br>20 nm | ETM1<br>10 nm |

TABLE 2

Results

| Ex. | EQE (%) 1000 cd/$m^2$ | Voltage (V) 1000 cd/$m^2$ | Colour | EL-FWHM [eV] |
|---|---|---|---|---|
| Ref-BF1 | 6.3 | 4.5 | blue | 0.17 |
| Ref-BF2 | 7.9 | 4.3 | blue | 0.43 |
| BF1 | 8.4 | 4.3 | blue | 0.15 |
| BF2 | 7.9 | 4.2 | blue | 0.15 |
| BF3 | 8.2 | 4.2 | blue | 0.15 |
| BF4 | 6.6 | 4.4 | deep blue | 0.13 |
| BF5 | 7.9 | 4.6 | blue | 0.15 |
| BF6 | 7.3 | 4.4 | deep blue | 0.13 |
| BF7 | 8.3 | 4.3 | blue | 0.15 |
| BF8 | 8.0 | 4.4 | blue | 0.16 |
| BF9 | 8.6 | 4.5 | blue | 0.15 |
| BF10 | 7.9 | 4.3 | blue | 0.13 |
| BF11 | 8.8 | 4.3 | blue | 0.15 |
| BF12 | 7.6 | 4.4 | blue | 0.14 |
| BF13 | 7.9 | 4.4 | blue | 0.15 |
| BF14 | 8.3 | 4.3 | blue | 0.16 |
| BF15 | 7.8 | 4.3 | blue | 0.15 |
| BF16 | 7.7 | 4.4 | blue | 0.14 |
| BF17 | 7.6 | 4.4 | blue | 0.14 |
| BF18 | 8.1 | 4.3 | blue | 0.16 |
| BF19 | 8.5 | 4.3 | blue | 0.15 |
| BF20 | 8.9 | 4.2 | blue | 0.13 |

Hyperphosphorescence OLED Components:

All materials are applied by thermal vapour deposition in a vacuum chamber. The emission layer(s) (EML) always consist(s) of at least one matrix material (host material) TMM, a (phosphorescent) sensitizer PS and a fluorescent emitter ES or EAS. The matrix material (host material) TMM may consist of two components that are evaporated as a mixture (premixed host, e.g. TMM2), the components and the composition is likewise shown in table 10. Sensitizers and fluorescent emitter ES or EAS are added to the host material TMM in a particular proportion by volume by coevaporation. Details given in such a form as TMM:PS (5%):ES or EAS(3%) mean here that the material TMM is present in the layer in a proportion by volume of 92%, PS in a proportion of 5% and ES or EAS in a proportion of 3%.

Blue Hyperphosphorescence OLED Components BH:

The OLEDs basically have the following layer structure:

substrate hole injection layer 1 (HIL1) composed of HTM2 doped with 5% NDP-9 (commercially available from Novaled), 20 nm hole transport layer 1 (HTL1) composed of HTM2, 30 nm hole transport layer 2 (HTL2), see table 3 emission layer (EML), see table 3 electron transport layer (ETL2), see table 3 electron transport layer (ETL1) composed of ETM1 (50%) and ETM2 (50%), 20 nm electron injection layer (EIL) composed of ETM2, 1 nm cathode composed of aluminium, 100 nm

TABLE 3

Construction of blue hyperphosphorescence OLED components

| Ex. | HTL2 | EML | ETL2 |
|---|---|---|---|
| BH1 | HTM3 10 nm | TMM1:PS1(7%):ES37(1.5%) 25 nm | ETM3 10 nm |
| BH2 | HTM3 10 nm | TMM1:PS1(7%):ES37(2%) 25 nm | ETM3 10 nm |
| BH3 | HTM3 10 nm | TMM1:PS1(7%):EAS19(2%) 25 nm | ETM3 10 nm |
| BH4 | HTM3 10 nm | TMM1:PS3(7%):ES80(2%) 25 nm | ETM3 10 nm |
| BH5 | HTM3 10 nm | TMM1:PS3(7%):EAS46(2%) 25 nm | ETM3 10 nm |
| BH6 | HTM3 10 nm | TMM1:PS3(7%):EAS42(2%) 25 nm | ETM3 10 nm |

TABLE 4

Results

| Ex. | EQE (%) 100 cd/m$^2$ | Voltage (V) 100 cd/m$^2$ | Colour | EL-FWHM [eV] |
|---|---|---|---|---|
| BH1 | 13.4 | 3.4 | blue | 0.16 |
| BH2 | 11.1 | 3.4 | blue | 0.16 |
| BH3 | 12.8 | 3.3 | blue | 0.17 |
| BH4 | 20.1 | 3.2 | blue | 0.17 |
| BH5 | 23.4 | 3.2 | blue | 0.16 |
| BH6 | 21.2 | 3.3 | blue | 0.17 |

Green Hyperphosphorescence OLED Components GH:

The OLEDs basically have the following layer structure:

substrate hole injection layer 1 (HIL1) composed of HTM2 doped with 5% NDP-9 (commercially available from Novaled), 20 nm hole transport layer 1 (HTL1) composed of HTM2, 30 nm hole transport layer 2 (HTL2), see table 5 emission layer (EML), see table 5 electron transport layer (ETL2), see table 5 electron transport layer (ETL1) composed of ETM1 (50%) and ETM2 (50%), 30 nm electron injection layer (EIL) composed of ETM2, 1 nm cathode composed of aluminium, 100 nm

TABLE 5

Construction of green hyperphosphorescence OLED components

| Ex. | HTL2 | EML | ETL2 |
|---|---|---|---|
| GH1 | HTM3 10 nm | TMM1:PS1(8%):ES39(2%) 25 nm | ETM3 10 nm |
| GH2 | HTM3 10 nm | TMM1:PS3(8%):ES39(2%) 25 nm | ETM3 10 nm |

TABLE 6

Results

| Ex. | EQE (%) 100 cd/m$^2$ | Voltage (V) 100 cd/m$^2$ | Colour | EL-FWHM [eV] |
|---|---|---|---|---|
| GH1 | 19.3 | 3.4 | green | 0.16 |
| GH2 | 22.4 | 3.3 | green | 0.16 |

Orange-Red Hyperphosphorescence OLED Components RH:

The OLEDs basically have the following layer structure:

substrate hole injection layer 1 (HIL1) composed of HTM1 doped with 5% NDP-9 (commercially available from Novaled), 20 nm hole transport layer 1 (HTL1) composed of HTM1, 30 nm hole transport layer 2 (HTL2), see table 7 emission layer (EML), see table 7 electron transport layer (ETL2), see table 7 electron transport layer (ETL1) composed of ETM1 (50%) and ETM2 (50%), 45 nm electron injection layer (EIL) composed of ETM2, 1 nm cathode composed of aluminium, 100 nm

TABLE 7

Construction of orange-red hyperphosphorescence OLED components

| Ex. | HTL2 | EML | ETL2 |
|---|---|---|---|
| RH1 | HTM2 10 nm | TMM2:PS2(8%):ES67(2%) 20 nm | ETM1 10 nm |

TABLE 8

Results

| Ex. | EQE (%) 100 cd/m$^2$ | Voltage (V) 100 cd/m$^2$ | Colour | EL-FWHM [eV] |
|---|---|---|---|---|
| RH1 | 20.2 | 3.2 | red | 0.15 |

2) Solution-Processed Components:

The production of solution-based OLEDs is fundamentally described in the literature, for example in WO 2004/037887 and WO 2010/097155. The examples that follow combined the two production processes (application from the gas phase and solution processing), such that layers up to and including emission layer were processed from solution and the subsequent layers (hole blocker layer/electron transport layer) were applied by vapour deposition under reduced pressure. For this purpose, the previously described general methods are matched to the circumstances described here (layer thickness variation, materials) and combined as follows.

The construction used is thus as follows:

substrate

ITO, 50 nm

PEDOT, 20 nm hole transport layer HIL-Sol, composed of HTM-Sol, 20 nm emission layer composed of SMB4(97%) and ES(3%) or EAS(3%), 50 nm electron transport layer (ETL1) composed of ETM1 (50%) and ETM2 (50%), 25 nm cathode composed of aluminium, 100 nm Substrates used are glass plaques coated with structured ITO (indium tin oxide) of thickness 50 nm. For better processing, these are coated with the buffer (PEDOT) Clevios P VP AI 4083 (Heraeus Clevios GmbH, Leverkusen); PEDOT is at the top. Spin-coating is effected under air from water. The layer is subsequently baked at 180° C. for 10 minutes. The hole transport layer and the emission layer are applied to the glass plates thus coated. The hole transport layer is the polymer HTM-Sol of the structure shown in table 10, which was synthesized according to WO 2010/097155. The polymer is dissolved in toluene, such that the solution typically has a solids content of about 5 g/l when, as is the case here, the layer thickness of 20 nm typical of a device is to be achieved by means of spin-coating. The layers are spun on in an inert gas atmosphere, argon in the present case, and baked at 180° C. for 60 min.

The emission layer is always composed of at least one matrix material (host material) and an emitting dopant (emitter). Details given in such a form as SMB4 (97%) and ES or EAS (3%) mean here that the material SMB4 is present in the emission layer in a proportion by weight of 97% and the dopant ES or EAS in a proportion by weight of 3%. The mixture for the emission layer is dissolved in toluene or chlorobenzene. The typical solids content of such solutions is about 18 g/l when, as here, the layer thickness of 50 nm which is typical of a device is to be achieved by means of spin-coating. The layers are spun on in an inert gas atmosphere, argon in the present case, and baked at 140 to 160° C. for 10 minutes. The materials used are shown in table 10.

The materials for the electron transport layer and for the cathode are applied by thermal vapour deposition in a vacuum chamber. The electron transport layer, for example, may consist of more than one material, the materials being added to one another by co-evaporation in a particular proportion by volume. Details given in such a form as ETMF (50%) and ETM2 (50%) mean here that the ETM1 and ETM2 materials are present in the layer in a proportion by volume of 50% each. The materials used in the present case are shown in table 10.

TABLE 9

Results for the solution-processed OLEDs at 1000 cd/m$^2$

| Ex. | Dopant | EQE (%) | Voltage (V) | Colour | EL-FWHM [eV] |
|---|---|---|---|---|---|
| Sol-BF1 | ES15 | 7.8 | 4.4 | blue | 0.15 |

TABLE 10

Structural formulae of the materials used

HTM1

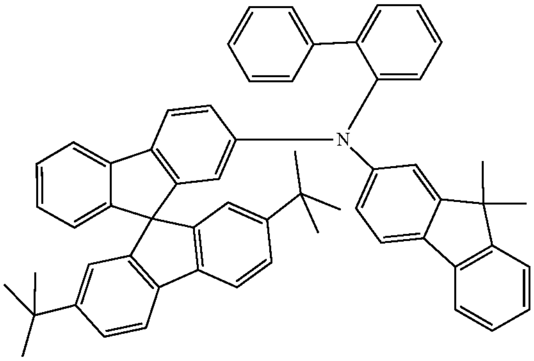 [SMILES: CC(C)(C)c1ccc2c(c1)C1(c3ccccc3-c3ccc(N(c4ccc5c(c4)C(C)(C)c4ccccc4-5)c4ccccc4-c4ccccc4)cc31)c1cc(C(C)(C)C)ccc1-2]

[1365840-52-3]

HTM2

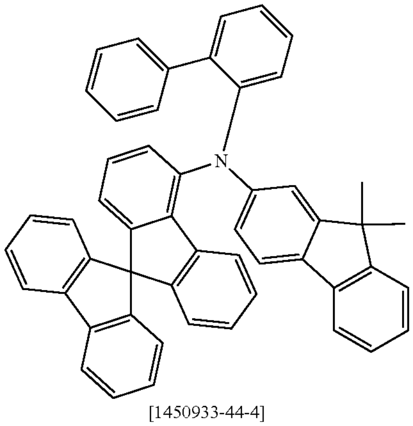

[1450933-44-4]

TABLE 10-continued
| Structural formulae of the materials used |
| --- |
HTM3
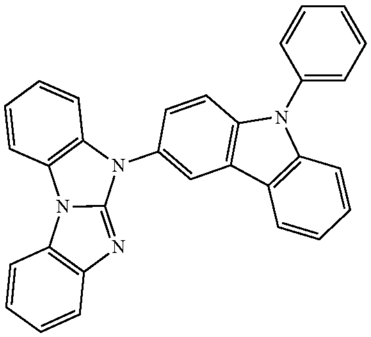 [SMILES: c1ccc(-n2c3ccccc3c3cc(-n4c5ccccc5n5c6ccccc6nc45)ccc32)cc1]
[1401068-29-8]
SMB1
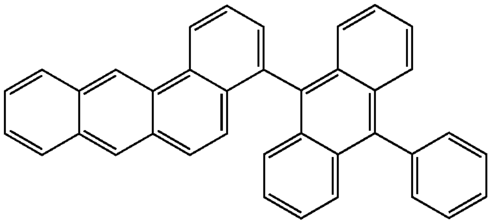 [SMILES: c1ccc(-c2c3ccccc3c(-c3cccc4c3ccc3cc5ccccc5cc34)c3ccccc23)cc1]
[1087346-88-0]
SMB2
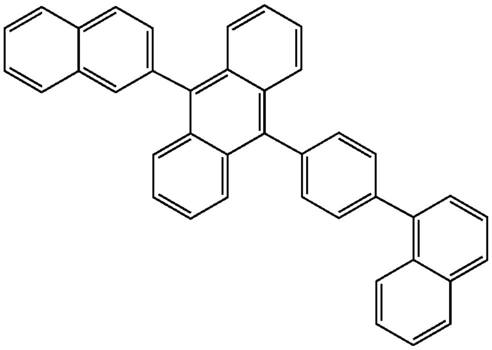 [SMILES: c1ccc2cc(-c3c4ccccc4c(-c4ccc(-c5cccc6ccccc56)cc4)c4ccccc34)ccc2c1]
[667940-34-3]
SMB3
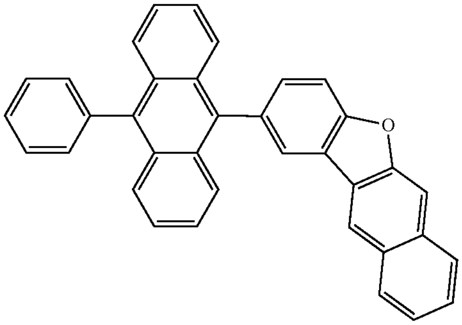 [SMILES: c1ccc(-c2c3ccccc3c(-c3ccc4oc5cc6ccccc6cc5c4c3)c3ccccc23)cc1]
[1627916-48-6]

TABLE 10-continued
| Structural formulae of the materials used |
|---|
| SMB4<br>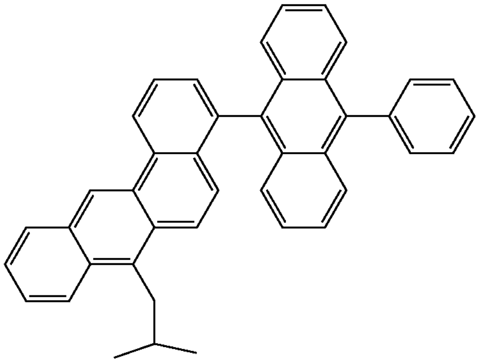 [SMILES: CC(C)Cc1c2ccccc2cc2c1ccc1c(-c3c4ccccc4c(-c4ccccc4)c4ccccc34)cccc12]<br>[1818872-85-3] |
| TMM1/ETM3<br>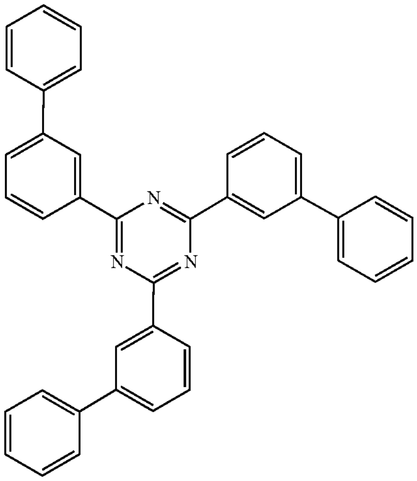 [SMILES: c1ccc(-c2cccc(-c3nc(-c4cccc(-c5ccccc5)c4)nc(-c4cccc(-c5ccccc5)c4)n3)c2)cc1]<br>[1201800-83-0] |
| TMM2<br>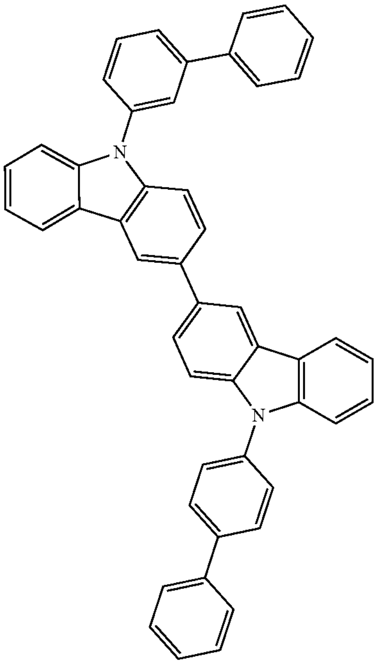 [SMILES: c1ccc(-c2ccc(-n3c4ccccc4c4cc(-c5ccc6c(c5)c5ccccc5n6-c5cccc(-c6ccccc6)c5)ccc43)cc2)cc1]<br>[1643476-29-2] (40%) |

TABLE 10-continued
| Structural formulae of the materials used |
| --- |
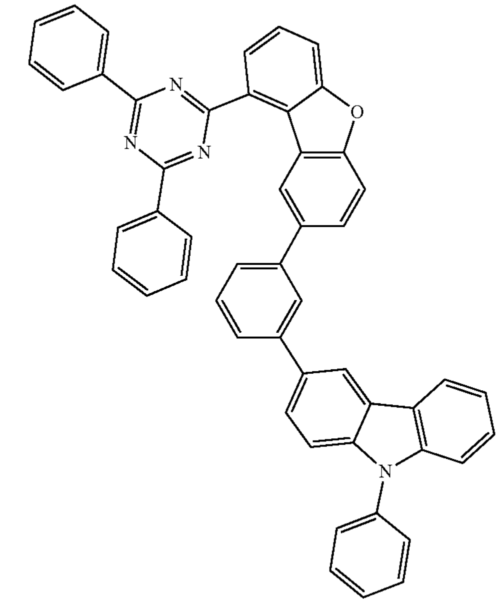 [SMILES: c1ccc(-c2nc(-c3ccccc3)nc(-c3cccc4oc5ccc(-c6cccc(-c7ccc8c(c7)c7ccccc7n8-c7ccccc7)c6)cc5c34)n2)cc1]
[1822310-86-0] (60%)
Ref.-D1
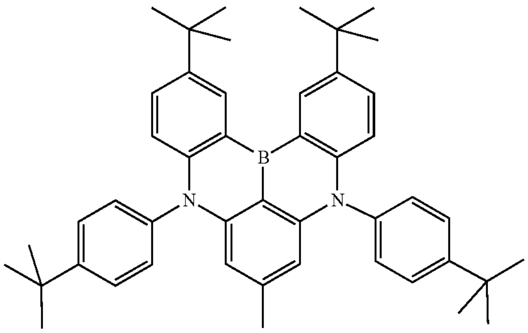 [SMILES: Cc1cc2c3c(c1)N(c1ccc(C(C)(C)C)cc1)c1ccc(C(C)(C)C)cc1B3c1cc(C(C)(C)C)ccc1N2c1ccc(C(C)(C)C)cc1]
[1805802-42-9]
Ref.-D2
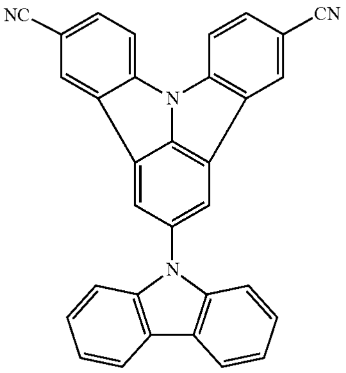 [SMILES: N#Cc1ccc2c(c1)c1cc(-n3c4ccccc4c4ccccc43)cc3c4cc(C#N)ccc4n2c13]
[2222555-03-3]

TABLE 10-continued
| Structural formulae of the materials used | |
|---|---|
| 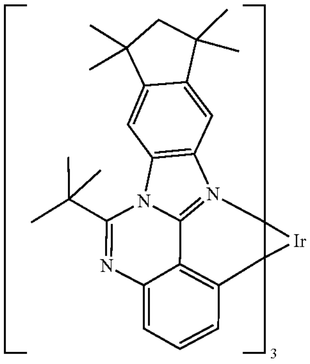<br>[1541114-98-0] | PS1 |
| 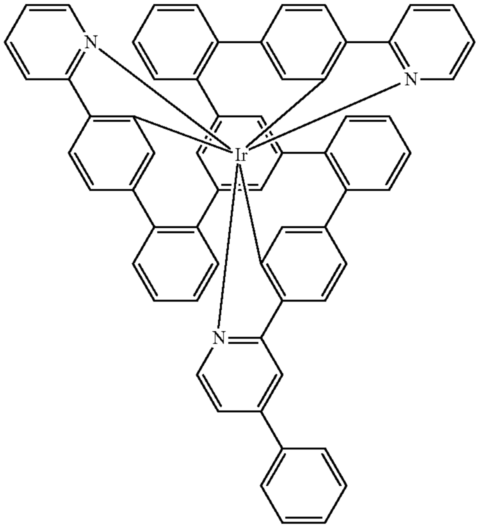<br>[2245865-85-2] | PS2 |
| 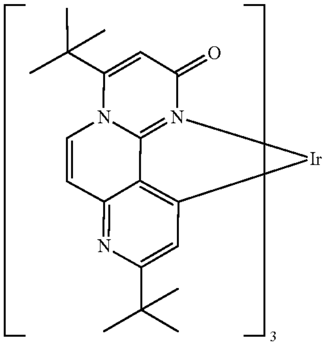<br>[1615218-73-9] | PS3 |

TABLE 10-continued

| Structural formulae of the materials used | |
|---|---|
| 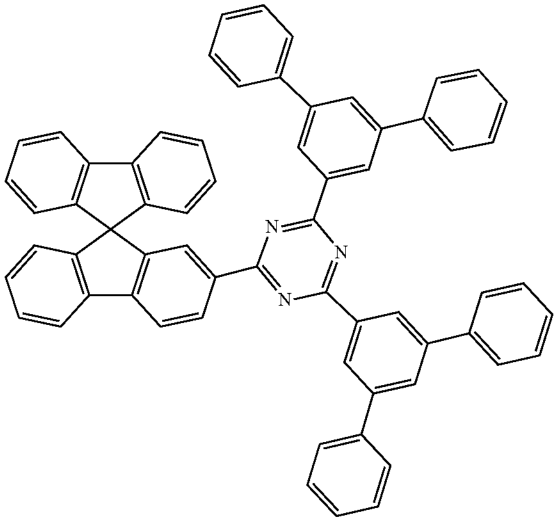 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]<br>[1233200-52-6] | ETM1 |
| 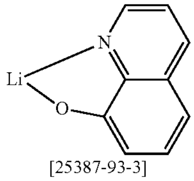<br>[25387-93-3] | ETM2 |
| 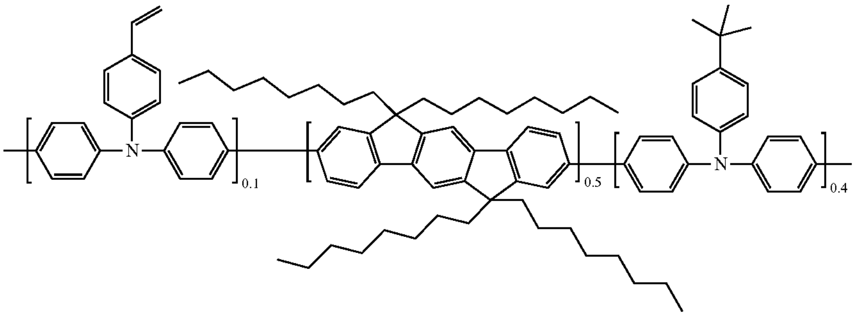 | HTM-Sol |

The abbreviations of the inventive compounds that are used in the tables set out above in relation to the OLED components relate to the abbreviations provided in the above synthesis examples.

By comparison with the references, the inventive compounds shown narrower electroluminescence spectra, recognizable by the smaller or equal EL-FWHM values (ELectroluminescence-Full Width Half Maximum—width of the EL emission spectra in eV at half the peak height). Narrower electroluminescence spectra lead to a distinct improvement in colour purity (lower CIE y values). Moreover, EQE values (External Quantum Efficiencies) are distinctly greater and operating voltages are lower compared to the reference, which leads to a distinct improvement in power efficiencies of the device and hence to lower power consumption.

Production of Components for Colour Conversion

The compounds of the invention can be used for colour conversion. For this purpose, compounds are incorporated into a composition which is then processed by known methods (spin-coating, slit-coating, screenprinting, nozzle printing, inkjet printing, etc.) to give pixels or two-dimensional layers. The compositions typically consist of cross-linkable components (monomers, oligomers, polymers), for example based on acrylates, acrylamide, polyesters, silicones etc., and one or more thermally or photochemically activatable starter components. It is additionally possible to introduce further components such as organic auxiliaries (antioxidants, stabilizers, levelling aids, viscosity moderators, etc.) or inorganic fillers ($SiO_2$, $TiO_2$, $Al_2O_3$, etc.).

General Production Procedure for the Composition and Derived Layers:

0.5 g of the inventive compound ES or EAS, 0.2 g of titanium dioxide ($TiO_2$ ToyoColor, from Toyo Ink Group) and 10 g of OE-6550 Optical Encapsulant (from Dow Corning) are homogenized at 40° C. with very good stirring (magnetic stirrer) under the action of ultrasound (ultrasound bath). Layers of layer thickness about 15 m are produced by knife-coating and then cured by baking under a nitrogen atmosphere (150° C., 1 hour).

Spectral Measurement of the Layers:

Fluorescence spectra and EQE values (external quantum efficiency, EQE=photons emitted/photons are absorbed) of the layers are ascertained in a fluorescence spectrometer (09920, Hamamatsu photonics) with an Ulbricht sphere and fibre optics (excitation wavelength OWL: 420-440 nm for blue, 450 nm for green, yellow and red emitters, reference measurement under air at room temperature).

Results

Table 11 summarizes the results:

| Ex. | Material | Colour | FWHM [eV] | EQE [%] |
|---|---|---|---|---|
| CCG1 | ES39 | deep green | 0.16 | 26.4 |
| CCG2 | ES65 | yellow | 0.15 | 26.8 |
| CCG3 | ES66 | yellow | 0.14 | 27.6 |
| CCG4 | ES84 | green | 0.15 | 29.6 |
| CCR2 | ES67 | red | 0.15 | 25.0 |
| CCB3 | ES5 | deep blue | 0.14 | 25.2 |
| CCB4 | ES13 | blue | 0.15 | 27.4 |
| CCB5 | ES16 | blue | 0.15 | 25.6 |
| CCB6 | ES17 | blue | 0.15 | 27.3 |
| CCB7 | ES19 | blue | 0.14 | 28.6 |
| CCB8 | ES20 | deep blue | 0.14 | 24.3 |
| CCB9 | ES22 | deep blue | 0.15 | 24.0 |
| CCB10 | ES26 | deep blue | 0.15 | 26.7 |
| CCB11 | ES29 | blue | 0.15 | 32.1 |
| CCB12 | ES32 | blue | 0.16 | 34.0 |
| CCB13 | ES33 | blue | 0.15 | 29.4 |
| CCB14 | ES35 | blue | 0.15 | 30.1 |
| CCB15 | ES36 | deep blue | 0.15 | 29.6 |
| CCB16 | ES45 | deep blue | 0.14 | 21.6 |
| CCB17 | ES46 | blue | 0.14 | 33.5 |
| CCB18 | ES53 | blue | 0.14 | 30.3 |
| CCB19 | ES57 | blue | 0.15 | 31.4 |
| CCB20 | EAS5 | deep blue | 0.15 | 29.9 |
| CCB21 | EAS16 | deep blue | 0.17 | 25.8 |
| CCB22 | EAS25 | deep blue | 0.16 | 24.9 |
| CCB23 | EAS33A | deep blue | 0.15 | 26.8 |
| CCB24 | EAS39 | deep blue | 0.15 | 27.8 |
| CCB25 | EAS40B | blue | 0.15 | 31.0 |
| CCB26 | EAS42 | blue | 0.15 | 30.3 |
| CCB27 | ES72 | blue | 0.19 | 31.4 |
| CCB28 | ES74 | blue | 0.14 | 29.9 |
| CCB29 | ES75 | blue | 0.14 | 30.4 |
| CCB30 | ESA45A | blue | 0.15 | 29.1 |
| CCB31 | ES80 | blue | 0.14 | 28.9 |
| CCB32 | ES81 | blue | 0.18 | 28.7 |
| CCB33 | ES85 | blue | 0.15 | 30.3 |
| CCB34 | ES89 | deep blue | 0.16 | 31.2 |

The invention claimed is:

1. A compound comprising at least one structure of the formula (I),

Formula (I)

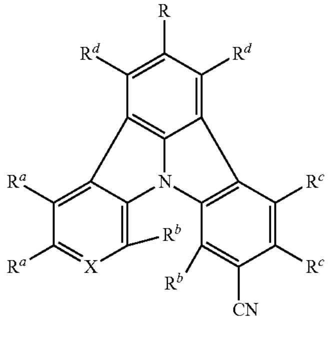

where the symbols and indices used are as follows:

X is the same or different at each instance and is N, C—CN, C—Y—$R^y$ or $CR^b$;

Y is the same or different at each instance and is CO, P(═O)$R^a$, SO, $SO_2$, C(O)O, C(S)O, C(O)S, C(═O)$NR^a$, C(═O)NAr;

R is the same or different at each instance and is H, D, OH, F, Cl, Br, I, CN, $NO_2$, $N(Ar)_2$, $N(R^e)_2$, C(═O)$N(Ar)_2$, C(═O)$N(R^e)_2$, $C(Ar)_3$, $C(R^e)_3$, $Si(Ar)_3$, $Si(R^e)_3$, $B(Ar)_2$, $B(R^e)_2$, C(═O)Ar, C(═O)$R^e$, P(═O)$(Ar)_2$, P(═O)$(R^e)_2$, $P(Ar)_2$, $P(R^e)_2$, S(═O)Ar, S(═O)$R^e$, S(═O)$_2$Ar, S(═O)$_2R^e$, $OSO_2ArR^e$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may each be substituted by one or more $R^e$ radicals, where one or more nonadjacent $CH_2$ groups may be replaced by $R^eC$═$CR^e$, C≡C, $Si(R^e)_2$, C═O, C═S, C═Se, C═$NR^e$, —C(═O)O—, —C(═O)$N^e$—, $NR^e$, P(═O)($R^e$), —O—, —S—, SO or $SO_2$, or an aromatic or heteroaromatic ring system which has 5 to 60 aromatic ring atoms and may be substituted in each case by one or more $R^e$ radicals, or an aryloxy or heteroaryloxy group which has 5 to 60 aromatic ring atoms and may be substituted by one or more $R^e$ radicals, or an arylthio or heteroarylthio group which has 5 to 60 aromatic ring atoms and may be substituted by one or more $R^e$ radicals, or a diarylamino, arylheteroarylamino, diheteroarylamino group which has 5 to 60 aromatic ring atoms and may be substituted by one or more $R^e$ radicals, or an arylalkyl or heteroarylalkyl group which has 5 to 60 aromatic ring atoms and 1 to 10 carbon atoms in the alkyl radical and may be substituted by one or more $R^e$ radicals; at the same time, any R radical may form a ring system with a further group;

Ar is the same or different at each instance and is an aromatic or heteroaromatic ring system which has 5 to 60 aromatic ring atoms and may be substituted by one or more $R^e$ radicals; at the same time, it is possible for two Ar radicals bonded to the same carbon atom, silicon atom, nitrogen atom, phosphorus atom or boron atom also to be joined together via a bridge by a single bond or a bridge selected from $B(R^e)$, $C(R^e)_2$, $Si(R^e)_2$, C═O, C═$NR^e$, C═$C(R^e)_2$, O, S, S═O, $SO_2$, $N(R^e)$, $P(R^e)$ and P(═O)$R^e$;

$R^a$, $R^b$, $R^c$, $R^d$, $R^e$ is the same or different at each instance and is H, D, OH, F, Cl, Br, I, CN, $NO_2$, $N(Ar')_2$, $N(R^1)_2$, C(═O)$N(Ar')_2$, C(═O)$N(R^1)_2$, $C(Ar')_3$, $C(R^1)_3$, $Si(Ar')_3$, $Si(R^1)_3$, $B(Ar')_2$, $B(R^1)_2$, C(═O)Ar', C(═O)$R^1$, P(═O)$(Ar')_2$, P(═O)$(R^1)_2$, $P(Ar')_2$, $P(R^1)_2$, S(═O)Ar', S(═O)$R^1$, S(═O)$_2$Ar', S(═O)$_2R^1$, $OSO_2Ar'$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^1$ radicals, where one or more nonadjacent $CH_2$ groups may be replaced by $R^1C$═$CR^1$, C═C, $Si(R^1)_2$, C═O, C═S, C═Se, C═$NR^1$, —C(═O)O—, —C(═O)$NR^1$—, $NR^1$, P (═O) ($R^1$), —O—, —S—, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two $R^a$, $R^b$, $R^d$, $R^e$ radicals may also form a ring system together or with a further group;

$R^y$ is the same or different at each instance and is $C(Ar')_3$, $C(R^1)_3$, $Si(Ar')_3$, $Si(R^1)_3$, $N(Ar')_2$, $N(R^1)_2$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^1$ radicals, where one or more nonadjacent $CH_2$ groups may be replaced by $R^1C{=}CR^1$, C≡C, $Si(R^1)_2$, C═O, C═S, C═Se, $C{=}NR^1$, —C(═O)O—, $—C({=}O)NR^1—$, $NR^1$, $P({=}O)(R^1)$, —O—, —S—, SO or $SO_2$, where any $CH_2$ group bonded to the Y radical may not be replaced by C═O, C═S, C═Se, $C—NR^1$, —C(═O)O—, $—C({=}O)NR^1—$, P(═O) $(R^1)$, SO or $SO_2$, where any $CH_2$ group bonded to the Y radical may optionally not be replaced by $Si(R^1)_2$, C═O, C═S, C═Se, $C{=}NR^1$, —C(═O)O—, $—C({=}O)NR^1—$, $NR^1$, $P({=}O)(R^1)$, —O—, —S—, SO or $SO_2$, or an aromatic or heteroaromatic ring system which has 5 to 60 aromatic ring atoms and may be substituted in each case by one or more $R^1$ radicals; at the same time, two $R^y$ radicals may also form a ring system with one another, or one $R^y$ radical together with one $R^a$, $R^b$, $R^c$, $R^c$, $R^e$ radical;

Ar' is the same or different at each instance and is an aromatic or heteroaromatic ring system which has 5 to 60 aromatic ring atoms and may be substituted by one or more $R^1$ radicals; at the same time, it is possible for two Ar' radicals bonded to the same carbon atom, silicon atom, nitrogen atom, phosphorus atom or boron atom also to be joined together via a bridge by a single bond or a bridge selected from $B(R^1)$, $C(R^1)_2$, $Si(R^1)_2$, C═O, $C{=}NR^1$, $C{=}C(R^1)_2$, O, S, S═O, $SO_2$, $N(R^1)$, $P(R^1)$ and P(═O) $R^1$;

$R^1$ is the same or different at each instance and is H, D, F, Cl, Br, I, CN, $NO_2$, $N(Ar'')_2$, $N(R^2)_2$, C(═O)Ar'', C(═O) $R^2$, $P({=}O)(Ar'')_2$, $P(Ar'')_2$, $B(Ar'')_2$, $B(R^2)_2$, $C(Ar'')_3$, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by $—R^2C—CR^2—$, —C═C—, $Si(R^2)_2$, C═O, C—S, C═Se, $C{=}NR^2$, —C(═O)O—, $—C({=}O)NR^2—$, $NR^2$, $P({=}O)(R^2)$, —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more, $R^1$ radicals together may form a ring system; at the same time, one or more $R^1$ radicals may form a ring system with a further part of the compound;

Ar'' is the same or different at each instance and is an aromatic or heteroaromatic ring system which has 5 to 30 aromatic ring atoms and may be substituted by one or more $R^2$ radicals; at the same time, it is possible for two Ar'' radicals bonded to the same carbon atom, silicon atom, nitrogen atom, phosphorus atom or boron atom also to be joined together via a bridge by a single bond or a bridge selected from $B(R^2)$, $C(R^2)_2$, $Si(R^2)_2$, C═O, $C{=}NR^2$, $C{=}C(R^2)_2$, O, S, S—O, $SO_2$, $N(R^2)$, $P(R^2)$ and $P({=}O)R^2$;

$R^2$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, two or more, substituents $R^2$ together may form a ring system;

wherein two $R^e$ radicals together with the further groups to which the two $R^e$ radicals bind form a fused ring, an aliphatic or heteroaliphatic ring having 3 to 20 ring atoms or an aromatic or heteroaromatic ring having 5 to 13 ring atoms.

2. The compound according to claim 1, wherein at least one of the R, $R^a$, $R^b$, $R^c$, $R^d$, $R^e$ radicals are not H.

3. The compound according to claim 1, wherein at least one of the $R^a$, $R^c$ radicals are a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^1$ radicals, where one or more nonadjacent $CH_2$ groups may be replaced by $R^1C{=}CR^1$, C═C, $Si(R^1)_2$, C═O, C═S, C═Se, $C{=}NR^1$,-C(═O)O—, —C(═O) $NR^1—$, $NR^1$, $P({=}O)(R^1)$, —O—, —S—, SO or $SO_2$.

4. The compound according to claim 1, wherein the R radical is an aromatic or heteroaromatic ring system which has 5 to 13 aromatic ring atoms and may be substituted by one or more $R^e$ radicals.

5. The compound according to claim 1, wherein two $R^a$ radicals together with the further groups to which the two $R^a$ radicals bind form a fused ring, an aliphatic or heteroaliphatic ring having 3 to 20 ring atoms or an aromatic or heteroaromatic ring having 5 to 13 ring atoms.

6. The compound according to claim 1, comprising at least one structure of the formulae (I-1) to (I-83), Formula (I-1)

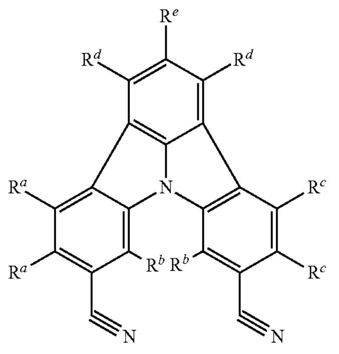

-continued
Formula (I-2)
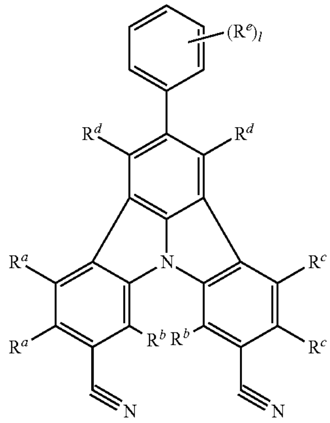
Formula (I-3)
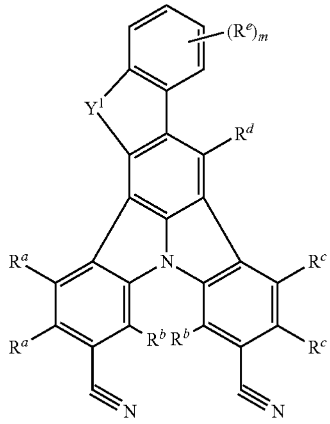
Formula (I-4)
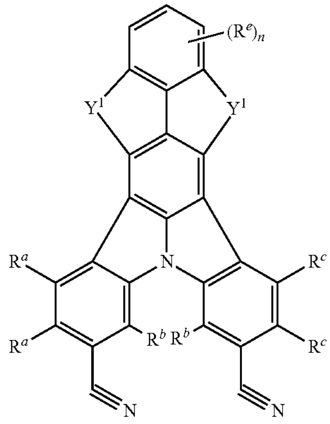
Formula (I-5)
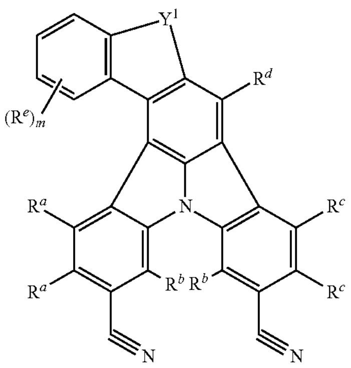
-continued
Formula (I-6)
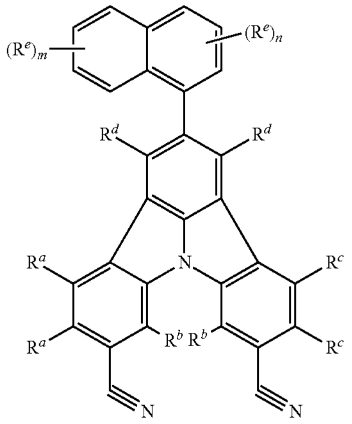
Formula (I-7)
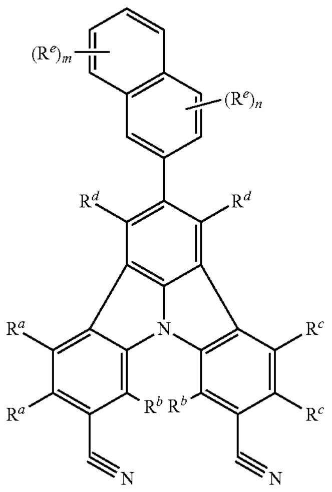
Formula (I-8)
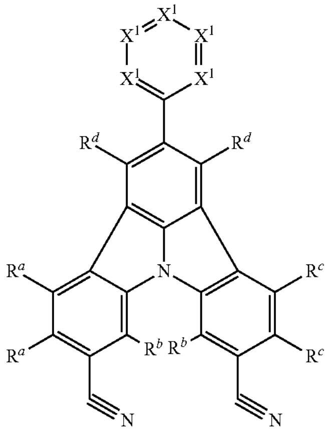

-continued
Formula (I-9)
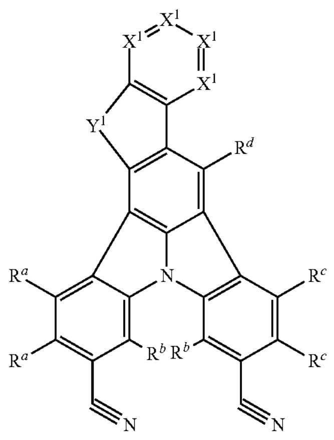
Formula (I-10)
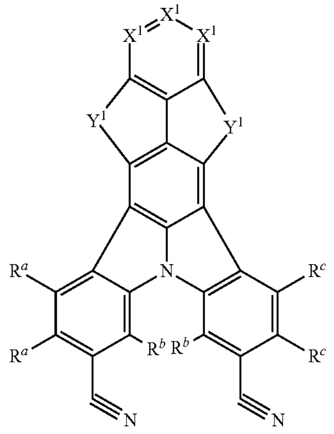
Formula (I-11)
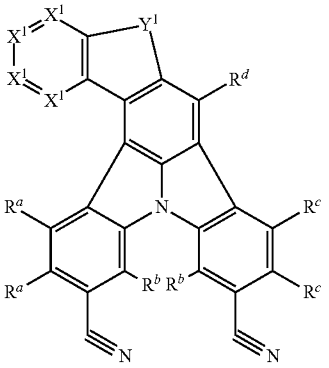
-continued
Formula (I-12)
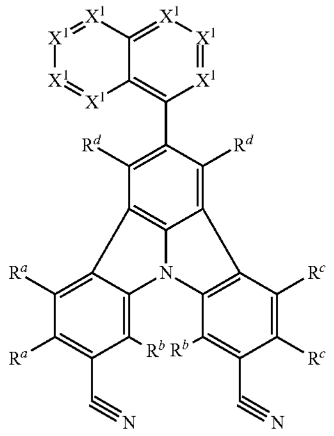
Formula (I-13)
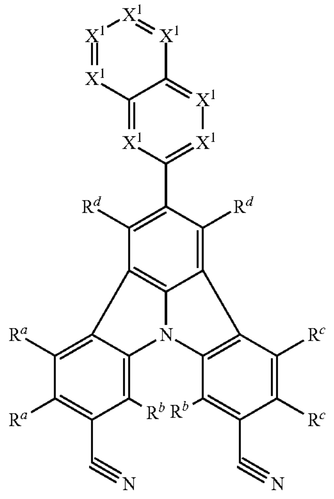
Formula (I-14)
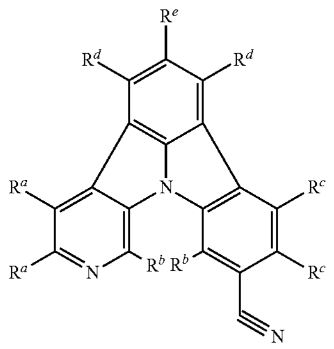

-continued
Formula (I-15)
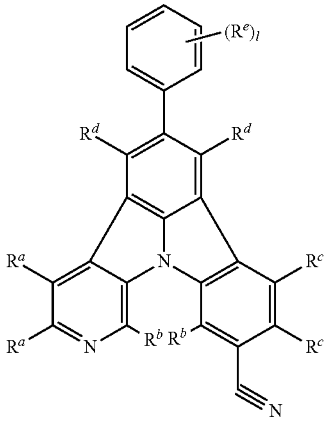
Formula (I-16)
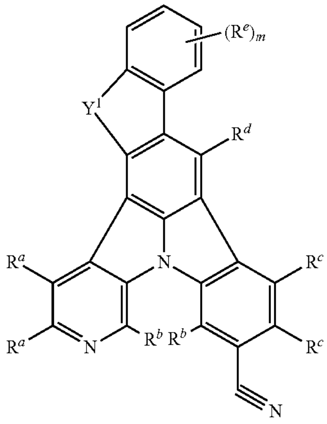
Formula (I-17)
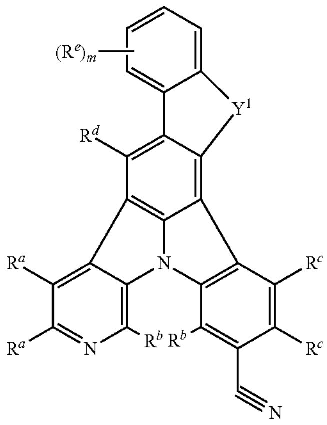
-continued
Formula (I-18)
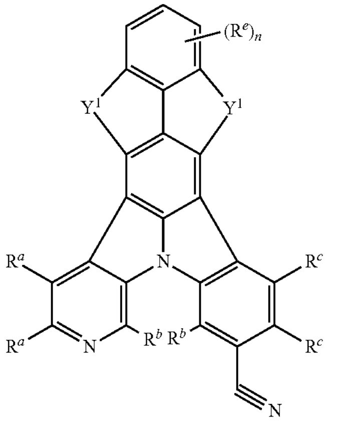
Formula (I-19)
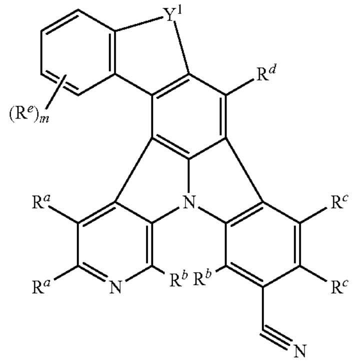
Formula (I-20)
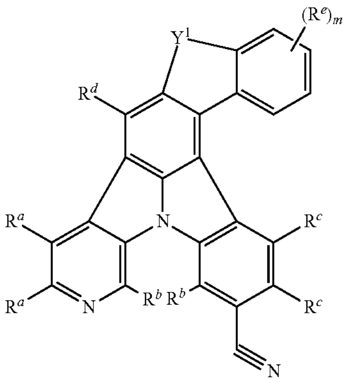
Formula (I-21)
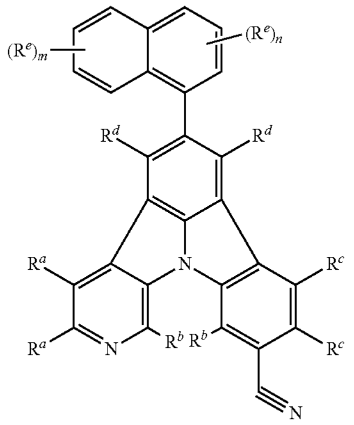

-continued
Formula (I-22)
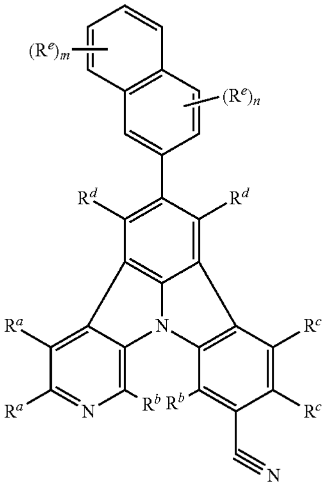
Formula (I-23)
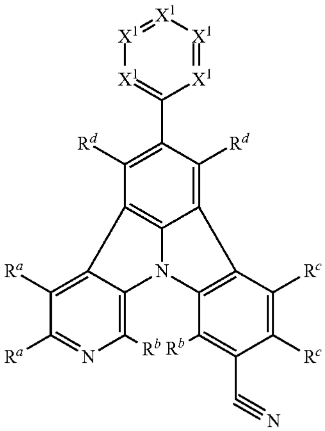
Formula (I-24)
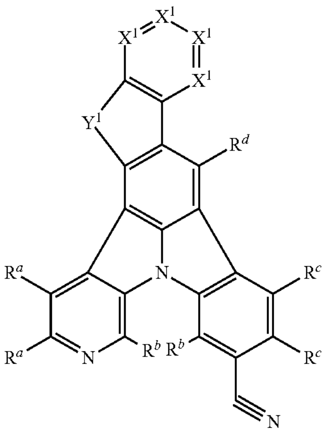
-continued
Formula (I-25)
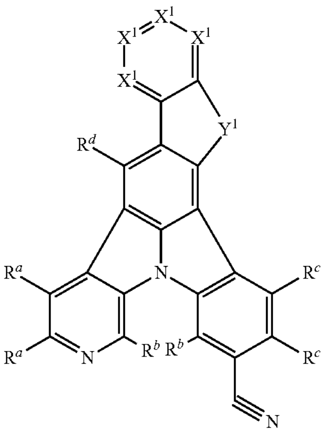
Formula (I-26)
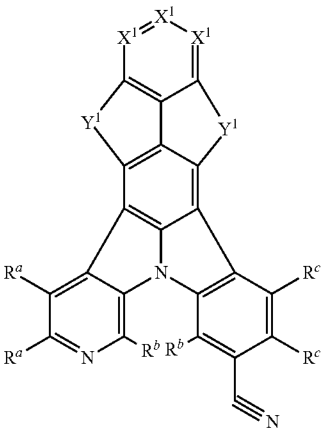
Formula (I-27)
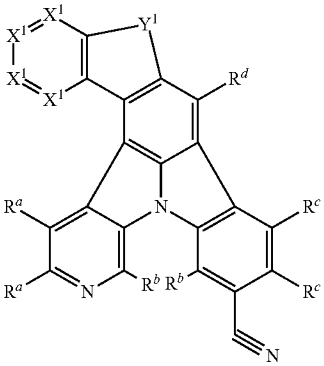
Formula (I-28)
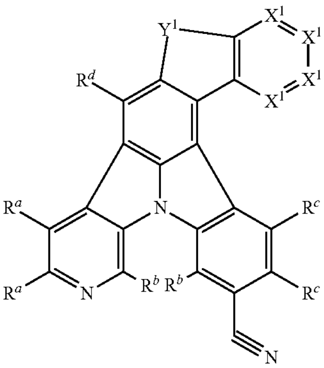

-continued
Formula (I-29)
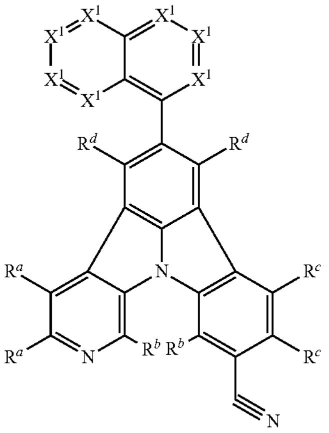
Formula (I-30)
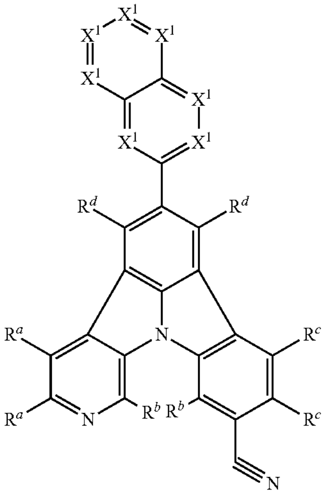
Formula (I-31)
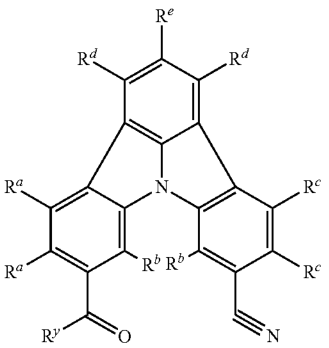
-continued
Formula (I-32)
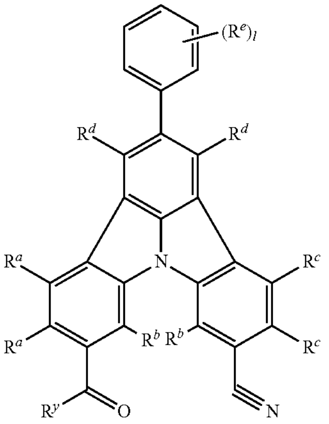
Formula (I-33)
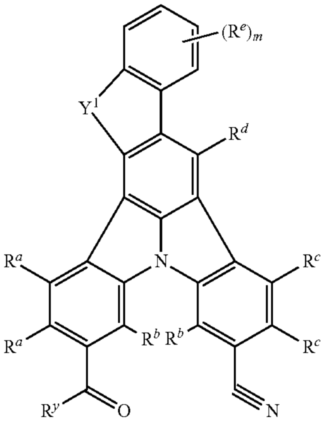
Formula (I-34)
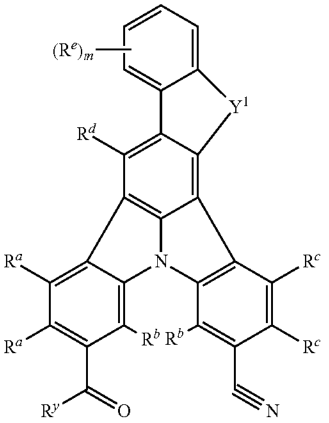

-continued
Formula (I-35)
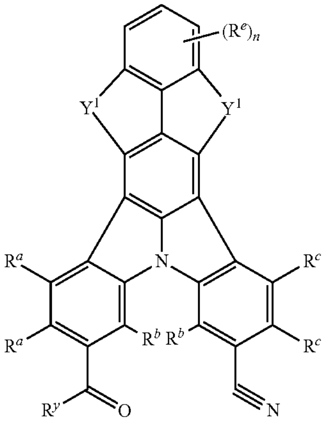
Formula (I-36)
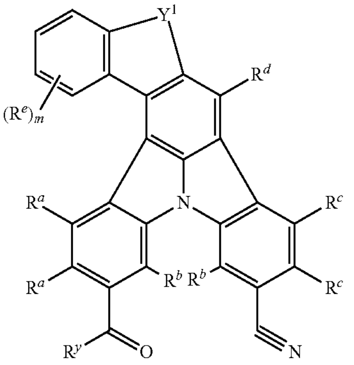
Formula (I-37)
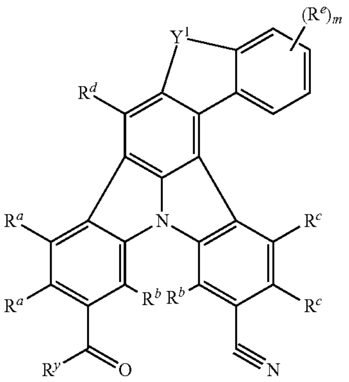
Formula (I-38)
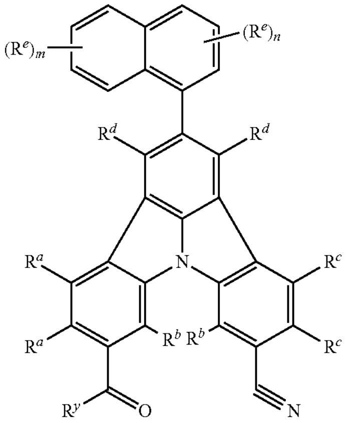
-continued
Formula (I-39)
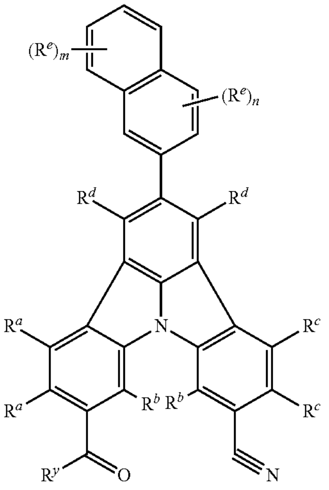
Formula (I-40)
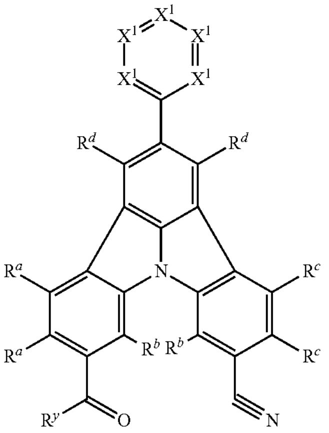
Formula (I-41)
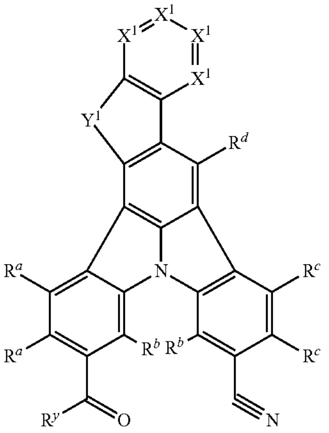

-continued
Formula (I-42)
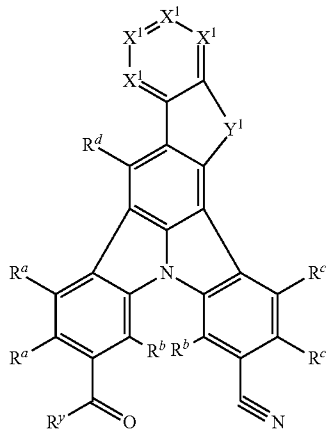
Formula (I-43)
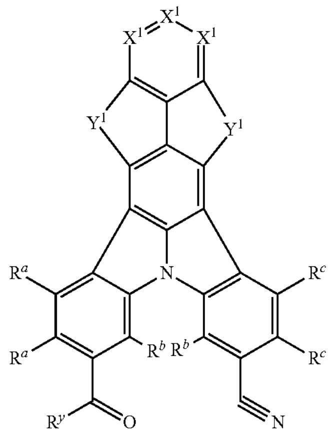
Formula (I-44)
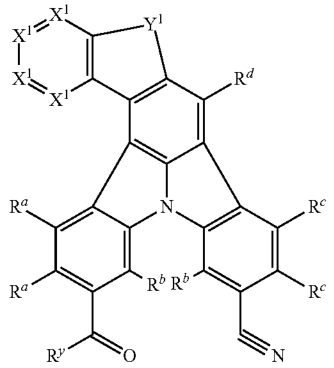
Formula (I-45)
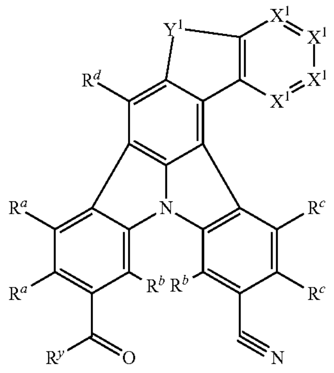
-continued
Formula (I-46)
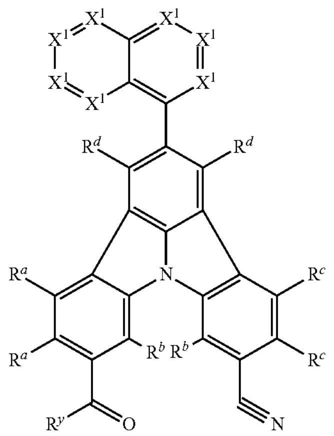
Formula (I-47)
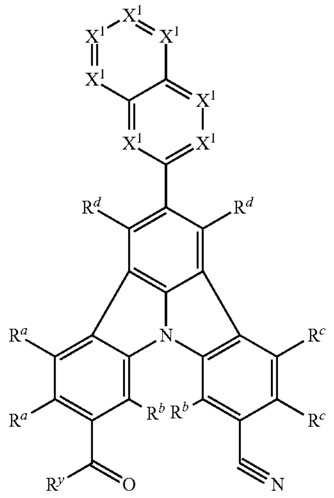
Formula (I-48)
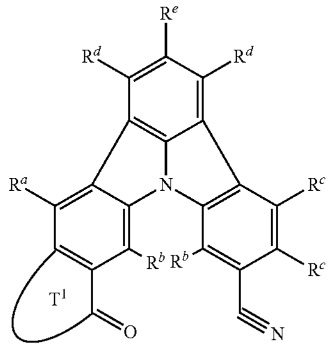

-continued
Formula (I-49)
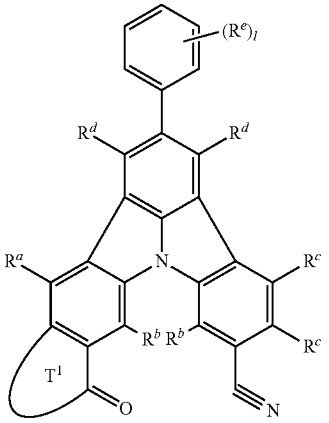
Formula (I-50)
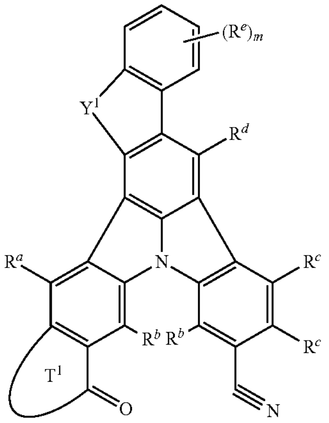
Formula (I-51)
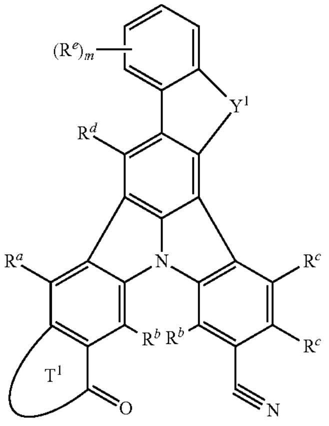
-continued
Formula (I-52)
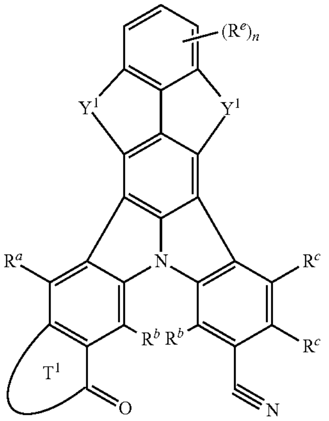
Formula (I-53)
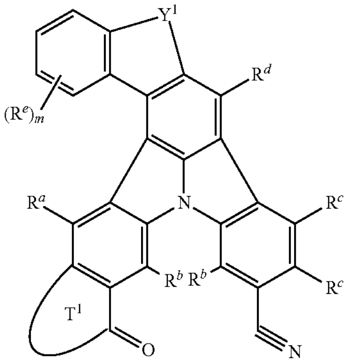
Formula (I-54)
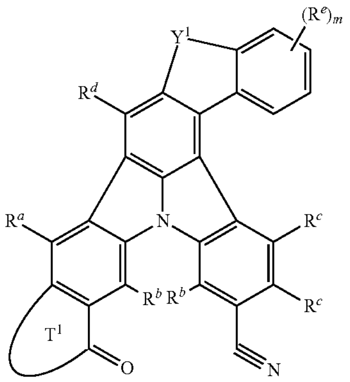
Formula (I-55)
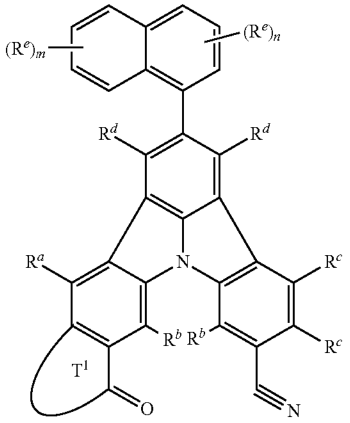

-continued
Formula (I-56)
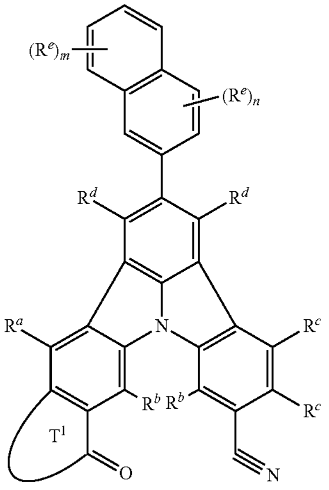
Formula (I-57)
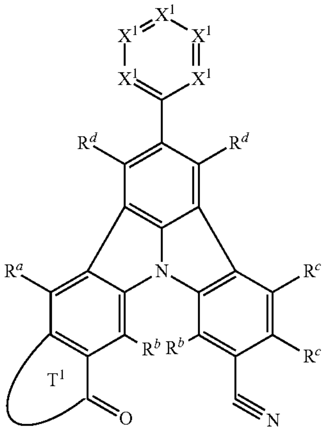
Formula (I-58)
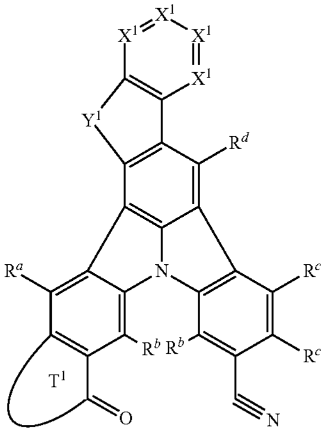
-continued
Formula (I-59)
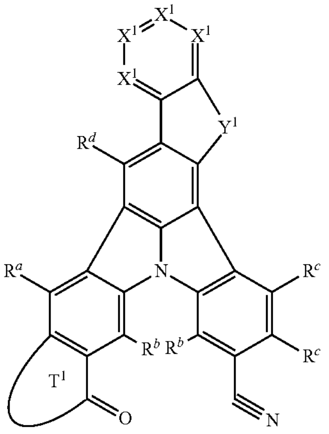
Formula (I-60)
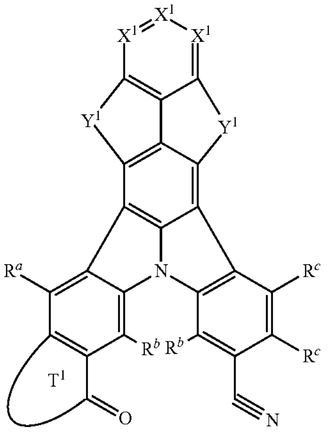
Formula (I-61)
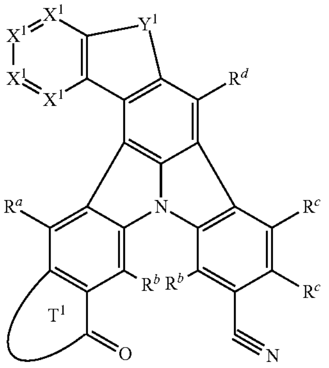
Formula (I-62)
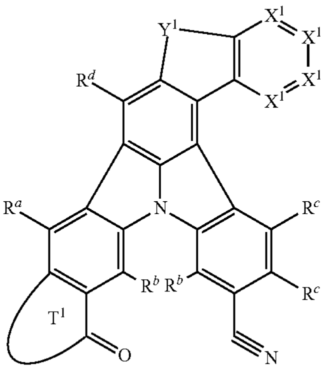

-continued
Formula (I-63)
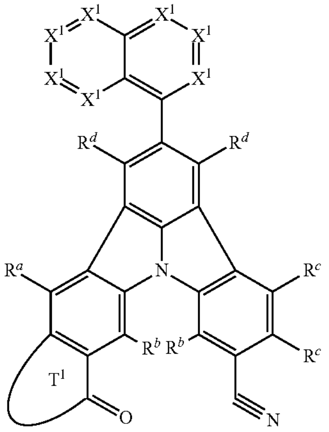
Formula (I-64)
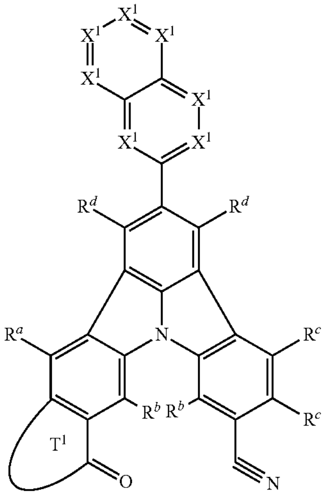
Formula (I-65)
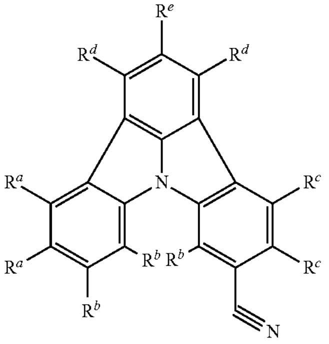
-continued
Formula (I-66)
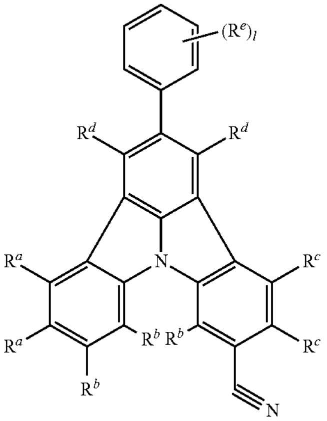
Formula (I-67)
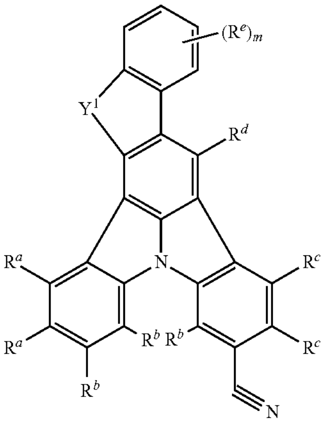
Formula (I-68)
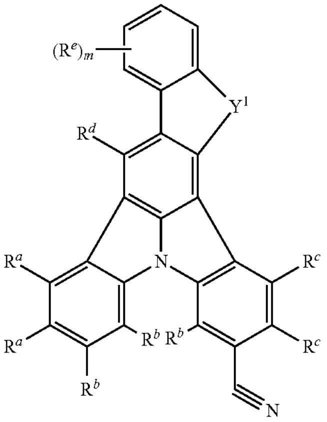

-continued
Formula (I-69)
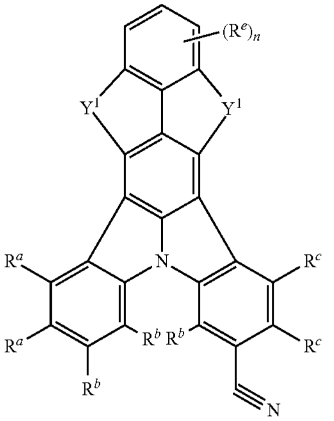
Formula (I-70)
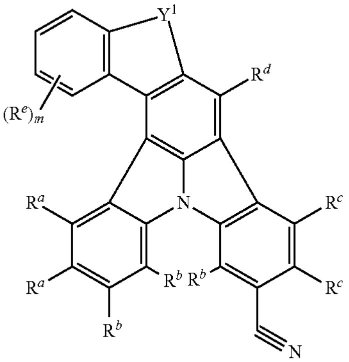
Formula (I-71)
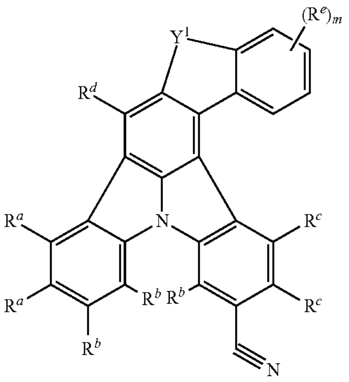
Formula (I-72)
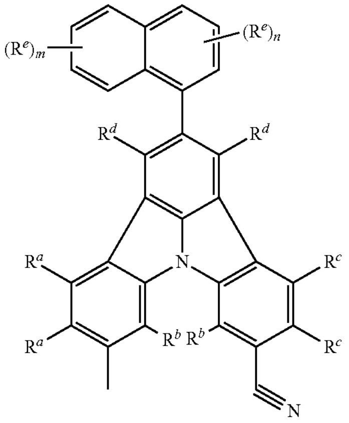
-continued
Formula (I-73)
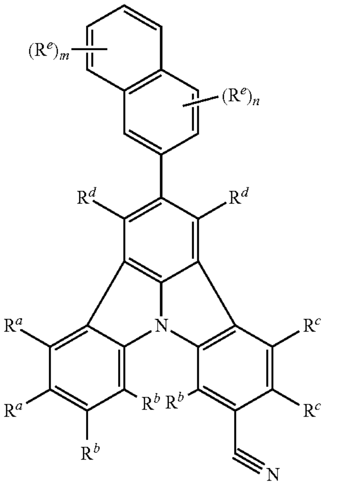
Formula (I-74)
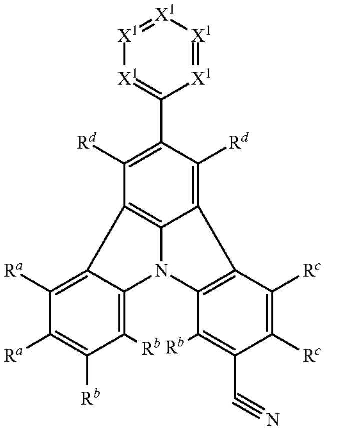
Formula (I-75)
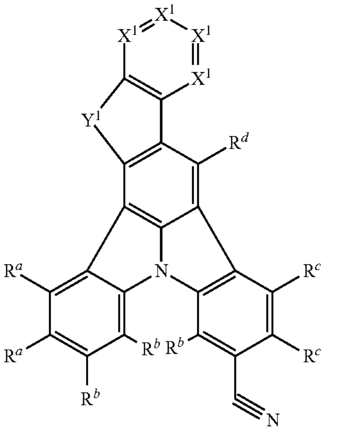

-continued
Formula (I-76)
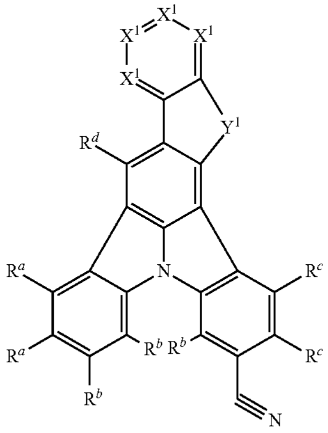
Formula (I-77)
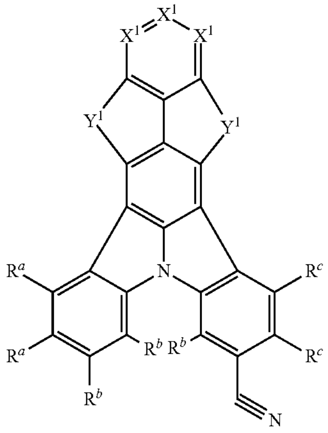
Formula (I-78)
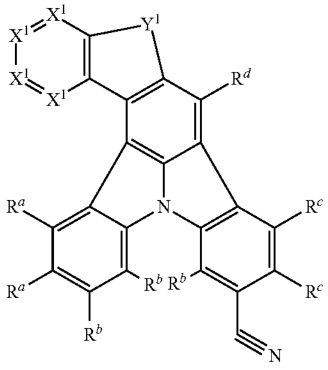
Formula (I-79)
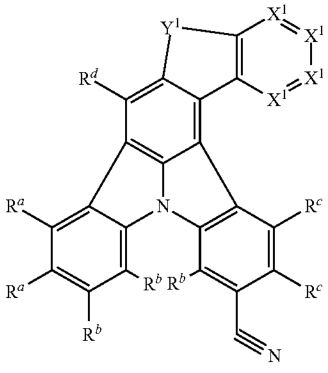
-continued
Formula (I-80)
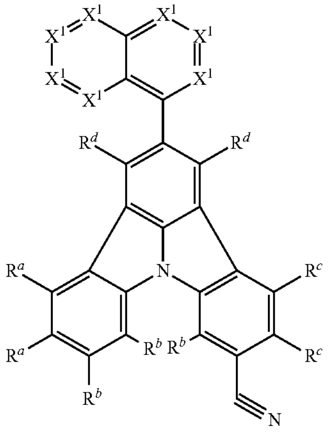
Formula (I-81)
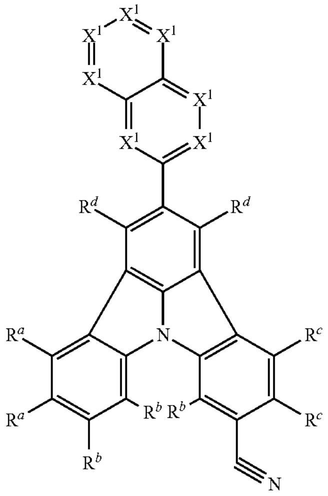
Formula (I-82)
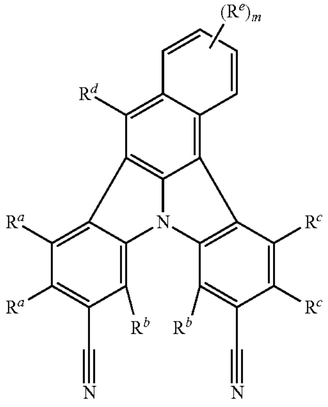

-continued

Formula (I-83)

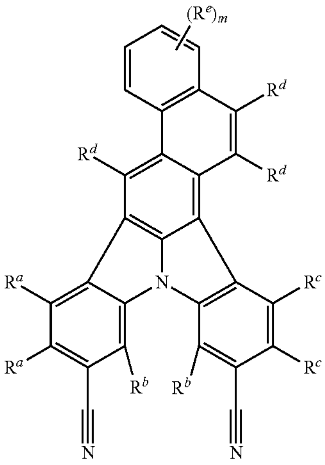

wherein the symbols $R^a$, $R^b$, $R^c$, $R^d$, $R^e$ and $R^y$ have the definitions given in claim 1 and the further symbols and indices used are as follows:

$X^1$ is the same or different at each instance and is N or $CR^e$, with the proviso that not more than two of the $X^1$ groups in one cycle are N;

$Y^1$ is the same or different at each instance and is $C(R^e)_2$, $(R^e)_2C—C(R^e)_2$, $(R^e)C═C(R^e)$, $NR^e$, $NAr^e$, O, S, SO, $SO_2$, Se, P(O) $R^e$, $BR^e$ or $Si(R^e)_2$;

$T^1$ is the same or different at each instance and is a fused ring, an aliphatic or heteroaliphatic ring having 3 to 20, or an aromatic or heteroaromatic ring having 5 to 13 ring atoms, which may be substituted by one or more $R^1$ radicals, where $R^1$ has the definition given in claim 1;

n is 0, 1, 2 or 3; and m is 0, 1, 2, 3 or 4.

7. The compound according to claim 1, wherein at least two R, $R^a$, $R^b$, $R^c$, $R^d$, $R^e$, $R^y$ radicals together with the further groups to which the two R, $R^a$, $R^b$, $R^c$, $R^d$, $R^e$, $R^y$ radicals bind form a fused ring, where the two R, $R^a$, $R^b$, $R^c$, $R^d$, $R^e$, $R^y$ radicals form at least one structure of the following formulae (Cy-1) to (Cy-10), Formula (Cy-1)

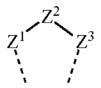

Formula (Cy-2)

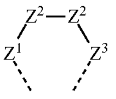

Formula (Cy-3)

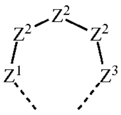

Formula (Cy-4)

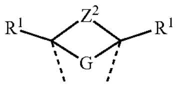

Formula (Cy-5)

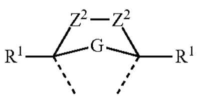

-continued

Formula (Cy-6)

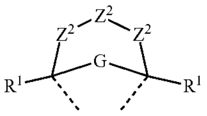

Formula (Cy-7)

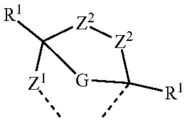

Formula (Cy-8)

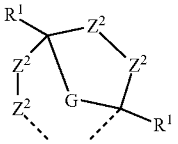

Formula (Cy-9)

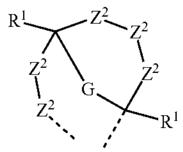

Formula (Cy-10)

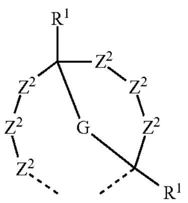

where $R^1$ and $R^2$ have the definitions given in claim 1, the dotted bonds represent the sites of attachment to the atoms of the groups to which the two R, $R^a$, $R^b$, $R^c$, $R^d$, $R^e$, $R^y$ radicals bind, and in addition:

$Z^1$, $Z^3$ is the same or different at each instance and is $C(R^3)_2$, O, S, $NR^3$ or C(—O);

$Z^2$ is $C(R^1)_2$, O, S, $NR^1$ or C(═O), where two adjacent groups $Z^2$ represent-$CR^1$═$CR^1$— or an ortho-bonded arylene or heteroarylene group having 5 to 14 aromatic ring atoms which may be substituted by one or more $R^1$ radicals;

G is an alkylene group which has 1, 2 or 3 carbon atoms and may be substituted by one or more $R^1$ radicals, —$CR^1$═$CR^1$— or an ortho-bonded arylene or heteroarylene group which has 5 to 14 aromatic ring atoms and may be substituted by one or more $R^1$ radicals;

$R^1$ is the same or different at each instance and is H, D, F, Cl, Br, I, CN, $NO_2$, $N(Ar'')_2$, $N(R^2)_2$, C(═O) Ar'', C(═O) $R^2$, $P(═O)(Ar'')_2$, $P(Ar'')_2$, $B(Ar'')_2$, $B(R^2)_2$, $C(Ar'')_3$, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by —$R^2C$—$CR^2$—, —C═C—, $Si(R^2)_2$, C═O, C═S, C═Se, C═$NR^2$, —C(═O)O—, —C(═O)$NR^2$—, $NR^2$, P(═O)($R^2$), —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two $R^3$ radicals which are bonded to the same carbon atom together may form an aliphatic or aromatic ring system and thus span a spiro system; in addition, $R^3$ may form a ring system with an R, $R^a$, $R^c$, $R^d$, $R^e$ or $R^1$ radical;

with the proviso that no two heteroatoms in these groups are bonded directly to one another and no two C═O groups are bonded directly to one another.

8. The compound according to claim 1, wherein at least two R, $R^a$, $R^b$, $R^c$, $R^d$, $R^e$, $R^y$ radicals together with the further groups to which the two R, $R^a$, $R^b$, $R^c$, $R^d$, $R^e$, $R^y$ radicals bind form a fused ring, where the two R, $R^a$, $R^b$, $R^c$, $R^d$, $R^e$, $R^y$ radicals form at least one structure of the formulae (RA-1) to (RA-13)

Formula RA-1

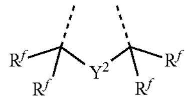

Formula RA-2

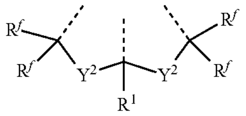

Formula RA-3

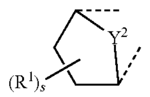

Formula RA-4

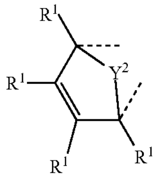

Formula RA-5

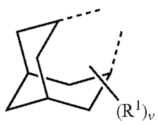

Formula RA-6

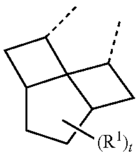

Formula RA-7

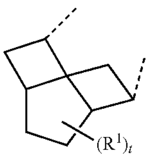

-continued

Formula RA-8

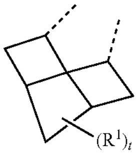

Formula RA-9

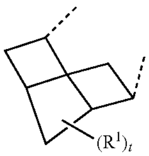

Formula RA-10

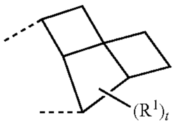

Formula RA-11

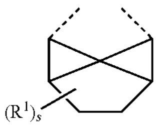

Formula RA-12

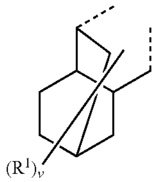

Formula RA-13

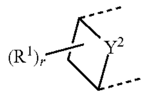

where $R^1$ has the definition set out above, the dotted bonds represent the sites of attachment to the atoms of the groups to which the two R, $R^a$, $R^b$, $R^c$, $R^d$, $R^e$, $R^y$ radicals bind, and the further symbols have the following definition:

$Y^2$ is the same or different at each instance and is $C(R^1)_2$, $(R^1)_2C—C(R^1)_2$, $(R^1)C—C(R^1)$, $NR^1$, NAr', O or S;

$R^f$ is the same or different at each instance and is F, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may in each case be substituted by one or more $R^2$ radicals, where one or more nonadjacent $CH_2$ groups may be replaced by $R^2C—CR^2$, C≡C, $Si(R^2)_2$, C═O, C═S, C═Se, $C═NR^2$, —C(═O)O—, $—C(═O)NR^2—$, $NR^2$, $P(═O)(R^1)$, —O—, —S—, SO or $SO_2$, or an aromatic or heteroaromatic ring system which has 5 to 60 aromatic ring atoms and may be substituted in each case by one or more $R^2$ radicals, or an aryloxy or heteroaryloxy group which has 5 to 60 aromatic ring atoms and may be substituted by one or more $R^2$ radicals; at the same time, two $R^f$ radicals together or one $R^f$ radical together with an $R^1$ radical or with a further group may form a ring system;

r is 0, 1, 2, 3 or 4;

s is 0, 1, 2, 3, 4, 5 or 6;

t is 0, 1, 2, 3, 4, 5, 6, 7 or 8; and

V is 0, 1, 2, 3, 4, 5, 6, 7, 8 or 9.

9. The compound according to claim 1, wherein at least two R, $R^a$, $R^b$, $R^c$, $R^d$, $R^e$, $R^y$ radicals together with the further groups to which the two R, $R^a$, $R^b$, $R^c$, $R^d$, $R^e$, $R^y$ radicals bind form a fused ring, where the two R, $R^a$, $R^b$, $R^c$, $R^d$, $R^e$, $R^y$ radicals form the structures of the formulae (RB)

Formula RB

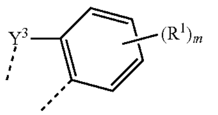

where $R^1$ has the definition set out in claim 1, the dotted bonds represent the bonding sites via which the two R, $R^a$, $R^b$, $R^e$, $R^d$, $R^e$, $R^y$ radicals bind, the index m is 0, 1, 2, 3 or 4, and $Y^3$ is $C(R^1)_2$, $NR^1$, NAr', $BR^1$, BAr', O or S.

10. The compound according to claim 1, wherein R or Ar is the same or different at each instance and is selected from phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, indolocarbazole, pyridine, pyrimidine, pyrazine, pyridazine, triazine, quinoline, isoquinoline, quinazoline, quinoxaline, phenanthrene or triphenylene, each of which may be substituted by one or more $R^e$ radicals.

11. The compound according to claim 1, wherein the compound is symmetric in relation to the $R^a$ and $R^c$ radicals.

12. The compound according to claim 1, wherein the $R^e$ and/or $R^d$ radical represents, comprises, or forms together with an $R^d$ or $R^e$ radical, at least one group selected from $C(Ar')_3$, $C(R^1)_3$, $Si(Ar')_3$, $Si(R^1)_3$, $B(R^1)$ 2 that may be substituted by one or more $R^1$ radicals.

13. The compound according to claim 6, wherein the compound comprises exactly two or exactly three structures of formula (I) and/or (I-1) to (I-81).

14. A formulation comprising at least one compound according to claim 1 and at least one further compound.

15. A composition comprising at least one compound according to claim 1 and at least one further compound selected from the group consisting of fluorescent emitters, phosphorescent emitters, emitters that exhibit TADF, host materials, electron transport materials, electron injection materials, hole conductor materials, hole injection materials, electron blocker materials and hole blocker materials.

16. The composition according to claim 15, wherein the at least one further compound is a TADF host material and/or at least one further compound is a phosphorescent emitter (triplet emitter).

17. A process for preparing the compound according to claim 1, which comprises synthesizing a base skeleton having an aromatic amino group and at least one aromatic or heteroaromatic radical is introduced.

18. An electronic device comprising at least one compound according to claim 1.

19. A compound comprising at least one structure of the formula (I),

Formula (I)

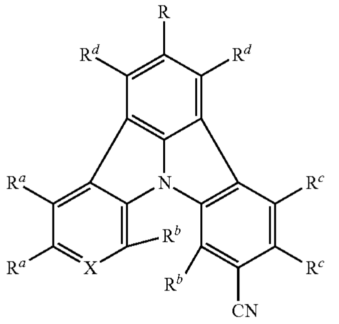

where the symbols and indices used are as follows:

X is the same or different at each instance and is N, C—CN, C—Y—$R^y$ or $CR^b$;

Y is the same or different at each instance and is CO, P(═O)$R^a$, SO, $SO_2$, C(O) O, C(S) O, C(O) S, C(—O) $NR^a$, C(═O)NAr;

R is the same or different at each instance and is H, D, OH, F, Cl, Br, I, CN, $NO_2$, $N(Ar)_2$, $N(R^e)_2$, C(═O)$N(Ar)_2$, C(═O)$N(R^e)_2$, $C(Ar)_3$, $C(R^e)_3$, $Si(Ar)_3$, $Si(R^e)_3$, $B(Ar)_2$, $B(R^e)_2$, C(═O) Ar, C(═O) $R^e$, P(═O) $(Ar)_2$, P(═O)$(R^e)_2$, $P(Ar)_2$, $P(R^e)_2$, S(═O) Ar, S(═O)$R^e$, S(═O)$_2$Ar, S(═O)$_2R^e$, $OSO_2Ar$, $OSO_2R^e$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may each be substituted by one or more $R^e$ radicals, where one or more nonadjacent $CH_2$ groups may be replaced by $R^e$C═C$R^e$, C≡C, $Si(R^e)_2$, C═O, C═S, C═Se, C═$NR^e$, —C(═O)O—, —C(═O) $N^e$—, $NR^e$, P(═O)($R^e$), —O—, —S—, SO or $SO_2$, or an aromatic or heteroaromatic ring system which has 5 to 60 aromatic ring atoms and may be substituted in each case by one or more $R^e$ radicals, or an aryloxy or heteroaryloxy group which has 5 to 60 aromatic ring atoms and may be substituted by one or more $R^e$ radicals, or an arylthio or heteroarylthio group which has 5 to 60 aromatic ring atoms and may be substituted by one or more $R^e$ radicals, or a diarylamino, arylheteroarylamino, diheteroarylamino group which has 5 to 60 aromatic ring atoms and may be substituted by one or more $R^e$ radicals, or an arylalkyl or heteroarylalkyl group which has 5 to 60 aromatic ring atoms and 1 to 10 carbon atoms in the alkyl radical and may be substituted by one or more $R^e$ radicals; at the same time, any R radical may form a ring system with a further group;

Ar is the same or different at each instance and is an aromatic or heteroaromatic ring system which has 5 to 60 aromatic ring atoms and may be substituted by one or more $R^e$ radicals; at the same time, it is possible for two Ar radicals bonded to the same carbon atom, silicon atom, nitrogen atom, phosphorus atom or boron atom also to be joined together via a bridge by a single bond or a bridge selected from $B(R^e)$, $C(R^e)_2$, $Si(R^e)_2$, C═O, C═$NR^e$, C═$C(R^e)_2$, O, S, S═O, $SO_2$, $N(R^e)$, $P(R^e)$ and P(═O) $R^e$;

$R^a$, $R^b$, $R^c$, $R^d$, $R^e$ is the same or different at each instance and is H, D, OH, F, Cl, Br, I, CN, $NO_2$, $N(Ar')_2$, $N(R^1)_2$, $C(=O)N(Ar')_2$, $C(=O)N(R^1)_2$, $C(Ar')_3$, $C(R^1)_3$, $Si(Ar')_3$, $Si(R^1)_3$, $B(Ar')_2$, $B(R^1)_2$, C(=O) Ar', C(=O) $R^1$, $P(=O)(Ar')_2$, P(=O) $(R^1)_2$, $P(Ar')_2$, $P(R^1)_2$, S(=O) Ar', S(=O) $R^1$, $S(=O)_2Ar'$, $S(=O)_2R^1$, $OSO_2Ar'$, $OSO_2R^1$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^1$ radicals, where one or more nonadjacent $CH_2$ groups may be replaced by $R^1C$—$CR^1$, C≡C, $Si(R^1)_2$, C=O, C=S, C=Se, C=$NR^1$, —C(=O)O—, —C(=O)$NR^1$—, $NR^1$, P(=O)($R^1$), —O—, —S—, SO or $SO_2$, or an aromatic or heteroaromatic ring system which has 5 to 60 aromatic ring atoms and may be substituted in each case by one or more $R^1$ radicals, or an aryloxy or heteroaryloxy group which has 5 to 60 aromatic ring atoms and may be substituted by one or more $R^1$ radicals; at the same time, two $R^a$, $R^b$, $R^d$, $R^e$ radicals may also form a ring system together or with a further group;

$R^y$ is the same or different at each instance and is $C(Ar')_3$, $C(R^1)_3$, $Si(Ar')_3$, $Si(R^1)_3$, $N(Ar')_2$, $N(R^1)_2$, a straight-chain alkyl, alkoxy or thioalkoxy group having 1 to 40 carbon atoms or an alkenyl or alkynyl group having 2 to 40 carbon atoms or a branched or cyclic alkyl, alkoxy or thioalkoxy group having 3 to 20 carbon atoms, where the alkyl, alkoxy, thioalkoxy, alkenyl or alkynyl group may be substituted in each case by one or more $R^1$ radicals, where one or more nonadjacent $CH_2$ groups may be replaced by $R^1C$=$CR^1$, C≡C, $Si(R^1)_2$, C=O, C=S, C=Se, C=$NR^1$, —C(=O)O—, —C(=O)$NR^1$—, $NR^1$, P(=O)($R^1$), —O—, —S—, SO or $SO_2$, where any $CH_2$ group bonded to the Y radical may not be replaced by C=O, C=S, C=Se, C=$NR^1$, —C(=O)O—, —C(=O)$NR^1$—, P(=O) ($R^1$), SO or $SO_2$, where any $CH_2$ group bonded to the Y radical may optionally not be replaced by $Si(R^1)_2$, C=O, C=S, C=Se, C=$NR^1$, —C(=O)O—, —C(=O)$NR^1$—, $NR^1$, P(=O) ($R^1$), —O—, —S—, SO or $SO_2$, or an aromatic or heteroaromatic ring system which has 5 to 60 aromatic ring atoms and may be substituted in each case by one or more $R^1$ radicals; at the same time, two $R^y$ radicals may also form a ring system with one another, or one $R^y$ radical together with one $R^a$, $R^b$, $R^c$, $R^d$, $R^e$ radical;

Ar' is the same or different at each instance and is an aromatic or heteroaromatic ring system which has 5 to 60 aromatic ring atoms and may be substituted by one or more $R^1$ radicals; at the same time, it is possible for two Ar' radicals bonded to the same carbon atom, silicon atom, nitrogen atom, phosphorus atom or boron atom also to be joined together via a bridge by a single bond or a bridge selected from $B(R^1)$, $C(R^1)_2$, $Si(R^1)_2$, C=O, C=$NR^1$, C=$C(R^1)_2$, O, S, S=O, $SO_2$, $N(R^1)$, $P(R^1)$ and P(=O) $R^1$;

$R^1$ is the same or different at each instance and is H, D, F, Cl, Br, I, CN, $NO_2$, $N(Ar'')_2$, $N(R^2)_2$, C(=O)Ar'', C(=O) $R^2$, $P(=O)(Ar'')_2$, $P(Ar'')_2$, $B(Ar'')_2$, $B(R^2)_2$, $C(Ar'')_3$, $C(R^2)_3$, $Si(Ar'')_3$, $Si(R^2)_3$, a straight-chain alkyl, alkoxy or thioalkoxy group having 1 to 40 carbon atoms or a branched or cyclic alkyl, alkoxy or thioalkoxy group having 3 to 40 carbon atoms or an alkenyl group having 2 to 40 carbon atoms, each of which may be substituted by one or more $R^2$ radicals, where one or more nonadjacent $CH_2$ groups may be replaced by —$R^2C$=$CR^2$—, —C≡C—, $Si(R^2)_2$, C=O, C=S, C=Se, C=$NR^2$, —C(=O)O—, —C(=O)$NR^2$—, $NR^2$, P(=O)($R^2$), —O—, —S—, SO or $SO_2$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^2$ radicals, or an aryloxy or heteroaryloxy group which has 5 to 60 aromatic ring atoms and may be substituted by one or more $R^2$ radicals, or an aralkyl or heteroaralkyl group which has 5 to 60 aromatic ring atoms and may be substituted by one or more $R^2$ radicals, or a combination of these systems; at the same time, two or more, $R^1$ radicals together may form a ring system; at the same time, one or more $R^1$ radicals may form a ring system with a further part of the compound;

Ar'' is the same or different at each instance and is an aromatic or heteroaromatic ring system which has 5 to 30 aromatic ring atoms and may be substituted by one or more $R^2$ radicals; at the same time, it is possible for two Ar'' radicals bonded to the same carbon atom, silicon atom, nitrogen atom, phosphorus atom or boron atom also to be joined together via a bridge by a single bond or a bridge selected from $B(R^2)$, $C(R^2)_2$, $Si(R^2)_2$, C=O, C=$NR^2$, C—$C(R^2)_2$, O, S, S=O, $SO_2$, $N(R^2)$, $P(R^2)$ and P(=O) $R^2$;

$R^2$ is the same or different at each instance and is selected from the group consisting of H, D, F, CN, an aliphatic hydrocarbyl radical having 1 to 20 carbon atoms or an aromatic or heteroaromatic ring system which has 5 to 30 aromatic ring atoms and in which one or more hydrogen atoms may be replaced by D, F, Cl, Br, I or CN and which may be substituted by one or more alkyl groups each having 1 to 4 carbon atoms; at the same time, two or more, substituents $R^2$ together may form a ring system;

wherein two $R^c$ radicals together with the further groups to which the two $R^c$ radicals bind form a fused ring; and wherein the R radical is not H.

* * * * *